US010392438B2

(12) United States Patent
Bennett et al.

(10) Patent No.: US 10,392,438 B2
(45) Date of Patent: Aug. 27, 2019

(54) BISPECIFIC ANTIBODIES

(71) Applicant: Pfizer Inc., New York, NY (US)

(72) Inventors: Eric M. Bennett, Arlington, MA (US); Nathan Higginson-Scott, Boston, MA (US); Lioudmila Tchistiakova, Stoneham, MA (US); Kimberly A. Marquette, Somerville, MA (US); Janet E. Paulsen, Londonderry, NH (US); Ruth E. Gimeno, Carmel, IN (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 15/309,879

(22) PCT Filed: May 13, 2015

(86) PCT No.: PCT/IB2015/053537
§ 371 (c)(1),
(2) Date: Nov. 9, 2016

(87) PCT Pub. No.: WO2015/173756
PCT Pub. Date: Nov. 19, 2015

(65) Prior Publication Data
US 2018/0179285 A1   Jun. 28, 2018

Related U.S. Application Data

(60) Provisional application No. 62/159,201, filed on May 8, 2015, provisional application No. 62/150,680, filed on Apr. 21, 2015, provisional application No. 61/994,720, filed on May 16, 2014.

(51) Int. Cl.
*C07K 16/00* (2006.01)
*C07K 16/28* (2006.01)
*C07K 16/24* (2006.01)
*A61P 27/16* (2006.01)

(52) U.S. Cl.
CPC .......... *C07K 16/2863* (2013.01); *A61P 27/16* (2018.01); *C07K 16/00* (2013.01); *C07K 16/24* (2013.01); *C07K 16/244* (2013.01); *C07K 2317/24* (2013.01); *C07K 2317/31* (2013.01); *C07K 2317/35* (2013.01); *C07K 2317/522* (2013.01); *C07K 2317/55* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| 5,731,168 A | 3/1998 | Carter et al. |
| 7,183,076 B2 | 2/2007 | Arathoon et al. |
| 7,750,122 B2 | 7/2010 | Cho et al. |
| 2002/0039995 A1 | 4/2002 | Gao |
| 2008/0269466 A1 | 10/2008 | Humphreys |
| 2010/0150914 A1 | 6/2010 | Wang et al. |
| 2010/0256340 A1 | 10/2010 | Brinkmann |
| 2012/0009621 A1 | 1/2012 | Yamasaki |
| 2014/0200331 A1* | 7/2014 | Corper .................. C07K 16/36 530/387.3 |

FOREIGN PATENT DOCUMENTS

| WO | 199852976 | 11/1998 |
| WO | 200034317 | 6/2000 |
| WO | 2009089004 | 7/2009 |
| WO | 20110117653 | 9/2011 |
| WO | 2011143545 | 11/2011 |
| WO | 20130096291 | 6/2013 |
| WO | 2014081955 A1 | 5/2014 |
| WO | 2014150973 | 9/2014 |
| WO | 2015173756 A2 | 11/2015 |

OTHER PUBLICATIONS

Davies et al: "Fab Assembly: An analysis of different Ch1:CL combinations", Progress in Immunology VI : Sixth International Congress of Immunology, pp. 145-149, 1986.
Klein et al: "Progress in overcoming the chain association issue in bispecific heterodimeric IgG antibodies", MABS, vol. 4, No. 6, pp. 653-663, 2012.
Lewis et al: "Generation of bispecific IgG antibodies by structure-based design of an orthogonal Fab interface", Nature Biotechnology, vol. 32, No. 2, pp. 191-198, 2014.
Lewis et al: "Supplemental Information: Generation of bispecific IgG antibodies by structure-based design of an orthogonal Fab interface", Nature Biotechnology, vol. 32, No. 2, 2014 doi:10.1038/nbt.2797.
Liu et al: "A Novel Antibody Engineering Strategy for Making Monovalent Bispecific Heterodimeric IgG Antibodies by Electrostatic Steering Mechanism", Journal of Biological Chemistry, vol. 290, No. 12, pp. 7535-7562, 2015.
Liu et al: "Disulfide bond structures of IgG molecules: Structural variations, chemical modifications and possible impacts to stability and biological function", MABS, vol. 4, No. 1, pp. 17-23, 2012.
Luo et al: "Design and Applications of Bispecific Heterodimers: Molecular Imaging and beyond" Molecular Pharmacuetics, vol. 11, No. 6, pp. 1750-1761, 2014.
Muller et al: "The first constant domain (CH1 and CL) of an antibody used as heterodimerization domain for bispecific miniantibodies", FEBS Letters, vol. 422, No. 2, pp. 259-264, 1998.
International Search Report and the Written Opinion, PCT/IB2015/053537, dated Dec. 2, 2015; 23 pages.

(Continued)

Primary Examiner — Sean E Aeder

(57) ABSTRACT

The present invention relates to engineered heteromultimeric proteins, and more specifically, to methods for producing and purifying heterodimeric proteins, such as bispecific antibodies and. Methods for producing and purifying such engineered heterodimeric proteins and their use in diagnostics and therapeutics are also provided. The present invention also relates to a humanized antibody that specifically binds human TrkB and methods for producing and using the antibody to, inter alia, treat a hearing loss disorder.

24 Claims, 62 Drawing Sheets

Specification includes a Sequence Listing.

(56) References Cited

OTHER PUBLICATIONS

Abhinandan et al: "Analysis and prediction of VH/VL packing in antibodies", Protein Engineering, Design & Selection, vol. 23, No. 9, pp. 689-697, 2010.
Corrada et al: "Energetic and Dynamic Aspects of the Affinity Maturation Process: Characterizing Improved Variants from the Bevacizumab Antibody with Molecular Simulations," Journal of Chemical Information and Modeling, vol. 53, pp. 2937-2950, 2013.
Dani et al: "MODIP revisited: re-evaluation and refinement of an automated procedure for modeling of disulfide bonds in proteins," Protein Engineering, vol. 16, No. 3, pp. 187-193, 2003.
Das et al: "Macromolecular Modeling with Rosetta," Annual Review of Biochemistry, vol. 77, pp. 363-82, 2008.
Eswar et al: "Tools for comparative protein structure modeling and analysis," Nucleic Acids Research, vol. 31, No. 13, pp. 3375-3380, 2003.
Feige et al: "An Unfolded CH1 Domain Controls the Assembly and Secretion of IgG Antibodies," Molecular Cell, vol. 34, pp. 569-579, 2009.
Friedman et al: "Neurotrophin Signaling via Trks and p75," Experimental Cell Research, vol. 253, pp. 131-142, 1999.
Kostelny et al: "Formation of a bispecific antibody by the use of leucine zippers," Journal of Immunology, vol. 148, pp. 1547-1553, 1992.
Krivov et al: "Improved prediction of protein side-chain conformations with SCWRL4," Proteins, vol. 77, pp. 778-795, 2009.
Laskowski: "PDBsum: summaries and analyses of PDB structures," Nucleic Acids Research, vol. 29, No. 1, pp. 221-222, 2001.
Liberman and Kujawa: "Adding Insult to Injury: Cochlear Nerve Degeneration after 'Temporary' Noise-Induced Hearing Loss," Journal of Neuroscience, vol. 29, No. 45, pp. 14077-14085, 2009.
Meltser et al: "TrkB-Mediated Protection against Circadian Sensitivity to Noise Trauma in the Murine Cochlea," Current Biology, vol. 24, pp. 658-663, 2014.
Qian et al: "Novel Agonist Monoclonal Antibodies Activate TrkB Receptors and Demonstrate Potent Neurotrophic Activities," Journal of Neuroscience, vol. 26, No. 37, pp. 9394-9403, 2006.
Saphire et al: "Crystal Structure of a Neutralizing Human IgG Against HIV-1: A Template for Vaccine Design," Science, vol. 293, pp. 1155-1159, 2001.
Schimmang et al: "Lack of Bdnf and TrkB signalling in the postnatal cochlea leads to a spatial reshaping of innervation along the tonotopic axis and hearing loss," Development, vol. 130, pp. 4741-4750, 2003.
Smith et al: "Predicting the Tolerated Sequences for Proteins and Protein Interfaces Using RosettaBackrub Flexible Backbone Design," PLoS One, vol. 6, No. 7, e20451,.
Songsivilai et al: "Bispecific antibody: a tool for diagnosis and treatment of disease," Clinical Exp Immunology, vol. 79, pp. 315-321, 1990.
Wise et al: "Resprouting and Survival of Guinea Pig Cochlear Neurons in Response to the Administration of the Neurotrophins Brain-Derived Neurotrophic Factor and Neurotrophin-3," Journal of Comparative Neurology, vol. 487, pp. 147-165, 2005.
Zhang et al: "TM-align: a protein structure alignment algorithm based on the TM-score," Nucleic Acids Research, vol. 33, No. 7, pp. 2302-2309, 2005.
Zhang et al: "Cyclic-AMP Response Element-Based Signaling Assays for Characterization of Trk Family Tyrosine Kinases Modulators," Neurosignals, vol. 15, pp. 26-39, 2006-2007.
Kleywegt et al: "Detection, delineation, measurement and display of cavities in macromolecular structures," ACTA Crystallographica Section D, vol. 50, No. 2, pp. 178-185, 1994.
Lewis et al. "Generation of bispecific IgG antibodies by structure-based design of an orthogonal Fab interface" 2014, vol. 32, No. 2, pp. 191-202.
Mazor et al. "Improving target cell specificity using a novel monovalent bispecific IgG design" MAbs. 2015;7(2):377-89.
Regula et al. "Variable heavy-variable light domain and Fab-arm CrossMabs with charged residue exchanges to enforce correct light chain assembly." Protein Engineering, Design and Selection, 2018, vol. 31, No. 7-8, pp. 289-299.
Schaefer et al. "Immunoglobulin domain crossover as a generic approach for the production of bispecific IgG antibodies." PNAS, 2011, vol. 108, No. 27, pp. 11187-11192.
Shen et al. "Conjugation site modulates the in vivo stability and therapeutic activity of antibody-drug conjugates." Nature Biotechnology, 2012, vol. 30. No. 2, pp. 184-189.
Strop et al. "Generating Bispecific Human IgG1 and IgG2 Antibodies from Any Antibody Pair" J. Mole. Biol., 2012, vol. 420, pp. 204-219.

* cited by examiner

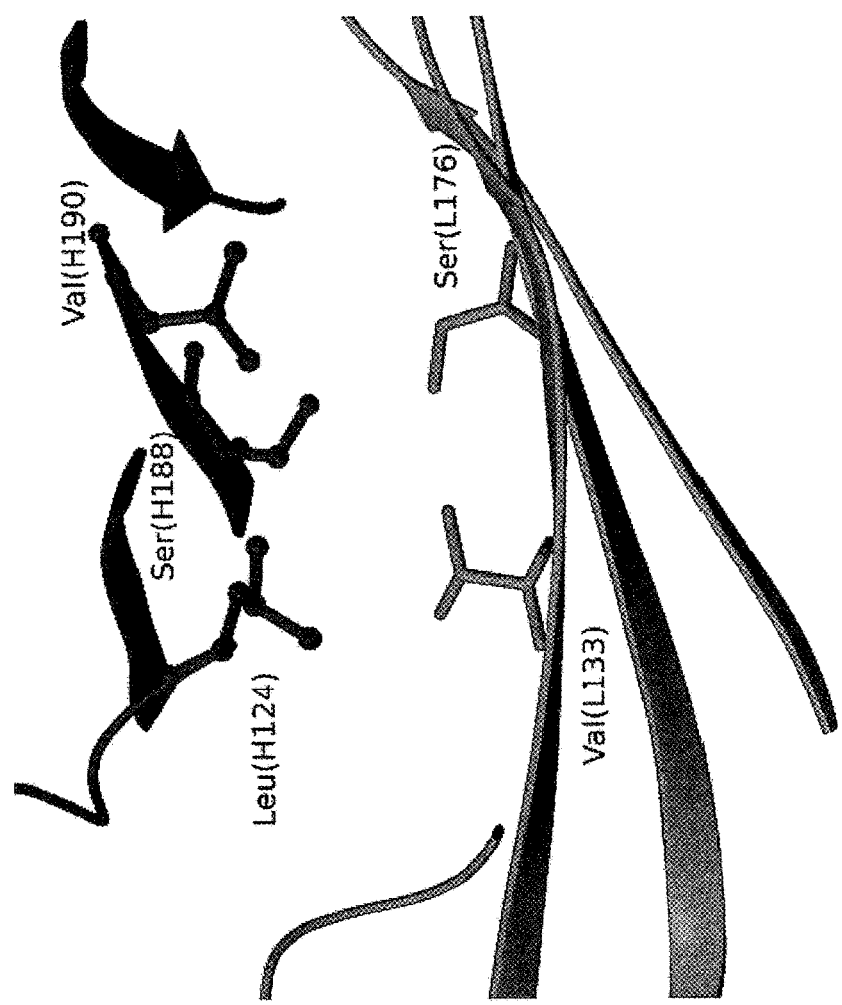

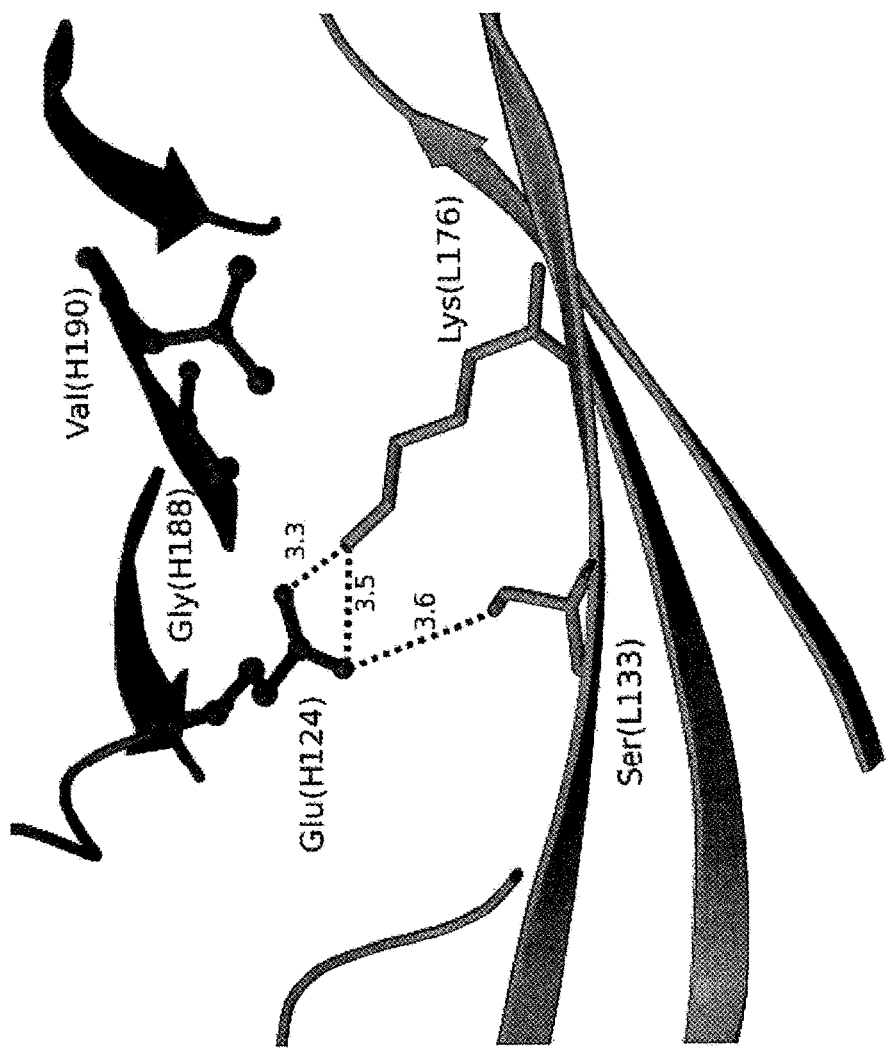

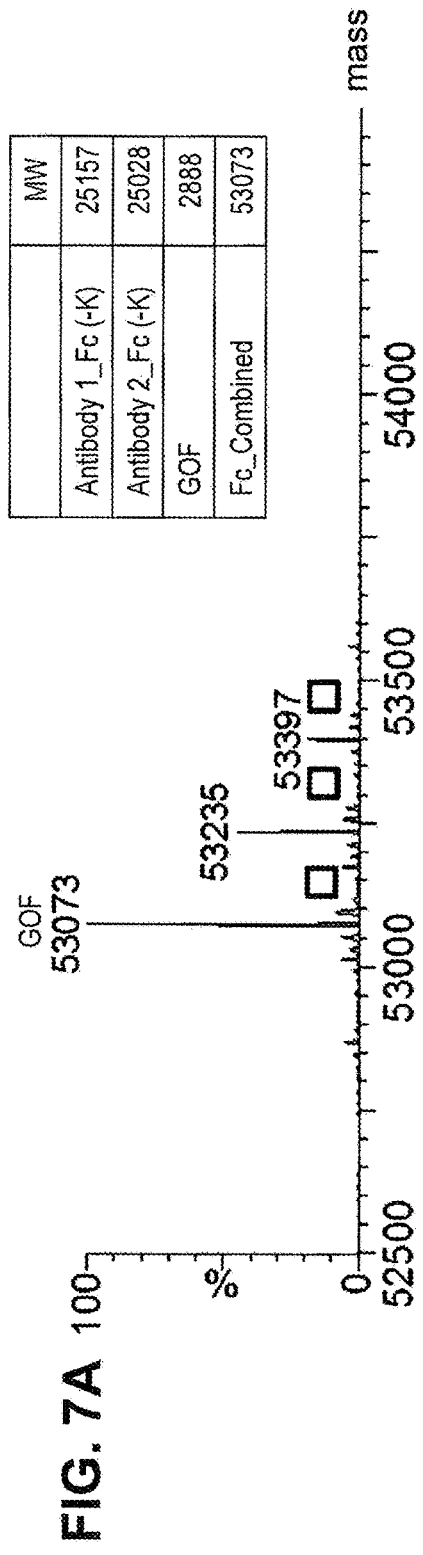
FIG. 7A
FIG. 7B

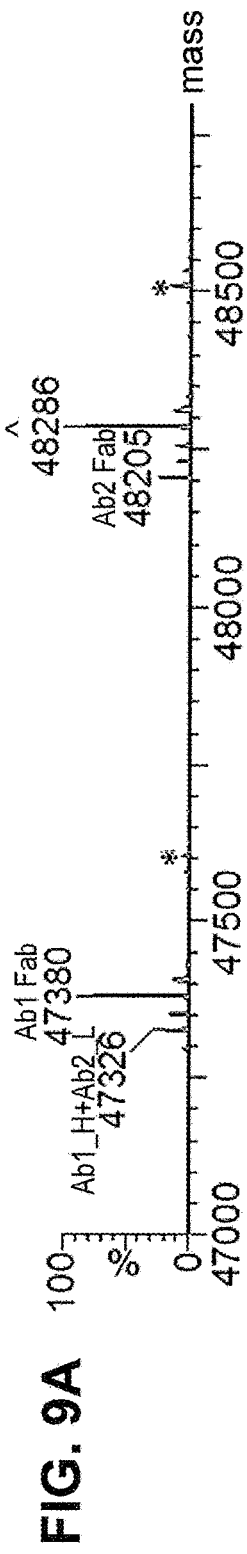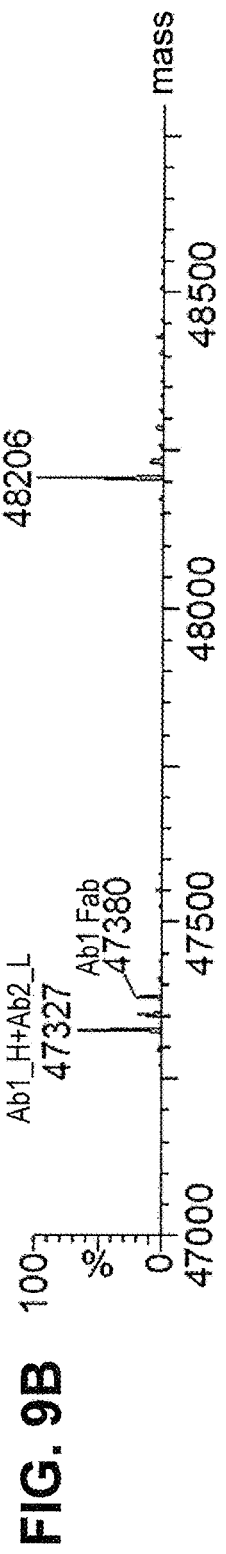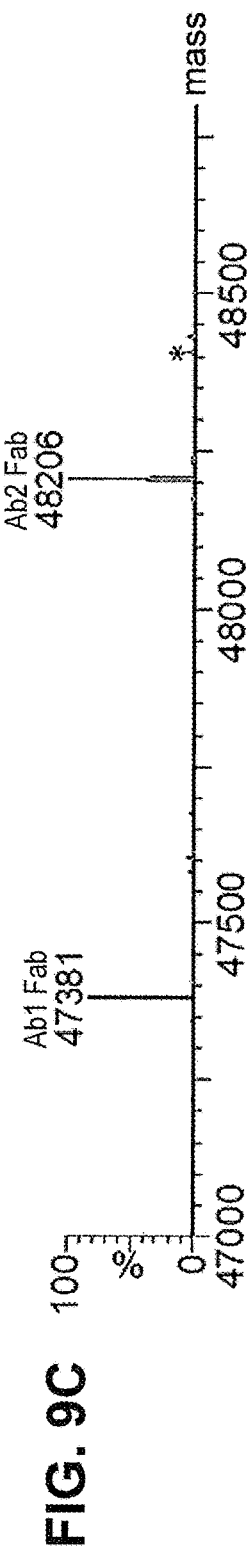

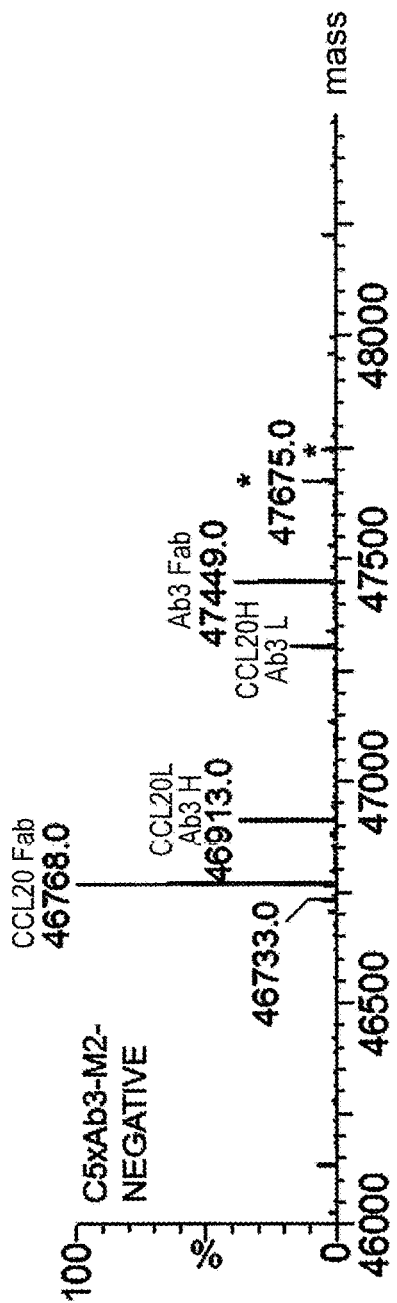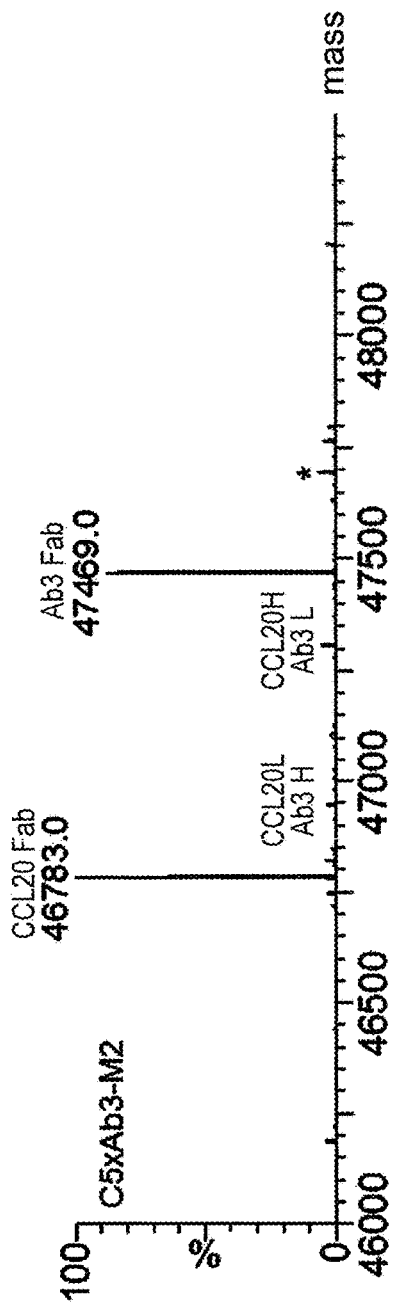
FIG. 11A
FIG. 11B

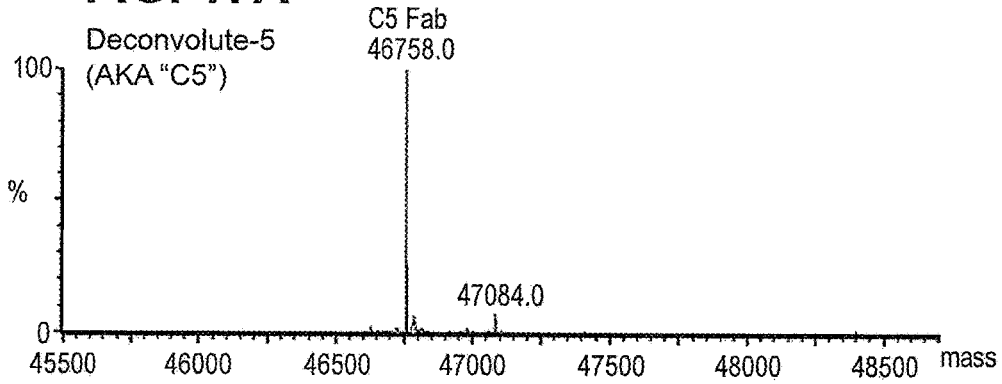
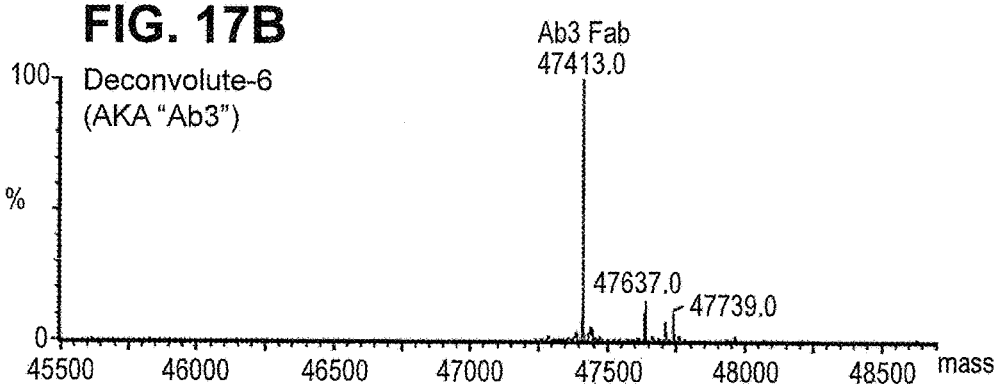
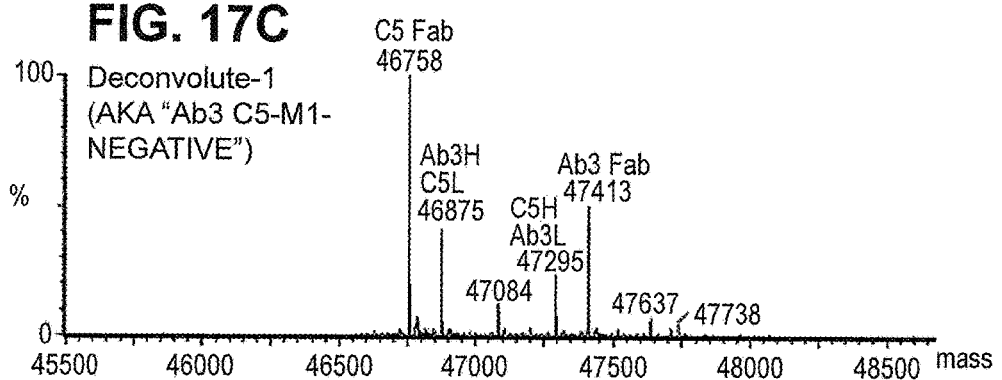

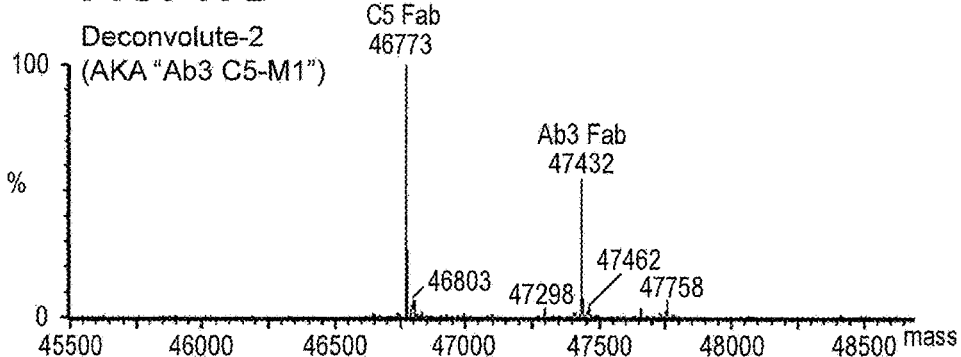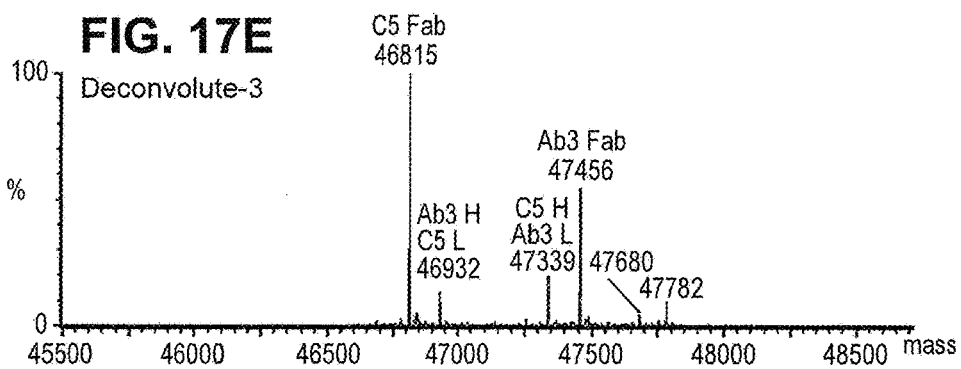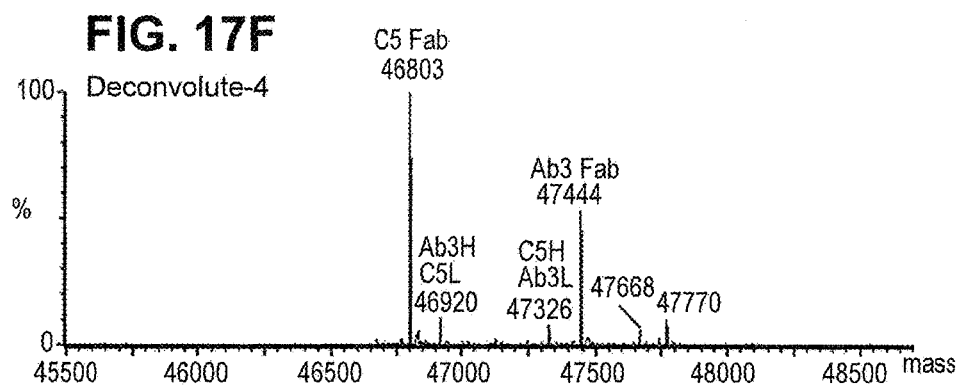

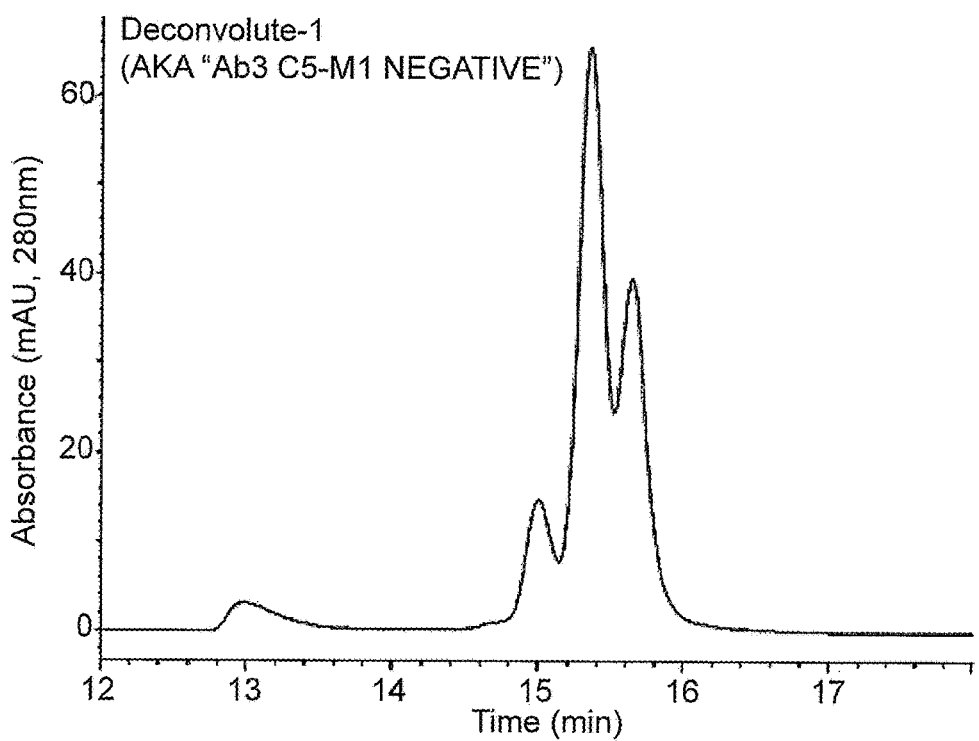
FIG. 18A Deconvolute-1 (AKA "Ab3 C5-M1 NEGATIVE")
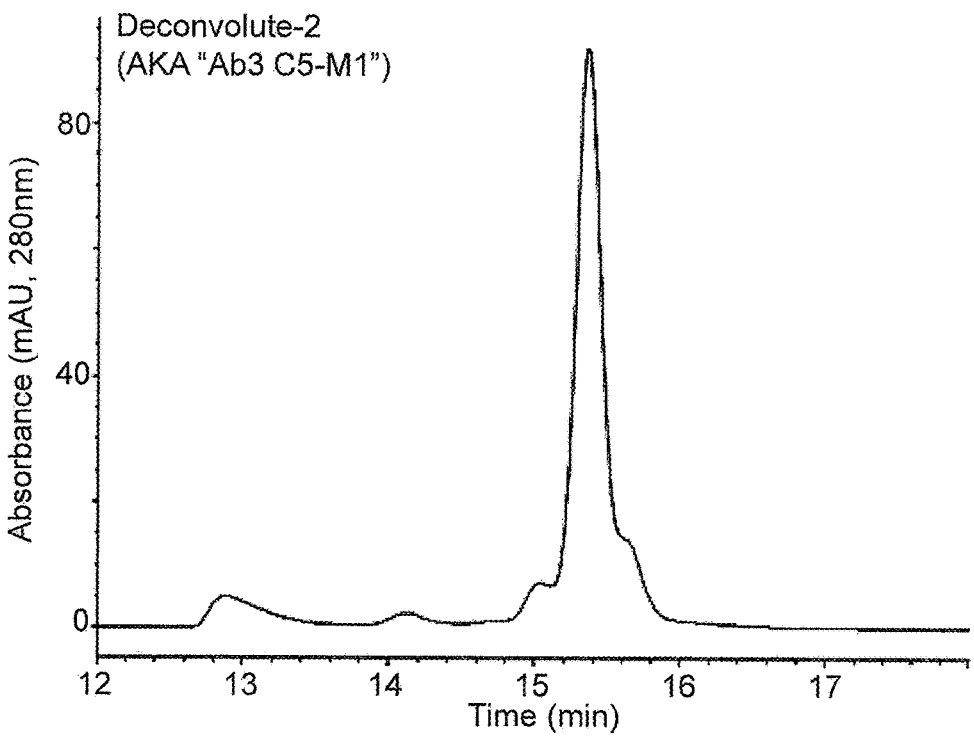
FIG. 18B Deconvolute-2 (AKA "Ab3 C5-M1")

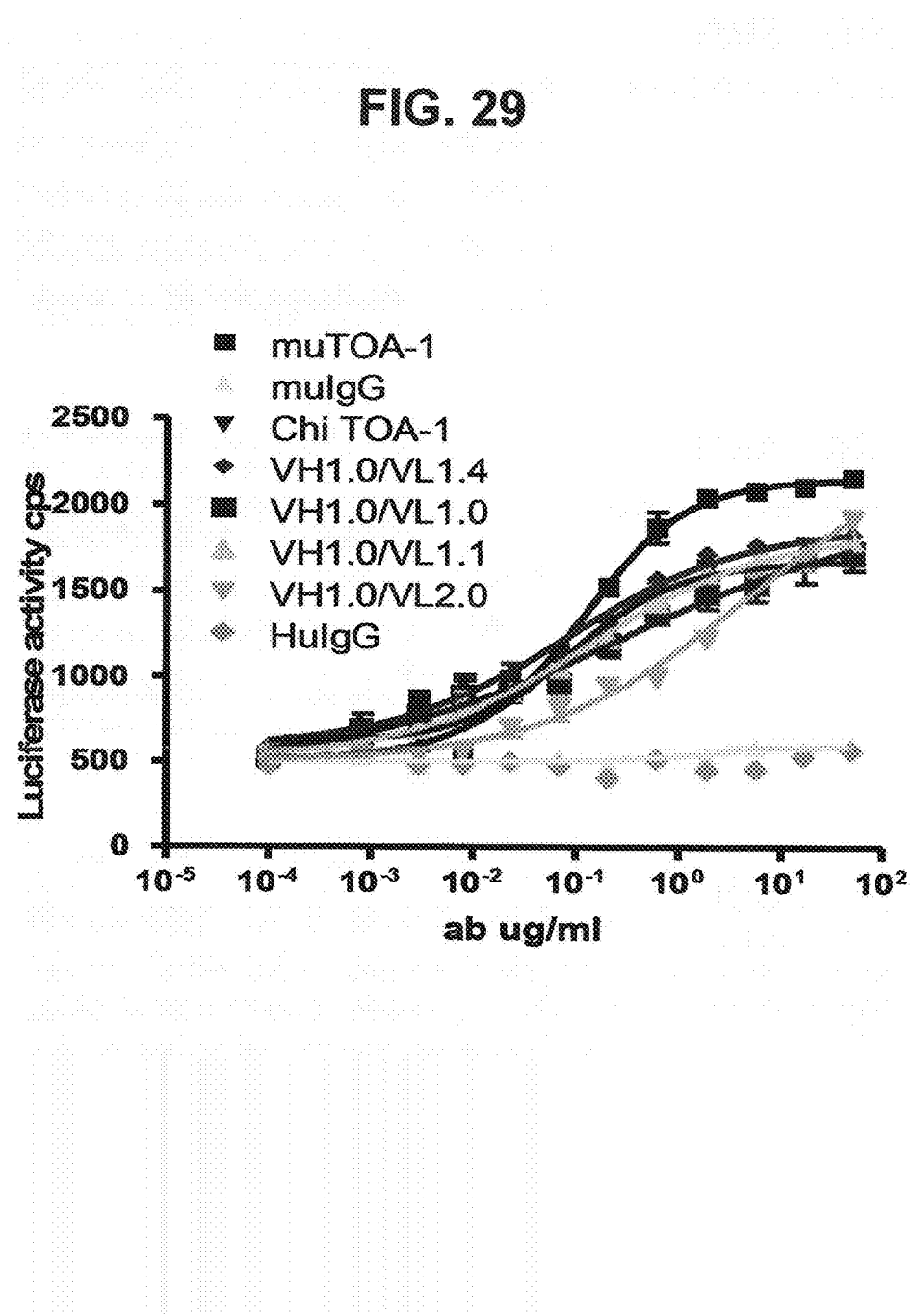

rhuTrkB-CRE cells rmuTrkB-CRE cells

Differentiated
Human SH-SY5Y
Neuroblastoma
Cells rhuTrkB-CRE cells

FIG. 37

FIG. 47
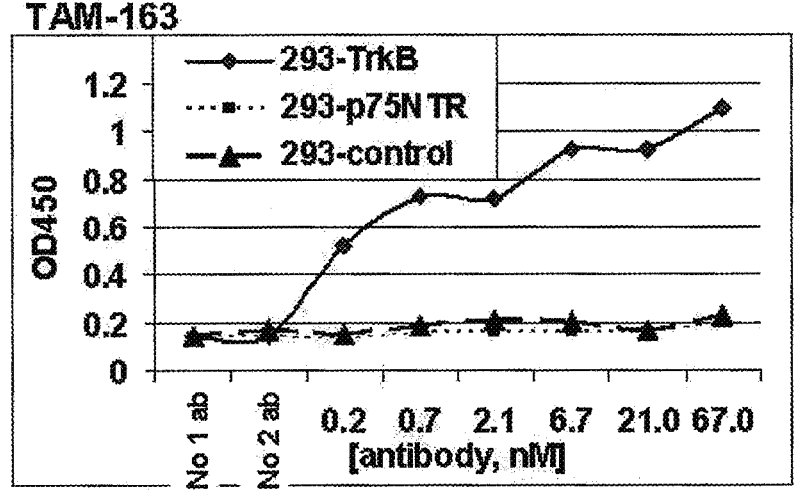
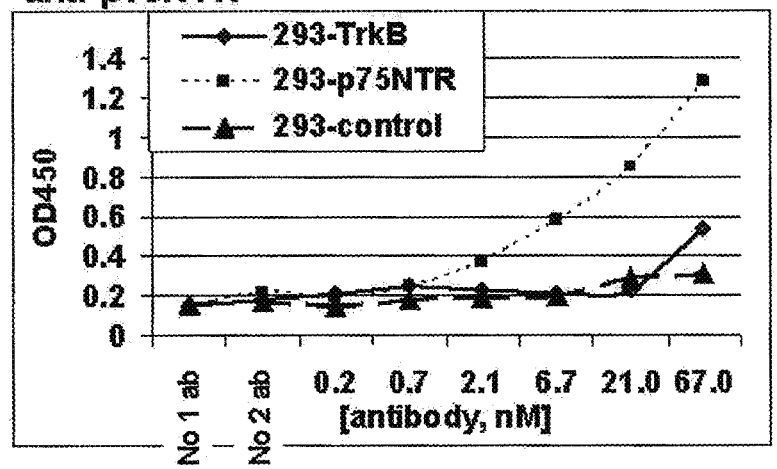

SEQUENCE LISTING

<160> NUMBER OF SEQ ID NOS: 147

<210> SEQ ID NO 1
<211> LENGTH: 103
<212> TYPE: PRT
<213> ORGANISM: Artificial Sequence
<220> FEATURE:
<223> OTHER INFORMATION: Synthetic Construct

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 2
<211> LENGTH: 103
<212> TYPE: PRT
<213> ORGANISM: Artificial Sequence
<220> FEATURE:
<223> OTHER INFORMATION: Synthetic Construct

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
            100

<210> SEQ ID NO 3
<211> LENGTH: 101
<212> TYPE: PRT
<213> ORGANISM: Artificial Sequence
<220> FEATURE:
<223> OTHER INFORMATION: Synthetic Construct

<400> SEQUENCE: 3

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys
            100

<210> SEQ ID NO 4
<211> LENGTH: 101
<212> TYPE: PRT
<213> ORGANISM: Artificial Sequence
<220> FEATURE:
<223> OTHER INFORMATION: Synthetic Construct

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys
            100

<210> SEQ ID NO 5
<211> LENGTH: 103
<212> TYPE: PRT
<213> ORGANISM: Artificial Sequence
<220> FEATURE:
<223> OTHER INFORMATION: Synthetic Construct

<400> SEQUENCE: 5

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro
            100
```

```
<210> SEQ ID NO 6
<211> LENGTH: 103
<212> TYPE: PRT
<213> ORGANISM: Artificial Sequence
<220> FEATURE:
<223> OTHER INFORMATION: Synthetic Construct

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly
            100

<210> SEQ ID NO 7
<211> LENGTH: 104
<212> TYPE: PRT
<213> ORGANISM: Artificial Sequence
<220> FEATURE:
<223> OTHER INFORMATION: Synthetic Construct

<400> SEQUENCE: 7

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro
            100

<210> SEQ ID NO 8
<211> LENGTH: 104
<212> TYPE: PRT
<213> ORGANISM: Artificial Sequence
<220> FEATURE:
<223> OTHER INFORMATION: Synthetic Construct

<400> SEQUENCE: 8

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45
```

Asp Ile Ser Ser Thr Arg Gly Phe Pro Ser Val Leu Arg Gly Gly Lys
            50                  55                  60

Tyr Ala Ala Thr Ser Gln Val Leu Leu Pro Ser Lys Asp Val Met Ala
65                  70                  75                  80

Gly Thr Asp Glu His Val Val Cys Lys Val Gln His Pro Asn Gly Asn
                85                  90                  95

Lys Glu Lys Asn Val Pro Leu Pro
            100

<210> SEQ ID NO 9
<211> LENGTH: 107
<212> TYPE: PRT
<213> ORGANISM: Artificial Sequence
<220> FEATURE:
<223> OTHER INFORMATION: Synthetic Construct

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Synthetic Construct

<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Val Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 11
<211> LENGTH: 107
<212> TYPE: PRT

```
<213> ORGANISM: Artificial Sequence
<220> FEATURE:
<223> OTHER INFORMATION: Synthetic Construct

<400> SEQUENCE: 11

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 12
<211> LENGTH: 105
<212> TYPE: PRT
<213> ORGANISM: Artificial Sequence
<220> FEATURE:
<223> OTHER INFORMATION: Synthetic Construct

<400> SEQUENCE: 12

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 13
<211> LENGTH: 110
<212> TYPE: PRT
<213> ORGANISM: Artificial Sequence
<220> FEATURE:
<223> OTHER INFORMATION: Synthetic Construct

<400> SEQUENCE: 13

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60
```

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 14
<211> LENGTH: 109
<212> TYPE: PRT
<213> ORGANISM: Artificial Sequence
<220> FEATURE:
<223> OTHER INFORMATION: Synthetic Construct

<400> SEQUENCE: 14

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105

<210> SEQ ID NO 15
<211> LENGTH: 110
<212> TYPE: PRT
<213> ORGANISM: Artificial Sequence
<220> FEATURE:
<223> OTHER INFORMATION: Synthetic Construct

<400> SEQUENCE: 15

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Gln Phe Lys Trp Tyr
            35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 16
<211> LENGTH: 110
<212> TYPE: PRT
<213> ORGANISM: Artificial Sequence
<220> FEATURE:
<223> OTHER INFORMATION: Synthetic Construct

<400> SEQUENCE: 16

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 17
<211> LENGTH: 112
<212> TYPE: PRT
<213> ORGANISM: Artificial Sequence
<220> FEATURE:
<223> OTHER INFORMATION: Synthetic Construct

<400> SEQUENCE: 17

Val Ile Ala Glu Leu Pro Pro Lys Val Ser Val Phe Val Pro Pro Arg
1               5                   10                  15

Asp Gly Phe Phe Gly Asn Pro Arg Lys Ser Lys Leu Ile Cys Gln Ala
            20                  25                  30

Thr Gly Phe Ser Pro Arg Gln Ile Gln Val Ser Trp Leu Arg Glu Gly
        35                  40                  45

Lys Gln Val Gly Ser Gly Val Thr Thr Asp Gln Val Gln Ala Glu Ala
    50                  55                  60

Lys Glu Ser Gly Pro Thr Thr Tyr Lys Val Thr Ser Thr Leu Thr Ile
65                  70                  75                  80

Lys Glu Ser Asp Trp Leu Gly Gln Ser Met Phe Thr Cys Arg Val Asp
                85                  90                  95

His Arg Gly Leu Thr Phe Gln Gln Asn Ala Ser Ser Met Cys Val Pro
            100                 105                 110

<210> SEQ ID NO 18
<211> LENGTH: 107
<212> TYPE: PRT
<213> ORGANISM: Artificial Sequence
<220> FEATURE:
<223> OTHER INFORMATION: Synthetic Construct

<400> SEQUENCE: 18

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

```
Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 19
<211> LENGTH: 107
<212> TYPE: PRT
<213> ORGANISM: Artificial Sequence
<220> FEATURE:
<223> OTHER INFORMATION: Synthetic Construct

<400> SEQUENCE: 19

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 20
<211> LENGTH: 107
<212> TYPE: PRT
<213> ORGANISM: Artificial Sequence
<220> FEATURE:
<223> OTHER INFORMATION: Synthetic Construct

<400> SEQUENCE: 20

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Met Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 21
<211> LENGTH: 107
<212> TYPE: PRT
<213> ORGANISM: Artificial Sequence
<220> FEATURE:
<223> OTHER INFORMATION: Synthetic Construct

<400> SEQUENCE: 21

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

Asn Asn Tyr Asn Thr Thr Pro Pro Met Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Synthetic Construct

<400> SEQUENCE: 22

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 23
<211> LENGTH: 106
<212> TYPE: PRT
<213> ORGANISM: Artificial Sequence
<220> FEATURE:
<223> OTHER INFORMATION: Synthetic Construct

<400> SEQUENCE: 23

Asp Gln Asp Thr Ala Ile Arg Val Phe Ala Ile Pro Pro Ser Phe Ala
1               5                   10                  15

Ser Ile Phe Leu Thr Lys Ser Thr Lys Leu Thr Cys Leu Val Thr Asp
            20                  25                  30

Leu Thr Thr Tyr Asp Ser Val Thr Ile Ser Trp Thr Arg Gln Asn Gly
        35                  40                  45

Glu Ala Val Lys Thr His Thr Asn Ile Ser Glu Ser His Pro Asn Ala
50                  55                  60

Thr Phe Ser Ala Val Gly Glu Ala Ser Ile Cys Glu Asp Asp Trp Asn
65                  70                  75                  80

Ser Gly Glu Arg Phe Thr Cys Thr Val Thr His Thr Asp Leu Pro Ser
                85                  90                  95

```
Pro Leu Lys Gln Thr Ile Ser Arg Pro Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: Synthetic Construct

<400> SEQUENCE: 24

Arg Thr Val Ala Ala Pro Ser Val Phe Ile Phe Pro Pro Ser Asp Glu
1               5                   10                  15

Gln Leu Lys Ser Gly Thr Ala Ser Val Ser Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Asp Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 25
<211> LENGTH: 107
<212> TYPE: PRT
<213> ORGANISM: Artificial Sequence
<220> FEATURE:
<223> OTHER INFORMATION: Synthetic Construct

<400> SEQUENCE: 25

Arg Thr Val Ala Ala Pro Ser Val Phe Ile Phe Pro Pro Ser Asp Glu
1               5                   10                  15

Gln Leu Lys Ser Gly Thr Ala Ser Val Ser Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Lys Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 26
<211> LENGTH: 107
<212> TYPE: PRT
<213> ORGANISM: Artificial Sequence
<220> FEATURE:
<223> OTHER INFORMATION: Synthetic Construct

<400> SEQUENCE: 26

Arg Thr Val Ala Ala Pro Ser Val Phe Ile Phe Pro Pro Ser Asp Lys
1               5                   10                  15
```

```
Gln Leu Lys Ser Gly Thr Ala Ser Val Val Cys Ile Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Cys Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105
```

<210> SEQ ID NO 27
<211> LENGTH: 107
<212> TYPE: PRT
<213> ORGANISM: Artificial Sequence
<220> FEATURE:
<223> OTHER INFORMATION: Synthetic Construct

<400> SEQUENCE: 27

```
Arg Thr Val Ala Ala Pro Ser Val Phe Ile Phe Pro Pro Ser Asp Cys
1               5                   10                  15

Gln Leu Lys Ser Gly Thr Ala His Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105
```

<210> SEQ ID NO 28
<211> LENGTH: 107
<212> TYPE: PRT
<213> ORGANISM: Artificial Sequence
<220> FEATURE:
<223> OTHER INFORMATION: Synthetic Construct

<400> SEQUENCE: 28

```
Arg Thr Val Ala Ala Pro Ser Val Phe Ile Phe Pro Pro Ser Asp Glu
1               5                   10                  15

Gln Leu Lys Ser Gly Thr Ala His Val Val Cys Ile Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Cys Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105
```

```
<210> SEQ ID NO 29
<211> LENGTH: 107
<212> TYPE: PRT
<213> ORGANISM: Artificial Sequence
<220> FEATURE:
<223> OTHER INFORMATION: Synthetic Construct

<400> SEQUENCE: 29

Arg Thr Val Ala Ala Pro Ser Val Cys Ile Phe Pro Pro Ser Asp Glu
1               5                   10                  15

Gln Leu Lys Ser Gly Thr Ala His Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105

<210> SEQ ID NO 30
<211> LENGTH: 107
<212> TYPE: PRT
<213> ORGANISM: Artificial Sequence
<220> FEATURE:
<223> OTHER INFORMATION: Synthetic Construct

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Asp Val Ser Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Cys Ser Ser Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105

<210> SEQ ID NO 31
<211> LENGTH: 107
<212> TYPE: PRT
<213> ORGANISM: Artificial Sequence
<220> FEATURE:
<223> OTHER INFORMATION: Synthetic Construct

<400> SEQUENCE: 31

Arg Thr Val Ala Ala Pro Ser Val Phe Ile Phe Pro Pro Ser Asp Cys
1               5                   10                  15

Gln Leu Lys Ser Gly Thr Ala Ser Val Met Cys Leu Leu Asn Asn Phe
            20                  25                  30
```

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Gly Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105

<210> SEQ ID NO 32
<211> LENGTH: 107
<212> TYPE: PRT
<213> ORGANISM: Artificial Sequence
<220> FEATURE:
<223> OTHER INFORMATION: Synthetic Construct

<400> SEQUENCE: 32

Arg Thr Val Ala Ala Pro Ser Val Cys Ile Phe Pro Pro Ser Asp Cys
 1               5                  10                  15

Gln Leu Lys Ser Gly Thr Ala Asp Val Ser Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Cys Ser Ser Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105

<210> SEQ ID NO 33
<211> LENGTH: 103
<212> TYPE: PRT
<213> ORGANISM: Artificial Sequence
<220> FEATURE:
<223> OTHER INFORMATION: Synthetic Construct

<400> SEQUENCE: 33

Ala Ser Thr Lys Gly Pro Ser Val Phe Pro Lys Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Ser Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 34

```
<211> LENGTH: 103
<212> TYPE: PRT
<213> ORGANISM: Artificial Sequence
<220> FEATURE:
<223> OTHER INFORMATION: Synthetic Construct

<400> SEQUENCE: 34

Ala Ser Thr Lys Gly Pro Ser Val Phe Pro Glu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Gly Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 35
<211> LENGTH: 103
<212> TYPE: PRT
<213> ORGANISM: Artificial Sequence
<220> FEATURE:
<223> OTHER INFORMATION: Synthetic Construct

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Cys Pro Ala Val Leu Gln Ser Ser Gly Leu Tyr Ser
    50                  55                  60

Leu Ser Ser Ile Val Thr Val Pro Ser Ser Ser Leu Gly Thr Gln Thr
65                  70                  75                  80

Tyr Ile Cys Asn Val Asn His Lys Pro Ser Asn Thr Lys Val Asp Asp
                85                  90                  95

Lys Val Glu Pro Lys Ser Ser
            100

<210> SEQ ID NO 36
<211> LENGTH: 103
<212> TYPE: PRT
<213> ORGANISM: Artificial Sequence
<220> FEATURE:
<223> OTHER INFORMATION: Synthetic Construct

<400> SEQUENCE: 36

Ala Ser Thr Lys Gly Pro Ser Val Cys Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Ser
            100
```

<210> SEQ ID NO 37
<211> LENGTH: 103
<212> TYPE: PRT
<213> ORGANISM: Artificial Sequence
<220> FEATURE:
<223> OTHER INFORMATION: Synthetic Construct

<400> SEQUENCE: 37

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys His Val Lys Asp Tyr
                 20                  25                  30

Phe Pro Glu Pro Val Thr Val Ser Trp Asn Ser Gly Ala Leu Thr Ser
             35                  40                  45

Gly Val His Thr Cys Pro Ala Val Leu Asp Ser Ser Gly Leu Tyr Glu
 50                  55                  60

Leu Ser Ser Ile Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Ser
            100
```

<210> SEQ ID NO 38
<211> LENGTH: 103
<212> TYPE: PRT
<213> ORGANISM: Artificial Sequence
<220> FEATURE:
<223> OTHER INFORMATION: Synthetic Construct

<400> SEQUENCE: 38

```
Ala Ser Thr Lys Gly Pro Ser Val Phe Pro Leu Ala Pro Ser Ser Lys
 1               5                  10                  15

Ser Thr Ser Gly Gly Thr Ala Cys Leu Gly Cys Leu Val Ser Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Glu
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Ser
            100
```

<210> SEQ ID NO 39
<211> LENGTH: 103
<212> TYPE: PRT
<213> ORGANISM: Artificial Sequence

```
<220> FEATURE:
<223> OTHER INFORMATION: Synthetic Construct

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Ser Val Lys Asp Tyr
            20                  25                  30

Phe Pro Glu Pro Val Thr Val Ser Trp Asn Ser Gly Ala Leu Thr Ser
        35                  40                  45

Gly Val His Thr Cys Pro Ala Val Leu Gln Ser Ser Gly Leu Tyr Ser
    50                  55                  60

Leu Trp Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser
            100

<210> SEQ ID NO 40
<211> LENGTH: 103
<212> TYPE: PRT
<213> ORGANISM: Artificial Sequence
<220> FEATURE:
<223> OTHER INFORMATION: Synthetic Construct

<400> SEQUENCE: 40

Ala Ser Thr Lys Gly Pro Ser Val Cys Pro Leu Ala Pro Ser Ser Lys
1               5                   10                  15

Ser Thr Ser Gly Gly Thr Ala Ala Leu Gly Cys Ser Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Trp Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser
            100

<210> SEQ ID NO 41
<211> LENGTH: 103
<212> TYPE: PRT
<213> ORGANISM: Artificial Sequence
<220> FEATURE:
<223> OTHER INFORMATION: Synthetic Construct

<400> SEQUENCE: 41

Ala Ser Thr Lys Gly Pro Ser Val Cys Pro Leu Ala Pro Ser Ser Lys
1               5                   10                  15

Ser Thr Ser Gly Gly Thr Ala Cys Leu Gly Cys Ser Val Lys Asp Tyr
            20                  25                  30

Phe Pro Glu Pro Val Thr Val Ser Trp Asn Ser Gly Ala Leu Thr Ser
        35                  40                  45

Gly Val His Thr Cys Pro Ala Val Leu Gln Ser Ser Gly Leu Tyr Ser
    50                  55                  60
```

```
Leu Trp Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Ser
            100
```

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

```
Asp Lys Thr His Thr Cys Pro Pro Cys Pro
1               5                   10
```

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

```
Glu Lys Thr His Thr Cys Pro Glu Cys Pro
1               5                   10
```

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

```
Arg Lys Thr His Thr Cys Pro Arg Cys Pro
1               5                   10
```

<210> SEQ ID NO 45
<211> LENGTH: 110
<212> TYPE: PRT
<213> ORGANISM: Artificial Sequence
<220> FEATURE:
<223> OTHER INFORMATION: Synthetic Construct

<400> SEQUENCE: 45

```
Ala Pro Glu Ala Ala Gly Ala Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

```
<210> SEQ ID NO 46
<211> LENGTH: 107
<212> TYPE: PRT
<213> ORGANISM: Artificial Sequence
<220> FEATURE:
<223> OTHER INFORMATION: Synthetic Construct

<400> SEQUENCE: 46

Gly Gln Pro Arg Glu Pro Gln Val Cys Thr Leu Pro Pro Ser Arg Glu
1               5                   10                  15

Glu Met Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 47
<211> LENGTH: 107
<212> TYPE: PRT
<213> ORGANISM: Artificial Sequence
<220> FEATURE:
<223> OTHER INFORMATION: Synthetic Construct

<400> SEQUENCE: 47

Gly Gln Pro Arg Glu Pro Gln Val Tyr Thr Leu Pro Pro Cys Arg Glu
1               5                   10                  15

Glu Met Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 48
<211> LENGTH: 107
<212> TYPE: PRT
<213> ORGANISM: Artificial Sequence
<220> FEATURE:
<223> OTHER INFORMATION: Synthetic Construct

<400> SEQUENCE: 48

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Glu Val Lys Gly Phe
            20                  25                  30

Tyr Pro Ser Asp Ile Ala Val Glu Trp Glu Ser Asn Gly Gln Pro Glu
```

```
                35                  40                  45
Asn Asn Tyr Lys Thr Thr Pro Pro Val Leu Asp Ser Asp Gly Ser Phe
         50                  55                  60
Phe Leu Tyr Ser Lys Leu Thr Val Asp Lys Ser Arg Trp Gln Gln Gly
 65                  70                  75                  80
Asn Val Phe Ser Cys Ser Val Met His Glu Ala Leu His Asn His Tyr
                 85                  90                  95
Thr Gln Lys Ser Leu Ser Leu Ser Pro Gly Lys
            100                 105
```

<210> SEQ ID NO 49
<211> LENGTH: 107
<212> TYPE: PRT
<213> ORGANISM: Artificial Sequence
<220> FEATURE:
<223> OTHER INFORMATION: Synthetic Construct

<400> SEQUENCE: 49

```
Gly Gln Pro Arg Glu Pro Gln Val Tyr Thr Leu Pro Pro Ser Arg Glu
 1               5                  10                  15
Glu Met Thr Lys Asn Gln Val Ser Leu Thr Cys Leu Val Lys Gly Phe
                20                  25                  30
Tyr Pro Ser Asp Ile Ala Val Glu Trp Glu Ser Asn Gly Gln Pro Glu
             35                  40                  45
Asn Asn Tyr Lys Thr Thr Pro Pro Val Leu Asp Ser Asp Gly Ser Phe
         50                  55                  60
Phe Leu Tyr Ser Arg Leu Thr Val Asp Lys Ser Arg Trp Gln Gln Gly
 65                  70                  75                  80
Asn Val Phe Ser Cys Ser Val Met His Glu Ala Leu His Asn His Tyr
                 85                  90                  95
Thr Gln Lys Ser Leu Ser Leu Ser Pro Gly Lys
            100                 105
```

<210> SEQ ID NO 50
<211> LENGTH: 120
<212> TYPE: PRT
<213> ORGANISM: Artificial Sequence
<220> FEATURE:
<223> OTHER INFORMATION: Synthetic Construct

<400> SEQUENCE: 50

```
Gln Val Gln Leu Val Gln Ser Gly Ala Glu Val Lys Lys Pro Gly Ser
 1               5                  10                  15
Ser Val Lys Val Ser Cys Lys Ala Ser Gly Gly Thr Phe Ser Ser Tyr
                20                  25                  30
Ala Ile Ser Trp Val Arg Gln Ala Pro Gly Gln Gly Leu Glu Trp Met
             35                  40                  45
Gly Gly Ile Ile Pro Ile Phe Gly Thr Ala Asn Tyr Ala Gln Lys Phe
         50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Gly Gly Ser Ile Thr Gly Thr Thr Pro Phe Asp Tyr Trp Gly Arg
            100                 105                 110
Gly Thr Leu Val Thr Val Ser Ser
            115                 120
```

```
<210> SEQ ID NO 51
<211> LENGTH: 118
<212> TYPE: PRT
<213> ORGANISM: Artificial Sequence
<220> FEATURE:
<223> OTHER INFORMATION: Synthetic Construct

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Ala Tyr
            20                  25                  30

Phe Met Asn Trp Val Arg Gln Ala Pro Gly Lys Gly Leu Glu Trp Val
        35                  40                  45

Ala Arg Ile Asn Pro Asn Asn Gly Asp Thr Phe Tyr Thr Gln Lys Phe
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Asp Tyr Phe Gly Ala Met Asp Tyr Trp Gly Gln Gly Thr
            100                 105                 110

Leu Val Thr Val Ser Ser
        115

<210> SEQ ID NO 52
<211> LENGTH: 107
<212> TYPE: PRT
<213> ORGANISM: Artificial Sequence
<220> FEATURE:
<223> OTHER INFORMATION: Synthetic Construct

<400> SEQUENCE: 52

Ala Ile Gln Leu Thr Gln Ser Pro Ser Ser Leu Thr Ala Ser Val Gly
1               5                   10                  15

Asp Arg Val Thr Ile Thr Cys Arg Ala Ser Gln Phe Ala Ser Asn Asp
            20                  25                  30

Val Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Glu Phe Thr Phe Thr Ile Ser Ser Leu Gln Pro
65                  70                  75                  80

Glu Asp Phe Ala Thr Tyr Tyr Cys Leu Gln Asp Tyr Thr Tyr Pro Leu
                85                  90                  95

Thr Phe Gly Gln Gly Thr Lys Val Glu Ile Lys
            100                 105

<210> SEQ ID NO 53
<211> LENGTH: 107
<212> TYPE: PRT
<213> ORGANISM: Artificial Sequence
<220> FEATURE:
<223> OTHER INFORMATION: Synthetic Construct

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Asn
```

```
                20                  25                  30
Leu His Trp Tyr Gln Gln Lys Pro Gly Lys Ala Pro Lys Leu Leu Ile
            35                  40                  45

Lys Ser Ala Ser Leu Ala Ile Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Asn
                85                  90                  95

Thr Phe Gly Gly Gly Thr Lys Val Glu Ile Lys
            100                 105

<210> SEQ ID NO 54
<211> LENGTH: 330
<212> TYPE: PRT
<213> ORGANISM: Artificial Sequence
<220> FEATURE:
<223> OTHER INFORMATION: Synthetic Construct

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 55
<211> LENGTH: 330
<212> TYPE: PRT
<213> ORGANISM: Artificial Sequence
<220> FEATURE:
<223> OTHER INFORMATION: Synthetic Construct

<400> SEQUENCE: 55

Ala Ser Thr Lys Gly Pro Ser Val Phe Pro Lys Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Ser Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Glu Glu
225                 230                 235                 240

Met Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

Gln Lys Ser Leu Ser Leu Ser Pro Gly Lys
            325                 330

<210> SEQ ID NO 56
<211> LENGTH: 330
<212> TYPE: PRT
<213> ORGANISM: Artificial Sequence
<220> FEATURE:
<223> OTHER INFORMATION: Synthetic Construct

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Glu Glu
225                 230                 235                 240

Met Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 57
<211> LENGTH: 330
<212> TYPE: PRT
<213> ORGANISM: Artificial Sequence
<220> FEATURE:
<223> OTHER INFORMATION: Synthetic Construct

<400> SEQUENCE: 57

```
Ala Ser Thr Lys Gly Pro Ser Val Phe Pro Lys Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Ser Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Arg Lys Thr His Thr Cys Pro Arg Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 58
<211> LENGTH: 330
<212> TYPE: PRT
<213> ORGANISM: Artificial Sequence
<220> FEATURE:
<223> OTHER INFORMATION: Synthetic Construct

<400> SEQUENCE: 58

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Arg Lys Thr His Thr Cys Pro Arg Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 59
<211> LENGTH: 330
<212> TYPE: PRT
<213> ORGANISM: Artificial Sequence
<220> FEATURE:
<223> OTHER INFORMATION: Synthetic Construct

<400> SEQUENCE: 59

```
Ala Ser Thr Lys Gly Pro Ser Val Phe Pro Glu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Gly Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Cys Arg Glu Glu
225                 230                 235                 240

Met Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 60
<211> LENGTH: 330
<212> TYPE: PRT
<213> ORGANISM: Artificial Sequence
<220> FEATURE:
<223> OTHER INFORMATION: Synthetic Construct

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Cys Arg Glu Glu
225                 230                 235                 240

Met Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Val Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

```
<210> SEQ ID NO 61
<211> LENGTH: 330
<212> TYPE: PRT
<213> ORGANISM: Artificial Sequence
<220> FEATURE:
<223> OTHER INFORMATION: Synthetic Construct

<400> SEQUENCE: 61
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Cys Pro Ala Val Leu Gln Ser Ser Gly Leu Tyr Ser
    50                  55                  60

Leu Ser Ser Ile Val Thr Val Pro Ser Ser Ser Leu Gly Thr Gln Thr
65                  70                  75                  80

Tyr Ile Cys Asn Val Asn His Lys Pro Ser Asn Thr Lys Val Asp Asp
                85                  90                  95

Lys Val Glu Pro Lys Ser Ser Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Cys Arg Glu Glu
225                 230                 235                 240

Met Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 62
<211> LENGTH: 330
<212> TYPE: PRT
<213> ORGANISM: Artificial Sequence
<220> FEATURE:
<223> OTHER INFORMATION: Synthetic Construct

<400> SEQUENCE: 62

Ala Ser Thr Lys Gly Pro Ser Val Cys Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

```
Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Cys Arg Glu Glu
225                 230                 235                 240

Met Thr Lys Asn Gln Val Ser Leu Ser Cys Ala Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Val Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 63
<211> LENGTH: 330
<212> TYPE: PRT
<213> ORGANISM: Artificial Sequence
<220> FEATURE:
<223> OTHER INFORMATION: Synthetic Construct

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys His Val Lys Asp Tyr
            20                  25                  30

Phe Pro Glu Pro Val Thr Val Ser Trp Asn Ser Gly Ala Leu Thr Ser
            35                  40                  45

Gly Val His Thr Cys Pro Ala Val Leu Asp Ser Ser Gly Leu Tyr Glu
        50                  55                  60

Leu Ser Ser Ile Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Cys Arg Glu Glu
225                 230                 235                 240

Met Thr Lys Asn Gln Val Ser Leu Ser Cys Ala Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Val Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 64
<211> LENGTH: 330
<212> TYPE: PRT
<213> ORGANISM: Artificial Sequence
<220> FEATURE:
<223> OTHER INFORMATION: Synthetic Construct

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Cys Leu Gly Cys Leu Val Ser Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Glu
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Ser Asp Lys Thr His Thr Cys Pro Pro Cys
        100                 105                 110

Pro Ala Pro Glu Ala Ala Gly Ala Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Cys Arg Glu Glu
225                 230                 235                 240

Met Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 65
<211> LENGTH: 330
<212> TYPE: PRT
<213> ORGANISM: Artificial Sequence
<220> FEATURE:
<223> OTHER INFORMATION: Synthetic Construct

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Ser Val Lys Asp Tyr
                20                  25                  30

Phe Pro Glu Pro Val Thr Val Ser Trp Asn Ser Gly Ala Leu Thr Ser
            35                  40                  45

Gly Val His Thr Cys Pro Ala Val Leu Gln Ser Ser Gly Leu Tyr Ser
        50                  55                  60

Leu Trp Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Cys Arg Glu Glu
225                 230                 235                 240

Met Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 66
<211> LENGTH: 330
<212> TYPE: PRT
<213> ORGANISM: Artificial Sequence
<220> FEATURE:
<223> OTHER INFORMATION: Synthetic Construct

<400> SEQUENCE: 66

Ala Ser Thr Lys Gly Pro Ser Val Cys Pro Leu Ala Pro Ser Ser Lys
1               5                   10                  15

Ser Thr Ser Gly Gly Thr Ala Ala Leu Gly Cys Ser Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Trp Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Cys Arg Glu Glu
225                 230                 235                 240
```

```
Met Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 67
<211> LENGTH: 330
<212> TYPE: PRT
<213> ORGANISM: Artificial Sequence
<220> FEATURE:
<223> OTHER INFORMATION: Synthetic Construct

<400> SEQUENCE: 67

Ala Ser Thr Lys Gly Pro Ser Val Cys Pro Leu Ala Pro Ser Ser Lys
1               5                   10                  15

Ser Thr Ser Gly Gly Thr Ala Cys Leu Gly Cys Ser Val Lys Asp Tyr
                20                  25                  30

Phe Pro Glu Pro Val Thr Val Ser Trp Asn Ser Gly Ala Leu Thr Ser
            35                  40                  45

Gly Val His Thr Cys Pro Ala Val Leu Gln Ser Ser Gly Leu Tyr Ser
        50                  55                  60

Leu Trp Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Cys Arg Glu Glu
225                 230                 235                 240

Met Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 68
<211> LENGTH: 330
<212> TYPE: PRT
<213> ORGANISM: Artificial Sequence
<220> FEATURE:
<223> OTHER INFORMATION: Synthetic Construct

<400> SEQUENCE: 68

Ala Ser Thr Lys Gly Pro Ser Val Phe Pro Glu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Gly Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Glu Lys Thr His Thr Cys Pro Glu Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Glu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 69
<211> LENGTH: 330
<212> TYPE: PRT
<213> ORGANISM: Artificial Sequence
<220> FEATURE:
<223> OTHER INFORMATION: Synthetic Construct

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Glu Lys Thr His Thr Cys Pro Glu Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Glu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 70
<211> LENGTH: 450
<212> TYPE: PRT
<213> ORGANISM: Artificial Sequence
<220> FEATURE:
<223> OTHER INFORMATION: Synthetic Construct

<400> SEQUENCE: 70

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Ser Ile Thr Gly Thr Thr Pro Phe Asp Tyr Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 71
<211> LENGTH: 450
<212> TYPE: PRT
<213> ORGANISM: Artificial Sequence
<220> FEATURE:
<223> OTHER INFORMATION: Synthetic Construct

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Ser Ile Thr Gly Thr Thr Pro Phe Asp Tyr Trp Gly Arg
            100                 105                 110

Gly Thr Leu Val Thr Val Ser Ser Ala Ser Thr Lys Gly Pro Ser Val
        115                 120                 125

Phe Pro Glu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Gly Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

```
Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Glu Glu Met Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 72
<211> LENGTH: 450
<212> TYPE: PRT
<213> ORGANISM: Artificial Sequence
<220> FEATURE:
<223> OTHER INFORMATION: Synthetic Construct

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Ser Ile Thr Gly Thr Thr Pro Phe Asp Tyr Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Cys Arg Glu Glu Met Thr Lys Asn Gln Val Ser Leu
    355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 73
<211> LENGTH: 450
<212> TYPE: PRT
<213> ORGANISM: Artificial Sequence
<220> FEATURE:
<223> OTHER INFORMATION: Synthetic Construct

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Gly Gly Ser Ile Thr Gly Thr Thr Pro Phe Asp Tyr Trp Gly Arg
            100                 105                 110

Gly Thr Leu Val Thr Val Ser Ser Ala Ser Thr Lys Gly Pro Ser Val
            115                 120                 125

Phe Pro Glu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Gly Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Glu
210                 215                 220

Lys Thr His Thr Cys Pro Glu Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Glu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 74
<211> LENGTH: 450
<212> TYPE: PRT
<213> ORGANISM: Artificial Sequence
<220> FEATURE:
<223> OTHER INFORMATION: Synthetic Construct

<400> SEQUENCE: 74

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Ser Ile Thr Gly Thr Thr Pro Phe Asp Tyr Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Glu
210                 215                 220

Lys Thr His Thr Cys Pro Glu Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Glu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
```

```
                       405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 75
<211> LENGTH: 448
<212> TYPE: PRT
<213> ORGANISM: Artificial Sequence
<220> FEATURE:
<223> OTHER INFORMATION: Synthetic Construct

<400> SEQUENCE: 75

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Ser Phe Thr Ala Tyr
            20                  25                  30
Phe Met Asn Trp Val Arg Gln Ala Pro Gly Lys Gly Leu Glu Trp Val
        35                  40                  45
Ala Arg Ile Asn Pro Asn Asn Gly Asp Thr Phe Tyr Thr Gln Lys Phe
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Arg Asp Tyr Phe Gly Ala Met Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Ala Ala Gly Ala Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
```

```
                305                 310                 315                 320
Lys Cys Lys Val Ser Asn Lys Ala Leu Pro Ala Pro Ile Glu Lys Thr
                    325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 76
<211> LENGTH: 214
<212> TYPE: PRT
<213> ORGANISM: Artificial Sequence
<220> FEATURE:
<223> OTHER INFORMATION: Synthetic Construct

<400> SEQUENCE: 76

Ala Ile Gln Leu Thr Gln Ser Pro Ser Ser Leu Thr Ala Ser Val Gly
1               5                   10                  15

Asp Arg Val Thr Ile Thr Cys Arg Ala Ser Gln Phe Ala Ser Asn Asp
                20                  25                  30

Val Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Pro Arg Phe Ser Gly
        50                  55                  60

Ser Gly Ser Gly Thr Glu Phe Thr Phe Thr Ile Ser Ser Leu Gln Pro
65              70                  75                  80

Glu Asp Phe Ala Thr Tyr Tyr Cys Leu Gln Asp Tyr Thr Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 77
<211> LENGTH: 214
<212> TYPE: PRT
<213> ORGANISM: Artificial Sequence
<220> FEATURE:
<223> OTHER INFORMATION: Synthetic Construct

<400> SEQUENCE: 77
```

| | | | | | | | | | | | | | | | |
|---|---|---|---|---|---|---|---|---|---|---|---|---|---|---|---|
| Ala | Ile | Gln | Leu | Thr | Gln | Ser | Pro | Ser | Ser | Leu | Thr | Ala | Ser | Val | Gly |
| 1 | | | | 5 | | | | | 10 | | | | | 15 | |
| Asp | Arg | Val | Thr | Ile | Thr | Cys | Arg | Ala | Ser | Gln | Phe | Ala | Ser | Asn | Asp |
| | | | 20 | | | | | 25 | | | | | 30 | | |
| Val | Gly | Trp | Tyr | Gln | Gln | Lys | Pro | Gly | Lys | Ala | Pro | Lys | Leu | Leu | Ile |
| | | | 35 | | | | | 40 | | | | | 45 | | |
| Tyr | Ala | Ala | Ser | Ser | Leu | Gln | Ser | Gly | Val | Pro | Pro | Arg | Phe | Ser | Gly |
| | 50 | | | | | 55 | | | | | 60 | | | | |
| Ser | Gly | Ser | Gly | Thr | Glu | Phe | Thr | Phe | Thr | Ile | Ser | Ser | Leu | Gln | Pro |
| 65 | | | | | 70 | | | | | 75 | | | | | 80 |
| Glu | Asp | Phe | Ala | Thr | Tyr | Tyr | Cys | Leu | Gln | Asp | Tyr | Thr | Tyr | Pro | Leu |
| | | | | 85 | | | | | 90 | | | | | 95 | |
| Thr | Phe | Gly | Gln | Gly | Thr | Lys | Val | Glu | Ile | Lys | Arg | Thr | Val | Ala | Ala |
| | | | | 100 | | | | | 105 | | | | | 110 | |
| Pro | Ser | Val | Phe | Ile | Phe | Pro | Pro | Ser | Asp | Glu | Gln | Leu | Lys | Ser | Gly |
| | | | 115 | | | | | 120 | | | | | 125 | | |
| Thr | Ala | Ser | Val | Ser | Cys | Leu | Leu | Asn | Asn | Phe | Tyr | Pro | Arg | Glu | Ala |
| | 130 | | | | | 135 | | | | | 140 | | | | |
| Lys | Val | Gln | Trp | Lys | Val | Asp | Asn | Ala | Leu | Gln | Ser | Gly | Asn | Ser | Gln |
| 145 | | | | | 150 | | | | | 155 | | | | | 160 |
| Glu | Ser | Val | Thr | Glu | Gln | Asp | Ser | Lys | Asp | Ser | Thr | Tyr | Ser | Leu | Lys |
| | | | | 165 | | | | | 170 | | | | | 175 | |
| Ser | Thr | Leu | Thr | Leu | Ser | Lys | Ala | Asp | Tyr | Glu | Lys | His | Lys | Val | Tyr |
| | | | | 180 | | | | | 185 | | | | | 190 | |
| Ala | Cys | Glu | Val | Thr | His | Gln | Gly | Leu | Ser | Ser | Pro | Val | Thr | Lys | Ser |
| | | | 195 | | | | | 200 | | | | | 205 | | |
| Phe | Asn | Arg | Gly | Glu | Cys | | | | | | | | | | |
| | | | 210 | | | | | | | | | | | | |

```
<210> SEQ ID NO 78
<211> LENGTH: 214
<212> TYPE: PRT
<213> ORGANISM: Artificial Sequence
<220> FEATURE:
<223> OTHER INFORMATION: Synthetic Construct

<400> SEQUENCE: 78
```

| | | | | | | | | | | | | | | | |
|---|---|---|---|---|---|---|---|---|---|---|---|---|---|---|---|
| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |
| Asp | Arg | Val | Thr | Ile | Thr | Cys | Arg | Ala | Ser | Gln | Thr | Ile | Ser | Asn | Asn |
| | | | 20 | | | | | 25 | | | | | 30 | | |
| Leu | His | Trp | Tyr | Gln | Gln | Lys | Pro | Gly | Lys | Ala | Pro | Lys | Leu | Leu | Ile |
| | | | 35 | | | | | 40 | | | | | 45 | | |
| Lys | Ser | Ala | Ser | Leu | Ala | Ile | Ser | Gly | Val | Pro | Ser | Arg | Phe | Ser | Gly |
| | 50 | | | | | 55 | | | | | 60 | | | | |
| Ser | Gly | Ser | Gly | Thr | Asp | Phe | Thr | Leu | Thr | Ile | Ser | Ser | Leu | Gln | Pro |
| 65 | | | | | 70 | | | | | 75 | | | | | 80 |
| Glu | Asp | Phe | Ala | Thr | Tyr | Tyr | Cys | Gln | Gln | Ser | Asn | Ser | Trp | Pro | Asn |
| | | | | 85 | | | | | 90 | | | | | 95 | |

```
Thr Phe Gly Gly Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 79
<211> LENGTH: 9
<212> TYPE: PRT
<213> ORGANISM: Artificial Sequence
<220> FEATURE:
<223> OTHER INFORMATION: Synthetic Construct

<400> SEQUENCE: 79

```
Cys Cys Val Glu Cys Pro Pro Cys Pro
1               5
```

<210> SEQ ID NO 80
<211> LENGTH: 57
<212> TYPE: PRT
<213> ORGANISM: Artificial Sequence
<220> FEATURE:
<223> OTHER INFORMATION: Synthetic Construct

<400> SEQUENCE: 80

```
Leu Gly Asp Thr Thr His Thr Cys Pro Arg Cys Pro Glu Pro Lys Ser
1               5                   10                  15
Cys Asp Thr Pro Pro Cys Pro Arg Cys Pro Glu Pro Lys Ser Cys
                20                  25                  30
Asp Thr Pro Pro Cys Pro Arg Cys Pro Glu Pro Lys Ser Cys Asp
            35                  40                  45
Thr Pro Pro Cys Pro Arg Cys Pro
    50                  55
```

<210> SEQ ID NO 81
<211> LENGTH: 7
<212> TYPE: PRT
<213> ORGANISM: Artificial Sequence
<220> FEATURE:
<223> OTHER INFORMATION: Synthetic Construct

<400> SEQUENCE: 81

```
Pro Pro Cys Pro Ser Cys Pro
1               5
```

<210> SEQ ID NO 82
<211> LENGTH: 43
<212> TYPE: PRT
<213> ORGANISM: Artificial Sequence
<220> FEATURE:
<223> OTHER INFORMATION: Synthetic Construct

<400> SEQUENCE: 82

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Glu Val Lys Gly Phe
            20                  25                  30

Tyr Pro Ser Asp Ile Ala Val Glu Trp Glu Ser
        35                  40

<210> SEQ ID NO 83
<211> LENGTH: 64
<212> TYPE: PRT
<213> ORGANISM: Artificial Sequence
<220> FEATURE:
<223> OTHER INFORMATION: Synthetic Construct

<400> SEQUENCE: 83

Asn Gly Gln Pro Glu Asn Asn Tyr Lys Thr Thr Pro Pro Val Leu Asp
1               5                   10                  15

Ser Asp Gly Ser Phe Phe Leu Tyr Ser Lys Leu Thr Val Asp Lys Ser
            20                  25                  30

Arg Trp Gln Gln Gly Asn Val Phe Ser Cys Ser Val Met His Glu Ala
        35                  40                  45

Leu His Asn His Tyr Thr Gln Lys Ser Leu Ser Leu Ser Pro Gly Lys
    50                  55                  60

<210> SEQ ID NO 84
<211> LENGTH: 43
<212> TYPE: PRT
<213> ORGANISM: Artificial Sequence
<220> FEATURE:
<223> OTHER INFORMATION: Synthetic Construct

<400> SEQUENCE: 84

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser
        35                  40

<210> SEQ ID NO 85
<211> LENGTH: 64
<212> TYPE: PRT
<213> ORGANISM: Artificial Sequence
<220> FEATURE:
<223> OTHER INFORMATION: Synthetic Construct

<400> SEQUENCE: 85

Asn Gly Gln Pro Glu Asn Asn Tyr Lys Thr Thr Pro Pro Val Leu Asp
1               5                   10                  15

Ser Asp Gly Ser Phe Phe Leu Tyr Ser Arg Leu Thr Val Asp Lys Ser
            20                  25                  30

Arg Trp Gln Gln Gly Asn Val Phe Ser Cys Ser Val Met His Glu Ala
        35                  40                  45

Leu His Asn His Tyr Thr Gln Lys Ser Leu Ser Leu Ser Pro Gly Lys
    50                  55                  60

<210> SEQ ID NO 86
<211> LENGTH: 107
<212> TYPE: PRT

<213> ORGANISM: Artificial Sequence
<220> FEATURE:
<223> OTHER INFORMATION: Synthetic Construct

<400> SEQUENCE: 86

```
Gly Gln Pro Arg Glu Pro Gln Val Tyr Thr Leu Pro Pro Ser Arg Glu
1               5                   10                  15
Glu Met Thr Lys Asn Gln Val Ser Leu Thr Cys Leu Val Lys Gly Phe
            20                  25                  30
Tyr Pro Ser Asp Ile Ser Val Glu Trp Glu Ser Asn Gly Gln Pro Glu
        35                  40                  45
Asn Asn Tyr Lys Thr Thr Pro Pro Met Leu Asp Ser Asp Gly Ser Phe
    50                  55                  60
Phe Leu Tyr Ser Arg Leu Thr Val Asp Lys Ser Arg Trp Gln Gln Gly
65                  70                  75                  80
Asn Val Phe Ser Cys Ser Val Met His Glu Ala Leu His Asn His Tyr
                85                  90                  95
Thr Gln Lys Ser Leu Ser Leu Ser Pro Gly Lys
            100                 105
```

<210> SEQ ID NO 87
<211> LENGTH: 107
<212> TYPE: PRT
<213> ORGANISM: Artificial Sequence
<220> FEATURE:
<223> OTHER INFORMATION: Synthetic Construct

<400> SEQUENCE: 87

```
Gly Gln Pro Arg Glu Pro Gln Val Tyr Thr Leu Pro Pro Ser Arg Glu
1               5                   10                  15
Glu Met Thr Lys Asn Gln Val Ser Leu Thr Cys Glu Val Lys Gly Phe
            20                  25                  30
Tyr Pro Ser Asp Ile Ser Val Glu Trp Glu Ser Asn Gly Gln Pro Glu
        35                  40                  45
Asn Asn Tyr Lys Thr Thr Pro Pro Met Leu Asp Ser Asp Gly Ser Phe
    50                  55                  60
Phe Leu Tyr Ser Lys Leu Thr Val Asp Lys Ser Arg Trp Gln Gln Gly
65                  70                  75                  80
Asn Val Phe Ser Cys Ser Val Met His Glu Ala Leu His Asn His Tyr
                85                  90                  95
Thr Gln Lys Ser Leu Ser Leu Ser Pro Gly Lys
            100                 105
```

<210> SEQ ID NO 88
<211> LENGTH: 107
<212> TYPE: PRT
<213> ORGANISM: Artificial Sequence
<220> FEATURE:
<223> OTHER INFORMATION: Synthetic Construct

<400> SEQUENCE: 88

```
Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
```

```
Thr Tyr Ser Leu Asp Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 89
<211> LENGTH: 107
<212> TYPE: PRT
<213> ORGANISM: Artificial Sequence
<220> FEATURE:
<223> OTHER INFORMATION: Synthetic Construct

<400> SEQUENCE: 89

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Lys Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 90
<211> LENGTH: 214
<212> TYPE: PRT
<213> ORGANISM: Artificial Sequence
<220> FEATURE:
<223> OTHER INFORMATION: Synthetic Construct

<400> SEQUENCE: 90

Ala Ile Gln Leu Thr Gln Ser Pro Ser Ser Leu Thr Ala Ser Val Gly
 1               5                  10                  15

Asp Arg Val Thr Ile Thr Cys Arg Ala Ser Gln Phe Ala Ser Asn Asp
                 20                  25                  30

Val Gly Trp Tyr Gln Lys Pro Gly Lys Ala Pro Lys Leu Leu Ile
             35                  40                  45

Tyr Ala Ala Ser Ser Leu Gln Ser Gly Val Pro Pro Arg Phe Ser Gly
 50                  55                  60

Ser Gly Ser Gly Thr Glu Phe Thr Phe Thr Ile Ser Ser Leu Gln Pro
 65                  70                  75                  80

Glu Asp Phe Ala Thr Tyr Tyr Cys Leu Gln Asp Tyr Tyr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
```

```
            145                 150                 155                 160
Glu Ser Val Thr Glu Gln Asp Ser Lys Asp Ser Thr Tyr Ser Leu Lys
                    165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 91
<211> LENGTH: 103
<212> TYPE: PRT
<213> ORGANISM: Artificial Sequence
<220> FEATURE:
<223> OTHER INFORMATION: Synthetic Construct

<400> SEQUENCE: 91

Ala Ser Thr Lys Gly Pro Ser Val Phe Pro Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 92
<211> LENGTH: 103
<212> TYPE: PRT
<213> ORGANISM: Artificial Sequence
<220> FEATURE:
<223> OTHER INFORMATION: Synthetic Construct

<400> SEQUENCE: 92

Ala Ser Thr Lys Gly Pro Ser Val Phe Pro Glu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 93
<211> LENGTH: 330
```

```
<212> TYPE: PRT
<213> ORGANISM: Artificial Sequence
<220> FEATURE:
<223> OTHER INFORMATION: Synthetic Construct

<400> SEQUENCE: 93

Ala Ser Thr Lys Gly Pro Ser Val Phe Pro Lys Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Glu Glu
225                 230                 235                 240

Met Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 94
<211> LENGTH: 330
<212> TYPE: PRT
<213> ORGANISM: Artificial Sequence
<220> FEATURE:
<223> OTHER INFORMATION: Synthetic Construct

<400> SEQUENCE: 94
```

Ala Ser Thr Lys Gly Pro Ser Val Phe Pro Glu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Cys Arg Glu Glu
225                 230                 235                 240

Met Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 95
<211> LENGTH: 450
<212> TYPE: PRT
<213> ORGANISM: Artificial Sequence
<220> FEATURE:
<223> OTHER INFORMATION: Synthetic Construct

<400> SEQUENCE: 95

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

```
Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Gly Gly Ser Ile Thr Gly Thr Thr Pro Phe Asp Tyr Trp Gly Arg
                100                 105                 110

Gly Thr Leu Val Thr Val Ser Ser Ala Ser Thr Lys Gly Pro Ser Val
            115                 120                 125

Phe Pro Glu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Glu Glu Met Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

Gly Lys
    450

<210> SEQ ID NO 96
<211> LENGTH: 214
<212> TYPE: PRT
<213> ORGANISM: Artificial Sequence
<220> FEATURE:
<223> OTHER INFORMATION: Synthetic Construct

<400> SEQUENCE: 96

Ala Ile Gln Leu Thr Gln Ser Pro Ser Ser Leu Thr Ala Ser Val Gly
1               5                   10                  15

Asp Arg Val Thr Ile Thr Cys Arg Ala Ser Gln Phe Ala Ser Asn Asp
            20                  25                  30

Val Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Glu Phe Thr Phe Thr Ile Ser Ser Leu Gln Pro
65                  70                  75                  80

Glu Asp Phe Ala Thr Tyr Tyr Cys Leu Gln Asp Tyr Thr Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Lys Gln Leu Lys Ser Gly
        115                 120                 125

Thr Ala Ser Val Val Cys Ile Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Cys
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser
    210

<210> SEQ ID NO 97
<211> LENGTH: 214
<212> TYPE: PRT
<213> ORGANISM: Artificial Sequence
<220> FEATURE:
<223> OTHER INFORMATION: Synthetic Construct

<400> SEQUENCE: 97

Ala Ile Gln Leu Thr Gln Ser Pro Ser Ser Leu Thr Ala Ser Val Gly
1               5                   10                  15

Asp Arg Val Thr Ile Thr Cys Arg Ala Ser Gln Phe Ala Ser Asn Asp
            20                  25                  30

Val Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Glu Phe Thr Phe Thr Ile Ser Ser Leu Gln Pro
65                  70                  75                  80

```
Glu Asp Phe Ala Thr Tyr Tyr Cys Leu Gln Asp Tyr Thr Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Cys Gln Leu Lys Ser Gly
            115                 120                 125

Thr Ala His Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser
    210
```

<210> SEQ ID NO 98
<211> LENGTH: 214
<212> TYPE: PRT
<213> ORGANISM: Artificial Sequence
<220> FEATURE:
<223> OTHER INFORMATION: Synthetic Construct

<400> SEQUENCE: 98

```
Ala Ile Gln Leu Thr Gln Ser Pro Ser Ser Leu Thr Ala Ser Val Gly
1               5                   10                  15

Asp Arg Val Thr Ile Thr Cys Arg Ala Ser Gln Phe Ala Ser Asn Asp
            20                  25                  30

Val Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Glu Phe Thr Phe Thr Ile Ser Ser Leu Gln Pro
65                  70                  75                  80

Glu Asp Phe Ala Thr Tyr Tyr Cys Leu Gln Asp Tyr Thr Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala His Val Val Cys Ile Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Cys
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser
    210
```

<210> SEQ ID NO 99
<211> LENGTH: 214
<212> TYPE: PRT
<213> ORGANISM: Artificial Sequence
<220> FEATURE:
<223> OTHER INFORMATION: Synthetic Construct

<400> SEQUENCE: 99

```
Ala Ile Gln Leu Thr Gln Ser Pro Ser Ser Leu Thr Ala Ser Val Gly
1               5                   10                  15

Asp Arg Val Thr Ile Thr Cys Arg Ala Ser Gln Phe Ala Ser Asn Asp
            20                  25                  30

Val Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Glu Phe Thr Phe Thr Ile Ser Ser Leu Gln Pro
65                  70                  75                  80

Glu Asp Phe Ala Thr Tyr Tyr Cys Leu Gln Asp Tyr Thr Tyr Pro Leu
                85                  90                  95

Thr Phe Gly Gln Gly Thr Lys Val Glu Ile Lys Arg Thr Val Ala Ala
            100                 105                 110

Pro Ser Val Cys Ile Phe Pro Pro Ser Asp Glu Gln Leu Lys Ser Gly
        115                 120                 125

Thr Ala His Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser
        210
```

<210> SEQ ID NO 100
<211> LENGTH: 214
<212> TYPE: PRT
<213> ORGANISM: Artificial Sequence
<220> FEATURE:
<223> OTHER INFORMATION: Synthetic Construct

<400> SEQUENCE: 100

```
Ala Ile Gln Leu Thr Gln Ser Pro Ser Ser Leu Thr Ala Ser Val Gly
1               5                   10                  15

Asp Arg Val Thr Ile Thr Cys Arg Ala Ser Gln Phe Ala Ser Asn Asp
            20                  25                  30

Val Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Glu Phe Thr Phe Thr Ile Ser Ser Leu Gln Pro
65                  70                  75                  80

Glu Asp Phe Ala Thr Tyr Tyr Cys Leu Gln Asp Tyr Thr Tyr Pro Leu
```

```
                    85                  90                  95
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Asp Val Ser Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Cys
                165                 170                 175

Ser Ser Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser
    210

<210> SEQ ID NO 101
<211> LENGTH: 450
<212> TYPE: PRT
<213> ORGANISM: Artificial Sequence
<220> FEATURE:
<223> OTHER INFORMATION: Synthetic Construct

<400> SEQUENCE: 101

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Ser Ile Thr Gly Thr Thr Pro Phe Asp Tyr Trp Gly Arg
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Cys Pro Ala Val
                165                 170                 175

Leu Gln Ser Ser Gly Leu Tyr Ser Leu Ser Ser Ile Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Asp Lys Val Glu Pro Lys Ser Ser Asp
    210                 215                 220

Lys Thr His Thr Cys Pro Pro Cys Pro Ala Pro Glu Ala Ala Gly Ala
```

```
            225                 230                 235                 240
    Pro Ser Val Phe Leu Phe Pro Lys Pro Lys Asp Thr Leu Met Ile
                    245                 250                 255
    Ser Arg Thr Pro Glu Val Thr Cys Val Val Val Asp Val Ser His Glu
                    260                 265                 270
    Asp Pro Glu Val Lys Phe Asn Trp Tyr Val Asp Gly Val Glu Val His
                    275                 280                 285
    Asn Ala Lys Thr Lys Pro Arg Glu Glu Gln Tyr Asn Ser Thr Tyr Arg
                    290                 295                 300
    Val Val Ser Val Leu Thr Val Leu His Gln Asp Trp Leu Asn Gly Lys
    305                 310                 315                 320
    Glu Tyr Lys Cys Lys Val Ser Asn Lys Ala Leu Pro Ala Pro Ile Glu
                    325                 330                 335
    Lys Thr Ile Ser Lys Ala Lys Gly Gln Pro Arg Glu Pro Gln Val Tyr
                    340                 345                 350
    Thr Leu Pro Pro Cys Arg Glu Glu Met Thr Lys Asn Gln Val Ser Leu
                    355                 360                 365
    Ser Cys Ala Val Lys Gly Phe Tyr Pro Ser Asp Ile Ala Val Glu Trp
                    370                 375                 380
    Glu Ser Asn Gly Gln Pro Glu Asn Asn Tyr Lys Thr Thr Pro Pro Val
    385                 390                 395                 400
    Leu Asp Ser Asp Gly Ser Phe Phe Leu Val Ser Lys Leu Thr Val Asp
                    405                 410                 415
    Lys Ser Arg Trp Gln Gln Gly Asn Val Phe Ser Cys Ser Val Met His
                    420                 425                 430
    Glu Ala Leu His Asn His Tyr Thr Gln Lys Ser Leu Ser Leu Ser Pro
                    435                 440                 445
    Gly Lys
        450

<210> SEQ ID NO 102
<211> LENGTH: 450
<212> TYPE: PRT
<213> ORGANISM: Artificial Sequence
<220> FEATURE:
<223> OTHER INFORMATION: Synthetic Construct

<400> SEQUENCE: 102

Gln Val Gln Leu Val Gln Ser Gly Ala Glu Val Lys Lys Pro Gly Ser
    1               5                   10                  15
    Ser Val Lys Val Ser Cys Lys Ala Ser Gly Gly Thr Phe Ser Ser Tyr
                    20                  25                  30
    Ala Ile Ser Trp Val Arg Gln Ala Pro Gly Gln Gly Leu Glu Trp Met
                    35                  40                  45
    Gly Gly Ile Ile Pro Ile Phe Gly Thr Ala Asn Tyr Ala Gln Lys Phe
    50                  55                  60
    Gln Gly Arg Val Thr Ile Thr Ala Asp Glu Ser Thr Ser Thr Ala Tyr
    65                  70                  75                  80
    Met Glu Leu Ser Ser Leu Arg Ser Glu Asp Thr Ala Val Tyr Tyr Cys
                    85                  90                  95
    Ala Gly Gly Ser Ile Thr Gly Thr Thr Pro Phe Asp Tyr Trp Gly Arg
                    100                 105                 110
    Gly Thr Leu Val Thr Val Ser Ser Ala Ser Thr Lys Gly Pro Ser Val
                    115                 120                 125
    Cys Pro Leu Ala Pro Ser Ser Lys Ser Thr Ser Gly Gly Thr Ala Ala
```

```
                130                 135                 140
Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Ser Asp
        210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Cys Arg Glu Glu Met Thr Lys Asn Gln Val Ser Leu
            355                 360                 365

Ser Cys Ala Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 103
<211> LENGTH: 450
<212> TYPE: PRT
<213> ORGANISM: Artificial Sequence
<220> FEATURE:
<223> OTHER INFORMATION: Synthetic Construct

<400> SEQUENCE: 103

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
```

```
                35                  40                  45
Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Gly Gly Ser Ile Thr Gly Thr Thr Pro Phe Asp Tyr Trp Gly Arg
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys His Val Lys Asp Tyr Phe Pro Glu Pro Val Thr Val Ser
145                 150                 155                 160

Trp Asn Ser Gly Ala Leu Thr Ser Gly Val His Thr Cys Pro Ala Val
                165                 170                 175

Leu Asp Ser Ser Gly Leu Tyr Glu Leu Ser Ser Ile Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Ser Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Cys Arg Glu Glu Met Thr Lys Asn Gln Val Ser Leu
                355                 360                 365

Ser Cys Ala Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450
```

<210> SEQ ID NO 104
<211> LENGTH: 450
<212> TYPE: PRT
<213> ORGANISM: Artificial Sequence
<220> FEATURE:
<223> OTHER INFORMATION: Synthetic Construct

<400> SEQUENCE: 104

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Ser Ile Thr Gly Thr Thr Pro Phe Asp Tyr Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Cys
    130                 135                 140

Leu Gly Cys Leu Val Ser Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Glu Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Ser Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Glu Glu Met Thr Lys Asn Gln Val Ser Leu
        355                 360                 365
```

-continued

Ser Cys Ala Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 105
<211> LENGTH: 450
<212> TYPE: PRT
<213> ORGANISM: Artificial Sequence
<220> FEATURE:
<223> OTHER INFORMATION: Synthetic Construct

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Ser Ile Thr Gly Thr Thr Pro Phe Asp Tyr Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Ser Val Lys Asp Tyr Phe Pro Glu Pro Val Thr Val Ser
145                 150                 155                 160

Trp Asn Ser Gly Ala Leu Thr Ser Gly Val His Thr Cys Pro Ala Val
                165                 170                 175

Leu Gln Ser Ser Gly Leu Tyr Ser Leu Trp Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Ser Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Cys Arg Glu Met Thr Lys Asn Gln Val Ser Leu
                355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 106
<211> LENGTH: 411
<212> TYPE: PRT
<213> ORGANISM: Artificial Sequence
<220> FEATURE:
<223> OTHER INFORMATION: Synthetic Construct

<400> SEQUENCE: 106

Ala Thr Gly Gly Gly Ala Thr Gly Gly Ala Gly Cys Thr Gly Thr Ala
1               5                   10                  15

Thr Cys Thr Thr Thr Cys Thr Cys Thr Thr Thr Cys Thr Cys Cys Thr
                20                  25                  30

Gly Thr Cys Ala Gly Thr Ala Ala Cys Thr Gly Thr Ala Gly Gly Thr
                35                  40                  45

Gly Thr Gly Thr Thr Cys Thr Cys Thr Gly Ala Gly Gly Thr Thr Cys
            50                  55                  60

Ala Gly Cys Thr Gly Cys Ala Gly Cys Ala Gly Thr Cys Thr Gly Gly
65                  70                  75                  80

Ala Cys Cys Thr Gly Ala Gly Cys Thr Gly Gly Thr Gly Ala Ala Gly
                85                  90                  95

Cys Cys Thr Gly Gly Gly Gly Cys Thr Thr Cys Ala Ala Thr Gly Ala
                100                 105                 110

Ala Gly Ala Thr Ala Thr Cys Cys Thr Gly Cys Ala Ala Gly Ala Cys
            115                 120                 125

Thr Thr Cys Thr Gly Gly Thr Thr Ala Cys Thr Cys Ala Thr Thr Thr
        130                 135                 140

Ala Cys Thr Gly Cys Cys Thr Ala Cys Thr Thr Ala Thr Gly Ala
145                 150                 155                 160

Ala Cys Thr Gly Gly Gly Thr Gly Ala Ala Gly Cys Ala Gly Ala Gly
                165                 170                 175
```

```
Cys Cys Ala Thr Gly Gly Ala Ala Gly Ala Gly Cys Cys Thr Thr
            180                 185                 190
Gly Ala Gly Thr Gly Gly Ala Thr Gly Gly Ala Cys Gly Thr Ala
            195                 200                 205
Thr Thr Ala Ala Thr Cys Cys Ala Ala Cys Ala Ala Thr Gly Gly
210                 215                 220
Thr Gly Ala Cys Ala Cys Thr Thr Thr Cys Thr Ala Cys Ala Cys
225                 230                 235                 240
Cys Ala Gly Ala Ala Gly Thr Thr Cys Ala Ala Gly Gly Cys Ala
            245                 250                 255
Ala Gly Gly Cys Cys Ala Cys Ala Thr Gly Ala Cys Thr Gly Thr
            260                 265                 270
Ala Gly Ala Cys Ala Ala Ala Thr Cys Cys Thr Cys Thr Ala Cys
            275                 280                 285
Ala Cys Ala Gly Cys Cys Cys Ala Cys Ala Thr Gly Gly Ala Ala
            290                 295                 300
Thr Cys Cys Thr Gly Ala Gly Cys Cys Thr Gly Ala Cys Ala Thr Cys
305                 310                 315                 320
Thr Gly Ala Gly Gly Ala Cys Thr Cys Thr Gly Cys Ala Ala Thr Cys
            325                 330                 335
Thr Ala Thr Thr Ala Thr Thr Gly Thr Gly Gly Ala Ala Gly Ala Ala
            340                 345                 350
Gly Gly Gly Ala Thr Thr Ala Thr Thr Thr Cys Gly Gly Gly Gly Cys
            355                 360                 365
Thr Ala Thr Gly Gly Ala Cys Thr Ala Cys Thr Gly Gly Gly Gly Thr
            370                 375                 380
Cys Ala Ala Gly Gly Ala Ala Cys Cys Thr Cys Ala Gly Thr Cys Ala
385                 390                 395                 400
Cys Cys Gly Thr Cys Thr Cys Cys Thr Cys Ala
            405                 410
```

<210> SEQ ID NO 107
<211> LENGTH: 137
<212> TYPE: PRT
<213> ORGANISM: Artificial Sequence
<220> FEATURE:
<223> OTHER INFORMATION: Synthetic Construct

<400> SEQUENCE: 107

```
Met Gly Trp Ser Cys Ile Phe Leu Phe Leu Leu Ser Val Thr Val Gly
1               5                   10                  15
Val Phe Ser Glu Val Gln Leu Gln Gln Ser Gly Pro Glu Leu Val Lys
            20                  25                  30
Pro Gly Ala Ser Met Lys Ile Ser Cys Lys Thr Ser Gly Tyr Ser Phe
        35                  40                  45
Thr Ala Tyr Phe Met Asn Trp Val Lys Gln Ser His Gly Lys Ser Leu
    50                  55                  60
Glu Trp Ile Gly Arg Ile Asn Pro Asn Asn Gly Asp Thr Phe Tyr Thr
65                  70                  75                  80
Gln Lys Phe Lys Gly Lys Ala Thr Leu Thr Val Asp Lys Ser Ser Asn
                85                  90                  95
Thr Ala His Met Glu Leu Leu Ser Leu Thr Ser Glu Asp Ser Ala Ile
            100                 105                 110
Tyr Tyr Cys Gly Arg Arg Asp Tyr Phe Gly Ala Met Asp Tyr Trp Gly
        115                 120                 125
```

Gln Gly Thr Ser Val Thr Val Ser Ser
    130                 135

<210> SEQ ID NO 108
<211> LENGTH: 381
<212> TYPE: DNA
<213> ORGANISM: Artificial Sequence
<220> FEATURE:
<223> OTHER INFORMATION: Synthetic Construct

<400> SEQUENCE: 108

```
atggttttca cacctcagat acttggactt atgcttttt ggatttcagc ctccagaggt    60
gctattgtgc taattcagtc tccagccacc ctgtctgtga ctccaggaga tagcgtcagt   120
ctttcctgca gggccagcca aactattagt aacaacctac actggtatca acaaaaatca   180
catgagtctc caaggcttct catcaagtct gcttccctgg ccatctctgg atcccctcc    240
aggttcagtg gcagtggatc aggacagat ttcactctca gtatcagcag tgtggagact    300
gaagattttg gaatgtattt ctgtcaacag agtaacagct ggccgaacac gttcggcggg   360
gggaccaagc tggaaataaa a                                             381
```

<210> SEQ ID NO 109
<211> LENGTH: 127
<212> TYPE: PRT
<213> ORGANISM: Artificial Sequence
<220> FEATURE:
<223> OTHER INFORMATION: Synthetic Construct

<400> SEQUENCE: 109

Met Val Phe Thr Pro Gln Ile Leu Gly Leu Met Leu Phe Trp Ile Ser
1               5                   10                  15

Ala Ser Arg Gly Ala Ile Val Leu Ile Gln Ser Pro Ala Thr Leu Ser
            20                  25                  30

Val Thr Pro Gly Asp Ser Val Ser Leu Ser Cys Arg Ala Ser Gln Thr
        35                  40                  45

Ile Ser Asn Asn Leu His Trp Tyr Gln Gln Lys Ser His Glu Ser Pro
    50                  55                  60

Arg Leu Leu Ile Lys Ser Ala Ser Leu Ala Ile Ser Gly Ile Pro Ser
65                  70                  75                  80

Arg Phe Ser Gly Ser Gly Ser Gly Thr Asp Phe Thr Leu Ser Ile Ser
                85                  90                  95

Ser Val Glu Thr Glu Asp Phe Gly Met Tyr Phe Cys Gln Gln Ser Asn
            100                 105                 110

Ser Trp Pro Asn Thr Phe Gly Gly Gly Thr Lys Leu Glu Ile Lys
        115                 120                 125

<210> SEQ ID NO 110
<211> LENGTH: 321
<212> TYPE: DNA
<213> ORGANISM: Artificial Sequence
<220> FEATURE:
<223> OTHER INFORMATION: Synthetic Construct

<400> SEQUENCE: 110

```
gatattgtgc taattcagtc tccagccacc ctgtctgtga ctccaggaga tagcgtcagt    60
ctttcctgca gggccagcca aactattagt aacaacctac actggtatca acaaaaatca   120
catgagtctc caaggcttct catcaagtct gcttccctgg ccatctctgg atcccctcc    180
aggttcagtg gcagtggatc aggacagat ttcactctca gtatcagcag tgtggagact    240
```

```
gaagattttg gaatgtattt ctgtcaacag agtaacagct ggccgaacac gttcggcggg    300
gggaccaagg tggaaataaa a                                              321
```

<210> SEQ ID NO 111
<211> LENGTH: 107
<212> TYPE: PRT
<213> ORGANISM: Artificial Sequence
<220> FEATURE:
<223> OTHER INFORMATION: Synthetic Construct

<400> SEQUENCE: 111

```
Asp Ile Val Leu Ile Gln Ser Pro Ala Thr Leu Ser Val Thr Pro Gly
1               5                   10                  15

Asp Ser Val Ser Leu Ser Cys Arg Ala Ser Gln Thr Ile Ser Asn Asn
            20                  25                  30

Leu His Trp Tyr Gln Gln Lys Ser His Glu Ser Pro Arg Leu Leu Ile
        35                  40                  45

Lys Ser Ala Ser Leu Ala Ile Ser Gly Ile Pro Ser Arg Phe Ser Gly
    50                  55                  60

Ser Gly Ser Gly Thr Asp Phe Thr Leu Ser Ile Ser Ser Val Glu Thr
65                  70                  75                  80

Glu Asp Phe Gly Met Tyr Phe Cys Gln Gln Ser Asn Ser Trp Pro Asn
                85                  90                  95

Thr Phe Gly Gly Gly Thr Lys Val Glu Ile Lys
            100                 105
```

<210> SEQ ID NO 112
<211> LENGTH: 354
<212> TYPE: DNA
<213> ORGANISM: Artificial Sequence
<220> FEATURE:
<223> OTHER INFORMATION: Synthetic Construct

<400> SEQUENCE: 112

```
gaggtgcagc tggtggagtc tgggggaggc ttggtccagc ctggggggtc cctgagactc    60
tcctgtgcag cctctggtta ctcatttact gcctacttta tgaactgggt ccgccaggct   120
ccagggaagg ggctggagtg ggtggcccgt attaatccca acaatggtga cactttctac   180
acccagaagt tcaagggccg attcaccatc tccagagaca cgccaagaa ctcactgtat    240 ctgcaaatga acagcctgag agccgaggac accgctgtgt attactgtgc cagaagggat   300
tatttcgggg ctatggacta ctggggtcaa ggaaccttgg tcaccgtctc ctca         354
```

<210> SEQ ID NO 113
<211> LENGTH: 118
<212> TYPE: PRT
<213> ORGANISM: Artificial Sequence
<220> FEATURE:
<223> OTHER INFORMATION: Synthetic Construct

<400> SEQUENCE: 113

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Tyr Ser Phe Thr Ala Tyr
            20                  25                  30

Phe Met Asn Trp Val Arg Gln Ala Pro Gly Lys Gly Leu Glu Trp Val
        35                  40                  45

Ala Arg Ile Asn Pro Asn Asn Gly Asp Thr Phe Tyr Thr Gln Lys Phe
    50                  55                  60
```

Lys Gly Arg Phe Thr Ile Ser Val Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Asp Tyr Phe Gly Ala Met Asp Tyr Trp Gly Gln Gly Thr
            100                 105                 110

Leu Val Thr Val Ser Ser
        115

<210> SEQ ID NO 114
<211> LENGTH: 354
<212> TYPE: DNA
<213> ORGANISM: Artificial Sequence
<220> FEATURE:
<223> OTHER INFORMATION: Synthetic Construct

<400> SEQUENCE: 114

| gaggtgcagc | tggtggagtc | tgggggaggc | ttggtccagc | ctgggggtc | cctgagactc | 60 |
| tcctgtgcaa | cctctggtta | ctcatttact | gcctacttta | tgaactgggt | ccgccaggct | 120 |
| ccagggaagg | ggctggagtg | ggtggcccgt | attaatccca | acaatggtga | cactttctac | 180 |
| acccagaagt | tcaagggccg | attcaccatc | tccgtggaca | acgccaagaa | ctcagcctat | 240 |
| ctgcaaatga | acagcctgag | agccgaggac | accgctgtgt | attactgtgc | cagaagggat | 300 |
| tatttcgggg | ctatggacta | ctggggtcaa | ggaaccttgg | tcaccgtctc | ctca | 354 |

<210> SEQ ID NO 115
<211> LENGTH: 118
<212> TYPE: PRT
<213> ORGANISM: Artificial Sequence
<220> FEATURE:
<223> OTHER INFORMATION: Synthetic Construct

<400> SEQUENCE: 115

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Thr Ala Tyr
            20                  25                  30

Phe Met Asn Trp Val Gln Gln Ala Pro Gly Lys Gly Leu Glu Trp Met
        35                  40                  45

Gly Arg Ile Asn Pro Asn Asn Gly Asp Thr Phe Tyr Thr Gln Lys Phe
    50                  55                  60

Lys Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Arg Asp Tyr Phe Gly Ala Met Asp Tyr Trp Gly Gln Gly Thr
            100                 105                 110

Leu Val Thr Val Ser Ser
        115

<210> SEQ ID NO 116
<211> LENGTH: 354
<212> TYPE: DNA
<213> ORGANISM: Artificial Sequence
<220> FEATURE:
<223> OTHER INFORMATION: Synthetic Construct

<400> SEQUENCE: 116

```
gaggtccagc tggtgcagtc tggggctgag gtgaagaagc tggggctac agtgaaaatc    60 tcctgcaagg tctccggtta ctcattact gcctacttta tgaactgggt gcaacaggcc   120
cctggaaaag ggctggagtg gatgggacgt attaatccca caatggtga cactttctac   180 acccagaagt tcaagggcag agtcaccata accgctgaca cctctacaga cacagcctac   240
atggagctga gcagcctgcg ctctgaggac accgccgtgt attactgtgc aacaagggat   300
tatttcgggg ctatggacta ctggggtcaa ggaaccttgg tcaccgtctc ctca          354
```

<210> SEQ ID NO 117
<211> LENGTH: 107
<212> TYPE: PRT
<213> ORGANISM: Artificial Sequence
<220> FEATURE:
<223> OTHER INFORMATION: Synthetic Construct

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Asn
            20                  25                  30

Leu His Trp Tyr Gln Gln Lys Pro Gly Lys Ala Pro Lys Leu Leu Ile
        35                  40                  45

Tyr Ser Ala Ser Leu Ala Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Asn
                85                  90                  95

Thr Phe Gly Gly Gly Thr Lys Val Glu Ile Lys
            100                 105

<210> SEQ ID NO 118
<211> LENGTH: 321
<212> TYPE: DNA
<213> ORGANISM: Artificial Sequence
<220> FEATURE:
<223> OTHER INFORMATION: Synthetic Construct

<400> SEQUENCE: 118

```
gacatccaga tgacccagtc tccatcctcc ctgtctgcat ctgtcggaga cagagtcacc    60
atcacttgca gggccagcca aactattagt aacaacctgc actggtatca gcagaaacca   120
ggcaaagccc ctaagctcct gatctattct gcttccctgg ccatctctgg agtcccatcc   180
cgcttcagcg gcagcggatc cggcacagat ttcactctca ccatcagcag cctgcaacct   240
gaagattttg caacttacta ctgtcaacag agtaacagct ggcccaacac cttcggcgga   300
gggaccaagg tggaaataaa a                                              321
```

<210> SEQ ID NO 119
<211> LENGTH: 107
<212> TYPE: PRT
<213> ORGANISM: Artificial Sequence
<220> FEATURE:
<223> OTHER INFORMATION: Synthetic Construct

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Asn
            20                  25                  30

```
                20                  25                  30
Leu His Trp Tyr Gln Gln Lys Pro Gly Glu Ser Pro Lys Leu Leu Ile
            35                  40                  45

Lys Ser Ala Ser Leu Ala Ile Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Asn
                85                  90                  95

Thr Phe Gly Gly Gly Thr Lys Val Glu Ile Lys
            100                 105

<210> SEQ ID NO 120
<211> LENGTH: 321
<212> TYPE: DNA
<213> ORGANISM: Artificial Sequence
<220> FEATURE:
<223> OTHER INFORMATION: Synthetic Construct

<400> SEQUENCE: 120
gacatccaga tgacccagtc tccatcctcc ctgtctgcat ctgtcggaga cagagtcacc      60
atcacttgca gggccagcca aactattagt aacaacctgc actggtatca gcagaaacca     120
ggcgagtccc ctaagctcct gatcaagtct gcttccctgg ccatctctgg agtcccatcc     180
cgcttcagcg gcagcggatc cggcacagat ttcactctca ccatcagcag cctgcaacct     240
gaagattttg caacttacta ctgtcaacag agtaacagct ggcccaacac cttcggcgga     300
gggaccaagg tggaaataaa a                                                321

<210> SEQ ID NO 121
<211> LENGTH: 107
<212> TYPE: PRT
<213> ORGANISM: Artificial Sequence
<220> FEATURE:
<223> OTHER INFORMATION: Synthetic Construct

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Asn
            20                  25                  30

Leu His Trp Tyr Gln Gln Lys Pro Gly Glu Ala Pro Lys Leu Leu Ile
        35                  40                  45

Tyr Ser Ala Ser Leu Ala Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Asn
                85                  90                  95

Thr Phe Gly Gly Gly Thr Lys Val Glu Ile Lys
            100                 105

<210> SEQ ID NO 122
<211> LENGTH: 321
<212> TYPE: DNA
<213> ORGANISM: Artificial Sequence
<220> FEATURE:
<223> OTHER INFORMATION: Synthetic Construct

<400> SEQUENCE: 122
```

```
gacatccaga tgacccagtc tccatcctcc ctgtctgcat ctgtcggaga cagagtcacc      60
atcacttgca gggccagcca aactattagt aacaacctgc actggtatca gcagaaacca     120
ggcgaggccc ctaagctcct gatctattct gcttccctgg ccatctctgg agtcccatcc     180
cgcttcagcg gcagcggatc cggcacagat ttcactctca ccatcagcag cctgcaacct     240
gaagattttg caacttacta ctgtcaacag agtaacagct ggcccaacac cttcggcgga     300
gggaccaagg tggaaataaa a                                               321
```

<210> SEQ ID NO 123
<211> LENGTH: 107
<212> TYPE: PRT
<213> ORGANISM: Artificial Sequence
<220> FEATURE:
<223> OTHER INFORMATION: Synthetic Construct

<400> SEQUENCE: 123

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Asn
            20                  25                  30

Leu His Trp Tyr Gln Gln Lys Pro Gly Lys Ser Pro Lys Leu Leu Ile
        35                  40                  45

Tyr Ser Ala Ser Leu Ala Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Asn
                85                  90                  95

Thr Phe Gly Gly Gly Thr Lys Val Glu Ile Lys
            100                 105
```

<210> SEQ ID NO 124
<211> LENGTH: 321
<212> TYPE: DNA
<213> ORGANISM: Artificial Sequence
<220> FEATURE:
<223> OTHER INFORMATION: Synthetic Construct

<400> SEQUENCE: 124

```
gacatccaga tgacccagtc tccatcctcc ctgtctgcat ctgtcggaga cagagtcacc      60
atcacttgca gggccagcca aactattagt aacaacctgc actggtatca gcagaaacca     120
ggcaaatccc ctaagctcct gatctattct gcttccctgg ccatctctgg agtcccatcc     180
cgcttcagcg gcagcggatc cggcacagat ttcactctca ccatcagcag cctgcaacct     240
gaagattttg caacttacta ctgtcaacag agtaacagct ggcccaacac cttcggcgga     300
gggaccaagg tggaaataaa a                                               321
```

<210> SEQ ID NO 125
<211> LENGTH: 321
<212> TYPE: DNA
<213> ORGANISM: Artificial Sequence
<220> FEATURE:
<223> OTHER INFORMATION: Synthetic Construct

<400> SEQUENCE: 125

```
gacatccaga tgacccagtc tccatcctcc ctgtctgcat ctgtcggaga cagagtcacc      60
atcacttgca gggccagcca aactattagt aacaacctgc actggtatca gcagaaacca     120
```

```
ggcaaagccc ctaagctcct gatcaagtct gcttccctgg ccatctctgg agtcccatcc    180
cgcttcagcg gcagcggatc cggcacagat tcactctca ccatcagcag cctgcaacct    240
gaagattttg caacttacta ctgtcaacag agtaacagct ggcccaacac cttcggcgga    300
gggaccaagg tggaaataaa a                                              321
```

<210> SEQ ID NO 126
<211> LENGTH: 107
<212> TYPE: PRT
<213> ORGANISM: Artificial Sequence
<220> FEATURE:
<223> OTHER INFORMATION: Synthetic Construct

<400> SEQUENCE: 126

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Asn
            20                  25                  30

Leu His Trp Tyr Gln Gln Lys Pro His Lys Ala Pro Lys Leu Leu Ile
        35                  40                  45

Tyr Ser Ala Ser Leu Ala Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Asn
                85                  90                  95

Thr Phe Gly Gly Gly Thr Lys Val Glu Ile Lys
            100                 105
```

<210> SEQ ID NO 127
<211> LENGTH: 321
<212> TYPE: DNA
<213> ORGANISM: Artificial Sequence
<220> FEATURE:
<223> OTHER INFORMATION: Synthetic Construct

<400> SEQUENCE: 127

```
gacatccaga tgacccagtc tccatcctcc ctgtctgcat ctgtcggaga cagagtcacc    60
atcacttgca gggccagcca aactattagt aacaacctgc actggtatca gcagaaacca    120
cacaaagccc ctaagctcct gatctattct gcttccctgg ccatctctgg agtcccatcc    180
cgcttcagcg gcagcggatc cggcacagat tcactctca ccatcagcag cctgcaacct    240
gaagattttg caacttacta ctgtcaacag agtaacagct ggcccaacac cttcggcgga    300
gggaccaagg tggaaataaa a                                              321
```

<210> SEQ ID NO 128
<211> LENGTH: 107
<212> TYPE: PRT
<213> ORGANISM: Artificial Sequence
<220> FEATURE:
<223> OTHER INFORMATION: Synthetic Construct

<400> SEQUENCE: 128

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Asn
            20                  25                  30

Leu His Trp Tyr Gln Gln Lys Pro Gly Glu Ser Pro Lys Leu Leu Ile
```

```
                35                  40                  45
Tyr Ser Ala Ser Leu Ala Ile Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Asn Ser Trp Pro Asn
                 85                  90                  95
Thr Phe Gly Gly Gly Thr Lys Val Glu Ile Lys
            100                 105
```

<210> SEQ ID NO 129
<211> LENGTH: 321
<212> TYPE: DNA
<213> ORGANISM: Artificial Sequence
<220> FEATURE:
<223> OTHER INFORMATION: Synthetic Construct

<400> SEQUENCE: 129

```
gacatccaga tgacccagtc tccatcctcc ctgtctgcat ctgtcggaga cagagtcacc      60
atcacttgca gggccagcca aactattagt aacaacctgc actggtatca gcagaaacca     120
ggcgagtccc ctaagctcct gatctattct gcttccctgg ccatctctgg agtcccatcc     180
cgcttcagcg gcagcggatc cggcacagat ttcactctca ccatcagcag cctgcaacct     240
gaagattttg caacttacta ctgtcaacag agtaacagct ggcccaacac cttcggcgga     300
gggaccaagg tggaaataaa a                                                321
```

<210> SEQ ID NO 130
<211> LENGTH: 107
<212> TYPE: PRT
<213> ORGANISM: Artificial Sequence
<220> FEATURE:
<223> OTHER INFORMATION: Synthetic Construct

<400> SEQUENCE: 130

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Thr Ile Ser Asn Asn
             20                  25                  30
Leu His Trp Tyr Gln Gln Lys Pro Gly Lys Ser Pro Lys Leu Leu Ile
         35                  40                  45
Lys Ser Ala Ser Leu Ala Ile Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Asn Ser Trp Pro Asn
                 85                  90                  95
Thr Phe Gly Gly Gly Thr Lys Val Glu Ile Lys
            100                 105
```

<210> SEQ ID NO 131
<211> LENGTH: 321
<212> TYPE: DNA
<213> ORGANISM: Artificial Sequence
<220> FEATURE:
<223> OTHER INFORMATION: Synthetic Construct

<400> SEQUENCE: 131

```
gacatccaga tgacccagtc tccatcctcc ctgtctgcat ctgtcggaga cagagtcacc      60
```

```
atcacttgca gggccagcca aactattagt aacaacctgc actggtatca gcagaaacca    120
ggcaaatccc ctaagctcct gatcaagtct gcttccctgg ccatctctgg agtcccatcc    180
cgcttcagcg gcagcggatc cggcacagat ttcactctca ccatcagcag cctgcaacct    240
gaagattttg caacttacta ctgtcaacag agtaacagct ggcccaacac cttcggcgga    300
gggaccaagg tggaaataaa a                                              321
```

<210> SEQ ID NO 132
<211> LENGTH: 107
<212> TYPE: PRT
<213> ORGANISM: Artificial Sequence
<220> FEATURE:
<223> OTHER INFORMATION: Synthetic Construct

<400> SEQUENCE: 132

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Asn
            20                  25                  30

Leu His Trp Tyr Gln Gln Lys Pro Gly Glu Ala Pro Lys Leu Leu Ile
        35                  40                  45

Lys Ser Ala Ser Leu Ala Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Asn
                85                  90                  95

Thr Phe Gly Gly Gly Thr Lys Val Glu Ile Lys
            100                 105
```

<210> SEQ ID NO 133
<211> LENGTH: 321
<212> TYPE: DNA
<213> ORGANISM: Artificial Sequence
<220> FEATURE:
<223> OTHER INFORMATION: Synthetic Construct

<400> SEQUENCE: 133

```
gacatccaga tgacccagtc tccatcctcc ctgtctgcat ctgtcggaga cagagtcacc     60
atcacttgca gggccagcca aactattagt aacaacctgc actggtatca gcagaaacca    120
ggcgaggccc ctaagctcct gatcaagtct gcttccctgg ccatctctgg agtcccatcc    180
cgcttcagcg gcagcggatc cggcacagat ttcactctca ccatcagcag cctgcaacct    240
gaagattttg caacttacta ctgtcaacag agtaacagct ggcccaacac cttcggcgga    300
gggaccaagg tggaaataaa a                                              321
```

<210> SEQ ID NO 134
<211> LENGTH: 107
<212> TYPE: PRT
<213> ORGANISM: Artificial Sequence
<220> FEATURE:
<223> OTHER INFORMATION: Synthetic Construct

<400> SEQUENCE: 134

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Ile Ser Asn Asn
            20                  25                  30
```

```
Leu His Trp Tyr Gln Gln Lys Pro Gly Gln Ala Pro Arg Leu Leu Ile
        35                  40                  45

Tyr Ser Ala Ser Leu Ala Ile Ser Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Ser Asn Ser Trp Pro Asn
                 85                  90                  95

Thr Phe Gly Gly Gly Thr Lys Val Glu Ile Lys
                100                 105
```

<210> SEQ ID NO 135
<211> LENGTH: 321
<212> TYPE: DNA
<213> ORGANISM: Artificial Sequence
<220> FEATURE:
<223> OTHER INFORMATION: Synthetic Construct

<400> SEQUENCE: 135

```
gaaatcgtga tgacacagtc tccagccacc ctgtctgtgt ctccaggcga acgcgccacc      60
ctgtcctgca gggccagcca aactattagt aacaacctgc actggtacca gcagaaacct     120
ggccaggctc ccaggctcct gatctattct gcttccctgg ccatctctgg catcccagcc     180
cgcttcagcg gcagcggatc cggcacagag ttcactctca ccatcagcag cctgcagtcc     240
gaagattttg ctgtgtatta ctgtcaacag agtaacagct ggcccaacac cttcggcgga     300
gggaccaagg tggaaataaa a                                                321
```

<210> SEQ ID NO 136
<211> LENGTH: 796
<212> TYPE: PRT
<213> ORGANISM: Artificial Sequence
<220> FEATURE:
<223> OTHER INFORMATION: Synthetic Construct

<400> SEQUENCE: 136

```
Met Leu Arg Gly Gly Arg Arg Gly Gln Leu Gly Trp His Ser Trp Ala
 1               5                  10                  15

Ala Gly Pro Gly Ser Leu Leu Ala Trp Leu Ile Leu Ala Ser Ala Gly
                20                  25                  30

Ala Ala Pro Cys Pro Asp Ala Cys Cys Pro His Gly Ser Ser Gly Leu
            35                  40                  45

Arg Cys Thr Arg Asp Gly Ala Leu Asp Ser Leu His His Leu Pro Gly
 50                  55                  60

Ala Glu Asn Leu Thr Glu Leu Tyr Ile Glu Asn Gln Gln His Leu Gln
 65                  70                  75                  80

His Leu Glu Leu Arg Asp Leu Arg Gly Leu Gly Glu Leu Arg Asn Leu
                 85                  90                  95

Thr Ile Val Lys Ser Gly Leu Arg Phe Val Ala Pro Asp Ala Phe His
                100                 105                 110

Phe Thr Pro Arg Leu Ser Arg Leu Asn Leu Ser Phe Asn Ala Leu Glu
            115                 120                 125

Ser Leu Ser Trp Lys Thr Val Gln Gly Leu Ser Leu Gln Glu Leu Val
        130                 135                 140

Leu Ser Gly Asn Pro Leu His Cys Ser Cys Ala Leu Arg Trp Leu Gln
145                 150                 155                 160

Arg Trp Glu Glu Glu Gly Leu Gly Gly Val Pro Glu Gln Lys Leu Gln
                165                 170                 175
```

-continued

```
Cys His Gly Gln Gly Pro Leu Ala His Met Pro Asn Ala Ser Cys Gly
            180                 185                 190

Val Pro Thr Leu Lys Val Gln Val Pro Asn Ala Ser Val Asp Val Gly
            195                 200                 205

Asp Asp Val Leu Leu Arg Cys Gln Val Glu Gly Arg Gly Leu Glu Gln
210                 215                 220

Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                245                 250                 255

Asp Leu Asn Arg Lys Asn Val Thr Cys Trp Ala Glu Asn Asp Val Gly
            260                 265                 270

Arg Ala Glu Val Ser Val Gln Val Asn Val Ser Phe Pro Ala Ser Val
            275                 280                 285

Gln Leu His Thr Ala Val Glu Met His His Trp Cys Ile Pro Phe Ser
            290                 295                 300

Val Asp Gly Gln Pro Ala Pro Ser Leu Arg Trp Leu Phe Asn Gly Ser
305                 310                 315                 320

Val Leu Asn Glu Thr Ser Phe Ile Phe Thr Glu Phe Leu Glu Pro Ala
                325                 330                 335

Ala Asn Glu Thr Val Arg His Gly Cys Leu Arg Leu Asn Gln Pro Thr
            340                 345                 350

His Val Asn Asn Gly Asn Tyr Thr Leu Leu Ala Ala Asn Pro Phe Gly
            355                 360                 365

Gln Ala Ser Ala Ser Ile Met Ala Ala Phe Met Asp Asn Pro Phe Glu
            370                 375                 380

Phe Asn Pro Glu Asp Pro Ile Pro Val Ser Phe Ser Pro Val Asp Thr
385                 390                 395                 400

Asn Ser Thr Ser Gly Asp Pro Val Glu Lys Lys Asp Glu Thr Pro Phe
                405                 410                 415

Gly Val Ser Val Ala Val Gly Leu Ala Val Phe Ala Cys Leu Phe Leu
            420                 425                 430

Ser Thr Leu Leu Leu Val Leu Asn Lys Cys Gly Arg Arg Asn Lys Phe
            435                 440                 445

Gly Ile Asn Arg Pro Ala Val Leu Ala Pro Glu Asp Gly Leu Ala Met
450                 455                 460

Ser Leu His Phe Met Thr Leu Gly Gly Ser Ser Leu Ser Pro Thr Glu
465                 470                 475                 480

Gly Lys Gly Ser Gly Leu Gln Gly His Ile Ile Glu Asn Pro Gln Tyr
                485                 490                 495

Phe Ser Asp Ala Cys Val His His Ile Lys Arg Arg Asp Ile Val Leu
            500                 505                 510

Lys Trp Glu Leu Gly Glu Gly Ala Phe Gly Lys Val Phe Leu Ala Glu
            515                 520                 525

Cys His Asn Leu Leu Pro Glu Gln Asp Lys Met Leu Val Ala Val Lys
            530                 535                 540

Ala Leu Lys Glu Ala Ser Glu Ser Ala Arg Gln Asp Phe Gln Arg Glu
545                 550                 555                 560

Ala Glu Leu Leu Thr Met Leu Gln His Gln His Ile Val Arg Phe Phe
                565                 570                 575

Gly Val Cys Thr Glu Gly Arg Pro Leu Leu Met Val Phe Glu Tyr Met
            580                 585                 590
```

Arg His Gly Asp Leu Asn Arg Phe Leu Arg Ser His Gly Pro Asp Ala
            595                 600                 605

Lys Leu Leu Ala Gly Gly Glu Asp Val Ala Pro Gly Pro Leu Gly Leu
610                 615                 620

Gly Gln Leu Leu Ala Val Ala Ser Gln Val Ala Ala Gly Met Val Tyr
625                 630                 635                 640

Leu Ala Gly Leu His Phe Val His Arg Asp Leu Ala Thr Arg Asn Cys
            645                 650                 655

Leu Val Gly Gln Gly Leu Val Val Lys Ile Gly Asp Phe Gly Met Ser
            660                 665                 670

Arg Asp Ile Tyr Ser Thr Asp Tyr Tyr Arg Val Gly Gly Arg Thr Met
            675                 680                 685

Leu Pro Ile Arg Trp Met Pro Pro Glu Ser Ile Leu Tyr Arg Lys Phe
690                 695                 700

Thr Thr Glu Ser Asp Val Trp Ser Phe Gly Val Val Leu Trp Glu Ile
705                 710                 715                 720

Phe Thr Tyr Gly Lys Gln Pro Trp Tyr Gln Leu Ser Asn Thr Glu Ala
            725                 730                 735

Ile Asp Cys Ile Thr Gln Gly Arg Glu Leu Glu Arg Pro Arg Ala Cys
            740                 745                 750

Pro Pro Glu Val Tyr Ala Ile Met Arg Gly Cys Trp Gln Arg Glu Pro
            755                 760                 765

Gln Gln Arg His Ser Ile Lys Asp Val His Ala Arg Leu Gln Ala Leu
            770                 775                 780

Ala Gln Ala Pro Pro Val Tyr Leu Asp Val Leu Gly
785                 790                 795

<210> SEQ ID NO 137
<211> LENGTH: 822
<212> TYPE: PRT
<213> ORGANISM: Artificial Sequence
<220> FEATURE:
<223> OTHER INFORMATION: Synthetic Construct

<400> SEQUENCE: 137

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
            35                  40                  45

Ser Pro Gly Ile Val Ala Phe Pro Arg Leu Glu Pro Asn Ser Val Asp
50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
            85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
            115                 120                 125

Ser Leu Ser Arg Lys His Phe Arg His Leu Asp Leu Ser Glu Leu Ile
            130                 135                 140

Leu Val Gly Asn Pro Phe Thr Cys Ser Cys Asp Ile Met Trp Ile Lys
145                 150                 155                 160

```
Thr Leu Gln Glu Ala Lys Ser Ser Pro Asp Thr Gln Asp Leu Tyr Cys
            165                 170                 175
Leu Asn Glu Ser Ser Lys Asn Ile Pro Leu Ala Asn Leu Gln Ile Pro
        180                 185                 190
Asn Cys Gly Leu Pro Ser Ala Asn Leu Ala Ala Pro Asn Leu Thr Val
    195                 200                 205
Glu Glu Gly Lys Ser Ile Thr Leu Ser Cys Ser Val Ala Gly Asp Pro
210                 215                 220
Val Pro Asn Met Tyr Trp Asp Val Gly Asn Leu Val Ser Lys His Met
225                 230                 235                 240
Asn Glu Thr Ser His Thr Gln Gly Ser Leu Arg Ile Thr Asn Ile Ser
                245                 250                 255
Ser Asp Asp Ser Gly Lys Gln Ile Ser Cys Val Ala Glu Asn Leu Val
            260                 265                 270
Gly Glu Asp Gln Asp Ser Val Asn Leu Thr Val His Phe Ala Pro Thr
        275                 280                 285
Ile Thr Phe Leu Glu Ser Pro Thr Ser Asp His His Trp Cys Ile Pro
    290                 295                 300
Phe Thr Val Lys Gly Asn Pro Lys Pro Ala Leu Gln Trp Phe Tyr Asn
305                 310                 315                 320
Gly Ala Ile Leu Asn Glu Ser Lys Tyr Ile Cys Thr Lys Ile His Val
                325                 330                 335
Thr Asn His Thr Glu Tyr His Gly Cys Leu Gln Leu Asp Asn Pro Thr
            340                 345                 350
His Met Asn Asn Gly Asp Tyr Thr Leu Ile Ala Lys Asn Glu Tyr Gly
        355                 360                 365
Lys Asp Glu Lys Gln Ile Ser Ala His Phe Met Gly Trp Pro Gly Ile
    370                 375                 380
Asp Asp Gly Ala Asn Pro Asn Tyr Pro Asp Val Ile Tyr Glu Asp Tyr
385                 390                 395                 400
Gly Thr Ala Ala Asn Asp Ile Gly Asp Thr Thr Asn Arg Ser Asn Glu
                405                 410                 415
Ile Pro Ser Thr Asp Val Thr Asp Lys Thr Gly Arg Glu His Leu Ser
            420                 425                 430
Val Tyr Ala Val Val Val Ile Ala Ser Val Val Gly Phe Cys Leu Leu
        435                 440                 445
Val Met Leu Phe Leu Leu Lys Leu Ala Arg His Ser Lys Phe Gly Met
    450                 455                 460
Lys Gly Pro Ala Ser Val Ile Ser Asn Asp Asp Ser Ala Ser Pro
465                 470                 475                 480
Leu His His Ile Ser Asn Gly Ser Asn Thr Pro Ser Ser Glu Gly
                485                 490                 495
Gly Pro Asp Ala Val Ile Ile Gly Met Thr Lys Ile Pro Val Ile Glu
            500                 505                 510
Asn Pro Gln Tyr Phe Gly Ile Thr Asn Ser Gln Leu Lys Pro Asp Thr
        515                 520                 525
Phe Val Gln His Ile Lys Arg His Asn Ile Val Leu Lys Arg Glu Leu
    530                 535                 540
Gly Glu Gly Ala Phe Gly Lys Val Phe Leu Ala Glu Cys Tyr Asn Leu
545                 550                 555                 560
Cys Pro Glu Gln Asp Lys Ile Leu Val Ala Val Lys Thr Leu Lys Asp
                565                 570                 575
Ala Ser Asp Asn Ala Arg Lys Asp Phe His Arg Glu Ala Glu Leu Leu
```

-continued

```
                580                 585                 590
Thr Asn Leu Gln His Glu His Ile Val Lys Phe Tyr Gly Val Cys Val
        595                 600                 605

Glu Gly Asp Pro Leu Ile Met Val Phe Glu Tyr Met Lys His Gly Asp
610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
                645                 650                 655

Ala Gln Gln Ile Ala Ala Gly Met Val Tyr Leu Ala Ser Gln His Phe
            660                 665                 670

Val His Arg Asp Leu Ala Thr Arg Asn Cys Leu Val Gly Glu Asn Leu
        675                 680                 685

Leu Val Lys Ile Gly Asp Phe Gly Met Ser Arg Asp Val Tyr Ser Thr
    690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
            740                 745                 750

Pro Trp Tyr Gln Leu Ser Asn Asn Glu Val Ile Glu Cys Ile Thr Gln
        755                 760                 765

Gly Arg Val Leu Gln Arg Pro Arg Thr Cys Pro Gln Glu Val Tyr Glu
    770                 775                 780

Leu Met Leu Gly Cys Trp Gln Arg Glu Pro His Met Arg Lys Asn Ile
785                 790                 795                 800

Lys Gly Ile His Thr Leu Leu Gln Asn Leu Ala Lys Ala Ser Pro Val
                805                 810                 815

Tyr Leu Asp Ile Leu Gly
            820

<210> SEQ ID NO 138
<211> LENGTH: 826
<212> TYPE: PRT
<213> ORGANISM: Artificial Sequence
<220> FEATURE:
<223> OTHER INFORMATION: Synthetic Construct

<400> SEQUENCE: 138

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
```

```
            115                 120                 125
Ser Leu Ser Arg Lys His Phe Arg His Leu Asp Leu Ser Glu Leu Ile
130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
                180                 185                 190

Asn Cys Gly Leu Pro Ser Ala Asn Leu Ala Ala Pro Asn Leu Thr Val
                195                 200                 205

Glu Glu Gly Lys Ser Ile Thr Leu Ser Cys Ser Val Ala Gly Asp Pro
210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
                260                 265                 270

Gly Glu Asp Gln Asp Ser Val Asn Leu Thr Val Val Asn Val Ser Phe
                275                 280                 285

Pro Ala Ser Val Gln Leu His Thr Ala Val Glu Met His His Trp Cys
                290                 295                 300

Ile Pro Phe Ser Val Asp Gly Gln Pro Ala Pro Ser Leu Arg Trp Leu
305                 310                 315                 320

Phe Asn Gly Ser Val Leu Asn Glu Thr Ser Phe Ile Phe Thr Glu Phe
                325                 330                 335

Leu Glu Pro Ala Ala Asn Glu Thr Val Arg His Gly Cys Leu Arg Leu
                340                 345                 350

Asn Gln Pro Thr His Val Asn Asn Gly Asn Tyr Thr Leu Leu Ala Ala
                355                 360                 365

Asn Pro Phe Gly Gln Ala Ser Ala Ser Ile Met Ala Ala Phe Met Gly
                370                 375                 380

Trp Pro Gly Ile Asp Asp Gly Ala Asn Pro Asn Tyr Pro Asp Val Ile
385                 390                 395                 400

Tyr Glu Asp Tyr Gly Thr Ala Ala Asn Asp Ile Gly Asp Thr Thr Asn
                405                 410                 415

Arg Ser Asn Glu Ile Pro Ser Thr Asp Val Thr Asp Lys Thr Gly Arg
                420                 425                 430

Glu His Leu Ser Val Tyr Ala Val Val Ile Ala Ser Val Val Gly
                435                 440                 445

Phe Cys Leu Leu Val Met Leu Phe Leu Leu Lys Leu Ala Arg His Ser
                450                 455                 460

Lys Phe Gly Met Lys Gly Pro Ala Ser Val Ile Ser Asn Asp Asp Asp
465                 470                 475                 480

Ser Ala Ser Pro Leu His His Ile Ser Asn Gly Ser Asn Thr Pro Ser
                485                 490                 495

Ser Ser Glu Gly Gly Pro Asp Ala Val Ile Ile Gly Met Thr Lys Ile
                500                 505                 510

Pro Val Ile Glu Asn Pro Gln Tyr Phe Gly Ile Thr Asn Ser Gln Leu
                515                 520                 525

Lys Pro Asp Thr Phe Val Gln His Ile Lys Arg His Asn Ile Val Leu
530                 535                 540
```

```
Lys Arg Glu Leu Gly Glu Gly Ala Phe Gly Lys Val Phe Leu Ala Glu
545                 550                 555                 560

Cys Tyr Asn Leu Cys Pro Glu Gln Asp Lys Ile Leu Val Ala Val Lys
            565                 570                 575

Thr Leu Lys Asp Ala Ser Asp Asn Ala Arg Lys Asp Phe His Arg Glu
        580                 585                 590

Ala Glu Leu Leu Thr Asn Leu Gln His Glu His Ile Val Lys Phe Tyr
    595                 600                 605

Gly Val Cys Val Glu Gly Asp Pro Leu Ile Met Val Phe Glu Tyr Met
610                 615                 620

Lys His Gly Asp Leu Asn Lys Phe Leu Arg Ala His Gly Pro Asp Ala
625                 630                 635                 640

Val Leu Met Ala Glu Gly Asn Pro Pro Thr Glu Leu Thr Gln Ser Gln
                645                 650                 655

Met Leu His Ile Ala Gln Gln Ile Ala Ala Gly Met Val Tyr Leu Ala
            660                 665                 670

Ser Gln His Phe Val His Arg Asp Leu Ala Thr Arg Asn Cys Leu Val
        675                 680                 685

Gly Glu Asn Leu Leu Val Lys Ile Gly Asp Phe Gly Met Ser Arg Asp
    690                 695                 700

Val Tyr Ser Thr Asp Tyr Tyr Arg Val Gly Gly His Thr Met Leu Pro
705                 710                 715                 720

Ile Arg Trp Met Pro Pro Glu Ser Ile Met Tyr Arg Lys Phe Thr Thr
                725                 730                 735

Glu Ser Asp Val Trp Ser Leu Gly Val Val Leu Trp Glu Ile Phe Thr
            740                 745                 750

Tyr Gly Lys Gln Pro Trp Tyr Gln Leu Ser Asn Asn Glu Val Ile Glu
        755                 760                 765

Cys Ile Thr Gln Gly Arg Val Leu Gln Arg Pro Arg Thr Cys Pro Gln
    770                 775                 780

Glu Val Tyr Glu Leu Met Leu Gly Cys Trp Gln Arg Glu Pro His Met
785                 790                 795                 800

Arg Lys Asn Ile Lys Gly Ile His Thr Leu Leu Gln Asn Leu Ala Lys
                805                 810                 815

Ala Ser Pro Val Tyr Leu Asp Ile Leu Gly
            820                 825

<210> SEQ ID NO 139
<211> LENGTH: 798
<212> TYPE: PRT
<213> ORGANISM: Artificial Sequence
<220> FEATURE:
<223> OTHER INFORMATION: Synthetic Construct

<400> SEQUENCE: 139

Met Leu Arg Gly Gly Arg Arg Gly Gln Leu Gly Trp His Ser Trp Ala
1               5                   10                  15

Ala Gly Pro Gly Ser Leu Leu Ala Trp Leu Ile Leu Ala Ser Ala Gly
            20                  25                  30

Ala Ala Pro Cys Pro Asp Ala Cys Cys Pro His Gly Ser Ser Gly Leu
        35                  40                  45

Arg Cys Thr Arg Asp Gly Ala Leu Asp Ser Leu His His Leu Pro Gly
    50                  55                  60

Ala Glu Asn Leu Thr Glu Leu Tyr Ile Glu Asn Gln Gln His Leu Gln
65                  70                  75                  80
```

```
His Leu Glu Leu Arg Asp Leu Arg Gly Leu Gly Glu Leu Arg Asn Leu
                 85                  90                  95

Thr Ile Val Lys Ser Gly Leu Arg Phe Val Ala Pro Asp Ala Phe His
            100                 105                 110

Phe Thr Pro Arg Leu Ser Arg Leu Asn Leu Ser Phe Asn Ala Leu Glu
        115                 120                 125

Ser Leu Ser Trp Lys Thr Val Gln Gly Leu Ser Leu Gln Glu Leu Val
130                 135                 140

Leu Ser Gly Asn Pro Leu His Cys Ser Cys Ala Leu Arg Trp Leu Gln
145                 150                 155                 160

Arg Trp Glu Glu Glu Gly Leu Gly Gly Val Pro Glu Gln Lys Leu Gln
                165                 170                 175

Cys His Gly Gln Gly Pro Leu Ala His Met Pro Asn Ala Ser Cys Gly
            180                 185                 190

Val Pro Thr Leu Lys Val Gln Val Pro Asn Ala Ser Val Asp Val Gly
        195                 200                 205

Asp Asp Val Leu Leu Arg Cys Gln Val Glu Gly Arg Gly Leu Glu Gln
        210                 215                 220

Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                245                 250                 255

Asp Leu Asn Arg Lys Asn Val Thr Cys Trp Ala Glu Asn Asp Val Gly
            260                 265                 270

Arg Ala Glu Val Ser Val Gln Val Asn Val Leu Thr Val His Phe Ala
        275                 280                 285

Pro Thr Ile Thr Phe Leu Glu Ser Pro Thr Ser Asp His His Trp Cys
        290                 295                 300

Ile Pro Phe Thr Val Lys Gly Asn Pro Lys Pro Ala Leu Gln Trp Phe
305                 310                 315                 320

Tyr Asn Gly Ala Ile Leu Asn Glu Ser Lys Tyr Ile Cys Thr Lys Ile
                325                 330                 335

His Val Thr Asn His Thr Glu Tyr His Gly Cys Leu Gln Leu Asp Asn
            340                 345                 350

Pro Thr His Met Asn Asn Gly Asp Tyr Thr Leu Ile Ala Lys Asn Glu
        355                 360                 365

Tyr Gly Lys Asp Glu Lys Gln Ile Ser Ala His Phe Met Asp Asn Pro
370                 375                 380

Phe Glu Phe Asn Pro Glu Asp Pro Ile Pro Val Ser Phe Ser Pro Val
385                 390                 395                 400

Asp Thr Asn Ser Thr Ser Gly Asp Pro Val Glu Lys Lys Asp Glu Thr
                405                 410                 415

Pro Phe Gly Val Ser Val Ala Val Gly Leu Ala Val Phe Ala Cys Leu
            420                 425                 430

Phe Leu Ser Thr Leu Leu Leu Val Leu Asn Lys Cys Gly Arg Arg Asn
        435                 440                 445

Lys Phe Gly Ile Asn Arg Pro Ala Val Leu Ala Pro Glu Asp Gly Leu
450                 455                 460

Ala Met Ser Leu His Phe Met Thr Leu Gly Gly Ser Ser Leu Ser Pro
465                 470                 475                 480

Thr Glu Gly Lys Gly Ser Gly Leu Gln Gly His Ile Ile Glu Asn Pro
                485                 490                 495
```

Gln Tyr Phe Ser Asp Ala Cys Val His His Ile Lys Arg Arg Asp Ile
                500                 505                 510

Val Leu Lys Trp Glu Leu Gly Glu Gly Ala Phe Gly Lys Val Phe Leu
515                 520                 525

Ala Glu Cys His Asn Leu Leu Pro Glu Gln Asp Lys Met Leu Val Ala
                530                 535                 540

Val Lys Ala Leu Lys Glu Ala Ser Glu Ser Ala Arg Gln Asp Phe Gln
545                 550                 555                 560

Arg Glu Ala Glu Leu Leu Thr Met Leu Gln His Gln His Ile Val Arg
                565                 570                 575

Phe Phe Gly Val Cys Thr Glu Gly Arg Pro Leu Leu Met Val Phe Glu
                580                 585                 590

Tyr Met Arg His Gly Asp Leu Asn Arg Phe Leu Arg Ser His Gly Pro
                595                 600                 605

Asp Ala Lys Leu Leu Ala Gly Gly Glu Asp Val Ala Pro Gly Pro Leu
                610                 615                 620

Gly Leu Gly Gln Leu Leu Ala Val Ala Ser Gln Val Ala Ala Gly Met
625                 630                 635                 640

Val Tyr Leu Ala Gly Leu His Phe Val His Arg Asp Leu Ala Thr Arg
                645                 650                 655

Asn Cys Leu Val Gly Gln Gly Leu Val Val Lys Ile Gly Asp Phe Gly
                660                 665                 670

Met Ser Arg Asp Ile Tyr Ser Thr Asp Tyr Tyr Arg Val Gly Gly Arg
                675                 680                 685

Thr Met Leu Pro Ile Arg Trp Met Pro Pro Glu Ser Ile Leu Tyr Arg
                690                 695                 700

Lys Phe Thr Thr Glu Ser Asp Val Trp Ser Phe Gly Val Val Leu Trp
705                 710                 715                 720

Glu Ile Phe Thr Tyr Gly Lys Gln Pro Trp Tyr Gln Leu Ser Asn Thr
                725                 730                 735

Glu Ala Ile Asp Cys Ile Thr Gln Gly Arg Glu Leu Glu Arg Pro Arg
                740                 745                 750

Ala Cys Pro Pro Glu Val Tyr Ala Ile Met Arg Gly Cys Trp Gln Arg
                755                 760                 765

Glu Pro Gln Gln Arg His Ser Ile Lys Asp Val His Ala Arg Leu Gln
                770                 775                 780

Ala Leu Ala Gln Ala Pro Pro Val Tyr Leu Asp Val Leu Gly
785                 790                 795

<210> SEQ ID NO 140
<211> LENGTH: 824
<212> TYPE: PRT
<213> ORGANISM: Artificial Sequence
<220> FEATURE:
<223> OTHER INFORMATION: Synthetic Construct

<400> SEQUENCE: 140

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
                20                  25                  30

Pro Thr Ser Cys Lys Cys Ser Ala Ser Arg Ile Trp Cys Ser Asp Pro
                35                  40                  45

Ser Pro Gly Ile Val Ala Phe Pro Arg Leu Glu Pro Asn Ser Val Asp
                50                  55                  60

-continued

```
Pro Glu Asn Ile Thr Glu Ile Phe Ile Ala Asn Gln Lys Arg Leu Glu
 65                  70                  75                  80

Ile Ile Asn Glu Asp Asp Val Glu Ala Tyr Val Gly Leu Arg Asn Leu
                 85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Pro Asn Ala
            180                 185                 190

Ser Cys Gly Val Pro Thr Leu Lys Val Gln Val Pro Asn Ala Ser Val
        195                 200                 205

Asp Val Gly Asp Val Leu Leu Arg Cys Gln Val Glu Gly Arg Gly Gly
    210                 215                 220

Leu Glu Gln Ala Gly Trp Ile Leu Thr Glu Leu Glu Gln Ser Ala Thr
225                 230                 235                 240

Val Met Lys Ser Gly Leu Pro Ser Leu Gly Leu Thr Leu Ala Asn
                245                 250                 255

Val Thr Ser Asp Leu Asn Arg Lys Asn Val Thr Cys Trp Ala Glu Asn
            260                 265                 270

Asp Val Gly Arg Ala Glu Val Ser Val Gln Val Asn Val His Phe Ala
        275                 280                 285

Pro Thr Ile Thr Phe Leu Glu Ser Pro Thr Ser Asp His His Trp Cys
    290                 295                 300

Ile Pro Phe Thr Val Lys Gly Asn Pro Lys Pro Ala Leu Gln Trp Phe
305                 310                 315                 320

Tyr Asn Gly Ala Ile Leu Asn Glu Ser Lys Tyr Ile Cys Thr Lys Ile
                325                 330                 335

His Val Thr Asn His Thr Glu Tyr His Gly Cys Leu Gln Leu Asp Asn
            340                 345                 350

Pro Thr His Met Asn Asn Gly Asp Tyr Thr Leu Ile Ala Lys Asn Glu
        355                 360                 365

Tyr Gly Lys Asp Glu Lys Gln Ile Ser Ala His Phe Met Gly Trp Pro
    370                 375                 380

Gly Ile Asp Asp Gly Ala Asn Pro Asn Tyr Pro Asp Val Ile Tyr Glu
385                 390                 395                 400

Asp Tyr Gly Thr Ala Ala Asn Asp Ile Gly Asp Thr Thr Asn Arg Ser
                405                 410                 415

Asn Glu Ile Pro Ser Thr Asp Val Thr Asp Lys Thr Gly Arg Glu His
            420                 425                 430

Leu Ser Val Tyr Ala Val Val Val Ile Ala Ser Val Val Gly Phe Cys
        435                 440                 445

Leu Leu Val Met Leu Phe Leu Leu Lys Leu Ala Arg His Ser Lys Phe
    450                 455                 460

Gly Met Lys Gly Pro Ala Ser Val Ile Ser Asn Asp Asp Ser Ala
465                 470                 475                 480

Ser Pro Leu His His Ile Ser Asn Gly Ser Asn Thr Pro Ser Ser Ser
```

485                 490                 495
Glu Gly Gly Pro Asp Ala Val Ile Ile Gly Met Thr Lys Ile Pro Val
                500                 505                 510

Ile Glu Asn Pro Gln Tyr Phe Gly Ile Thr Asn Ser Gln Leu Lys Pro
            515                 520                 525

Asp Thr Phe Val Gln His Ile Lys Arg His Asn Ile Val Leu Lys Arg
        530                 535                 540

Glu Leu Gly Glu Gly Ala Phe Gly Lys Val Phe Leu Ala Glu Cys Tyr
545                 550                 555                 560

Asn Leu Cys Pro Glu Gln Asp Lys Ile Leu Val Ala Val Lys Thr Leu
                565                 570                 575

Lys Asp Ala Ser Asp Asn Ala Arg Lys Asp Phe His Arg Glu Ala Glu
            580                 585                 590

Leu Leu Thr Asn Leu Gln His Glu His Ile Val Lys Phe Tyr Gly Val
        595                 600                 605

Cys Val Glu Gly Asp Pro Leu Ile Met Val Phe Glu Tyr Met Lys His
610                 615                 620

Gly Asp Leu Asn Lys Phe Leu Arg Ala His Gly Pro Asp Ala Val Leu
625                 630                 635                 640

Met Ala Glu Gly Asn Pro Pro Thr Glu Leu Thr Gln Ser Gln Met Leu
                645                 650                 655

His Ile Ala Gln Gln Ile Ala Ala Gly Met Val Tyr Leu Ala Ser Gln
            660                 665                 670

His Phe Val His Arg Asp Leu Ala Thr Arg Asn Cys Leu Val Gly Glu
        675                 680                 685

Asn Leu Leu Val Lys Ile Gly Asp Phe Gly Met Ser Arg Asp Val Tyr
690                 695                 700

Ser Thr Asp Tyr Tyr Arg Val Gly Gly His Thr Met Leu Pro Ile Arg
705                 710                 715                 720

Trp Met Pro Pro Glu Ser Ile Met Tyr Arg Lys Phe Thr Thr Glu Ser
                725                 730                 735

Asp Val Trp Ser Leu Gly Val Val Leu Trp Glu Ile Phe Thr Tyr Gly
            740                 745                 750

Lys Gln Pro Trp Tyr Gln Leu Ser Asn Asn Glu Val Ile Glu Cys Ile
        755                 760                 765

Thr Gln Gly Arg Val Leu Gln Arg Pro Arg Thr Cys Pro Gln Glu Val
770                 775                 780

Tyr Glu Leu Met Leu Gly Cys Trp Gln Arg Glu Pro His Met Arg Lys
785                 790                 795                 800

Asn Ile Lys Gly Ile His Thr Leu Leu Gln Asn Leu Ala Lys Ala Ser
                805                 810                 815

Pro Val Tyr Leu Asp Ile Leu Gly
            820

<210> SEQ ID NO 141
<211> LENGTH: 794
<212> TYPE: PRT
<213> ORGANISM: Artificial Sequence
<220> FEATURE:
<223> OTHER INFORMATION: Synthetic Construct

<400> SEQUENCE: 141

Met Leu Arg Gly Gly Arg Arg Gly Gln Leu Gly Trp His Ser Trp Ala
1               5                   10                  15

Ala Gly Pro Gly Ser Leu Leu Ala Trp Leu Ile Leu Ala Ser Ala Gly

```
                20              25              30
Ala Ala Pro Cys Pro Asp Ala Cys Cys Pro His Gly Ser Ser Gly Leu
            35              40              45
Arg Cys Thr Arg Asp Gly Ala Leu Asp Ser Leu His His Leu Pro Gly
        50              55              60
Ala Glu Asn Leu Thr Glu Leu Tyr Ile Glu Asn Gln Gln His Leu Gln
 65              70              75              80
His Leu Glu Leu Arg Asp Leu Arg Gly Leu Gly Glu Leu Arg Asn Leu
                85              90              95
Thr Ile Val Lys Ser Gly Leu Arg Phe Val Ala Pro Asp Ala Phe His
            100             105             110
Phe Thr Pro Arg Leu Ser Arg Leu Asn Leu Ser Phe Asn Ala Leu Glu
        115             120             125
Ser Leu Ser Trp Lys Thr Val Gln Gly Leu Ser Leu Gln Glu Leu Val
130             135             140
Leu Ser Gly Asn Pro Leu His Cys Ser Cys Ala Leu Arg Trp Leu Gln
145             150             155             160
Arg Trp Glu Glu Glu Gly Leu Gly Gly Val Pro Glu Gln Lys Leu Gln
            165             170             175
Cys His Gly Gln Gly Pro Leu Ala His Met Gln Ile Pro Asn Cys Gly
            180             185             190
Leu Pro Ser Ala Asn Leu Ala Ala Pro Asn Leu Thr Val Glu Glu Gly
            195             200             205
Lys Ser Ile Thr Leu Ser Cys Ser Val Ala Gly Asp Pro Val Pro Asn
            210             215             220
Met Tyr Trp Asp Val Gly Asn Leu Val Ser Lys His Met Asn Glu Thr
225             230             235             240
Ser His Thr Gln Gly Ser Leu Arg Ile Thr Asn Ile Ser Ser Asp Asp
            245             250             255
Ser Gly Lys Gln Ile Ser Cys Val Ala Glu Asn Leu Val Gly Glu Asp
            260             265             270
Gln Asp Ser Val Asn Leu Thr Val Ser Phe Pro Ala Ser Val Gln Leu
            275             280             285
His Thr Ala Val Glu Met His His Trp Cys Ile Pro Phe Ser Val Asp
            290             295             300
Gly Gln Pro Ala Pro Ser Leu Arg Trp Leu Phe Asn Gly Ser Val Leu
305             310             315             320
Asn Glu Thr Ser Phe Ile Phe Thr Glu Phe Leu Glu Pro Ala Ala Asn
            325             330             335
Glu Thr Val Arg His Gly Cys Leu Arg Leu Asn Gln Pro Thr His Val
            340             345             350
Asn Asn Gly Asn Tyr Thr Leu Leu Ala Ala Asn Pro Phe Gly Gln Ala
            355             360             365
Ser Ala Ser Ile Met Ala Ala Phe Met Asp Asn Pro Phe Glu Phe Asn
            370             375             380
Pro Glu Asp Pro Ile Pro Val Ser Phe Ser Pro Val Asp Thr Asn Ser
385             390             395             400
Thr Ser Gly Asp Pro Val Glu Lys Lys Asp Glu Thr Pro Phe Gly Val
            405             410             415
Ser Val Ala Val Gly Leu Ala Val Phe Ala Cys Leu Phe Leu Ser Thr
            420             425             430
Leu Leu Leu Val Leu Asn Lys Cys Gly Arg Arg Asn Lys Phe Gly Ile
            435             440             445
```

```
Asn Arg Pro Ala Val Leu Ala Pro Glu Asp Gly Leu Ala Met Ser Leu
            450                 455                 460
His Phe Met Thr Leu Gly Ser Ser Leu Ser Pro Thr Glu Gly Lys
465                 470                 475                 480
Gly Ser Gly Leu Gln Gly His Ile Ile Glu Asn Pro Gln Tyr Phe Ser
                    485                 490                 495
Asp Ala Cys Val His His Ile Lys Arg Arg Asp Ile Val Leu Lys Trp
                500                 505                 510
Glu Leu Gly Glu Gly Ala Phe Gly Lys Val Phe Leu Ala Glu Cys His
            515                 520                 525
Asn Leu Leu Pro Glu Gln Asp Lys Met Leu Val Ala Val Lys Ala Leu
        530                 535                 540
Lys Glu Ala Ser Glu Ser Ala Arg Gln Asp Phe Gln Arg Glu Ala Glu
545                 550                 555                 560
Leu Leu Thr Met Leu Gln His Gln His Ile Val Arg Phe Phe Gly Val
                565                 570                 575
Cys Thr Glu Gly Arg Pro Leu Leu Met Val Phe Glu Tyr Met Arg His
                580                 585                 590
Gly Asp Leu Asn Arg Phe Leu Arg Ser His Gly Pro Asp Ala Lys Leu
            595                 600                 605
Leu Ala Gly Gly Glu Asp Val Ala Pro Gly Pro Leu Gly Leu Gly Gln
        610                 615                 620
Leu Leu Ala Val Ala Ser Gln Val Ala Ala Gly Met Val Tyr Leu Ala
625                 630                 635                 640
Gly Leu His Phe Val His Arg Asp Leu Ala Thr Arg Asn Cys Leu Val
                645                 650                 655
Gly Gln Gly Leu Val Val Lys Ile Gly Asp Phe Gly Met Ser Arg Asp
                660                 665                 670
Ile Tyr Ser Thr Asp Tyr Tyr Arg Val Gly Gly Arg Thr Met Leu Pro
            675                 680                 685
Ile Arg Trp Met Pro Pro Glu Ser Ile Leu Tyr Arg Lys Phe Thr Thr
        690                 695                 700
Glu Ser Asp Val Trp Ser Phe Gly Val Val Leu Trp Glu Ile Phe Thr
705                 710                 715                 720
Tyr Gly Lys Gln Pro Trp Tyr Gln Leu Ser Asn Thr Glu Ala Ile Asp
                725                 730                 735
Cys Ile Thr Gln Gly Arg Glu Leu Glu Arg Pro Arg Ala Cys Pro Pro
                740                 745                 750
Glu Val Tyr Ala Ile Met Arg Gly Cys Trp Gln Arg Glu Pro Gln Gln
            755                 760                 765
Arg His Ser Ile Lys Asp Val His Ala Arg Leu Gln Ala Leu Ala Gln
        770                 775                 780
Ala Pro Pro Val Tyr Leu Asp Val Leu Gly
785                 790

<210> SEQ ID NO 142
<211> LENGTH: 2469
<212> TYPE: DNA
<213> ORGANISM: Artificial Sequence
<220> FEATURE:
<223> OTHER INFORMATION: Synthetic Construct

<400> SEQUENCE: 142
atgtcgtcct ggacgaggtg gcatggaccc gccatggcgc ggctctgggg cttctgctgg      60
```

```
ctggttgtgg gcttctggag ggccgctctc gcctgtccca cgtcctgcaa gtgcaccgcc    120
tctcggatct ggtgcagcga cccttctccg ggcatcgtgg cgtttccgag gttggagcct    180
aatagtgcag accctgagaa catcaccgaa atttacattg ccaatcagaa aaggttggaa    240
atcatcaacg aagatgatgt cgaagcttac gcaggactga aaaatctgac aattgtggat    300
tctggattaa aatttgtggc tcataaagcg tttctgaaaa cagcaacttt acagcacatc    360
aattttactc gaaataaact gaccagcttg tctaggaaac atttcgtca ccttgatttg    420
tctgaactga tcctggtggg caatccattt acatgctcct gtgacattat gtggatcaag    480
actcttcagg agactaaatc cagcccagaa actcaggatt gtactgcct aaatgaaagc    540
agcaagaata ttcccctggc aaacctgcag atacccaatt gtggtttgcc atcagcaaat    600
ttggccgcac ctaacctcac tgtggargag ggaaggtcta tcacattatc ttgcagtgtc    660
tcaggcgatc cggttccgaa tttgtactgg gatgtcggta atctggtttc caagcatatg    720
aatgaaacga gccacacaca gggctcctta aggataacta acatttcatc tgatgacagt    780
ggaaagcaga tctcctgtgt ggcagaaaat cttgtaggag aagaccaaga ttctgtcaac    840
ctcactgtac attttgctcc aactatcaca tttctcgaat ctccaacctc agaccaccac    900
tggtgcattc cattcactgt gaaaggcaac cccaaaccag ctcttcagtg gttctataat    960
ggggcgatac tgaatgagtc caagtacatc tgtactaaaa tccatgttac caatcacacg   1020
gagtaccatg gctgcctcca gctggataat cctactcaca tgaacaatgg ggactacaag   1080
ttagtagcca agaacgagta tgggaaggat gagaaacaga tttctgctca cttcatgggc   1140
tggcctggaa tcgtagatgg tgccaaccca aattatcctg atgtaattta tgaagattat   1200
gggactgcag cgaatgacat tggggacacc acgaacagaa gtaacgaaat ccctccaca   1260
gatgtggcg acaaaagcgg tcgggaacat ctttcggtct atgctgtggt ggtcattgcg   1320
tctgtggtgg gattttgtct gctggtgatg ctgtttctgc tgaagttggc aagacactcc   1380
aagtttggca tgaaaggccc agcttcagtt atcagcaatg atgatgactc tgccagccca   1440
ctccaccaca tctccaatgg gagtaacacc ccatcatctt cagagggcgg ccccgatgcc   1500
gtcattattg gaatgaccaa gattcctgtc attgaaaatc cccagtactt tggcatcacc   1560
aacagtcagc tcaagccaga cacatttgtt caacacatca gcgacataa cattgttctg   1620
aaaagggagc taggcgaagg agcctttgga aaagttttcc tagctgaatg ctataacctc   1680
tgtcctgagc aggacaagat cttggtggca gtgaagacgc tgaaggacgc cagtgacaac   1740
gcccgcaagg acttccaccg tgaggcagag ctgctgacca cctccagca cgagcacatt   1800
gtcaagttct acggtgtctg tgtggagggc gacccactca tcatggtctt tgagtacatg   1860
aagcacgggg atctcaacaa gttcctcagg gcccacgggc tgacgctgt gctgatggcc   1920
gaaggcaacc cgccgacaga gctgacgcag tcccagatgc tgcacatcgc ccagcagata   1980
gcagcgggca tggtctacct ggcgtcccaa cactttgtgc accgagatct ggccacccgg   2040
aactgcctgg tcggtgagaa cctcctggtg aaaatcgggg acttcgggat gtcccgggac   2100
gtgtacagca ctgactacta cagggtcggt ggccacacga tgttacccat cgctggatg   2160
cctccagaga gcatcatgta caggaagttc accacagaaa gtgatgtctg gagcctggga   2220
gtcgtgttgt gggagatctt cacgtacggc aaacagccct ggtaccagct gtccaacaac   2280
gaggtgatag aatgcatcac tcagggccga gtcttgcagc gacctagaac atgcccccag   2340
gaggtgtatg agttgatgct ggggtgctgg cagcgagagc cccacatgag gaagaacatc   2400
aagggcatcc acaccctcct tcagaacttg gccaaggcat ctccggtcta cctggatatt   2460
``` ctgggctag 2469

<210> SEQ ID NO 143
<211> LENGTH: 822
<212> TYPE: PRT
<213> ORGANISM: Artificial Sequence
<220> FEATURE:
<223> OTHER INFORMATION: Synthetic Construct

<400> SEQUENCE: 143

```
Met Ser Ser Trp Thr Arg Trp His Gly Pro Ala Met Ala Arg Leu Trp
1               5                   10                  15

Gly Phe Cys Trp Leu Val Val Gly Phe Trp Arg Ala Ala Leu Ala Cys
            20                  25                  30

Pro Thr Ser Cys Lys Cys Thr Ala Ser Arg Ile Trp Cys Ser Asp Pro
        35                  40                  45

Ser Pro Gly Ile Val Ala Phe Pro Arg Leu Glu Pro Asn Ser Ala Asp
    50                  55                  60

Pro Glu Asn Ile Thr Glu Ile Tyr Ile Ala Asn Gln Lys Arg Leu Glu
65                  70                  75                  80

Ile Ile Asn Glu Asp Asp Val Glu Ala Tyr Ala Gly Leu Lys Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Thr Lys Ser Ser Pro Glu Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Arg Ser Ile Thr Leu Ser Cys Ser Val Ser Gly Asp Pro
    210                 215                 220

Val Pro Asn Leu Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350
```

His Met Asn Asn Gly Asp Tyr Lys Leu Val Ala Lys Asn Glu Tyr Gly
            355                 360                 365

Lys Asp Glu Lys Gln Ile Ser Ala His Phe Met Gly Trp Pro Gly Ile
370                 375                 380

Val Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
            405                 410                 415

Ile Pro Ser Thr Asp Val Ala Asp Lys Ser Gly Arg Glu His Leu Ser
            420                 425                 430

Val Tyr Ala Val Val Val Ile Ala Ser Val Val Gly Phe Cys Leu Leu
            435                 440                 445

Val Met Leu Phe Leu Leu Lys Leu Ala Arg His Ser Lys Phe Gly Met
        450                 455                 460

Lys Gly Pro Ala Ser Val Ile Ser Asn Asp Asp Ser Ala Ser Pro
465                 470                 475                 480

Leu His His Ile Ser Asn Gly Ser Asn Thr Pro Ser Ser Glu Gly
                485                 490                 495

Gly Pro Asp Ala Val Ile Gly Met Thr Lys Ile Pro Val Ile Glu
            500                 505                 510

Asn Pro Gln Tyr Phe Gly Ile Thr Asn Ser Gln Leu Lys Pro Asp Thr
            515                 520                 525

Phe Val Gln His Ile Lys Arg His Asn Ile Val Leu Lys Arg Glu Leu
        530                 535                 540

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
            565                 570                 575

Ala Ser Asp Asn Ala Arg Lys Asp Phe His Arg Glu Ala Glu Leu Leu
            580                 585                 590

Thr Asn Leu Gln His Glu His Ile Val Lys Phe Tyr Gly Val Cys Val
        595                 600                 605

Glu Gly Asp Pro Leu Ile Met Val Phe Glu Tyr Met Lys His Gly Asp
610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
            645                 650                 655

Ala Gln Gln Ile Ala Ala Gly Met Val Tyr Leu Ala Ser Gln His Phe
            660                 665                 670

Val His Arg Asp Leu Ala Thr Arg Asn Cys Leu Val Gly Glu Asn Leu
        675                 680                 685

Leu Val Lys Ile Gly Asp Phe Gly Met Ser Arg Asp Val Tyr Ser Thr
        690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
            725                 730                 735

Trp Ser Leu Gly Val Val Leu Trp Glu Ile Phe Thr Tyr Gly Lys Gln
            740                 745                 750

Pro Trp Tyr Gln Leu Ser Asn Asn Glu Val Ile Glu Cys Ile Thr Gln
        755                 760                 765

Gly Arg Val Leu Gln Arg Pro Arg Thr Cys Pro Gln Glu Val Tyr Glu

Leu Met Leu Gly Cys Trp Gln Arg Glu Pro His Met Arg Lys Asn Ile
785                 790                 795                 800

Lys Gly Ile His Thr Leu Leu Gln Asn Leu Ala Lys Ala Ser Pro Val
            805                 810                 815

Tyr Leu Asp Ile Leu Gly
            820

<210> SEQ ID NO 144
<211> LENGTH: 2469
<212> TYPE: DNA
<213> ORGANISM: Artificial Sequence
<220> FEATURE:
<223> OTHER INFORMATION: Synthetic Construct

<400> SEQUENCE: 144

```
atgtcgtcct ggacgaggtg gcatggaccc gccatggcgc ggctctgggg cttctgctgg      60
ctggtcgtgg gcttctggag ggctgccctc gcctgtccca cgtcctgcaa atgcagcgcc     120
tctaggatct ggtgcagcga cccttctccg ggcatcgtgg cgtttccgag gttggagccc     180
aacagtgcag accctgagaa catcaccgaa atttacattg ccaatcagaa aaggttggaa     240
atcatcaatg aagatgatgt tgaagcttat gcaggactga agaatctgac gattgtggac     300
tctggattaa atttgtggc tcataaagca tttctgaaaa acagcaactt acagcacatc     360
aattttaccc gaaataaact gacaagcttg tctaggaaac attttcgtca ccttgacttg     420
tctgagctga tcctggtggg caatccattt acatgttcct gtgatattat gtggatcaag     480
actcttcagg agactaaatc cagcccagaa actcaggatt tgtactgcct aaatgaaagc     540
agcaagaata ttccccctggc aaacctgcag atacccaatt gtggtttgcc atcagcaaat     600
ttggctgcac ctaacctcac cgtggaggag ggaaagtcta tcacattatc ttgtagtgtt     660
gcaggcgatc cagttccgaa tttgtactgg atgtcggta atctggtttc caaacatatg     720
aatgaaacaa gccacatgca gggctccttg aggataacta cattcatc tgatgacagt     780
ggaaaacaaa tctcctgtgt ggcagaaaat cttgtaggag aagaccaaga ttctgtcaac     840
ctcactgtac attttgctcc aactatcaca tttctcgaat ctccaacctc agaccaccac     900
tggtgcattc cattcactgt gaaaggcaac cccaaaccag cgcttcagtg gttctataac     960
ggggcaatat tgaatgagtc caaatacatc tgtactaaaa tccatgttac caatcacacg    1020
gagtaccatg gctgcctcca gctggataat cccactcaca tgaacaatgg ggactacaag    1080
ttagtagcca agaatgagta tgggaaagat gagaaacaga tttctgctca cttcatgggc    1140
tggcctggaa ttgatgatgg tgccaaccca aattatcccg acgtaattta tgaagattac    1200
gggactgcag caaatgacat tgggacacc acaaacagaa gtaacgaaat cccttctaca    1260
gatgttgctg acaaaagcgg tcgggaacat ctttcggtct atgctgtggt ggtaattgca    1320
tctgtggtgg atttgtgtct gctggtgatg ctgtttctgc tgaagttggc aagacactcc    1380
aagtttggca tgaaaggccc agcttcagtt atcagcaatg atgatgactc tgccagcccc    1440
ctccaccaca tctccaatgg gagtaacacc ccatcatctt cagagggcgg ccccgatgcc    1500
gtcatcattg aatgaccaa gatccctgtc attgaaaatc cccagtactt tggcatcacc    1560
aacagtcagc tcaagccaga cacatttgtt cagcacatca agagacataa cattgttctg    1620
aaaagggagc taggcgaagg agcctttgga aaagttttcc tagctgaatg ctataacctc    1680
tgtcctgagc aggacaagat cttggtggca gtgaagacac tgaaggatgc cagtgacaac    1740
```

```
gcacgcaagg actttcaccg cgaggctgag ctgctgacca acctccagca cgagcacatc    1800
gtcaagttct atggtgtctg cgtggagggt gacccgctca tcatggtctt tgagtacatg    1860
aagcacgggg acctcaacaa gttcctcagg gcccatgggc tgatgctgt gctgatggcc    1920 gaaggcaacc cgccgacgga gctcacccag tcccagatgc tgcacattgc ccagcagata    1980
gcagcaggaa tggtctacct ggcgtcccag cactttgtgc accgagatct ggccacccgc    2040
aactgcctgg ttggcgagaa cctcctggtg aaaatcgggg acttcgggat gtcccgggac    2100
gtgtacagca ccgactacta cagggtcggt ggccacacaa tgctgcccat cgctggatg    2160 cctccagaga gcatcatgta caggaagttc accacagaaa gtgatgtctg gagcctggga    2220
gtcgtgttat gggagatctt cacgtacggc aaacagccct ggtaccagct gtccaacaac    2280
gaggtgatag aatgcatcac gcagggccga gtcttgcagc gacctagaac gtgcccccag    2340
gaggtctatg agttgatgct ggggtgctgg cagcgggagc cccatatgag gaaaaacatc    2400
aagggtatcc acaccctcct tcagaacttg gccaaggcat ctccagtcta cctggatatt    2460
ctaggctag                                                             2469
```

<210> SEQ ID NO 145
<211> LENGTH: 822
<212> TYPE: PRT
<213> ORGANISM: Artificial Sequence
<220> FEATURE:
<223> OTHER INFORMATION: Synthetic Construct

<400> SEQUENCE: 145

```
Met Ser Ser Trp Thr Arg Trp His Gly Pro Ala Met Ala Arg Leu Trp
1               5                   10                  15

Gly Phe Cys Trp Leu Val Val Gly Phe Trp Arg Ala Ala Leu Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Ala Asp
    50                  55                  60

Pro Glu Asn Ile Thr Glu Ile Tyr Ile Ala Asn Gln Lys Arg Leu Glu
65                  70                  75                  80

Ile Ile Asn Glu Asp Asp Val Glu Ala Tyr Ala Gly Leu Lys Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Thr Lys Ser Ser Pro Glu Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Leu Tyr Trp Asp Val Gly Asn Leu Val Ser Lys His Met
```

```
            225                 230                 235                 240
Asn Glu Thr Ser His Met Gln Gly Ser Leu Arg Ile Thr Asn Ile Ser
                    245                 250                 255

Ser Asp Asp Ser Gly Lys Gln Ile Ser Cys Val Ala Glu Asn Leu Val
                260                 265                 270

Gly Glu Asp Gln Asp Ser Val Asn Leu Thr Val His Phe Ala Pro Thr
            275                 280                 285

Ile Thr Phe Leu Glu Ser Pro Thr Ser Asp His His Trp Cys Ile Pro
        290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Lys Leu Val Ala Lys Asn Glu Tyr Gly
        355                 360                 365

Lys Asp Glu Lys Gln Ile Ser Ala His Phe Met Gly Trp Pro Gly Ile
370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Ala Asp Lys Ser Gly Arg Glu His Leu Ser
            420                 425                 430

Val Tyr Ala Val Val Val Ile Ala Ser Val Val Gly Phe Cys Leu Leu
        435                 440                 445

Val Met Leu Phe Leu Leu Lys Leu Ala Arg His Ser Lys Phe Gly Met
450                 455                 460

Lys Gly Pro Ala Ser Val Ile Ser Asn Asp Asp Asp Ser Ala Ser Pro
465                 470                 475                 480

Leu His His Ile Ser Asn Gly Ser Asn Thr Pro Ser Ser Glu Gly
                485                 490                 495

Gly Pro Asp Ala Val Ile Ile Gly Met Thr Lys Ile Pro Val Ile Glu
            500                 505                 510

Asn Pro Gln Tyr Phe Gly Ile Thr Asn Ser Gln Leu Lys Pro Asp Thr
        515                 520                 525

Phe Val Gln His Ile Lys Arg His Asn Ile Val Leu Lys Arg Glu Leu
530                 535                 540

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
                565                 570                 575

Ala Ser Asp Asn Ala Arg Lys Asp Phe His Arg Glu Ala Glu Leu Leu
            580                 585                 590

Thr Asn Leu Gln His Glu His Ile Val Lys Phe Tyr Gly Val Cys Val
        595                 600                 605

Glu Gly Asp Pro Leu Ile Met Val Phe Glu Tyr Met Lys His Gly Asp
610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
                645                 650                 655
```

```
Ala Gln Gln Ile Ala Ala Gly Met Val Tyr Leu Ala Ser Gln His Phe
            660                 665                 670

Val His Arg Asp Leu Ala Thr Arg Asn Cys Leu Val Gly Glu Asn Leu
            675                 680                 685

Leu Val Lys Ile Gly Asp Phe Gly Met Ser Arg Asp Val Tyr Ser Thr
    690                 695                 700

Asp Tyr Tyr Arg Val Gly Gly His Thr Met Leu Pro Ile Arg Trp Met
705             710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
            740                 745                 750

Pro Trp Tyr Gln Leu Ser Asn Asn Glu Val Ile Glu Cys Ile Thr Gln
            755                 760                 765

Gly Arg Val Leu Gln Arg Pro Arg Thr Cys Pro Gln Glu Val Tyr Glu
    770                 775                 780

Leu Met Leu Gly Cys Trp Gln Arg Glu Pro His Met Arg Lys Asn Ile
785             790                 795                 800

Lys Gly Ile His Thr Leu Leu Gln Asn Leu Ala Lys Ala Ser Pro Val
                805                 810                 815

Tyr Leu Asp Ile Leu Gly
            820

<210> SEQ ID NO 146
<211> LENGTH: 41
<212> TYPE: DNA
<213> ORGANISM: Artificial Sequence
<220> FEATURE:
<223> OTHER INFORMATION: Synthetic Construct

<400> SEQUENCE: 146
ggatccgccg ccaccatgtc gtcctggacg aggtggcatg g        41

<210> SEQ ID NO 147
<211> LENGTH: 39
<212> TYPE: DNA
<213> ORGANISM: Artificial Sequence
<220> FEATURE:
<223> OTHER INFORMATION: Synthetic Construct

<400> SEQUENCE: 147
gcggccgcct agcccagaat atccaggtag accggagat          39
```

BISPECIFIC ANTIBODIES

CROSS-REFERENCE TO RELATED APPLICATIONS

This application is the U.S. National Phase of International Application No. PCT/32015/053537, filed May 13, 2015 and published in English, which claims the benefit of U.S. provisional application No. 61/994,720, filed May 16, 2014, U.S. provisional application No. 62/150,680, filed Apr. 21, 2015, and U.S. provisional application No. 62/159,201, filed May 8, 2015. The complete content of all of the above-referenced patent applications are hereby incorporated by reference for all purposes.

REFERENCE TO SEQUENCE LISTING

This application contains a Sequence Listing which has been submitted electronically in ASCII format and is hereby incorporated by reference in its entirety. Said ASCII copy, created on Nov. 3$^{rd}$, 2016, is named PC71995A_Seq_Listing_ST25.txt and is 269,724 bytes in size.

FIELD

The present invention relates to engineered bispecific antibodies and related polypeptides, multimeric forms thereof, and methods of making such proteins.

BACKGROUND

Antibodies having binding specificities for at least two different antigens, called bispecific antibodies (BsAbs), have been engineered. Unlike classical antibodies which comprise two identical heterodimer (i.e. a light chain portion and a heavy chain portion) "arms" wherein each arm comprises an antigen binding site (e.g. a Fab region), bispecific antibodies have different sequences in each of the two arms (e.g. Fab regions) so that each arm of the Y-shaped molecule binds to a different antigen or different epitope of the same antigen.

By binding two different antigenic molecules or different epitopes of the same antigen, BsAbs offer a wide variety of clinical applications as targeting agents for in vitro and in vivo diagnostics and immunotherapies. Bispecific antibodies are also advantageous for in vitro or in vivo diagnoses of various disease states, including cancer. For example, one arm of the BsAb can be engineered to bind a tumor-associated antigen and the other arm to bind a detectable marker.

BsAbs can be used to direct a patient's cellular immune defense mechanisms to a tumor cell or an infectious agent (e.g. virally infected cells such as HIV or influenza virus; protozoa such as *Toxoplasma gondii*). In particular, one can redirect immune modulated cytotoxicity by engineering one arm of the BsAb to bind to a desired target (e.g. a tumor cell or pathogen) and the other arm of the BsAb to bind to a cytotoxic trigger molecule, such as the T-cell receptor or a Fc gamma receptor, thereby activating downstream immune effector pathways. Using this strategy, BsAbs which bind to the Fc gamma RIII have been shown to mediate tumor cell killing by natural killer (NK) cell/large granular lymphocyte (LGL) cells in vitro and to prevent tumor growth in vivo. Alternatively, targeting two separate antigens or targets related to the therapeutic indication can enhance specificity and reduce unwanted interaction, thereby widening the therapeutic index.

Although bispecific antibodies posses certain advantages over canonical bivalent monospecific classical antibodies, use of bispecific antibodies has been hindered by the expense in obtaining BsAbs in sufficient quantity and purity.

To produce multispecific proteins, e.g. bispecific antibodies and other heterodimers or heteromultimers, it is desirable to use methods that favor formation of the desired heteromultimer over homomultimer(s). One method for obtaining Fc-containing BsAbs remains the hybrid hybridoma technique, in which two antibodies are co-expressed. However, this approach is inefficient with respect to yield and purity, the desired heteromultimer often being difficult to further purify from a relatively large level of contaminant comprising improperly paired polypeptide chains.

Other techniques to favor heteromultimer formation and reduce improper matching involve engineering sterically complementary mutations in multimerization domains at the $C_H3$ domain interface, referred to as a "knobs-into-holes" strategy as described by Ridgway et al. (U.S. Pat. No. 5,731,168) and Merchant et al. (U.S. Pat. No. 7,183,076).

Techniques that replace one or more residues that make up the $C_H3$-$C_H3$ interface in both $C_H3$ domains with a charged amino acid for promoting the heterodimer formation have also been described by Strop et al. (WO2011/143545).

A recent review also discusses various approaches for overcoming chain association issues when generating bispecific antibodies (Klein et al., mAbs 4(6): 653-663 (2012)).

However, most of these techniques are directed to ensuring proper pairing of the heavy chain polypeptides and do not address the further matching of each light chain polypeptide with its corresponding heavy chain polypeptide to provide a functional antigen-binding site. Thus, production of desired bispecific antibodies remains a technically difficult and costly process not commercially feasible due to the high cost of goods.

Therefore, there is a long-felt need in the art for methods for engineering bispecific antibody fragments and/or full length BsAbs which enable the BsAbs to be expressed and recovered directly and/or efficiently from recombinant cell culture and/or which may be produced with efficient yields and purities at commercially reasonable costs.

SUMMARY OF THE INVENTION

E1. According to a first embodiment of the invention, there is provided a heterodimeric protein, comprising:
  (i) a first $C_HC_L$ domain ($C_HC_L$), comprising a first $C_H1$ domain ($C_H1$) and a first $C_L$ domain ($C_L$), wherein the first $C_H1$ and the first $C_L$ interact together at a first $C_HC_L$ interface;
  (ii) a second $C_HC_L$, comprising a second $C_H1$ and a second $C_L$, wherein the second $C_H1$ and the second $C_L$ interacting together at a second $C_HC_L$ interface;
wherein the first $C_H1$ differs from the second $C_H1$ by at least one $C_H1$ mutant residue in the first $C_H1$; and the first $C_L$ differs from the second $C_L$ by at least one $C_L$ mutant residue in the first $C_L$;
such that the $C_H1$ mutant residue and the $C_L$ mutant residue of the first $C_HC_L$ interact with each other in preference to the corresponding residue positions on the second $C_HC_L$, the interacting mutant residues of the first $C_H1$ and first $C_L$ thereby forming a first complementary residue set.

Described below are a number of further embodiments (E) of this first embodiment of the invention, where for convenience E1 is identical thereto.

E2. The heterodimeric protein according to E1, wherein the second $C_H1$ differs from the first $C_H1$ by at least one $C_H1$ mutant residue in the second $C_H1$; and the second $C_L$ differs from the first $C_L$ by at least one $C_L$ mutant residue in the second $C_L$; such that the $C_H1$ mutant residue and the $C_L$ mutant residue of the second $C_HC_L$ interact with each other in preference to the corresponding residue positions on the first $C_HC_L$, the interacting mutant residues of the second $C_H1$ and second $C_L$ thereby forming a second complementary residue set.

E3. A heterodimeric protein, comprising
 (i) a first $C_H1$ domain ($C_H1$) and a first $C_L$ domain ($C_L$), the first $C_H1$ and the first $C_L$ interacting together at a first $C_HC_L$ interface to form a first $C_HC_L$ domain ($C_HC_L$),
 (ii) a second $C_H1$ domain ($C_H1$) and a second $C_L$ domain ($C_L$), the second $C_H1$ and the second $C_L$ interacting together at a second $C_HC_L$ interface to form a second $C_HC_L$ domain ($C_HC_L$);
wherein the first $C_H1$ is engineered to differ from the second $C_H1$ by at least one $C_H1$ mutant residue in the first $C_H1$; and the first $C_L$ is engineered to differ from the second $C_L$ by at least one $C_L$ mutant residue in the first $C_L$;
such that the $C_H1$ mutant residue and the $C_L$ mutant residue of the first $C_HC_L$ interact with each other in preference to the corresponding residue positions on the second $C_HC_L$, the interacting mutant residues of the first $C_H1$ and first $C_L$ thereby forming a first complementary residue set.

E4. The heterodimeric protein according to E3, wherein the second $C_H1$ is engineered to differ from the first $C_H1$ by at least one $C_H1$ mutant residue in the second $C_H1$; and the second $C_L$ is engineered to differ from the first $C_L$ by at least one $C_L$ mutant residue in the second $C_L$; such that the $C_H1$ mutant residue and the $C_L$ mutant residue of the second $C_HC_L$ preferentially interact with each other over the corresponding residue positions on the first $C_HC_L$, the interacting mutant residues of the second $C_H1$ and second $C_L$ thereby forming a second complementary residue set.

E5. The heterodimeric protein according to any one of E1-E4, wherein the solvent accessible surface area of the first complementary residue set is less than 225 $Å^2$ as measured using a 2.5 Å probe.

E6. The heterodimeric protein according to any one of E1-E5, wherein the solvent accessible surface area of the first complementary residue set is less than 220 $Å^2$ as measured using a 2.5 Å probe.

E7. The heterodimeric protein according to any one of E1-E6, wherein the solvent accessible surface area of the first complementary residue set is less than 150 $Å^2$ as measured using a 2.5 Å probe.

E8. The heterodimeric protein according to any one of E1-E7, wherein the solvent accessible surface area of the first complementary residue set is less than 100 $Å^2$ as measured using a 2.5 Å probe.

E9. The heterodimeric protein according to any one of E1-E8, wherein the solvent accessible surface area of the first complementary residue set is less than 50 $Å^2$ as measured using a 2.5 Å probe.

E10. The heterodimeric protein according to any one of E1-E9, wherein the solvent accessible surface area of the first complementary residue set is less than 20 $Å^2$ as measured using a 2.5 Å probe.

E11. The heterodimeric protein according to any one of E1-E10, wherein the solvent accessible surface area of the first complementary residue set is less than 10 $Å^2$ as measured using a 2.5 Å probe.

E12. The heterodimeric protein according to any one of E1-E11, wherein the solvent accessible surface area of the first complementary residue set is less than 5 $Å^2$ as measured using a 2.5 Å probe.

E12. The heterodimeric protein according to any one of E1-E12, wherein the solvent accessible surface area of the first complementary residue set is less than 1 $Å^2$ as measured using a 2.5 Å probe.

E13. The heterodimeric protein according to any one of E1-E12, wherein the solvent accessible surface area of the second complementary residue set is less than 225 $Å^2$ as measured using a 2.5 Å probe.

E14. The heterodimeric protein according to any one of E1-E13, wherein the solvent accessible surface area of the second complementary residue set is less than 220 $Å^2$ as measured using a 2.5 Å probe.

E15. The heterodimeric protein according to any one of E1-E14, wherein the solvent accessible surface area of the second complementary residue set is less than 150 $Å^2$ as measured using a 2.5 Å probe.

E16. The heterodimeric protein according to any one of E1-E15, wherein the solvent accessible surface area of the second complementary residue set is less than 100 $Å^2$ as measured using a 2.5 Å probe.

E17. The heterodimeric protein according to any one of E1-E16, wherein the solvent accessible surface area of the second complementary residue set is less than 50 $Å^2$ as measured using a 2.5 Å probe.

E18. The heterodimeric protein according to any one of E1-E17, wherein the solvent accessible surface area of the second complementary residue set is less than 20 $Å^2$ as measured using a 2.5 Å probe.

E19. The heterodimeric protein according to any one of E1-E18, wherein the solvent accessible surface area of the second complementary residue set is less than 10 $Å^2$ as measured using a 2.5 Å probe.

E20. The heterodimeric protein according to any one of E1-E19, wherein the solvent accessible surface area of the second complementary residue set is less than 5 $Å^2$ as measured using a 2.5 Å probe.

E21. The heterodimeric protein according to any one of E1-E20, wherein the solvent accessible surface area of the second complementary residue set is less than 1 $Å^2$ as measured using a 2.5 Å probe.

E21. The heterodimeric protein according to any one of E1-E20, wherein the solvent accessible surface area of the first or the second complementary residue set is about 0 $Å^2$ as measured using a 2.5 Å probe.

E22. The heterodimeric protein according to any one of E1-E21, wherein the mutant residues of the first complementary residue set are different to the mutant residues of the second complementary residue set.

E23. The heterodimeric protein according to any one of E1-E22, wherein formation of the first $C_HC_L$ and second $C_HC_L$ preferentially occurs over formation of a $C_HC_L$ comprised of either the first $C_H1$ and second $C_L$, or second $C_H1$ and first $C_L$.

E24. The heterodimeric protein according to any one of E1-E23, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 4-fold.

E25. The heterodimeric protein according to any one of E1-E24, wherein the first $C_H1$ is attached to a first variable heavy domain ($V_H$), and the first $C_L$ is attached to a first variable light domain ($V_L$), and the second $C_H1$ is attached to a second $V_H$, and the second $C_L$ is attached to a second $V_L$, E26. The heterodimeric protein according to any one of E1-E25, wherein the preferential formation of first $C_HC_L$ and second $C_HC_L$ does not rely on complementary pairing of the variable domains.

E27. The heterodimeric protein according to any one of E1-E26, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 5-fold.

E28. The heterodimeric protein according to any one of E1-E27, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 6-fold.

E29. The heterodimeric protein according to any one of E1-E28, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 8-fold.

E30. The heterodimeric protein according to any one of E1-E29, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 10-fold.

E31. The heterodimeric protein according to any one of E1-E30, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 15-fold.

E32. The heterodimeric protein according to any one of E1-E31, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 20-fold.

E33. The heterodimeric protein according to any one of E1-E32, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 25-fold.

E34. The heterodimeric protein according to any one of E1-E33, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 30-fold.

E35. The heterodimeric protein according to any one of E1-E34, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 40-fold.

E36. The heterodimeric protein according to any one of E1-E35, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 50-fold.

E37. The heterodimeric protein according to any one of E1-E36, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 60-fold.

E38. The heterodimeric protein according to any one of E1-E37, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 80-fold.

E39. The heterodimeric protein according to any one of E1-E38, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 90-fold.

E40. The heterodimeric protein according to any one of E1-E39, wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about 100-fold.

E41. The heterodimeric protein according to any one of E25-E39, wherein the preferential formation of the first $C_HC_L$ and second $C_HC_L$ occurs in the absence of any complementary pairing in the variable domains.

E42. The heterodimeric protein according to any one of E25-E41, wherein the first $V_H$, first $V_L$, first $C_H$ and first $C_L$ combined together form a first Fab, and the second $V_H$, second $V_L$, second $C_H1$, and second $C_L$ combined together form a second Fab.

E43. The heterodimeric protein according to E42, wherein the preferential formation of first Fab and second Fab does not rely on complementary pairing of the variable domains.

E44. The heterodimeric protein according to any one of E42-E43, wherein the preferential formation of first Fab and second Fab occurs in the absence of any complementary pairing in the variable domains.

E44. The heterodimeric protein according to any one of E1-E43, wherein the preferential formation of first $C_HC_L$ and second $C_HC_L$ relies on complementary pairing of the complementary residue sets.

E45. The heterodimeric protein according to any one of E1-E46, wherein at least one of the $C_L$ domains is a kappa domain.

E46. The heterodimeric protein according to any one of E1-E45, wherein both the first $C_L$ and the second $C_L$ is a kappa domain.

E47. The heterodimeric protein according to any one of E1-E46, wherein the complementary residue sets comprise a positively or negatively charged residue in one domain, and either a polar residue, or an oppositely charged residue in the other domain.

E48. The heterodimeric protein according to any one of E1-E47, wherein the locations of the complementary residue sets are selected from the group consisting of: $C_H1$-124 and $C_L$-176; (ii) $C_H1$-188 and $C_L$-178; (iii) $C_H1$-143 and $C_L$-178; (iv) $C_H1$-143 and $C_L$-131; (v) $C_H1$-221 and $C_L$-123; (vi) $C_H1$-145 and $C_L$-131; (vii) $C_H1$-179 and $C_L$-131; (viii) $C_H1$-186 and $C_L$-131; and (ix) $C_H1$-188 and $C_L$-133, according to Kabat numbering.

E49. The heterodimeric protein according to E48, wherein the mutation at the $C_H1$ position is selected from the group consisting of W, H, K, R, S and T, and the mutation at the $C_L$ position is selected from the group consisting of S, M, D and E.

E50. The heterodimeric protein according to E49, wherein the mutation at the $C_H1$ position is selected from the group consisting of E, and D, and the mutation at the $C_L$ position is selected from the group consisting of H, K, and R.

E51. The heterodimeric protein according to any one of E49-E50, wherein the complementary residue sets further comprise one or more mutations selected from the group consisting of: $C_H1$-143D, $C_H1$-145S, $C_H1$-186A, $C_H1$-186E, $C_H1$-188G, $C_H1$-143S, $C_H1$-190S, $C_H1$-190I, $C_L$-133S, $C_L$-135I, $C_L$-176G, $C_L$-176M, and $C_L$-178G, $C_L$-178S.

E52. The heterodimeric protein according to any one of E1-E51, wherein the first and second complementary residue sets are selected from two of the following groups: $C_H1$-124K, $C_L$-176D, $C_H1$-190S, $C_L$-133S; (ii) $C_H1$-124K, $C_L$-176D, $C_L$-133S; (iii) $C_H1$-124E, $C_L$-176K; (iv) $C_H1$-124E, $C_L$-176K, $C_H1$-188G; (v) $C_H1$-188E, $C_L$-178K, $C_H1$-143E; (vi) $C_H1$-188K, $C_L$-178D, $C_H1$-143D; (vii) $C_H1$-143K, $C_L$-178D; (viii) $C_H1$-143D, $C_L$-178R; (ix) $C_H1$-143K, $C_L$-178D; (x) $C_H1$-143D, $C_L$-178K; (xi) $C_H1$-143D, $C_L$-178K, $C_L$-176M; (xii) $C_H1$-143E, $C_L$-131R; (xiii) $C_H1$-143R, $C_L$-131E; (xiv) $C_H1$-143R, $C_L$-131E, $C_H1$-186A; (xv) $C_H1$-221D, $C_L$-123K; (xvi) $C_H1$-221D, $C_L$-123K, $C_H1$-190I, $C_L$-135I; (xvii) $C_H1$-145E, $C_L$-131H; (xviii) $C_H1$-143H, $C_H1$-179D, $C_H1$-186E, $C_L$-131H; (xix) $C_H1$-145E, $C_L$-131H; (xx) $C_H1$-186E, $C_L$-131H, $C_H1$-145S; (xxi) $C_H1$-143S, $C_L$-131D, $C_H1$-188W, $C_L$-133S, 178S; (xxii) $C_H1$-143S, $C_H1$-188W, $C_L$-133M, $C_L$-176G, $C_L$-178G; (xxiii) $C_H1$-143H, $C_H1$-179D, $C_H1$-186E, $C_L$-131H, $C_H1$-190I, $C_L$-135I, (xxiv) $C_H1$-186E, $C_L$-131H, $C_H1$-145S; (xxv) $C_H1$-143S, $C_L$-131D, $C_H1$-188W, $C_L$-133S, $C_L$-176C; (xxvi) $C_H1$-143S, $C_H1$-188W, 133M, $C_L$-178G, $C_L$-176G; (xxvii) $C_H1$-143S, $C_H1$-188W, $C_L$-131D.

E53. The heterodimeric protein according to any one of E1-E52, comprising an engineered disulfide bond between the first $C_H1$ and the first $C_L$, and or the second $C_H1$ and the second $C_L$.

E54. The heterodimeric protein according to E53, wherein the engineered disulfide bond is located at one or more of the following positions (i) $C_H1$-122 and $C_L$-123; (ii) $C_H1$-139 and $C_L$-116; and (iii) $C_H1$-174 and $C_L$-176.

E55. The heterodimeric protein according to any one of E53-E54, wherein a wild type disulfide bond has been removed, by mutating one or both of $C_H1$-C230 and $C_L$-214 to any residue except C, on the first $C_HC_L$ and/or second $C_HC_L$.

E56. The heterodimeric protein according to E55, wherein the first and/or second $C_H1$-C230 and first, and/or second $C_L$-C214 are mutated to S.

E57. The heterodimeric protein according to any one of E1-E56, wherein the first $C_HC_L$ comprises residues from one of the following groups: (i) $C_H1$-124K, $C_L$-176D, $C_H1$-190S, $C_L$-133S; (ii) $C_H1$-124K, $C_L$-176D, $C_L$-133S; (iii) $C_H1$-124K, $C_L$-176K, $C_L$-133S; (iv) $C_H1$-124E, $C_L$-176K, $C_H1$-188G, $C_L$-133S; (v) $C_H1$-188E, $C_L$-178K, $C_H1$-143E; (v) $C_H1$-188K, $C_L$-178D, $C_H1$-143D; (vi) $C_H1$-143K, $C_L$-178D; (vii) $C_H1$-143D, $C_L$-178R; (viii) $C_H1$-143K, $C_L$-178D; (ix) $C_H1$-143D, $C_L$-178K; (x) $C_H1$-143D, $C_L$-178K, $C_L$-176M; (xi) $C_H1$-143E, $C_L$-131R; (xii) $C_H1$-143R, $C_L$-131E; (xiii) $C_H1$-143R, $C_L$-131E, $C_H1$-186A; (xiv) $C_H1$-221D, $C_L$-123K; (xv) $C_H1$-221D, $C_L$-123K, $C_H1$-190I, $C_L$-135I, $C_H1$-174C, $C_H1$-230S, $C_L$-176C, $C_L$-214S; (xvi) $C_H1$-145E, $C_L$-131H; (xvii) $C_H1$-143H, $C_H1$-179D, $C_H1$-186E, $C_L$-131H; (xviii) $C_H1$-122C, $C_H1$-145E, $C_H1$-230S, $C_L$-123C, $C_L$-131H, $C_L$-214S; (xix) $C_H1$-186E, $C_L$-131H, $C_H1$-145S; (xx) $C_H1$-143S, $C_L$-131D, $C_H1$-188W, $C_L$-133S, $C_L$-178S; (xxi) $C_H1$-143S, $C_H1$-188W, $C_L$-133M, $C_L$-176G, $C_L$-178G; (xxii) $C_H1$-143H, $C_H1$-179D, $C_H1$-186E, $C_L$-131H, $C_H1$-190I, $C_L$-135I, $C_H1$-174C, $C_H1$-230S, $C_L$-176C, $C_L$-214S; (xxiii) $C_H1$-186E, $C_L$-131H, $C_H1$-145S, $C_H1$-139C, $C_H1$-230S, $C_L$-116C, $C_L$-214S; (xxiv) $C_H1$-143S, $C_L$-131D, $C_H1$-188W, $C_L$-133S, $C_L$-178S, $C_H1$-174C, $C_H1$-230S, $C_L$-176C, $C_L$-214S; (xxv) $C_H1$-143S, $C_H1$-188W, $C_H1$-122C, $C_H1$-230S, $C_L$-133M, $C_L$-178G, $C_L$-176G, $C_L$-123C, $C_L$-214S; (xxvi) $C_H1$-143S, $C_H1$-188W, $C_H1$-122C, $C_H1$-139C, $C_H1$-174C, $C_H1$-230S, $C_L$-133S, $C_L$-178S, $C_L$-131D, $C_L$-116C, $C_L$-123C, $C_L$-176C, $C_L$-214S.

E58. The heterodimeric protein according to E57, wherein the second $C_HC_L$ comprises residues from one of groups i-xxvii, provided the first and second $C_HC_L$ do not both comprises residues from the same group.

E59. The heterodimeric protein according to any one of E1-E58, wherein the first $C_H1$ is connected to a first $C_H2$ domain ($C_H2$), which is connected to a first $C_H3$ domain ($C_H3$), and the second $C_H1$ is connected to second $C_H2$, which is connected to a second $C_H3$.

E60. The heterodimeric protein according to E59, wherein the first $C_H3$ and second $C_H3$ comprises a first $C_H3$ mutant residue and second $C_H3$ mutant residue respectively, the first $C_H3$ mutant residue and second $C_H3$ mutant residues being engineered to differ from each other, and preferentially interact with each other and thereby form $C_H3$ heterodimers over the formation of $C_H3$ homodimers.

E61. The heterodimeric protein according to any one of E1-E60, wherein the first $C_H1$ is attached to a first variable heavy domain ($V_H$), and the first $C_L$ is attached to a first variable light domain ($V_L$), and the second $C_H1$ is attached to a second $V_H$, and the second $C_L$ is attached to a second $V_L$, and wherein the first $V_H$ comprises $V_H$-Q39 and $V_H$-Q105.

E62. The heterodimeric protein according to any one of E1-E61, wherein the first $C_H1$ is attached to a first variable heavy domain ($V_H$), and the first $C_L$ is attached to a first variable light domain ($V_L$), and the second $C_H1$ is attached to a second $V_H$, and the second $C_L$ is attached to a second $V_L$, and wherein the second $V_H$ comprises $V_H$-Q39 and $V_H$-Q105.

E63. The heterodimeric protein according to any one of E1-E62, wherein the first $C_H1$ is attached to a first variable heavy domain ($V_H$), and the first $C_L$ is attached to a first variable light domain ($V_L$), and the second $C_H1$ is attached to a second $V_H$, and the second $C_L$ is attached to a second $V_L$, and wherein the first $V_L$ comprises: (i) $V_L$-Q38; and (ii) one of $V_L$-Q1; $V_L$-S1, $V_L$-D1, $V_L$-E1, $V_L$-A1, or $V_L$-N1; and (iii) one of $V_L$-T42, $V_L$-Q42, or $V_L$-K42.

E64. The heterodimeric protein according to any one of E1-E63, wherein the first $C_H1$ is attached to a first variable heavy domain ($V_H$), and the first $C_L$ is attached to a first variable light domain ($V_L$), and the second $C_H1$ is attached to a second $V_H$, and the second $C_L$ is attached to a second $V_L$, and wherein the second $V_L$ comprises: (i) $V_L$-Q38; and (ii) one of $V_L$-Q1; $V_L$-S1, $V_L$-D1, $V_L$-E1, $V_L$-A1, or $V_L$-N1; and (iii) one of $V_L$-T42, $V_L$-Q42, or $V_L$-K42.

E65. The heterodimeric protein according to any one of E1-E64, wherein the first $C_HC_L$ comprises $C_H1$-124K, $C_L$-176D, $C_H1$-190S, and $C_L$-133S.

E66. The heterodimeric protein according to any one of E1-E65, wherein the second $C_HC_L$ comprises $C_H1$-124E, $C_L$-176K, $C_H1$-188G, and $C_L$-133S.

E67. The heterodimeric protein according to any one of E1-E66, wherein the first $C_HC_L$ comprises $C_H1$-124K, $C_L$-176D, $C_H1$-190S, and $C_L$-133S, and the second $C_HC_L$ comprises $C_H1$-124E, $C_L$-176K, $C_H1$-188G, and $C_L$-133S.

E68. A bispecific antibody comprising a heterodimeric protein as in any one of E1-E67.

E69. The bispecific antibody as set forth in E66, wherein the first $C_HC_L$ comprises $C_H1$-124K, $C_L$-176D, $C_H1$-190S, and $C_L$-133S.

E70. The bispecific antibody as set forth in any one of E68-E69, wherein the second $C_HC_L$ comprises $C_H1$-124E, $C_L$-176K, $C_H1$-188G, and $C_L$-133S.

E71. The bispecific antibody as set forth in any one of E68-E70, wherein the first $C_HC_L$ comprises $C_H1$-124K, $C_L$-176D, $C_H1$-190S, and $C_L$-133S, and the second $C_HC_L$ comprises $C_H1$-124E, $C_L$-176K, $C_H1$-188G, and $C_L$-133S.

E72. A nucleic acid encoding the heterodimeric protein according to any one of E1-E65, or a bispecific antibody according to any one of E68-E71.

E73. A vector comprising the nucleic acid according to E72.

E74. A cell comprising the nucleic acid according to E72, or comprising the vector according to E71.

E75. A method of making the heterodimeric protein, according to any one of E1-E67, comprising: (i) cotransfecting a cell line with one or more vectors to express the first $C_H1$, the first $C_L$ of the first $C_HC_L$; and the second $C_H1$, and the second $C_L$ of the second $C_HC_L$; (ii) culturing the cell line under conditions to express the one or more vectors and that allow the first $C_HC_L$ and second $C_HC_L$ to assemble; and (iii) purifying the heterodimeric protein from the cell culture.

E76. The method of E75, wherein the cell line is cotransfected with vectors that express the first $C_H1$, first $C_L$, second $C_H1$, and second $C_L$ in a 1:1:1:1 ratio.

BRIEF DESCRIPTION OF THE DRAWINGS

FIG. 7 depicts mass spectrometric analysis of bispecific antibody Ab1/Ab2 Fc domain (panel A) and of a control Ab1/Ab2 containing HC heterodimerizing mutations but no Fab arm $C_H/C_L$ interface mutations. Expected molecular weight of Fc (consisting of heavy chain from Ab 1 & 2) were detected in both cases whilst no heavy chain homodimers were detected.

FIG. 9 depicts a graph showing a mass spectrometric analysis of Fab components from ion exchange fractionated heterodimeric bispecific antibody Ab1/Ab2 (derived in FIG. 8B). Panel 9A shows that peak 2B from FIG. 8B contains enriched bispecific Ab1/Ab2 with correctly paired light chains in each Fab arm, but with a post translational modification in the Ab2 Fab arm. Panel 9B shows Peak 2A from FIG. 8B to has enriched incorrect light chain pairing (antibody 1 heavy chain combined antibody 2 light chain), Panel 9C shows peak 1 from FIG. 8B. This peak represents only correctly paired bispecific Ab1/Ab2 Fab arms with no post-translational modifications. Key: * potential incomplete leader sequence processing; ^ Ab2 Fab with a post-translational modification.

FIG. 11 depicts a graph showing mass spectrometric analysis of dual arm Fab fragment of constructs C5XAb3-M2 (panel 11B) and C5XAb3-M2-NEGATIVE (panel 11A). Significant reduction of incorrectly paired light chain between C5 & Ab3 was observed in construct C5XAb3-M2 compared to C5XAb3-M2-NEGATIVE. Key: * potential incomplete leader sequence processing.

FIG. 17 depicts graphs showing mass spectrometric analysis of dual arm Fab fragments designed to show the impact of subsets of the S1 and S1_rev mutations. Panels A and B show original monospecific antibodies with no $C_H1/C_L$ mutations. A bispecific combining the two parent antibodies has significant mispairing in the absence of the S1 and S1_rev mutations (Panel C) but nearly eliminated mispairing when S1 and S1_rev are used (Panel D). Using various subsets of the S1 and S1_rev mutations results in antibodies (Panels E and F) with reduced mispairing relative to Panel C, but still lower fidelity than the full S1 and S1_rev design used in Panel D. The peaks corresponding to mispaired Fabs are labled as "Ab3H C5L" and "C5H Ab3L" while the correct pairings are labeled as "C5 Fab" and "Ab3 Fab".

This figure further illustrates the two semi-functional and one non-functional permutations that are avoided by the present invention. That is, the present inventions reduce the probability that that a first $C_H1$ ($1\text{-}C_H1$) and a second $C_H$ ($2\text{-}C_L$) will associate to form a third $C_HC_L$ (FIG. 1B, left arm) compared with the favored pairings shown herein and in FIG. 1A. Similarly, the present invention reduces the likelihood of formation of a fourth $C_HC_L$ (comprising a second $2\text{-}C_H1$ and a $1\text{-}C_L$) as illustrated in FIG. 1C (right arm). Likewise, the present invention reduces the formation of a non-functional antibody (e.g., FIG. 1B) comprising a third $C_HC_L$ in one arm and a fourth $C_HC_L$ in the other arm.

Figure 23:
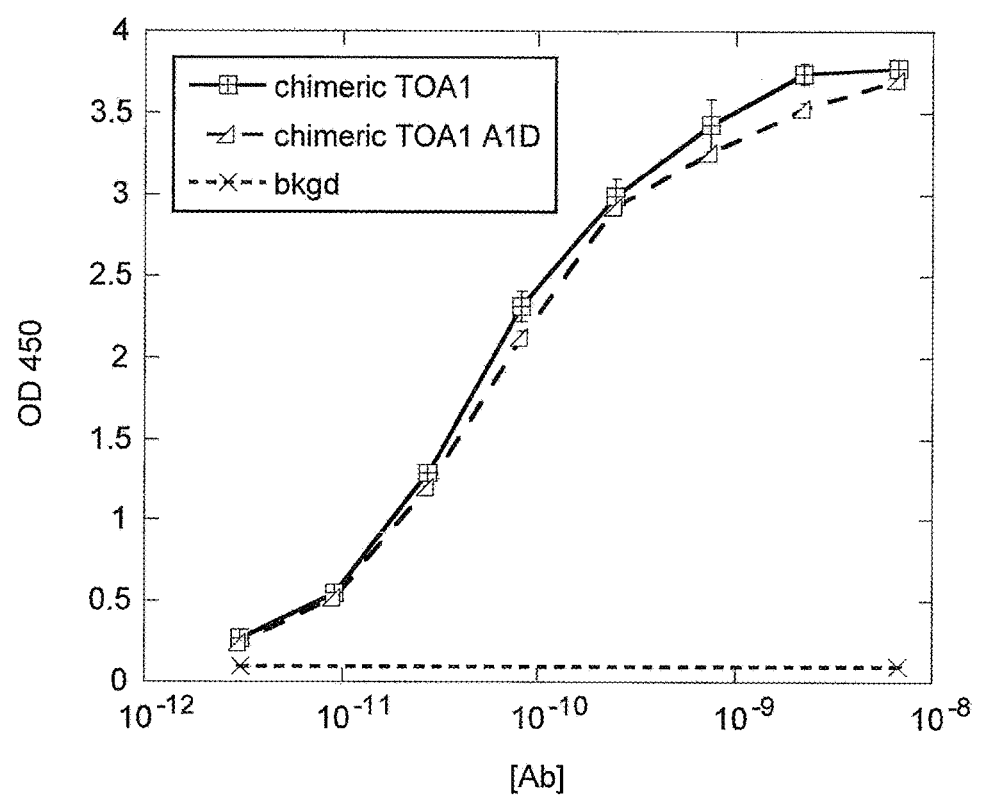

FIG. 23: Chimeric TOA-1 antibody binds human TrkB

Figure 24:
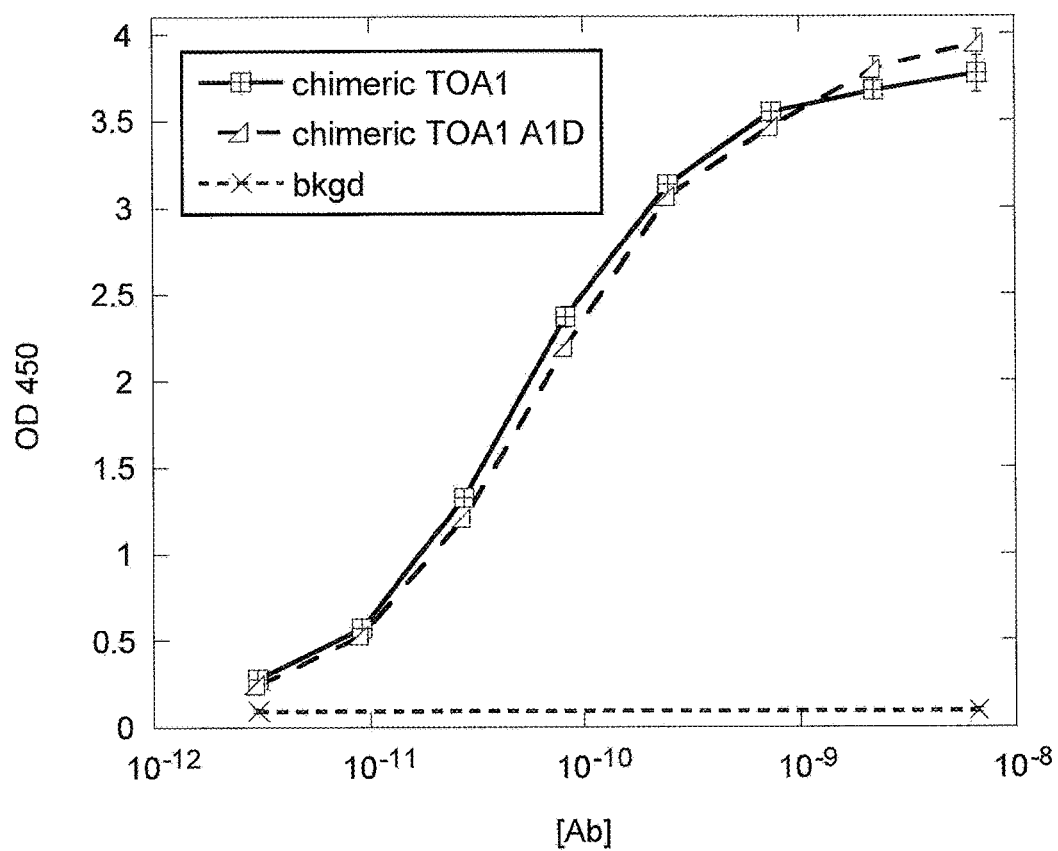

FIG. 24: Chimeric TOA-1 antibody binds mouse TrkB

Figure 25:
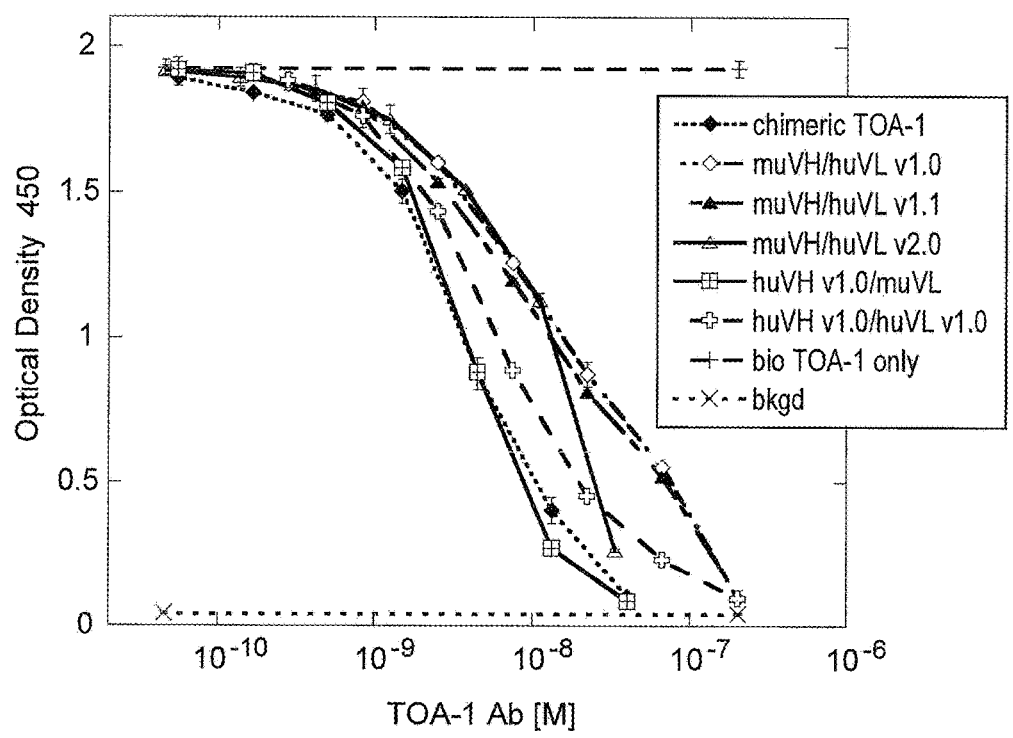

FIG. 25: Humanized TOA-1 variants compete with biotinylated chimeric TOA-1 for binding to human TrkB FIG. 26: Humanized TOA-1 variants compete with biotinylated chimeric TOA-1 for binding to human TrkB FIG. 27: Humanized TOA-1 variants compete with biotinylated chimeric TOA-1 for binding to human TrkB FIG. 28: Humanized TOA-1 version 1.0/1.4 fully retains human TrkB binding properties relative to parental TOA-1 antibody FIG. 29: Agonist activity of Anti-TrkB TOA-1 antibodies FIG. 30: Humanized TOA-1 activates the TrkB signalling cascade FIG. 31: The TOA-1 and BDNF binding sites on hTrkB overlap FIG. 32: TOA-1 binding to chimeric TrkB-TrkA receptors FIG. 33: Anti-TrkB antibodies bind to mouse, cat and dog TrkB FIG. 34: TOA-1 antibodies do not bind to TrkA or TrkC FIG. 35: Humanized TOA-1 does not bind to p75

Figure 36:
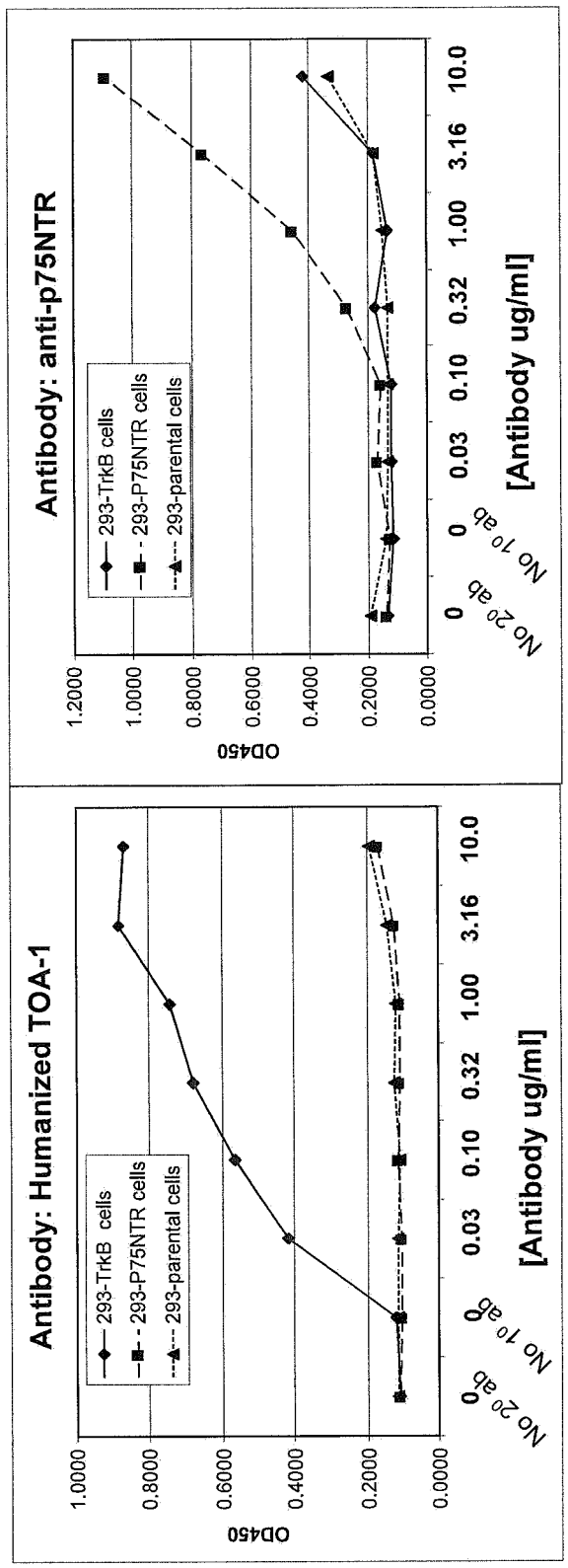

FIG. 36: Humanized TOA-1 does not bind to p75

Figure 37:
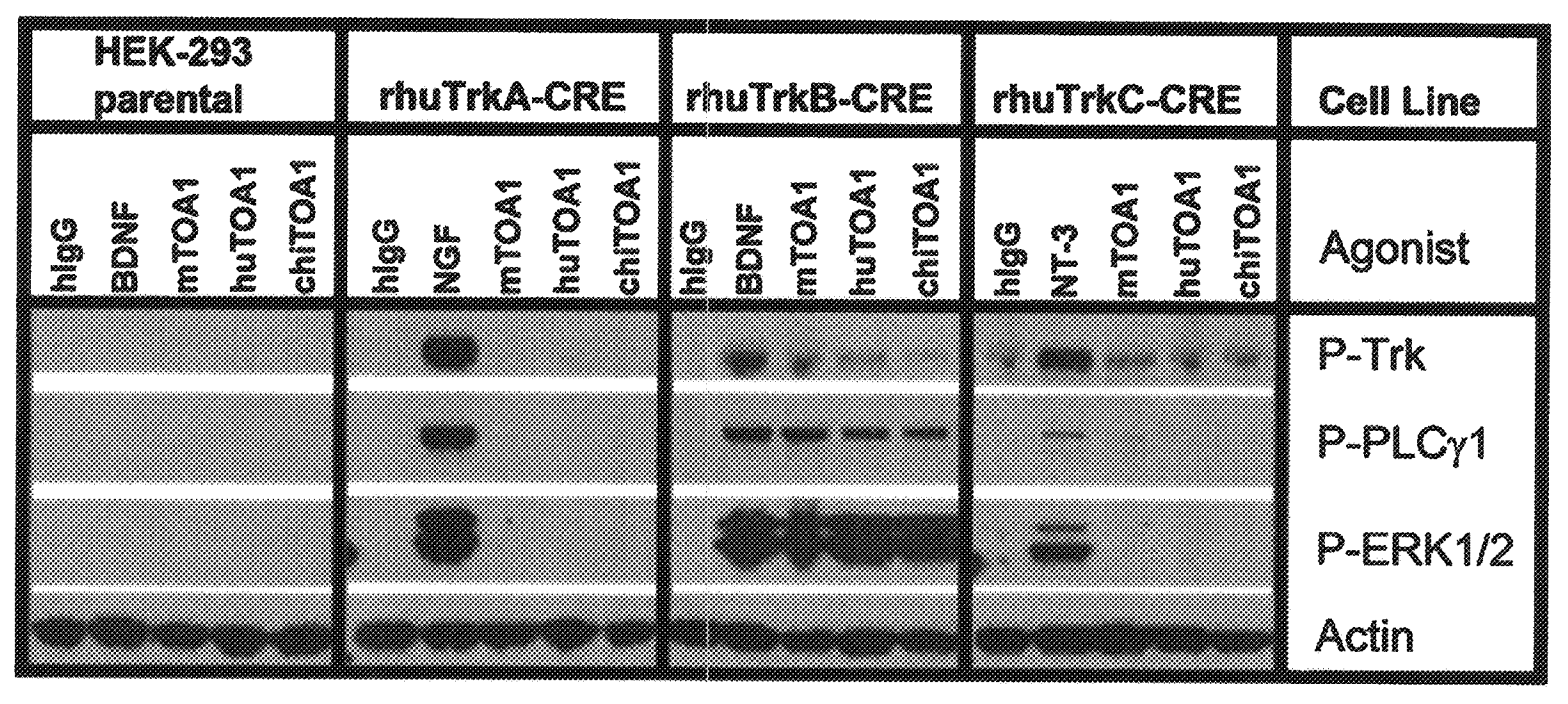

FIG. 37: TOA-1 does not activate the TrkA or TrkC signaling cascades

Figure 38:
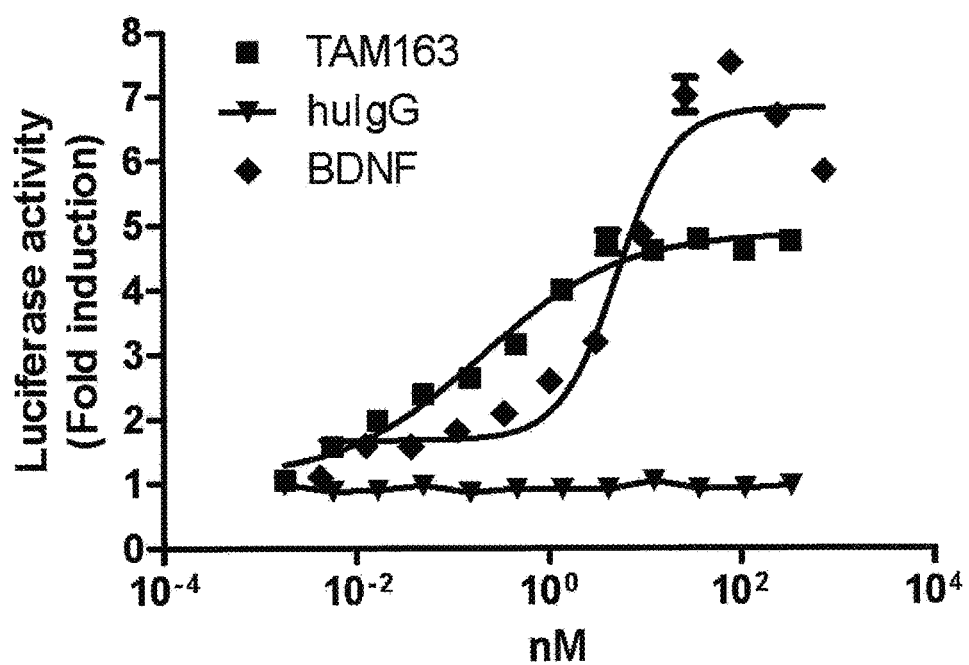

FIG. 38. TAM-163 activates the Cre-luciferase reporter gene in hTrkB cells

Figure 39:
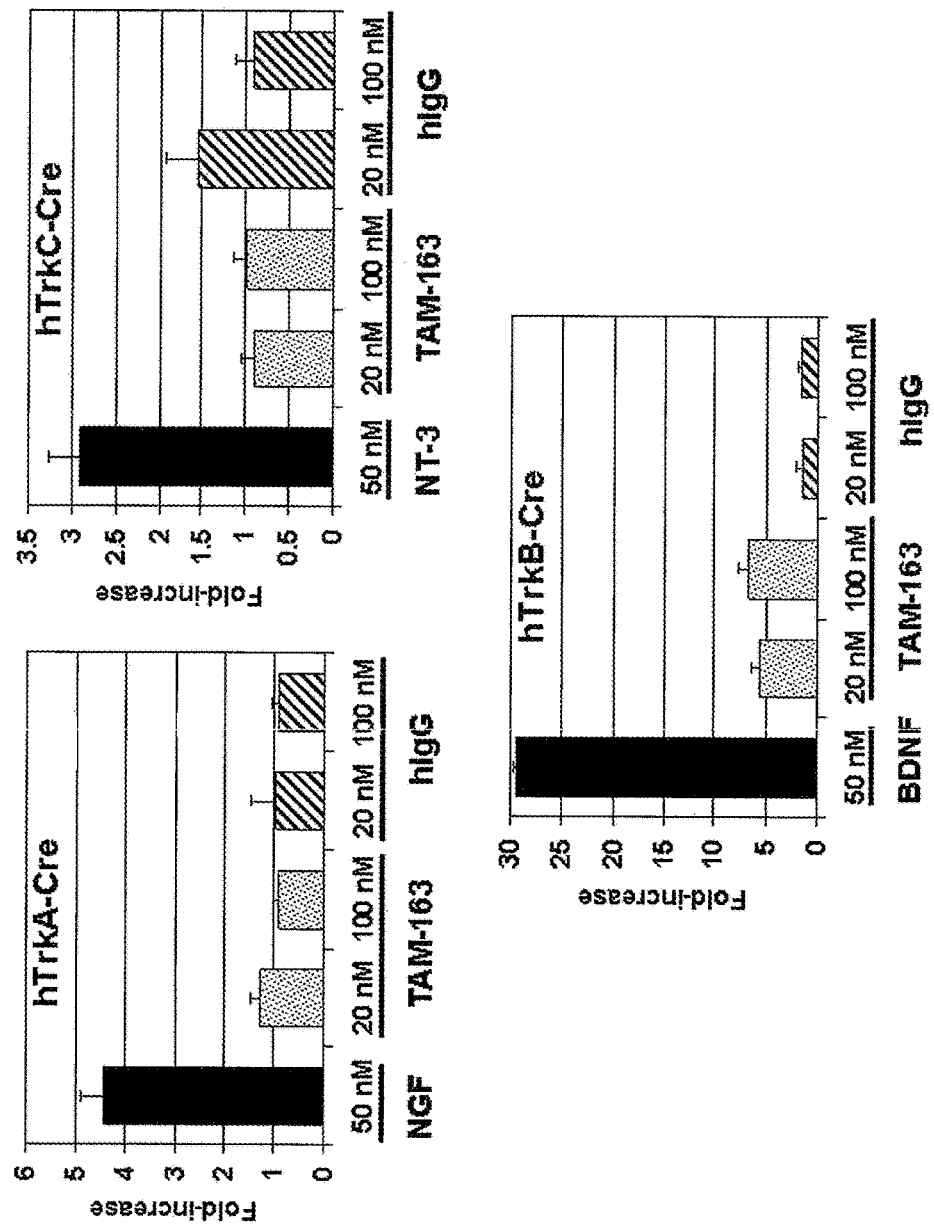
Figure 49:
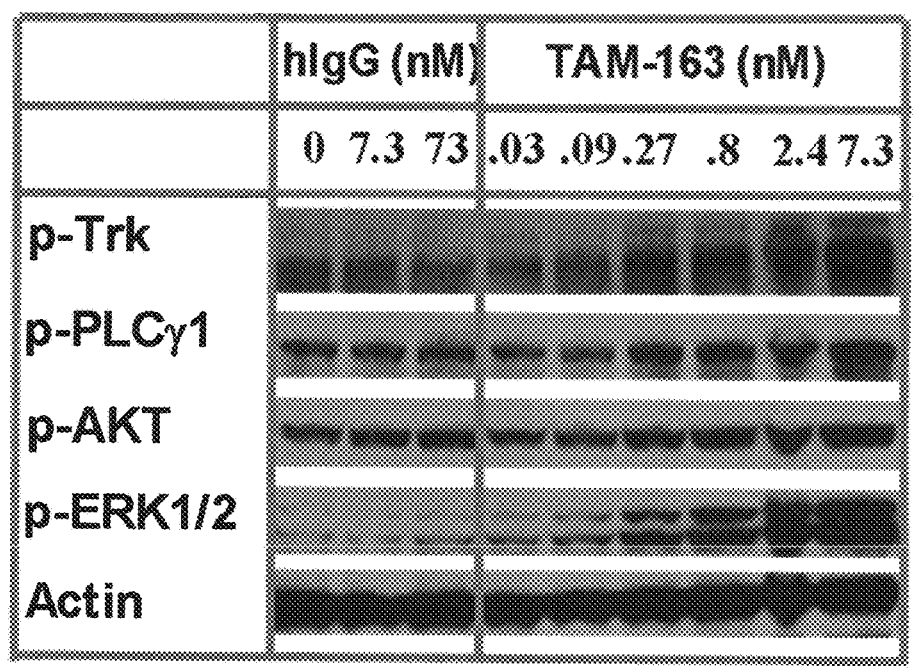
Figure 50:
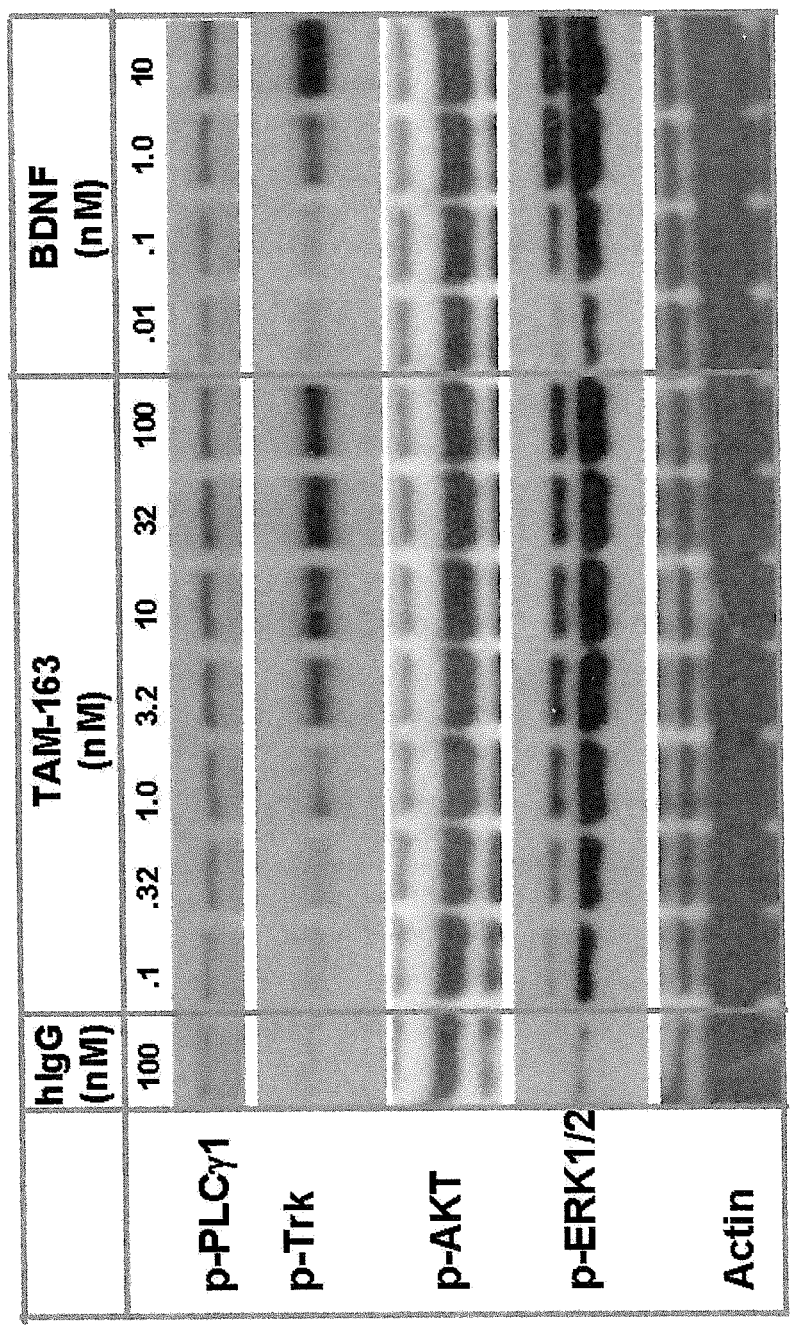

FIG. 39. TAM-163 does not activate the Cre-luciferase reporter gene in hTrkA-Cre and hTrkC-Cre cells FIG. 40. TAM-163 activates hTrkB, but not hTrkA or hTrkC in the SHC1 recruitment assay FIG. 41. FIG. 1. TAM-163 activates TrkB-dependent phosphorylation events in hTrkB-Cre cells FIG. 42 TAM-163 does not activate Trk-dependent phosphorylation events in hTrkA-Cre or hTrkC-Cre cells FIG. 43. TAM-163 activates Trk-dependent phosphorylation events in human neuroblastoma SH-SY5Y cells FIG. 44. TAM-163 induces internalization of TrkB in hTrkB-Cre and in human neuroblastoma SH-SY5Y cells FIG. 45. TAM-163 induces degradation of TrkB in hTrkB-Cre and in human neuroblastoma SH-SY5Y cells FIG. 46. TAM-163 does not bind to human p75NTR—FACS analysis FIG. 47. TAM-163 does not bind human p75NTR—cell-based ELISA FIG. 48. TAM-163 binds to mouse, dog and cat TrkB with high affinity FIG. 49. TAM-163 activates TrkB-dependent signaling in cells transfected with mouse TrkB FIG. 50. TAM-163 activates TrkB-dependent signaling in cells transfected with dog TrkB

DETAILED DESCRIPTION

In some aspects, the invention relates to a heterodimeric protein comprising (i) a first $C_H1$ domain ($C_H1$) and a first $C_L$ domain ($C_L$), the first $C_H1$ and the first $C_L$ interacting together at a first $C_HC_L$ interface to form a first $C_HC_L$ domain ($C_HC_L$); (ii) a second $C_H1$ domain ($C_H1$) and a second $C_L$ domain ($C_L$), the second $C_H1$ and the second $C_L$ interacting together at a second $C_HC_L$ interface to form a second $C_HC_L$; wherein the first $C_H1$ is engineered to differ from the second $C_H1$ by at least one $C_H1$ mutant residue in the first $C_H1$; and the first $C_L$ is engineered to differ from the second $C_L$ by at least one $C_L$ mutant residue in the first $C_L$; such that the $C_H1$ mutant residue and the $C_L$ mutant residue of the first $C_HC_L$ interact with each other in preference to the corresponding residue positions on the second $C_HC_L$, the interacting mutant residues of the first $C_H1$ and first $C_L$ thereby forming a first complementary residue set.

In some aspects, the second $C_H1$ is engineered to differ from the first $C_H1$ by at least one $C_H1$ mutant residue in the second $C_H1$; and the second $C_L$ is engineered to differ from the first $C_L$ by at least one $C_L$ mutant residue in the second $C_L$; such that the $C_H1$ mutant residue and the $C_L$ mutant residue of the second $C_HC_L$ preferentially interact with each other over the corresponding residue positions on the first $C_HC_L$, the interacting mutant residues of the second $C_H1$ and second $C_L$ thereby forming a second complementary residue set.

The first $C_H1$ may be engineered to differ from wild type $C_H1$. The second $C_H1$ may be engineered to differ from wild type $C_H1$. The first $C_L$ may be engineered to differ from wild type $C_L$. The second $C_L$ may be engineered to differ from wild type $C_L$.

The first $C_H1$ may comprise at least one $C_H1$ mutant residue engineered to differ from the corresponding position on the second $C_H1$. The first $C_L$ may comprise at least one $C_L$ mutant residue engineered to differ from the corresponding position on the second $C_L$. The second $C_H1$ may comprise at least one $C_H1$ mutant residue engineered to differ from the corresponding position on the first $C_H1$. The second $C_L$ may comprise at least one $C_L$ mutant residue engineered to differ from the corresponding position on the first $C_L$.

In some aspects of the invention, the identity of the mutant residues of the first complementary residue set are different from the identity of the mutant residues of the second complementary residue set. In some aspects, the location of the mutant residues of the first complementary residue set are different from the location of the mutant residues of the second complementary residue set (locations according to Kabat numbering as described herein). In some aspects of the invention, the identity and location of the mutant residues of the first complementary residue set are different to the identity and location of the mutant residues of the second complementary residue set.

Preferential Formation of Heterodimers

Providing a second complementary residue set in the second $C_HC_L$ further decreases the risk of mis-pairing of the domains. This strategy may be more effective when there is little overlap between the engineered mutations of the different domains. In some aspects, the first complementary residue set of the first $C_HC_L$ are located at different positions relative to the location of the second complementary residue set of the second $C_HC_L$.

Accordingly, in some aspects of the invention, formation of the first $C_HC_L$ and second $C_HC_L$ preferentially occurs over formation of a $C_HC_L$ comprised of either the first $C_H1$ and second $C_L$ (hereinafter referred to as a third $C_HC_L$), or second $C_H1$ and first $C_L$ (hereinafter referred to as a fourth $C_HC_L$).

Figure 1A:
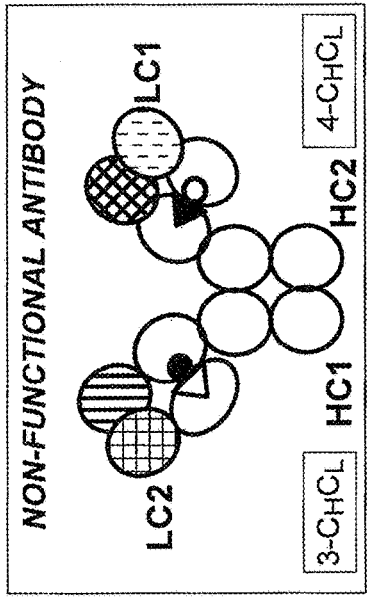
FIG. 1 depicts potential products that may result from attempting to generate bispecific antibody via coexpression of 2 different antibody light chains and 2 different antibody heavy chains, where the $C_H3$ interface is engineered using established technology to favor heterodimer formation, but the heavy/light chain interface is devoid of the mutations of the present invention. LC1 paired with HC1 provides a Fab arm binding one epitope, and LC2 paired with HC2 provides a Fab arm binding a distinct epitope, possibly on a different antigen. LC1 paired with HC2, or LC2 paired with HC1, results in a Fab with reduced or no binding to those epitopes. A: correct pairing of a representative bispecific antibody, showing on the left arm, a combination of first $V_H$ and first $V_L$ (represented by heavy vertical stripes and light vertical dashes respectively) through preferential formation of first $C_HC_L$ (facilitated by the interaction of a first complementary residue set, depicted by filled and unfilled circles), and on the right arm, a combination of second $V_H$ and second $V_L$ (represented by heavy diagonal hatching and light check pattern respectively) through preferential formation of the second $C_HC_L$ (facilitated by the interaction of a second complementary residue set, depicted by filled and unfilled triangles). B: incorrect pairing of a bispecific antibody, showing on the left arm, a combination of first $V_H$ and second $V_L$ (represented by heavy vertical stripes and light check pattern respectively) through formation of a third $C_HC_L$, and on the right arm, a combination of second $V_H$ and first $V_L$ (represented by heavy diagonal hatching and light vertical dashes respectively) through formation of a fourth $C_HC_L$. C and D each show semi-functional bispecific antibodies, where either the left or right arm has paired correctly, and the other arm has paired incorrectly.
Figure 1B:
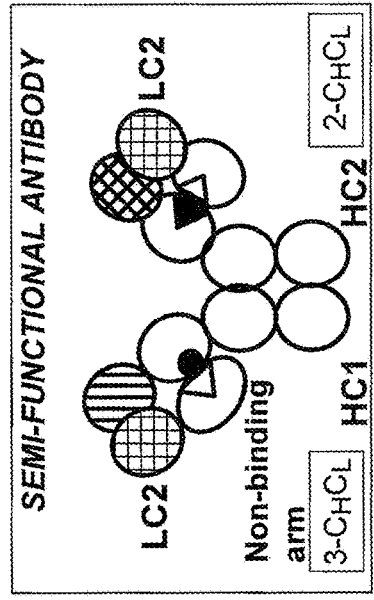
Figure 1C:
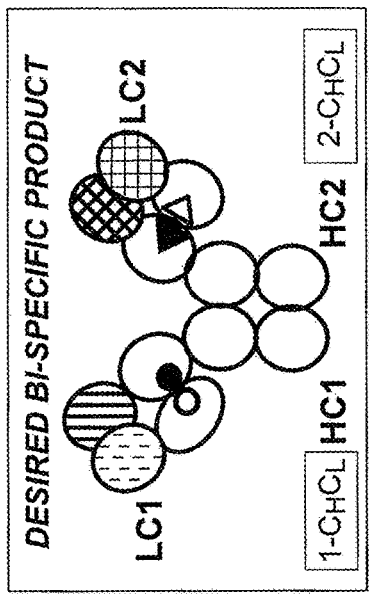
Figure 1D:
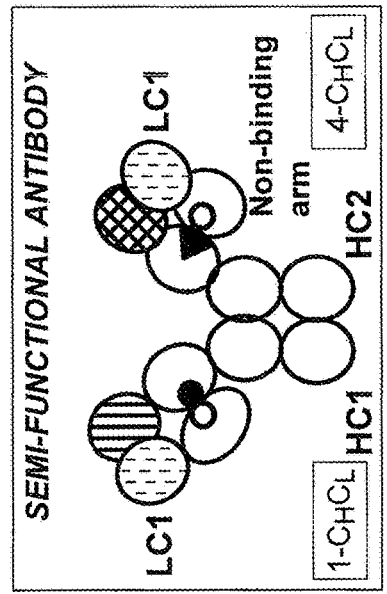
Figure 22:
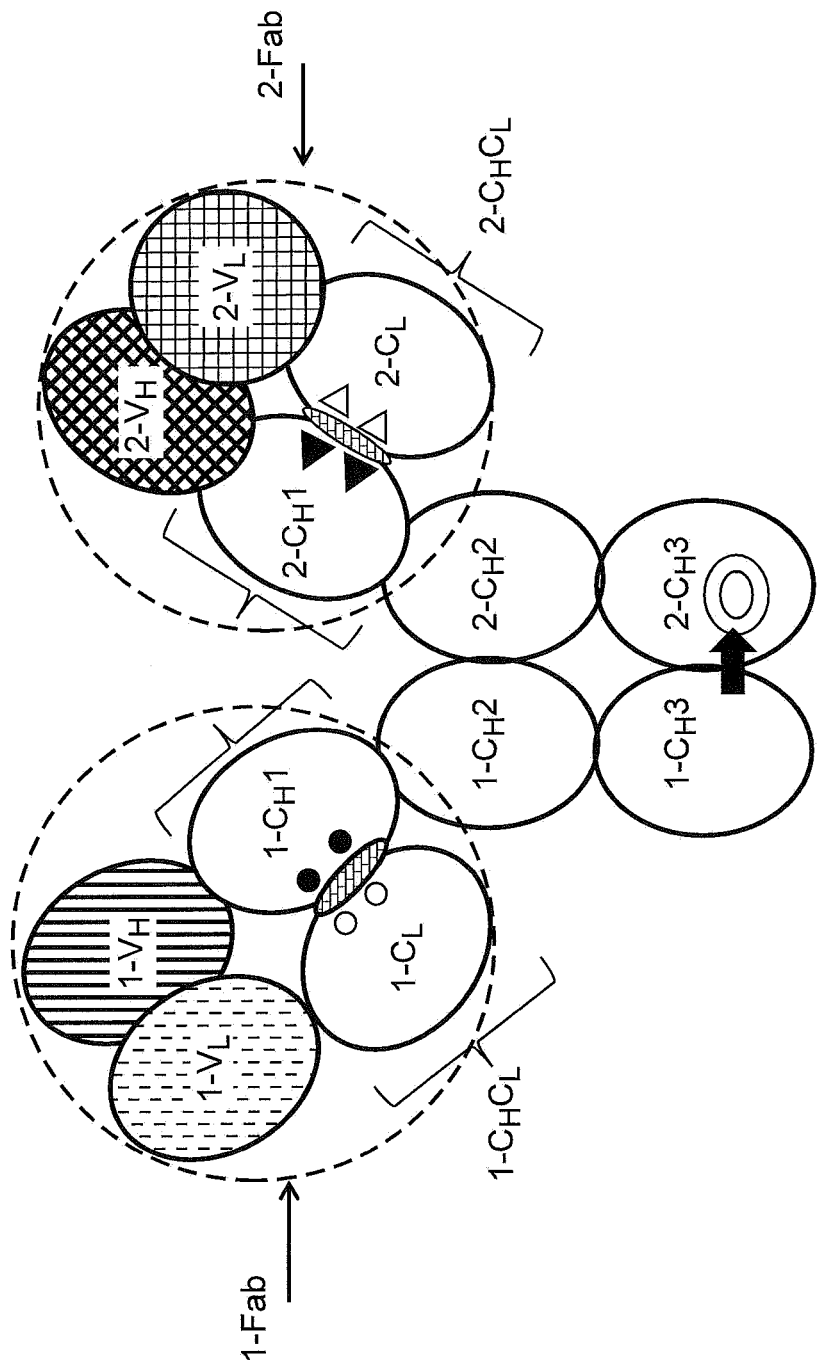
FIG. 22 depicts a bispecific antibody according to the invention. The domains are labelled as follows: $1\text{-}V_L$ first variable light domain; $1\text{-}V_H$: first variable light domain. $1\text{-}C_L$: first constant light domain. $1\text{-}C_H1$: first constant heavy 1 domain. $1\text{-}C_H2$: first constant heavy 2 domain. $1\text{-}C_H3$: first constant heavy 3 domain. $2\text{-}V_L$ second variable light domain; $2\text{-}V_H$: second variable light domain. $2\text{-}C_L$: second constant light domain. $2\text{-}C_H1$: second constant heavy 1 domain. $2\text{-}C_H2$: second constant heavy 2 domain. $2\text{-}C_H3$: second constant heavy 3 domain. The first $C_HC_L$ and second $C_HC_L$ domains are indicated between the braces ($1\text{-}C_HC_L$, and $2\text{-}C_HC_L$ respectively) and encompass the respective $C_L$ and $C_H$ domains. The dotted oval lines capture the four domains ($V_L$, $V_H$, $C_L$, $C_H1$) that make up the first and second Fab (1-Fab and 2-Fab respectively). The first $C_HC_L$ interface and second $C_HC_L$ interface are patterned in brickwork. Mutant residues in the $C_L$ and $C_H1$ domains are represented by filled and unfilled circles and triangles (the set of filled and unfilled circles represent the complementary residue set of the first Fab and the set of filled and unfilled triangles represent the complementary residue set of the second Fab). The 'knobs and holes' pairing of the first $C_H3$ and second $C_H3$ domains is represented by an arrow and ring.

FIG. 1A and FIG. 22 illustrate a correctly paired antibody (comprising first $C_HC_L$ and second $C_HC_L$. Improperly paired domains are also depicted: a third $C_HC_L$ (comprising a first $C_H1$ and a second $C_L$) is shown as the left arm of FIGS. 1B, and 1D, and a fourth $C_HC_L$ (comprising a second $C_H1$ and a first $C_L$) is shown as the right arm of FIGS. 1B, and 1C. Similarly, switching the right hand and left hand light chains of FIG. 22 would result in a non-functional antibody comprising third $C_HC_L$ and fourth $C_HC_L$.

Favorably, formation of the first and second $C_HC_L$ preferentially occurs over formation of the third and fourth $C_HC_L$ by at least about 4-fold. In some aspects, formation of the first and second $C_HC_L$ preferentially occurs over formation of the third and fourth $C_HC_L$ by at least about 5-fold. In some aspects, formation of the first and second $C_HC_L$ preferentially occurs over formation of the third and fourth $C_HC_L$ by at least about 6-fold. In some aspects, formation of the first and second $C_HC_L$ preferentially occurs over formation of the third and fourth $C_HC_L$ by at least about 7-fold. In some aspects, formation of the first and second $C_HC_L$ preferentially occurs over formation of the third and fourth $C_HC_L$ by at least about 8-fold. In some aspects, formation of the first and second $C_HC_L$ preferentially occurs over formation of the third and fourth $C_HC_L$ by at least about 9-fold. In some aspects, formation of the first and second $C_HC_L$ preferentially occurs over formation of the third and fourth $C_HC_L$ by at least about 10-fold. In some aspects, formation of the first and second $C_HC_L$ preferentially occurs over formation of the third and fourth $C_HC_L$ by at least about 12-fold. In some aspects, formation of the first and second $C_HC_L$ preferentially occurs over formation of the third and fourth $C_HC_L$ by at least about 15-fold. In some aspects, formation of the first and second $C_HC_L$ preferentially occurs over formation of the third and fourth $C_HC_L$ by at least about 20-fold. In some aspects, formation of the first and second $C_HC_L$ preferentially occurs over formation of the third and fourth $C_HC_L$ by at least about 25-fold. In some aspects, formation of the first and second $C_HC_L$ preferentially occurs over formation of the third and fourth $C_HC_L$ by at least about 30-fold. In some aspects, formation of the first and second $C_HC_L$ preferentially occurs over formation of the third and fourth $C_HC_L$ by at least about 35-fold. In some aspects, formation of the first and second $C_HC_L$ preferentially occurs over formation of the third and fourth $C_HC_L$ by at least about 40-fold. In some aspects, formation of the first and second $C_HC_L$ preferentially occurs over formation of the third and fourth $C_HC_L$ by at least about 50-fold. In some aspects, formation of the first and second $C_HC_L$ preferentially occurs over formation of the third and fourth $C_HC_L$ by at least about 60-fold. In some aspects, formation of the first and second $C_HC_L$ preferentially occurs over formation of the third and fourth $C_HC_L$ by at least about 70-fold. In some aspects, formation of the first and second $C_HC_L$ preferentially occurs over formation of the third and fourth $C_HC_L$ by at least about 75-fold. In some aspects, formation of the first and second $C_HC_L$ preferentially occurs over formation of the third and fourth $C_HC_L$ by at least about 80-fold. In some aspects, formation of the first and second $C_HC_L$ preferentially occurs over formation of the third and fourth $C_HC_L$ by at least about 85-fold. In some aspects, formation of the first and second $C_HC_L$ preferentially occurs over formation of the third and fourth $C_HC_L$ by at least about 90-fold. In some aspects, formation of the first and second $C_HC_L$ preferentially occurs over formation of the third and fourth $C_HC_L$ by at least about 95-fold. In some aspects, formation of the first and second $C_HC_L$ preferentially occurs over formation of the third and fourth $C_HC_L$ by at least about 99-fold. In some aspects, formation of the first and second $C_HC_L$ preferentially occurs over formation of the third and fourth $C_HC_L$ by at least about 100-fold. In some aspects, formation of the first and second $C_HC_L$ preferentially occurs over formation of the third and fourth $C_HC_L$ by at least about 200-fold. In some aspects, formation of the first and second $C_HC_L$ preferentially occurs over formation of the third and fourth $C_HC_L$ by at least about 500-fold. In some aspects, formation of the first and second $C_HC_L$ preferentially occurs over formation of the third and fourth $C_HC_L$ by at least about 1000-fold.

In some aspects, formation of the first and second $C_HC_L$ preferentially occurs over formation of the third and fourth $C_HC_L$ at a ratio of at least about 4 to about 1. In some aspects, formation of the first and second $C_HC_L$ preferentially occurs over formation of the third and fourth $C_HC_L$ at a ratio of at least about 5 to about 1. In some aspects, formation of the first and second $C_HC_L$ preferentially occurs over formation of the third and fourth $C_HC_L$ at a ratio of at least about 6 to about 1. In some aspects, formation of the first and second $C_HC_L$ preferentially occurs over formation of the third and fourth $C_HC_L$ at a ratio of at least about 7 to about 1. In some aspects, formation of the first and second $C_HC_L$ preferentially occurs over formation of the third and fourth $C_HC_L$ at a ratio of at least about 8 to about 1. In some aspects, formation of the first and second $C_HC_L$ preferentially occurs over formation of the third and fourth $C_HC_L$ at a ratio of at least about 9 to about 1. In some aspects, formation of the first and second $C_HC_L$ preferentially occurs over formation of the third and fourth $C_HC_L$ at a ratio of at least about 10 to about 1. In some aspects, formation of the first and second $C_HC_L$ preferentially occurs over formation of the third and fourth $C_HC_L$ at a ratio of at least about 12 to about 1. In some aspects, formation of the first and second $C_HC_L$ preferentially occurs over formation of the third and fourth $C_HC_L$ at a ratio of at least about 15 to about 1. In some aspects, formation of the first and second $C_HC_L$ preferentially occurs over formation of the third and fourth $C_HC_L$ at a ratio of at least about 20 to about 1. In some aspects, formation of the first and second $C_HC_L$ preferentially occurs over formation of the third and fourth $C_HC_L$ at a ratio of at least about 25 to about 1. In some aspects, formation of the first and second $C_HC_L$ preferentially occurs over formation of the third and fourth $C_H C_L$ at a ratio of at least about 30 to about 1. In some aspects, formation of the first and second $C_H C_L$ preferentially occurs over formation of the third and fourth $C_H C_L$ at a ratio of at least about 35 to about 1. In some aspects, formation of the first and second $C_H C_L$ preferentially occurs over formation of the third and fourth $C_H C_L$ at a ratio of at least about 40 to about 1. In some aspects, formation of the first and second $C_H C_L$ preferentially occurs over formation of the third and fourth $C_H C_L$ at a ratio of at least about 45 to about 1. In some aspects, formation of the first and second $C_H C_L$ preferentially occurs over formation of the third and fourth $C_H C_L$ at a ratio of at least about 50 to about 1. In some aspects, formation of the first and second $C_H C_L$ preferentially occurs over formation of the third and fourth $C_H C_L$ at a ratio of at least about 55 to about 1. In some aspects, formation of the first and second $C_H C_L$ preferentially occurs over formation of the third and fourth $C_H C_L$ at a ratio of at least about 60 to about 1. In some aspects, formation of the first and second $C_H C_L$ preferentially occurs over formation of the third and fourth $C_H C_L$ at a ratio of at least about 65 to about 1. In some aspects, formation of the first and second $C_H C_L$ preferentially occurs over formation of the third and fourth $C_H C_L$ at a ratio of at least about 70 to about 1. In some aspects, formation of the first and second $C_H C_L$ preferentially occurs over formation of the third and fourth $C_H C_L$ at a ratio of at least about 75 to about 1. In some aspects, formation of the first and second $C_H C_L$ preferentially occurs over formation of the third and fourth $C_H C_L$ at a ratio of at least about 80 to about 1. In some aspects, formation of the first and second $C_H C_L$ preferentially occurs over formation of the third and fourth $C_H C_L$ at a ratio of at least about 85 to about 1. In some aspects, formation of the first and second $C_H C_L$ preferentially occurs over formation of the third and fourth $C_H C_L$ at a ratio of at least about 90 to about 1. In some aspects, formation of the first and second $C_H C_L$ preferentially occurs over formation of the third and fourth $C_H C_L$ at a ratio of at least about 95 to about 1. In some aspects, formation of the first and second $C_H C_L$ preferentially occurs over formation of the third and fourth $C_H C_L$ at a ratio of at least about 99 to about 1. In some aspects, formation of the first and second $C_H C_L$ preferentially occurs over formation of the third and fourth $C_H C_L$ at a ratio of at least about 100 to about 1. In some aspects, formation of the first and second $C_H C_L$ preferentially occurs over formation of the third and fourth $C_H C_L$ at a ratio of at least about 200 to about 1. In some aspects, formation of the first and second $C_H C_L$ preferentially occurs over formation of the third and fourth $C_H C_L$ at a ratio of at least about 500 to about 1. In some aspects, formation of the first and second $C_H C_L$ preferentially occurs over formation of the third and fourth $C_H C_L$ at a ratio of at least about 1000 to about 1. In some aspects, formation of the first and second $C_H C_L$ preferentially occurs over formation of the third and fourth $C_H C_L$ at a ratio of at least about 2000 to about 1. In some aspects, formation of the first and second $C_H C_L$ preferentially occurs over formation of the third and fourth $C_H C_L$ at a ratio of at least about 5000 to about 1.

The level of 'correct' heterodimer light chain pairing (i.e. first and second $C_H C_L$ formed) relative to 'incorrect' light chain pairing (i.e. third and fourth $C_H C_L$ formed) may be measured by Liquid Chromatography Mass Spectrometry (LCMS). A bispecific antibody preparation may be purified by protein A chromatography and preparative size exclusion chromatography to remove any aggregates or lower molecular weight components is digested with LysC enzyme to release each Fab arm and the Fc as independent fragments (3 fragments total). LCMS may then be used to measure the empirical mass of each Fab arm and the Fc and values obtained are compared to the theoretical mass of the two possible correct Fab arms and the two possible incorrect Fab arms and for the Fc a comparison to theoretical mass of homodimer vs heterodimer Fc is made. The signal intensity for each fragment can be converted to a % of total intensity of all fragments detected above background noise allowing for a ratio comparison of correct Fab product to incorrect Fab product. In a separate approach, post protein A bispecific antibody preparation elute can be fractionated using ion exchange or HIC chromatography and eluted fractions identified using LCMS. Identified peaks are then assigned % AUC from A280 measurements associated with the chromatography step. Ion exchange chromatography or hydrophobic interaction chromatography fractionate bispecific IgG containing correct and incorrect light chain pairings based on differential charge or hydrophobicity properties. The % area under curve from the resulting A280 chromatograms can be used to quantitate the amount of correct product.

Solvent Accessible Surface Area

When introducing non-wild type human residues (such as the complementary residue sets herein; see below) into antibodies intended for administration to human patients, there is a risk that the human immune system will recognize the modified residues as foreign and generate antibodies against the therapeutic (an anti-drug antibody or ADA response, which may result in faster clearance, reduced activity of circulating therapeutic, or both). In order to be recognized by the ADA, the non-human residues of the therapeutic antibody must be accessible to the ADA. Minimizing the surface area accessible to the ADA would be expected to reduce the ability of the ADA to interact with the therapeutic antibody.

In some aspects, the solvent accessible surface area of the first complementary residue set is less than 225 $Å^2$ as measured using a 2.5 Å probe. In some aspects, the solvent accessible surface area of the second complementary residue set is less than 225 $Å^2$ as measured using a 2.5 Å probe. In some aspects, the solvent accessible surface area of the first complementary residue set is less than 220 $Å^2$ as measured using a 2.5 Å probe. In some aspects, the solvent accessible surface area of the second complementary residue set is less than 220 $Å^2$ as measured using a 2.5 Å probe. In some aspects, the solvent accessible surface area of the first complementary residue set is less than 150 $Å^2$ as measured using a 2.5 Å probe. In some aspects, the solvent accessible surface area of the second complementary residue set is less than 150 $Å^2$ as measured using a 2.5 Å probe. In some aspects, the solvent accessible surface area of the first complementary residue set is less than 120 $Å^2$ as measured using a 2.5 Å probe. In some aspects, the solvent accessible surface area of the second complementary residue set is less than 120 $Å^2$ as measured using a 2.5 Å probe. In some aspects, the solvent accessible surface area of the first complementary residue set is less than 100 $Å^2$ as measured using a 2.5 Å probe. In some aspects, the solvent accessible surface area of the second complementary residue set is less than 100 $Å^2$ as measured using a 2.5 Å probe. In some aspects, the solvent accessible surface area of the first complementary residue set is less than 80 $Å^2$ as measured using a 2.5 Å probe. In some aspects, the solvent accessible surface area of the second complementary residue set is less than 80 $Å^2$ as measured using a 2.5 Å probe. In some aspects, the solvent accessible surface area of the first complementary residue set is less than 50 $Å^2$ as measured using a 2.5 Å probe. In some aspects, the solvent accessible surface area of the second complementary residue set is less than 50 Å² as measured using a 2.5 Å probe. In some aspects, the solvent accessible surface area of the first complementary residue set is less than 40 Å² as measured using a 2.5 Å probe. In some aspects, the solvent accessible surface area of the second complementary residue set is less than 40 Å² as measured using a 2.5 Å probe. In some aspects, the solvent accessible surface area of the first complementary residue set is less than 30 Å² as measured using a 2.5 Å probe. In some aspects, the solvent accessible surface area of the second complementary residue set is less than 30 Å² as measured using a 2.5 Å probe. In some aspects, the solvent accessible surface area of the first complementary residue set is less than 20 Å² as measured using a 2.5 Å probe. In some aspects, the solvent accessible surface area of the second complementary residue set is less than 20 Å² as measured using a 2.5 Å probe. In some aspects, the solvent accessible surface area of the first complementary residue set is less than 10 Å² as measured using a 2.5 Å probe. In some aspects, the solvent accessible surface area of the second complementary residue set is less than 10 Å² as measured using a 2.5 Å probe. In some aspects, the solvent accessible surface area of the first complementary residue set is less than 5 Å² as measured using a 2.5 Å probe. In some aspects, the solvent accessible surface area of the second complementary residue set is less than 5 Å² as measured using a2.5 Å probe. In some aspects, the solvent accessible surface area of the first complementary residue set is less than 2 Å² as measured using a 2.5 Å probe. In some aspects, the solvent accessible surface area of the second complementary residue set is less than 2 Å² as measured using a 2.5 Å probe. In some aspects, the solvent accessible surface area of the first complementary residue set is less than 1 Å² as measured using a 2.5 Å probe. In some aspects, the solvent accessible surface area of the second complementary residue set is less than 1 Å² as measured using a 2.5 Å probe.

In some aspects, the solvent accessible surface area is measured using the surface area algorithm in Maestro 9.6, 9.7, or 9.9 (Schrodinger, LLC.). The resolution may be 0.3. Preferably, the solvent accessible surface area of the first complementary residue set is less than 50 Å² as measured using a 2.5 Å probe at high resolution (for example, a resolution of 0.3), using the surface area algorithm in Maestro 9.6, 9.7, or 9.9 (Schrodinger, LLC.).

It is well known in the art that mutation of a single side chain can improve antibody binding potency by an order of magnitude or more. For example, a His/Tyr substitution with an accessible surface area of ~90 Å² is known to cause a >10-fold binding improvement of bevacizumab (J. Chem. Inf. Model. 53(11), 2937-50 (2013)). However, it is well known in the art that even smaller surface changes can have similar effects. An alanine side chain has an accessible surface area of ~20 Å². A mutation to alanine can be sufficient to change binding affinity between two proteins by greater than an order of magnitude. For example, see Mabs 3(5), 479-486 (2011). Thus, a small mutated surface area may be sufficient to allow the immune system to produce an anti-drug antibody (ADA) which recognizes an engineered biotherapeutic antibody, while having significant selectivity against binding native human antibodies.

The solvent accessible surface area (SASA) is the surface of a biomolecule accessible to a solvent (typically water). SASA can be calculated by using the 'rolling ball' algorithm developed by Shrake & Rupley in 1973, which models a sphere approximating the size of the solvent molecule to 'probe' the surface of the molecule. A typical value for the sphere radius is 1.4 Å, as this corresponds to the approximate radius of a water molecule. However, a larger value (such as 2.5 Å, as used herein) may be appropriate, when taking into account the experimental uncertainties in atom positions inherent in a crystal structure, or if the molecular entity, whose access to biomolecule's surface is in question, is larger than a water molecule (for example, the biomolecules of the potential host's immune system).

One aspect of the present invention is to provide a means of generating and maintaining bispecific heterogeneous antibodies or Fab fragments thereof through the use of engineered mutations in the $C_H1$ and $C_L$ domains. However, introducing non-canonical residues into antibodies for in vivo use risks triggering a host immune response. It is therefore advantageous to minimize the extent to which introduced or engineered residues to an antibody or Fab fragment thereof can potentially trigger a host immune response. Accordingly, the solvent accessible surface area of a complementary residue set of some aspects of the invention is less than 50 Å² as measured using a 2.5 Å probe.

In some aspects, the solvent accessible surface area of a complementary residue set of the invention is less than 45 Å² as measured using a 2.5 Å probe. In some aspects, the solvent accessible surface area of a complementary residue set of the invention is less than 40 Å² as measured using a 2.5 Å probe. In some aspects, the solvent accessible surface area of a complementary residue set of the invention is less than 35 Å² as measured using a 2.5 Å probe. In some aspects, the solvent accessible surface area of a complementary residue set of the invention is less than 30 Å² as measured using a 2.5 Å probe. In some aspects, the solvent accessible surface area of a complementary residue set of the invention is less than 25 Å² as measured using a 2.5 Å probe. In some aspects, the solvent accessible surface area of a complementary residue set of the invention is less than 20 Å² as measured using a 2.5 Å probe. In some aspects, the solvent accessible surface area of a complementary residue set of the invention is less than 15 Å² as measured using a 2.5 Å probe. In some aspects, the solvent accessible surface area of a complementary residue set of the invention is less than 10 Å² as measured using a 2.5 Å probe. In some aspects, the solvent accessible surface area of a complementary residue set of the invention is less than 9 Å² as measured using a 2.5 Å probe. In some aspects, the solvent accessible surface area of a complementary residue set of the invention is less than 8 Å² as measured using a 2.5 Å probe. In some aspects, the solvent accessible surface area of a complementary residue set of the invention is less than 7 Å² as measured using a 2.5 Å probe. In some aspects, the solvent accessible surface area of a complementary residue set of the invention is less than 6 Å² as measured using a 2.5 Å probe. In some aspects, the solvent accessible surface area of a complementary residue set of the invention is less than 5 Å² as measured using a 2.5 Å probe. In some aspects, the solvent accessible surface area of a complementary residue set of the invention is less than 4 Å² as measured using a 2.5 Å probe. In some aspects, the solvent accessible surface area of a complementary residue set of the invention is less than 3 Å² as measured using a 2.5 Å probe. In some aspects, the solvent accessible surface area of a complementary residue set of the invention is less than 2 Å² as measured using a 2.5 Å probe. In some aspects, the solvent accessible surface area of a complementary residue set of the invention is less than 1 Å² as measured using a 2.5 Å probe. In some aspects, the solvent accessible surface area of a complementary residue set of the invention is less than 0.5 Å² as measured using a 2.5 Å probe. In some aspects, the solvent accessible surface area of a complementary residue set of the invention is about 0 Å$^2$ as measured using a 2.5 Å probe.

Variable Domain

In some aspects, the first $C_H1$ is attached to a first variable heavy domain ($V_H$), and the first $C_L$ is attached to a first variable light domain ($V_L$), and the second $C_H1$ is attached to a second $V_H$, and the second $C_L$ is attached to a second $V_L$. When combined, the first $V_H$, first $V_L$, first $C_H1$, and first $C_L$ form a first Fab. When combined, the second $V_H$, second $V_L$, second $C_H1$, and second $C_L$ form a second Fab.

In some aspects, the first $V_H$ is connected to the first $C_H1$, which in turn is connected to the first $C_H2$, which in turn is connected to the first $C_H3$, thereby forming a first heavy chain. In some aspects, the second $V_H$ is connected to the second $C_H1$, which in turn is connected to the second $C_H2$, which in turn is connected to the second $C_H3$, thereby forming a second heavy chain.

In some aspects, the first $V_L$ is connected to the first $C_L$, thereby forming a first light chain. In some aspects, the second $V_L$ is connected to the second $C_L$, thereby forming a second light chain.

In some aspects, the invention provides for preferential formation of a first Fab and second Fab that does not rely on complementary pairing of the variable domains.

Where the preferential formation of heterodimeric protein domain interactions is discussed as not relying on complementary residue pairing of the variable domains, this means that the complementary pairing of, for example, a first $C_H1$ and a first $C_L$ domain is sufficient to effect preferential formation of a first $C_HC_L$ (or a first Fab). Additonal engineered residues in one or more of the variable or constant domains may provide additive effects to increase the fidelity of the preferential formation of the desired domain pairing.

In some aspects, the first complementary residue set is necessary for preferential formation of the first $C_HC_L$. In some aspects, the first complementary residue set is necessary for preferential formation of the first Fab. In some aspects, the second complementary residue set is necessary for preferential formation of the second $C_HC_L$. In some aspects, the second complementary residue set is necessary for preferential formation of the second Fab.

In some aspects, the first complementary residue set is sufficient for preferential formation of the first $C_HC_L$. In some aspects, the first complementary residue set is sufficient for preferential formation of the first Fab. In some aspects, the second complementary residue set is sufficent for preferential formation of the second $C_HC_L$. In some aspects, the second complementary residue set is sufficient for preferential formation of the second Fab.

In some aspects, the invention provides for preferential formation of a first Fab and second Fab that does not rely on complementary pairing of the variable domains such that formation of the first and second $C_HC_L$ preferentially occurs over formation of the third and fourth $C_HC_L$ at a ratio of at least about 4 to about 1, and may occur at a ratio of at least a value selected from the group 4, 5, 6, 7, 8, 9, 10, 12, 20, 25, 30, 35, 40, 45, 50, 55, 60, 65, 70, 75, 80, 85, 90, 95, 100, 200, 500, 1000, 2000, and 5000 to 1.

There are some instances of known $V_L/V_H$ pairs that have a natural affinity with each other. Accordingly, in some aspects the invention provides for preferential formation of a first Fab and second Fab that does not rely on the any of the variable domains comprising engineered mutant residues that form complementary residue sets. In some aspects, the multimeric proteins of the invention do not comprise mutations in any of the variable domains that are engineered to increase complementary pairing above that of the non-engineered or wild type $V_L/V_H$ framework sequences.

There are multiple advantages realized by avoiding inserting mutant residues of complementary residue sets into variable domains. For example, it is sometimes advantageous to use different germline frameworks for the variable region. Sequence variations in each germline present differing local environments for any mutations made in the variable domain; mutations which work in some frameworks may not work in other frameworks (for example, problems with expression, aggregation, stability, or other physical properties could occur). Also, mutations in the $V_L/V_H$ interface (the area most likely to affect pairing specificity) are near CDRs and may affect the relative orientation of $V_L$ and $V_H$ in subtle ways that differ from antibody to antibody, and between frameworks. A subtle variation in $V_L/V_H$ orientation may be tolerated by some antibodies, but not others. In addition, mutating multiple regions of the protein surface (both variable and constant domains) provides additional opportunities for the patient's immune system to recognize the antibody as foreign, and reject it via an anti-drug antibody response (ADA). Two possible results of an ADA response are a faster rate of clearance of the therapeutic from the patient, and neutralization of the drug's ability to bind its intended target (Jawa et. al, Clin. Immunol. 149(3), 534-55 (2013)). In the development of bispecific antibodies, it is desirable to take steps to minimize the probability of the patient's immune system mounting an ADA response. While there are some computational models for predicting T cell ADA response, accurate tools for conformational epitopes are lacking. Therefore, given the limited accuracy of in silico predictions, it is preferable to limit modifications of high-fidelity bispecific IgG molecules to the $C_H1$ and $C_L$ domains rather than mutating multiple domains as required by the Lewis et al. method (see below).

In some aspects, the first $V_H$ comprises $V_H$-Q39 (as in DP54 or DP75) or $V_H$-Q105 (as in human J segments other than JH2). In some aspects, the second $V_H$ comprises $V_H$-Q39 (as in DP54 or DP75) or $V_H$-Q105 (as in human J segments other than JH2).

In some aspects, the first $V_L$ comprises one or more of: (i) $V_L$-Q38 (as in DPK9 or DPL16); and (ii) one of $V_L$-Q1 (as in DPL7), $V_L$-S1 (as in DPL16), $V_L$-D1 (as in DPK9), $V_L$-E1 (as in DPK23), $V_L$-A1 (as in DPK3), or $V_L$-N1 (as in DPK2); and (iii) one of $V_L$-T42 (as in DPL7), $V_L$-Q42 (as in DPL16), or $V_L$-K42 (as in DPK9).

In some aspects, the second $V_L$ comprises one or more of: (i) $V_L$-Q38 (as in DPK9 or DPL16); and (ii) one of $V_L$-Q1 (as in DPL7), $V_L$-S1 (as in DPL16), $V_L$-D1 (as in DPK9), $V_L$-E1 (as in DPK23), $V_L$-A1 (as in DPK3), or $V_L$-N1 (as in DPK2); and (iii) one of $V_L$-T42 (as in DPL7), $V_L$-Q42 (as in DPL16), or $V_L$-K42 (as in DPK9).

In some aspects, the first $V_H$ comprises $V_H$-Q39 (as in DP54 or DP75) and $V_H$-Q105 (as in human J segments other than JH2). In some aspects, the second $V_H$ comprises $V_H$-Q39 (as in DP54 or DP75) and $V_H$-Q105 (as in human J segments other than JH2). In some aspects, both the first and second $V_H$ comprise these residues.

In some aspects, the first $V_L$ comprises: (i) $V_L$-Q38 (as in DPK9 or DPL16); and (ii) one of $V_L$-Q1 (as in DPL7), $V_L$-S1 (as in DPL16), $V_L$-D1 (as in DPK9), $V_L$-E1 (as in DPK23), $V_L$-A1 (as in DPK3), or $V_L$-N1 (as in DPK2); and (iii) one of $V_L$-T42 (as in DPL7), $V_L$-Q42 (as in DPL16), or $V_L$-K42 (as in DPK9).

In some aspects, the second $V_L$ comprises: (i) $V_L$-Q38 (as in DPK9 or DPL16); and (ii) one of $V_L$-Q1 (as in DPL7), $V_L$-S1 (as in DPL16), $V_L$-D1 (as in DPK9), $V_L$-E1 (as in DPK23), $V_L$-A1 (as in DPK3), or $V_L$-N1 (as in DPK2); and (iii) one of $V_L$-T42 (as in DPL7), $V_L$-Q42 (as in DPL16), or $V_L$-K42 (as in DPK9).

In some aspects, both the first $V_L$ and second $V_L$ comprise the above residues.

Lewis et al. (Nat. Biotechnol. 32, 191-98 (2014), or "Lewis publication" hereafter) reported mutations in the $C_H1$, $C_L$, $V_L$, and $V_H$ domains which attempted to address the issue of pairing light chains with the proper heavy chains. In a related patent application, WO2014150973, bispecific antibodies are disclosed which all involve at least one mutation of a variable domain. The Lewis publication states: "Our method requires the introduction of multiple mutations into conserved framework regions of both variable and constant domains." The authors further noted that in their experience, "variable domains dominated the specific assembly of heavy chains and light chains". They hypothesized that during the protein folding pathway, the variable domains may "recognize one another first and drive the $C_L$ domain to interact with unfolded $C_H1$", such that the heavy/light chain pairing is largely determined by interactions of $V_H$ and $V_L$, before $C_H1$ and $C_L$ interact. That hypothesis would explain their observation that mutations in the variable region were required.

In contrast, the present invention provides heterodimeric proteins (e.g. bispecific antibodies) which require no mutations of the CDRs or even the remainder of the variable region, and yet achieve high fidelity of chain pairing. Thus, relative to recent art in the field, specifically Lewis and WO2014150973, the heterodimeric proteins and bispecific antibodies of the present invention are unexpected and provide significant beneficial advantages.

As is known in the art, interactions between an antibody and its antigen are driven primarily by the CDR loops. While not all CDR loops participate in antigen binding for all antigens, when designing a method of antibody engineering to try and achieve high fidelity bispecific chain pairing, mutation of positions within the CDRs and variable region is a disadvantage due to the risk of negatively affecting antibody binding affinity. For cases involving the simultaneous production of multiple Fab sequences (or a bispecific IgG) rather than a single Fab, the various embodiments of WO2014150973 all envision mutating the CDR2 region of the heavy chain as defined by Kabat ("the residue which is four amino acids upstream of the first residue of HFR3 according to Kabat" is mutated to glutamate, where HFR3 refers to framework 3 of the heavy chain). The heterodimeric proteins and bispecific antibodies of the present invention do not involve modification of the CDRs, and thus avoid this risk. In addition, position 1 of the light chain variable region (which is mutated to Arg during production of four-chain mixtures according to the claims of WO2014/150973A1) is near the CDR1 and CDR3 loops, which means that mutations at this position may also affect binding affinity to some antigens. In PDB entry 4LLY, a crystal structure described in the Lewis publication, the side chain of position 1 is disordered beyond Cβ, but the backbone atoms are within 5 Å of CDR L1 and within 6 Å of CDR L3, and Cβ is oriented towards the face of the Fab containing the majority of the CDR residues (ie, where antigen is expected to bind). In contrast, the heterodimeric proteins and bispecific antibodies of the present invention do not involve mutation of this position, or of any other position in the variable domain, thus avoiding the risk of disturbing CDR positioning and/or antigen binding which exists when mutating nearby framework residues.

In principle, heterodimer-favoring mutations could be included in either of the major interface regions between the heavy and light chain, which are the interface between the $C_H1$ and $C_L$ domains, and the interface between the variable heavy and variable light domains. However, as noted in part above, mutations in the $C_H1/C_L$ interface are highly preferred for development of a robust bispecific platform. Mutations in the variable domain interface may affect the conformation of the CDR loops: because the CDR loops form part of the variable domain interface, they may interact (either directly or indirectly through nearby residues) with mutations made in the variable domains. If such interactions with heterodimer-enhancing mutations alter the CDR loop conformations in ways which affect antibody affinity, these heterodimer mutations will prove to be poor candidates for reliable use across a broad range of antibodies.

In addition, it is known that the relative orientation of the two variable domains is not constant among all antibodies; the angle between the two domains can vary by at least 30 degrees between antibodies (Abhinandan and Martin, Protein Eng Des Sel. 23(9), 689-97, (2010)). These changes necessarily alter the detailed pattern of contacts between residues in the variable domains, and correspondingly alter the range of amino acid substitutions that would be tolerated in the interface.

Given these facts, if variable domain mutations were used in a heterodimer-favoring platform design, it would be difficult to demonstrate robust and reliable applicability without testing a large number of examples covering the various CDR conformations and variable domain orientation angles encountered in common practice in known antibody structures. Accordingly, one of the advantages in generating heterodimers and bispecific anitbodies according to the present invention is to rely solely on modifying the $C_H1/C_L$ interface. None of the embodiments of the present invention require pairing with modifications of the variable domains as an essential feature to achieve useful levels of pairing fidelity.

The present invention advantageously provides that the preferential formation of first Fab and second Fab relies on complementary pairing of the complementary residue sets.

In some aspects, preferential formation refers to the formation of a first Fab (or first $C_HC_L$) comprising the first $C_H1$ and first $C_L$ to a greater extent than the formation of a Fab (or $C_HC_L$) comprising the first $C_H1$ with a second $C_L$, or a second $C_H1$ with a first $C_L$.

In some aspects, preferential formation refers to the formation of a second Fab (or second $C_HC_L$) comprising the second $C_H1$ and second $C_L$ to a greater extent than the formation of a Fab (or $C_HC_L$) comprising the first $C_H1$ with a second $C_L$, or a second $C_H1$ with a first $C_L$.

In some aspects, at least one of the $C_L$ domains is a kappa domain. In some aspects, at least one of the $C_L$ domains is a lambda domain. In some aspects, both of the $C_L$ domains are kappa domains. In some aspects, both of the $C_L$ domains are lambda domains. In some aspects, one of the $C_L$ domains is a kappa domain, and the other $C_L$ domain is a lambda domain.

In some aspects, the present invention provides for heterodimeric proteins and bispecific antibodies wherein formation of the first $C_HC_L$ and second $C_HC_L$ preferentially occurs over formation of a $C_HC_L$ comprised of either the first $C_H1$ and second $C_L$, or second $C_H1$ and first $C_L$, by at least about an amount selected from the group consisting of 4-fold, 5-fold, 6-fold, 8-fold, 10-fold, 15-fold, 20-fold, 25-fold, 30-fold, 40-fold, 50-fold, 60-fold, 80-fold, 90-fold, 100-fold, 150-fold, and 200-fold.

The determination of correct $C_H C_L$ pairing may be made by mass spectrometry analysis.

Complementary Residue Sets

In some aspects, the complementary residue sets comprise a positively or negatively charged residue in one domain, and an oppositely charged residue in the other domain. In some aspects, the complementary residue sets comprise a positively charged residue in one domain, and negatively charged residue in the other domain. In some aspects, the complementary residue sets comprise a positively or negatively charged residue in one domain, and either a polar residue, or oppositely charged residue, in the other domain. Positively charged residues may be selected from the group consisting of H, K and R. Negatively charged residues may be selected form the group consisting of E and D. For the avoidance of doubt, negatively charged residues are said to be oppositely charged to positively charged residues, and vice versa. Polar residues may be selected from the group consisting of S, T, M, Q, N, W, and Y. Polar residues may be selected from the group consisting of S, T, M, Q, N, and W. Polar residues may be selected from the group consisting of S, T, M, Q, N, and Y. Polar residues may be selected from the group consisting of S, T, M, W, and Y. Polar residues may be selected from the group consisting of S, T, M, W, and Y. Polar residues may be selected from the group consisting of S, T, M, and W. Polar residues may be selected from the group consisting of S, M, W, and Y. Polar residues may be selected from the group consisting of S, M, and W. Polar residues may be selected from the group consisting of S and T. In some aspects, M is not considered to be a polar residue.

For example, the $C_H1$ mutant residue may comprise a positively or negatively charged residue, and the $C_L$ mutant residue may comprise either a polar residue, or an oppositely charged residue. The $C_L$ mutant residue may comprise a positively or negatively charged residue, and the $C_H1$ mutant residue may comprise either a polar residue, or an oppositely charged residue. The $C_L$ mutant residue may comprise a positively charged residue, and the $C_H1$ mutant residue may comprise a negatively charged residue. The $C_H1$ mutant residue may comprise a positively charged residue, and the $C_L$ mutant residue may comprise a negatively charged residue.

In some aspects of the invention, the complementary residue sets may comprise a $C_H1$ mutant residue and a $C_L$ mutant residue whose oppositely charged side chains promote electrostatic interaction. Favorably, the altered charge polarity of the respective $C_H1$ and $C_L$ domains resulting from the engineered mutant residues supports the formation of the first or second Fab, and similarly, a repulsive charge interaction resulting from one or more of the engineered mutant residues suppresses the formation of the third or fourth Fab.

In some aspects, the locations of the complementary residue sets are selected from the group consisting of: (i) $C_H1$-124 and $C_L$-176; (ii) $C_H1$-188 and $C_L$-178; (iii) $C_H1$-143 and $C_L$-178; (iv) $C_H1$-143 and $C_L$-131; (v) $C_H1$-221 and $C_L$-123; (vi) $C_H1$-145 and $C_L$-131; (vi) $C_H1$-179 and $C_L$-131; (vii) $C_H1$-186 and $C_L$-131; and (viii) $C_H1$-143 and $C_L$-133, according to Kabat numbering as defined herein.

In some aspects, the complementary residue set comprises $C_H1$-124 and $C_L$-176. In some aspects, the complementary residue set comprises $C_H1$-188 and $C_L$-178. In some aspects, the complementary residue set comprises $C_H1$-143 and $C_L$-178. In some aspects, the complementary residue set comprises $C_H1$-143 and $C_L$-131. In some aspects, the complementary residue set comprises $C_H1$-221 and $C_L$-123. In some aspects, the complementary residue set comprises $C_H1$-145 and $C_L$-131. In some aspects, the complementary residue set comprises $C_H1$-179 and $C_L$-131. In some aspects, the complementary residue set comprises $C_H1$-145, $C_H1$-179, $C_H1$-186 and $C_L$-131. In some aspects, the complementary residue set comprises $C_H1$-143, $C_H1$-179, $C_H1$-186, and $C_L$-131. In some aspects, the complementary residue set comprises $C_H1$-186 and $C_L$-131. In some aspects, the complementary residue set comprises $C_H1$-143 and $C_L$-133.

In some aspects, the mutation at the $C_H1$ position is selected from the group consisting of W, H, K, R, S and T, and the mutation at the $C_L$ position is selected from the group consisting of S, M, D and E.

In some aspects, the mutation at the $C_H1$ position is selected from the group consisting of E, and D, and the mutation at the $C_L$ position is selected from the group consisting of H, K, and R.

In some aspects, one or more of the complementary residue sets further comprise one or more further mutations.

In some aspects, one or more of the complementary residue sets comprise one or more further mutations selected from the group consisting of: $C_H1$-143D, $C_H1$-145S, $C_H1$-186A, $C_H1$-186E, $C_H1$-188G, $C_H1$-188W, $C_H1$-190S, $C_H1$-190I, $C_L$-133S, $C_L$-135I, $C_L$-176G, $C_L$-176M, and $C_L$-178S.

In some aspects, one or more of the complementary residue sets comprise further mutations located at one or more positions selected from the group consisting of: $C_H1$-143, $C_H1$-145, $C_H1$-186, $C_H1$-188, $C_H1$-188, $C_H1$-190, $C_H1$-190, $C_L$-133, $C_L$-135, $C_L$-176, $C_L$-176, and $C_L$-178, according to Kabat numbering as described herein.

In some aspects, one or more of the complementary residue sets comprise a further $C_H1$ mutant residue at $C_H1$-143. The mutant residue at $C_H1$-143 may be selected from the group consisting of H, K, R, E, and D. The mutant residue at $C_H1$-143 may be selected from the group consisting of E, and D. The mutant residue at $C_H1$-143 may be E. The mutant residue at $C_H1$-143 may be D.

In some aspects, one or more of the complementary residue sets comprise a further $C_H1$ mutant residue at $C_H1$-145. The mutant residue at $C_H1$-145 may be selected from the group consisting of S, T, M, Q, N, E, D, W, or Y. The mutant residue at $C_H1$-145 may be selected from the group consisting of S, T, M, Q, N, E, or D. The mutant residue at $C_H1$-145 may be selected from the group consisting of S, T, M, Q, or N. The mutant residue at $C_H1$-145 may be selected from the group consisting of S, T, or M. The mutant residue at $C_H1$-145 may be S. The mutant residue at $C_H1$-145 may be T.

In some aspects, one or more of the complementary residue sets comprise a further $C_H1$ mutant residue at $C_H1$-186. The mutant residue at $C_H1$-186 may be selected from the group consisting of G, A, L, V, I, W, F, or Y. The mutant residue at $C_H1$-186 may be selected from the group consisting of G, A, L, V, I, or W. The mutant residue at $C_H1$-186 may be selected from the group consisting of G, A, L, V, or I. The mutant residue at $C_H1$-186 may be selected from the group consisting of G, A, V, or L. The mutant residue at $C_H1$-186 may be selected from the group consisting of G, A, or V. The mutant residue at $C_H1$-186 may be selected from the group consisting of G, or A. The mutant residue at $C_H1$-186 may be selected from the group consisting of A, or W. The mutant residue at $C_H1$-186 may be selected from the group consisting of F, Y, or W. The mutant residue at $C_H1$-186 may W. The mutant residue at $C_H1$-186 may A.

In some aspects, one or more of the complementary residue sets comprise a further $C_H1$ mutant residue at $C_H1$-188. The mutant residue at $C_H1$-188 may be selected from the group consisting of G, A, L, V, I, W, F, or Y. The mutant residue at $C_H1$-188 may be selected from the group consisting of G, A, L, V, I, or W. The mutant residue at $C_H1$-188 may be selected from the group consisting of G, A, L, V, or I. The mutant residue at $C_H1$-188 may be selected from the group consisting of G, A, V, or L. The mutant residue at $C_H1$-188 may be selected from the group consisting of G, or A. The mutant residue at $C_H1$-188 may be selected from the group consisting of G, A, or W. The mutant residue at $C_H1$-188 may be selected from the group consisting of G, or W. The mutant residue at $C_H1$-188 may be selected from the group consisting of F, Y, or W. The mutant residue at $C_H1$-188 may be W. The mutant residue at $C_H1$-188 may be A. The mutant residue at $C_H1$-188 may be G.

In some aspects, one or more of the complementary residue sets comprise a further $C_H1$ mutant residue at $C_H1$-190. The mutant residue at $C_H1$-190 may be selected from the group consisting of S, T, I, L. The mutant residue at $C_H1$-190 may be selected from the group consisting of I or L. The mutant residue at $C_H1$-190 may be selected from the group consisting of S or T. The mutant residue at $C_H1$-190 may be selected from the group consisting of S or I. The mutant residue at $C_H1$-190 may be T. The mutant residue at $C_H1$-190 may be L. The mutant residue at $C_H1$-190 may be I. The mutant residue at $C_H1$-190 may be S.

In some aspects, one or more of the complementary residue sets comprise a further $C_L$ mutant residue at $C_L$-133. The mutant residue at $C_L$-133 may be selected from the group consisting of S, T, Q or M. The mutant residue at $C_L$-133 may be S. The mutant residue at $C_L$-133 may be T. The mutant residue at $C_L$-133 may be M. The mutant residue at $C_L$-133 may be Q.

In some aspects, one or more of the complementary residue sets comprise a further $C_L$ mutant residue at $C_L$-135. The mutant residue at $C_L$-135 may be selected from the group consisting of I, T, or M. The mutant residue at $C_L$-135 may be I.

In some aspects, one or more of the complementary residue sets comprise a further $C_L$ mutant residue at $C_L$-176. The mutant residue at $C_L$-135 may be selected from the group consisting of G, A, V, I, L, M, N. or T. The mutant residue at $C_L$-176 may be selected from the group consisting of G, A, V, I, L, or M. The mutant residue at $C_L$-176 may be selected from the group consisting of G, A, V, L, or M. The mutant residue at $C_L$-176 may be selected from the group consisting of G, A, V, or M. The mutant residue at $C_L$-176 may be selected from the group consisting of G, A, or M. The mutant residue at $C_L$-176 may be selected from the group consisting of G, or M. The mutant residue at $C_L$-176 may be G. The mutant residue at $C_L$-176 may be A. The mutant residue at $C_L$-176 may be M. The mutant residue at $C_L$-176 may be N.

In some aspects, one or more of the complementary residue sets comprise a further $C_L$ mutant residue at $C_L$-178. The mutant residue at $C_L$-135 may be selected from the group consisting of G, S, V, or A. The mutant residue at $C_L$-135 may be S.

In some aspects, wherein the first and second complementary residue sets are selected from two of the following groups: (i) $C_H1$-124K, $C_L$-176D; (ii) $C_H1$-124K, $C_L$-176D, $C_H1$-190S, $C_L$-133S; (iii) $C_H1$-124K, $C_L$-176D, $C_L$-133S; (iv) $C_H1$-124E, $C_L$-176K; (v) $C_H1$-124E, $C_L$-176K, $C_H1$-188G; (vi) $C_H1$-188E, $C_L$-178K, $C_H1$-143E; (vii) $C_H1$-188K, $C_L$-178D, $C_H1$-143D; (viii) $C_H1$-143K, $C_L$-178D; (ix) $C_H1$-143D, $C_L$-178R; (x) $C_H1$-143K, $C_L$-178D; (xi) $C_H1$-143D, $C_L$-178K; (xii) $C_H1$-143D, $C_L$-178K, $C_L$-176M; (xiii) $C_H1$-143E, $C_L$-131R; (xiv) $C_H1$-143R, $C_L$-131E; (xv) $C_H1$-143R, $C_L$-131E, $C_H1$-186A; (xvi) $C_H1$-221D, $C_L$-123K; (xvii) $C_H1$-221D, $C_L$-123K, $C_H1$-190I, $C_L$-135I; (xviii) $C_H1$-145E, $C_L$-131H; (xvix) $C_H1$-143H, $C_H1$-179D, $C_H1$-186E, $C_L$-131H; (xix) $C_H1$-145E, $C_L$-131H; (xx) $C_H1$-186E, $C_L$-131H, $C_H1$-145S; (xxi) $C_H1$-143S, $C_L$-131D, $C_H1$-188W, $C_L$-133S, $C_L$-178S; (xxii) $C_H1$-143S, $C_H1$-188W, $C_L$-133M, $C_L$-176G, $C_L$-178G; (xxiii) $C_H1$-143H, $C_H1$-179D, $C_H1$-186E, $C_L$-131H, $C_H1$-190I, $C_L$-135I, (xxiv) $C_H1$-186E, $C_L$-131H, $C_H1$-145S; (xxv) $C_H1$-143S, $C_L$-131D, $C_H1$-188W, $C_L$-133S, $C_L$-176C; (xxvi) $C_H1$-143S, $C_H1$-188W, $C_L$-133M, $C_L$-178G, $C_L$-176G; (xxvii) $C_H1$-143S, $C_H1$-188W, $C_L$-131D.

Novel Disulfide Linkage

In some aspects, the invention provides for a novel disulfide bond between the first $C_H1$ and the first $C_L$, and/or the second $C_H1$ and the second $C_L$. The novel disulfide bond may be located at one or more of the following positions (i) $C_H1$-122 and $C_L$-123; (ii) $C_H1$-139 and $C_L$-116; and (iii) $C_H1$-174 and $C_L$-176.

The wild type disulfide bond may be removed, by mutating one or both of $C_H1$-C230 and $C_L$-214 to any residue except C, on either or both of the first $C_HC_L$ and/or second $C_HC_L$. In some aspects, the $C_L$-C214 is deleted in either or both of the first and/or second $C_HC_L$. In some aspects, the $C_H1$-C230 is deleted in either or both of the first and/or second $C_HC_L$.

In some aspects, the first and/or second $C_H1$-C230 and first, and/or second $C_L$-C214 are mutated to S. In some aspects, the first $C_HC_L$ comprises $C_H1$-C230S and $C_L$-C214S, and further comprises one or more of the following residue pairs: $C_H1$-122C and $C_L$-123C; $C_H1$-139C and $C_L$-116C; and $C_H1$-174C and $C_L$-176C. In some aspects, the second $C_HC_L$ comprises $C_H1$-C230S and $C_L$-C214S, and further comprises one or more of the following residue pairs: $C_H1$-122C and $C_L$-123C; $C_H1$-139C and $C_L$-116C; and $C_H1$-174C and $C_L$-176C. Favorably, the first $C_HC_L$ and second $C_HC_L$ do not comprise novel cytokine mutations located at the same corresponding positions.

In some aspects, wherein a given $C_HC_L$ comprises $C_H1$-174C and $C_L$-176C, the given $C_HC_L$ further comprises $C_H1$-190I and $C_L$-135I.

$C_H/C_L$ Mutations

In some aspects, the first $C_HC_L$ and/or second $C_HC_L$ comprises residues from one of the following groups: (i) $C_H1$-124K, $C_L$-176D, $C_H1$-190S, $C_L$-133S; (ii) $C_H1$-124E, $C_L$-176K, $C_H1$-188G, $C_L$-133S; (iii) $C_H1$-124K, $C_L$-176D, $C_L$-133S; (iv) $C_H1$-124E, $C_L$-176K, $C_L$-133S; (v) $C_H1$-188E, $C_L$-178K, $C_H1$-143E; (vi) $C_H1$-188K, $C_L$-178D, $C_H1$-143D; (vii) $C_H1$-143K, $C_L$-178D; (viii) $C_H1$-143D, $C_L$-178R; (ix) $C_H1$-143K, $C_L$-178D; (x) $C_H1$-143D, $C_L$-178K; (xi) $C_H1$-143D, $C_L$-178K, $C_L$-176M; (xii) $C_H1$-143E, $C_L$-131R; (xiii) $C_H1$-143R, $C_L$-131E; (xiv) $C_H1$-143R, $C_L$-131E, $C_H1$-186A; (xv) $C_H1$-221D, $C_L$-123K; (xvi) $C_H1$-221K, $C_L$-123K, $C_H1$-190I, $C_L$-135I, $C_H1$-174C, $C_H1$-230S, $C_L$-176C, $C_L$-214S; (xvii) $C_H1$-145E, $C_L$-131H; (xviii) $C_H1$-143H, $C_H1$-179D, $C_H1$-186E, $C_L$-131H; (xix) $C_H1$-122C, $C_H1$-145E, $C_H1$-230S, $C_L$-123C, $C_L$-131H, $C_L$-214S; (xx) $C_H1$-186E, $C_L$-131H, $C_H1$-145S; (xxi) $C_H1$-143S, $C_L$-131D, $C_H1$-188W, $C_L$-133S, $C_L$-178S; (xxii) $C_H1$-143S, $C_H1$-188W, $C_L$-133M, $C_L$-176G, $C_L$-178G; (xxiii) $C_H1$-143H, $C_H1$-179D, $C_H1$-186E, $C_L$-131H, $C_H1$-190I, $C_L$-135I, $C_H1$-174C, $C_H1$-230S, $C_L$-176C, $C_L$-214S; (xxiv) $C_H1$-186E, $C_L$-131H, $C_H1$-145S, $C_H1$-139C, $C_H1$-230S, $C_L$-116C, $C_L$-214S; (xxv) $C_H1$-143S, $C_L$-131D, $C_H1$-188W, $C_L$-133S, $C_L$-178S, $C_H1$-174C, $C_H1$-230S, $C_L$-176C, $C_L$-214S; (xxvi) $C_H$1-221D, 123K, $C_H$1-190I, $C_L$-135I, $C_H$1-174C, $C_H$1-230S, $C_L$-176C, $C_L$-214S; (xxvii) $C_H$1-143S, $C_H$1-188W, $C_H$1-122C, $C_H$1-139C, $C_H$1-174C, $C_H$1-230S, $C_L$-133S, $C_L$-178S, $C_L$-131D, $C_L$-116C, $C_L$-123C, $C_L$-176C, $C_L$-214S.

Favorably, the first and second Fab do not both comprise residues from the same group.

In some aspects, the first $C_HC_L$ and/or second $C_HC_L$ comprises the residues $C_H$1-124K, $C_L$-176D, $C_H$1-190S, and $C_L$-133S. In some aspects, the first $C_HC_L$ and/or second $C_HC_L$ comprise the residues $C_H$1-124K, and $C_L$-176D. In some aspects, the first $C_HC_L$ and/or second $C_HC_L$ comprises the residues $C_H$1-124K, $C_L$-176E. In some aspects, the first $C_HC_L$ and/or second $C_HC_L$ comprise the residues $C_H$1-124R, $C_L$-176D. In some aspects, the first $C_HC_L$ and/or second $C_HC_L$ comprise the residues $C_H$1-124R, $C_L$-176E.

In some aspects, the first $C_HC_L$ and/or second $C_HC_L$ comprise the residues $C_H$1-124E, $C_L$-176K, $C_H$1-188G, and $C_L$-133S. In some aspects, the first $C_HC_L$ and/or second $C_HC_L$ comprise the residues $C_H$1-124E, and $C_L$-176K. In some aspects, the first $C_HC_L$ and/or second $C_HC_L$ comprise the residues $C_H$1-124E, and $C_L$-176R. In some aspects, the first $C_HC_L$ and/or second $C_HC_L$ comprise the residues $C_H$1-124D, and $C_L$-176K. In some aspects, the first $C_HC_L$ and/or second $C_HC_L$ comprise the residues $C_H$1-124D, and $C_L$-176R.

In some aspects, the first $C_HC_L$ and/or second $C_HC_L$ comprise the residues $C_H$1-188E, $C_L$-178K, and $C_H$1-143E. In some aspects, the first $C_HC_L$ and/or second $C_HC_L$ comprise the residues $C_H$1-188E, and $C_L$-178K. In some aspects, the first $C_HC_L$ and/or second $C_HC_L$ comprise the residues $C_H$1-188D, and $C_L$-178K. In some aspects, the first $C_HC_L$ and/or second $C_HC_L$ comprise the residues $C_H$1-188E, $C_L$-178R. In some aspects, the first $C_HC_L$ and/or second $C_HC_L$ comprise the residues $C_H$1-188D, $C_L$-178R.

In some aspects, the first $C_HC_L$ and/or second $C_HC_L$ comprise the residues $C_H$1-188K, $C_L$-178D, and $C_H$1-143D. In some aspects, the first $C_HC_L$ and/or second $C_HC_L$ comprise the residues $C_H$1-188K, $C_L$-178D. In some aspects, the first $C_HC_L$ and/or second $C_HC_L$ comprise the residues $C_H$1-188R, $C_L$-178D. In some aspects, the first $C_HC_L$ and/or second $C_HC_L$ comprise the residues $C_H$1-188K, $C_L$-178E. In some aspects, the first $C_HC_L$ and/or second $C_HC_L$ comprise the residues $C_H$1-188R, $C_L$-178E.

In some aspects, the first $C_HC_L$ and/or second $C_HC_L$ comprise the residues $C_H$1-143K, and $C_L$-178D. In some aspects, the first $C_HC_L$ and/or second $C_HC_L$ comprise the residues $C_H$1-143K, and $C_L$-178E. In some aspects, the first $C_HC_L$ and/or second $C_HC_L$ comprise the residues $C_H$1-143R, and $C_L$-178D. In some aspects, the first $C_HC_L$ and/or second $C_HC_L$ comprise the residues $C_H$1-143R, and $C_L$-178E.

In some aspects, the first $C_HC_L$ and/or second $C_HC_L$ comprise the residues $C_H$1-143D, and $C_L$-178R. In some aspects, the first $C_HC_L$ and/or second $C_HC_L$ comprise the residues $C_H$1-143E, and $C_L$-178R. In some aspects, the first $C_HC_L$ and/or second $C_HC_L$ comprise the residues $C_H$1-143D, and $C_L$-178K. In some aspects, the first $C_HC_L$ and/or second $C_HC_L$ comprise the residues $C_H$1-143E, and $C_L$-178K.

In some aspects, the first $C_HC_L$ and/or second $C_HC_L$ comprise the residues $C_H$1-143D, $C_L$-178K, and $C_L$-176M.

In some aspects, the first $C_HC_L$ and/or second $C_HC_L$ comprise the residues $C_H$1-143E, and $C_L$-131R. In some aspects, the first $C_HC_L$ and/or second $C_HC_L$ comprise the residues $C_H$1-143D, and $C_L$-131R. In some aspects, the first $C_HC_L$ and/or second $C_HC_L$ comprise the residues $C_H$1-143E, and $C_L$-131K. In some aspects, the first $C_HC_L$ and/or second $C_HC_L$ comprise the residues $C_H$1-143D, and $C_L$-131K.

In some aspects, the first $C_HC_L$ and/or second $C_HC_L$ comprise the residues $C_H$1-143R, $C_L$-131E, and $C_H$1-186A. In some aspects, the first $C_HC_L$ and/or second $C_HC_L$ comprise the residues $C_H$1-143R, and $C_L$-131E. In some aspects, the first $C_HC_L$ and/or second $C_HC_L$ comprise the residues $C_H$1-143K, and $C_L$-131E. In some aspects, the first $C_HC_L$ and/or second $C_HC_L$ comprise the residues $C_H$1-143R, and $C_L$-131D. In some aspects, the first $C_HC_L$ and/or second $C_HC_L$ comprise the residues $C_H$1-143K, and $C_L$-131D.

In some aspects, the first $C_HC_L$ and/or second $C_HC_L$ comprise the residues $C_H$1-221D, $C_L$-123K, $C_H$1-190I, $C_L$-135I, $C_H$1-174C, $C_H$1-230S, $C_L$-176C, and $C_L$-214S. In some aspects, the first $C_HC_L$ and/or second $C_HC_L$ comprise the residues $C_H$1-221D, and $C_L$-123K. In some aspects, the first $C_HC_L$ and/or second $C_HC_L$ comprise the residues $C_H$1-221E, and $C_L$-123K. In some aspects, the first $C_HC_L$ and/or second $C_HC_L$ comprise the residues $C_H$1-221D, and $C_L$-123R. In some aspects, the first $C_HC_L$ and/or second $C_HC_L$ comprise the residues $C_H$1-221E, and $C_L$-123R.

In some aspects, the first $C_HC_L$ and/or second $C_HC_L$ comprise the residues $C_H$1-145E, and $C_L$-131H. In some aspects, the first $C_HC_L$ and/or second $C_HC_L$ comprise the residues $C_H$1-145D, and $C_L$-131H. In some aspects, the first $C_HC_L$ and/or second $C_HC_L$ comprise the residues $C_H$1-145E, and $C_L$-131K. In some aspects, the first $C_HC_L$ and/or second $C_HC_L$ comprise the residues $C_H$1-145E, and $C_L$-131R. In some aspects, the first $C_HC_L$ and/or second $C_HC_L$ comprise the residues $C_H$1-145D, and $C_L$-131K. In some aspects, the first $C_HC_L$ and/or second $C_HC_L$ comprise the residues $C_H$1-145E, and $C_L$-131H.

In some aspects, the first $C_HC_L$ and/or second $C_HC_L$ comprise the residues $C_H$1-143H, $C_H$1-179D, $C_H$1-186E, and $C_L$-131H. In some aspects, the first $C_HC_L$ and/or second $C_HC_L$ comprise the residues $C_H$1-143E, $C_H$1-179D, $C_H$1-186E, and $C_L$-131H. In some aspects, the first $C_HC_L$ and/or second $C_HC_L$ comprise the residues $C_H$1-143D, $C_H$1-179D, $C_H$1-186D, and $C_L$-131H. In some aspects, the first $C_HC_L$ and/or second $C_HC_L$ comprise the residues $C_H$1-143H, $C_H$1-179D, $C_H$1-186D, and $C_L$-131H. In some aspects, the first $C_HC_L$ and/or second $C_HC_L$ comprise the residues $C_H$1-143H, $C_H$1-179E, $C_H$1-186D, and $C_L$-131H. In some aspects, the first $C_HC_L$ and/or second $C_HC_L$ comprise the residues $C_H$1-143H, $C_H$1-179E, $C_H$1-186E, and $C_L$-131H. In some aspects, the first $C_HC_L$ and/or second $C_HC_L$ comprise the residues $C_H$1-143H, $C_H$1-179E, $C_H$1-186D, and $C_L$-131H. In some aspects, the first $C_HC_L$ and/or second $C_HC_L$ comprise the residues $C_H$1-143H, $C_H$1-179E, $C_H$1-186E, and $C_L$-131H.

In some aspects, the first $C_HC_L$ and/or second $C_HC_L$ comprise the residues $C_H$1-145E, $C_L$-131H, $C_H$1-122C, $C_H$1-230S, $C_L$-123C, and $C_L$-214S.

In some aspects, the first $C_HC_L$ and/or second $C_HC_L$ comprise the residues $C_H$1-186E, $C_L$-131H, and $C_H$1-145S. In some aspects, the first $C_HC_L$ and/or second $C_HC_L$ comprise the residues $C_H$1-186E, and $C_L$-131H. In some aspects, the first $C_HC_L$ and/or second $C_HC_L$ comprise the residues $C_H$1-186D, and $C_L$-131H.

In some aspects, the first $C_HC_L$ and/or second $C_HC_L$ comprise the residues $C_H$1-143S, $C_L$-131D, $C_H$1-188W, $C_L$-133S, and $C_L$-178S. In some aspects, the first $C_HC_L$ and/or second $C_HC_L$ comprise the residues $C_H$1-143S, $C_H$1-188W, and $C_L$-131D. In some aspects, the first $C_HC_L$ and/or second $C_HC_L$ comprise the residues $C_H$1-143T, $C_H$1-188W, and $C_L$-131D. In some aspects, the first $C_HC_L$ and/or second $C_HC_L$ comprise the residues $C_H$1-143S, $C_H$1-188W, and $C_L$-131E. In some aspects, the first $C_HC_L$ and/or second $C_HC_L$ comprise the residues $C_H1$-143T, $C_H1$-188W, and $C_L$-131E.

In some aspects, the first $C_HC_L$ and/or second $C_HC_L$ comprise the residues $C_H1$-143S, $C_H1$-188W, $C_L$-133M, $C_L$-176G, and $C_L$-178G. In some aspects, the first $C_HC_L$ and/or second $C_HC_L$ comprise the residues $C_H1$-143S, $C_H1$-188W, and $C_L$-133M. In some aspects, the first $C_HC_L$ and/or second $C_HC_L$ comprise the residues $C_H1$-143T, $C_H1$-188W, and $C_L$-133M.

In some aspects, the first $C_HC_L$ and/or second $C_HC_L$ comprise the residues $C_H1$-143H, $C_H1$-179D, $C_H1$-186E, $C_L$-131H, $C_H$-190I, $C_L$-135I, $C_H1$-174C, $C_H1$-230S, 176C, and $C_L$-214S. In some aspects, the first $C_HC_L$ and/or second $C_HC_L$ comprise the residues $C_H1$-143H, $C_H1$-179D, $C_H1$-186E, and $C_L$-131H. In some aspects, the first $C_HC_L$ and/or second $C_HC_L$ comprise the residues $C_H1$-143H, $C_H1$-179E, $C_H1$-186E, and $C_L$-131H. In some aspects, the first $C_HC_L$ and/or second $C_HC_L$ comprise the residues $C_H1$-143H, $C_H1$-179D, $C_H1$-186D, and $C_L$-131H. In some aspects, the first $C_HC_L$ and/or second $C_HC_L$ comprise the residues $C_H1$-143H, $C_H1$-179E, $C_H1$-186D, and $C_L$-131H.

In some aspects, the first $C_HC_L$ and/or second $C_HC_L$ comprise the residues $C_H$-186E, $C_L$-131H, $C_H$-145S, $C_H1$-139C, $C_H1$-230S, $C_L$-116C, and $C_L$-214S.

In some aspects, the first $C_HC_L$ and/or second $C_HC_L$ comprise the residues $C_H1$-143S, $C_L$-131D, $C_H1$-188W, $C_L$-133S, $C_L$-178S, $C_H1$-174C, $C_H1$-230S, $C_L$-176C, and $C_L$-214S.

In some aspects, the first $C_HC_L$ and/or second $C_HC_L$ comprise the residues $C_H1$-143S, $C_H1$-188W, $C_L$-133M, $C_L$-178G, $C_L$-176G, $C_H1$-122C, $C_H1$-230S, $C_L$-123C, and $C_L$-214S.

In some aspects, the first $C_HC_L$ and/or second $C_HC_L$ comprise the residues $C_H1$-143S, $C_L$-131D, $C_H1$-188W, $C_L$-133S, $C_L$-178S, $C_H1$-122C, $C_H$-139C, $C_H$-174C, $C_H1$-230S, $C_L$-116C, $C_L$-123C, $C_L$-176C, and $C_L$-214S.

In some aspects, the invention comprises a $C_H1$ domain comprising a sequence identical to SEQ ID NO:1, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:2, by at least an amount selected from the group consisting of 85%, 86%, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:3, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:4, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:5, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:6, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:7, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:8, by at least an amount selected from the group consisting of 85%, 86, 87%, 88%, 89%, 90%, 91%, 92%, 93%, 94%, 95%, 96%, 97%, 98%, and 99%.

In some aspects, the invention comprises a $C_H1$ domain comprising a sequence identical to SEQ ID NO:33, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:34, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:35, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:36, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:37, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:38, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:39, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:40, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H1$ domain comprising a sequence identical to SEQ ID NO:41, by at least an amount selected from the group consisting of 85%, 86, 87%, 88%, 89%, 90%, 91%, 92%, 93%, 94%, 95%, 96%, 97%, 98%, and 99%.

In some aspects, the invention comprises a $C_L$ domain comprising a sequence identical to SEQ ID NO:9, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_L$ domain comprising a sequence identical to SEQ ID NO:10, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_L$ domain comprising a sequence identical to SEQ ID NO:11, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_L$ domain comprising a sequence identical to SEQ ID NO:12, by at least an amount selected from the group consisting of 85%, 86, 87%, 88%, 89%, 90%, 91%, 92%, 93%, 94%, 95%, 96%, 97%, 98%, and 99%.

In some aspects, the invention comprises a $C_L$ domain comprising a sequence identical to SEQ ID NO:24, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_L$ domain comprising a sequence identical to SEQ ID NO:25, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_L$ domain comprising a sequence identical to SEQ ID NO:26, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_L$ domain comprising a sequence identical to SEQ ID NO:27, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_L$ domain comprising a sequence identical to SEQ ID NO:28, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_L$ domain comprising a sequence identical to SEQ ID NO:29, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_L$ domain comprising a sequence identical to SEQ ID NO:30, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_L$ domain comprising a sequence identical to SEQ ID NO:31, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_L$ domain comprising a sequence identical to SEQ ID NO:32, by at least an amount selected from the group consisting of 85%, 86, 87%, 88%, 89%, 90%, 91%, 92%, 93%, 94%, 95%, 96%, 97%, 98%, and 99%.

Modification to constant domains of antibodies to produce heterodimers are disclosed in U.S. Pat. No. 5,731,168, WO2009089004, and WO2011143545, each of whose contents is herein incorporated in its entirety.

$C_H2$ and $C_H3$ Domains

In some aspects, the first $C_H1$ is connected to a first $C_H2$ domain ($C_H2$), and the second $C_H1$ is connected to second $C_H2$. The first and second $C_H2$ may each comprise a first and second $C_H2$ mutant residue respectively, the first and second $C_H2$ mutant residues being engineered to differ from each other, and preferentially interact with each other and thereby form $C_H2$ heterodimers preferentially over the formation of $C_H2$ homodimers.

In some aspects, the heterodimeric protein of the invention further comprises a first $C_H2$ region and second $C_H2$ region, which interact together to form a $C_H2$ interface, wherein one or more amino acids within the $C_H2$ interface destabilize homodimer formation and are not electrostatically unfavorable to homodimer formation.

In some aspects, the first $C_H1$ or $C_H2$ is connected to a first $C_H3$ domain ($C_H3$), and the second $C_H1$ or $C_H2$ is connected to second $C_H3$. The first and second $C_H3$ may each comprise a first and second $C_H3$ mutant residue respectively, the first and second $C_H3$ mutant residues being engineered to differ from each other, and preferentially interact with each other and thereby form $C_H3$ heterodimers preferentially over the formation of $C_H3$ homodimers. Techniques involving replacing one or more residues that make up the $C_H3$-$C_H3$ interface in both $C_H3$ domains with a charged amino acid for promoting the heterodimer formation have also been described in WO2009/089004.

In some aspects, the heterodimeric protein of the invention further comprises a first $C_H3$ region and a second $C_H3$ region, which interact together to form a $C_H3$ interface, wherein one or more amino acids within the $C_H3$ interface destabilizes homodimer formation and are not electrostatically unfavorable to homodimer formation. In some embodiments, the engineered $C_H3$ interface sterically favors heterodimer formation over homodimer formation. In some embodiments, the engineered $C_H3$ interface electrostatically favors heterodimer formation over homodimer formation.

In some embodiments, the amino acid modification in the first $C_H3$ polypeptide is an amino acid substitution at $C_H3$-391, and the amino acid modification in the second $C_H3$ polypeptide is an amino acid substitution at $C_H3$-441 (according to the numbering of SEQ ID NO:18). In some embodiments, the amino acid modification in the first $C_H3$ polypeptide is $C_H3$-441R and the amino acid modification in the second $C_H3$ polypeptide is $C_H3$-391E or $C_H3$-391D (for greater detail, see WO2011/143545). In some embodiments, the bispecific antibodies further comprise amino acid modification in the first hinge region at positions $C_H2$-D232 and $C_H2$-P241 of SEQ ID NO: 42 (hinge IgG1), or $C_H2$-C233, $C_H2$-E237, and $C_H2$-P241 of SEQ ID NO: 79 (IgG2 hinge sequence) in one arm, and the substituted/replaced amino acid in the first hinge region has an opposite charge to the corresponding amino acid in the second hinge region in another arm (for greater detail, see WO2011/143545). For example, the amino acid modification in the hinge region can be $C_H2$-D232R, $C_H2$-D232E, $C_H2$-P241R, and/or $C_H2$-P241E. In another example, the amino acid modification in the hinge region can be $C_H2$-C233D, $C_H2$-C233E, $C_H2$-C233K, $C_H2$-C223R, $C_H2$-E237E, $C_H2$-E237K, $C_H2$-E237R, $C_H2$-P241D, $C_H2$-P241E, $C_H2$-P241K, and/or $C_H2$-P228R. In some aspects, the $C_H3$ domain is selected from the group consisting of SEQ ID NO:82, 83, 84, and 85.

In some aspects, the invention comprises a $C_H2$ domain comprising a sequence identical to SEQ ID NO:13, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H2$ domain comprising a sequence identical to SEQ ID NO:14, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H2$ domain comprising a sequence identical to SEQ ID NO:15, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H2$ domain comprising a sequence identical to SEQ ID NO:16, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H2$ domain comprising a sequence identical to SEQ ID NO:17, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H2$ domain comprising a sequence identical to SEQ ID NO:45, by at least an amount selected from the group consisting of 85%, 86, 87%, 88%, 89%, 90%, 91%, 92%, 93%, 94%, 95%, 96%, 97%, 98%, and 99%.

In some aspects, the invention comprises a $C_H3$ domain comprising a sequence identical to SEQ ID NO:18, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H3$ domain comprising a sequence identical to SEQ ID NO:19, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H3$ domain comprising a sequence identical to SEQ ID NO:20, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H3$ domain comprising a sequence identical to SEQ ID NO:21, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H3$ domain comprising a sequence identical to SEQ ID NO:22, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H3$ domain comprising a sequence identical to SEQ ID NO:23, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H3$ domain comprising a sequence identical to SEQ ID NO:46, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H3$ domain comprising a sequence identical to SEQ ID NO:47, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H3$ domain comprising a sequence identical to SEQ ID NO:48, by at least an amount selected from the group consisting of 85%, 86, 87%, 88%, 89%, 90%, 91%, 92%, 93%, 94%, 95%, 96%, 97%, 98%, and 99%. In some aspects, the invention comprises a $C_H3$ domain comprising a sequence identical to SEQ ID NO:49, by at least an amount selected from the group consisting of 85%, 86, 87%, 88%, 89%, 90%, 91%, 92%, 93%, 94%, 95%, 96%, 97%, 98%, and 99%.

In some aspects, the invention further comprises a IgG hinge region between the $C_H1$ and $C_H2$ region. The IgG hinge region may comprise SEQ ID NO:42. The IgG hinge region may comprise SEQ ID NO:43. The IgG hinge region may comprise SEQ ID NO:44. The IgG hinge region may be a IgG2 hinge region, and may comprise SEQ ID NO:79.

Ig Isotype and Subclass

In some embodiments, the heterodimeric protein may comprise one or more IgA domains. In some embodiments, the heterodimeric protein may comprise one or more IgD domains. In some embodiments, the heterodimeric protein may comprise one or more IgE domains. In some embodiments, the heterodimeric protein may comprise one or more IgG domains. In some embodiments, the heterodimeric protein may comprise one or more IgM domains.

In some embodiments, at least one Fab is an IgA1, or IgA2. In some embodiments, at least one Fab is an IgG1, IgG2, IgG3, or IgG4. In some embodiments, the IgG Fab comprises a human IgG Fab (e.g. $IgG_1$, $IgG_2$, $IgG_3$, or $IgG_4$). In some embodiments, the first and second Fab are the same subclass (i.e. both are $IgG_1$, or both are $IgG_2$, or both are $IgG_3$, or both are $IgG_4$).

In alternative embodiments, the first Fab is of a different subclass to the second Fab (i.e. the first Fab and second Fab may each be of a different subclass, and each may be selected from the group consisting of $IgG_1$, $IgG_2$, $IgG_3$, $IgG_4$, $IgA_1$ or $IgA_2$). For example, the antibody of the invention may comprise a first Fab from one antibody sub-class (for example, selected from the group consisting of $IgG_1$, $IgG_2$, $IgG_3$, $IgG_4$, $IgA_1$ or IgA2), and a second Fab from a different sub-class (for example, selected from the group consisting of $IgG_1$, $IgG_2$, $IgG_3$, $IgG_4$, $IgA_1$ or $IgA_2$, provided the second Fab is of a different subclass to the first Fab), and first and second $C_H2$ domains and first and second $C_H3$ domains from a single antibody class (for example, selected from the group consisting of $IgG_1$, $IgG_2$, $IgG_3$, $IgG_4$, $IgA_1$ or $IgA_2$).

In another aspect of the invention, the antibody or Fab region thereof (e.g., bispecific antibody) as described herein comprises a full-length human antibody, wherein a first antibody variable domain of the antibody or Fab thereof is capable of recruiting the activity of a human immune effector cell by specifically binding to an effector antigen located on the human immune effector cell, wherein a second antibody variable domain of the heterodimeric protein is capable of specifically binding to a target antigen. In some embodiments, the human antibody has an $IgG_1$, $IgG_2$, $IgG_3$, or $IgG_4$ isotype.

Except where indicated otherwise by context, the terms "first" and "second", and variations thereof, are merely generic identifiers, and are not to be taken as identifying a specific or a particular $C_H1$, $C_L$, $V_H$, $V_L$, $C_H2$, $C_H3$, or Fab.

In another aspect of the invention, a heterodimeric protein disclosed herein may be deimmunized to reduce immunogenicity upon administration to a subject using known techniques such as those described, e.g. in PCT Publication WO98/52976 and WO00/34317.

In other embodiments, a heterodimeric protein may be modified or derivatized, such as by making a fusion antibody or immunoadhesin that comprises all or a portion of the heterodimeric polypeptide, e.g. bispecific antibody disclosed herein, linked to another polypeptide or molecular agent. Heteromultimeric, e.g. heterodimeric polypeptides disclosed herein (e.g., bispecific antibodies) may be modified or derivatized, for example, to extend in vivo half-lives, by producing more stable fusion molecules and/or by treatment with biocompatible polymers such as polyethylene glycol (PEG), commonly referred to as "pegylation," or by any of a number of other engineering methods well known in the art.

A heterodimeric protein may be derivatized with a chemical group, including but not limited to polyethylene glycol (PEG), a methyl or ethyl group, an ester, a carbohydrate group and the like, using well known techniques. These chemical groups (and others like them which have been used to stability therapeutic compounds in vivo) are useful to improve the biological characteristics of the heterodimeric polypeptide, e.g., to increase serum half-life and bioactivity.

A heterodimeric protein may also be labeled using any of a multitude of methods known in the art. As used herein, the terms "label" or "labeled" refers to incorporation of another molecule in the antibody. In one embodiment, the label is a detectable marker, e.g., incorporation of a radio labeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.
Nucleic Acids and Methods of Producing Polypeptides and Heterodimeric Proteins of the Invention In some embodiments, different nucleic acid molecules encode one or more chains or portions of the heterodimeric protein, e.g. bispecific antibody disclosed herein. In other embodiments, the same nucleic acid molecule encodes a heterodimeric protein disclosed herein.

In one aspect, the present invention provides a nucleic acid sequence encoding one of the chains of a heterodimeric protein disclosed herein, or portion thereof as described above. Nucleic acid molecules of the invention include nucleic acids that hybridize under highly stringent conditions, such as those at least about 70%, 75%, 80%, 85%, 90%, 95%, 97%, 98% or 99% or more identical to a nucleic acid sequence of the invention.

In some aspects, the nucleic acid is DNA. In some aspects, the nucleic acid is RNA. In some aspects, the nucleic acid is mRNA. In some aspects, the nucleic acid is a non-natural nucleic acid, such as PNA (peptide nucleic acid), morpholino and locked nucleic acid, glycol nucleic acid, and threose nucleic acid.

In a further aspect, the present invention provides a vector comprising a nucleic acid sequence encoding one or more of the chains or portions of the heteromultimeric or heterodimeric protein disclosed herein, or portion thereof as described herein.

In a further aspect, the present invention provides a vector suitable for expressing one or more of the chains or portions of the heterodimeric protein disclosed herein, or portion thereof as described herein. In some aspects, the invention provides for a vector that comprises a nucleic acid of the invention.

In another embodiment, a nucleic acid molecule of the invention is used as a probe or PCR primer for a specific amino acid sequence, e.g. a specific antibody sequence such as in the hinge and constant heavy domain sequences. For instance, the nucleic acid can be used as a probe in diagnostic methods or as a PCR primer to amplify regions of DNA that could be used, inter alia, to isolate additional nucleic acid molecules encoding useful sequences. In some embodiments, the nucleic acid molecules are oligonucleotides. In some embodiments, the oligonucleotides are from hinge and constant domain regions of the heavy and light chains of an antibody of interest. In some embodiments, the oligonucleotides encode all or a part of one or more of the modified Fab regions of the heterodimeric polypeptide, e.g. bispecific antibodies or fragments thereof of the invention as described herein.

Recombinant expression vectors of the invention may, in some embodiments, carry regulatory sequences that control the expression of antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g. the adenovirus major late promoter (AdMLP)), polyoma and strong mammalian promoters such as native immunoglobulin and actin promoters.

In addition to the antibody chain genes and regulatory sequences, the recombinant expression vectors of the invention may carry additional sequences, such as sequences that regulate replication of the vector in host cells (e.g. origins of replication) and selectable marker genes. For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr⁻ host cells with methotrexate selection/amplification), the neo gene (for G418 selection), and the glutamate synthetase gene.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

In some aspects, the invention comprises a nucleic acid encoding at least one $C_H1$, or $C_L$ of the invention. The invention further provides for nucleic acids that encode for a Fab of the invention. In some aspects, the invention provides for a nucleic acid that encodes for a first Fab of the invention. In some aspects, the invention provides for a nucleic acid that encodes for a second Fab of the invention.

In some aspects, the invention provides for a nucleic acid that encodes a first heavy chain of the invention. In some aspects, the invention provides for a nucleic acid that encodes a second heavy chain of the invention. In some aspects, the invention provides for a nucleic acid that encodes a first light chain of the invention. In some aspects, the invention provides for a nucleic acid that encodes a second light chain of the invention.

In some aspects, the invention provides for a cell that comprises a vector of the invention. In some aspects, the invention provides for a cell that comprises a nucleic acid of the invention. In some aspects, the invention provides for a cell that expresses a nucleic acid of the invention.

Favorably, the invention provides for a cell that expresses a heterodimeric protein as herein described. Co-expressing the first $C_HC_L$ and second $C_HC_L$ in the same cell takes advantage of the complementary residue sets that allow for correct formation of the heteromultimeric protein. In some aspects, this permits a bispecific antibody to be expressed and generated in a fully assembled form, and requires little to no additional purification or processing steps over what would be typically required for purification of a monoclonal antibody.

In some aspects, bispecific antibodies of the invention may be used in mRNA replacement therapy or RNA transcript therapy. Accordingly, in some aspects, the invention comprises a cell, or vector, comprising one or more nucleic acids encoding one or more polypeptide chains of the invention, such that expression of the polypeptide chains of the invention in vivo result in the generation of a bispecific antibody in vivo. Delivery mechanisms for such vectors include lipid based systems and nanoparticles (see for example, WO2010053572, WO2012170930 and WO2011068810, each of whose contents is incorporated entirely).

In some aspects, the invention further comprises a transfer vehicle, defined herein as any of the standard pharmaceutical carriers, diluents, excipients and the like which can be used in connection with the administration of biologically active agents, including nucleic acids. The compositions and in particular the transfer vehicles described herein are capable of delivering nucleic acids of the invention to the target cell. In some embodiments, the transfer vehicle is a lipid nanoparticles, suitable for transferring mRNA to a target cell.

In some aspects, the invention comprises an mRNA encoding a bispecific antibody of the invention, a transfer vehicle and, optionally, an agent to facilitate contact with, and subsequent transfection of a target cell.

In some embodiments the mRNA encoding one or more polypeptides of the invention can comprise one or more modifications that confer stability to the mRNA (e.g., compared to a wild-type or native version of the mRNA). For example, the nucleic acids of the present invention may comprise modifications to one or both of the 5' and 3' untranslated regions. Such modifications may include, but are not limited to, the inclusion of a partial sequence of a cytomegalovirus (CMV) immediate-early 1 (IE1) gene, a poly A tail, a Capl structure or a sequence encoding human growth hormone (hGH)). In some embodiments, the mRNA is modified to decrease mRNA immunogenicity.

In some embodiments, the mRNA of the invention have undergone a chemical or biological modification to render them more stable. Exemplary modifications to an mRNA include the depletion of a base (e.g. by deletion or by the substitution of one nucleotide for another) or modification of a base, for example, the chemical modification of a base. In some aspects, a poly A tail can be added to an mRNA molecule thus rendering the mRNA more stable.

In some aspects, the transfer vehicle in the compositions of the invention is a liposomal transfer vehicle, e.g. a lipid nanoparticle. The transfer vehicle may be selected and/or prepared to optimize delivery of the mRNA to a target cell. For example, if the target cell is a hepatocyte the properties of the transfer vehicle (e.g., size, charge and/or pH) may be optimized to effectively deliver such transfer vehicle to the target cell, reduce immune clearance and/or promote retention in that target cell. Alternatively, if the target cell is the central nervous system (e.g. mRNA administered for the treatment of neurodegenerative diseases may specifically target brain or spinal tissue), selection and preparation of the transfer vehicle must consider penetration of, and retention within the blood brain barrier and/or the use of alternate means of directly delivering such transfer vehicle to such target cell. In some aspects, the compositions of the present invention may be combined with agents that facilitate the transfer of exogenous mRNA (e.g. agents which disrupt or improve the permeability of the blood brain barrier and thereby enhance the transfer of exogenous mRNA to the target cells).

The use of liposomal transfer vehicles to facilitate the delivery of nucleic acids to target cells is contemplated by the present invention. In some aspects, the transfer vehicle is formulated as a lipid nanoparticle. Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides). Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, dendrimers and polyethylenimine.

The invention contemplates the use of lipid nanoparticles as transfer vehicles comprising a cationic lipid to encapsulate and/or enhance the delivery of mRNA into the target cell that will act as a depot for protein production. As used herein, the phrase "cationic lipid" refers to any of a number of lipid species that can a net positive charge at a selected pH, such as physiological pH.

In one aspect, this invention provides a strategy for enhancing the formation of a bispecific antibody, by altering or engineering an interface between the light chain and the heavy chain of one or more Fab regions of the antibody. In some embodiments, one or more residues that make up the $C_H1/C_L$ interface of the one more Fab regions are replaced with residues such that the modified residues favor pairing of the specific heavy and light chain of the modified Fab region over mispairing with heavy chains or light chains of other Fab regions in the protein. In one embodiment, the modifications introduce novel disulfide bridges in the Fab region. In another embodiment, the modifications introduce disrupting mutations that disrupt the native interface between the $C_H1$ and $C_L$ domains of a Fab region, as well as restoring modifications that introduce non-native stable interactions at the interface. In another embodiment, the disrupting mutations may introduce both novel disulfide bridges and disrupting and restoring mutations.

In some embodiments, the formation of the heterodimeric protein comprising one or more amino acid modifications in the $C_H1/C_L$ interface of one or more Fab regions disclosed herein is substantially increased in comparison to the wild-type heterodimeric protein without such modifications. In some embodiments, the formation of the heterodimeric protein comprising one or more amino acid modifications in $C_H1/C_L$ interface of at least one Fab region is at least about any of 51%, 55%, 60%, 65%, 70%, 75%, 80%, 85%, 90%, 95%, 97%, 99%, or 100% in comparison to the wild-type heterodimeric protein without such modifications.

In another aspect, the present invention also provides methods of producing a heteromultimeric protein, e.g. a heterodimeric protein of the invention, such as a bispecific antibody. In some embodiments, the method comprises the steps of:

a) cotransfecting a cell line with vectors expressing each heavy chain and each light chain of each Fab region of the protein;

b) culturing the cell line under conditions to express each heavy chain and each light chain of each Fab region of the protein and that allow the heteromultimeric protein to assemble; and c) purifying the heteromultimeric protein from the cell culture. In some embodiments, the cell line is cotransfected with vectors that express the heavy chain and the light chain of each Fab region in a 1:1:1:1 ratio.

In some embodiments, the method comprises the steps of:
(i) cotransfecting a cell line with one or more vectors to express the first $C_H1$, the first $C_L$ of the first $C_HC_L$; and the second $C_H1$, and the second $C_L$ of the second $C_HC_L$;
(i) culturing the cell line under conditions to express the one or more vectors and that allow the first $C_HC_L$ and second $C_HC_L$ to assemble; and
(ii) purifying the heteromultimeric protein from the cell culture.

In some aspects, the cell line is cotransfected with vectors that express the first $C_H1$, first $C_L$, second $C_H1$, and second $C_L$ in a 1:1:1:1 ratio.

The skilled artisan can readily determine, using well-known techniques, the relative amounts of molecules or antibodies to use according to the methods disclosed herein.

In the methods disclosed herein, incubations may be performed across a range of temperatures. Such temperatures will be recognized by those skilled in the art and will include, for example, incubation temperatures at which deleterious physical changes such as denaturation or decomposition do not occur in the mixed molecules or antibodies. In certain embodiments, the incubations are performed at about 37° C.

Any of a number of host cells may be used in methods of the invention. Such cells are known in the art (some of which are described herein) or can be determined empirically with respect to suitability for use in methods of the invention using routine techniques known in the art. In certain embodiments, the host cell is prokaryotic. In some embodiments, a host cell is a gram-negative bacteria cell. In other embodiments, a host cell is E. coli. In some embodiments, the E. coli is of a strain deficient in endogenous protease activities. In some embodiments, the genotype of an E. coli host cell lacks degP and prc genes and harbors a mutant spr gene. In other embodiments of the invention, the host cell is mammalian, for example, a Chinese Hamster Ovary (CHO) cell.

In some embodiments, methods of the invention further comprise expressing in a host cell a polynucleotide or recombinant vector encoding a molecule the expression of which in the host cell enhances yield of a bispecific antibody or a heterodimeric protein of the invention. For example, such molecule can be a chaperone protein. In one embodiment, said molecule is a prokaryotic polypeptide selected from the group consisting of DsbA, DsbC, DsbG and FkpA. In some embodiments of these methods, the polynucleotide encodes both DsbA and DsbC.

In one aspect, the present invention provides recombinant host cells allowing the recombinant expression of the antibodies of the invention or portions thereof. Antibodies produced by such recombinant expression in such recombinant host cells are referred to herein as "recombinant antibodies". The present invention also provides progeny cells of such host cells, and antibodies produced by same. The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein. Such cell may comprise a vector according to the invention as described above.

In another aspect, the present invention provides a method for making an antibody or portion thereof as described above. According to one embodiment, said method comprises culturing a cell transfected or transformed with a vector as described above, and retrieving said antibody or portion thereof. Nucleic acid molecules encoding antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455. Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NSO cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Suitable plant host cells may include, e.g., *Nicotiana, Arabidopsis*, duckweed, corn, wheat, potato, etc. Suitable bacterial host cells may include, e.g., *E. coli* and *Streptomyces* species. Suitable yeast host cells may include, e.g., *Schizosaccharomyces pombe, Saccharomyces cerevisiae* and *Pichia pastoris*.

Expression of polypeptides of the invention or portions thereof from production cell lines can be enhanced using a number of known techniques. For example, the glutamine synthetase gene expression system (the GS system) is a common approach for enhancing expression under certain conditions. The GS system is discussed in whole or in part in connection with EP0216846, EP0256055, EP0323997, and EP0338841.

It is likely that polypeptides comprising Fc polypeptides or Fc regions and immunoglobulin-like hinge polypeptides, such as antibodies, as expressed by different cell lines or in transgenic animals, will differ from each other in their glycosylation patterns. All such "glycoforms" of polypeptides of the invention, including all heterodimers of polypeptides comprising immunoglobulin-like hinge sequences, bispecific polypeptides, antibodies and the like, are considered to be part of the instant invention, regardless of their glycosylation state, and more generally, regardless of the presence or absence of any post-translational modification(s).

In some embodiments, heterodimeric protein is an antibody, a maxibody, a monobody, a peptibody, an Fc fusion protein, or Fab region of any of the foregoing. In some embodiments, the heterodimeric protein is a bispecific antibody.

The heterodimeric protein thereof may comprise one or more human domains. The heterodimeric protein may comprise one or more humanized Ig domains. The heterodimeric protein may comprise one or more murine Ig domains. The heterodimeric protein may comprise one or more Ig domains originating from a species selected from the group consisting of human, monkey, mouse, rat, hamster, guinea pig, rabbit, dog, cat, donkey, goat, camel, cow, horse, pig, chicken, and shark.

In some aspects, the antibodies of the invention are mammalian, avian, or Squaliform in origin (notwithstanding the method used to generate any artificially mutated or otherwise engineered versions). The mammalian, avian, or squaliform species may be human, mouse, rabbit, rat, rodent, pig, cow, sheep, goat, donkey, horse, camel, llama, primate, monkey, dog, cat, chicken, or spiny dogfish. The antibodies of the invention may be humanized.

In some aspects, the invention comprises mutant antibodies and portions thereof, wherein a mutant is defined as sequence that has been engineered or altered to a sequence other than its natural canonical sequence, such that certain embodiments of polypeptides of the invention specifically excludes naturally occurring sequences that fall within the scope of the definition. In some aspects, therefore, the present invention relates to polypeptides of the invention comprising mutations to enable heterodimeric Ig-domain pairing such that the Ig domain polypeptide sequence differs from its naturally occurring corresponding sequence.

Antibody $C_H1$ domains may be selected from the group consisting of $C_H\alpha1$, $C_H\delta1$, $C_H\varepsilon1$, $C_H\gamma1$, and $C_H\mu1$.

In some aspects, the constant light chain ($C_L$) domain of the invention is connected to a variable light chain ($V_L$) domain. Together, these may comprise an antibody light chain. The $C_L$ domain may be a $C_L\kappa$ (constant light chain kappa). The $C_L$ domain may be a $C_L\lambda$ (constant light chain lambda).

In some aspects, the $C_H1$ domain of the invention is connected to a variable heavy chain ($V_H$) domain. Together, these may comprise the heavy chain portion of a Fab molecule. In some aspects, the $V_H$ and $C_H1$ domains are connected to the remainder of the $C_H$ domains typical for that particular Ig isotype (i.e. $C_H\alpha1$ may be connected to $C_H\alpha2$, and $C_H\alpha3$; $C_H\delta1$ may be connected to $C_H\delta2$ and $C_H\delta3$; $C_H\varepsilon1$ may be connected to $C_H\varepsilon2$, $C_H\varepsilon3$, and $C_H\varepsilon4$; $C_H\gamma1$ may be connected to $C_H\gamma2$, and $C_H\gamma3$; $C_H\mu1$ may be connected to $C_H\mu2$, $C_H\mu3$, and $C_H\mu4$).

In some aspects, the invention provides for an isolated host cell that recombinantly produces an antibody of the present invention. The present invention provides for an isolated polynucleotide comprising a nucleotide sequence encoding proteins, domains and antibodies of the present invention, and vectors comprising said polynucleotides. In some aspects, the invention provides for a method of producing an antibody, immunoglobulin domain, or protein, comprising culturing a host cell under conditions that result in production of the antibody, immunoglobulin domain, or protein, and isolating the antibody, immunoglobulin domain, or protein, from the host cell or culture.

The invention provides improved methods, compositions, kits and articles of manufacture for generating heteromultimeric complex molecules, more preferably, heterodimeric proteins, such as, e.g. a bispecific antibody. The invention provides methods to make and to purify heteromultimeric complex molecules in yields and purities desirable for commercial manufacture of biotherapeutics. The invention makes possible efficient production of complex molecules that, in turn, can be used for diagnosing and/or treating various disorders or conditions where use of multispecific antibodies is desirable and/or required. Details of methods, compositions, kits and articles of manufacture of the invention are provided herein.

Methods of Using Proteins of the Invention

The present invention also provides various therapeutic applications for the proteins of the invention. In one aspect, the proteins of the invention can be used for treating various diseases (e.g. cancer, autoimmune diseases, or viral infections) by binding the first protein (e.g. first human antibody variable domain) to an effector antigen and by binding the second protein (e.g. second human antibody variable domain) to a target antigen. For example, the proteins of the invention can be used for redirecting cytotoxicity, delivering thrombolytic agents to clots, for delivering immunotoxins to tumor cells, or for converting enzyme activated prodrugs at a target site (e.g. a tumor).

In another aspect, the proteins of the invention can be used for increasing specificity of a therapeutic agent and/or modulating synergistic or additive pathways (e.g. metabolic or biochemical pathways). For example, the proteins of the invention can engage receptor/receptor, receptor/ligand, ligand/ligand, cell/cell, ligand/payload, receptor/payload, or single receptor.

Pharmaceutical Compositions

The invention provides a pharmaceutical composition comprising proteins of the invention of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, polyalcohols such as mannitol, sorbitol, or sodium chloride in the composition, and may include pharmaceutically acceptable substances such as wetting or minor amounts of auxiliary substances such as wetting or emulsifying agents, preservatives or buffers, which enhance the shelf life or effectiveness of the antibody or antibody portion.

In certain embodiments, the proteins of the invention may be present in a neutral form (including zwitter ionic forms) or as a positively or negatively-charged species. In some embodiments, the polypeptides may be complexed with a counterion to form a "pharmaceutically acceptable salt," which refers to a complex comprising one or more polypeptides and one or more counterions, where the counterions are derived from pharmaceutically acceptable inorganic and organic acids and bases.

The compositions of this invention may be in a variety of forms. These include, for example, liquid, semi-solid and solid dosage forms, such as liquid solutions (e.g. injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with antibodies in general. The preferred mode of administration is parenteral (e.g. intravenous, subcutaneous, intraperitoneal, intramuscular). In a preferred embodiment, the protein of the invention is administered by intravenous infusion or injection. In another preferred embodiment, the protein of the invention is administered by intramuscular or subcutaneous injection.

The pharmaceutical composition may further comprise another component, such as an anti-tumor agent or an imaging reagent. Another aspect of the present invention provides kits comprising antibodies of the invention and pharmaceutical compositions comprising these antibodies. A kit may include, in addition to the antibody or pharmaceutical composition, diagnostic or therapeutic agents. A kit may also include instructions for use in a diagnostic or therapeutic method. In some embodiments, the kit includes the antibody or a pharmaceutical composition thereof and a diagnostic agent. In other embodiments, the kit includes the antibody or a pharmaceutical composition thereof and one or more therapeutic agents, such as an additional antineoplastic agent, anti-tumor agent or chemotherapeutic agent.

These agents and compounds of the invention can be combined with pharmaceutically acceptable vehicles such as saline, Ringer's solution, dextrose solution, and the like. The particular dosage regimen, i.e. dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy, 20th Ed., Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic compounds of the invention are generally placed into a container having a sterile access port, for example, an intravenous solution bag or vial having a stopper pierceable by a hypodermic injection needle.

An exemplary, non-limiting pharmaceutical composition of the invention is a formulation as a sterile aqueous solution having a pH that ranges from about 5.0 to about 6.5 and comprising from about 1 mg/mL to about 200 mg/mL of a composition comprising a heterodimeric protein of the invention, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dihydrate.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders.

The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compounds and compositions of the invention may be used in conjunction with established treatments for the relevant indication.

Therapeutic Methods of the Invention

Therapeutic methods are also provided by the invention. A therapeutic method comprises administering a compound or composition of the invention to a subject in need thereof.

As used herein, an "effective dosage" or "effective amount" of drug, compound, or pharmaceutical composition is an amount sufficient to affect any one or more beneficial or desired results. For prophylactic use, beneficial or desired results include eliminating or reducing the risk, lessening the severity, or delaying the outset of the disease, including biochemical, histological and/or behavioural symptoms of the disease, its complications and intermediate pathological phenotypes presenting during development of the disease. For therapeutic use, beneficial or desired results include clinical results such as reducing tumor size, spread, vasculature of tumors, or one or more symptoms of cancer or other diseases associated with increased angiogenesis, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, and horses.

For administration to human subjects, the total monthly dose of an antibody of the invention is typically in the range of about 0.5 to about 1200 mg per patient, depending on the mode of administration. For example, an intravenous monthly dose may require about 1 to about 1000 mg/patient. The total monthly dose may be administered in single or divided doses and may, at the physician's discretion, fall outside of the typical range given herein.

An exemplary, non-limiting range for a therapeutically or prophylactically effective amount of a heterodimeric protein, e.g. a bispecific antibody or portion thereof, disclosed herein is about 1 to about 1000 mg/patient/month. In certain embodiments, the heterodimeric protein may be administered at about 1 to about 200 or about 1 to about 150 mg/patient/month.

Administration of compounds of the invention in accordance with the method in the present invention can be continuous or intermittent, depending, for example, upon the recipient's physiological condition, whether the purpose of the administration is therapeutic or prophylactic, and other factors known to skilled practitioners. The administration of a compound of the invention may be essentially continuous over a preselected period of time or may be in a series of spaced doses.

Antibodies

An "Antibody" is an immunoglobulin molecule capable of specific binding to a target or antigen, such as a carbohydrate, polynucleotide, lipid, polypeptide, etc., through at least one antigen-binding site, located in the variable region of the immunoglobulin molecule.

As used herein, unless otherwise indicated by context, the term is intended to encompass not only intact polyclonal or monoclonal antibodies comprising two identical full-length heavy chain polypeptides and two identical light chain polypeptides, but also fragments thereof (such as Fab, Fab', F(ab')$_2$, Fv), single chain (ScFv) and domain antibodies (dAbs), including shark and camelid antibodies, and fusion proteins comprising an antibody portion, multivalent antibodies, multispecific antibodies (e.g. bispecific antibodies so long as they exhibit the desired biological activity) and antibody fragments as described herein, and any other modified configuration of the immunoglobulin molecule that comprises an antigen recognition site, for example without limitation, minibodies, maxibodies, monobodies, peptibodies, intrabodies, diabodies, triabodies, tetrabodies, v-NAR and bis-scFv.

Antigen-binding portions may be produced by recombinant DNA techniques or by enzymatic or chemical cleavage of intact antibodies. Antigen-binding portions include, inter alia, Fab, Fab', F(ab')2, Fv, dAb, and complementarity determining region (CDR) fragments, single-chain antibodies (scFv), chimeric antibodies, diabodies and polypeptides that contain at least a portion of an Ig that is sufficient to confer specific antigen binding to the polypeptide.

The immunoglobulin (Ig) domain is a type of protein domain that typically consists of a 2-layer sandwich of between 7 and 9 β-strands arranged in two β-sheets (although variations on these arrangements are known). A β-strand is a stretch of polypeptide chain typically 3 to 10 amino acids long with backbone in an almost fully extended conformation. β sheets consist of β-strands connected laterally by at least two or three backbone hydrogen bonds, forming a generally twisted, pleated sheet. The backbone of a strand switches repeatedly between interacting with its two opposite neighboring strands in the sheet, or between sheet and non-sheet interactions for strands at the sheet edge. Members of the Ig superfamily are found in hundreds of proteins of different functions. Examples include antibodies, the giant muscle kinase titin and receptor tyrosine kinases. Ig-like domains may be involved in protein—protein and protein—ligand interactions.

An immunoglobulin (Ig) is a heteromultimeric molecule. In a naturally occurring Ig, each multimer is composed primarily of identical pairs of polypeptide chains, each pair having one "light" (about 25 kDa) and one "heavy" chain (about 50-70 kDa).

The amino-terminal portion of each chain includes a variable region, of about 100 to 110 or more amino acids primarily responsible for antigen recognition. The carboxy-terminal portion of each chain defines a constant region primarily responsible for effector function. Human light chains are classified as κ and λ light chains. Heavy chains are classified as α, δ, ε, γ, and μ, and define the antibody's isotype as IgA, IgD, IgE, IgG, IgM, respectively. Several of these classes may be further subdivided into isotypes: IgG1, IgG2, IgG3, IgG4, IgA1, and IgA2.

Within light and heavy chains, the variable and constant regions are joined by a "J" region of about 12 or more amino acids, with the heavy chain also including a "D" region of about 10 more amino acids (in the context of an entire antibody sequence, the D and J regions are sometimes considered as parts of the variable region after they have been joined). The variable regions of each light/heavy chain pair form the antibody binding site such that an intact Ig has 2 binding sites.

Each domain in an antibody molecule has a similar structure of two β-sheets packed tightly against each other in a compressed antiparallel β-barrel. This conserved structure is termed the immunoglobulin (Ig) fold. The Ig fold of constant domains contains two β sheets packed against each other, with each strand separated by a contiguous polypeptide string; these contiguous polypeptide strings typically comprise α-helices, loops, turns, and short, sharp turns between two β-sheets called β-hairpins.

Variable domains exhibit the same general structure of relatively conserved framework regions (FR) joined by 3 hypervariable regions, also called complementarity determining regions or CDRs. The CDRs from the 2 chains of each pair are aligned by the framework regions, enabling binding to a specific epitope. From N-terminus to C-terminus, both light and heavy chains comprise the domains FR1, CDR1, FR2, CDR2, FR3, CDR3 and FR4.

The identity of the amino acid residues in a particular antibody that make up a CDR can be determined using methods well known in the art. For example, antibody CDRs may be identified as the hypervariable regions originally defined by Kabat et al (Kabat et al., 1991, Sequences of Proteins of Immunological Interest, 5th ed., Public Health Service, NIH, Washington D.C., NIH Publication No. 91-3242). The positions of the CDRs may also be identified as the structural loop structures described by Chothia and others (Chothia et al., 1989, Nature 342:877-883). Other approaches to CDR identification include the "AbM definition," which is a compromise between Kabat and Chothia and is derived the Abysis program (www.abysis.org), or the "contact definition" of CDRs based on observed antigen contacts, set forth in MacCallum et al., 1996, J. Mol. Biol., 262:732-745. North has identified canonical CDR conformations using a different preferred set of CDR definitions (North et al., 2011, J. Mol. Biol, 406: 228-256). In another approach, referred to herein as the "conformational definition" of CDRs, the positions of the CDRs may be identified as the residues that make enthalpic contributions to antigen binding (Makabe et al., 2008, Journal of Biological Chemistry, 283:1156-1166). Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs (or other residue of the antibody) may be defined in accordance with any of Kabat, Chothia, North, extended, AbM, contact, and/or conformational definitions.

Except where indicated otherwise explicitly or by context, all $C_H1$ residue numbering positions herein described are according to the numbering of SEQ ID NO:1, and all $C_L$ residue positions are herein described according to the numbering of SEQ ID NO:9. This numbering is most closely related to the numbering of Kabat, which is used herein except (a) in cases such as IgM domain where certain experimental data has shown Kabat to be incorrect, (b) when Kabat's reference is internally inconsistent, or (c) when otherwise noted. In the original Kabat reference, position 107A is the first residue of the $C_L$. Many light chain sequences do not have any residue assigned to position 107A and many also do not have a residue at position 108. The first residue of $C_L$ is the first residue numbered greater than 107, whatever that may be.

A $C_H1$ domain is a region of protein sequence, preferably at least 80 residues in length, and having more than 85% of its residues in common with one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41. In some aspects, a $C_H1$ domain is protein sequence having more than 85% of its residues in common with SEQ ID NO:1.

A $C_H2$ domain is a is a region of protein sequence, preferably at least 80 residues in length, and having more than 85% of its residues in common with one or more of SEQ ID NO:13, SEQ ID NO:14, SEQ ID NO:15, SEQ ID NO:16, SEQ ID NO:17, or SEQ ID NO:45. In some aspects, a $C_H2$ domain is protein sequence having more than 85% of its residues in common with SEQ ID NO:13.

A hinge region is a region of protein sequence having more than 80% identity with one or more of SEQ ID NO:42, SEQ ID NO:43, SEQ ID NO:44, SEQ ID NO:79, SEQ ID NO:80, or SEQ ID NO:81. In some aspects, a hinge region is protein sequence having more than 80% of its residues in common with SEQ ID NO:42.

A $C_H3$ domain is a region of protein sequence, preferably at least 80 residues in length, and having more than 85% of its residues in common with one or more of SEQ ID NO:18, SEQ ID NO:19, SEQ ID NO:20, SEQ ID NO:21, SEQ ID NO:22, SEQ ID NO:23, SEQ ID NO:46, SEQ ID NO:47, SEQ ID NO:48, or SEQ ID NO:49. In some aspects, a $C_H3$ domain is protein sequence having more than 85% of its residues in common with SEQ ID NO:18.

A $C_L$ domain is a region of protein sequence preferably at least 80 residues in length, and having more than 85% of its residues in common with one or more of SEQ ID NO:9, SEQ ID NO:10, SEQ ID NO:11, SEQ ID NO:12, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32. In some aspects, the $C_L$ domain is a $C_L$ kappa domain, and shares at least 85% identity with one or more of SEQ ID NO:9, SEQ ID NO:10, or SEQ ID NO:11. In some aspects, the $C_L$ domain is a $C_L$ lambda domain, and shares at least 85% identity with SEQ ID NO:12. In some aspects, a $C_L$ domain is protein sequence having more than 85% of its residues in common with SEQ ID NO:9.

Mammalian light chains are of two types, κ and λ, and in any given naturally occurring antibody molecule only one type occurs. Approximately twice as many κ as λ molecules are produced in humans but in other mammals this ratio can vary. Each free light chain molecule contains approximately 220 amino acids in a single polypeptide chain that is folded to form the constant and variable region domains.

During B cell development, a recombination event at the DNA level joins a single variable (V) segment with a joining (J) segment; the constant (C) segment is later joined by splicing at the RNA level. Recombination of many different V segments with several J segments provides a wide range of antigen recognition. Additional diversity is attained by junctional diversity, resulting from the random additional of nucleotides by terminal deoxynucleotidyltransferase, and by somatic hypermutation, which occurs during B cell maturation in the spleen and lymph nodes. Constant kappa (CLκ) regions are encoded by a single gene, whereas lambda constant (CLλ) regions are encoded by multiple genes, and undergo splicing. Several markers associated with particular polymorphic species of CLλ are known: IgCLλ1 (Mcg marker); IgLC2-IgCLλ2 (Kern-Oz-marker); IgCLλ 3 (Kern-Oz+ marker), and IgCLλ7, for example. The skilled person can easily establish all of the polymorphisms so far identified in human CLλ chains. The sequences of the present invention encompass other known polymorphisms of the CLκ and CLλ, and antibodies in general. Two polymorphic loci have been identified in the CLκ; CLκ-V/A$^{153}$ and CLκ-L/V$^{191}$. The three polymorphisms so far identified are: Km(1): CLκ-V$^{153}$/L$^{191}$; Km(1,2): CLκ-A$^{153}$/L$^{191}$; and Km(3): CLκ-A$^{153}$/V$^{191}$.

The term "Fc region" as used herein generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. The Fc sequence of an immunoglobulin generally comprises two constant domains, a $C_H2$ domain and a $C_H3$ domain, and optionally comprises a $C_H4$ domain. The term "Fc polypeptide" is used herein to refer to one of the polypeptides that makes up an Fc region. In some embodiments, an Fc polypeptide may be obtained or derived from any suitable immunoglobulin, such as from at least one of the various IgG1, IgG2, IgG3, or IgG4 subtypes, or from IgA, IgE, IgD or IgM. In some embodiments, an Fc polypeptide comprises part or all of a wild-type hinge sequence (generally at its N terminus). In some embodiments, an Fc polypeptide does not comprise a wild-type hinge sequence. An Fc polypeptide may comprise native or variant Fc sequences.

The "immunoglobulin-like hinge region," "immunoglobulin-like hinge sequence," and variations thereof, as used herein, refer to the hinge region and hinge sequence of an immunoglobulin-like or an antibody-like molecule (e.g. immunoadhesins). In some embodiments, the immunoglobulin-like hinge region can be from or derived from any IgG1, IgG2, IgG3, or IgG4 subtype, or from IgA, IgE, IgD or IgM, including chimeric forms thereof, e.g. a chimeric IgG1/2 hinge region.

"Antibody fragments" comprise only a portion of an intact antibody, wherein the portion preferably retains at least one, preferably most or all, of the functions normally associated with that portion when present in an intact antibody.

A "bivalent antibody" comprises two antigen binding sites per molecule (e.g. IgG). In some instances, the two binding sites have the same antigen specificities. However, bivalent antibodies may be bispecific (see below).

A "monovalent antibody" comprises one antigen binding site per molecule (e.g. IgG). In some instances, a monovalent antibody can have more than one antigen binding site, but the binding sites are from different antigens.

A "multispecific antibody" is one that targets more than one antigen or epitope. A "bispecific," "dual-specific" or "bifunctional" antibody is a hybrid antibody having two different antigen binding sites. Bispecific antibodies are a species of multispecific antibody and may be produced by a variety of methods including, but not limited to, fusion of hybridomas or linking of Fab' fragments. See, e.g. Songsivilai & Lachmann (1990), *Clin. Exp. Immunol.* 79:315-321; and Kostelny et al. (1992), *J. Immunol.* 148:1547-1553. The two binding sites of a bispecific antibody will bind to two different epitopes, which may reside on the same or different protein targets.

The phrase "antigen binding arm," "target molecule binding arm," and variations thereof, as used herein, refers to a component part of an antibody of the invention that has an ability to specifically bind a target molecule of interest. Generally and preferably, the antigen binding arm is a complex of immunoglobulin polypeptide sequences, e.g. CDR and/or variable domain sequences of an immunoglobulin light and heavy chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Further, in contrast to polyclonal antibody preparations that typically include different antibodies directed against different determinants (epitopes), each monoclonal antibody is directed against a single determinant on the antigen.

As used herein, the term "immunoadhesin" designates antibody-like or immunoglobulin-like molecules which combine the "binding domain" of a heterologous protein (an "adhesin", e.g. a receptor, ligand or enzyme) with the effector component of immunoglobulin constant domains. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as IgG1, IgG2, IgG3, or IgG4 subtypes, IgA, IgE, IgD or IgM.

A Fab fragment is a monovalent fragment consisting of the $V_L$, $V_H$, $C_L$ and $C_H1$ domains; a F(ab')2 fragment is a bivalent fragment comprising two Fab fragments linked by a disulfide bridge at the hinge region; a Fd fragment consists of the $V_H$ and $C_H1$ domains; an Fv fragment consists of the $V_L$ and $V_H$ domains of a single arm of an antibody; and a dAb fragment consists of a $V_H$ domain or a $V_L$ domain (e.g. human, camelid, or shark).

A single-chain antibody (scFv) is an antibody in which a $V_L$ and $V_H$ region are paired to form a monovalent molecule via a synthetic linker that enables them to be made as a single protein chain. Diabodies are bivalent, bispecific antibodies in which $V_H$ and $V_L$ domains are expressed on a single polypeptide chain, but using a linker that is too short to allow for pairing between the 2 domains on the same chain, thereby forcing the domains to pair with complementary domains of another chain and creating 2 antigen binding sites. One or more CDRs may be incorporated into a molecule either covalently or noncovalently to make it an immunoadhesin. An immunoadhesin may incorporate the CDR (s) as part of a larger polypeptide chain, may covalently link the CDR (s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring antibody has 2 identical binding sites, a single-chain antibody or Fab fragment has one binding site, while a "bispecific" or "bifunctional" antibody has 2 different binding sites.

An "isolated antibody" is an antibody that (1) is not associated with naturally-associated components, including other naturally-associated antibodies, that accompany it in its native state, (2) is free of other proteins from the same species, (3) is expressed by a cell that does not naturally express the antibody, or is expressed by a cell from a different species, or (4) does not occur in nature.

The term "human antibody" includes all antibodies that have one or more variable and constant regions derived from human Ig sequences. In some embodiments of the present invention, all of the variable and constant domains of the antibody are derived from human Ig sequences (a fully human antibody).

A humanized antibody is an antibody that is derived from a non-human species, in which certain amino acids have been mutated so as to avoid or abrogate an immune response in humans. Alternatively, a humanized antibody may be produced by fusing the constant domains from a human antibody to the variable domains of a non-human species.

The term "chimeric antibody" refers to an antibody that contains one or more regions from one antibody and one or more regions from one or more other antibodies. Each antibody may originate from seperate species (such as human and mouse).

The term "epitope" includes any molecular determinant capable of specific binding to an Ig or T-cell receptor. Epitopic determinants usually consist of surface groupings of atoms such as amino acids or sugar side chains and usually have specific 3 dimensional structural characteristics, as well as specific charge characteristics. An antibody is said to specifically bind an antigen when the dissociation constant is <1 uM, preferably <100 nM and more preferably: <10 nM.

Fully human antibodies are expected to minimize the immunogenic and allergic responses intrinsic to mouse or mouse-derivatized monoclonal antibodies (Mabs) and thus to increase the efficacy and safety of the administered antibodies. The use of fully human antibodies can be expected to provide a substantial advantage in the treatment of chronic and recurring human diseases, such as inflammation and cancer, which may require repeated antibody administrations.

In addition, fusion antibodies can be created in which 2 (or more) single-chain antibodies are linked to one another. This is useful if one wants to create a divalent or polyvalent antibody on a single polypeptide chain, or if one wants to create a bispecific antibody.

By "Fc fusion" as used herein is meant a protein wherein one or more polypeptides is operably linked to an Fc polypeptide. An Fc fusion combines the Fc region of an immunoglobulin with a fusion partner, which in general may be any protein, polypeptide or small molecule. Virtually any protein or small molecule may be linked to Fc to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, for example without limitation, an extracellular receptor that is implicated in disease.

One type of derivatized antibody is produced by cross-linking 2 or more antibodies (of the same type or of different types; e. g. to create bispecific antibodies). Suitable cross-linkers include those that are heterobifunctional, having 2 distinctly reactive groups separated by an appropriate spacer (e. g., m-maleimidobenzoyl-N-hydroxysuccinimide ester) or homobifunctional (e. g. disuccinimidyl suberate).

Another type of derivatized antibody is a labelled antibody. Useful detection agents with which an antibody or antibody portion of the invention may be derivatized include fluorescent compounds, including fluorescein, fluorescein isothiocyanate, rhodamine, 5-dimethylamine-1-napthalene-sulfonyl chloride, phycoerythrin, lanthanide phosphors and the like. An antibody may also be labelled with enzymes that are useful for detection, such as horseradish peroxidase, galactosidase, luciferase, alkaline phosphatase, glucose oxidase and the like. When an antibody is labelled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody may also be labelled with biotin, and detected through indirect measurement of avidin or streptavidin binding. An antibody may be labelled with a magnetic agent, such as gadolinium. An antibody may also be labelled with a predetermined polypeptide epitope recognized by a secondary reporter (e. g. leucine zipper pair sequences, binding sites for secondary antibodies, metal binding domains, epitope tags). In some embodiments, labels are attached by spacer arms of various lengths to reduce potential steric hindrance.

The antibody may also be derivatized with a chemical group such as polyethylene glycol (PEG), a methyl or ethyl group, or a carbohydrate group. These groups may be useful to improve the biological characteristics of the antibody, e.g. to increase serum half-life or to increase tissue binding.

Antibody Specificity

In some embodiments comprising antigen binding domains, at least the antigen binding domain (for example, but not limited to, an antibody variable region having all 6 CDRs, or an equivalent region that is at least 90 percent identical to an antibody variable region) is chosen from that found in: abagovomab, abatacept (ORENCIA®), abciximab (REOPRO®, c7E3 Fab), adalimumab (HUMIRA®), adecatumumab, alemtuzumab (CAMPATH®, MabCampath or Campath-1H), altumomab, afelimomab, anatumomab mafenatox, anetumumab, anrukizumab, apolizumab, arcitumomab, aselizumab, atlizumab, atorolimumab, bapineuzumab, basiliximab (SIMULECT®), bavituximab, bectumomab (LYMPHOSCAN®), belimumab (LYMPHO-STAT-B®), bertilimumab, besilesomab, βcept (ENBREL®), bevacizumab (AVASTIN®), biciromab brallobarbital, bivatuzumab mertansine, brentuximab vedotin (ADCETRIS®), canakinumab (ACZ885), cantuzumab mertansine, capromab (PROSTASCINT®), catumaxomab (REMOV ABC)), cedelizumab (CIMZIA®), certolizumab pegol, cetuximab (ERBITUX®), clenoliximab, dacetuzumab, dacliximab, daclizumab (ZENAPAX(®), denosumab (AMG 162), detumomab, dorlimomab aritox, dorlixizumab, duntumumab, durimulumab, durmulumab, ecromeximab, eculizumab (SOLIRIS®), edobacomab, edrecolomab (Mabl7-1A, PAN-OREX®), efalizumab (RAPTIVA®), efungumab (MY- COGRAB®), elsilimomab, enlimomab pegol, epitumomab cituxetan, efalizumab, epitumomab, epratuzumab, erlizumab, ertumaxomab (REXOMUN®), etaracizumab (etaratuzumab, VITAXIN®, ABEGRIN™), exbivirumab, fanolesomab (NEUTROSPEC®), faralimomab, felvizumab, fontolizumab (HUZAF®), galiximab, gantenerumab, gavilimomab (ABX-CBL®), gemtuzumab ozogamicin (MYLOTARG®), golimumab (CNTO 148), gomiliximab, ibalizumab (TNX-355), ibritumomab tiuxetan (ZEVALIN®), igovomab, imciromab, infliximab (REMICAD E®), inolimomab, inotuzumab ozogamicin, ipilimumab (YERVOY®, MDX-010), iratumumab, keliximab, labetuzumab, lemalesomab, lebrilizumab, lerdelimumab, lexatumumab (HGS-ETR2, ETR2-ST01), lexitumumab, libivirumab, lintuzumab, lucatumumab, lumiliximab, mapatumumab (HGS-ETRI, TRM-I), maslimomab, matuzumab (EMD72000), mepolizumab (BOSATRIA®), metelimumab, milatuzumab, minretumomab, mitumomab, morolimumab, motavizumab (NUMAX™), muromonab (OKT3), nacolomab tafenatox, naptumomab estafenatox, natalizumab (TYSABRI®, ANTEGREN®), nebacumab, nerelimomab, nimotuzumab (THERACIM hR3®, THERA-CIM-hR3®, THERALOC®), nofetumomab merpentan (VERLUMA®), ocrelizumab, odulimomab, ofatumumab, omalizumab (XOLAIR®), oregovomab (OVAREX®), otelixizumab, pagibaximab, palivizumab (SYNAGIS®), panitumumab (ABX-EGF, VECTIBIX®), pascolizumab, pemtumomab (THERAGYN®), pertuzumab (2C4, OMNITARG®), pexelizumab, pintumomab, ponezumab, priliximab, pritumumab, ranibizumab (LUCENTIS®), raxibacumab, regavirumab, reslizumab, rituximab (RITUXAN®, MabTHERA®), rovelizumab, ruplizumab, satumomab, sevirumab, sibrotuzumab, siplizumab (MEDI-507), sontuzumab, stamulumab (Myo-029), sulesomab (LEUKOSCAN®), tacatuzumab tetraxetan, tadocizumab, talizumab, taplitumomab paptox, tefibazumab (AUREXIS®), telimomab aritox, teneliximab, teplizumab, ticilimumab, tocilizumab (ACTEMRA®), toralizumab, tositumomab, trastuzumab (HERCEPTIN®), tremelimumab (CP-675,206), tucotuzumab celmoleukin, tuvirumab, urtoxazumab, ustekinumab (CNTO 1275), vapaliximab, veltuzumab, vepalimomab, visilizumab (NUVION®), volociximab (M200), votumumab (HUMASPECT®), zalutumumab, zanolimumab (HuMAX-CD4), ziralimumab, or zolimomab aritox.

In some embodiments comprising antigen binding domains, the antigen binding domain comprises a heavy and light chain variable domain having six CDRs, and/or competes for binding with an antibody selected from the preceding list. In some embodiments comprising antigen binding domains, the antigen binding domain binds the same epitope as the antibodies in the preceding list. In some embodiments comprising antigen binding domains, the antigen binding domain comprises a heavy and light chain variable domain having six total CDRs, and binds to the same antigen as the antibodies in the preceding list.

In some embodiments comprising antigen binding domains, at least the first antigen binding domain comprises a heavy and light chain variable domain having six (6) total CDRs, and specifically binds to an antigen selected from: PDGFRα, PDGFRβ, PDGF, VEGF, VEGF-A, VEGF-B, VEGF-C, VEGF-D, VEGF-E, VEGF-F, VEGFR1, VEGFR2, VEGFR3, FGF, FGF2, HGF, KDR, flt-1, FLK-1, Ang-2, Ang-1, PLGF, CEA, CXCL13, Baff, IL-21, CCL21, TNF-α, CXCL1, SDF-I, bFGF, MAC-I, IL23pl9, FPR, IGFBP4, CXCR3, TLR4, CXCR2, EphA2, EphA4, EphrinB2, EGFR(ErbBl), HER2(ErbB2 or pl85neu), HER3 (ErbB3), HER4 ErbB4 or tyro2), SCI, LRP5, LRP6, RAGE, s100A8, s100A9, Nav1.7, GLPI, RSV, RSV F protein, Influenza HA protein, Influenza NA protein, HMGBI, CD16, CD19, CD20, CD21, CD28, CD32, CD32b, CD64, CD79, CD22, ICAM-I, FGFRI, FGFR2, HDGF, EphB4, GITR, β-amyloid, hMPV, PIV-I, PIV-2, OX40L, IGFBP3, cMet, PD-I, PLGF, Neprolysin, CTD, IL-18, IL-6, CXCL-13, IL-IRI, IL-15, IL-4R, IgE, PAI-I, NGF, EphA2, uPARt, DLL-4, αvβ5, αvβ6, α5β1, α3β1, interferon receptor type I and type II, CD 19, ICOS, IL-17, Factor II, Hsp90, IGF, IGF-I, IGF-II, CD 19, GM-CSFR, PIV-3, CMV, IL-13, IL-9, and EBV.

In some embodiments comprising antigen binding domains, at least the first antigen binding domain specifically binds to a member (receptor or ligand) of the TNF superfamily. Various molecules include, but are not limited to Tumor Necrosis Factor-α("TNF-α"), Tumor Necrosis Factor-β ("TNF-β"), Lymphotoxin-α ("LT-α"), CD30 ligand, CD27 ligand, CD40 ligand, 4-1 BB ligand, Apo-1 ligand (also referred to as Fas ligand or CD95 ligand), Apo-2 ligand (also referred to as TRAIL), Apo-3 ligand (also referred to as TWEAK), osteoprotegerin (OPG), APRIL, RANK ligand (also referred to as TRANCE), TALL-I (also referred to as BlyS, BAFF or THANK), DR4, DR5 (also known as Apo-2, TRAIL-R2, TR6, Tango-63, hAPO8, TRICK2, or KILLER), DR6, DcRI, DcR2, DcR3 (also known as TR6 or M68), CARI, HVEM (also known as ATAR or TR2), GITR, ZTNFR-5, NTR-I, TNFLI, CD30, LTBr, 4-1BB receptor and TR9.

In some embodiments comprising antigen binding domains, at least the first antigen binding domain is capable of binding one or more targets chosen from 5T4, ABL, ABCB5, ABCFI, ACVRI, ACVRIB, ACVR2, ACVR2B, ACVRLI, ADORA2A, Aggrecan, AGR2, AICDA, AIFI, AIGI, AKAPI, AKAP2, AMH, AMHR2, angiogenin (ANG), ANGPTI, ANGPT2, ANGPTL3, ANGPTL4, Annexin A2, ANPEP, APC, APOCI, AR, aromatase, ATX, AXI, AZGPI (zinc-a-glycoprotein), B7.1, B7.2, B7-H1, BAD, BAFF, BAGI, BAII, BCR, BCL2, BCL6, BDNF, BLNK, BLRI (MDR15), BlyS, BMP1, BMP2, BMP3B (GDFIO), BMP4, BMP6, BMP7, BMP8, BMP9, BMP11, BMP12, BMPR1A, BMPR1B, BMPR2, BPAGI (plectin), BRCAI, C19orfIO (IL27w), C3, C4A, C5, C5R1, CANTI, CASPI, CASP4, CAVI, CCBP2 (D6/JAB61), CCLI (1-309), CCLI 1 (eotaxin), CCL13 (MCP-4), CCL15 (MIP-Id), CCL16 (HCC-4), CCL17 (TARC), CCL18 (PARC), CCL19 (MIP-3b), CCL2 (MCP-1), MCAF, CCL20 (MIP-3a), CCL21 (MEP-2), SLC, exodus-2, CCL22(MDC/STC-I), CCL23 (MPIF-I), CCL24 (MPIF-2/eotaxin-2), CCL25 (TECK), CCL26(eotaxin-3), CCL27 (CTACK/ILC), CCL28, CCL3 (MIP-Ia), CCL4 (MIP-Ib), CCL5(RANTES), CCL7 (MCP-3), CCL8 (mcp-2), CCNAI, CCNA2, CCNDI, CCNEI, CCNE2, CCRI (CKRI/HM145), CCR2 (mcp-IRB/RA), CCR3 (CKR3/CMKBR3), CCR4, CCR5(CMKBR5/ChemR13), CCR6 (CMKBR6/CKR-L3/STRL22/DRY6), CCR7 (CKR7/EBI1), CCR8 (CMKBR8/TERI/CKR-LI), CCR9 (GPR-9-6), CCRLI (VSHKI), CCRL2 (L-CCR), CD164, CD19, CDIC, CD20, CD200, CD-22, CD24, CD28, CD3, CD33, CD35, CD37, CD38, CD3E, CD3G, CD3Z, CD4, CD40, CD40L, CD44, CD45RB, CD46, CD52, CD69, CD72, CD74, CD79A, CD79B, CD8, CD80, CD81, CD83, CD86, CD105, CD137, CDHI (E-cadherin), CDCP1CDH10, CDH12, CDH13, CDH18, CDH19, CDH20, CDH5, CDH7, CDH8, CDH9, CDK2, CDK3, CDK4, CDK5, CDK6, CDK7, CDK9, CDKNIA (p21Wapl/Cipl), CDKNIB (p27Kipl), CDKNIC, CDKN2A (p16INK4a), CDKN2B, CDKN2C, CDKN3, CEBPB, CERI, CHGA, CHGB, Chitinase, CHSTIO, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLRI, CMKORI (RDCI), CNRI, COLI 8AI, COL1A1.COL4A3, COL6A1, CR2, Cripto, CRP, CSFI (M-CSF), CSF2 (GM-CSF), CSF3 (GCSF), CTLA4, CTL8, CTNNBI (b-catenin), CTSB (cathepsin B), CX3CL1 (SCYDI), CX3CR1 (V28), CXCLI (GROI), CXCLIO (IP-10), CXCLII (I-TAC/IP-9), CXCL12 (SDFI), CXCL13, CXCL 14, CXCL 16, CXCL2 (GRO2), CXCL3 (GR03), CXCL5 (ENA-78/LIX), CXCL6 (GCP-2), CXCL9 (MIG), CXCR3 (GPR9/CKR-L2), CXCR4, CXCR6 (TYMSTR/STRL33/Bonzo), CYB5, CYCI, Cyr61, CYSLTRI, c-Met, DAB2IP, DES, DKFZp451J0118, DNCLI, DPP4, E2F1, ECGFI5EDGI, EFNAI, EFNA3, EFNB2, EGF, ELAC2, ENG, endoglin, ENOI, EN02, EN03, EPHAI, EPHA2, EPHA3, EPHA4, EPHA5, EPHA6, EPHA7, EPHA8, EPHA9, EPHAIO, EPHBI, EPHB2, EPHB3, EPHB4, EPHB5, EPHB6, EPHRIN-AI, EPHRIN-A2, EPHRIN-A3, EPHRIN-A4, EPHRIN-A5, EPHRIN-A6, EPHRIN-BI, EPHRIN-B2, EPHRTN-B3, EPHB4, EPG, ERBB2 (Her-2), EREG, ERK8, Estrogen receptor, ESRI, ESR2, F3 (TF), FADD, farnesyltransferase, FasL, FASNf, FCER1A, FCER2, FCGR3A, FGF, FGFI (aFGF), FGFIO, FGFI 1, FGF12, FGF12B, FGF13, FGF14, FGF16, FGF17, FGF18, FGF19, FGF2 (bFGF), FGF20, FGF21 (such as mimAb1), FGF22, FGF23, FGF3 (int-2), FGF4 (HST), FGF5, FGF6 (HST-2), FGF7 (KGF), FGF8, FGF9, FGFR3, FIGF (VEGFD), FILI(EPSILON), FBLI (ZETA), FLJ12584, FLJ25530, FLRTI (fibronectin), FLTI, FLT-3, FOS, FOSLI(FRA-1), FY (DARC), GABRP (GABAa), GAGEBI, GAGECI, GALNAC4S-6ST, GATA3, GD2, GD3, GDF5, GDF8, GFII, GGTI, GM-CSF, GNASI, GNRHI, GPR2 (CCRIO), GPR31, GPR44, GPR81 (FKSG80), GRCCIO (CIO), gremlin, GRP, GSN (Gelsolin), GSTPI, HAVCR2, HDAC, HDAC4, HDAC5, HDAC7A, HDAC9, Hedgehog, HGF, HIFIA, HIPI, histamine and histamine receptors, HLA-A, HLA-DRA, HM74, HMOXI, HSP90, HUMCYT2A, ICEBERG, ICOSL, ID2, IFN-a, IFNAI, IFNA2, IFNA4, IFNA5, EFNA6, BFNA7, IFNBI, IFNgamma, IFNWI, IGBPI, IGFI, IGFIR, IGF2, IGFBP2, IGFBP3, IGFBP6, DL-I, ILIO, ILIORA, ILIORB, IL-1, ILIRI (CD121a), ILIR2(CD121b), IL-IRA, IL-2, IL2RA (CD25), IL2RB(CD122), IL2RG(CD132), IL-4, IL-4R (CD123), IL-5, IL5RA(CD125), IL3RB(CD131), IL-6, IL6RA (CD126), IL6RB(CD130), IL-7, IL7RA(CD127), IL-8, CXCRI (IL8RA), CXCR2 (IL8RB/CD128), IL-9, IL9R (CD129), IL-10, IL10RA(CD210), IL10RB (CDW210B), IL-11, ILI IRA, IL-12, IL-12A, IL-12B, IL-12RB1, IL-12RB2, IL-13, IL13RA1, IL13RA2, IL14, IL15, IL15RA, 1L16, IL17, IL17A, IL17B, IL17C, IL17R, IL18, IL18BP, IL18R1, IL18RAP, IL19, ILIA, ILIB, ILI-FIO, IL1F5, IL1F6, IL1F7, IL1F8, DL1F9, ILIHYI, ILIRI, IL1R2, ILIRAP, ILIRAPLI, ILI RAPL2, ILIRLI, ILI RL2, ILIRN, IL2, IL20, IL20RA, IL21R, IL22, IL22R, IL22RA2, IL23, DL24, IL25, IL26, IL27, IL28A, IL28B, IL29, IL2RA, IL2RB, IL2RG, IL3, IL30, IL3RA, IL4, IL4R, IL6ST (glycoprotein 130), ILK, INHA, INHBA, INSL3, INSL4, IRAKI, IRAK2, ITGA1, ITGA2, ITGA3, ITGA6 (α6 integrin), ITGAV, ITGB3, ITGB4 (β4 integrin), JAKI, JAK3, JTB, JUN, K6HF, KAII, KDR, KIM-1, KITLG, KLFS (GC Box BP), KLF6, KLKIO, KLK12, KLK13, KLK14, KLK15, KLK3, KLK4, KLKS, KLK6, KLK9, KRTI, KRT19 (Keratin 19), KRT2A, KRTHB6 (hair-specific type II keratin), LAMA5, LEP (leptin), Lingo-p75, Lingo-Troy, LPS, LRPS, LRP6, LTA (TNF-b), LTB, LTB4R (GPR16), LTB4R2, LTBR, MACMARCKS, MAG or Omgp, MAP2K7 (c-Jun), MCP-I, MDK, MIBI, midkine, MIF, MISRII, MJP-2, MK, MKI67 (Ki-67), MMP2, MMP9, MS4A1, MSMB, MT3 (metallothionectin-Ui), mTOR, MTSSI, MUCI (mucin), MYC, MYD88, NCK2, neurocan, neuregulin-1, neuropilin-1, NFKBI, NFKB2, NGFB (NGF), NGFR, NgR-Lingo, NgR-Nogo66 (Nogo), NgR-p75, NgR-Troy, NMEI (NM23A), NOTCH, NOTCHI, NOX5, NPPB, NROBI, NROB2, NRIDI, NR1D2, NR1H2, NR1H3, NR1H4, NR1I2, NR1I3, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRPI, NRP2, NT5E, NTN4, OCT-1, ODZ1, OPN1, OPN2, OPRDI, P2RX7, PAP, PARTI, PATE, PAWR, PCA3, PCDGF, PCNA, PDGFA, PDGFB, PDGFRA, PDGFRB, PECAMI, peg-asparaginase, PF4 (CXCL4), Plexin B2 (PLXNB2), PGF, PGR, phosphacan, PIAS2, PI3 Kinase, PIK3CG, PLAU (uPA), PLG5PLXDCI, PKC, PKC-β, PPBP (CXCL7), PPID, PRI, PRKCQ, PRKDI, PRL, PROC, PROK2, pro-NGF, prosaposin, PSAP, PSCA, PTAFR, PTEN, PTGS2 (COX-2), PTN, RAC2 (P21Rac2), RANK, RANK ligand, RARB, RGSI, RGS13, RGS3, RNFI10 (ZNF144), Ron, R0B02, RXR, selectin, S100A2, S100A8, S100A9, SCGB 1D2 (lipophilin B), SCGB2A1 (mammaglobin 2), SCGB2A2 (mammaglobin 1), SCYEI (endothelial Monocyte-activating cytokine), SDF2, SERPENA1, SERPINA3, SERPINB5 (maspin), SERPINEI (PAI-I), SERPINFI, SHIP-I, SHIP-2, SHBI, SHB2, SHBG, SfcAZ, SLC2A2, SLC33A1, SLC43A1, SLIT2, SPPI, SPRRIB (SprI), ST6GAL1, STABI, STATE, STEAP, STEAP2, SULF-1, Sulf-2, TB4R2, TBX21, TCPIO, TDGFI, TEK, TGFA, TGFBI, TGFBIII, TGFB2, TGFB3, TGFBI, TGFBRI, TGFBR2, TGFBR3, THIL, THBSI (thrombospondin-1), THBS2/THBS4, THPO, TIE (Tie-1), TIMP3, tissue factor, TIKI2, TLR10, TLR2, TLR3, TLR4, TLR5, TLR6JLR7, TLR8, TLR9, TM4SF1, TNF, TNF-a, TNFAIP2 (B94), TNFAIP3, TNFRSFIIA, TNFRSFIA, TNFRSFIB, TNFRSF21, TNFRSF5, TNFRSF6 (Fas), TNFRSF7, TNFRSF8, TNFRSF9, TNFSFIO (TRAIL), TNFSFI 1 (TRANCE), TNFSF12 (APO3L), TNFSF13 (April), TNFSF13B, TNFSF14 (HVEM-L), TNFSF15 (VEGI), TNFSF 18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TLR2, TLR4, TLR9, TOP2A (topoisomerase lia), TP53, TPMI, TPM2, TRADD, TRAFI, TRAF2, TRAF3, TRAF4, TRAF5, TRAF6, TRKA, TREMI, TREM2, TRPC6, TROY, TSLP, TWEAK, Tyrosinase, uPAR, VEGF, VEGFB, VEGFC, versican, VHL C5, VLA-4, Wnt-1, XCLI (lymphotactin), XCL2 (SCM-Ib), XCRI (GPR5/CCXCRI), YYI, and ZFPM2.

Definitions

Generally, nomenclatures used in connection with, and techniques of, biochemistry, analytical chemistry, synthetic organic chemistry, medicinal and pharmaceutical chemistry, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Reactions and purification techniques are performed according to manufacturer's specifications, as commonly accomplished in the art or as described herein. As used herein, the 20 natural, or conventional, amino acids and their abbreviations follow IUPAC single letter and three letter codes.

A "complementary residue set", as used herein, refers to at least one amino acid in a $C_H$-1 domain, and at least one amino acid in the $C_L$ domain that are engineered to interact with each other. By interacting with each other, they drive their respective domains to heterodimerize and form an interface comprising at least some of the interaction between the residues of the complementary residue set. The interaction may be characterized by a salt bridge, electrostatic interaction, or van der Waals force. A complementary residue set may comprise more than one engineered residue in each domain.

Any given residue within a complementary residue set will be within 5 Å of at least one other residue of that complementary residue set.

In the context of complementary residue sets, two residues are said to interact if at least one atom of each residue is within 5 Å of each other. Residue interaction may be characterized as either a salt bridge, electrostatic interaction, or van der Waals force. For avoidance of doubt, in other contexts it is recognized that interatomic forces may act over longer distances.

"Complementary pairing" between domains refers to the interaction of those two domains, at least in part, through a complementary residue set.

"Engineered", as used herein, refers to the deliberate mutation of residues that are not found in the predominant wild type sequence, and may be an engineered insertion, deletion or substitution mutation.

A "heteromultimer", "heteromultimeric complex", or "heteromultimeric polypeptide" is a molecule comprising at least a first polypeptide and a second polypeptide, wherein the second polypeptide differs in amino acid sequence from the first polypeptide by at least one amino acid residue. The heteromultimer can comprise a "heterodimer" formed by the first and second polypeptide or can form higher order tertiary structures where polypeptides in addition to the first and second polypeptide are present.

A "heterodimer," "heterodimeric protein," "heterodimeric complex," or "heteromultimeric polypeptide" is a molecule comprising a first polypeptide and a second polypeptide, wherein the second polypeptide differs in amino acid sequence from the first polypeptide by at least one amino acid residue.

In the context of the invention, the term heterodimeric is used to indicate a heteromultimer comprising at least two polypeptides with differing amino acid sequences; but it will be readily appreciated that in many embodiments, particularly those where the invention relates to IgG antibodies and similar molecules, heterodimeric proteins of the invention may equally be referred to as heteromultimeric proteins, as there will necessarily be four distinct polypeptides (the first heavy and light chain, and the second heavy and light chain).

"Polypeptide," "peptide," and "protein" are used interchangeably to refer to a polymer of amino acid residues. As used herein, these terms apply to amino acid polymers in which one or more amino acid residues is an artificial chemical analog of a corresponding naturally occurring amino acid. These terms also apply to naturally occurring amino acid polymers. Amino acids can be in the L-form or D-form as long as the binding and other desired characteristics of the peptide are maintained. A polypeptide may be monomeric or polymeric. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

Unless indicated otherwise by a "D" prefix, e.g. D-Ala or N-Me-D-Ile, or written in lower case format, e.g. a, i, l, (D versions of Ala, Ile, Leu), the stereochemistry of the α-carbon of the amino acids and aminoacyl residues in peptides described in this specification and the appended claims is the natural or "L" configuration.

All peptide sequences are written according to the generally accepted convention whereby the α-N-terminal amino acid residue is on the left and the α-C-terminal amino acid residue is on the right. As used herein, the term "N-terminus" refers to the free α-amino group of an amino acid in a peptide, and the term "C-terminus" refers to the free α-carboxylic acid terminus of an amino acid in a peptide. A peptide which is N-term inated with a group refers to a peptide bearing a group on the α-amino nitrogen of the N-terminal amino acid residue. An amino acid which is C-terminated with a group refers to an amino acid bearing a group on the carboxyl moiety, such as a methyl group resulting in a methyl ester.

As used herein, "biological activity" refers to the in vivo activities of a compound, composition, or other mixture, or physiological responses that result upon in vivo administration of a compound, composition or other mixture. Biological activity thus encompasses therapeutic effects, diagnostic effects and pharmaceutical activity of such compounds, compositions, and mixtures.

The term "biologically compatible" as used herein means something that is biologically inert or non reactive with intracellular and extra cellular biological molecules, and non toxic.

"About" or "approximately," when used in connection with a measurable numerical variable, refers to the indicated value of the variable and to all values of the variable that are within the experimental error of the indicated value (e.g. within the 95% confidence interval for the mean) or within 10 percent of the indicated value, whichever is greater. Numeric ranges are inclusive of the numbers defining the range.

The term "identity," as known in the art, refers to a relationship between the sequences of two or more polypeptide molecules or two or more nucleic acid molecules, as determined by comparing the sequences. In the art, "identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by a particular mathematical model of computer programs (i. e. "algorithms").

The term "similarity" is a related concept, but in contrast to "identity", refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, 10 out of 20 identical amino acids, and the remainder are all nonconservative substitutions, then the percent identity and similarity would both be 50%. If in the same example, there are 5 more positions where there are conservative substitutions, then the percent identity remains 50%, but the percent similarity would be 75% (15 out of 20). Therefore, in cases where there are conservative substitutions, the degree of similarity between two polypeptide sequences will be higher than the percent identity between those two sequences.

The term "conservative amino acid substitution" refers to a substitution of a native amino acid residue with a nonnative residue such that there is little or no effect on the polarity, charge, and approximate volume of the amino acid residue at that position. For example, a conservative substitution results from the replacement of a non-polar residue in a polypeptide with any other non-polar residue. The term may also refer to a substitution identified as frequently occurring between highly similar proteins, as in the BLOSUM62 matrix or related matrices (PNAS, USA 89(22), 10915-9, 1992).

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g. bacterial vectors having a bacterial origin of replication and episomal mammalian vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid molecule," which may be used interchangeably herein, refers to a polymeric, possibly isolated, form of nucleosides or nucleotides of at least 10 bases in length. The term includes single and double stranded forms. The nucleotides can be deoxyribonucleotides, ribonucleotides, modified nucleotides or bases, and/or their analogs, or any substrate that can be incorporated into a polymer by DNA or RNA polymerase, or by a synthetic reaction.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g. methyl phosphonates, phosphotriesters, phosphoamidates, carbamates, etc.) and with charged linkages (e.g. phosphorothioates, phosphorodithioates, etc.), those containing pendant moieties, such as, for example, proteins (e.g. nucleases, toxins, antibodies, signal peptides, ply-L-lysine, etc.), those with intercalators (e.g. acridine, psoralen, etc.), those containing chelators (e.g. metals, radioactive metals, boron, oxidative metals, etc.), those containing alkylators, those with modified linkages (e.g. alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

A reference to a nucleotide sequence as used herein encompasses its complement unless otherwise specified. Thus, a reference to a nucleic acid having a particular sequence should be understood to encompass its complementary strand, with its complementary sequence, unless otherwise defined by context.

"Cell" or "cell line," as used herein, includes various types of cells that can be used to express a heterodimeric protein, a polypeptide or a nucleic acid of the invention, e.g. prokaryotic cells, eukaryotic cells, mammalian cells, rat cells, human cells.

The term "purify," and grammatical variations thereof, is used to mean the removal, whether completely or partially, of at least one impurity from a mixture containing the polypeptide and one or more impurities, which thereby improves the level of purity of the polypeptide in the composition (i.e. by decreasing the amount (ppm) of impurity(ies) in the composition).

The terms "ion-exchange" and "ion-exchange chromatography" refer to a chromatographic process in which an ionizable solute of interest (e.g. a protein of interest in a mixture) interacts with an oppositely charged ligand linked (e.g. by covalent attachment) to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange, anion exchange, and mixed mode chromatographies.

A "blocking" antibody or an "antagonist" antibody is one which inhibits or reduces biological activity of the antigen it binds. An "agonist antibody", as used herein, is an antibody which mimics at least one of the functional activities of a polypeptide of interest.

The term "immune effector cell" or "effector cell" as used herein refers to a cell within the natural repertoire of cells in the human immune system which can be activated to affect the viability of a target cell. The viability of a target cell can include cell survival, proliferation, and/or ability to interact with other cells.

Salt bridges are a type of noncovalent interaction. A salt bridge involves close-range direct interactions between two atoms with opposite formal charges. In the context of protein structure, salt bridges most often form between the anionic carboxylate ($RCOO^-$) of either aspartic acid or glutamic acid and the cationic ammonium ($RNH_3^+$) from lysine or the guanidinium ($RNHC(NH_2)_2^+$) of arginine, with histidine another possibility. However, other amino acids may participate depending on changes to their pKa values and locations in the polypeptide chain (the N and C terminal residues may be ionized, and thus capable of salt bridge formation, regardless of amino acid type).

Electrostatic interactions are noncovalent interactions between atoms having nonzero charge. They may have favorable, unfavorable, or neutral interaction energies and may involve atoms which have formal charges, or which are polarized despite the lack of formal charge. Hydrogen bonds, salt bridges, and pi-cation stacking are examples of electrostatic interactions frequently observed in protein structures.

Structural alignments, which are usually specific to protein and sometimes RNA sequences, use information about the secondary and tertiary structure of the protein or RNA molecule to aid in aligning the sequences. These methods are used for two or more sequences and typically produce local alignments; however, because they depend on the availability of structural information, they can only be used for sequences whose corresponding structures are known (usually through X-ray crystallography or NMR spectroscopy). Because both protein and RNA structure is more evolutionarily conserved than sequence, structural alignments can be more reliable between sequences that are very distantly related and that have diverged so extensively that sequence comparison cannot reliably detect their similarity. Where there is no available structural data on one of the proteins, a comparison can still be made if structural data is available on one or preferably more closely related proteins, such as immunoglobulins across species, and in particular antibody constant domains across species and subtype.

Structural alignments are used as the "gold standard" because they explicitly align regions of the protein sequence that are structurally similar rather than relying exclusively on sequence information. A commonly used algorithm for structural alignments is TM-ALIGN (Zhang and Skolnick, *Nucleic Acids Research,* 33: 2302-2309 (2005)), which assigns increased weight to the most similar regions of the structure during superposition.

Sequence Alignment

Where structural alignment with protein sequences of the invention is not possible, for example due to an absence of target sequence NMR or crystal structure data, sequence alignment may be used. The skilled person is familiar with sequence alignment tools (such as BLAST, CLUSTAL and others known to the skilled person, such as those described herein), and is able to align sequences, particularly antibody constant domain sequences according to known structural motifs, especially due to the large number of exemplary structural studies already existent for immunoglobulin domains, antibodies and antibody constant domains in particular, across subtype and species.

Computational approaches to sequence alignment generally fall into two categories: global alignments and local alignments. Calculating a global alignment is a form of global optimization that "forces" the alignment to span the entire length of all query sequences. By contrast, local alignments identify regions of similarity within long sequences that are often widely divergent overall. Local alignments are often preferable, but can be more difficult to calculate because of the additional challenge of identifying the regions of similarity. A variety of computational algorithms have been applied to the sequence alignment problem. These include slow but formally correct methods like dynamic programming and also efficient, heuristic algorithms or probabilistic methods designed for large-scale database search, that do not guarantee to find best matches.

Global alignments, which attempt to align every residue in every sequence, are most useful when the sequences in the query set are similar and of roughly equal size. A general global alignment technique is the Needleman-Wunsch algorithm, which is based on dynamic programming. Local alignments are more useful for dissimilar sequences that are suspected to contain regions of similarity or similar sequence motifs within their larger sequence context. The Smith-Waterman algorithm is a general local alignment method also based on dynamic programming.

Pairwise sequence alignment methods are used to find the best-matching piecewise (local) or global alignments of two query sequences. The three primary methods of producing pairwise alignments are dot-matrix methods, dynamic programming, and word methods; however, multiple sequence alignment techniques can also align pairs of sequences. Although each method has its individual strengths and weaknesses, all three pairwise methods have difficulty with highly repetitive sequences of low information content—especially where the number of repetitions differ in the two sequences to be aligned. One way of quantifying the utility of a given pairwise alignment is the 'maximum unique match' (MUM), or the longest subsequence that occurs in both query sequences. Longer MUM sequences typically reflect closer relatedness. Preferred methods to determine identity and/or similarity are designed to give the largest match between the sequences tested. Methods to determine identity and similarity are codified in publicly available computer programs. Preferred computer program methods to determine identity and similarity between two sequences include, but are not limited to, the GCG program package, including GAP (Devereux et al., Nuc. Acids Res. 12: 387 (1984); Genetics Computer Group, University of Wisconsin, Madison, Wis.), BLASTP, BLASTN, and FASTA (Atschul et al., J. Mol. Biol. 215: 403-10 (1990)). The BLAST X program is publicly available from the National Center for Biotechnology Information (NCBI) and other sources (Altschul et al., BLAST Manual (NCB NLM NIH, Bethesda, Md.); Altschul et al., 1990, supra). The well-known Smith Waterman algorithm may also be used to determine identity.

By way of example, using the computer algorithm GAP (Genetics Computer Group), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. Preferred parameters for polypeptide sequence comparison include the following: Algorithm: Needleman and Wunsch, J. Mol. Biol. 48: 443-53 (1970). Comparison matrix: BLOSUM 62 from Henikoff et al., Proc. Natl. Acad. Sci. U.S.A 89: 10915-19 (1992).

Other exemplary algorithms, gap opening penalties, gap extension penalties, comparison matrices, thresholds of similarity, etc. may be used by those of skill in the art, including those set forth in the Program Manual, WisconsinPackage, Version 9, September, 1997. The particular choices to be made will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

For specific protein families with conserved structure, other alignment algorithms are available. In the case of antibodies, various algorithms for assigning Kabat numbering are available. The algorithm implemented in the 2012 release of Abysis (www.abysis.org) is used herein to assign Kabat numbering to variable regions unless otherwise noted.

The term "percent sequence identity" in the context of nucleic acid sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version10.0, Genetics Computer Group (GCG), Madison, Wis. FASTA, which includes, e.g. the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:185-219 (2000); Pearson, *Methods Enzymol.* 266:227-258 (1996); Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

TABLE 1

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
| 1 | IgG1 CH1 numbered from residue 111 to 231 (with insertions 162A, 162B, and 162C after position 162) | ---ASTKGPS VFPLAPSSKS --TSGGTAAL GCLVKDYFPE PVTV-SW--- -N---SGALT SG-VHTFPAV LQS-SGLYSL SSVVTVPSSS LGT--Q-TYI CNVNHKPSNT KVDKKV--EP KSC- |
| 2 | IgG1 CH1 G1m3 using the numbering range of Seq 1 | ---ASTKGPS VFPLAPSSKS --TSGGTAAL GCLVKDYFPE PVTV-SW--- -N---SGALT SG-VHTFPAV LQS-SGLYSL SSVVTVPSSS LGT--Q-TYI CNVNHKPSNT KVDKRV--EP KSC- |
| 3 | IgG2 CH1 using the numbering range of Seq 1 | ---ASTKGPS VFPLAPCSRS --TSESTAAL GCLVKDYFPE PVTV-SW--- -N---SGALT SG-VHTFPAV LQS-SGLYSL SSVVTVPSSN FGT--Q-TYT CNVDHKPSNT KVDKTV--ER K--- |
| 4 | IgG2 CH1 G2m23 using the numbering range of Seq 1 | ---ASTKGPS VFPLAPCSRS --TSESTAAL GCLVKDYFPE PVTV-SW--- -N---SGALT SG-VHTFPAV LQS-SGLYSL SSVVTVTSSN FGT--Q-TYT CNVDHKPSNT KVDKTV--ER K--- |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
| 5 | IgG3 CH1 using the numbering range of Seq 1 | ---ASTKGPS VFPLAPCSRS --TSGGTAAL GCLVKDYFPE PVTV-SW----N---SGALT SG-VHTFPAV LQS-SGLYSL SSVVTVPSSS LGT--Q-TYT CNVNHKPSNT KVDKRV--EL KTP- |
| 6 | IgG4 CH1 using the numbering range of Seq 1 | ---ASTKGPS VFPLAPCSRS --TSESTAAL GCLVKDYFPE PVTV-SW----N---SGALT SG-VHTFPAV LQS-SGLYSL SSVVTVPSSS LGT--K-TYT CNVDHKPSNT KVDKRV--ES KYG- |
| 7 | IgM CH1 seq1 numbered from residue 111 to 226 (with insertions 162A, 162B, and 162C after position 162) | ---GSASAPT LFPLVSCENS P-SDTSSVAV GCLAQDFLPD SITL-SW----KYKNNSDIS S--TRGFPSV LRG--GKYAA TSQVLLPSKD VMQGTDEHVV CKVQH-PNGN --KEKNVPLP |
| 8 | IgM CH1 seq2 using the numbering range of Seq 7 | ---GSASAPT LFPLVSCENS P-SDTSSVAV GCLAQDFLPD SITF-SW----KYKNNSDIS S--TRGFPSV LRG--GKYAA TSQVLLPSKD VMAGTDEHVV CKVQH-PNGN --KEKNVPLP |
| 9 | CL-Kappa-KM3 numbered from position 101 to 215 | -------RTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC- |
| 10 | CL-Kappa-KM1 using the numbering range of Seq 9 | -------RTV AAPSVFIFPP SDEQLKSGTA SVVCLLNNFY PREAKVQWKV DNVLQSGNSQ ESVTEQDSKD STYSLSSTLT LSKADYEKHK LYACEVTHQG LSSPVTKSFN RGEC- |
| 11 | CL-Kappa-KM1, 2 using the numbering range of Seq 9 | -------RTV AAPSVFIFPP SDEQLKSGTA SVVCLLNNFY PREAKVQWKV DNALQSGNSQ ESVTEQDSKD STYSLSSTLT LSKADYEKHK LYACEVTHQG LSSPVTKSFN RGEC- |
| 12 | CL-Lambda using the numbering range of Seq 9 | -------QPK AAPSVTLFPP SSEELQANKA TLVCLISDFY PGAVTVAWKA DSSPVKAGVE TTTPSKQS-N NKYAASSYLS LTPEQWKSHR SYSCQVTHEG --STVEKTVA PTECS |
| 13 | IgG1 CH2 numbered from 241 to 360B with insertions 266A, 302A, 316A, 316B, 360A, and 360B | ---APELLGG PSVFLFPPKP KDTLMI-SRT PEVTCVVVDV SHEDPEVKFN WYV--DG--V EVH-NAKTKP REEQYN---- STYRVVSVLT VLHQDWLNGK EYKCKVSNKA LPAPIEKTI- SKAK-- |
| 14 | IgG2 CH2 using the numbering range of Seq 13 | ---APPVA-G PSVFLFPPKP KDTLMI-SRT PEVTCVVVDV SHEDPEVQFN WYV--DG--V EVH-NAKTKP REEQFN---- STFRVVSVLT VVHQDWLNGK EYKCKVSNKG LPAPIEKTI- SKTK-- |
| 15 | IgG3 CH2 using the numbering range of Seq 13 | ---APELLGG PSVFLFPPKP KDTLMI-SRT PEVTCVVVDV SHEDPEVQFK WYV--DG--V EVH-NAKTKP REEQYN---- STFRVVSVLT VLHQDWLNGK EYKCKVSNKA LPAPIEKTI- SKTK-- |
| 16 | IgG4 CH2 using the numbering range of Seq 13 | ---APEFLGG PSVFLFPPKP KDTLMI-SRT PEVTCVVVDV SQEDPEVQFN WYV--DG--V EVH-NAKTKP REEQFN---- STYRVVSVLT VLHQDWLNGK EYKCKVSNKG LPSSIEKTI- SKAK-- |
| 17 | IgM CH2 using the numbering range of Seq 13 | ----VIAELP PKVSVFVPPR DGFFGN-PRK SKLICQATGF S--PRQIQVS WLR--EG--K QVGSGVTTDQ VQAEAKESGP TTYKVTSTLT IKESDWLGQS MFTCRVDHRG L--TFQQNA- SSMCVP |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
| 18 | IgG1 CH3 numbered from 361 to 478 with insertion 398A | G-QPREPQVY TLPPSREE-- MTKNQVSLTC LVKGFYPS-D IAV--EWES- NG--QPENNY KTTPPVLDS- D--GSFFLYS KLTVDKSRWQ QGNVFSCSVM HEALHNHYTQ KSLSLSPGK |
| 19 | IgG1 CH3 alternate isotype using the numbering range of Seq 18 | G-QPREPQVY TLPPSRDE-- LTKNQVSLTC LVKGFYPS-D IAV--EWES- NG--QPENNY KTTPPVLDS- D--GSFFLYS KLTVDKSRWQ QGNVFSCSVM HEALHNHYTQ KSLSLSPGK |
| 20 | IgG2 CH3 using the numbering range of Seq 18 | G-QPREPQVY TLPPSREE-- MTKNQVSLTC LVKGFYPS-D IAV--EWES- NG--QPENNY KTTPPMLDS- D--GSFFLYS KLTVDKSRWQ QGNVFSCSVM HEALHNHYTQ KSLSLSPGK |
| 21 | IgG3 CH3 using the numbering range of Seq 18 | G-QPREPQVY TLPPSREE-- MTKNQVSLTC LVKGFYPS-D IAV--EWES- SG--QPENNY NTTPPMLDS- D--GSFFLYS KLTVDKSRWQ QGNIFSCSVM HEALHNRFTQ KSLSLSPGK |
| 22 | IgG4 CH3 using the numbering range of Seq 18 | G-QPREPQVY TLPPSQEE-- MTKNQVSLTC LVKGFYPS-D IAV--EWES- NG--QPENNY KTTPPVLDS- D--GSFFLYS RLTVDKSRWQ EGNVFSCSVM HEALHNHYTQ KSLSLSLGK |
| 23 | IgM CH3 using the numbering range of Seq 18 | D-QDTAIRVF AIPPSFASI- FLTKSTKLTC LVTDLTTYDS VTI--SWTRQ NG--EAV-KT HTNISESHP- N--ATFSAVG EASICEDDWN SGERFTCTVT HTDLPSP-LK QTISRPK- |
| 24 | CL-V133S-S176D using the numbering range of Seq 9 | -------RTV AAPSVFIFPP SDEQLKSGTA SV*S*CLLNNFY PREAKVQWKV DNALQSGNSQ ESVTEQDSKD STYSL*D*STLT LSKADYEKHK VYACEVTHQG LSSPVTKSFN RGEC |
| 25 | CL-V133S-S176K using the numbering range of Seq 9 | -------RTV AAPSVFIFPP SDEQLKSGTA SV*S*CLLNNFY PREAKVQWKV DNALQSGNSQ ESVTEQDSKD STYSL*K*STLT LSKADYEKHK VYACEVTHQG LSSPVTKSFN RGEC |
| 26 | CL-L1.1 using the numbering range of Seq 9 | -------RTV AAPSVFIFPP SDKQLKSGTA SVVCILNNFY PREAKVQWKV DNALQSGNSQ ESVTEQDSKD STYSLCSTLT LSKADYEKHK VYACEVTHQG LSSPVTKSFN RGES |
| 27 | CL-L4.1 using the numbering range of Seq 9 | -------RTV AAPSVFIFPP SDCQLKSGTA HVVCLLNNFY PREAKVQWKV DNALQSGNSQ ESVTEQDSKD STYSLSSTLT LSKADYEKHK VYACEVTHQG LSSPVTKSFN RGES |
| 28 | CL-L4.2 using the numbering range of Seq 9 | -------RTV AAPSVFIFPP SDEQLKSGTA HVVCILNNFY PREAKVQWKV DNALQSGNSQ ESVTEQDSKD STYSLCSTLT LSKADYEKHK VYACEVTHQG LSSPVTKSFN RGES |
| 29 | CL-L4.3 using the numbering range of Seq 9 | -------RTV AAPSVCIFPP SDEQLKSGTA HVVCLLNNFY PREAKVQWKV DNALQSGNSQ ESVTEQDSKD STYSLSSTLT LSKADYEKHK VYACEVTHQG LSSPVTKSFN RGES |
| 30 | CL-H10.1 using the numbering range of Seq 9 | -------RTV AAPSVFIFPP SDEQLKSGTA DVSCLLNNFY PREAKVQWKV DNALQSGNSQ ESVTEQDSKD STYSLCSSLT LSKADYEKHK VYACEVTHQG LSSPVTKSFN RGES |
| 31 | CL-H10.4 using the numbering range of Seq 9 | -------RTV AAPSVFIFPP SDCQLKSGTA SVMCLLNNFY PREAKVQWKV DNALQSGNSQ ESVTEQDSKD STYSLGSGLT LSKADYEKHK VYACEVTHQG LSSPVTKSFN RGES |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
| 32 | CL-5.6 using the numbering range of Seq 9 | -------RTV AAPSVCIFPP SDCQLKSGTA DVSCLLNNFY PREAKVQWKV DNALQSGNSQ ESVTEQDSKD STYSLCSSLT LSKADYEKHK VYACEVTHQG LSSPVTKSFN RGES |
| 33 | CH1-L124K-V190S numbered from residue 111 to 230 (with insertions 162A, 162B, and 162C after position 162) | ---ASTKGPS VFP*K*APSSKS --TSGGTAAL GCLVKDYFPE PVTV-SW--- -N---SGALT SG-VHTFPAV LQS-SGLYSL SS*S*VTVPSSS LGT--Q-TYI CNVNHKPSNT KVDKKV--EP KSC |
| 34 | CH1-L124E-S188G numbered using the range of Seq 33 | ---ASTKGPS VFP*E*APSSKS --TSGGTAAL GCLVKDYFPE PVTV-SW--- -N---SGALT SG-VHTFPAV LQS-SGLYSL *G*SVVTVPSSS LGT--Q-TYI CNVNHKPSNT KVDKKV--EP KSC |
| 35 | CH1-L1.1 numbered using the range of Seq 33 | ---ASTKGPS VFPLAPSSKS --TSGGTAAL GCLVKDYFPE PVTV-SW--- -N---SGALT SG-VHTCPAV LQS-SGLYSL SSIVTVPSSS LGT--Q-TYI CNVNHKPSNT KVDDKV--EP KSS |
| 36 | CH1-L4.1 numbered using the range of Seq 33 | ---ASTKGPS VCPLAPSSKS --TSGGTAAL GCLVEDYFPE PVTV-SW--- -N---SGALT SG-VHTFPAV LQS-SGLYSL SSVVTVPSSS LGT--Q-TYI CNVNHKPSNT KVDKKV--EP KSS |
| 37 | CH1-L4.2 numbered using the range of Seq 33 | ---ASTKGPS VFPLAPSSKS --TSGGTAAL GCHVKDYFPE PVTV-SW--- -N---SGALT SG-VHTCPAV LDS-SGLYEL SSIVTVPSSS LGT--Q-TYI CNVNHKPSNT KVDKKV--EP KSS |
| 38 | CH1-L4.3 numbered using the range of Seq 33 | ---ASTKGPS VFPLAPSSKS --TSGGTACL GCLVSDYFPE PVTV-SW--- -N---SGALT SG-VHTFPAV LQS-SGLYEL SSVVTVPSSS LGT--Q-TYI CNVNHKPSNT KVDKKV--EP KSS |
| 39 | CH1-H10.1 numbered using the range of Seq 33 | ---ASTKGPS VFPLAPSSKS --TSGGTAAL GCSVKDYFPE PVTV-SW--- -N---SGALT SG-VHTCPAV LQS-SGLYSL WSVVTVPSSS LGT--Q-TYI CNVNHKPSNT KVDKKV--EP KSS |
| 40 | CH1-H10.4 numbered using the range of Seq 33 | ---ASTKGPS VCPLAPSSKS --TSGGTAAL GCSVKDYFPE PVTV-SW--- -N---SGALT SG-VHTFPAV LQS-SGLYSL WSVVTVPSSS LGT--Q-TYI CNVNHKPSNT KVDKKV--EP KSS |
| 41 | CH1-5.6 numbered using the range of Seq 33 | ---ASTKGPS VCPLAPSSKS --TSGGTACL GCSVKDYFPE PVTV-SW--- -N---SGALT SG-VHTCPAV LQS-SGLYSL WSVVTVPSSS LGT--Q-TYI CNVNHKPSNT KVDKKV--EP KSS |
| 42 | IGG1-HINGE numbered from 231 to 243 | -D--KTHTCP PCP |
| 43 | IgG1-HINGE-EE numbered using the range of Seq 42 | -E--KTHTCP ECP |
| 44 | IGG1-HINGE-RR numbered using the range of Seq 42 | -R--KTHTCP RCP |
| 45 | CH2-WINTER numbered using the range of Seq 13 | ---APEAAGA PSVFLFPPKP KDTLMI-SRT PEVTCVVVDV SHEDPEVKFN WYV--DG--V EVH-NAKTKP REEQYN---- STYRVVSVLT VLHQDWLNGK EYKCKVSNKA LPAPIEKTI- SKAK-- |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for C$_H$1 (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
| --- | --- | --- |
| 46 | CH3-CW numbered using the range of Seq 18 ("knob") | G-QPREPQVC TLPPSREE-- MTKNQVSLWC LVKGFYPS-D IAV--EWES- NG--QPENNY KTTPPVLDS- D--GSFFLYS KLTVDKSRWQ QGNVFSCSVM HEALHNHYTQ KSLSLSPGK |
| 47 | CH3-CSAV numbered using the range of Seq 18 ("hole") | G-QPREPQVY TLPPCREE-- MTKNQVSLSC AVKGFYPS-D IAV--EWES- NG--QPENNY KTTPPVLDS- D--GSFFLVS KLTVDKSRWQ QGNVFSCSVM HEALHNHYTQ KSLSLSPGK |
| 48 | CH3-E numbered using the range of Seq 18 | G-QPREPQVY TLPPSREE-- MTKNQVSLTC EVKGFYPS-D IAV--EWES- NG--QPENNY KTTPPVLDS- D--GSFFLYS KLTVDKSRWQ QGNVFSCSVM HEALHNHYTQ KSLSLSPGK |
| 49 | CH3-R numbered using the range of Seq 18 | G-QPREPQVY TLPPSREE-- MTKNQVSLTC LVKGFYPS-D IAV--EWES- NG--QPENNY KTTPPVLDS- D--GSFFLYS RLTVDKSRWQ QGNVFSCSVM HEALHNHYTQ KSLSLSPGK |
| 50 | C5-VH numbered from 1 to 113 with insertions 52A, 82A, 82B, 82C, 100A, 100B, 100C | QVQLVQSGAE VKKPGSSVKV SCKASGGTFS SYAISWVRQA PGQGLEWMGG IIPIFGTANY AQKFQGRVTI TADESTSTAY MELSSLRSED TAVYYCAGGS ITGTTPPFDYW GRGTLVTVSS |
| 51 | TAM-163 VH numbered using the range of Seq 50 | EVQLVESGGG LVQPGGSLRL SCAASGYSFT AYFMNWVRQA PGKGLEWVAR INPNNGDTFY TQKFKGRFTI SRDNAKNSLY LQMNSLRAED TAVYYCARRD YFGAM--DYW GQGTLVTVSS |
| 52 | C5-VL numbered from 1 to 107 | AIQLTQSPSS LTASVGDRVT ITCRASQFAS NDVGWYQQKP GKAPKLLIYA ASSLQSGVPP RFSGSGSGTE FTFTISSLQP EDFATYYCLQ DYTYPLTFGQ GTKVEIK |
| 53 | TAM-163 VL numbered from 1 to 107 | DIQMTQSPSS LSASVGDRVT ITCRASQTIS NNLHWYQQKP GKAPKLLIKS ASLAISGVPS RFSGSGSGTD FTLTISSLQP EDFATYYCQQ SNSWPNTFGG GTKVEIK |
| 54 | SeqID:1, 42, 45, 18 numbered from 111 to 478 (with insertions 162A, 162B, 162C, 26)A, 302A, 316A, 316B, 398A) | ---ASTKGPS VFPLAPSSKS --TSGGTAAL GCLVKDYFPE PVTV-SW--- -N---SGALT SG VHTFPAV LQS-SGLYSL SSVVTVPSSS LGT--Q-TYI CNVNHKPSNT KVDKKV--EP KSC-D--KTH TCPPCPAPEA AGAPSVFLFP PKPKDTLMI- SRTPEVTCVV VDVSHEDPEV KFNWYV--DG --VEVH-NAK TKPREEQYN- ---STYRVVS VLTVLHQDWL NGKEYKCKVS NKALPAPIEK TI-SKAKG-Q PREPQVYTLP PSREE--MTK NQVSLTCLVK GFYPS-DIAV --EWES-NG- -QPENNYKTT PPVLDS-D-- GSFFLYSKLT VDKSRWQQGN VFSCSVMHEA LHNHYTQKSL SLSPGK |
| 55 | SeqID:33, 42, 45, 46 using the numbering range of Seq 54 | ---ASTKGPS VFPKAPSSKS --TSGGTAAL GCLVKDYFPE PVTV-SW--- -N---SGALT SG-VHTFPAV LQS-SGLYSL SSSVTVPSSS LGT--Q-TYI CNVNHKPSNT KVDKKV--EP KSC-D--KTH TCPPCPAPEA AGAPSVFLFP PKPKDTLMI- SRTPEVTCVV VDVSHEDPEV KFNWYV--DG --VEVH-NAK TKPREEQYN- ---STYRVVS VLTVLHQDWL NGKEYKCKVS NKALPAPIEK TI-SKAKG-Q PREPQVCTLP PSREE--MTK NQVSLWCLVK GFYPS-DIAV --EWES-NG- -QPENNYKTT PPVLDS-D-- GSFFLYSKLT VDKSRWQQGN VFSCSVMHEA LHNHYTQKSL SLSPGK |
| 56 | SeqID:1, 42, 45, 46 using the numbering range of Seq 54 | ---ASTKGPS VFPLAPSSKS --TSGGTAAL GCLVKDYFPE PVTV-SW--- -N---SGALT SG-VHTFPAV LQS-SGLYSL SSVVTVPSSS LGT--Q-TYI CNVNHKPSNT KVDKKV--EP KSC-D--KTH TCPPCPAPEA AGAPSVFLFP PKPKDTLMI- SRTPEVTCVV VDVSHEDPEV KFNWYV--DG --VEVH-NAK TKPREEQYN- ---STYRVVS VLTVLHQDWL NGKEYKCKVS NKALPAPIEK TI-SKAKG-Q PREPQVCTLP PSREE--MTK NQVSLWCLVK GFYPS-DIAV |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
|  |  | --EWES-NG- -QPENNYKTT PPVLDS-D-- GSFFLYSKLT VDKSRWQQGN VFSCSVMHEA LHNHYTQKSL SLSPGK |
| 57 | SeqID:33, 44, 45, 49 using the numbering range of Seq 54 | ---ASTKGPS VFPKAPSSKS --TSGGTAAL GCLVKDYFPE PVTV-SW--- -N---SGALT SG-VHTFPAV LQS-SGLYSL SSSVTVPSSS LGT--Q-TYI CNVNHKPSNT KVDKKV--EP KSC-R--KTH TCPRCPAPEA AGAPSVFLFP PKPKDTLMI- SRTPEVTCVV VDVSHEDPEV KFNWYV--DG --VEVH-NAK TKPREEQYN- ---STYRVVS VLTVLHQDWL NGKEYKCKVS NKALPAPIEK TI-SKAKG-Q PREPQVYTLP PSREE--MTK NQVSLTCLVK GFYPS-DIAV --EWES-NG- -QPENNYKTT PPVLDS-D-- GSFFLYSRLT VDKSRWQQGN VFSCSVMHEA LHNHYTQKSL SLSPGK |
| 58 | SeqID:1, 44, 45, 49 using the numbering range of Seq 54 | ---ASTKGPS VFPLAPSSKS --TSGGTAAL GCLVKDYFPE PVTV-SW--- -N---SGALT SG-VHTFPAV LQS-SGLYSL SSSVTVPSSS LGT--Q-TYI CNVNHKPSNT KVDKKV--EP KSC-R--KTH TCPRCPAPEA AGAPSVFLFP PKPKDTLMI- SRTPEVTCVV VDVSHEDPEV KFNWYV--DG --VEVH-NAK TKPREEQYN- ---STYRVVS VLTVLHQDWL NGKEYKCKVS NKALPAPIEK TI-SKAKG-Q PREPQVYTLP PSREE--MTK NQVSLTCLVK GFYPS-DIAV --EWES-NG- -QPENNYKTT PPVLDS-D-- GSFFLYSRLT VDKSRWQQGN VFSCSVMHEA LHNHYTQKSL SLSPGK |
| 59 | SeqID:34, 42, 45, 47 using the numbering range of Seq 54 | ---ASTKGPS VFPEAPSSKS --TSGGTAAL GCLVKDYFPE PVTV-SW--- -N---SGALT SG-VHTFPAV LQS-SGLYSL SSVVTVPSSS LGT--Q-TYI CNVNHKPSNT KVDKKV--EP KSC-D--KTH TCPPCPAPEA AGAPSVFLFP PKPKDTLMI- SRTPEVTCVV VDVSHEDPEV KFNWYV--DG --VEVH-NAK TKPREEQYN- ---STYRVVS VLTVLHQDWL NGKEYKCKVS NKALPAPIEK TI-SKAKG-Q PREPQVYTLP PCREE--MTK NQVSLSCAVK GFYPS-DIAV --EWES-NG- -QPENNYKTT PPVLDS-D-- GSFFLVSKLT VDKSRWQQGN VFSCSVMHEA LHNHYTQKSL SLSPGK |
| 60 | SeqID:1, 42, 45, 47 using the numbering range of Seq 54 | ---ASTKGPS VFPLAPSSKS --TSGGTAAL GCLVKDYFPE PVTV-SW--- -N---SGALT SG-VHTFPAV LQS-SGLYSL SSVVTVPSSS LGT--Q-TYI CNVNHKPSNT KVDKKV--EP KSC-D--KTH TCPPCPAPEA AGAPSVFLFP PKPKDTLMI- SRTPEVTCVV VDVSHEDPEV KFNWYV--DG --VEVH-NAK TKPREEQYN- ---STYRVVS VLTVLHQDWL NGKEYKCKVS NKALPAPIEK TI-SKAKG-Q PREPQVYTLP PCREE--MTK NQVSLSCAVK GFYPS-DIAV --EWES-NG- -QPENNYKTT PPVLDS-D-- GSFFLVSKLT VDKSRWQQGN VFSCSVMHEA LHNHYTQKSL SLSPGK |
| 61 | SeqID:35, 42, 45, 47 using the numbering range of Seq 54 | ---ASTKGPS VFPLAPSSKS --TSGGTAAL GCLVKDYFPE PVTV-SW--- -N---SGALT SG-VHTCPAV LQS-SGLYSL SSIVTVPSSS LGT--Q-TYI CNVNHKPSNT KVDDKV--EP KSS-D--KTH TCPPCPAPEA AGAPSVFLFP PKPKDTLMI- SRTPEVTCVV VDVSHEDPEV KFNWYV--DG --VEVH-NAK TKPREEQYN- ---STYRVVS VLTVLHQDWL NGKEYKCKVS NKALPAPIEK TI-SKAKG-Q PREPQVYTLP PCREE--MTK NQVSLSCAVK GFYPS-DIAV --EWES-NG- -QPENNYKTT PPVLDS-D-- GSFFLVSKLT VDKSRWQQGN VFSCSVMHEA LHNHYTQKSL SLSPGK |
| 62 | SeqID:36, 42, 45, 47 using the numbering range of Seq 54 | ---ASTKGPS VCPLAPSSKS --TSGGTAAL GCLVEDYFPE PVTV-SW--- -N---SGALT SG-VHTFPAV LQS-SGLYSL SSVVTVPSSS LGT--Q-TYI CNVNHKPSNT KVDKKV--EP KSS-D--KTH TCPPCPAPEA AGAPSVFLFP PKPKDTLMI- SRTPEVTCVV VDVSHEDPEV KFNWYV--DG --VEVH-NAK TKPREEQYN- ---STYRVVS VLTVLHQDWL NGKEYKCKVS NKALPAPIEK TI-SKAKG-Q PREPQVYTLP PCREE--MTK NQVSLSCAVK GFYPS-DIAV --EWES-NG- -QPENNYKTT PPVLDS-D-- GSFFLVSKLT VDKSRWQQGN VFSCSVMHEA LHNHYTQKSL SLSPGK |
| 63 | SeqID:37, 42, 45, 47 using the numbering range of Seq 54 | ---ASTKGPS VFPLAPSSKS --TSGGTAAL GCHVKDYFPE PVTV-SW--- -N---SGALT SG-VHTCPAV LDS-SGLYEL SSIVTVPSSS LGT--Q-TYI CNVNHKPSNT KVDKKV--EP KSS-D--KTH TCPPCPAPEA AGAPSVFLFP PKPKDTLMI- SRTPEVTCVV VDVSHEDPEV KFNWYV--DG --VEVH-NAK |

TABLE 1-continued

Sequence list. Dashes ("-") indicate gaps introduced to align the various
allotype and isotype domains with Kabat numbering. Alignments were adjusted so that
boundaries (spaces) between blocks of 10 residues always fall between residue
numbering positions ending in "0" and residue numbering positions ending in "1".
Where a domain does not begin with a residue whose numbering position ends with "1",
phonypadding gaps were inserted to adjust the alignment. For example, for C_H1 (Seq ID
1) the Kabat domain begins at position 114. Three gap characters were inserted to put
the alignment in the correct frame (starting with position 111). These three gap residues
(corresponding to Kabat positions 111-113) are properly part of the VH domain and
would generally be occupied by real amino acids belonging to the VH in a full antibody
sequence. Similar padding gaps may be found at the beginning and end of some other
sequences.
The sequences herein described for 29D7 (SEQ ID NOs: 51 and 53, and other
sequences that comprise those sequences) are those of the antibody TAM-163. All
examples herein described as using antibody 29D7 used the antibody TAM-163.

SEQUENCE LIST

| SEQ | Description | Sequence |
|---|---|---|
|  |  | TKPREEQYN- ---STYRVVS VLTVLHQDWL NGKEYKCKVS NKALPAPIEK<br>TI-SKAKG-Q PREPQVYTLP PCREE--MTK NQVSLSCAVK GFYPS-DIAV<br>--EWES-NG- -QPENNYKTT PPVLDS-D-- GSFFLVSKLT VDKSRWQQGN<br>VFSCSVMHEA LHNHYTQKSL SLSPGK |
| 64 | SeqID:38, 42, 45, 47<br>using the<br>numbering range of<br>Seq 54 | ---ASTKGPS VFPLAPSSKS --TSGGTACL GCLVSDYFPE PVTV-SW---<br>-N---SGALT SG-VHTFPAV LQS-SGLYEL SSVVTVPSSS LGT--Q-TYI<br>CNVNHKPSNT KVDKKV--EP KSS-D--KTH TCPPCPAPEA AGAPSVFLFP<br>PKPKDTLMI- SRTPEVTCVV VDVSHEDPEV KFNWYV--DG --VEVH-NAK<br>TKPREEQYN- ---STYRVVS VLTVLHQDWL NGKEYKCKVS NKALPAPIEK<br>TI-SKAKG-Q PREPQVYTLP PCREE--MTK NQVSLSCAVK GFYPS-DIAV<br>--EWES-NG- -QPENNYKTT PPVLDS-D-- GSFFLVSKLT VDKSRWQQGN<br>VFSCSVMHEA LHNHYTQKSL SLSPGK |
| 65 | SeqID:39, 42, 45, 47<br>using the<br>numbering range of<br>Seq 54 | ---ASTKGPS VFPLAPSSKS --TSGGTAAL GCSVKDYFPE PVTV-SW---<br>-N---SGALT SG-VHTCPAV LQS-SGLYSL WSVVTVPSSS LGT--Q-TYI<br>CNVNHKPSNT KVDKKV--EP KSS-D--KTH TCPPCPAPEA AGAPSVFLFP<br>PKPKDTLMI- SRTPEVTCVV VDVSHEDPEV KFNWYV--DG --VEVH-NAK<br>TKPREEQYN- ---STYRVVS VLTVLHQDWL NGKEYKCKVS NKALPAPIEK<br>TI-SKAKG-Q PREPQVYTLP PCREE--MTK NQVSLSCAVK GFYPS-DIAV<br>--EWES-NG- -QPENNYKTT PPVLDS-D-- GSFFLVSKLT VDKSRWQQGN<br>VFSCSVMHEA LHNHYTQKSL SLSPGK |
| 66 | SeqID:40, 42, 45, 47<br>using the<br>numbering range of<br>Seq 54 | ---ASTKGPS VCPLAPSSKS --TSGGTAAL GCSVKDYFPE PVTV-SW---<br>-N---SGALT SG-VHTFPAV LQS-SGLYSL WSVVTVPSSS LGT--Q-TYI<br>CNVNHKPSNT KVDKKV--EP KSS-D--KTH TCPPCPAPEA AGAPSVFLFP<br>PKPKDTLMI- SRTPEVTCVV VDVSHEDPEV KFNWYV--DG --VEVH-NAK<br>TKPREEQYN- ---STYRVVS VLTVLHQDWL NGKEYKCKVS NKALPAPIEK<br>TI-SKAKG-Q PREPQVYTLP PCREE--MTK NQVSLSCAVK GFYPS-DIAV<br>--EWES-NG- -QPENNYKTT PPVLDS-D-- GSFFLVSKLT VDKSRWQQGN<br>VFSCSVMHEA LHNHYTQKSL SLSPGK |
| 67 | SeqID:41, 42, 45, 47<br>using the<br>numbering range of<br>Seq 54 | ---ASTKGPS VCPLAPSSKS --TSGGTACL GCSVKDYFPE PVTV-SW---<br>-N---SGALT SG-VHTCPAV LQS-SGLYSL WSVVTVPSSS LGT--Q-TYI<br>CNVNHKPSNT KVDKKV--EP KSS-D--KTH TCPPCPAPEA AGAPSVFLFP<br>PKPKDTLMI- SRTPEVTCVV VDVSHEDPEV KFNWYV--DG --VEVH-NAK<br>TKPREEQYN- ---STYRVVS VLTVLHQDWL NGKEYKCKVS NKALPAPIEK<br>TI-SKAKG-Q PREPQVYTLP PCREE--MTK NQVSLSCAVK GFYPS-DIAV<br>--EWES-NG- -QPENNYKTT PPVLDS-D-- GSFFLVSKLT VDKSRWQQGN<br>VFSCSVMHEA LHNHYTQKSL SLSPGK |
| 68 | SeqID:34, 43, 45, 48<br>using the<br>numbering range of<br>Seq 54 | ---ASTKGPS VFPEAPSSKS --TSGGTAAL GCLVKDYFPE PVTV-SW---<br>-N---SGALT SG-VHTFPAV LQS-SGLYSL GSVVTVPSSS LGT--Q-TYI<br>CNVNHKPSNT KVDKKV--EP KSC-E--KTH TCPECPAPEA AGAPSVFLFP<br>PKPKDTLMI- SRTPEVTCVV VDVSHEDPEV KFNWYV--DG --VEVH-NAK<br>TKPREEQYN- ---STYRVVS VLTVLHQDWL NGKEYKCKVS NKALPAPIEK<br>TI-SKAKG-Q PREPQVYTLP PSREE--MTK NQVSLTCEVK GFYPS-DIAV<br>--EWES-NG- -QPENNYKTT PPVLDS-D-- GSFFLYSKLT VDKSRWQQGN<br>VFSCSVMHEA LHNHYTQKSL SLSPGK |
| 69 | SeqID:1, 43, 45, 48<br>using the<br>numbering range of<br>Seq 54 | ---ASTKGPS VFPLAPSSKS --TSGGTAAL GCLVKDYFPE PVTV-SW---<br>-N---SGALT SG-VHTFPAV LQS-SGLYSL SSVVTVPSSS LGT--Q-TYI<br>CNVNHKPSNT KVDKKV--EP KSC-E--KTH TCPECPAPEA AGAPSVFLFP<br>PKPKDTLMI- SRTPEVTCVV VDVSHEDPEV KFNWYV--DG --VEVH-NAK<br>TKPREEQYN- ---STYRVVS VLTVLHQDWL NGKEYKCKVS NKALPAPIEK<br>TI-SKAKG-Q PREPQVYTLP PSREE--MTK NQVSLTCEVK GFYPS-DIAV<br>--EWES-NG- -QPENNYKTT PPVLDS-D-- GSFFLYSKLT VDKSRWQQGN<br>VFSCSVMHEA LHNHYTQKSL SLSPGK |
| 70 | SeqID:50, 54<br>numbered from 1 to | QVQLVQSGAE VKKPGSSVKV SCKASGGTFS SYAISWVRQA PGQGLEWMGG<br>IIPIFGTANY AQKFQGRVTI TADESTSTAY MELSSLRSED TAVYYCAGGS |

TABLE 1-continued

Sequence list. Dashes ("-") indicate gaps introduced to align the various
allotype and isotype domains with Kabat numbering. Alignments were adjusted so that
boundaries (spaces) between blocks of 10 residues always fall between residue
numbering positions ending in "0" and residue numbering positions ending in "1". Where
a domain does not begin with a residue whose numbering position ends with "1",
phonypadding gaps were inserted to adjust the alignment. For example, for $C_H1$ (Seq ID
1) the Kabat domain begins at position 114. Three gap characters were inserted to put
the alignment in the correct frame (starting with position 111). These three gap residues
(corresponding to Kabat positions 111-113) are properly part of the VH domain and
would generally be occupied by real amino acids belonging to the VH in a full antibody
sequence. Similar padding gaps may be found at the beginning and end of some other
sequences.
The sequences herein described for 29D7 (SEQ ID NOs: 51 and 53, and other
sequences that comprise those sequences) are those of the antibody TAM-163. All
examples herein described as using antibody 29D7 used the antibody TAM-163.

SEQUENCE LIST

| SEQ | Description | Sequence |
|---|---|---|
| | 478 with insertions 52A, 82A, 82B, 82C, 100A, 100B, 100C, 162A, 162B, 162C, 266A 302A 316A, 316B, 398A, | ITGTTPFDYW GRGTLVTVSS ASTKGPSVFP LAPSSKS--T SGGTAALGCL<br>VKDYFPEPVT V-SW----N- --SGALTSG- VHTFPAVLQS -SGLYSLSSV<br>VTVPSSSLGT --Q-TYICNV NHKPSNTKVD KKV--EPKSC -D--KTHTCP<br>PCPAPEAAGA PSVFLFPPKP KDTLMI-SRT PEVTCVVVDV SHEDPEVKFN<br>WYV--DG--V EVH-NAKTKP REEQYN---- STYRVVSVLT VLHQDWLNGK<br>EYKCKVSNKA LPAPIEKTI- SKAKG-QPRE PQVYTLPPSR EE--MTKNQV<br>SLTCLVKGFY PS-DIAV--E WES-NG--QP ENNYKTTPPV LDS-D--GSF<br>FLYSKLTVDK SRWQQGNVFS CSVMHEALHN HYTQKSLSLS PGK |
| 71 | BegID:50, 59 using the numbering range of Seq 70 | QVQLVQSGAE VKKPGSSVKV SCKASGGTFS SYAISWVRQA PGQGLEWMGG<br>IIPIFGTANY AQKFQGRVTI TADESTSTAY MELSSLRSED TAVYYCAGGS<br>ITGTTPFDYW GRGTLVTVSS ASTKGPSVFP EAPSSKS--T SGGTAALGCL<br>VKDYFPEPVT V-SW----N- --SGALTSG- VHTFPAVLQS -SGLYSLGSV<br>VTVPSSSLGT --Q-TYICNV NHKPSNTKVD KKV--EPKSC -D--KTHTCP<br>PCPAPEAAGA PSVFLFPPKP KDTLMI-SRT PEVTCVVVDV SHEDPEVKFN<br>WYV--DG--V EVH-NAKTKP REEQYN---- STYRVVSVLT VLHQDWLNGK<br>EYKCKVSNKA LPAPIEKTI- SKAKG-QPRE PQVYTLPPCR EE--MTKNQV<br>SLSCAVKGFY PS-DIAV--E WES-NG--QP ENNYKTTPPV LDS-D--GSF<br>FLVSKLTVDK SRWQQGNVFS CSVMHEALHN HYTQKSLSLS PGK |
| 72 | SeqID:50, 60 using the numbering range of Seq 70 | QVQLVQSGAE VKKPGSSVKV SCKASGGTFS SYAISWVRQA PGQGLEWMGG<br>IIPIFGTANY AQKFQGRVTI TADESTSTAY MELSSLRSED TAVYYCAGGS<br>ITGTTPFDYW GRGTLVTVSS ASTKGPSVFP LAPSSKS--T SGGTAALGCL<br>VKDYFPEPVT V-SW----N- --SGALTSG- VHTFPAVLQS -SGLYSLSSV<br>VTVPSSSLGT --Q-TYICNV NHKPSNTKVD KKV--EPKSC -D--KTHTCP<br>PCPAPEAAGA PSVFLFPPKP KDTLMI-SRT PEVTCVVVDV SHEDPEVKFN<br>WYV--DG--V EVH-NAKTKP REEQYN---- STYRVVSVLT VLHQDWLNGK<br>EYKCKVSNKA LPAPIEKTI- SKAKG-QPRE PQVYTLPPCR EE--MTKNQV<br>SLSCAVKGFY PS-DIAV--E WES-NG--QP ENNYKTTPPV LDS-D--GSF<br>FLVSKLTVDK SRWQQGNVFS CSVMHEALHN HYTQKSLSLS PGK |
| 73 | SeqID:50, 68 using the numbering range of Seq 70 | QVQLVQSGAE VKKPGSSVKV SCKASGGTFS SYAISWVRQA PGQGLEWMGG<br>IIPIFGTANY AQKFQGRVTI TADESTSTAY MELSSLRSED TAVYYCAGGS<br>ITGTTPFDYW GRGTLVTVSS ASTKGPSVFP EAPSSKS--T SGGTAALGCL<br>VKDYFPEPVT V-SW----N- --SGALTSG- VHTFPAVLQS -SGLYSLGSV<br>VTVPSSSLGT --Q-TYICNV NHKPSNTKVD KKV--EPKSC -E--KTHTCP<br>ECPAPEAAGA PSVFLFPPKP KDTLMI-SRT PEVTCVVVDV SHEDPEVKFN<br>WYV--DG--V EVH-NAKTKP REEQYN---- STYRVVSVLT VLHQDWLNGK<br>EYKCKVSNKA LPAPIEKTI- SKAKG-QPRE PQVYTLPPSR EE--MTKNQV<br>SLTCEVKGFY PS-DIAV--E WES-NG--QP ENNYKTTPPV LDS-D--GSF<br>FLYSKLTVDK SRWQQGNVFS CSVMHEALHN HYTQKSLSLS PGK |
| 74 | SeqID:50, 69 using the numbering range of Seq 70 | QVQLVQSGAE VKKPGSSVKV SCKASGGTFS SYAISWVRQA PGQGLEWMGG<br>IIPIFGTANY AQKFQGRVTI TADESTSTAY MELSSLRSED TAVYYCAGGS<br>ITGTTPFDYW GRGTLVTVSS ASTKGPSVFP LAPSSKS--T SGGTAALGCL<br>VKDYFPEPVT V-SW----N- --SGALTSG- VHTFPAVLQS -SGLYSLSSV<br>VTVPSSSLGT --Q-TYICNV NHKPSNTKVD KKV--EPKSC -E--KTHTCP<br>ECPAPEAAGA PSVFLFPPKP KDTLMI-SRT PEVTCVVVDV SHEDPEVKFN<br>WYV--DG--V EVH-NAKTKP REEQYN---- STYRVVSVLT VLHQDWLNGK<br>EYKCKVSNKA LPAPIEKTI- SKAKG-QPRE PQVYTLPPSR EE--MTKNQV<br>SLTCEVKGFY PS-DIAV--E WES-NG--QP ENNYKTTPPV LDS-D--GSF<br>FLYSKLTVDK SRWQQGNVFS CSVMHEALHN HYTQKSLSLS PGK |
| 75 | SeqID:51, 54 using the numbering range of Seq 70 | EVQLVESGGG LVQPGGSLRL SCAASGYSFT AYFMNWVRQA PGKGLEWVAR<br>INPNNGDTFY TQKFKGRFTI SRDNAKNSLY LQMNSLRAED TAVYYCARRD<br>YFGAM--DYW GQGTLVTVSS ASTKGPSVFP LAPSSKS--T SGGTAALGCL<br>VKDYFPEPVT V-SW----N- --SGALTSG- VHTFPAVLQS -SGLYSLSSV<br>VTVPSSSLGT --Q-TYICNV NHKPSNTKVD KKV--EPKSC -D--KTHTCP<br>PCPAPEAAGA PSVFLFPPKP KDTLMI-SRT PEVTCVVVDV SHEDPEVKFN<br>WYV--DG--V EVH-NAKTKP REEQYN---- STYRVVSVLT VLHQDWLNGK<br>EYKCKVSNKA LPAPIEKTI- SKAKG-QPRE PQVYTLPPSR EE--MTKNQV |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for C_H1 (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
|  |  | SLTCLVKGFY PS-DIAV--E WES-NG--QP ENNYKTTPPV LDS-D--GSF FLYSKLTVDK SRWQQGNVFS CSVMHEALHN HYTQKSLSLS PGK |
| 76 | SeqID:52, 9 numbered from position 1 to 215 | AIQLTQSPSS LTASVGDRVT ITCRASQFAS NDVGWYQQKP GKAPKLLIYA ASSLQSGVPP RFSGSGSGTE FTFTISSLQP EDFATYYCLQ DYTYPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC- |
| 77 | SeqID:52, 25 using the numbering range of Seq 76 | AIQLTQSPSS LTASVGDRVT ITCRASQFAS NDVGWYQQKP GKAPKLLIYA ASSLQSGVPP RFSGSGSGTE FTFTISSLQP EDFATYYCLQ DYTYPLTFGQ GTKVEIKRTV AAPSVFIFPP SDEQLKSGTA SVVCLLNNFY PREAKVQWKV DNALQSGNSQ ESVTEQDSKD STYSLKSTLT LSKADYEKHK VYACEVTHQG LSSPVTKSFN RGEC- |
| 78 | SeqID:53, 9 using the numbering range of Seq 76 | DIQMTQSPSS LSASVGDRVT ITCRASQTIS NNLHWYQQKP GKAPKLLIKS ASLAISGVPS RFSGSGSGTD FTLTISSLQP EDFATYYCQQ SNSWPNTFGG GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC- |
| 79 | IgG2 Hinge using the numbering range of Seq 42 | -CC-V-E-CP PCP |
| 80 | IgG3 Hinge from 231 to 243 with insertions 241A through 241Z, then insertions 241AA through 241SS | -LGDTTHTCP RCPEPKSCDT PPPCPRCPEP KSCDTPPPCP RCPEPKSCDT PPPCPRCP |
| 81 | IgG4 Hinge using the numbering range of Seq 42 | ------PPCP SCP |
| 82 | IgG1 CH3 alternate allotype numbered from 361 to 478 with E391 | G-QPREPQVY TLPPSREE-- MTKNQVSLTC EVKGFYPS-D IAV--EWES- NG--QPENNY KTTPPVLDS- D--GSFFLYS KLTVDKSRWQ QGNVFSCSVM HEALHNHYTQ KSLSLSPGK |
| 83 | IgG1 CH3 alternate allotype numbered from 361 to 478 with R441 | G-QPREPQVY TLPPSREE-- MTKNQVSLTC LVKGFYPS-D IAV--EWES- NG--QPENNY KTTPPVLDS- D--GSFFLYS RLTVDKSRWQ QGNVFSCSVM HEALHNHYTQ KSLSLSPGK |
| 84 | IgG2 CH3 alternate allotype numbered from 361 to 478 with R441 | G-QPREPQVY TLPPSREE-- MTKNQVSLTC LVKGFYPS-D ISV--EWES- NG--QPENNY KTTPPMLDS- D--GSFFLYS RLTVDKSRWQ QGNVFSCSVM HEALHNHYTQ KSLSLSPGK |
| 85 | IgG2 CH3 alternate allotype numbered from 361 to 478 with E391 | G-QPREPQVY TLPPSREE-- MTKNQVSLTC EVKGFYPS-D ISV--EWES- NG--QPENNY KTTPPMLDS- D--GSFFLYS KLTVDKSRWQ QGNVFSCSVM HEALHNHYTQ KSLSLSPGK |
| 86 | CL-5176D using the numbering range of Seq 9 | -------RTV AAPSVFIFPP SDEQLKSGTA SVVCLLNNFY PREAKVQWKV DNALQSGNSQ ESVTEQDSKD STYSL$^D$STLT LSKADYEKHK VYACEVTHQG LSSPVTKSFN RGEC |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
| 87 | CL-5176K using the numbering range of Seq 9 | -------RTV AAPSVFIFPP SDEQLKSGTA SVVCLLNNFY PREAKVQWKV DNALQSGNSQ ESVTEQDSKD STYSL*K*STLT LSKADYEKHK VYACEVTHQG LSSPVTKSFN RGEC |
| 88 | CL-Deconvolute-05 arm using the numbering range of Seq 76 | AIQLTQSPSS LTASVGDRVT ITCRASQFAS NDVGWYQQKP GKAPKLLIYA ASSLQSGVPP RFSGSGSGTE FTFTISSLQP EDFATYYCLQ DYTYPLTFGQ GTKVEIKRTV AAPSVFIFPP SDEQLKSGTA SV*V*CLLNNFY PREAKVQWKV DNALQSGNSQ ESVTEQDSKD STYSL*K*STLT LSKADYEKHK VYACEVTHQG LSSPVTKSFN RGEC- |
| 89 | CH1-L124K numbered using the range of Seq 33 | ---ASTKGPS VFP*K*APSSKS --TSGGTAAL GCLVKDYFPE PVTV-SW--- -N---SGALT SG-VHTFPAV LQS-SGLYSL SSVVTVPSSS LGT--Q-TYI CNVNHKPSNT KVDKKV--EP KSC |
| 90 | CH1-L124E numbered using the range of Seq 33 | ---ASTKGPS VFP*E*APSSKS --TSGGTAAL GCLVKDYFPE PVTV-SW--- -N---SGALT SG-VHTFPAV LQS-SGLYSL SSVVTVPSSS LGT--Q-TYI CNVNHKPSNT KVDKKV--EP KSC |
| 91 | CH-L124K-Knob (aka Seq 89, 42, 45, 46) numbered using the range of Seq 54 | ---ASTKGPS VFP*K*APSSKS --TSGGTAAL GCLVKDYFPE PVTV-SW--- -N---SGALT SG-VHTFPAV LQS-SGLYSL SSVVTVPSSS LGT--Q-TYI CNVNHKPSNT KVDKKV--EP KSC-D--KTH TCPPCPAPEA AGAPSVFLFP PKPKDTLMI- SRTPEVTCVV VDVSHEDPEV KFNWYV--DG --VEVH-NAK TKPREEQYN- ---STYRVVS VLTVLHQDWL NGKEYKCKVS NKALPAPIEK TI-SKAKG-Q PREPQVCTLP PSREE--MTK NQVSLWCLVK GFYPS-DIAV --EWES-NG- -QPENNYKTT PPVLDS-D-- GSFFLYSKLT VDKSRWQQGN VFSCSVMHEA LHNHYTQKSL SLSPGK |
| 92 | CH-L124E-Hole (aka Seq 90, 42, 45, 47) numbered using the range of Seq 54 | ---ASTKGPS VFP*E*APSSKS --TSGGTAAL GCLVKDYFPE PVTV-SW--- -N---SGALT SG-VHTFPAV LQS-SGLYSL SSVVTVPSSS LGT--Q-TYI CNVNHKPSNT KVDKKV--EP KSC-D--KTH TCPPCPAPEA AGAPSVFLFP PKPKDTLMI- SRTPEVTCVV VDVSHEDPEV KFNWYV--DG --VEVH-NAK TKPREEQYN- ---STYRVVS VLTVLHQDWL NGKEYKCKVS NKALPAPIEK TI-SKAKG-Q PREPQVYTLP PCREE--MTK NQVSLSCAVK GFYPS-DIAV --EWES-NG- -QPENNYKTT PPVLDS-D-- GSFFLVSKLT VDKSRWQQGN VFSCSVMHEA LHNHYTQKSL SLSPGK |
| 93 | HC-05 Deconvolute 51 rev (aka Seq 50, 92 or 50,90, 42, 45, 47) using the numbering range of Seq 70 | QVQLVQSGAE VKKPGSSVKV SCKASGGTFS SYAISWVRQA PGQGLEWMGG IIPIFGTANY AQKFQGRVTI TADESTSTAY MELSSLRSED TAVYYCAGGS ITGTTPFDYW GRGTLVTVSS ASTKGPSVFP *E*APSSKS--T SGGTAALGCL VKDYFPEPVT V-SW----N- --SGALTSG- VHTFPAVLQS -SGLYSLSSV VTVPSSSLGT --Q-TYICNV NHKPSNTKVD KKV--EPKSC -D--KTHTCP PCPAPEAAGA PSVFLFPPKP KDTLMI-SRT PEVTCVVVDV SHEDPEVKFN WYV--DG--V EVH-NAKTKP REEQYN---- STYRVVSVLT VLHQDWLNGK EYKCKVSNKA LPAPIEKTI- SKAKG-QPRE PQVYTLPPCR EE--MTKNQV SLSCAVKGFY PS-DIAV--E WES-NG--QP ENNYKTTPPV LDS-D--GSF FLVSKLTVDK SRWQQGNVFS CSVMHEALHN HYTQKSLSLS PGK |
| 94 | LC-C5-T1 (aka Seq 52, 26) using the numbering range of Seq 76 | AIQLTQSPSS LTASVGDRVT ITCRASQFAS NDVGWYQQKP GKAPKLLIYA ASSLQSGVPP RFSGSGSGTE FTFTISSLQP EDFATYYCLQ DYTYPLTFGQ GTKVEIKRTV AAPSVFIFPP SDKQLKSGTA SVVCILNNFY PREAKVQWKV DNALQSGNSQ ESVTEQDSKD STYSLCSTLT LSKADYEKHK VYACEVTHQG LSSPVTKSFN RGES- |
| 95 | LC-C5-T2 (aka Seq 52, 27) using the numbering range of Seq 76 | AIQLTQSPSS LTASVGDRVT ITCRASQFAS NDVGWYQQKP GKAPKLLIYA ASSLQSGVPP RFSGSGSGTE FTFTISSLQP EDFATYYCLQ DYTYPLTFGQ GTKVEIKRTV AAPSVFIFPP SDCQLKSGTA HVVCLLNNFY PREAKVQWKV DNALQSGNSQ ESVTEQDSKD STYSLSSTLT LSKADYEKHK VYACEVTHQG LSSPVTKSFN RGES- |
| 96 | LC-C5-T3 (aka Seq 52, 28) using the | AIQLTQSPSS LTASVGDRVT ITCRASQFAS NDVGWYQQKP GKAPKLLIYA ASSLQSGVPP RFSGSGSGTE FTFTISSLQP EDFATYYCLQ DYTYPLTFGQ |

TABLE 1-continued

Sequence list. Dashes ("-") indicate gaps introduced to align the various
allotype and isotype domains with Kabat numbering. Alignments were adjusted so that
boundaries (spaces) between blocks of 10 residues always fall between residue
numbering positions ending in "0" and residue numbering positions ending in "1". Where
a domain does not begin with a residue whose numbering position ends with "1",
phonypadding gaps were inserted to adjust the alignment. For example, for $C_H1$ (Seq ID
1) the Kabat domain begins at position 114. Three gap characters were inserted to put
the alignment in the correct frame (starting with position 111). These three gap residues
(corresponding to Kabat positions 111-113) are properly part of the VH domain and
would generally be occupied by real amino acids belonging to the VH in a full antibody
sequence. Similar padding gaps may be found at the beginning and end of some other
sequences.
The sequences herein described for 29D7 (SEQ ID NOs: 51 and 53, and other
sequences that comprise those sequences) are those of the antibody TAM-163. All
examples herein described as using antibody 29D7 used the antibody TAM-163.

SEQUENCE LIST

| SEQ | Description | Sequence |
|---|---|---|
|  | numbering range of Seq 76 | GTKVEIKRTV AAPSVFIFPP SDEQLKSGTA HVVCILNNFY PREAKVQWKV<br>DNALQSGNSQ ESVTEQDSKD STYSLCSTLT LSKADYEKHK VYACEVTHQG<br>LSSPVTKSFN RGES- |
| 97 | LC-C5-T4 (aka Seq 52, 29) using the numbering range of Seq 76 | AIQLTQSPSS LTASVGDRVT ITCRASQFAS NDVGWYQQKP GKAPKLLIYA<br>ASSLQSGVPP RFSGSGSGTE FTFTISSLQP EDFATYYCLQ DYTYPLTFGQ<br>GTKVEIKRTV AAPSVCIFPP SDEQLKSGTA HVVCLLNNFY PREAKVQWKV<br>DNALQSGNSQ ESVTEQDSKD STYSLSSTLT LSKADYEKHK VYACEVTHQG<br>LSSPVTKSFN RGES- |
| 98 | LC-C5-T9 (aka Seq 52, 30) using the numbering range of Seq 76 | AIQLTQSPSS LTASVGDRVT ITCRASQFAS NDVGWYQQKP GKAPKLLIYA<br>ASSLQSGVPP RFSGSGSGTE FTFTISSLQP EDFATYYCLQ DYTYPLTFGQ<br>GTKVEIKRTV AAPSVFIFPP SDEQLKSGTA DVSCLLNNFY PREAKVQWKV<br>DNALQSGNSQ ESVTEQDSKD STYSLCSSLT LSKADYEKHK VYACEVTHQG<br>LSSPVTKSFN RGES- |
| 99 | HC-C5-T1 (aka Seq 50, 61) using the numbering range of Seq 70 | QVQLVQSGAE VKKPGSSVKV SCKASGGTFS SYAISWVRQA PGQGLEWMGG<br>IIPIFGTANY AQKFQGRVTI TADESTSTAY MELSSLRSED TAVYYCAGGS<br>ITGTTPFDYW GRGTLVTVSS ASTKGPSVFP LAPSSKS--T SGGTAALGCL<br>VKDYFPEPVT V-SW----N- --SGALTSG- VHTCPAVLQS -SGLYSLSSI<br>VTVPSSSLGT --Q-TYICNV NHKPSNTKVD DKV--EPKSS -D--KTHTCP<br>PCPAPEAAGA PSVFLFPPKP KDTLMI-SRT PEVTCVVVDV SHEDPEVKFN<br>WYV--DG--V EVH-NAKTKP REEQYN---- STYRVVSVLT VLHQDWLNGK<br>EYKCKVSNKA LPAPIEKTI- SKAKG-QPRE PQVYTLPPCR EE--MTKNQV<br>SLSCAVKGFY PS-DIAV--E WES-NG--QP ENNYKTTPPV LDS-D--GSF<br>FLVSKLTVDK SRWQQGNVFS CSVMHEALHN HYTQKSLSLS PGK |
| 100 | HC-C5-T2 (aka Seq 50, 62) using the numbering range of Seq 70 | QVQLVQSGAE VKKPGSSVKV SCKASGGTFS SYAISWVRQA PGQGLEWMGG<br>IIPIFGTANY AQKFQGRVTI TADESTSTAY MELSSLRSED TAVYYCAGGS<br>ITGTTPFDYW GRGTLVTVSS ASTKGPSVCP LAPSSKS--T SGGTAALGCL<br>VEDYFPEPVT V-SW----N- --SGALTSG- VHTCPAVLQS -SGLYSLSSI<br>VTVPSSSLGT --Q-TYICNV NHKPSNTKVD KKV--EPKSS -D--KTHTCP<br>PCPAPEAAGA PSVFLFPPKP KDTLMI-SRT PEVTCVVVDV SHEDPEVKFN<br>WYV--DG--V EVH-NAKTKP REEQYN---- STYRVVSVLT VLHQDWLNGK<br>EYKCKVSNKA LPAPIEKTI- SKAKG-QPRE PQVYTLPPCR EE--MTKNQV<br>SLSCAVKGFY PS-DIAV--E WES-NG--QP ENNYKTTPPV LDS-D--GSF<br>FLVSKLTVDK SRWQQGNVFS CSVMHEALHN HYTQKSLSLS PGK |
| 101 | HC-C5-T3 (aka Seq 50, 63) using the numbering range of Seq 70 | QVQLVQSGAE VKKPGSSVKV SCKASGGTFS SYAISWVRQA PGQGLEWMGG<br>IIPIFGTANY AQKFQGRVTI TADESTSTAY MELSSLRSED TAVYYCAGGS<br>ITGTTPFDYW GRGTLVTVSS ASTKGPSVFP LAPSSKS--T SGGTAALGCH<br>VKDYFPEPVT V-SW----N- --SGALTSG- VHTCPAVLDS -SGLYELSSI<br>VTVPSSSLGT --Q-TYICNV NHKPSNTKVD KKV--EPKSS -D--KTHTCP<br>PCPAPEAAGA PSVFLFPPKP KDTLMI-SRT PEVTCVVVDV SHEDPEVKFN<br>WYV--DG--V EVH-NAKTKP REEQYN---- STYRVVSVLT VLHQDWLNGK<br>EYKCKVSNKA LPAPIEKTI- SKAKG-QPRE PQVYTLPPCR EE--MTKNQV<br>SLSCAVKGFY PS-DIAV--E WES-NG--QP ENNYKTTPPV LDS-D--GSF<br>FLVSKLTVDK SRWQQGNVFS CSVMHEALHN HYTQKSLSLS PGK |
| 102 | HC-C5-T4 (aka Seq 50, 64) using the numbering range of Se q 70 | QVQLVQSGAE VKKPGSSVKV SCKASGGTFS SYAISWVRQA PGQGLEWMGG<br>IIPIFGTANY AQKFQGRVTI TADESTSTAY MELSSLRSED TAVYYCAGGS<br>ITGTTPFDYW GRGTLVTVSS ASTKGPSVFP LAPSSKS--T SGGTACLGCL<br>VSDYFPEPVT V-SW----N- --SGALTSG- VHTFPAVLQS -SGLYELSSV<br>VTVPSSSLGT --Q-TYICNV NHKPSNTKVD KKV--EPKSS -D--KTHTCP<br>PCPAPEAAGA PSVFLFPPKP KDTLMI-SRT PEVTCVVVDV SHEDPEVKFN<br>WYV--DG--V EVH-NAKTKP REEQYN---- STYRVVSVLT VLHQDWLNGK<br>EYKCKVSNKA LPAPIEKTI- SKAKG-QPRE PQVYTLPPCR EE--MTKNQV<br>SLSCAVKGFY PS-DIAV--E WES-NG--QP ENNYKTTPPV LDS-D--GSF<br>FLVSKLTVDK SRWQQGNVFS CSVMHEALHN HYTQKSLSLS PGK |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
| 103 | HC-C5-T9 (aka Seq 50, 65) using the numbering range of Seq 70 | QVQLVQSGAE VKKPGSSVKV SCKASGGTFS SYAISWVRQA PGQGLEWMGG IIPIFGTANY AQKFQGRVTI TADESTSTAY MELSSLRSED TAVYYCAGGS ITGTTPFDYW GRGTLVTVSS ASTKGPSVFP LAPSSKS--T SGGTAALGCS VKDYFPEPVT V-SW----N- --SGALTSG- VHTCPAVLQS -SGLYSLWSV VTVPSSSLGT --Q-TYICNV NHKPSNTKVD KKV--EPKSS -D--KTHTCP PCPAPEAAGA PSVFLFPPKP KDTLMI-SRT PEVTCVVVDV SHEDPEVKFN WYV--DG--V EVH-NAKTKP REEQYN---- STYRVVSVLT VLHQDWLNGK EYKCKVSNKA LPAPIEKTI- SKAKG-QPRE PQVYTLPPCR EE--MTKNQV SLSCAVKGFY PS-DIAV--E WES-NG--QP ENNYKTTPPV LDS-D--GSF FLVSKLTVDK SRWQQGNVFS CSVMHEALHN HYTQKSLSLS PGK |
| 104 | TOA-1 $V_H$ | ATGGGATGGAGCTGTATCTTTCTCTTTCCTGTCAGTAACTGTAGGT GTGTTCTCTGAGGTTCAGCTGCAGCAGTCTGGACCTGAGCTGGTGAA GCCTGGGGCTTCAATGAAGATATCCTGCAAGACTTCTGGTTACTCATT TACTGCCTACTTTATGAACTGGGTGAAGCAGAGCCATGGAAAGAGCC TTGAGTGGATTGGACGTATTAATCCCAACAATGGTGACACTTTCTACA CCCAGAAGTTCAAGGGCAAGGCCACATTGACTGTAGACAAATCCTCT AACACAGCCCACATGGAACTCCTGAGCCTGACATCTGAGGACTCTGC AATCTATTATTGTGGAAGAAGGGATTATTTCGGGGCTATGGACTACTG GGGTCAAGGAACCTCAGTCACCGTCTCCTCA |
| 105 | TOA-1 $V_H$ (leader, CDRs underlined and defined by Kabat) | *MGWSCIFLFLLSVTVGVFS*EVQLQQSGPELVKPGASMKISCKTSGYSFT AYFMNWVKQSHGKSLEWIGRINPNNGDTFYTQKFKGKATLTVDKSSNT AHMELLSLTSEDSAIYYCGRRDYFGAMDYWGQGTSVTVSS |
| 106 | TOA-1 $V_L$ | ATGGTTTTCACACCTCAGATACTTGGACTTATGCTTTTTTGGATTTCAG CCTCCAGAGGTGCTATTGTGCTAATTCAGTCTCCAGCCACCCTGTCT GTGACTCCAGGAGATAGCGTCAGTCTTTCCTGCAGGGCCAGCCAAA CTATTAGTAACAACCTACACTGGTATCAACAAAAATCACATGAGTCTC CAAGGCTTCTCATCAAGTCTGCTTCCCTGGCCATCTCTGGGATCCCC TCCAGGTTCAGTGGCAGTGGATCAGGGACAGATTTCACTCTCAGTAT CAGCAGTGTGGAGACTGAAGATTTTGGAATGTATTTCTGTCAACAGA GTAACAGCTGGCCGAACACGTTCGGCGGGGGGACCAAGCTGGAAAT AAAA |
| 107 | TOA-1 $V_L$ (leader, CDRs underlined defined by Kabat) | *MVFTPQILGLMLFWISASRGA*IVLIQSPATLSVTPGDSVSLSCRASQTISN NLHWYQQKSHESPRLLIKSASLAISGIPSRFSGSGSGTDFTLSISSVETED FGMYFCQQSNSWPNTFGGGTKLEIK |
| 108 | SEQ ID NO: 5 TOA-1 A1D $V_L$ | GATATTGTGCTAATTCAGTCTCCAGCCACCCTGTCTGTGACTCCAGG AGATAGCGTCAGTCTTTCCTGCAGGGCCAGCCAAACTATTAGTAACA ACCTACACTGGTATCAACAAAAATCACATGAGTCTCCAAGGCTTCTCA TCAAGTCTGCTTCCCTGGCCATCTCTGGGATCCCCTCCAGGTTCAGT GGCAGTGGATCAGGGACAGATTTCACTCTCAGTATCAGCAGTGTGGA GACTGAAGATTTTGGAATGTATTTCTGTCAACAGAGTAACAGCTGGCC GAACACGTTCGGCGGGGGGACCAAGGTGGAAATAAAA |
| 109 | TOA-1 A1D $V_L$ (leader, CDRs underlined defined by Kabat) | DIVLIQSPATLSVTPGDSVSLSCRASQTISNNLHWYQQKSHESPRLLIKSA SLAISGIPSRFSGSGSGTDFTLSISSVETEDFGMYFCQQSNSWPNTFGG GTKVEIK |
| 110 | huTOA-1 $V_H$ v1.0 | GAGGTGCAGCTGGTGGAGTCTGGGGGAGGCTTGGTCCAGCCTGGG GGGTCCCTGAGACTCTCCTGTGCAGCCTCTGGTTACTCATTTACTGC CTACTTTATGAACTGGGTCCGCCAGGCTCCAGGGAAGGGGCTGGAG TGGGTGGCCCGTATTAATCCCAACAATGGTGACACTTTCTACACCCA GAAGTTCAAGGGCCGATTCACCATCTCCAGAGACAACGCCAAGAACT CACTGTATCTGCAAATGAACAGCCTGAGAGCCGAGGACACCGCTGT GTATTACTGTGCCAGAAGGGATTATTTCGGGGCTATGGACTACTGGG GTCAAGGAACCTTGGTCACCGTCTCCTCA |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
| 111 | huTOA-1 $V_H$ v1.1 (CDRs underlined defined by AbM) | EVQLVESGGGLVQPGGSLRLSCATS<u>GYSFTAYFMN</u>WVRQAPGKGLEW VA<u>RINPNNGDTFYTQKFKG</u>RFTISVDNAKNSAYLQMNSLRAEDTAVYYC ARR<u>DYFGAMDY</u>WGQGTLVTVSS |
| 112 | huTOA-1 $V_H$ v1.1 | GAGGTGCAGCTGGTGGAGTCTGGGGGAGGCTTGGTCCAGCCTGGG GGGTCCCTGAGACTCTCCTGTGCAACCTCTGGTTACTCATTTACTGC CTACTTTATGAACTGGGTCCGCCAGGCTCCAGGGAAGGGGCTGGAG TGGGTGGCCCGTATTAATCCCAACAATGGTGACACTTTCTACACCCA GAAGTTCAAGGGCCGATTCACCATCTCCGTGGACAACGCCAAGAACT CAGCCTATCTGCAAATGAACAGCCTGAGAGCCGAGGACACCGCTGT GTATTACTGTGCCAGAAGGGATTATTTCGGGGCTATGGACTACTGGG GTCAAGGAACCTTGGTCACCGTCTCCTCA |
| 113 | huTOA-1 $V_H$ v2.0 (CDRs underlined defined by AbM) | EVQLVQSGAEVKKPGATVKISCKVS<u>GYSFTAYFMN</u>WVQQAPGKGLEW MG<u>RINPNNGDTFYTQKFKG</u>RVTITADTSTDTAYMELSSLRSEDTAVYYC ATR<u>DYFGAMDY</u>WGQGTLVTVSS |
| 114 | huTOA-1 $V_H$ v2.0 | GAGGTCCAGCTGGTGCAGTCTGGGGCTGAGGTGAAGAAGCCTGGG GCTACAGTGAAAATCTCCTGCAAGGTCTCCGGTTACTCATTTACTGCC TACTTTATGAACTGGGTGCAACAGGCCCCTGGAAAAGGGCTGGAGT GGATGGGACGTATTAATCCCAACAATGGTGACACTTTCTACACCCAG AAGTTCAAGGGCAGAGTCACCATAACCGCTGACACCTCTACAGACAC AGCCTACATGGAGCTGAGCAGCCTGCGCTCTGAGGACACCGCCGTG TATTACTGTGCAACAAGGGATTATTTCGGGGCTATGGACTACTGGGG TCAAGGAACCTTGGTCACCGTCTCCTCA |
| 115 | huTOA-1 $V_L$ v1.0 (CDRs underlined defined by AbM) | DIQMTQSPSSLSASVGDRVTITC<u>RASQTISNNLH</u>WYQQKPGKAPKWY<u>S ASLAIS</u>GVPSRFSGSGSGTDFTLTISSLQPEDFATYYC<u>QQSNSWPNT</u>FG GGTKVEIK |
| 116 | huTOA-1 $V_L$ v1.0 | GACATCCAGATGACCCAGTCTCCATCCTCCCTGTCTGCATCTGTCGG AGACAGAGTCACCATCACTTGCAGGGCCAGCCAAACTATTAGTAACA ACCTGCACTGGTATCAGCAGAAACCAGGCAAAGCCCCTAAGCTCCTG ATCTATTCTGCTTCCCTGGCCATCTCTGGAGTCCCATCCCGCTTCAG CGGCAGCGGATCCGGCACAGATTTCACTCTCACCATCAGCAGCCTG CAACCTGAAGATTTTGCAACTTACTACTGTCAACAGAGTAACAGCTGG CCCAACACCTTCGGCGGAGGGACCAAGGTGGAAATAAAA |
| 117 | huTOA-1 $V_L$ v1.1 (CDRs underlined defined by AbM) | DIQMTQSPSSLSASVGDRVTITC<u>RASQTISNNLH</u>WYQQKPGESPKLLIK<u>S ASLAIS</u>GVPSRFSGSGSGTDFTLTISSLQPEDFATYYC<u>QQSNSWPNT</u>FG GGTKVEIK |
| 118 | huTOA-1 $V_L$ v1.1 | GACATCCAGATGACCCAGTCTCCATCCTCCCTGTCTGCATCTGTCGG AGACAGAGTCACCATCACTTGCAGGGCCAGCCAAACTATTAGTAACA ACCTGCACTGGTATCAGCAGAAACCAGGCGAGTCCCCTAAGCTCCTG ATCAAGTCTGCTTCCCTGGCCATCTCTGGAGTCCCATCCCGCTTCAG CGGCAGCGGATCCGGCACAGATTTCACTCTCACCATCAGCAGCCTG CAACCTGAAGATTTTGCAACTTACTACTGTCAACAGAGTAACAGCTGG CCCAACACCTTCGGCGGAGGGACCAAGGTGGAAATAAAA |
| 119 | huTOA-1 $V_L$ v1.2 (CDRs underlined defined by AbM) | DIQMTQSPSSLSASVGDRVTITC<u>RASQTISNNLH</u>WYQQKPGEAPKWY<u>S ASLAIS</u>GVPSRFSGSGSGTDFTLTISSLQPEDFATYYC<u>QQSNSWPNT</u>FG GGTKVEIK |
| 120 | huTOA-1 $V_L$ v1.2 | GACATCCAGATGACCCAGTCTCCATCCTCCCTGTCTGCATCTGTCGG AGACAGAGTCACCATCACTTGCAGGGCCAGCCAAACTATTAGTAACA ACCTGCACTGGTATCAGCAGAAACCAGGCGAGGCCCCTAAGCTCCT GATCTATTCTGCTTCCCTGGCCATCTCTGGAGTCCCATCCCGCTTCA GCGGCAGCGGATCCGGCACAGATTTCACTCTCACCATCAGCAGCCT GCAACCTGAAGATTTTGCAACTTACTACTGTCAACAGAGTAACAGCTG GCCCAACACCTTCGGCGGAGGGACCAAGGTGGAAATAAAA |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
| 121 | huTOA-1 $V_L$ v1.3 (CDRs underlined defined by AbM) | DIQMTQSPSSLSASVGDRVTITC<u>RASQTISNNLH</u>WYQQKPGKSPKWY<u>S ASLAI</u>SGVPSRFSGSGSGTDFTLTISSLQPEDFATYYC<u>QQSNSWPNT</u>FG GGTKVEIK |
| 122 | SEQ ID NO: 20 huTOA-1 $V_L$ v1.3 | GACATCCAGATGACCCAGTCTCCATCCTCCCTGTCTGCATCTGTCGG AGACAGAGTCACCATCACTTGCAGGGCCAGCCAAACTATTAGTAACA ACCTGCACTGGTATCAGCAGAAACCAGGCAAATCCCCTAAGCTCCTG ATCTATTCTGCTTCCCTGGCCATCTCTGGAGTCCCATCCCGCTTCAG CGGCAGCGGATCCGGCACAGATTTCACTCTCACCATCAGCAGCCTG CAACCTGAAGATTTTGCAACTTACTACTGTCAACAGAGTAACAGCTGG CCCAACACCTTCGGCGGAGGGACCAAGGTGGAAATAAAA |
| 123 | huTOA-1 $V_L$ v1.4 | GACATCCAGATGACCCAGTCTCCATCCTCCCTGTCTGCATCTGTCGG AGACAGAGTCACCATCACTTGCAGGGCCAGCCAAACTATTAGTAACA ACCTGCACTGGTATCAGCAGAAACCAGGCAAAGCCCCTAAGCTCCTG ATCAAGTCTGCTTCCCTGGCCATCTCTGGAGTCCCATCCCGCTTCAG CGGCAGCGGATCCGGCACAGATTTCACTCTCACCATCAGCAGCCTG CAACCTGAAGATTTTGCAACTTACTACTGTCAACAGAGTAACAGCTGG CCCAACACCTTCGGCGGAGGGACCAAGGTGGAAATAAAA |
| 124 | huTOA-1 $V_L$ v1.5 (CDRs underlined defined by AbM) | DIQMTQSPSSLSASVGDRVTITC<u>RASQTISNNLH</u>WYQQKPHKAPKWY<u>S ASLAI</u>SGVPSRFSGSGSGTDFTLTISSLQPEDFATYYC<u>QQSNSWPNT</u>FG GGTKVEIK |
| 125 | huTOA-1 $V_L$ v1.5 | GACATCCAGATGACCCAGTCTCCATCCTCCCTGTCTGCATCTGTCGG AGACAGAGTCACCATCACTTGCAGGGCCAGCCAAACTATTAGTAACA ACCTGCACTGGTATCAGCAGAAACCACACAAAGCCCCTAAGCTCCTG ATCTATTCTGCTTCCCTGGCCATCTCTGGAGTCCCATCCCGCTTCAG CGGCAGCGGATCCGGCACAGATTTCACTCTCACCATCAGCAGCCTG CAACCTGAAGATTTTGCAACTTACTACTGTCAACAGAGTAACAGCTGG CCCAACACCTTCGGCGGAGGGACCAAGGTGGAAATAAAA |
| 126 | huTOA-1 $V_L$ v1.6 (CDRs underlined defined by AbM) | DIQMTQSPSSLSASVGDRVTITC<u>RASQTISNNLH</u>WYQQKPGESPKWY<u>S ASLAI</u>SGVPSRFSGSGSGTDFTLTISSLQPEDFATYYC<u>QQSNSWPNT</u>FG GGTKVEIK |
| 127 | huTOA-1 $V_L$ v1.6 | GACATCCAGATGACCCAGTCTCCATCCTCCCTGTCTGCATCTGTCGG AGACAGAGTCACCATCACTTGCAGGGCCAGCCAAACTATTAGTAACA ACCTGCACTGGTATCAGCAGAAACCAGGCGAGTCCCCTAAGCTCCTG ATCTATTCTGCTTCCCTGGCCATCTCTGGAGTCCCATCCCGCTTCAG CGGCAGCGGATCCGGCACAGATTTCACTCTCACCATCAGCAGCCTG CAACCTGAAGATTTTGCAACTTACTACTGTCAACAGAGTAACAGCTGG CCCAACACCTTCGGCGGAGGGACCAAGGTGGAAATAAAA |
| 128 | huTOA-1 $V_L$ v1.7 (CDRs underlined defined by AbM) | DIQMTQSPSSLSASVGDRVTITC<u>RASQTISNNLH</u>WYQQKPGKSPKLLIK<u>S ASLAI</u>SGVPSRFSGSGSGTDFTLTISSLQPEDFATYYC<u>QQSNSWPNT</u>FG GGTKVEIK |
| 129 | huTOA-1 $V_L$ v1.7 | GACATCCAGATGACCCAGTCTCCATCCTCCCTGTCTGCATCTGTCGG AGACAGAGTCACCATCACTTGCAGGGCCAGCCAAACTATTAGTAACA ACCTGCACTGGTATCAGCAGAAACCAGGCAAATCCCCTAAGCTCCTG ATCAAGTCTGCTTCCCTGGCCATCTCTGGAGTCCCATCCCGCTTCAG CGGCAGCGGATCCGGCACAGATTTCACTCTCACCATCAGCAGCCTG CAACCTGAAGATTTTGCAACTTACTACTGTCAACAGAGTAACAGCTGG CCCAACACCTTCGGCGGAGGGACCAAGGTGGAAATAAAA |
| 130 | huTOA-1 $V_L$ v1.8 (CDRs underlined defined by AbM) | DIQMTQSPSSLSASVGDRVTITC<u>RASQTISNNLH</u>WYQQKPGEAPKLLIK<u>S ASLAI</u>SGVPSRFSGSGSGTDFTLTISSLQPEDFATYYC<u>QQSNSWPNT</u>FG G GTKVEIK |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
| 131 | huTOA-1 $V_L$ v1.8 | GACATCCAGATGACCCAGTCTCCATCCTCCCTGTCTGCATCTGTCGG<br>AGACAGAGTCACCATCACTTGCAGGGCCAGCCAAACTATTAGTAACA<br>ACCTGCACTGGTATCAGCAGAAACCAGGCGAGGCCCCTAAGCTCCT<br>GATCAAGTCTGCTTCCCTGGCCATCTCTGGAGTCCCATCCCGCTTCA<br>GCGGCAGCGGATCCGGCACAGATTTCACTCTCACCATCAGCAGCCT<br>GCAACCTGAAGATTTTGCAACTTACTACTGTCAACAGAGTAACAGCTG<br>GCCCAACACCTTCGGCGGAGGGACCAAGGTGGAAATAAAA |
| 132 | huTOA-1 $V_L$ v2.0 (CDRs underlined defined by AbM) | EIVMTQSPATLSVSPGERATLSC<u>RASQTISNNLH</u>WYQQKPGQAPRLLIY<u>S<br>ASLAIS</u>GIPARFSGSGSGTEFTLTISSLQSEDFAVYYC<u>QQSNSWPNTF</u>GG<br>GTKVEIK |
| 133 | huTOA-1 $V_L$ v2.0 | GAAATCGTGATGACACAGTCTCCAGCCACCCTGTCTGTGTCTCCAGG<br>CGAACGCGCCACCCTGTCCTGCAGGGCCAGCCAAACTATTAGTAACA<br>ACCTGCACTGGTACCAGCAGAAACCTGGCCAGGCTCCCAGGCTCCT<br>GATCTATTCTGCTTCCCTGGCCATCTCTGGCATCCCAGCCCGCTTCA<br>GCGGCAGCGGATCCGGCACAGAGTTCACTCTCACCATCAGCAGCCT<br>GCAGTCCGAAGATTTTGCTGTGTATTACTGTCAACAGAGTAACAGCT<br>GGCCCAACACCTTCGGCGGAGGGACCAAGGTGGAAATAAAA |
| 134 | Human TrkA, NP_002520<br>NP_002520 Length: 796<br>Jun. 8, 2009 11:29 Type:<br>P Check: 1056 .. | MLRGGRRGQL GWHSWAAGPG SLLAWLILAS AGAAPCPDAC<br>CPHGSSGLRC TRDGALDSLH HLPGAENLTE LYIENQQHLQ<br>HLELRDLRGL GELRNLTIVK SGLRFVAPDA FHFTPRLSRL<br>NLSFNALESL SWKTVQGLSL QELVLSGNPL HCSCALRWLQ<br>RWEEEGLGGV PEQKLQCHGQ GPLAHMPNAS CGVPTLKVQV<br>PNASVDVGDD VLLRCQVEGR GLEQAGWILT ELEQSATVMK<br>SGGLPSLGLT LANVTSDLNR KNVTCWAEND VGRAEVSVQV<br>NVSFPASVQL HTAVEMHHWC IPPFSVDGQPA PSLRWLFNGS<br>VLNETSFIFT EFLEPAANET VRHGCLRLNQ PTHVNNGNYT<br>LLAANPFGQA SASIMAAFMD NPPEFNPEDP IPVSFSPVDT<br>NSTSGDPVEK KDETPFGVSV AVGLAVFACL FLSTLLLVLN<br>KCGRRNKFGI NRPAVLAPED GLAMSLHFMT LGGSSLSPTE<br>GKGSGLQGHI IENPQYFSDA CVHHIKRRDI VLKWELGEGA<br>FGKVFLAECH NLLPEQDKML VAVKALKEAS ESARQDFQRE<br>AELLTMLQHQ HIVRFFGVCT EGRPLLMVFE YMRHGDLNRF<br>LRSHGPDAKL LAGGEDVAPG PLGLGQLLAV ASQVAAGMVY<br>LAGLHFVHRD LATRNCLVGQ GLVVKIGDFG MSRDIYSTDY<br>YRVGGRTMLP IRWMPPESIL YRKFTTESDV WSFGVVLWEI<br>FTYGKQPWYQ LSNTEAIDCI TQGRELERPR ACPPEVYAIM<br>RGCWQREPQQ RHSIKDVHAR LQALAQAPPV YLDVLG |
| 135 | Human TrkB,<br>NP_001018074<br>NP_001018074 Length:<br>822 Dec. 1, 2007<br>13:31 Type: P Check:<br>9157 | MSSWIRWHGP AMARLWGFCW LVVGFWRAAF ACPTSCKCSA<br>SRIWCSDPSP GIVAFPRLEP NSVDPENITE IFIANQKRLE IINEDDVEAY<br>VGLRNLTIVD SGLKFVAHKA FLKNSNLQHI NFTRNKLTSL<br>SRKHFRHLDL SELILVGNPF TCSCDIMWIK TLQEAKSSPD<br>TQDLYCLNES SKNIPLANLQ IPNCGLPSAN LAAPNLTVEE<br>GKSITLSCSV AGDPVPNMYW DVGNLVSKHM NETSHTQGSL<br>RITNISSDDS GKQISCVAEN LVGEDQDSVN LTVHFAPTIT<br>FLESPTSDHH WCIPFTVKGN PKPALQWFYN GAILNESKYI<br>CTKIHVTNHT EYHGCLQLDN PTHMNNGDYT LIAKNEYGKD<br>EKQISAHFMG WPGIDDGANP NYPDVIYEDY GTAANDIGDT<br>TNRSNEIPST DVTDKTGREH LSVYAVVVIA SVVGFCLLVM<br>LFLLKLARHS KFGMKGPASV ISNDDDSASP LHHISNGSNT<br>PSSSEGGPDA VIIGMTKIPV IENPQYFGIT NSQLKPDTFV QHIKRHNIVL<br>KRELGEGAFG KVFLAECYNL CPEQDKILVA VKTLKDASDN<br>ARKDFHREAE LLTNLQHEHI VKFYGVCVEG DPLIMVFEYM<br>KHGDLNKFLR AHGPDAVLMA EGNPPTELTQ SQMLHIAQQI<br>AAGMVYLASQ HFVHRDLATR NCLVGENLLV KIGDFGMSRD<br>VYSTDYYRVG GHTMLPIRWM PPESIMYRKF TTESDVWSLG |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
| | | VVLWEIFTYG KQPWYQLSNN EVIECITQGR VLQRPRTCPQ |
| | | EVYELMLGCW QREPHMRKNI KGIHTLLQNL AKASPVYLDI LG |
| 136 | Chimeric TrkB (d5TrkA) | MSSWIRWHGP AMARLWGFCW LVVGFWRAAF ACPTSCKCSA |
| | | SRIWCSDPSP GIVAFPRLEP NSVDPENITE IFIANQKRLE IINEDDVEAY |
| | | VGLRNLTIVD SGLKFVAHKA FLKNSNLQHI NFTRNKLTSL |
| | | SRKHFRHLDL SELILVGNPF TCSCDIMWIK TLQEAKSSPD |
| | | TQDLYCLNES SKNIPLANLQ IPNCGLPSAN LAAPNLTVEE |
| | | GKSITLSCSV AGDPVPNMYW DVGNLVSKHM NETSHTQGSL |
| | | RITNISSDDS GKQISCVAEN LVGEDQDSVN LTVVNVSFPA |
| | | SVQLHTAVEM HHWCIPFSVD GQPAPSLRWL FNGSVLNETS |
| | | FIFTEFLEPA ANETVRHGCL RLNQPTHVNN GNYTLLAANP |
| | | FGQASASIMA AFMGWPGIDD GANPNYPDVI YEDYGTAAND |
| | | IGDTTNRSNE IPSTDVTDKT GREHLSVYAV VVIASVVGFC |
| | | LLVMLFLLKL ARHSKFGMKG PASVISNDDD SASPLHHISN |
| | | GSNTPSSSEG GPDAVIIGMT KIPVIENPQY FGITNSQLKP |
| | | DTFVQHIKRH NIVLKRELGE GAFGKVFLAE CYNLCPEQDK |
| | | ILVAVKTLKD ASDNARKDFH REAELLTNLQ HEHIVKFYGV |
| | | CVEGDPLIMV FEYMKHGDLN KFLRAHGPDA VLMAEGNPPT |
| | | ELTQSQMLHI AQQIAAGMVY LASQHFVHRD LATRNCLVGE |
| | | NLLVKIGDFG MSRDVYSTDY YRVGGHTMLP IRWMPPESIM |
| | | YRKFTTESDV WSLGVVLWEI FTYGKQPWYQ LSNNEVIECI |
| | | TQGRVLQRPR TCPQEVYELM LGCWQREPHM RKNIKGIHTL |
| | | LQNLAKASPV YLDILG* |
| 137 | Chimeric TrkA (d5TrkB) | MLRGGRRGQL GWHSWAAGPG SLLAWLILAS AGAAPCPDAC |
| | | CPHGSSGLRC TRDGALDSLH HLPGAENLTE LYIENQQHLQ |
| | | HLELRDLRGL GELRNLTIVK SGLRFVAPDA FHFTPRLSRL |
| | | NLSFNALESL SWKTVQGLSL QELVLSGNPL HCSCALRWLQ |
| | | RWEEEGLGGV PEQKLQCHGQ GPLAHMPNAS CGVPTLKVQV |
| | | PNASVDVGDD VLLRCQVEGR GLEQAGWILT ELEQSATVMK |
| | | SGGLPSLGLT LANVTSDLNR KNVTCWAEND VGRAEVSVQV |
| | | NVLTVHFAPT ITFLESPTSD HHWCIPFTVK GNPKPALQWF |
| | | YNGAILNESK YICTKIHVTN HTEYHGCLQL DNPTHMNNGD |
| | | YTLIAKNEYG KDEKQISAHF MDNPFEFNPE DPIPVSFSPV |
| | | DTNSTSGDPV EKKDETPFGV SVAVGLAVFA CLFLSTLLLV |
| | | LNKCGRRNKF GINRPAVLAP EDGLAMSLHF MTLGGSSLSP |
| | | TEGKGSGLQG HIIENPQYFS DACVHHIKRR DIVLKWELGE |
| | | GAFGKVFLAE CHNLLPEQDK MLVAVKALKE ASESARQDFQ |
| | | REAELLTMLQ HQHIVRFFGV CTEGRPLLMV FEYMRHGDLN |
| | | RFLRSHGPDA KLLAGGEDVA PGPLGLGQLL AVASQVAAGM |
| | | VYLAGLHFVH RDLATRNCLV GQGLVVKIGD FGMSRDIYST |
| | | DYYRVGGRTM LPIRWMPPES ILYRKFTTES DVWSFGVVLW |
| | | EIFTYGKQPW YQLSNTEAID CITQGRELER PRACPPEVYA |
| | | IMRGCWQREP QQRHSIKDVH ARLQALAQAP PVYLDVLG* |
| 138 | Chimeric TrkB (d4TrkA) | MSSWIRWHGP AMARLWGFCW LVVGFWRAAF ACPTSCKCSA |
| | | SRIWCSDPSP GIVAFPRLEP NSVDPENITE IFIANQKRLE IINEDDVEAY |
| | | VGLRNLTIVD SGLKFVAHKA FLKNSNLQHI NFTRNKLTSL |
| | | SRKHFRHLDL SELILVGNPF TCSCDIMWIK TLQEAKSSPD |
| | | TQDLYCLNES SKNIPLANLP NASCGVPTLK VQVPNASVDV |
| | | GDDVLLRCQV EGRGLEQAGW ILTELEQSAT VMKSGGLPSL |
| | | GLTLANVTSD LNRKNVTCWA ENDVGRAEVS VQVNVHFAPT |
| | | ITFLESPTSD HHWCIPFTVK GNPKPALQWF YNGAILNESK |
| | | YICTKIHVTN HTEYHGCLQL DNPTHMNNGD YTLIAKNEYG |
| | | KDEKQISAHF MGWPGIDDGA NPNYPDVIYE DYGTAANDIG |
| | | DTTNRSNEIP STDVTDKTGR EHLSVYAVVV IASVVGFCLL |
| | | VMLFLLKLAR HSKFGMKGPA SVISNDDDSA SPLHHISNGS |
| | | NTPSSSEGGP DAVIIGMTKI PVIENPQYFG ITNSQLKPDT FVQHIKRHNI |
| | | VLKRELGEGA FGKVFLAECY NLCPEQDKIL VAVKTLKDAS |
| | | DNARKDFHRE AELLTNLQHE HIVKFYGVCV EGDPLIMVFE |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for C$_H$1 (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
| | | YMKHGDLNKF LRAHGPDAVL MAEGNPPTEL TQSQMLHIAQ<br>QIAAGMVYLA SQHFVHRDLA TRNCLVGENL LVKIGDFGMS<br>RDVYSTDYYR VGGHTMLPIR WMPPESIMYR KFTTESDVWS<br>LGVVLWEIFT YGKQPWYQLS NNEVIECITQ GRVLQRPRTC<br>PQEVYELMLG CWQREPHMRK NIKGIHTLLQ NLAKASPVYL DILG* |
| 139 | Chimeric TrkA (d4TrkB) | MLRGGRRGQL GWHSWAAGPG SLLAWLILAS AGAAPCPDAC<br>CPHGSSGLRC TRDGALDSLH HLPGAENLTE LYIENQQHLQ<br>HLELRDLRGL GELRNLTIVK SGLRFVAPDA FHFTPRLSRL<br>NLSFNALESL SWKTVQGLSL QELVLSGNPL HCSCALRWLQ<br>RWEEEGLGGV PEQKLQCHGQ GPLAHMQIPN CGLPSANLAA<br>PNLTVEEGKS ITLSCSVAGD PVPNMYWDVG NLVSKHMNET<br>SHTQGSLRIT NISSDDSGKQ ISCVAENLVG EDQDSVNLTV<br>SFPASVQLHT AVEMHHWCIP FSVDGQPAPS LRWLFNGSVL<br>NETSFIFTEF LEPAANETVR HGCLRLNQPT HVNNGNYTLL<br>AANPFGQASA SIMAAFMDNP FEFNPEDPIP VSFSPVDTNS<br>TSGDPVEKKD ETPFGVSVAV GLAVFACLFL STLLLVLNKC<br>GRRNKFGINR PAVLAPEDGL AMSLHFMTLG GSSLSPTEGK<br>GSGLQGHIIE NPQYFSDACV HHIKRRDIVL KWELGEGAFG<br>KVFLAECHNL LPEQDKMLVA VKALKEASES ARQDFQREAE<br>LLTMLQHQHI VRFFGVCTEG RPLLMVFEYM RHGDLNRFLR<br>SHGPDAKLLA GGEDVAPGPL GLGQLLAVAS QVAAGMVYLA<br>GLHFVHRDLA TRNCLVGQGL VVKIGDFGMS RDIYSTDYYR<br>VGGRTMLPIR WMPPESILYR KFTTESDVWS FGVVLWEIFT<br>YGKQPWYQLS NTEAIDCITQ GRELERPRAC PPEVYAIMRG<br>CWQREPQQRH SIKDVHARLQ ALAQAPPVYL DVLG* |
| 140 | TrkB, Cat (*Felis domesticus*) nucleotide | ATGTCGTCCTGGACGAGGTGGCATGGACCCGCCATGGCGCGGCTCT<br>GGGGCTTCTGCTGGCTGGTTGTGGGCTTCTGGAGGGCCGCTCTCGC<br>CTGTCCCACGTCCTGCAAGTGCACCGCCTCTCGGATCTGGTGCAGC<br>GACCCTTCTCCGGGCATCGTGGCGTTTCCGAGGTTGGAGCCTAATA<br>GTGCAGACCCTGAGAACATCACCGAAATTTACATTGCCAATCAGAAA<br>AGGTTGGAAATCATCAACGAAGATGATGTCGAAGCTTACGCAGGACT<br>GAAAAATCTGACAATTGTGGATTCTGGATTAAAATTTGTGGCTCATAA<br>AGCGTTTCTGAAAAACAGCAACTTACAGCACATCAATTTTACTCGAAA<br>TAAACTGACCAGCTTGTCTAGGAAACATTTTCGTCACCTTGATTTGTC<br>TGAACTGATCCTGGTGGGCAATCCATTTACATGCTCCTGTGACATTAT<br>GTGGATCAAGACTCTTCAGGAGACTAAATCCAGCCCAGAAACTCAGG<br>ATTTGTACTGCCTAAATGAAAGCAGCAAGAATATTCCCTGGCAAACC<br>TGCAGATACCCAATTGTGGTTTGCCATCAGCAAATTTGGCCGCACCT<br>AACCTCACTGTGGAGGAGGGAAGGTCTATCACATTATCTTGCAGTGT<br>CTCAGGCGATCCGGTTCCGAATTTGTACTGGGATGTCGGTAATCTGG<br>TTTCCAAGCATATGAATGAAACGAGCCACACACAGGGCTCCTTAAGG<br>ATAACTAACATTTCATCTGATGACAGTGGAAAGCAGATCTCCTGTGTG<br>GCAGAAAATCTTGTAGGAGAAGACCAAGATTCTGTCAACCTCACTGT<br>ACATTTTGCTCCAACTATCACATTTCTGAATCTCCAACCTCAGACCA<br>CCACTGGTGCATTCCATTCACTGTGAAAGGCAACCCCAAACCAGCTC<br>TTCAGTGGTTCTATAATGGGGCGATACTGAATGAGTCCAAGTACATCT<br>GTACTAAAATCCATGTTACCAATCACACGGAGTACCATGGCTGCCTC<br>CAGCTGGATAATCCTACTCACATGAACAATGGGGACTACAAGTTAGT<br>AGCCAAGAACGAGTATGGGAAGGATGAGAAACAGATTTCTGCTCACT<br>TCATGGGCTGGCCTGGAATCGTAGATGGTGCCAACCCAAATTATCCT<br>GATGTAATTTATGAAGATTATGGGACTGCAGCGAATGACATTGGGGA<br>CACCACGAACAGAAGTAACGAAATCCCTTCCACAGATGTGGCGGACA<br>AAAGCGGTCGGGACATCTTTCGGTCTATGCTGTGGTGGTCATTGCG<br>TCTGTGGTGGGATTTTGTCTGCTGGTGATGCTGTTTCTGCTGAAGTT<br>GGCAAGACACTCCAAGTTGGCATGAAAGGCCCAGCTTCAGTTATCA<br>GCAATGATGATGACTCTGCCAGCCCACTCCACCACATCTCCAATGGG<br>AGTAACACCCCATCATCTTCAGAGGGCGGCCCCGATGCCGTCATTAT<br>TGGAATGACCAAGATTCCTGTCATTGAAAATCCCCAGTACTTTGGCAT<br>CACCAACAGTCAGCTCAAGCCAGACACATTTGTTCAACACATCAAGC |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
|  |  | GACATAACATTGTTCTGAAAAGGGAGCTAGGCGAAGGAGCCTTTGGA<br>AAAGTTTTCCTAGCTGAATGCTATAACCTCTGTCCTGAGCAGGACAAG<br>ATCTTGGTGGCAGTGAAGACGCTGAAGGACGCCAGTGACAACGCCC<br>GCAAGGACTTCCACCGTGAGGCAGAGCTGCTGACCAACCTCCAGCA<br>CGAGCACATTGTCAAGTTCTACGGTGTCTGTGTGGAGGGCGACCCA<br>CTCATCATGGTCTTTGAGTACATGAAGCACGGGGATCTCAACAAGTT<br>CCTCAGGGCCCACGGGCCTGACGCTGTGCTGATGGCCGAAGGCAAC<br>CCGCCGACAGAGCTGACGCAGTCCCAGATGCTGCACATCGCCCAGC<br>AGATAGCAGCGGGCATGGTCTACCTGGCGTCCCAACACTTTGTGCAC<br>CGAGATCTGGCCACCCGGAACTGCCTGGTCGGTGAGAACCTCCTGG<br>TGAAAATCGGGGACTTCGGGATGTCCCGGGACGTGTACAGCACTGA<br>CTACTACAGGGTCGGTGGCCACACGATGTTACCCATTCGCTGGATGC<br>CTCCAGAGAGCATCATGTACAGGAAGTTCACCACAGAAAGTGATGTC<br>TGGAGCCTGGGAGTCGTGTTGTGGGAGATCTTCACGTACGGCAAAC<br>AGCCCTGGTACCAGCTGTCCAACAACGAGGTGATAGAATGCATCACT<br>CAGGGCCGAGTCTTGCAGCGACCTAGAACATGCCCCCAGGAGGTGT<br>ATGAGTTGATGCTGGGGTGCTGGCAGCGAGAGCCCCACATGAGGAA<br>GAACATCAAGGGCATCCACACCCTCCTTCAGAACTTGGCCAAGGCAT<br>CTCCGGTCTACCTGGATATTCTGGGC<u>TAG</u> |
| 141 | TrkB, Cat (*Felis domesticus*) protein: | MSSWTRWHGPAMARLWGFCWLVVGFWRAALACPTSCKCTASRIWCS<br>DPSPGIVAFPRLEPNSADPENITEIYIANQKRLEIINEDDVEAYAGLKNLTIV<br>DSGLKFVAHKAFLKNSNLQHINFTRNKLTSLSRKHFRHLDLSELILVGNPF<br>TCSCDIMWIKTLQETKSSPETQDLYCLNESSKNIPLANLQIPNCGLPSANL<br>AAPNLTVEEGRSITLSCSVSGDPVPNLYWDVGNLVSKHMNETSHTQGS<br>LRITNISSDDSGKQISCVAENLVGEDQDSVNLTVHFAPTITFLESPTSDHH<br>WCIPFTVKGNPKPALQWFYNGAILNESKYICTKIHVTNHTEYHGCLQLDN<br>PTHMNNGDYKLVAKNEYGKDEKQISAHFMGWPGIVDGANPNYPDVIYE<br>DYGTAANDIGDTTNRSNEIPSTDVADKSGREHLSVYAVVVIASVVGFCLL<br>VMLFLLKLARHSKFGMKGPASVISNDDDSASPLHHISNGSNTPSSSEGG<br>PDAVIIGMTKIPVIENPQYFGITNSQLKPDTFVQHIKRHNIVLKRELGEGAF<br>GKVFLAECYNLCPEQDKILVAVKTLKDASDNARKDFHREAELLTNLQHE<br>HIVKFYGVCVEGDPLIMVFEYMKHGDLNKFLRAHGPDAVLMAEGNPPTE<br>LTQSQMLHIAQQIAAGMVYLASQHFVHRDLATRNCLVGENLLVKIGDFG<br>MSRDVYSTDYYRVGGHTMLPIRWMPPESIMYRKFTTESDVWSLGVVLW<br>EIFTYGKQPVVYQLSNNEVIECITQGRVLQRPRTCPQEVYELMLGCWQR<br>EPHMRKNIKGIHTLLQNLAKASPVYLDILG |
| 142 | TrkB, Dog (*Canis familiaris*, XM_851329) | <u>ATG</u>TCGTCCTGGACGAGGTGGCATGGACCCGCCATGGCGCGGCTCT<br>GGGGCTTCTGCTGGCTGGTCGTGGGCTTCTGGAGGGCTGCCCTCGC<br>CTGTCCCACGTCCTGCAAATGCAGCGCCTCTAGGATCTGGTGCAGC<br>GACCCTTCTCCGGGCATCGTGGCGTTTCCGAGGTTGGAGCCCAACA<br>GTGCAGACCCTGAGAACATCACCGAAATTTACATTGCCAATCAGAAA<br>AGGTTGGAAATCATCAATGAAGATGATGTTGAAGCTTATGCAGGACT<br>GAAGAATCTGACGATTGTGGACTCTGGATTAAAATTTGTGGCTCATAA<br>AGCATTTCTGAAAAACAGCAACTTACAGCACATCAATTTTACCCGAAA<br>TAAACTGACAAGCTTGTCTAGGAAACATTTTCGTCACCTTGACTTGTC<br>TGAGCTGATCCTGGTGGGCAATCCATTTACATGTTCCTGTGATATTAT<br>GTGGATCAAGACTCTTCAGGAGACTAAATCCAGCCCAGAAACTCAGG<br>ATTTGTACTGCCTAAATGAAAGCAGCAAGAATATTCCCCTGGCAAACC<br>TGCAGATACCCAATTGTGGTTTGCCATCAGCAAATTTGGCTGCACCTA<br>ACCTCACCGTGGAGGAGGGAAAGTCTATCACATTATCTTGTAGTGTT<br>GCAGGCGATCCAGTTCCGAATTTGTACTGGGATGTCGGTAATCTGGT<br>TTCCAAACATATGAATGAAACAAGCCACATGCAGGGCTCCTTGAGGA<br>TAACTAACATTTCATCTGATGACAGTGGAAAACAAATCTCCTGTGTGG<br>CAGAAAATCTTGTAGGAGAAGACCAAGATTCTGTCAACCTCACTGTAC<br>ATTTTGCTCCAACTATCACATTTCTCGAATCTCCAACCTCAGACCACC<br>ACTGGTGCATTCCATTCACTGTGAAAGGCAACCCCAAACCAGCGCTT<br>CAGTGGTTCTATAACGGGGCAATATTGAATGAGTCCAAATACATCTGT<br>ACTAAAAATCCATGTTACCAATCACACGGAGTACCATGGCTGCCTCCA<br>GCTGGATAATCCCACTCACATGAACAATGGGGACTACAAGTTAGTAG |

TABLE 1-continued

Sequence list. Dashes ("-") indicate gaps introduced to align the various allotype and isotype domains with Kabat numbering. Alignments were adjusted so that boundaries (spaces) between blocks of 10 residues always fall between residue numbering positions ending in "0" and residue numbering positions ending in "1". Where a domain does not begin with a residue whose numbering position ends with "1", phonypadding gaps were inserted to adjust the alignment. For example, for $C_H1$ (Seq ID 1) the Kabat domain begins at position 114. Three gap characters were inserted to put the alignment in the correct frame (starting with position 111). These three gap residues (corresponding to Kabat positions 111-113) are properly part of the VH domain and would generally be occupied by real amino acids belonging to the VH in a full antibody sequence. Similar padding gaps may be found at the beginning and end of some other sequences.

The sequences herein described for 29D7 (SEQ ID NOs: 51 and 53, and other sequences that comprise those sequences) are those of the antibody TAM-163. All examples herein described as using antibody 29D7 used the antibody TAM-163.

SEQUENCE LIST

| SEQ | Description | Sequence |
|---|---|---|
|  |  | CCAAGAATGAGTATGGGAAAGATGAGAAACAGATTTCTGCTCACTTC ATGGGCTGGCCTGGAATTGATGATGGTGCCAACCCAAATTATCCCGA CGTAATTTATGAAGATTACGGGACTGCAGCAAATGACATTGGGGACA CCACAAACAGAAGTAACGAAATCCCTTCTACAGATGTTGCTGACAAA GCGGTCGGGAACATCTTTCGGTCTATGCTGTGGTGGTAATTGCATCT GTGGTGGGATTTTGTCTGCTGGTGATGCTGTTTCTGCTGAAGTTGGC AAGACACTCCAAGTTTGGCATGAAAGGCCCAGCTTCAGTTATCAGCA ATGATGATGACTCTGCCAGCCCCTCCACCACATCTCCAATGGGAGT AACACCCCATCATCTTCAGAGGGCGGCCCCGATGCCGTCATCATTGG AATGACCAAGATCCCTGTCATTGAAAATCCCCAGTACTTTGGCATCAC CAACAGTCAGCTCAAGCCAGACACATTTGTTCAGCACATCAAGAGAC ATAACATTGTTCTGAAAAGGGAGCTAGGCGAAGGAGCCTTTGGAAAA GTTTTCCTAGCTGAATGCTATAACCTCTGTCCTGAGCAGGACAAGATC TTGGTGGCAGTGAAGACACTGAAGGATGCCAGTGACAACGCACGCA AGGACTTTCACCGCGAGGCTGAGCTGCTGACCAACCTCCAGCACGA GCACATCGTCAAGTTCTATGGTGTCTGCGTGGAGGGTGACCCGCTCA TCATGGTCTTTGAGTACATGAAGCACGGGGACCTCAACAAGTTCCTC AGGGCCCATGGGCCTGATGCTGTGCTGATGGCCGAAGGCAACCCGC CGACGGAGCTCACCCAGTCCCAGATGCTGCACATTGCCCAGCAGAT AGCAGCAGGAATGGTCTACCTGGCGTCCCAGCACTTTGTGCACCGA GATCTGGCCACCCGCAACTGCCTGGTTGGCGAGAACCTCCTGGTGA AAATCGGGGACTTCGGGATGTCCCGGGACGTGTACAGCACCGACTA CTACAGGGTCGGTGGCCACACAATGCTGCCCATTCGCTGGATGCCT CCAGAGAGCATCATGTACAGGAAGTTCACCACAGAAAGTGATGTCTG GAGCCTGGGAGTCGTGTTATGGGAGATCTTCACGTACGGCAAACAG CCCTGGTACCAGCTGTCCAACAACGAGGTGATAGAATGCATCACGCA GGGCCGAGTCTTGCAGCGACCTAGAACGTGCCCCCAGGAGGTCTAT GAGTTGATGCTGGGGTGCTGGCAGCGGGAGCCCCATATGAGGAAAA ACATCAAGGGTATCCACACCCTCCTTCAGAACTTGGCCAAGGCATCT CCAGTCTACCTGGATATTCTAGGC<u>TAG</u> |
| 143 | TrkB, Dog (*Canis familiaris*, XM_851329), amino acid sequence: | MSSWTRWHGPAMARLWGFCWLVVGFWRAALACPTSCKCSASRIWCS DPSPGIVAFPRLEPNSADPENITEIYIANQKRLEIINEDDVEAYAGLKNLTIV DSGLKFVAHKAFLKNSNLQHINFTRNKLTSLSRKHFRHLDLSELILVGNPF TCSCDIMWIKTLQETKSSPETQDLYCLNESSKNIPLANLQIPNCGLPSANL AAPNLTVEEGKSITLSCSVAGDPVPNLYWDVGNLVSKHMNETSHMQGS LRITNISSDDSGKQISCVAENLVGEDQDSVNLTVHFAPTITFLESPTSDHH WCIPFTVKGNPKPALQWFYNGAILNESKYICTKIHVTNHTEYHGCLQLDN PTHMNNGDYKLVAKNEYGKDEKQISAHFMGWPGIDDGANPNYPDVIYE DYGTAANDIGDTTNRSNEIPSTDVADKSGREHLSVYAVVVIASVVGFCLL VMLFLLKLARHSKFGMKGPASVISNDDDSASPLHHISNGSNTPSSSEGG PDAVIIGMTKIPVIENPQYFGITNSQLKPDTFVQHIKRHNIVLKRELGEGAF GKVFLAECYNLCPEQDKILVAVKTLKDASDNARKDFHREAELLTNLQHE HIVKFYGVCVEGDPLIMVFEYMKHGDLNKFLRAHGPDAVLMAEGNPPTE LTQSQMLHIAQQ1AAGMVYLASQHFVHRDLATRNCLVGENLLVKIGDFG MSRDVYSTDYYRVGGHTMLPIRWMPPESIMYRKFTTESDVWSLGVVLW EIFTYGKQPVVYQLSNNEVIECITQGRVLQRPRTCPQEVYELMLGCWQR EPHMRKNIKGIHTLLQNLAKASPVYLDILG |
| 144 | Cat TrkB For Primer | GGATCCGCCG CCACCATGTC GTCCTGGACG AGGTGGCATG G |
| 145 | Cat TrkB Rev Primer | GCGGCCGCCT AGCCCAGAAT ATCCAGGTAG ACCGGAGAT |
| 146 | Dog TrkB For Primer | GGATCCGCCG CCACCATGTC GTCCTGGACG AGGTGGCATG G |
| 147 | Dog TrkB Rev Primer | GCGGCCGCCT AGCCTAGAAT ATCCAGGTAG ACTGGAG |

EXAMPLES

Numbering of Residues

Figure 2:
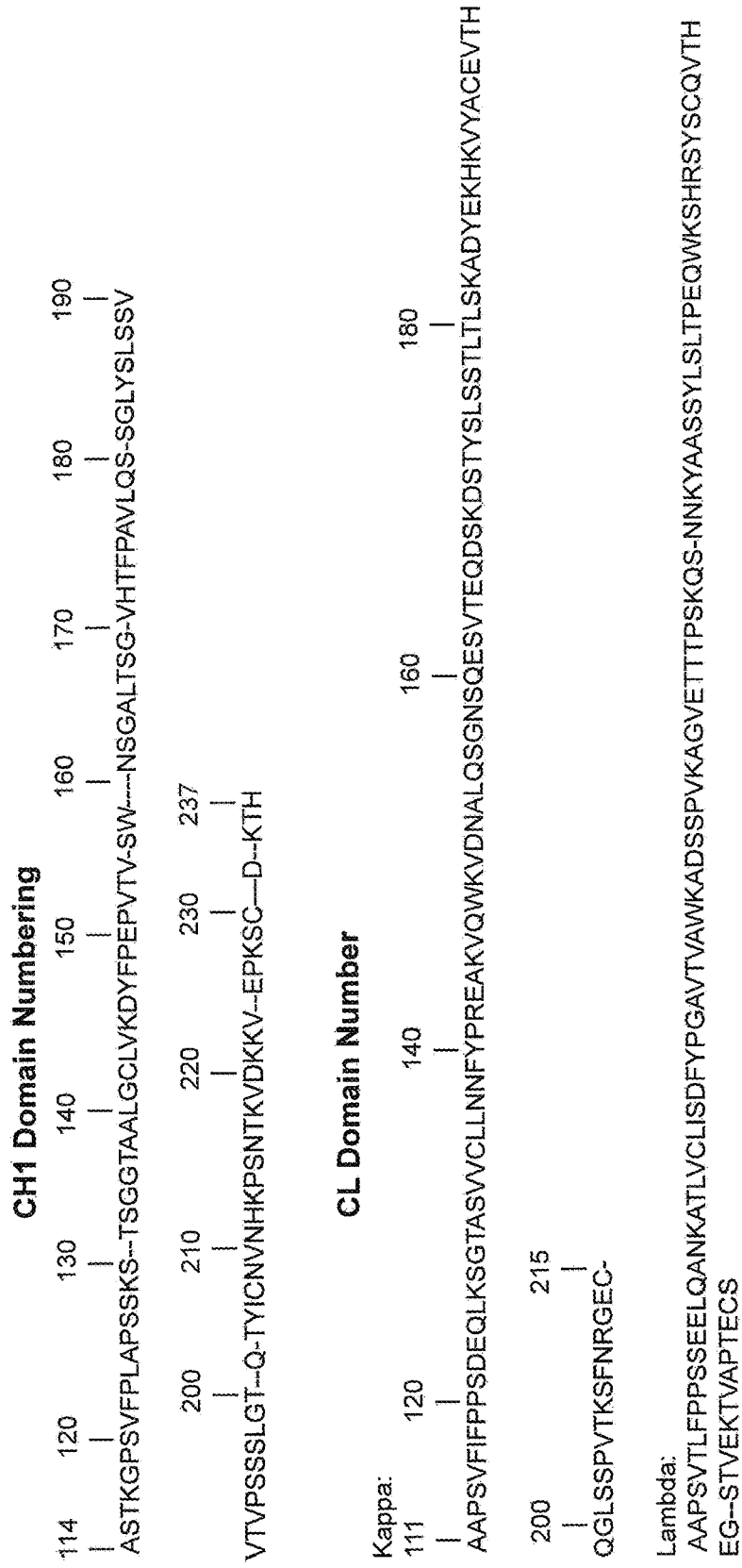
FIG. 2 depicts the sequence of wild type human IgG1 $C_H1$ (panel A), Kappa $C_L$ (panel B), and Lambda $C_L$ domains. The amino acid residues are numbered according to the Kabat numbering scheme. A dash ("-") indicates an amino acid position that is occupied only in a different type of antibody domain or in a different species.

Wild type amino acid residues are numbered using a Kabat-compatible numbering system, as illustrated in FIG. 2. As used herein, the mutations listed in the tables refer to the domain, followed by the residue position according to Kabat-compatible numbering (see for example SEQ ID NOs: 1 ($C_H1$), SEQ ID NO:9 ($C_L$), SEQ ID NO:13 ($C_H2$), and SEQ ID NO:18 ($C_H3$). The identity of wild type residues is noted in IUPAC single letter code before the residue position (e.g. $C_H1$-S188). The identity of mutant residues is noted after the residue position ($C_H1$-188E). Where relevant, both wild-type and mutant residue identity is provided ($C_H1$-S188E). In an alternative notation, the native amino acid may be listed first, followed by the chain and position in parentheses, followed by the substituted amino acid, for example, Ser(H188)Glu.

Example 1

Identification of Sites for Generating Heterodimer-Favoring Mutations in Antibodies The binding affinity between a protein and another molecule can often be changed by modifying the atoms in closest spatial proximity in the bound state. In native antibodies, a $C_H1$ and $C_L$ domain are bound to each other and the degree of binding can be significantly influenced by pairs of atoms, one atom in each domain, that are in close contact (less than 5.0 Å) in the bound state. Changes to the atoms involved in these binding pairs may lead to either increased or decreased binding. The specific atoms involved can be determined by methods such as NMR spectroscopy and protein x-ray crystallography. Atoms on one domain in close contact with the other domain may result in attractive or repulsive forces between the two domains depending on the nature of the atom and its local environment. In addition, for a residue (such as Gly) in a first domain having atoms within 12 Å of a second domain, close contacts with the second domain may occur if the residue is replaced by a different residue (such as Arg) which adopts a different conformation, and such a residue in the first domain is also considered a close contact residue herein. After modification, the new amino acid may be in close contact with residues on the second domain which were not previously in close contact with the first domain, and these residues are also considered close contact residues. For example, a mutation of Ala to Trp on the first domain may cause unfavorable steric interactions with the second domain, which may be relieved by changing a residue on the second domain, where the residue on the second domain was not in close contact prior to the introduction of Trp on the first domain. This principle may be used to design a novel $C_L$ (or $C_H1$) domain which does not interact with wild type $C_H1$ (or $C_L$) domain. A novel $C_H1$ (or $C_L$) domain which restores interactions with the novel $C_L$ (or $C_H1$) domain can then be constructed. A multispecific antibody can use one or more combinations of such novel $C_L$ and $C_H1$ domains to ensure correct pairing between each heavy chain and each light chain. Such designs may be based not just on steric interactions, but also electrostatic interactions, or both types of interactions.

Examination of a protein crystal structure using a graphical tool such as Maestro (Maestro, version 9.2, Schrodinger, LLC, New York, N.Y. (2011)) revealed the atoms in direct close contact by measuring inter-atomic distances using the criteria defined above. In the case of the crystal structure in Protein Data Bank (PDB) entry 3QQ9 (DOI: 10.2210/pdb3qq9/pdb), residues in the $C_L$ domain that are in close contact with the $C_H1$ domain include, but are not limited to: 116-119, 121, 123-124, 127, 129, 131, 133, 135-138, 160-164, 167, 174-176, 178, 180, 209 (using the numbering scheme described herein; see FIG. 2). The residues in $C_H1$ which are similarly in close contact with $C_L$ include, but are not limited to: 121-127, 137-140, 143, 145, 169, 172-180, 186, 188, 190, 192, 221 (using the numbering scheme described herein).

Due to uncertainty present in experimental measurements, and differences in the protein surface environment in different crystal forms, examination of other protein structures may show variations in relative atom positions such that examining these structures results in lists of residues substantially similar, but not identical, to the ones given here. For example, in PDB entry 1HZH (Saphire et al., Science 293:1155-59 (2001)) the structure contains two $C_H1$ domains with different local environments, and in one domain Lys221 is within 4.5 Å of its partner $C_L$ domain, while in the other $C_H1$ domain it is not. Determination of a close contact in one such $C_H1$/$C_L$ interface is sufficient to define a residue as a close contact residue.

Multiple computational methods are available for predicting the orientation of modified amino acid side chains, and the relative effect such changes may have on protein/protein interface binding affinity. However, different methods often give different results. In order to compensate for this variability across methods, several methods were employed to identify amino acid changes that could reduce the affinity of $C_H1$/$C_L$ binding. The list of potential amino acid residues that would be targeted was then refined based on inspection of structural models.

Example 2

Antibodies with Novel Covalent $C_H1$-$C_L$ Disulfide Linkages

Bispecific antibodies can contain different heavy and light chains in each Fab arm. For example, if a bispecific antibody has 2 Fab arms, each with a different LC and HC, producing a bispecific antibody can involve expression of 4 different polypeptides. Due to the possibility of light chains crossing over and pairing with the incorrect heavy chain, even if the heavy chains are modified to favor heterodimerization, cotransfection and expression of 4 different heavy and light chains can still result in undesirable products, as illustrated in FIG. 1.

The wild type interface between $C_H1$ and $C_L$ is stabilized by a covalent disulfide bond between $C_H1$-C230 and $C_L$-C214. During assembly of a bispecific antibody, if any incorrect HC/LC pairing occurs, the formation of this disulfide bond may help hold the incorrect pairing in place.

The present inventors postulated that if the mispaired antibody arms could not form the native disulfide, it may increase the opportunity for the mispaired chains to dissociate and find a correct partner. To explore this possibility, alternate positions for the disulfide bond were designed. In these designs, incorrectly paired $C_H1$ and $C_L$ domains cannot form a disulfide bond, because the cysteines are too far apart. When the correct $C_H1$/$C_L$ pairing occurs, a disulfide bond can form and help hold the pairing in place.

A custom method was developed to search the interface between $C_H1$ and $C_L$ and evaluate possible disulfide linkages. The method is similar to that of Dani et al. (*Prot. Eng.*

16(3): 187-93 (2003)) but performs additional types of analysis to rank the quality of each site.

Pairs of residues, one on each chain, were chosen where the two residues' alpha carbons are within 7.5 Å (Cα1-Cα2 distance), and the two residues' beta carbons are within 6.0 Å (Cβ1-Cβ2 distance). To remove pairs where the side chains are oriented away from each other, the distance between Cβ1 and Cβ2 was compared to the distance between Cβ1 and Cα2. If the former distance is larger, the side chains are partially oriented away from each other and thus poor candidates for forming a disulfide; if the former distance was larger by more than 0.5 Å the pair was dropped.

For surviving pairs, each putative disulfide was modeled structurally in Modeller (Eswar et al., *Nuc. Acids Res.* 31(13): 3375-80 (2003)) with 9 models built from randomized starting coordinates for the mutated atoms. A control model of the wild type was also constructed in Modeller. All models were superimposed back on the original crystal structure using TM-ALIGN (Zhang and Skolnick, *Nuc. Acids Res.* 33: 2302-9 (2005)). The models were checked for the introduction of void volumes in the protein core using VOIDOO (Kleywegt and Jones, *Acta Cryst, D* 50: 178-85 (1994)) with probe radii of 1.0 Å and 1.5 Å. Small or nonexistent voids were preferred. The Modeller DOPE Z-score was calculated, with mutant scores as low as for the wild type being preferred. The Ramachandran plots before and after mutation were compared using PROCHECK (Laskowski, *Nuc. Acids Res.* 29(1): 221-2 (2001)) to detect any degradation in backbone quality caused by the restraints of the covalent disulfide bond. The mutant model ranked best by the Modeller Objective function was compared to the wild type and the largest displacement of any backbone atom in the two residues being mutated was noted, with smaller displacements being preferred.

Finally, the $\chi1$, $\chi2$, and $\chi3$ angles of the mutant cysteines were computed and compared to a distribution of those angles in 4500 high-resolution crystal structures filtered at the 40% sequence identity level. Putative disulfides resulting in models with geometries deviating least from the experimentally observed distributions were preferred.

Several basic designs obtained from this process are listed in Table 2. Designs Cys2, Cys4, and Cys5 were ranked less favorably either by manual inspection or by the automated procedure described above, and were not pursued further. Design Cys 3 has two variants: Cys3a and Cys3b. In Cys3b, two additional nearby residues were changed to Ile to improve packing around the disulfide (V190I and L135I), because the F174C mutation was predicted to introduce a small cavity in the structure.

TABLE 1

Novel Cys Pairs Forming Inter-Domain Disulfide Bonds. Each row represents a combination of engineered amino acids in the $C_H1$ and $C_L$ domains predicted to result in the formation of a nonnatural disulfide bond between the two domains.

| Fab ID | $C_H1$ Residue(s) | $C_L$ Residue(s) | Base $C_L$ Sequence |
|---|---|---|---|
| Cys1 | A139C | F116C | κ |
| Cys2 | F174C | S162C | κ |
| Cys3a | F174C | S176C | κ or λ |
| Cys3b | F174C, V190I | L135I, S176C | κ or λ |
| Cys4 | V177C | Q160C | κ |
| Cys5 | P123C | S121C | κ or λ |
| Cys6 | F122C | E123C | κ or λ |
| Cys1λ | A139C | T116C | λ |

Example 3

Expression and Purification of Cys Altered Heavy/Light Chains

Antibody 29D7 was used as a platform to determine whether the three novel heavy/light chain disulfide bridge positions set out in Table 2 (Cys1, Cys3, Cys6) were capable of forming disulphide bonds. 29D7 is a bivalent, monospecific, monoclonal anti-tyrosine kinase receptor B (TrkB) IgG1 antibody (see Qian et al., *J. Neuroscience* 26(37): 9394-9403 (2006)).

A positive control with native disulphide bridge (between $C_H$-C230 and $C_L$-C214 "29D7") and a negative control with no bridge at all ($C_H$-C230S and $C_L$-C214S: "29D7 ΔCys") were also used in the assay design. 29D7 expression cassette genes were partially constructed using de novo gene synthesis and sub-cloned in frame with 29D7 heavy and light chain variable regions in expression vectors using restriction enzyme-ligation based cloning techniques. Light chain genes were cloned in pSMEN3 and heavy chain genes cloned in pSMED2. Suspension HEK293F cells (American Type Culture Collection) were cultured in serum-free Free-Style™ 293 expression medium (Life Technologies). Cells were maintained in a humidified incubator with 7% $CO_2$ at 37° C. Conditioned media were produced from a standard transient HEK293F transfection process. The conditioned media were filtered through a 0.2 μm filter prior to purification. Constructs expressed in the 30-50 mg/L range into conditioned media.

Example 4

Purification of 29D7 Antibodies Expressed in HEK293F Cells

Filtered conditioned media was loaded onto HiTrap™ Protein A HP column (GE Life Sciences) equilibrated with PBS-CMF (137 mM NaCl, 2.7 mM KCl, 8.1 mM $Na_2HPO4$, 2.7 mM $KH_2PO4$, pH 7.2). The resin was washed with 10 column volumes of PBS-CMF pH 7.2 before the antibody was eluted with 0-100% linear gradient of protein A Elution Buffer (20 mM citric acid, 150 mM NaCl, pH 2.5). Peak fractions were neutralized to pH 7.0 with 2M Tris-HCl pH 8.0 and pooled. The material was loaded onto HiLoad™ 16/60 Superdex™ 200 preparative size-exclusion column (GE Life Sciences) equilibrated in PBS-CMF pH 7.2. Peak fractions were pooled, concentrated using 30 kDa spin filters (Amicon) and 0.2 μm-filtered.

Figure 3:
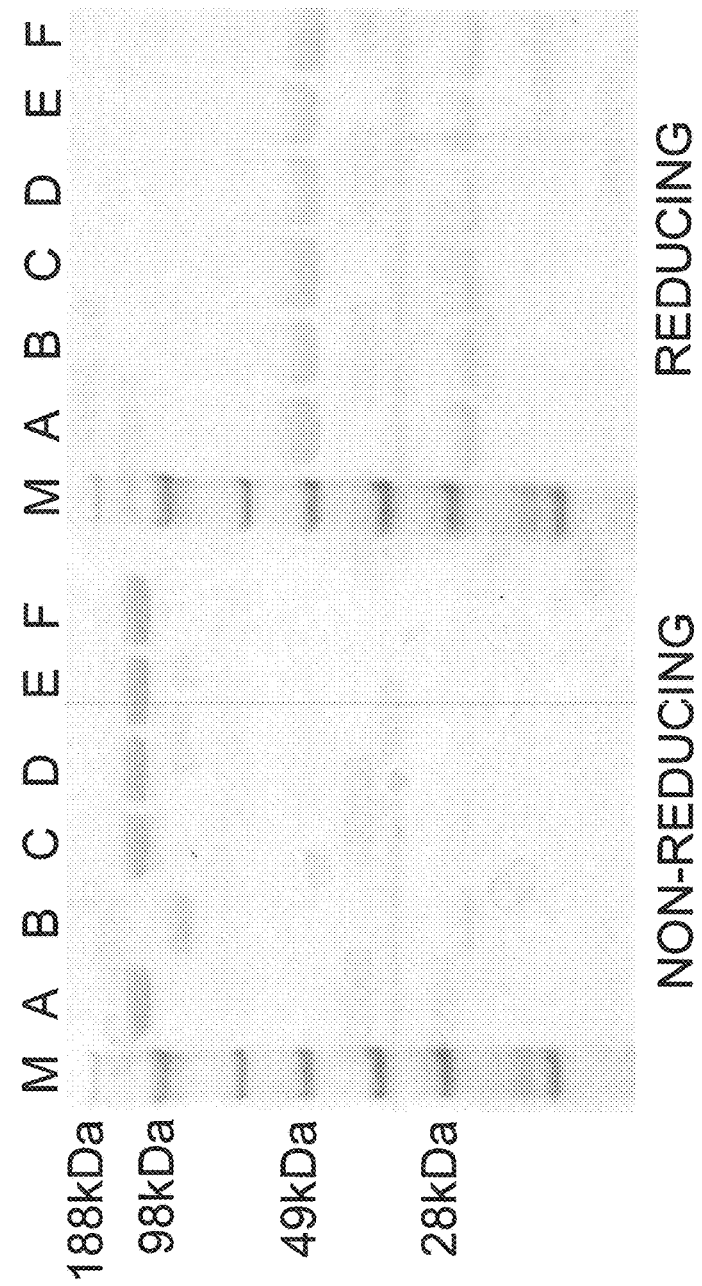
FIG. 3 depicts non-reducing and reducing SDS-PAGE analysis of wild-type 29D7 monoclonal IgG1 antibody with native disulphide bridge (A), no disulphide bridge (B) or with disulphide bridges in novel positions (C-F) as detailed in Table 1 for clones Cys1, Cys3a, Cys3b and Cys6 respectively. M; molecular weight marker.

Analytical SEC was performed using Superdex™ 200 10/300 GL column (GE Life Sciences) connected to Agilent 1100 Series HPLC system. Under non-reducing conditions, SDS-PAGE analysis (FIG. 3) revealed that the negative control, Ab 29D7 Cys Neg, driven by SDS denaturation, collapses into 100 kDa heavy and 25 kDa light chain components due to the lack of a heavy/light chain disulphide bridge. The positive control ("29D7") with native disulphide bridge exhibits a single band migrating between the 98 kDa and 188 kDa markers, presumably representing intact 150 kDa IgG1 molecule with heavy and light chains bound by a disulphide bridge. The four novel cysteine constructs described in Table 2 (29D7 Cys1, Cys 3a, Cys3b, and Cys6) behave in a similar fashion as the positive control, implying formation of a disulphide bridge at the positions set out in Table 2.

Example 5

Mass Spectrometry of Antibodies Having Altered Disulfide Linkages

To determine the effect of mutations introduced for novel covalent CH1-CL disulfide linkages, intact mass analysis of the various 29D7 constructs was carried out. Purified forms of antibody 29D7 containing the disulfide modifications listed in Table 2 as well as the positive and negative controls were deglycosylated in the presence of PNGaseF, followed by LC/MS as follows. Antibody was incubated with Lys-C (Wako Chemicals USA, Inc) at a protein:enzyme ratio of 400:1 and incubated at 37° C. for 20 mins. The digestion reaction was quenched with addition of 0.1% formic acid in water. The digested sample was analyzed by LC/MS analysis on an Agilent 1100 capillary HPLC coupled with Water Xevo G2 Q-TOF mass spectrometer. The analytes were loaded onto a Zorbax Poroshell 300SB C3 column (1.0 mm×75 mm, maintained at 80° C.) with 0.1% formic acid, and eluted using a gradient of 15-98% buffer B (0.1% formic acid in acetonitrile) at a flow rate of 65 μl/min over 4 mins. Mass spectrometric detection was carried out in positive, sensitivity mode with capillary voltage set at 3.3 kV. Data analysis were performed with MaxEnt 1 function in MassLynx.

Figures 4A, 4B, 4C:
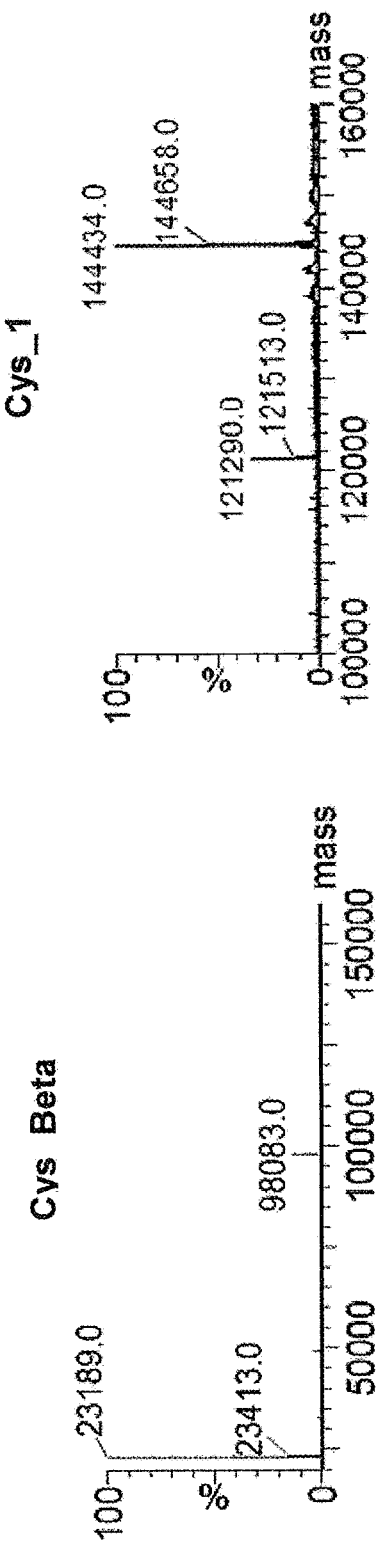
FIG. 4 depicts mass spectrometric analysis of constructs with engineered disulfides. Panel A: clone Cys_Beta, construct with wild type disulfides removed; Panel B: clone Cys_1; Panel C: clone Cys_3a; Panel D: clone Cys_3 b; Panel E: clone Cys_6.

For the 29D7 ΔCys, the base peak was assigned to monomeric light chain, which has a theoretical mass of 23190 Da (FIG. 4A). A secondary peak was assigned to a heavy chain dimer with a clipped lysine (theoretical mass 98086 Da). This result was consistent with initial design to disrupt formation of disulfide bond between CH1 and CL. The result for construct Cys1 is shown in FIG. 4B. The base peak corresponds to intact IgG with lysine clipping (theoretical weight 144438 Da). A partially intact IgG with two heavy chains and only one light chain (theoretical weight 121292 Da) was also observed. A similar result was obtained for construct Cys3a where base peak represents intact IgG with lysine clipping (theoretical weight 144404 Da) in addition to the detection of a partially intact IgG with two heavy chains and only one light chain (theoretical weight 121199 Da) (FIG. 4C).

Figure 4D:
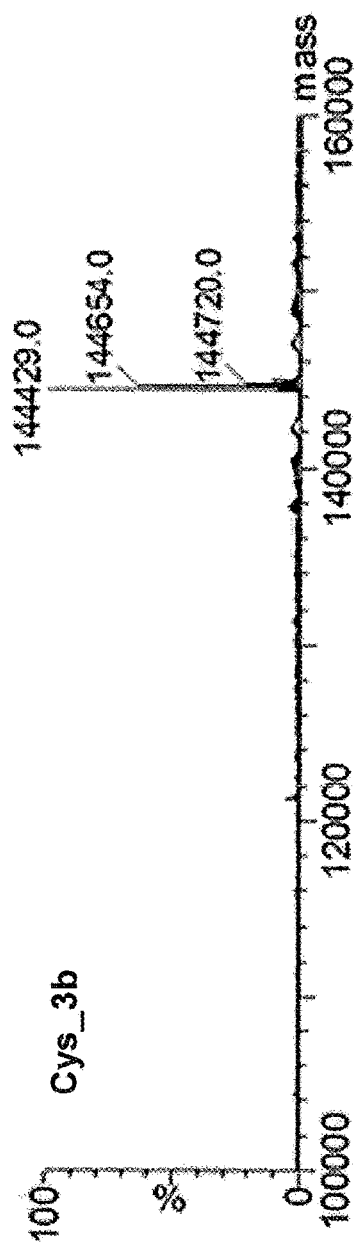
Figure 4E:
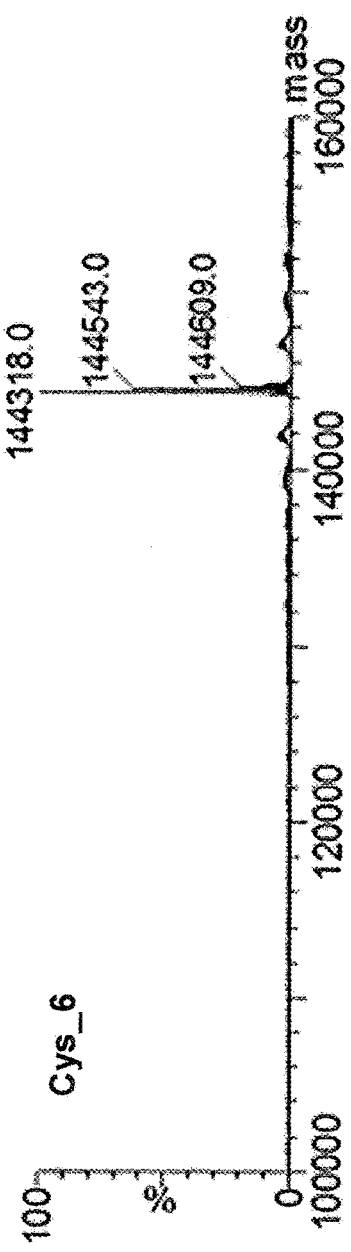

Two additional constructs showing majority as intact antibody with only residual partially intact IgG with two heavy chains and only one light chain are shown in FIGS. 4D & E.

Example 6

DSC Analysis of Antibodies Having Altered Disulfide Linkages

Thermal stability of antibodies was measured using Differential Scanning calorimetry (DSC). The 29D7 disulphide variant antibodies described in Table 2 were diluted in the same buffer (137 mM NaCl, 2.7 mM KCl, 8.1 mM $Na_2HPO_4$, and 1.47 mM $KH_2PO_4$, pH 7.2) to a concentration of 0.3 mg/mL. Samples and buffers (400 μL) were transferred to a 96 well deep well plate and placed in the autosampler of the DSC (Cap-DSC, Microcal/GE Healthcare). Following injection into the instrument, samples were heated from 10° C. to 110° C. at 100° C./hr. The data were buffer- and baseline corrected prior to fitting to three, non-two-state transitions to determine the melting temperatures (Table 2). All mutants were stable proteins with high $T_m$ values. Some differences could be observed in the $T_m1$ and $T_m2$, assigned to the $C_H2$ and $F_{ab}$ domains respectively.

TABLE 2

DSC Analysis of antibodies having altered disulfide linkages. Each melting temperature refers to the melting of a different key interface. In a canonical antibody, $T_M3$ is the temperature at which the interface of two $C_H3$ domains melts, $T_M1$ is the temperature at which the interface of the two $C_H2$ domains melts and $T_M2$ is the temperature at which the interface of the heavy and light chain melts.

| Construct | $T_m1$ (° C.) | $T_m2$ (° C.) | $T_m3$ (° C.) |
| --- | --- | --- | --- |
| 29D7 (WT) | 73.7 ± 0.3 | 77.9 ± 0.1 | 84.5 ± 0.1 |
| ΔCys | 73.3 ± 0.3 | 77.2 ± 0.1 | 84.6 ± 0.1 |
| Cys1 | 72.5 ± 0.2 | 75.7 ± 0.1 | 84.1 ± 0.1 |
| Cys3a | 72.8 ± 0.2 | 77.6 ± 0.1 | 84.6 ± 0.1 |
| Cys3b | 72.9 ± 0.2 | 77.7 ± 0.1 | 84.5 ± 0.1 |
| Cys6 | 71.7 ± 0.2 | 75.0 ± 0.1 | 84.2 ± 0.1 |

In conclusion, the mutants outlined in Table 2 with Fab ID's (Cys1, Cys3a, Cys3b and Cys6) have novel cysteine residues introduced in both the CH1 domain of the heavy chain and constant light domain of the kappa light chain and these cysteines are able to form a novel inter-chain disulphide bond which substitutes the intentionally removed native disulphide bond. These designs were then subsequently evaluated for their ability to favor correct light chain pairing in the bispecific antibody context with native disulphide bridge in one Fab arm and novel disulphide bridge in the other Fab arm.

Example 7

Disruptive Mutants Identified Using Rosetta Modelling

Multiple modeling methods were used to identify a set of mutations that could be classed as "disrupting mutations", in that the mutation disfavors pairing of the respective CL and CH domain. The mutations were evaluated by differential scanning calorimetry (DSC) (Table 5), (again, using antibody 29D7 as the test antibody). One modeling method involved using the interface energy method implemented in Rosetta (Das et al., *Ann. Rev. Biochemistry* 77:363-82 (2008)), version 2.3. Several protocols were used with varying degrees of flexibility in the protein. The "RFlex" protocol allowed side chains near the mutated residue to relax separately in the bound and unbound states. The "ExRFlex" protocol allowed finer extended sampling of amino acid side chain conformations (Rosetta options "-extrachi_cutoff 12", "-ex1 1", "-ex2 1", "-ex3 1", and "-ex4 1"). Amino acid changes predicted to disrupt the inter-chain binding affinity by more than 1 kcal/mol without causing unfavorable intra-chain energy of more than 10 kcal/mol were initially selected ("disrupting mutations"). Some mutations disrupted binding, but also caused an unfavorable intra-chain energy change (for example, +22 kcal/mol for $C_H1$-S188Y; see Table 3).

For $C_H1$-S188Y, inspection suggested that mutating L143 to a smaller residue could relieve this intra-chain strain. Rosetta predicted that combining $C_H1$-S188Y with $C_H1$-L143A would stabilize the $C_H1$ chain (−5.9 kcal/mol) while still disrupting interactions with the light chain. At some positions, such as $C_H1$-A139, all other amino acids were predicted to disrupt the complex (only a subset of results are shown in Table 3).

The total number of possible disrupting mutations obtained by modeling was too large for experimental testing, so disrupting mutations were further modeled for the feasibility of designing compensating mutations in the partner chain that could restore binding ("restoring mutations"). For each disrupting mutation, the protocol identified all close contact residues on the opposite chain as described above. For each disrupting mutation, up to several million candidate sequences with restoring mutations (all possible single and double restoring mutant combinations) were modeled in Rosetta. Representative amino acid positions where at least one Rosetta-predicted disrupting mutation was experimentally tested by DSC are shown in Table 3.

TABLE 3

Subset of Disrupting Mutations Identified by Rosetta Calculations. In the Fab ID column, "H" indicates mutations in the $C_H1$ domain of Ab 29D7. "L" indicated mutations in the $C_L$ domain of Ab 29D7. The numbers (10, 10b, 9 etc) refer to the different mutation constructs. $\Delta E$ is the predicted change in binding energy between $C_H1$ and $C_L$ due to the mutations listed, whereas self-chain $\Delta\Delta G$ reflects stabilization or disruption of the chain containing the mutations.

| Fab ID H/L | Protocol | Mutation | $\Delta E$ (kcal/mol) | Self-chain $\Delta\Delta G$ (kcal/mol) |
|---|---|---|---|---|
| H3 | RFlex | $C_H1$-A139F | >100 | −6.4 |
| H6 | RFlex | $C_H1$-A139H | >100 | −5.2 |
| H10 | RFlex | $C_H1$-S188W + $C_H1$-L143S | 57.7 | −5.9 |
| H10b | RFlex | $C_H1$-S188W | >100 | 22.2 |
| H10c | RFlex | $C_H1$-S188W + $C_H1$-L143A | 61.2 | −5.9 |
| H9 | RFlex | $C_H1$-S188Y + $C_H1$-L143A | 75.2 | −5.9 |
| H9b | RFlex | $C_H1$-S188Y | >100 | 22.1 |
| H9c | RFlex | $C_H1$-S188Y + $C_H1$-L143S | 73.6 | −5.8 |
| L1 | ExRFlex | $C_L$-E123K | 6.5 | |
| L3 | ExRFlex | $C_L$-S131M | 7.5 | |
| L4 | ExRFlex | $C_L$-S131H | 8.4 | |
| L5 | ExRFlex | $C_L$-S131P | 13.4 | |
| L8 | ExRFlex | $C_L$-L135W | 6.8 | |
| L11 | ExRFlex | $C_L$-S174Q | 16.1 | |
| L12 | ExRFlex | $C_L$-S174M | 34.6 | |
| L14 | ExRFlex | $C_L$-S176F | 46.1 | |

Example 8

Disruptive Mutants Identified Using SCWRL4 Modelling

A second modelling method involved using SCWRL4 (Krivov et al., Proteins 77(4): 778-95 (2009)) to predict the positions of side chains of mutated close contact residues in the interface, followed by energy minimization in Macro-Model (MacroModel, version 9.9, Schrodinger, LLC, New York, N.Y. (2012)). Two protocols were used with this method, with variations in the SCWRL step. For the "Base" method only the mutated side chains were adjusted, whereas for the "Repack" method all side chains were repacked. Results from the "Repack" method were preferred, as they were expected to indicate that a disruption would not be easily alleviated by minor side chain adjustments. The MacroModel step used the OPLS-2005 force field with GB/SA solvation, and allowed free movement of all hydrogen atoms and the mutated residue(s). Other atoms were restrained by a 100 kJ/mol-Å$^2$ restraint, but with 0.2 Å half-width flat bottom on the energy well. For each mutant the SCWRL4 and MacroModel calculations were performed on the bound state and on the unbound individual CH1 and CL domains, and the binding energy was computed as the energy difference between the bound and unbound forms. This method does not directly measure strain on the chain being mutated, so the most promising models were manually inspected for steric clashes, strained bond angles, or other signs of strain and compensating mutations were added where required. Approximately 40 different variants were modeled and assessed. Promising representative designs identified by this protocol are listed in Table 4 (some mutations were identified by both Rosetta and SCWRL4+ MacroModel).

TABLE 4

Subset of Disrupting Mutations Identified by SCWRL/MacroModel Calculations, using the "Repack" protocol. $\Delta E$ is the predicted change in binding energy between $C_H1$ and $C_L$ due to the mutations listed.

| Fab ID $C_H1/C_L$ | Mutation | $\Delta E$ (kJ/mol) |
|---|---|---|
| H2 | $C_H1$-L124R | 55.0 |
| H3 | $C_H1$-A139F | >100 |
| H6 | $C_H1$-A139H | 94.4 |
| H11 | $C_H1$-V190W | 39.0 |
| H14 | $C_H1$-K221E | 61.1 |
| H16 | $C_H1$-A139Y + $C_H1$-V190W | >100 |
| H17 | $C_H1$-V190W + $C_H1$-K221E | >100 |
| L1 | $C_L$-E123K | 49.0 |
| L3 | $C_L$-S131M | 17.5 |
| L4 | $C_L$-S131H | >100 |
| L5 | $C_L$-S131P | 84.1 |
| L8 | $C_L$-L135W | 22.2 |
| L11 | $C_L$-S174Q | >100 |
| L12 | $C_L$-S174M | 72.4 |
| L14 | $C_L$-S176F | 50.0 |

Example 9

Generation of Constructs from Modelling

Production of mutant Ab 29D2 constructs containing each disrupting mutation set (each row in Tables 3-4) was attempted. The $C_H1$ domain is intrinsically disordered, and adopts the normal folded IgG structure only after interaction with $C_L$. Prior to interaction with the $C_L$, heavy chains are retained in an unfolded state, bound to the chaperone binding immunoglobulin protein (BiP), in the endoplasmic reticulum (Feige et al., Mol. Cell 34(5): 569-79 (2009)). Thus, if the modelled designs fully disrupt the $C_H1/C_L$ interaction, no material would be isolatable for further characterization. Constructs H2, H3, H6, H10, H11, H16, H17, L1, L3, L4, L5, L8, L11, L12, and L14 expressed sufficiently for purification, indicating no more than partial disruption of $C_H1/C_L$ binding. Moderately reduced expression (<4 µg/mL as compared with parental expression of >15 µg/mL) was observed in COS cells for constructs L4 and L8. Expression of 9b, 9c, 10b, and 10c was not attempted.

Example 10

DSC of Expressed Constructs

Based on structural diversity of sites and selection of similar numbers of CH1 and CL sites, a subset of the expressed Ab 29D7 antibody variants of Example 9 was selected for examination by differential scanning calorimetry (DSC) (see Table 5 below). Constructs in PBS (137 mM NaCl, 2.7 mM KCl, 8.1 mM Na$_2$HPO$_4$, and 1.47 mM KH$_2$PO$_4$, pH 7.2) were diluted in the same buffer to a concentration of 0.3 mg/mL. Samples and buffers (400 µL) were transferred to a 96 well deep well plate and placed in the autosampler of the DSC (Cap-DSC, Microcal/GE Healthcare). Following injection into the instrument, samples were heated from 10° C. to 110° C. at 100° C./h.

The data were buffer- and baseline corrected prior to fitting to three, non-two-state transitions to determine the melting temperatures. Most changes were seen in the $T_m2$, the transition assigned to the $F_{ab}$ domain. Considering the standard errors shown in Table 5, all constructs in Table 5 were found to have at least slightly reduced thermal stability relative to antibodies lacking the disrupting mutation(s), indicating that mutations in the $C_H1/C_L$ interface destabilized the antibody. The constructs with the largest disruptions of $C_H1$ (H2 H10), and of $C_L$ (L1, L4), were selected for follow-up work.

In theory, a mispaired antibody with a restoring mutation (especially a 'hole' designed to accommodate a steric 'bump' on the opposite chain) on one chain and a native sequence on the other chain could still form. It was postulated that a disrupting mutation might have to be made on both the $C_H1$ and $C_L$ domain in order to disfavor all possible mispair combinations. Thus, L1 and L4 were chosen over H17, despite their smaller degree of disruption in the DSC experiment, because it was preferred to have multiple disrupting options for both $C_H1$ and $C_L$.

TABLE 5

Differential scanning calorimetry was used to measure melting temperatures of the various disruptive mutants (taken from Tables 3 and 4) to identify clones which had a lower Fab arm $T_m$ compared to wild-type antibody (29D7).

| Construct $C_H1/C_L$ | Mutations | $T_m2$ (° C.) | $T_m2$ (° C. ΔWT) |
|---|---|---|---|
| 29D7 (WT) | | 77.8 ± 0.1 | |
| H2 | $C_H1$-L124R | 69.7 ± 0.1 | −8.1 |
| H3 | $C_H1$-A139F | 77.2 ± 0.1 | −0.6 |
| H6 | $C_H1$-A139H | 76.6 ± 0.1 | −1.2 |
| H10 | $C_H1$-S188W + $C_H1$-L143S | 69.0 ± 0.1 | −8.8 |
| H11 | $C_H1$-V190W | 76.5 ± 0.1 | −1.3 |
| H16 | $C_H1$-A139Y + $C_H1$-V190W | 77.4 ± 0.1 | −0.4 |
| H17 | $C_H1$-V190W + $C_H1$-K221E | 72.1 ± 0.3 | −5.7 |
| L1 | $C_L$-E123K | 74.5 ± 0.1 | −3.3 |
| L4 | $C_L$-S131H | 75.2 ± 0.1 | −2.6 |
| L8 | $C_L$-L135W | 75.6 ± 0.1 | −2.2 |
| L11 | $C_L$-S174Q | 76.8 ± 0.1 | −1.0 |
| L12 | $C_L$-S174M | 76.6 ± 0.1 | −1.2 |
| L14 | $C_L$-S176F | 76.7 ± 0.1 | −1.1 |
| ΔCys | | 77.0 ± 0.1 | −0.8 |

Example 11

Restoring Mutants

Restoring mutations were designed using the SCWRL+MacroModel and Rosetta 2 protocols described above, or by using the Rosetta 3 Sequence Tolerance method (Smith and Kortemme, *PLoS One* 6(7): e20451 (2011)). With SCWRL+MacroModel, residues on the opposite chain from the disrupting mutations were identified by manual inspection and residues potentially increasing the spatial or electrostatic complementarity of the two chains were noted. Double or triple mutant combinations of these residues were enumerated exhaustively with SCWRL+MacroModel, and the binding energies were compared to the wild type sequence to identify amino acid substitutions which significantly reduced the binding energy loss caused by the disruptive mutation(s). On a modern computing cluster, this protocol is capable of evaluating tens of thousands of mutation combinations. For example, >1000 combinations of restoring mutations were considered for the H10 disruption example of Table 5. For the Rosetta 2 protocol, which evaluated up to millions of mutants, the search for restoring mutations was described above. The Rosetta 3 Sequence Tolerance method is not designed for finding disrupting mutations, but its design is appropriate for finding restoring mutations. A model of the disrupting mutation (constructed using one of the other methods) was provided as input, along with a list of nearby residues (determined by manual inspection) where mutations could ameliorate the disrupting effect. The primary output from this protocol is favorability rankings of amino acid types at each of the nearby sites; specific sequences containing these residues were then modeled using the sequence tolerance software and/or in SCWRL+MacroModel. In addition to the default Boltzmann-weighted sequence ranking implemented in the Sequence Tolerance package, a method was also used where statistics on amino acid frequency at each position were determined by a step function which applies a weight of 1 to the top-scoring 1% of sequences, and 0 weight to the remaining sequences.

For all protocols, a combination of the protocol energy scores and manual inspection of the models was used to select the best designs. Models in which the rotamers of the mutated side chains closely match known rotamers (from the rotomer data distributed with the Maestro software) were preferred during manual inspection. Multiple restoring designs were often plausible for a particular disrupting mutant. Representative restoring designs are shown in Table 6. In the case where a native salt bridge is being reversed, such as between $C_L$-E123 and $C_H1$-K221, the assignment of which residue is disrupting and which is restoring may be considered arbitrary.

In summary, for the disrupting sets of mutations chosen after confirmation by DSC (L1, L4, H2, H10) putative restoring mutations were identified using a combination of multiple computational modeling techniques. For L1, a salt bridge in the wild type sequence, reversal of the salt bridge (but with Glu replaced by Asp) was the only design judged to be worth testing. For the other three disrupting designs, multiple plausible restoring designs were identified.

TABLE 6

Example Designs with Disrupting and Restoring Mutations. Each row in the table represents a combination of mutant $C_H1$ and mutant $C_L$ domains predicted to associate more favorably than the disrupting mutant would associate with its wild type partner. The first two rows illustrate a case of charge swapping for reversing the orientation of a native salt bridge, where the mutation in either column can be considered disrupting in the absence of the other mutation.

| Fab ID | Disrupting Mutations | Restoring Mutations | Base CL Sequence |
|---|---|---|---|
| R1.1 | $C_L$-E123K | $C_H1$-K221D | K or λ |
| R1.1 | $C_H1$-K221D | $C_L$-E123K | K or λ |
| R4.1 | $C_L$-S131H | $C_H1$-K145E | K |

TABLE 6-continued Example Designs with Disrupting and Restoring Mutations. Each row in the table represents a combination of mutant $C_H1$ and mutant $C_L$ domains predicted to associate more favorably than the disrupting mutant would associate with its wild type partner. The first two rows illustrate a case of charge swapping for reversing the orientation of a native salt bridge, where the mutation in either column can be considered disrupting in the absence of the other mutation.

| Fab ID | Disrupting Mutations | Restoring Mutations | Base CL Sequence |
|---|---|---|---|
| R4.2 | $C_L$-S131H | $C_H1$-L143H + $C_H1$-Q179D + $C_H1$-S186E | K |
| R4.3 | $C_L$-S131H | $C_H1$-K145S + $C_H1$-S186E | K |
| H2.1 | $C_H1$-L124R | $C_L$-F118E + $C_L$-V133G + $C_L$-S176D | K or λ |
| H2.2 | $C_H1$-L124R | $C_L$-F118H + $C_L$-V133N + $C_L$-S176N | K or λ |
| H2.3 | $C_H1$-L124R | $C_L$-F118D + $C_L$-V133M + $C_L$-S176D | K or λ |
| H2.4 | $C_H1$-L124R | $C_L$-F118E + $C_L$-V133N | K or λ |
| R10.1 | $C_H1$-S188W + $C_H1$-L143S | $C_L$-V133S + $C_L$-T178S + $C_L$-S131D | K |
| R10.2 | $C_H1$-S188W + $C_H1$-L143S | $C_L$-V133S + $C_L$-T178G | K |
| R10.3 | $C_H1$-S188W + $C_H1$-L143S | $C_L$-V133Q + $C_L$-T178G + $C_L$-F118H | K |
| R10.4 | $C_H1$-S188W + $C_H1$-L143S | $C_L$-V133M + $C_L$-T178G + $C_L$-S176G | K |
| R4.1λ | $C_L$-T131H | $C_H1$-K145E | λ |
| R4.2λ | $C_L$-T131H | $C_H1$-L143H + $C_H1$-Q179D + $C_H1$-S186E | λ |
| R4.3λ | $C_L$-T131H | $C_H1$-K145S + $C_H1$-S186E | λ |
| R10.1λ | $C_H1$-S188W + $C_H1$-L143S | $C_L$-V133S + $C_L$-Y178S + $C_L$-T131D | λ |
| R10.2λ | $C_H1$-S188W + $C_H1$-L143S | $C_L$-V133S + $C_L$-Y178G | λ |
| R10.3λ | $C_H1$-S188W + $C_H1$-L143S | $C_L$-V133Q + $C_L$-Y178G + $C_L$-F118H | λ |
| R10.4λ | $C_H1$-S188W + $C_H1$-L143S | $C_L$-V133M + $C_L$-Y178G + $C_L$-S176G | λ |

Example 12

Designs with Disrupting, Restoring, and Novel Disulfide Mutations

An additional set of mutants consisted of incorporating the novel inter-chain disulphide bond designs highlighted in Table 2, with one or more of the designs listed in Table 6, where appropriate based on molecular modeling. In the cases where a novel disulphide was combined into the bispecific design, the native disulphide cysteine residues ($C_H1$-C230 and $C_L$-C214) were both mutated to serine residues to ablate the native disulphide bond.

Most of the combinations appeared complementary, but in some cases residues to be mutated were near each other (increasing risk of unexpected interactions between the mutations) or were identical. For example, the Cys6 design uses the mutation $C_L$-E123C, which means it is not compatible with the $C_L$-E123K constructs in Table 6. R4.2 and R10.3 both mutate residue $C_H1$-L143. R4.1 and R10.3 do not mutate the same residues, but are structurally adjacent, increasing the risk of unanticipated interactions between them; in the native structure, residue $C_L$-S131 used in R4.1 contacts $C_H1$-L143 used in R10.3. Example compatible designs are shown in the rows of Table 7, with the $C_H1$ and $C_L$ columns of each row constituting a paired design.

TABLE 7

Example Designs with Disrupting, Restoring, and Novel Disulfide Mutations. Each row in the table represents a combination of mutant $C_H1$ and mutant $C_L$ domains expected to associate more favorably than the disrupting mutant would associate with its wild type partner.

| Fab ID | $C_H1$ Mutations | $C_L$ Mutations | Base CL Sequence |
|---|---|---|---|
| T1 | K221D + F174C + V190I + C230S | E123K + S176C + L135I + C214S | K or λ |
| T2 | K145E + F122C + C230S | S131H + E123C + C214S | K |
| T3 | L143H + Q179D + S186E + F174C + V190I + C230S | S131H + L135I + S176C + C214S | K |
| T4 | K145S + S186E + A139C + C230S | S131H + F116C + C214S | K |
| T9 | S188W + L143S + F174C + C230S | V133S + T178S + S131D + S176C + C214S | K |
| T12 | S188W + L143S + F122C + C230S | V133M + T178G + S176G + E123C + C214S | K |
| T18 | S188W + L143S + F122C + A139C + F174C + C230S | V133S + T178S + S131D + F116C + E123C + S176C + C214S | K |
| T2λ | K145E + F122C + C230S | T131H + E123C + C214S | λ |
| T3λ | L143H + Q179D + S186E + F174C + V190I + C230S | T131H + L135I + S176C + C214S | λ |
| T4λ | K145S + S186E + A139C + C230S | T131H + T116C + C214S | λ |
| T9λ | S188W + L143S + F174C + C230S | V133S + Y178S + T131D + S176C + C214S | λ |
| T12λ | S188W + L143S + F122C + C230S | V133M + Y178G + S176G + E123C + C214S | λ |
| T18λ | S188W + L143S + F122C + A139C + F174C + C230S | V133S + Y178S + T131D + T116C + E123C + S176C + C214S | λ |

Example 13

Bispecific Antibodies Having Novel Electrostatic Interactions

One type of protein interface selectivity design involves electrostatic complementarity, where a positive charge on one side of an interface is paired with a negative charge on the other side of the interface. If an alternate variant of the interface is engineered in which the charges are reversed, selectivity can occur.

In the present example, the paired residues of each domain involved in existing $C_H$-$C_L$ domain salt bridges can be reversed between the interacting domains. One such example is E123K combined with K221D, as in Table 6. In the final bispecific, one binding arm of the antibody has the wild type salt bridge and one has the reversed salt bridge.

The dual-stage design process described above (first find a disrupting mutation or mutations as in Table 5, then find compensating restoring mutations as in Table 6) can also engineer electrostatic selectivity where only one of the two charged residues is present in the native protein, such as in the R4.1 design of Table 6. Here, the native residues are $C_L$-S131 and $C_H$1-K145. The first stage of the process finds a disrupting mutation of the same charge as the Lys, in this case $C_L$-S131H. Then, the second stage mutates the native Lys to the opposite charge as a restoring mutation, $C_H$1-K145E, which creates a favorable electrostatic interaction.

However, it is conceptually possible to design a de novo favorable electrostatic charge interaction where neither native residue is charged, and use this novel charge interaction to drive interface selectivity. In the absence of the second charged residue, introduction of the first charged residue might not be disruptive (unless for other reasons such as steric contact), and thus might not be found by the dual-stage process described above. Therefore, a different process for de novo electrostatic interaction engineering was also used.

A de novo electrostatic interaction could be placed either in the interface core, where there is little or no exposure to bulk solvent, or it could be placed at the boundary where solvent and both protein chains meet. Core regions, including the CH1/CL interface core, are generally hydrophobic and are not an ideal environment for charged side chains. Unless an optimal hydrogen bonding network that fully satisfies the hydrogen bonding potential of both residues can be engineered, the putative charged residues may have an energetic preference for interaction with solvent (where the CH1 and CL domains remain unbound) rather than each other. On the other hand, if a charge interaction is engineered on the periphery of the interface, charged residues (particularly Lys, Arg, and Glu) are sufficiently flexible that a charge/charge mispair might allow two similarly charged residues to orient away from each other, with the electrostatic repulsion significantly dampened by intervening solvent. Exposed residues also create a risk of unwanted clearance of a protein therapeutic if the immune system mounts an anti-drug antibody (ADA) response against the mutated exposed residues. An ideal case for de novo charge interaction design is a conformationally restricted pocket which does not allow significant side chain flexibility, but which is also sufficiently polar such that the interacting charged residues are stabilized by additional polar interactions with nearby residues or water molecules.

Figure 16:
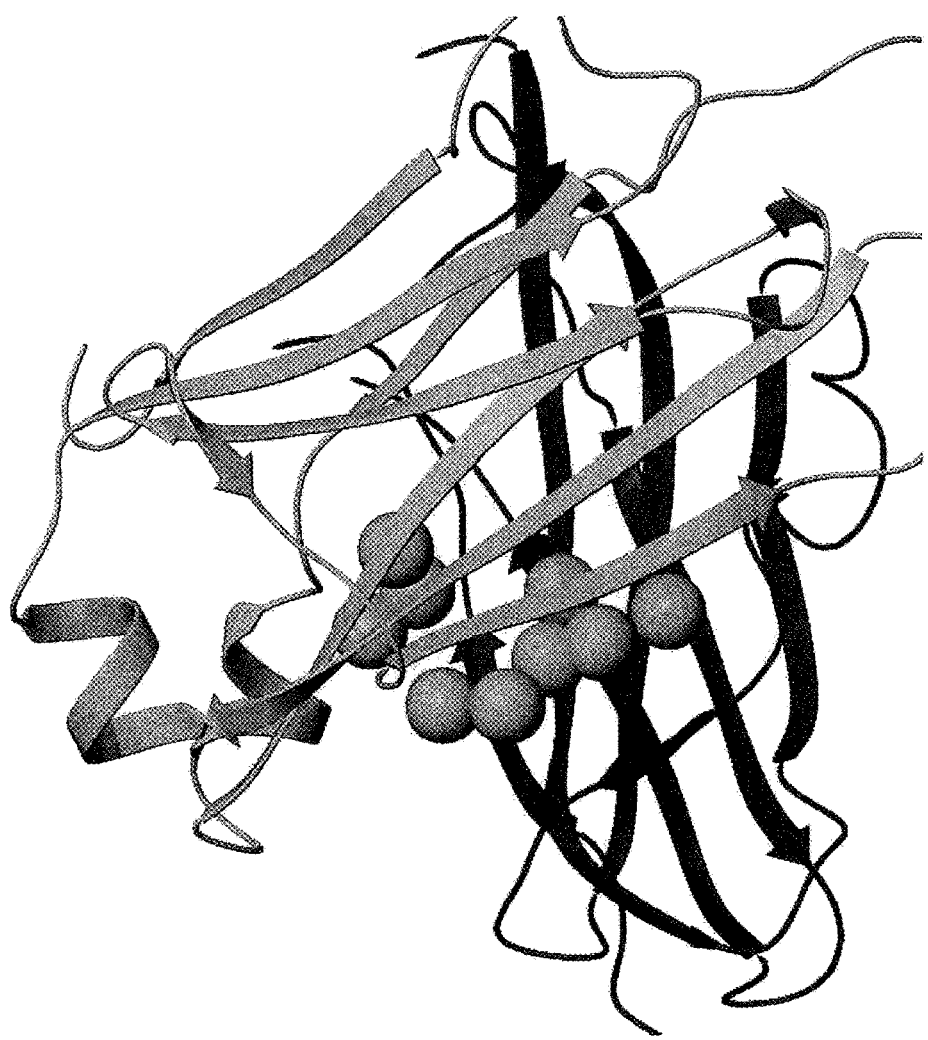
FIG. 16 depicts a mostly buried, solvated pocket between the $C_H1$ and $C_L$ domains of PDB entry 3QQ9. The light chain backbone, shown using a light gray ribbon, is in the front of the view, with the dark gray heavy chain backbone ribbon more to the back. Key water molecules defining this pocket are shown as spheres.
Figure 18C:
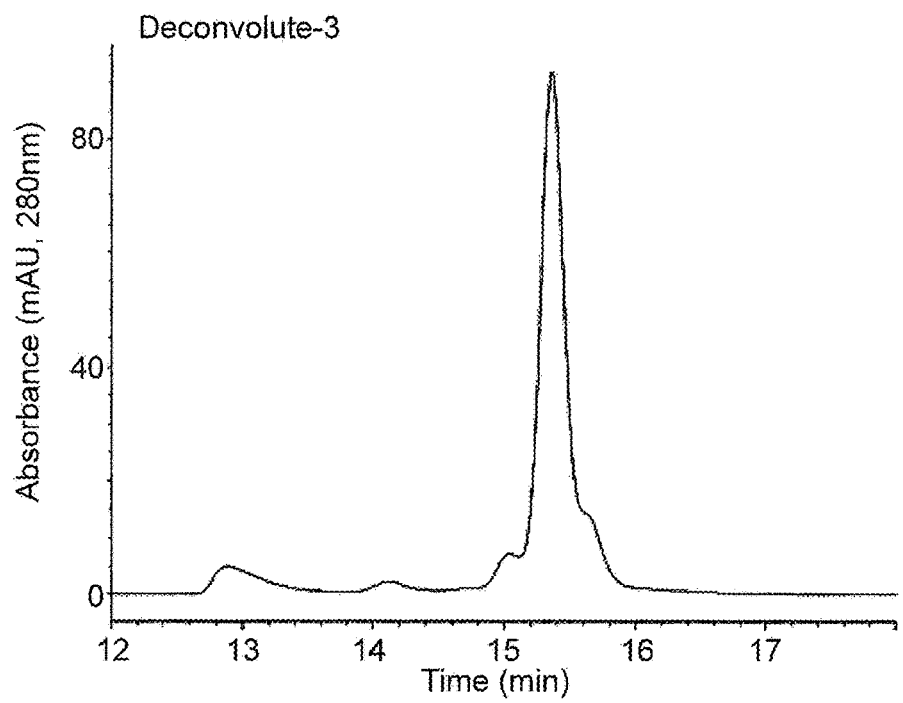
FIG. 18 depicts a graph showing separation of bispecific antibodies using hydrophobic chromatography. In Panel A, the C5 and Ab3 antibodies are combined into a bispecific incorporating only CH3 mutations for heavy chain heterodimerization, but no bispecific-favoring mutations in the heavy/light interface. There are three major peaks, indicating a heterogenous sample. In Panel B, the S1 and S1 rev designs are added to the heavy/light interface to disfavor mispairing of the wrong heavy and light chains; the sample homogeneity is greatly improved. If some of the secondary supporting mutations of the S1 and S1_rev designs are not utilized (Panels C and D), the sample has an intermediate level of heterogeneity. Panels E and F are controls showing the level of homogeneity observed with the monospecific versions of the two antibodies used to assemble the bispecific antibodies of Panels A-D.
Figure 18D:
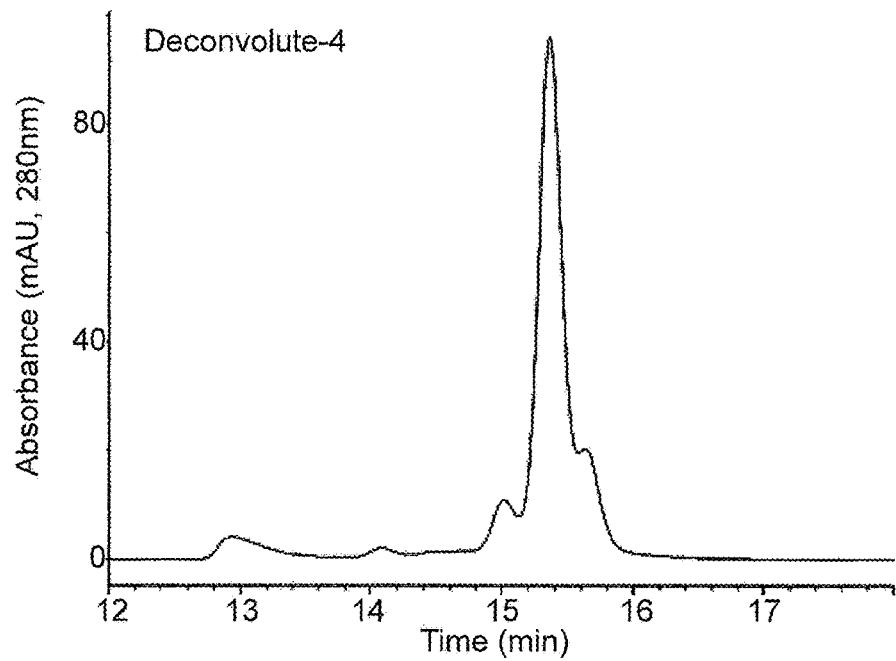
Figure 18E:
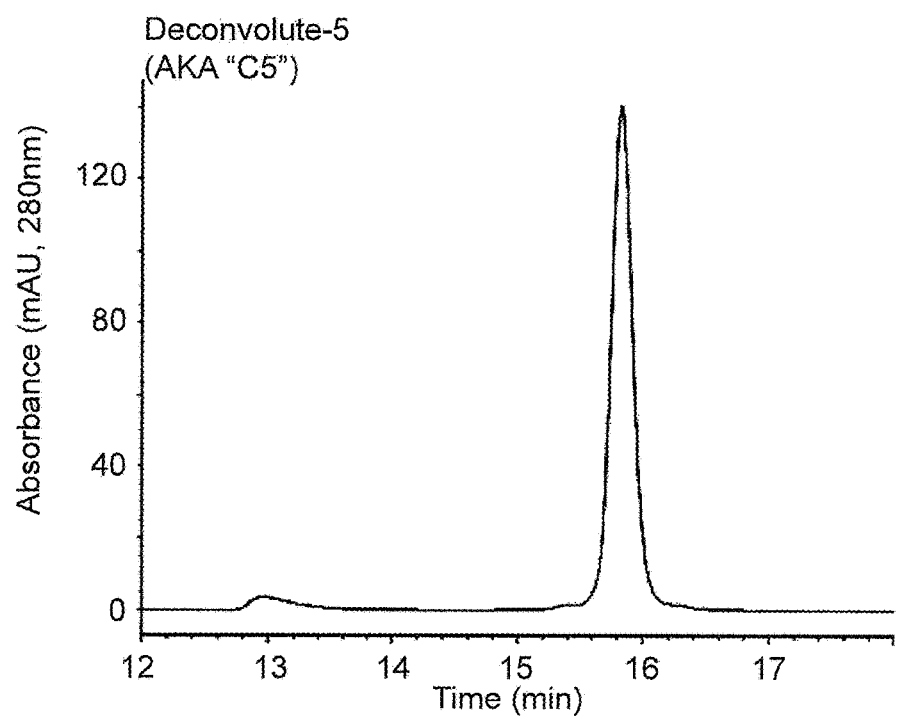
Figure 18F:
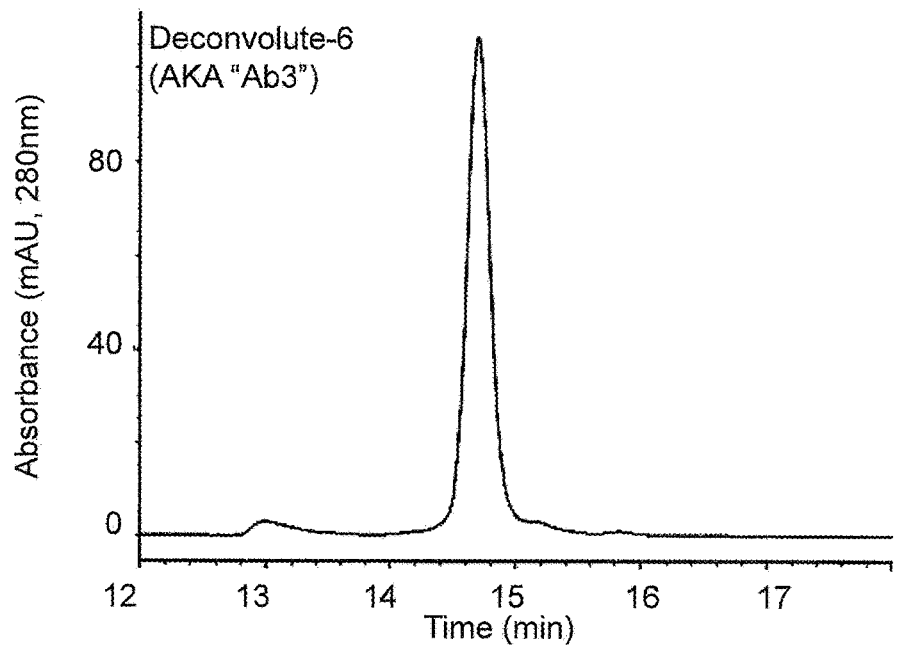
Figure 19A:
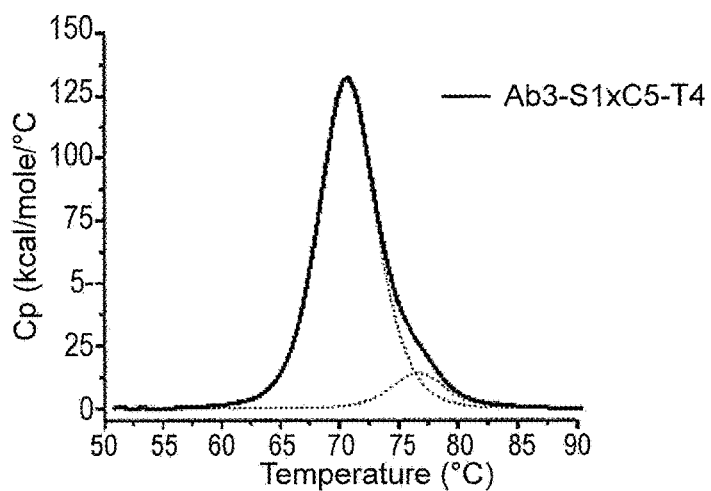
FIG. 19 depicts Differential Scanning calorimetry (DSC) curves for bispecific Fabs with various combinations of mutations in each Fab arm, as described in Table 23. The solid thick lines indicate raw data, while the thin dotted lines indicate the results of fitting the raw data to a two transition or three transition model, as appropriate. As summarized in Table 24, all Fabs showed good stability with their lowest transition above 65° C.
Figure 19B:
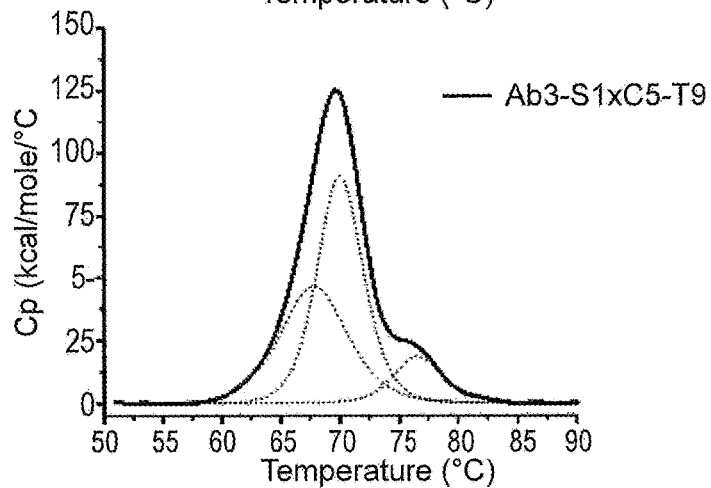
Figure 19C:
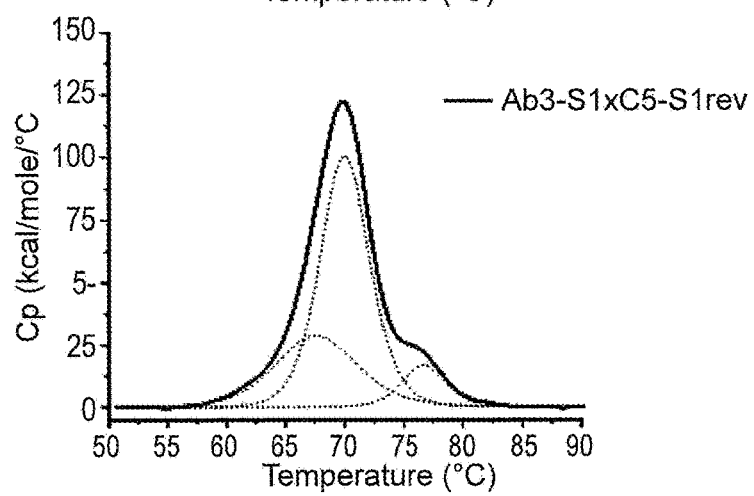
Figure 19D:
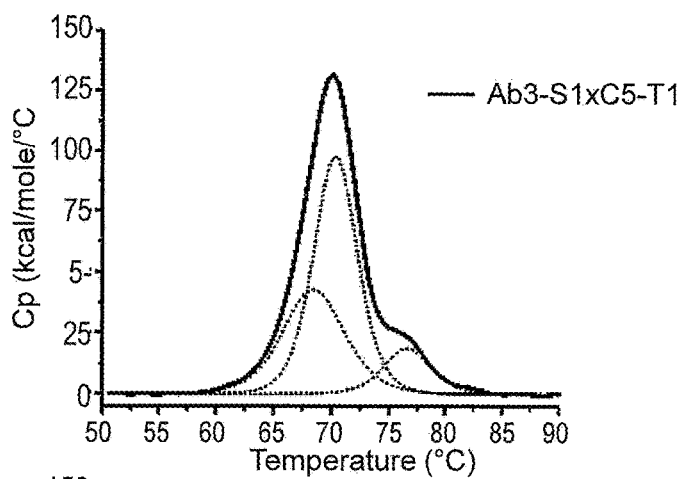
Figure 19E:
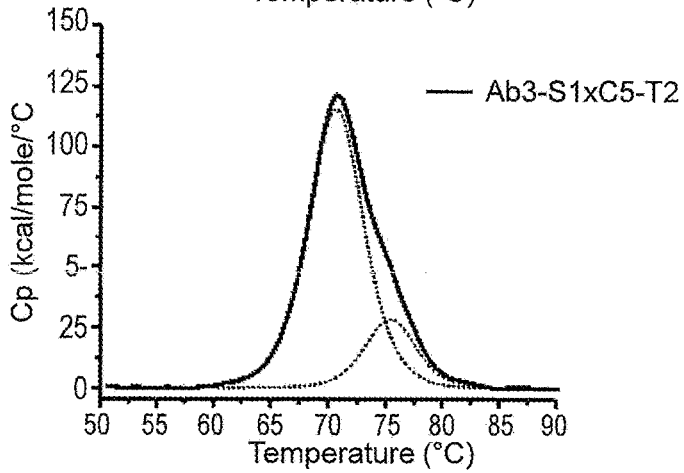
Figure 19F:
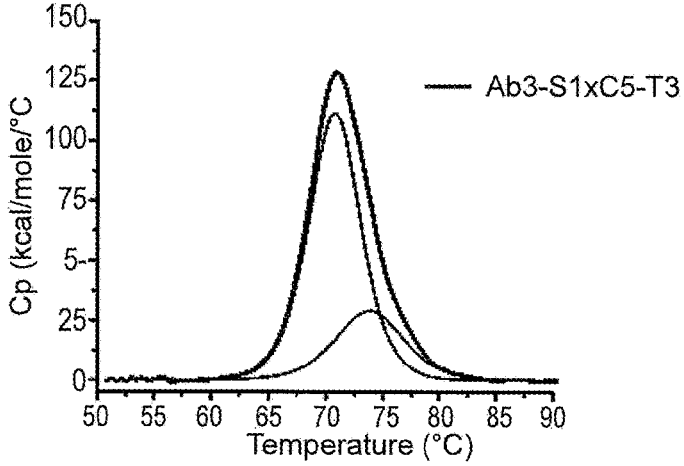
Figure 19G:
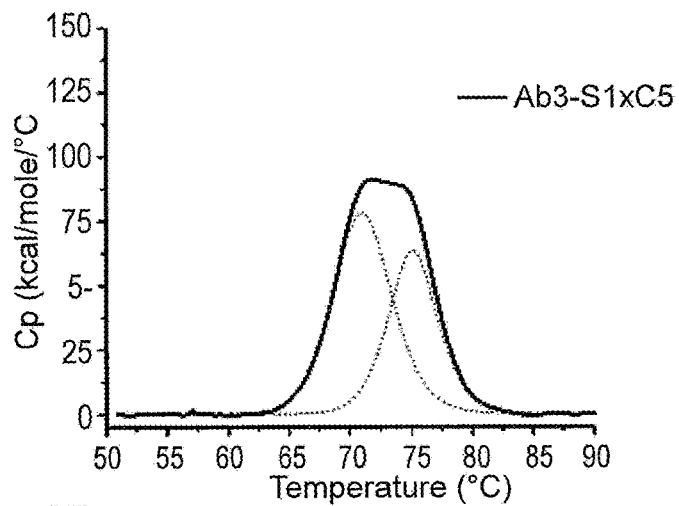
Figure 19H:
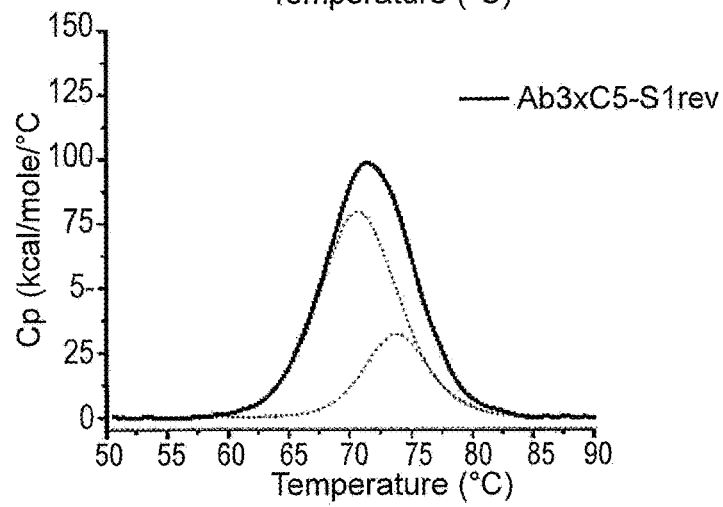
Figure 19I:
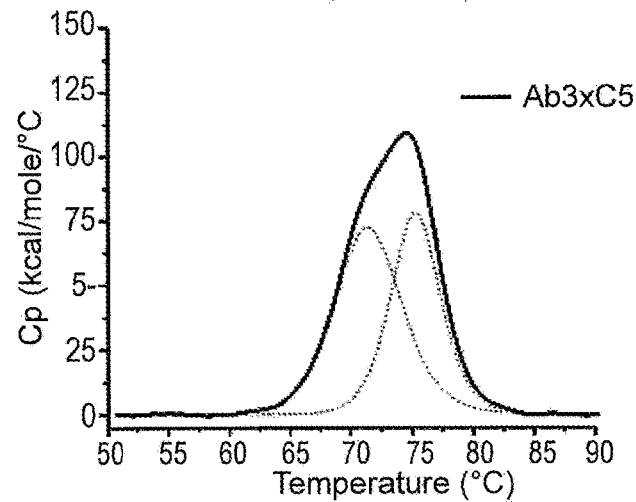
Figure 20A:
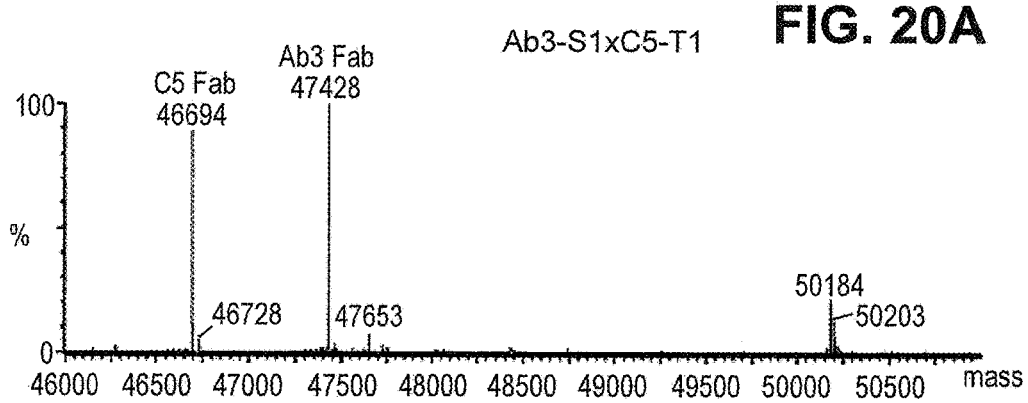
FIG. 20 depicts mass spectrographic analysis of dual arm Fab fragments with various combinations of designs in each Fab arm, as enumerated in Table 23. Bispecific antibodies with S1 in the Ab3 Fab arm and any of T1, T2, T3, T4, or T9 in the C5 Fab arm displayed high fidelity of heavy/light chain pairing (Panels A-E). A minor amount of mispairing (~3%) was detected in the sample combining S1 in one Fab arm with S1_rev in the other Fab arm (Panel F, mispair labeled as "C5 H Ab3 L"). If one Fab arm (Panels G-H) or both Fab arms (Panel I) did not contain a bispecific-favoring design, larger amounts of mispaired Fab (19% or higher) were detected.
Figure 20B:
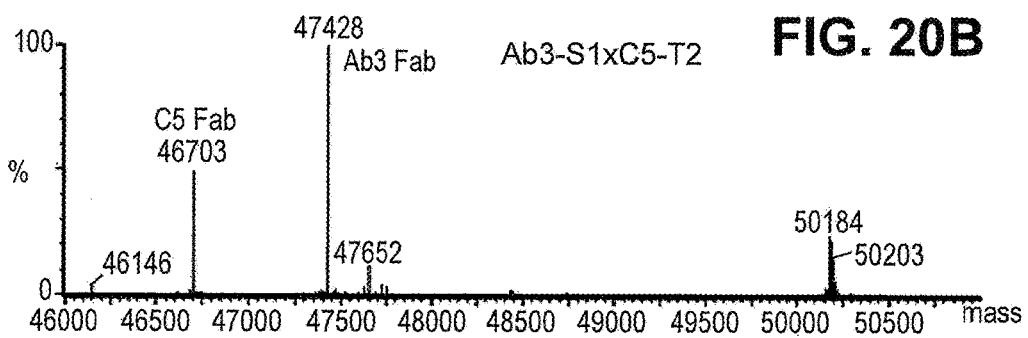
Figure 20C:
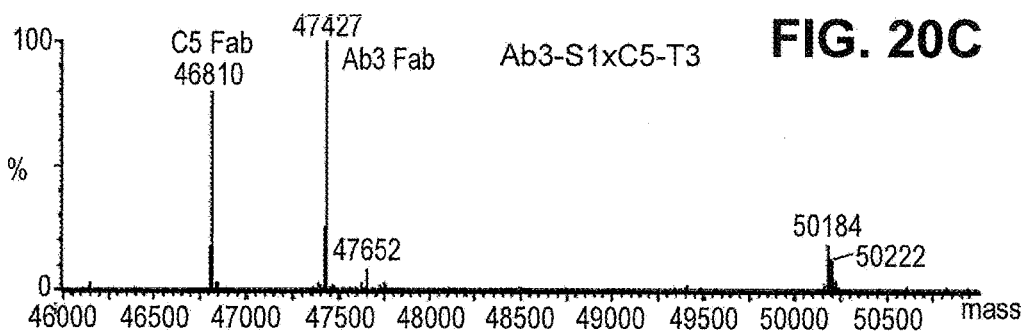
Figure 20D:
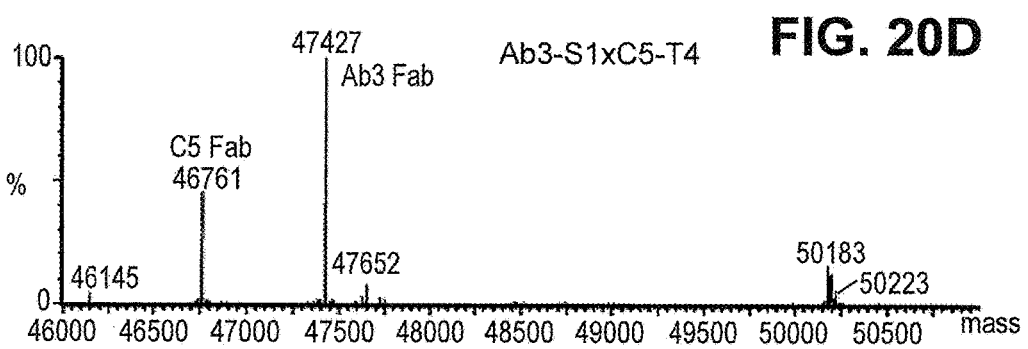
Figure 20E:
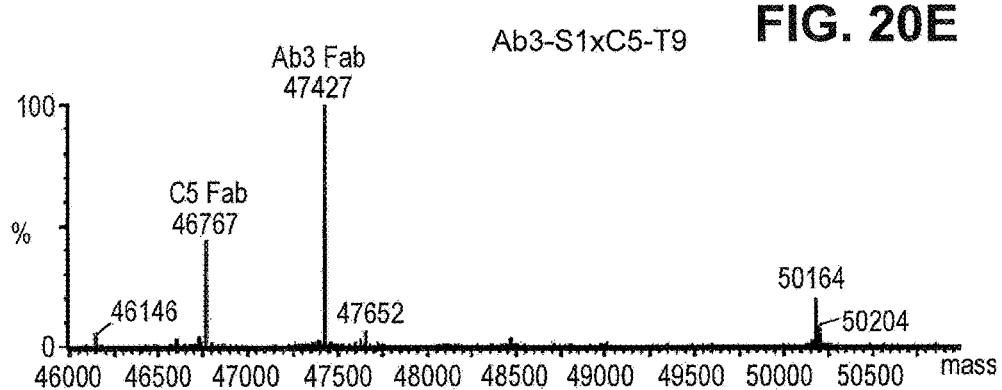
Figure 20F:
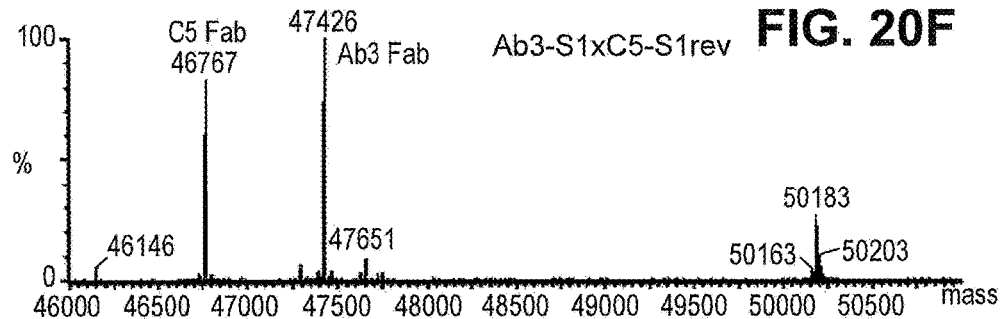
Figure 20G:
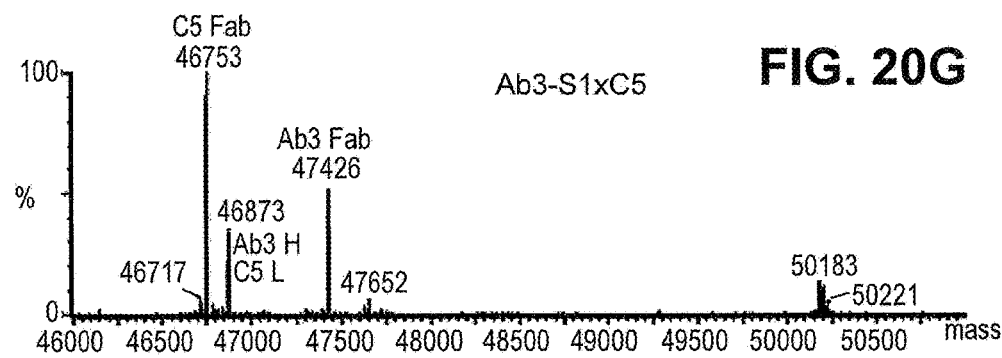
Figure 20H:
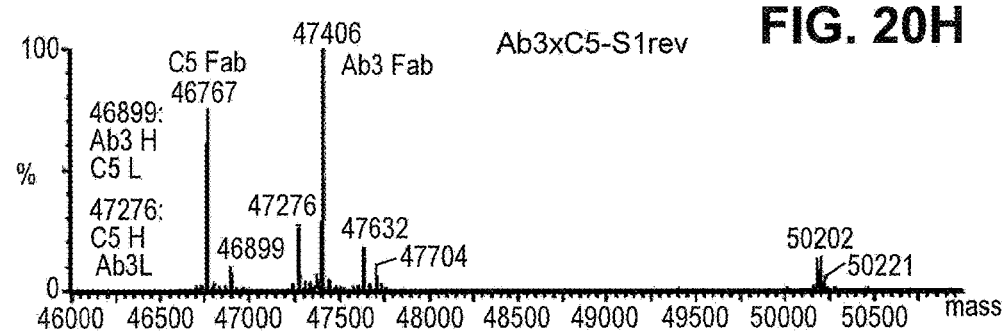
Figure 20I:
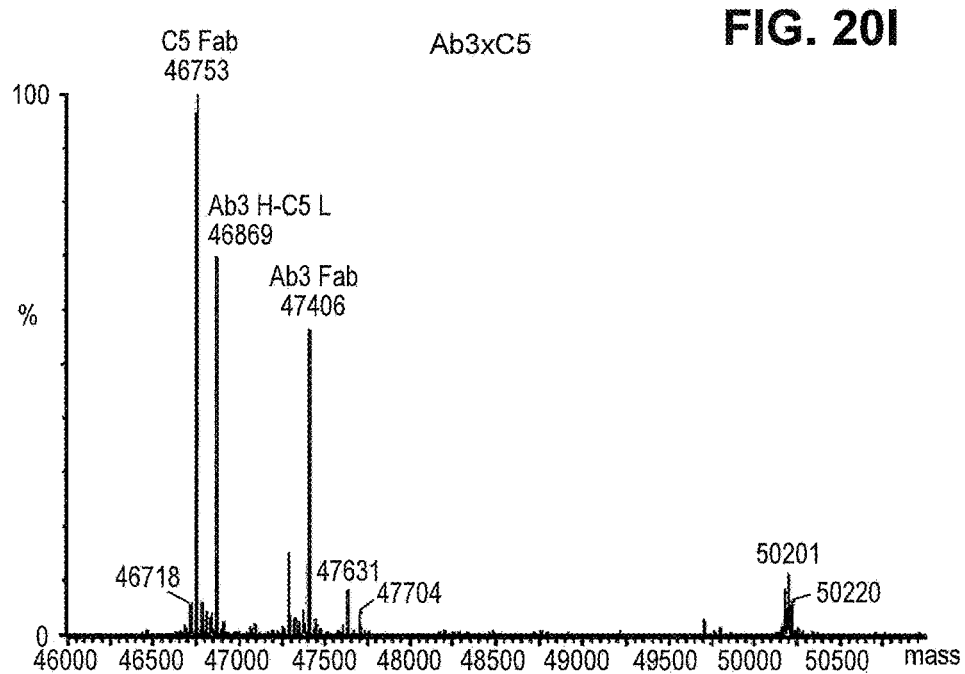
Figure 21A:
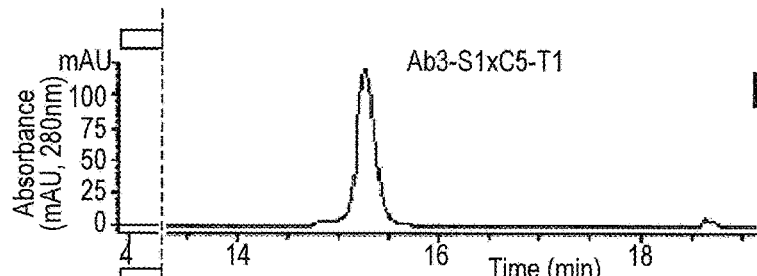
FIG. 21 depicts separation of bispecific antibodies using hydrophobic interaction chromatography. The antibodies are enumerated in Table 23. Bispecific antibodies with S1 in the Ab3 Fab arm and any of T1, T2, T3, T4, or T9 in the C5 Fab arm displayed high fidelity of heavy/light chain pairing (Panels A-E). A minor amount of mispairing is apparent as a small tail on the left side of the main peak. This tail on the peak is slightly larger for S1 on Ab3 paired with S1_rev on C5 (Panel F, see arrow). These results are consistent with the mass spectrographic analysis of Example 41 and FIG. 20. If one Fab arm (Panels G-H) or both Fab arms (Panel I) did not contain a bispecific-favoring design, larger amounts of mispaired Fab were detected, as indicated by the presence of additional peaks. For reference, Panels J-K show the corresponding profile of the monospecific Ab3 and C5 antibodies on which these bispecific designs were based.
Figure 21B:
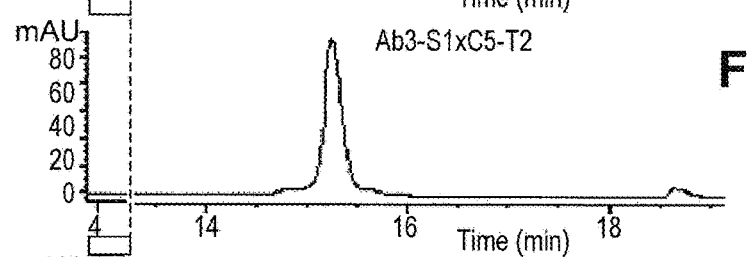
Figure 21C:
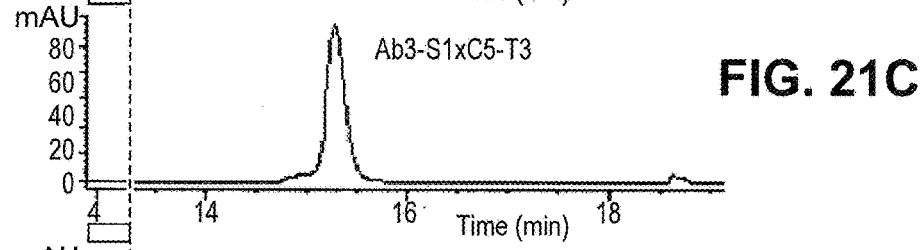
Figure 21D:
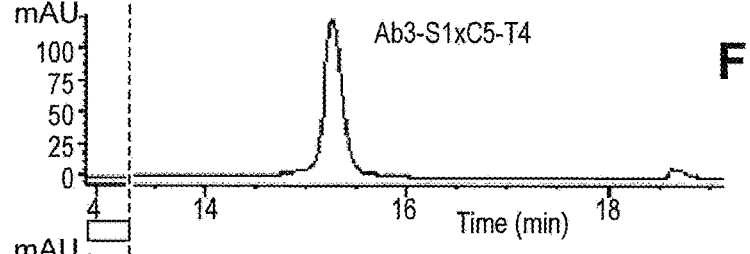
Figure 21E:
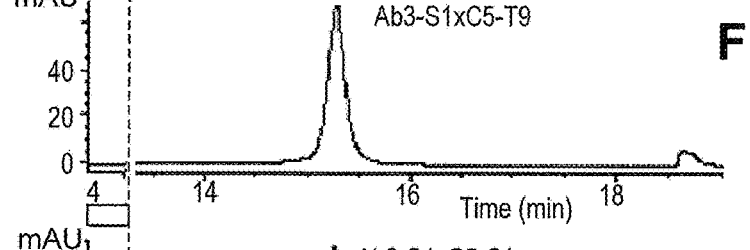
Figure 21F:
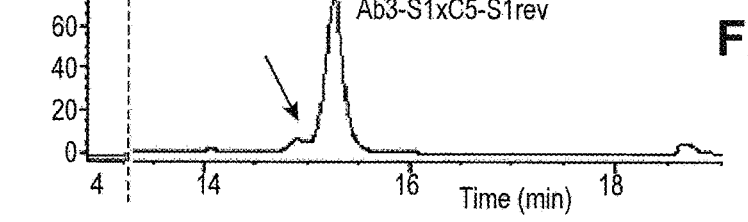
Figure 21G:
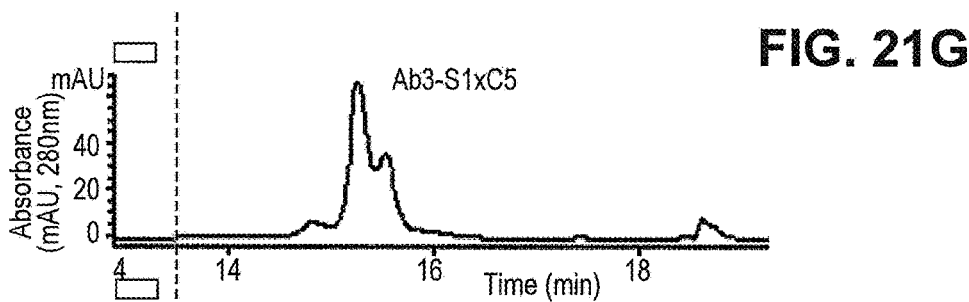
Figure 21H:
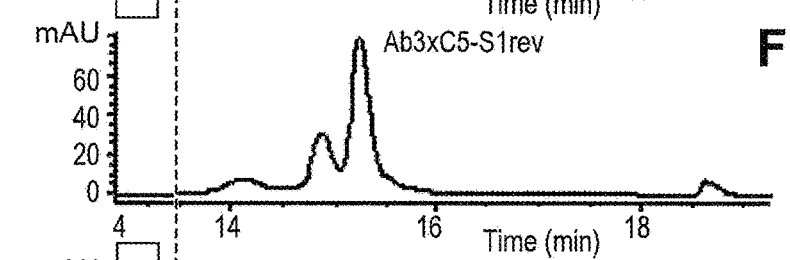
Figure 21I:
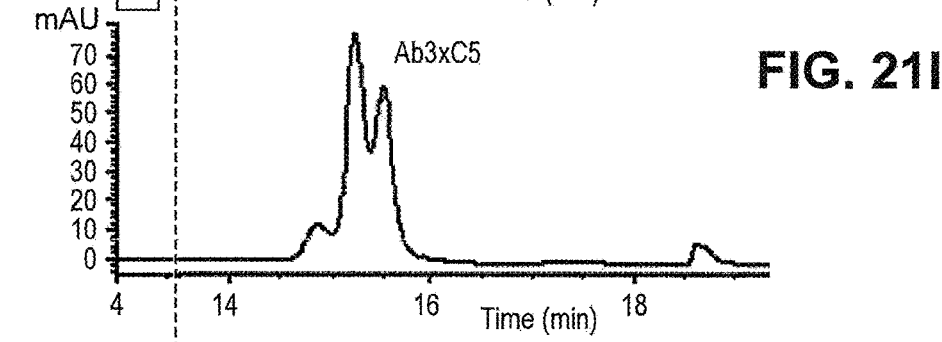
Figure 21J:
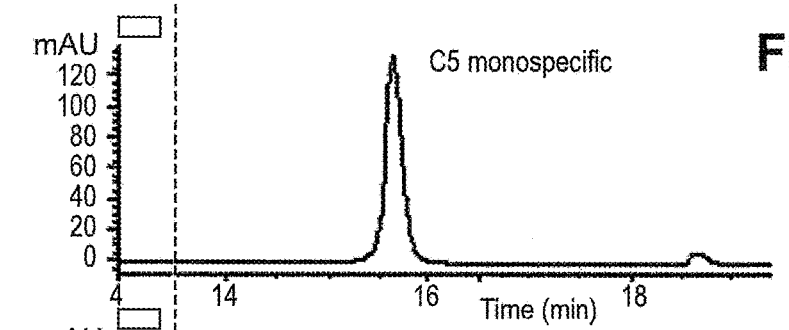
Figure 21K:
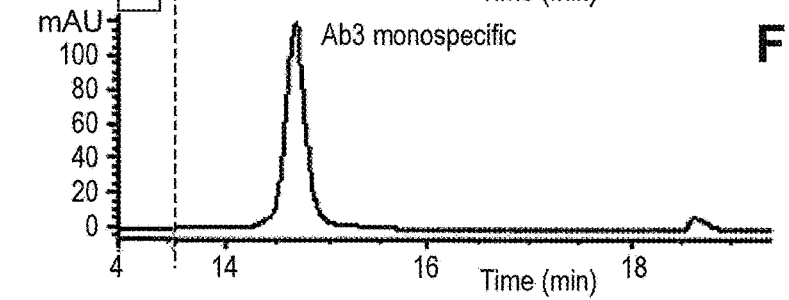

Such a region on the $C_H$1/$C_L$ interface was identified, and efforts were focused there. The $C_H$1/$C_L$ interface includes two pockets of water molecules which are in close contact with both domains and which are largely shielded from bulk solvent. In PDB entry 3QQ9, these water molecules include those labeled as residues $C_H$-292, $C_H$-319, $C_H$-498, $C_H$-504, $C_H$-544, $C_L$-254, $C_L$-279, $C_L$-359, and $C_L$-490 (FIG. 16). These waters contact protein side chains including $C_H$-L124, $C_H$-L143, $C_H$-K145, $C_H$-Q179, $C_H$-S186, $C_H$-S188, $C_L$-S131, $C_L$-V133, $C_L$-S162, $C_L$-S176, $C_L$-T178, and $C_L$-T180. Most of these residues are polar, but only $C_H$-K145 is charged. The SCWRL/MacroModel method was used to evaluate all possible double mutants of these residues involving one mutation to $C_H$1 and one mutation on $C_L$, and where the native residues were mutated to all possible combinations of Arg, Asp, Glu, and Lys. This procedure engineered both residues of a novel favorable charge interaction in a single design stage. Results from the protocol without full protein repacking were preferred, to favor designs that are readily accommodated by the native side chain rotamers without requiring significant adjustments. Additional residues in the pocket, such as $C_H$-F174, $C_H$-V177, $C_L$-F118, and $C_L$-Q128 were noted for reference but were not part of the initial design scan.

Figure 5B:
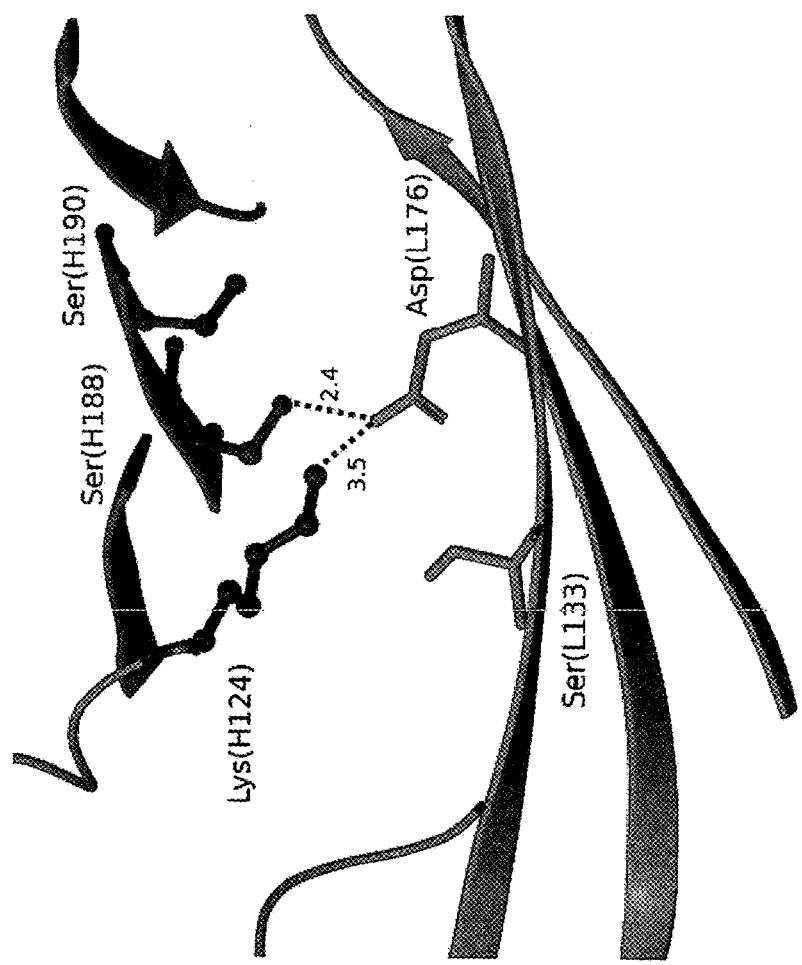
FIG. 5 depicts x-ray crystal structures of the interface region involved in design S1. Within each panel, the $C_H1$ domain is shown on top in dark gray with key residues rendered in ball and stick form. The $C_L$ domain is shown on the bottom in light gray with key resides rendered as tubes. Key interactions are indicated by dotted lines with distances in Angstroms. Panel A: the orientation of key residues $C_H1$-124 and $C_L$-S176, as well as the supporting residues $C_L$-V133, $C_H1$-S188, and $C_H1$-V190 in a native Fab arm comprising IgG1 $C_H1$ and kappa CL. Panel B: Design to be used in one Fab arm of a standard two-arm antibody, with mutations $C_H1$-L124K, $C_L$-S176D, $C_L$-V133S, and $C_H1$-V190S. Panel C: Design to be used in the other Fab arm of a standard two-arm antibody, with mutations $C_H1$-L124E, $C_L$-S176K, $C_L$-V133S, and $C_H1$-S188G. Without wishing to be bound by any particular theory, when the mutations shown in B and C are introduced into each of the two Fab arms of an antibody, heavy/light mispairing will be disfavored by Lys/Lys or Asp/Glu charge repulsion, and/or correct pairing will be encouraged by Lys/Asp or Lys/Glu charge attraction. Panel A depicts PDB entry 3QQ9, while panels B and C are unpublished crystal structures.

Inspection of the results showed that mutations at positions $C_H$-L124 and $C_L$-S176 were promising. The wild type orientations of these residues are shown in FIG. 5A. Modeling (not shown) indicated that a favorable electrostatic interaction could form from the combination $C_H$-L124K paired with $C_L$-S176D, and a reversed orientation of the charge interaction could form with $C_H$-L124E and $C_L$-S176K. However, some bad steric contacts were evident in each case. Manual inspection of the models suggested that for the former charge pair, mutations $C_H$-V190S and $C_L$-V133S would alleviate the strain and, in addition, $C_L$-S133 might form an additional hydrogen bond with position $C_H$-K124 and/or $C_L$-D176. Similarly, for the reversed orientation of the interaction, the mutations $C_H$-S188G and $C_L$-V133S were added to improve packing contacts. After production and experimental validation of these designs, the x-ray crystal structure of each charge pair design was determined, and the results are shown in panels B and C of FIG. 5.

The above procedure identified a number of additional potential charge interactions that could be favorably formed in either orientation ($V_H$ with a positive amino acid and $V_L$ with a negative amino acid, or the reverse, hence these may be considered 'reversible' charge interactions). Often, one or more mutated side chains made minor bad contacts with, or were prevented from adopted a preferred rotamer by, another nearby side chain. In these cases, the predicted double mutant structure was submitted to the Rosetta sequence tolerance protocol to optimize the other nearby surrounding residues.

The identified favorable charge interaction designs are shown in Table 8. Each row in this table is a design which can be used to modify a single $C_H$1/$C_L$ interface. However, the first column indicates preferred pairings of designs, where the two $C_H$1/$C_L$ interfaces of an antibody are separately engineered to each contain one of the two paired designs (a 'forward' and 'reverse' orientation of the charge interaction). The preferred pairings will result in overt charge/charge repulsion if either $C_L$ attempts to associate with the incorrect $C_H$1 domain.

TABLE 8

Charge Interaction Designs at the $C_H1/C_L$ Interface. Each row in the table lists a $C_H1/C_L$ residue pair predicted to form a favorable electrostatic interaction between the two domains, as described in Example 13. The fourth column lists any residues which may improve the behavior of the protein, which may include optimizing packing around the charged residues, heavy/light pairing selectivity, stability, expression, or other features. The "_rev" designation indicates reversal of the orientation of the charges on the $C_H$ and $C_L$ chains.

| Fab ID (Secondary Mutations included) | Pairing | $C_H1$ Mutation | $C_L$ Mutation | Secondary Mutations | Base $C_L$ Sequence |
|---|---|---|---|---|---|
| S1 | 1 | L124K | S176D | $C_L$-V133S, $C_H1$-V190S | K or λ |
| S1_rev | 1 | L124E | S176K | $C_L$-V133S, $C_H1$-S188G | K or λ |
| S3 | 3 | S188E | T178K | $C_H1$-L143E | K |
| S3_rev | 3 | S188K | T178D | $C_H1$-L143D | K |
| S4a | 4a | L143K | T178D | | K |
| S4a_rev | 4a | L143D | T178R | | K |
| S4b | 4b | L143K | T178D | | K |
| S4b_rev | 4b | L143D | T178K | $C_L$-S176M | K |
| S5 | 5 | L143E | S131R | | K |
| S5_rev | 5 | L143R | S131E | $C_H1$-S186A | K |
| S3λ | 3λ | S188E | Y178K | $C_H1$-L143E | λ |
| S3_revλ | 3λ | S188K | Y178D | $C_H1$-L143D | λ |
| S4aλ | 4aλ | L143K | Y178D | | λ |
| S4a_revλ | 4aλ | L143D | Y178R | | λ |
| S4bλ | 4bλ | L143K | Y178D | | λ |
| S4b_revλ | 4bλ | L143D | Y178K | $C_L$-S176M | λ |
| S5λ | 5λ | L143E | T131R | | λ |
| S5_revλ | 5λ | L143R | T131E | $C_H1$-S186A | λ |

Example 14

X-ray Crystal Structure of S1 and S1_rev

To confirm that the molecular modeling correctly predicted the formation of favorable electrostatic interactions, the x-ray crystal structures of the S1 and S1_rev designs from Table 8 were determined (FIG. 5, panels B and C). The designs were each expressed as recombinant Fab molecules (using antibody Ab1 for the variable domains) by transient transfection in HEK-293 cells. Fabs were purified from conditioned media by batch binding to Poros Protein A resin followed by elution with 0.1 M Glycine pH 2.5. Eluted Fab was then purified by size exclusion chromatography on a Superdex 200 16/60 column equilibrated with 20 mM Tris pH 7.0, 50 mM NaCl. S1 Fab was crystallized in 100 mM HEPES pH 7.5, 10% PEG 3350, 200 mM proline and crystallized in space group P21212 with unit cell edges of 106.7, 127.1, 84.5 Å. S1_rev formed crystals in space group P42212 (cell edges 118.4, 118.4, 84.2 Å) under conditions of 100 mM sodium Citrate pH 5.9, 14% PEG 6000.

Data were collected at beamline 17-ID at the Advanced Photon Source. Data were processed using Autoproc (Global Phasing Ltd.). The structures were solved by molecular replacement with Phaser (Phenix) using as a search model the structure of wild-type Fab solved previously in complex with its ligand (data not shown). The structures were refined using buster (Global Phasing Ltd.) and built using coot. The S1 designed Fab diffracted to 1.3 Å resolution and was refined to an R factor of 16.8% (19.0% Rfree). The S1_rev crystals diffracted to 2.1 Å resolution, and the structure was refined to an R factor of 17.8% (21.7% Rfree).

In the S1_rev design, $C_L$-K176 made favorable electrostatic contacts (3.3 Å and 3.5 Å, FIG. 5C) with both carboxyl oxygens of $C_H1$-E124. In the S1 design, $C_H1$-K124 made similar but slightly longer (3.5 Å and 3.7 Å) contacts with $C_L$-D176. This experimental result confirms the theoretical design, with both S1 and S1_rev having favorable electrostatic interactions between the key designed residues.

Example 15

Mixing of Fab Arm Engineering Designs

An additional set of combinations uses one Fab arm of the antibody engineered as in any of the rows from Table 7, and the other Fab arm of the antibody engineered using the S1 amino acid substitutions given in Table 8. Table 9 shows the resulting combinations.

TABLE 9

Combination of Electrostatic Interaction Design S1 from Table 8 and All Designs from Table 7.

| | Fab Arm 1 | | | Fab Arm 2 | | |
|---|---|---|---|---|---|---|
| Combination | $C_H1$ Mutations | $C_L$ Mutations | Fab ID (Table 7) | $C_H1$ Mutations | $C_L$ Mutations | Fab ID (Table 8) |
| 1 | K221D + F174C + V190I + C230S | E123K + S176C + L135I + C214S | T1 | L124K + V190S | S176D + V133S | S1 |
| 2 | K145E + F122C + C230S | S131H + E123C + C214S | T2 | L124K + V190S | S176D + V133S | S1 |
| 3 | L143H + Q179D + S186E + F174C + V190I + C230S | S131H + L135I + S176C + C214S | T3 | L124K + V190S | S176D + V133S | S1 |
| 4 | K145S + S186E + A139C + C230S | S131H + F116C + C214S | T4 | L124K + V190S | S176D + V133S | S1 |
| 5 | S188W + L143S + F174C + C230S | V133S + T178S + S131D + S176C + C214S | T9 | L124K + V190S | S176D + V133S | S1 |
| 6 | S188W + L143S + F122C + C230S | V133M + T178G + S176G + E123C + C214S | T12 | L124K + V190S | S176D + V133S | S1 |
| 7 | S188W + L143S + F122C + A139C + F174C + C230S | V133S + T178S + S131D + F116C + E123C + S176C + C214S | T18 | L124K + V190S | S176D + V133S | S1 |

TABLE 9-continued

Combination of Electrostatic Interaction Design S1 from Table 8 and All Designs from Table 7.

| | Fab Arm 1 | | | Fab Arm 2 | | |
|---|---|---|---|---|---|---|
| Combination | $C_H1$ Mutations | $C_L$ Mutations | Fab ID (Table 7) | $C_H1$ Mutations | $C_L$ Mutations | Fab ID (Table 8) |
| 2λ | K145E + F122C + C230S | T131H + E123C + C214S | T2λ (Table 12) | L124K V190S | S176D V133S | S1 |
| 3λ | L143H + Q179D + S186E + F174C + V190I + C230S | T131H + L135I + S176C + C214S | T3λ | L124K V190S | S176D V133S | S1 (Table 13) |
| 4λ | K145S + S186E + A139C + C230S | T131H + T116C + C214S | T4λ (Table 12) | L124K V190S | S176D V133S | S1 |
| 5λ | S188W + L143S + F174C + C230S | V133S + Y178S + T131D + S176C + C214S | T9λ | L124K V190S | S176D V133S | S1 |
| 6λ | S188W + L143S + F122C + C230S | V133M + Y178G + S176G + E123C + C214S | T12λ | L124K V190S | S176D V133S | S1 |
| 7λ | S188W + L143S + F122C + A139C + F174C + C230S | V133S + Y178S + T131D + T116C + E123C + S176C + C214S | T18λ | L124K V190S | S176D V133S | S1 |

Example 16

Design of Modified Bispecific Antibody Ab1/Ab2

Antibody 1 (Ab1) specific for antigen 1 (AG1) was mutated such that its Fab arm contained mutations in the CH1 and C-Kappa domains as denoted in Table 8 Fab ID S1, introducing a novel electrostatic interaction at the constant domain interface. Antibody 2 (Ab2) specific for antigen 2 (Ab2) was mutated such that its Fab arm contained mutations in the $C_H1$ and C-Kappa domains as denoted in Table 8 Fab ID S1_REV also introducing a novel electrostatic interaction at the domain interface. Knobs-into-holes mutations were introduced into the CH3 domain interface to bias heavy chain heterodimerization (see Ridgway et al., supra and Merchant et al., supra). In one $C_H3$ domain $C_H3$-Y370 was mutated to C and $C_H3$-T389 was mutated to W creating a steric protuberance (referred to as the "Knob" chain; residue numbering is compatible with Kabat, as opposed to the EU numbering of the original reference). In the opposite CH3 domain $C_H3$-S375 was mutated to C, $C_H3$-T389 to S, $C_H3$-L391 to A and $C_H3$-Y438 to V creating a cavity (referred to as the "Hole" chain) and therefore steric complementarity between the two different $C_H3$ domains. $C_H3$-C370 and $C_H3$-C375 form an inter-chain disulphide bond to stabilize the heterodimer. Appropriate controls were generated whereby the Fab heavy/light chain interfaces bore no mutations (wild type interfaces) but heavy chain heterodimerizing mutations were still present. A total of four chains comprising the heavy chain of Ab1, heavy chain of Ab2, light chain of Ab1 and light chain of Ab2 were simultaneously transfected into mammalian cells and the level of correct light chain pairing assessed via BIAcore based stoichiometry analysis, mass spectrometry and heterogeneity assessment by anion exchange chromatography. Biophysical analysis results were compared to a control containing the heavy chain heterodimerizing mutations but no mutations at the interface between the heavy and light chain. The isotype of the antibody was human IgG1 with hinge/$C_H2$ heavy chain mutations (L247A, L248A and G250A) that ablate effector functions. Additional mutation designs, as set out in Table 9, were also experimentally assessed using the Ab1/Ab2 antibody to evaluate for propensity for correct light chain pairing.

Example 17

Expression of Bispecific Antibodies

Bispecific antibody genes were constructed using de novo gene synthesis and restriction enzyme-ligation based cloning techniques. Light chain genes were cloned in pSMEN3 and heavy chain genes cloned in pSMED2. Suspension HEK293F cells (American Type Culture Collection) were cultured in serum-free FreeStyle™ 293 expression medium (Life Technologies). Cells were maintained in a humidified incubator with 7% $CO_2$ at 37° C. Conditioned media were produced from a standard transient HEK293F transfection process. The conditioned media were filtered through 0.2 μm filter prior to purification. Typically the bispecific antibodies expressed in the range of 5-50 mg/L into the conditioned medium.

Example 18

Purification of Antibodies Expressed in HEK293F Cells

Filtered conditioned media was loaded onto HiTrap™ Protein A HP column (GE Life Sciences) equilibrated with PBS-CMF (137 mM NaCl, 2.7 mM KCl, 8.1 mM $Na_2HPO_4$, 2.7 mM $KH_2PO_4$, pH 7.2). The resin was washed with 10 column volumes of PBS-CMF pH 7.2 before the antibody was eluted with 0-100% linear gradient of protein A Elution Buffer (20 mM citric acid, 150 mM NaCl, pH 2.5). Peak fractions were neutralized to pH 7.0 with 2M Tris-HC1 pH 8.0 and pooled. The material was loaded onto HiLoad™ 16/60 Superdex™ 200 preparative size-exclusion column (GE Life Sciences) equilibrated in PBS-CMF pH 7.2. Peak fractions were pooled, concentrated using 30 kDa spin filters (Amicon) and 0.2 μm-filtered.

Analytical SEC was performed using Superdex™ 200 10/300 GL column (GE Life Sciences) connected to Agilent 1100 Series HPLC system. Depending on the antibody v-domain combination, the typical % high molecular weight species ranged from 2-20% and no low molecular weight species were observed other than the predominant peak of interest representing the 150 kDa bispecific antibody species.

Example 19

Mass Spectrometric Analysis of Bispecific Antibody (Ab1/Ab2)

To confirm the generation of bispecific antibody, Fab fragments of Ab1 and Ab2 were analyzed by mass spectrometry. The molecular weights of Fab fragment from Ab1 and Ab2 are defined by their unique amino acid sequences, and accurate molecular weight determination provides evidence for the presence of correctly paired antibodies.

Bispecific antibody was incubated with Lys-C(Wako Chemicals USA, Inc) at a protein:enzyme ratio of 400:1 and incubated at 37° C. for 20 minutes. The digestion reaction was quenched with addition of 0.1% formic acid in water. The digested sample was analyzed by LC/MS analysis on an Aglient 1100 capillary HPLC coupled with Water Xevo G2 Q-TOF mass spectrometer. The analytes were loaded onto a Zorbax Poroshell 300SB C3 column (1.0 mm×75 mm, maintained at 80° C.) with 0.1% formic acid, and eluted using a gradient of 15-98% buffer B (0.1% formic acid in acetonitrile) at a flow rate of 65 μl/min over 4 minutes. Mass spectrometric detection was carried out in positive, sensitivity mode with capillary voltage set at 3.3 kV. Data analysis were performed with MaxEnt 1 function in Mass-Lynx.

Figure 6A:
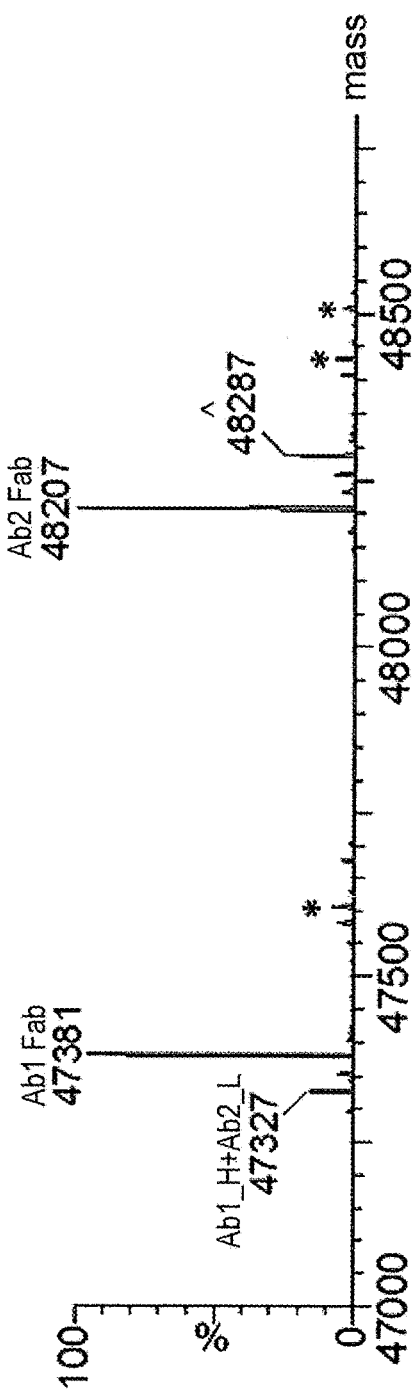
FIG. 6 depicts the results of mass spectrometric analysis of heterodimeric bispecific antibody Ab1/Ab2 comprising engineered favorable electrostatic interactions at the $C_H1$/$C_L$-Kappa interface of both Fab arms as described in Example 4 (panel A) and a control Ab1/Ab2 construct with native $C_H1$/$C_L$-Kappa interfaces (panel B). The novel electrostatic interaction mutations led to a significant reduction of incorrectly paired light chain in the isolated Fab fragments. Key: * potential incomplete leader sequence processing; ^ Correctly paired (both H and L chains) Ab2 Fab arm with a post-translational modification in the light chain.
Figure 6B:
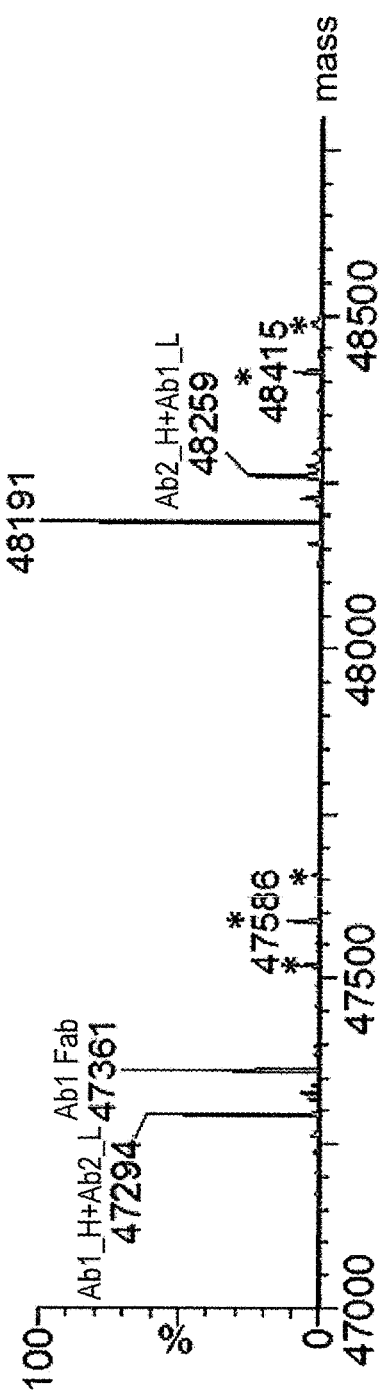

Fab analysis of bispecific antibody Ab1/Ab2 demonstrated that majority of detected Fab fragments are correctly paired Ab1 and Ab2 as shown in FIG. 6. There was a significant reduction of incorrectly paired light chain between Ab1 and Ab2 with the introduction of our novel mutations at the $C_H1/C_L$-Kappa interface. Fc analysis suggests that a majority of heavy chains are composed of one heavy chain from Ab 1 and one heavy chain from Ab 2. No heavy chain homodimers were detected (FIG. 7).

Example 20

Tandem Anion Exchange and Mass Spectrometric Analysis of Bispecific Antibody (Ab1/Ab 2)

Using an Agilent Infinity 1290 UHLPC (Agilent Technologies) fitted with a Q-STAT (Tosoh Bioscience), approximately 20 to 30 μg of Bispecific Ab1/Ab2 protein, purified by protein A and preparative SEC chromatography, was injected at a flow rate of 1 mL/min onto the column equilibrated in 20 mM Tris pH 8.6. The protein was then eluted with 1M NaCl in 20 mM Tris pH 8.6 over a 7 minute linear gradient from 0-100%.

Figure 8A:
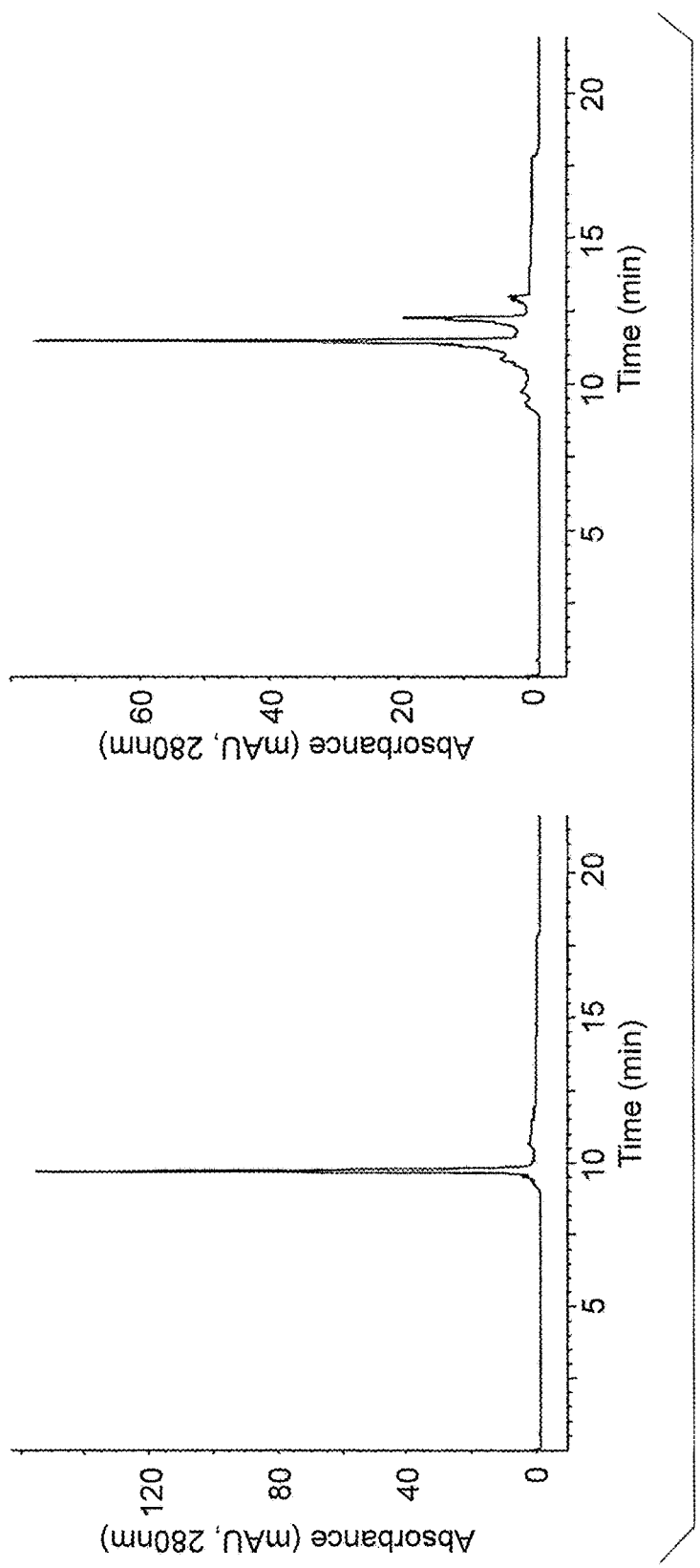
FIG. 8 depicts a graph showing the results from separation of bispecific antibody Ab1/Ab2 using anion-exchange chromatography. Anion-exchange chromatography was used to assess protein heterogeneity within the bispecific Ab1/Ab2 antibody preparation after protein A and preparative SEC chromatography. Analysis of the parental antibodies Ab1 and Ab2 are shown in panel A(i) and panel A(ii) respectively. Parental Ab1 displays an apparent single peak. Parental Ab2 shows a population of acidic and basic charge species which elute before and after the main peak, respectively. The heterodimeric bispecific Ab1/Ab2 antibody is shown in panel B. Fractions from Peak 1, Peak 2A and Peak 2B from the bispecific Ab1/Ab2 antibody (panel B) were analyzed by mass spectrometry.
Figure 8B:
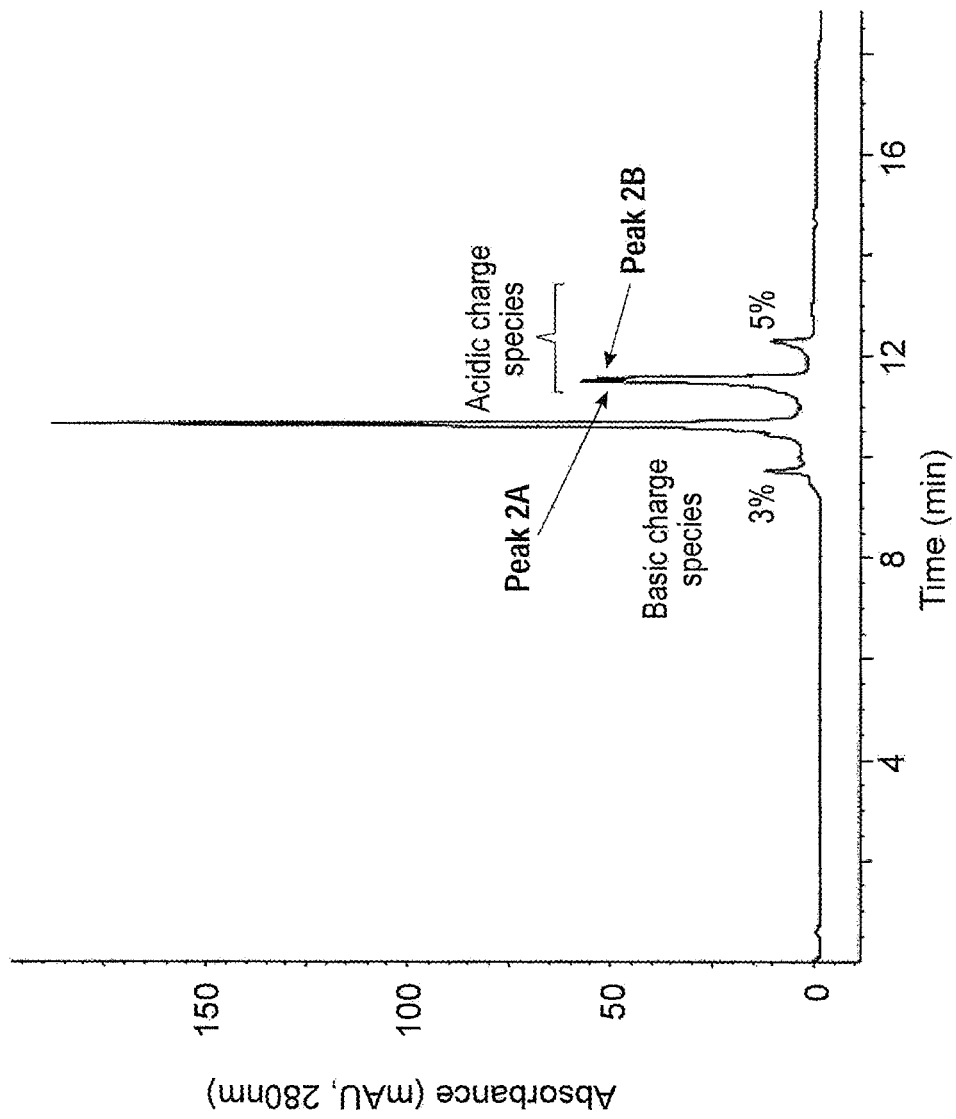

Protein was detected by absorption at 280 nm. The results of this analysis are shown in FIG. 8. The parental antibodies are shown in FIG. 8 panel A. Parental Ab1 (FIG. 8A(i)) displays an apparent homogenous single peak. The anion exchange chromatogram for Ab2 (FIG. 8A(ii)) shows a population of acidic and basic charge species which elute before and after the main peak respectively, representing heterogeneity caused by post-translational modifications within the Ab2 Fab arm that affect a proportion of the antibody preparation. The bispecific heterodimer Ab1/Ab2 antibody is shown in FIG. 8 panel B. This chromatogram shows the incorporation of the charge heterogeneity from the parental antibody (Ab2) into the bispecific antibody. The plot consists of a main peak (Peak 1) which represents approximately 60% of the protein species. Peak 2, which accounts for 32% of the remaining protein consists of two sub-peaks (Peak 2A and Peak 2B). The remaining 8% of protein is divided between two minor peaks.

Fractions containing or enriched for material from Peaks 1, 2A and 2B from bispecific Ab1/Ab2 fractionation were collected and processed for Fab arm isolation as described above and analyzed by mass spectrometry (FIG. 9). The analysis of the three anion exchange fractions revealed that peak 1 contained only two Fab arms with correct light chain pairing based on the expected MW. Fraction 2A is enriched for incorrectly paired Fab consisting of Ab 1 heavy chain and light chain from Ab 2 in addition to correctly paired ab 2 Fab. Fraction 2B consists of correctly paired Ab 1 Fab and correctly paired Ab 2 Fab but with the latter containing a post-translational modification inherited from the parental antibody.

Example 21

DSC Analysis

Bispecific antibody Ab1/Ab2 in PBS (137 mM NaCl, 2.7 mM KCl, 8.1 mM $Na_2HPO_4$, and 1.47 mM $KH_2PO_4$, pH 7.2) was diluted in the same buffer to a concentration of 0.3 mg/mL. Additionally, the protein was dialyzed overnight with two buffer changes into His: Sucrose (20 mM His, 8.5% sucrose, 50 mg/L EDTA, pH 6.0) using 10 kDa cut-off Slide-A-Lyzer dialysis cassettes and subsequently diluted to 0.3 mg/mL. Samples and buffers (400 μL) were transferred to a 96 well deep well plate and placed in the autosampler of the DSC (Cap-DSC, Microcal/GE Healthcare), Following injection into the instrument, samples were heated from 10° C. to 110° C. at 100° C./h. The data were buffer- and baseline corrected prior to fitting to two, non-two-state transitions to determine the melting temperatures, Graphically, the thermal profiles in PBS and His: Sucrose are broadly similar. This is also reflected in the Tm values obtained (Table 10).

TABLE 10

| Buffer | Tm1 (° C.) | Tm2 (° C.) |
| --- | --- | --- |
| PBS | 71.7 ± 0.1 | 75.9 ± 0.1 |
| His:Sucrose | 72.3 ± 0.2 | 76.6 ± 0.1 |

Example 22

Stability of Bispecific Antibody at High Concentrations

Bispecific antibody Ab1/Ab2 was dialyzed overnight with two buffer changes into His: Sucrose (20 mM His, 8.5% sucrose, 50 mg/L EDTA, pH 6.0) using 10 kDa cut-off Slide-A-Lyzer dialysis cassettes. The protein was transferred to a Vivaspin 500 concentrator, 10 kDa cut-off and spun at 14,000 g. The final concentration reached was 112 mg/mL. The sample was transferred to a plastic SEC vial and 20 μL mineral oil was overlaid. The sample was stored in the dark at room temperature. For each time point, the sample was placed in an Agilent 1200 and 1 µL was injected onto a TOSOH QC-PAK 300 column, using PBS (137 mM NaCl, 2.7 mM KCl, 8.1 mM $Na_2HPO_4$, and 1.47 mM $KH_2PO_4$, pH 7.2) as a running buffer, flow rate 0.5 mL/min, 15 min run. The area under the peak was monitored with each injection. The average recovery was 106±2%. Given the good recovery, the percent aggregate was obtained by comparing the area under the curve of the monomer peak with that of the aggregate peak. After 14 weeks at room temperature, only 2.4% aggregation was observed (Table 11).

TABLE 11

| | Time point | | | | | | | | |
|---|---|---|---|---|---|---|---|---|---|
| | Day 0 | Day 3 | Day 8 | Week 2 | Week 4 | Week 6 | Week 8 | Week 10 | Week 14 |
| % aggregation | 0 | 0.7 | 0.1 | 0.8 | 1 | 1.2 | 1.4 | 1.4 | 2.4 |

Example 23

BIAcore Analysis of Antibody 1 (Ab1)×Antibody 2 (Ab2) vs Cytokine 1× Cytokine 2

Fab Arm Mutations Used from Pair 1 from Table 8 (Fab ID S1 and S1_Rev)

Using a BIAcore Surface Plasmon Resonance biosensor (T200 model; GE Healthcare) an analysis of binding stoichiometry was conducted. The binding analysis took place using a running buffer consisting of phosphate buffered saline containing 300 mM NaCl, 3.4 mM EDTA and 0.01% Tween-20. 12,000 RU of an anti-human antibody (GE Healthcare) was immobilized via amine coupling chemistry to a CM5 carboxymethylated dextran chip (GE Healthcare) surface following manufacturer's instructions as supplied with the human antibody capture kit (part BR-1008-39, GE Healthcare). The anti-human antibody was amine coupled to both the reference and test flow cell. In order to measure binding stoichiometry, 100-200 RU of purified putative bispecific antibody was captured on the test flow cell at a flow rate of 10 uL/min for 30-60s at a concentration of 1-10 nM. Cytokine 1 was subsequently flowed over both flow cells at a flow rate of 50 uL/min saturating concentration over 100× the KD of the cytokine/antibody interaction, for 60s at which point the reaction had reached steady state. The cytokine and test antibody were stripped from the surface using 3M $MgCl_2$ which was exposed to the chip surface at 10 uL/min for 30-40s. The injection port was then washed with running buffer prior to the next cycle. The process described was then repeated using cytokine 2. Based on the molecular weight of the cytokine (MWC), the molecular weight of the antibody (MWA), the amount of test antibody captured (AB-RU) and the observed binding of cytokine at saturation (Rmax_Obs), the observed binding stoichiometry (OBST) was calculated. The equation for this was:

$$OBST = [Rmax\_Obs]/[(MWC/MWA) \times AB\text{-}RU].$$

In these studies, the known elements of the equation are the MW of the cytokine and antibody, the RU of antibody captured and the RU of cytokine binding at saturation, with the latter two variables measured experimentally. From that information, observed binding stoichiometry was calculated which infers the % of captured antibody molecules with correctly formed Fab arms for each respective antigen, since Fab arms with incorrect heavy/light chain pairing will result in no detectable binding of a given Fab arm to a given cytokine and hence a reduction in the pooled binding stoichiometry which represents the entire antibody population. This latter fact was verified from studies where antibody 1 heavy chain was transfected with antibody 2 light chain and vice versa and binding to each antigen tested by ELISA (data not shown). Data for Rmax_Obs was generated from reference subtracted data and adjusted for baseline drift caused by underlying dissociation of the antibody from the chip surface over time and for non-specific binding. The binding stoichiometries were normalized based on the saturation binding to the parental bivalent positive control antibody.

Saturation binding stoichiometries for cytokine 1 and cytokine 2 of putative bispecific antibodies were compared with bivalent monospecific positive controls and a control with no Fab arm engineering which exhibits all permutations of light chain pairing thus impacting the overall stoichiometry. The data (Table 12) show that the Fab arm engineered novel electrostatic interactions increase the correct light chain pairing to at least 90% with binding stoichiometries significantly closer to 1:1 compared to the negative control which lacks the Fab arm engineered electrostatic interactions for bias toward correct light chain association.

TABLE 12

Binding stoichiometries for antibody 1 x antibody 2 bispecific versus cytokine 1 and cytokine 2 utilising Fab arm mutations from pair 1, Table 8 (Fab ID S1 and S1_Rev).

| Clone | Cytokine 1 Binding Ratio | Cytokine 2 Binding Ratio |
|---|---|---|
| Ab1 | 2 (1.77*) | 0.00 |
| Ab2 | 0 | 2 (2.15*) |
| Ab1xAb2 v1.0 n = 1 | 0.88 | 0.97 |
| Ab1xAb2 v1.0 n = 2 | 0.90 | 1.02 |
| Ab1xAb2 v2.0*** n = 1 | 0.92 | 0.99 |
| Ab1xAb2 NEGATIVE** | 0.50 | 0.64 |

*Measured ratio, used to normalize bispecific ratios.
**Negative control with heavy chain heterodimerizing mutations but no Fab arm engineering for correct light chain association.
***Note for v2.0 Ab2 had a different antibody variable region framework compared with v1.0.

Example 24

Antibody 1 (Ab1)×Antibody 2 (Ab2) vs Cytokine 1× Cytokine 2—Assessment of Multiple Additional Designs Fab Arm Mutations Used from Table 7 in One Fab Arm and with Other Fab Arm Bearing Native Interface Using a BIAcore Surface Plasmon Resonance biosensor (T200 model; GE Healthcare) an analysis of binding stoichiometry was conducted. The binding analysis took place using a running buffer consisting of phosphate buffered saline containing 300 mM NaCl, 3.4 mM EDTA and 0.01% Tween-20. 12,000 RU of an anti-human antibody (GE Healthcare) was immobilized via amine coupling chemistry to a CM5 carboxymethylated dextran chip (GE Healthcare) surface following manufacturer's instructions as supplied with the human antibody capture kit (part BR-1008-39, GE Healthcare). The anti-human antibody was amine coupled to both the reference and test flow cell. In order to measure binding stoichiometry, 100-200 RU of putative bispecific antibody was captured from unpurified conditioned medium on the test flow cell at a flow rate of 10 uL/min for 30-60s at a concentration of 1-10 nM. Cytokine 1 was subsequently flowed over both flow cells at a flow rate of 50 uL/min saturating concentration over 100× the KD of the cytokine/antibody interaction, for 60s at which point the reaction had reached steady state. The cytokine and test antibody were stripped from the surface using 3M $MgCl_2$ which was exposed to the chip surface at 10 uL/min for 30-40s. The injection port was then washed with running buffer prior to the next cycle. The process described was then repeated using cytokine 2. Based on the molecular weight of the cytokine (MWC), the molecular weight of the antibody (MWA), the amount of test antibody captured (AB-RU) and the observed binding of cytokine at saturation (Rmax_Obs), the observed binding stoichiometry (OBST) was calculated. The equation for this was: OBST=[Rmax_Obs]/[(MWC/MWA)×AB-RU].

In these studies, the known elements of the equation are the MW of the cytokine and antibody, the RU of antibody captured and the RU of cytokine binding at saturation, with the latter two variables measured experimentally. From that information, observed binding stoichiometry was calculated which infers the % of captured antibody molecules with correctly formed Fab arms for each respective antigen, since Fab arms with incorrect heavy/light chain pairing will result in no detectable binding of a given Fab arm to a given cytokine and hence a reduction in the pooled binding stoichiometry which represents the entire antibody population. Data for Rmax_Obs was generated from reference subtracted data and adjusted for baseline drift caused by underlying dissociation of the antibody from the chip surface over time and for non-specific binding. The binding stoichiometries were normalized based on the saturation binding to the parental bivalent positive control antibody.

Saturation binding stoichiometries for cytokine 1 and cytokine 2 of putative bispecific antibodies were compared with a control with no Fab arm engineering which exhibits all permutations of light chain pairing thus impacting the overall stoichiometry. The data (Table 13) shows that the Fab arm engineered mutations from Table 7 increase the correct light chain pairing compared to the negative control which has native heavy/light chain Fab arm interface.

TABLE 13

Binding stoichiometries for antibody 1 x antibody 2 bispecific versus cytokine 1 and cytokine 2 utilising Fab arm mutations from Table 7 (Fab ID T1-T4, T9, T12 and T18).

| Clone | Cytokine 1 Binding Ratio | | Cytokine 2 Binding Ratio | |
|---|---|---|---|---|
| | N = 1 | N = 2 | N = 1 | N = 2 |
| Ab1xAb2 v1.0 T1 | 0.68 | 0.53 | 0.99 | 0.90 |
| Ab1xAb2 v1.0 T2 | 0.71 | 0.58 | 1.00 | 0.94 |
| Ab1xAb2 v1.0 T3 | 0.59 | 0.47 | 0.96 | 0.89 |
| Ab1xAb2 v1.0 T4 | 0.78 | 0.64 | 0.97 | 0.89 |
| Ab1xAb2 v1.0 T9 | 0.65 | 0.64 | 0.98 | 0.88 |
| Ab1xAb2 v1.0 T12 | 0.83 | ND | 0.64 | ND |

TABLE 13-continued

Binding stoichiometries for antibody 1 x antibody 2 bispecific versus cytokine 1 and cytokine 2 utilising Fab arm mutations from Table 7 (Fab ID T1-T4, T9, T12 and T18).

| Clone | Cytokine 1 Binding Ratio | | Cytokine 2 Binding Ratio | |
|---|---|---|---|---|
| | N = 1 | N = 2 | N = 1 | N = 2 |
| Ab1xAb2 v1.0 T18 | 0.79 | ND | 0.64 | ND |
| Ab1xAb2 NEGATIVE* | 0.36 | 0.37 | 0.86 | 0.85 |

*Negative control with heavy chain heterodimerizing mutations but no Fab arm engineering for correct light chain association Example 25

Antibody 1 (Ab1)×Antibody 2 (Ab2) vs Cytokine 1× Cytokine 2—Assessment of Multiple Additional Designs Fab Arm Mutations Used from Table 7 (in One Arm) and Electrostatic Interaction Mutation from Table 8 (Fab ID S1 in the Other Arm) as Summarized in Table 9

Using a BIAcore Surface Plasmon Resonance biosensor (T200 model; GE Healthcare) an analysis of binding stoichiometry was conducted. The binding analysis took place using a running buffer consisting of phosphate buffered saline containing 300 mM NaCl, 3.4 mM EDTA and 0.01% Tween-20. 12,000 RU of an anti-human antibody (GE Healthcare) was immobilized via amine coupling chemistry to a CM5 carboxymethylated dextran chip (GE Healthcare) surface following manufacturer's instructions as supplied with the human antibody capture kit (part BR-1008-39, GE Healthcare). The anti-human antibody was amine coupled to both the reference and test flow cell. In order to measure binding stoichiometry, 100-200 RU of putative bispecific antibody was captured from unpurified conditioned medium on the test flow cell at a flow rate of 10 uL/min for 30-60s at a concentration of 1-10 nM. Cytokine 1 was subsequently flowed over both flow cells at a flow rate of 50 uL/min saturating concentration over 100× the KD of the cytokine/antibody interaction, for 60s at which point the reaction had reached steady state. The cytokine and test antibody were stripped from the surface using 3M MgCl2 which was exposed to the chip surface at 10 uL/min for 30-40s. The injection port was then washed with running buffer prior to the next cycle. The process described was then repeated using cytokine 2. Based on the molecular weight of the cytokine (MWC), the molecular weight of the antibody (MWA), the amount of test antibody captured (AB-RU) and the observed binding of cytokine at saturation (Rmax_Obs), the observed binding stoichiometry (OBST) was calculated. The equation for this was: OBST=[Rmax_Obs]/[(MWC/MWA)×AB-RU].

In these studies, the known elements of the equation are the MW of the cytokine and antibody, the RU of antibody captured and the RU of cytokine binding at saturation, with the latter two variables measured experimentally. From that information, observed binding stoichiometry was calculated which infers the % of captured antibody molecules with correctly formed Fab arms for each respective antigen, since Fab arms with incorrect heavy/light chain pairing will result in no detectable binding of a given Fab arm to a given cytokine and hence a reduction in the pooled binding stoichiometry which represents the entire antibody population. Data for Rmax_Obs was generated from reference subtracted data and adjusted for baseline drift caused by underlying dissociation of the antibody from the chip surface over time and for non-specific binding. The binding stoichiometries were normalized based on the saturation binding to the parental bivalent positive control antibody.

Saturation binding stoichiometries for cytokine 1 and cytokine 2 of putative bispecific antibodies were compared with a control with no Fab arm engineering which exhibits all permutations of light chain pairing thus impacting the overall stoichiometry. The data (Table 14) shows that select Fab arm engineered mutations from Table 9 increase the correct light chain pairing compared to the negative control which has native heavy/light chain Fab arm interface.

TABLE 14

Binding stoichiometries for select antibody 1 × antibody 2 bispecific versus cytokine 1 (IL-13) and cytokine 2 (IL-4) utilising Fab arm mutations from Table 7 combined with electrostatic interaction pairing 1 from Table 8 as summarized in Table 9.

| Clone | Cytokine 1 (IL-13) Binding Ratio | | | Cytokine 2 (IL-4) Binding Ratio | | |
|---|---|---|---|---|---|---|
| | N = 1 | N = 2 | N = 3 | N = 1 | N = 2 | N = 3 |
| Ab1×Ab2 v1.0 T1* | 0.88 | 0.87 | 0.84 | 0.93 | 0.99 | 0.92 |
| Ab1×Ab2 v1.0 T2* | 0.93 | 0.91 | 0.83 | 0.98 | 1.04 | 0.97 |
| Ab1×Ab2 v1.0 T3* | 0.92 | 0.86 | 0.79 | 0.97 | 1.00 | 0.94 |
| Ab1×Ab2 v1.0 T4* | 0.96 | 0.87 | 0.83 | 0.99 | 1.02 | 0.99 |
| Ab1×Ab2 v1.0 T9* | 0.85 | 0.75 | 0.73 | 0.98 | 0.98 | 0.96 |
| Ab1×Ab2 NEGATIVE** | 0.47 | ND | ND | 0.81 | ND | ND |

*Select Fab ID's from Table 7 combined with electrostatic interaction Fab ID S1.
**Negative control with heavy chain heterodimerizing mutations but no Fab arm engineering for correct light chain association.

Example 26

Modified Bispecific Antibody C5×Ab3

An anti-CCL20 antibody (clone C5) specific for human CCL20 was isolated from a phage library and converted to IgG1 format. Its Fab arm contained mutations in the CH1 and C-Kappa domains as denoted in Table 8 Fab ID S1_Rev, introducing a novel electrostatic interaction at the constant domain interface. An anti-IL13 antibody (clone Ab3), specific for human IL13, was mutated such that its Fab arm contained mutations in the CH1 and C-Kappa domains as denoted in Table 8 Fab ID S1 also introducing a novel electrostatic interaction at the domain interface. Two different sets of mutations were introduced into the CH3 domain interface to bias heavy chain heterodimerization, either knobs-into-holes (see Ridgway et al., supra and Merchant et al., supra), termed Method 1 (M1) in the following examples, or the heterodimerization method disclosed in Strop et al., supra, and WO 2011/143545, termed Method 2 (M2). For M1, the anti-IL13 clone Ab3 heavy chain (with Fab ID S1), the $C_H3$ domain had the following mutations for heavy chain heterodimerization: $C_H3$-Y370 was mutated to C and $C_H3$-T389 was mutated to W creating a steric protuberance (referred to as the "Knob" chain). In the anti-CCL20 clone C5 heavy chain (with Fab ID S1_Rev) the $C_H3$ domain had the following mutations for heavy chain heterodimerization: $C_H3$-S375C, $C_H3$-T389S, $C_H3$-L391A and $C_H3$-Y438V creating a cavity (referred to as the "Hole" chain) and therefore steric complementarity between the two different $C_H3$ domains. The Cys-370 and Cys-375 form an inter-chain disulphide bond to stabilize the heterodimer. In the M2 design the mutations used include D232R, P441R, and K440R on the anti-IL13 Ab3 heavy chains and D'232E, P'441E, L'391E on the anti-CCL20 C5 heavy chains. Appropriate controls were generated whereby the Fab heavy/light chain interfaces bore no mutations (wild type interfaces) but heavy chain heterodimerizing mutations (method 1 or method 2) were still present. All antibodies were IgG1 isotype with hinge/$C_H2$ effector function ablating mutations (L247A, L248A and G250A). A total of four chains comprising the heavy chain of Ab3, heavy chain of C5, light chain of Ab3 and light chain of C5 were simultaneously transfected into mammalian cells and the level of correct light chain pairing was assessed via various biophysical analysis techniques compared to a control containing the heavy chain heterodimerizing mutations but no mutations at the interface between the heavy and light chain. Four separate expressions were carried out. The first (termed "Ab3×C5-M1") consists of the Fab arm mutations discussed above (Fab ID S1 and S1_Rev from Table 7) in combination with heavy chain heterodimerization method M1. The second expression is a control for the first (termed "Ab3×C5-M1-NEGATIVE") with no mutations in the Fab arms but with heavy chain heterodimerizing mutations present (method M1), The third expression (termed "Ab3×C5-M2") consists of the Fab arm mutations discussed above (Fab ID S1 and S1_Rev from Table 7) in combination with heavy chain heterodimerization method M2. The fourth expression is a control for the third (termed "Ab3×C5-M2-NEGATIVE") with no mutations in the Fab arms but with heavy chain heterodimerizing mutations present (method M2). By comparing the level of correct light chain pairing present in control versus test, the effect of the mutations can be assessed. Bispecific antibody CCL20×Ab3 was expressed and purified as discussed above in Examples 16 and 17 for Ab1/Ab2.

Example 27

Mass Spectrometric Analysis of Bispecific Antibody C5×Ab3

Fab generation and LC/MS analysis of dual arm antibody (C5 & Ab3) constructs were carried out using same methodology as described above for Ab1/Ab2. A total of four constructs as described above were analyzed to determine the existence of heavy and light chains based on Fab molecular weight measurement.

Figure 10A:
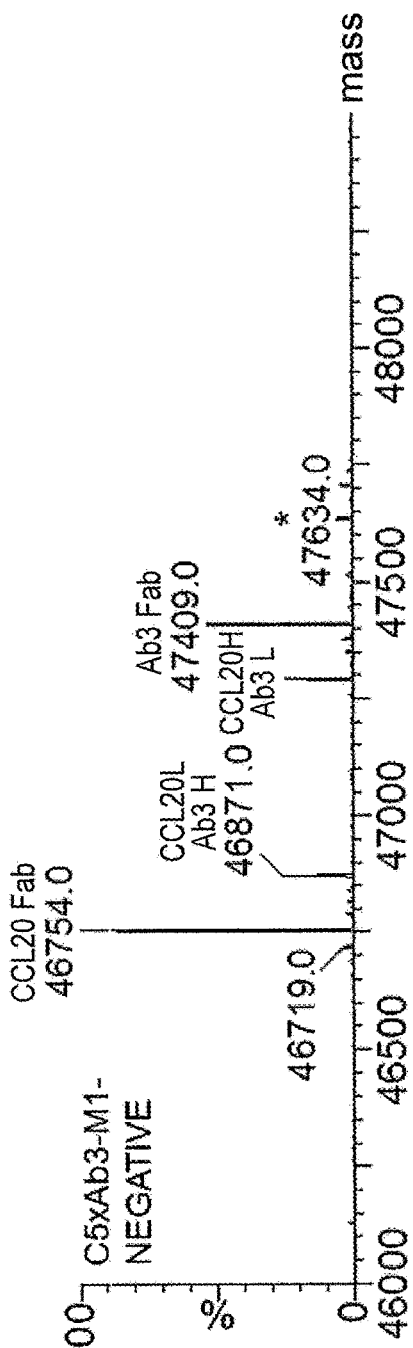
FIG. 10 depicts a graph showing mass spectrometric analysis of dual arm Fab fragment of constructs C5XAb3-M1 & C5XAb3-M1-NEGATIVE. Significant reduction of incorrectly paired light chain between C5 & Ab3 was observed in construct C5XAb3-M1 compared to C5XAb3-M1-NEGATIVE. Key: * potential incomplete leader sequence processing.
Figure 10B:
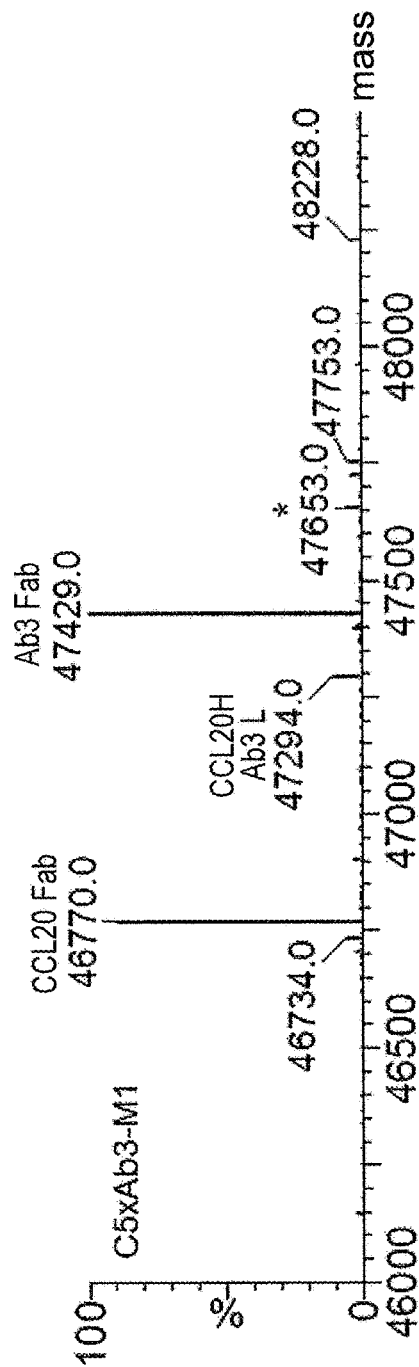

Deconvoluted mass spectra of C5×Ab3-M1 and C5×Ab3-M1-NEGATIVE constructs are shown in FIG. 10, where a significant amount of incorrectly paired Fab (C5 heavy chain with Ab3 Light chain & C5 light chain with Ab3 heavy chain) was detected in construct C5×Ab3-M1-NEGATIVE (24.8% of total intensity comes from incorrectly paired Fab). However, the amount of incorrectly paired Fab was reduced in the C5×Ab3-M1 which has the described electrostatic interaction mutations present in its Fab arms. The level of correctly light chain paired IgG rose to approximately 95%.

Data for constructs C5×Ab3-M2 and C5×Ab3-M2-NEGATIVE (FIG. 11) show that the intensities of incorrectly paired Fabs in construct C5×Ab3-M2-NEGATIVE amounts to 28.5%, where mis-paired Fab in construct C5×Ab3-M2 is reduced to 4.6%. The significant reduction of incorrect pairing demonstrates the effectiveness of engineered electrostatic interaction mutations.

Example 28

DSC Analysis

Proteins as listed in Table 15 below were received in PBS (137 mM NaCl, 2.7 mM KCl, 8.1 mM $Na_2HPO_4$, and 1.47 mM $KH_2PO_4$, pH 7.2) and diluted in the same buffer to a concentration of 0.3 mg/mL. Samples and buffers (400 µL) were transferred to a 96 well deep well plate and placed in the autosampler of the DSC (Cap-DSC, Microcal/GE Healthcare). Following injection into the instrument, samples were heated from 10° C. to 110° C. at 100° C./h. The data were buffer- and baseline corrected prior to fitting to two or three, non-two-state transitions to determine the melting temperatures. Overall these were all stable proteins with high Tm values.

TABLE 15

| Protein | $T_m1$ (° C.) | $T_m2$ (° C.) | $T_m3$ (° C.) |
|---|---|---|---|
| C5 | 73.6 ± 0.1 | 75.5 ± 0.1 | 83.9 ± 0.1 |
| Ab3 | 70.4 ± 0.1 | 74.1 ± 1.1 | 83.9 ± 0.1 |
| C5xAb3-M1 | 70.5 ± 0.1 | 71.5 ± 0.1 | n/a |
| C5xAb3-M2 | 70.5 ± 0.3 | 72.8 ± 0.2 | n/a |

Example 29 pH Reversibility

Proteins as listed in Table 16 below were received in PBS (137 mM NaCl, 2.7 mM KCl, 8.1 mM $Na_2HPO_4$, and 1.47 mM $KH_2PO_4$, pH 7.2) and diluted to 1 mg/mL using the same buffer. To two 20 µL aliquots, 0.8 µL PBS was added. Two further 20 µL aliquots were acidified to ~pH 3.5 by adding 0.8 µL of a 10x protein A elution buffer (200 mM citric acid, 1.5 M NaCl, pH 2.0). After 24 h at 4° C., a further 0.5 µL PBS was added to those samples that had had PBS added before, while the acidified samples were neutralized by addition of 0.5 µL of a 2 M Tris pH 8.0 buffer. Samples were loaded onto an Agilent 1200 system and 15 µL injected over a TOSOH QC-PAK 300 column, using PBS (137 mM NaCl, 2.7 mM KCl, 8.1 mM $Na_2HPO_4$, and 1.47 mM $KH_2PO_4$, pH 7.2) as a running buffer, flow rate 0.5 mL/min, 15 min run. The percent monomer from each injection was recorded and used to calculate the percent aggregate in each sample. No significant increases in aggregation were observed after acidification.

TABLE 16

| Sample | % aggregate neutral sample | % aggregate acidified sample |
|---|---|---|
| C5 | 0.85 ± 0.35 | 0.80 ± 0.14 |
| Ab3 | 0.55 ± 0.07 | 0.55 ± 0.07 |
| C5xAb3-M1 | 1.85 ± 0.07 | 1.75 ± 0.21 |
| C5xAb3-M2 | 0.85 ± 0.07 | 1.15 ± 0.07 |

Example 30

Forced Aggregation

Proteins as listed in Table 17 below were received in PBS (137 mM NaCl, 2.7 mM KCl, 8.1 mM $Na_2HPO_4$, and 1.47 mM $KH_2PO_4$, pH 7.2) and diluted to 1 mg/mL using the same buffer. Aliquots (20 µL) were placed in a 96 well plate, overlaid with 40 µL mineral oil and incubated at 40° C., 43.9° C., 50° C., 54° C., 60.1° C. and 64° C. in a gradient PCR block for 24 h. Following this, aliquots were loaded onto an Agilent 1200 system and 15 µL were injected over a TOSOH QC-PAK 300 column, using PBS (137 mM NaCl, 2.7 mM KCl, 8.1 mM $Na_2HPO_4$, and 1.47 mM $KH_2PO_4$, pH 7.2) as a running buffer, flow rate 0.5 mL/min, 15 min run. The percent monomer from each injection was recorded and used to calculate the percent aggregate in each sample. Where recovery was low due to significant aggregation, the peak area was used to calculate the percent of aggregate. The monovalent bispecifics showed significant aggregation from 54° C., while the bivalent bispecifics were still stable at this temperature. Monovalent C5xAb3-M2 was more aggregation prone than C5xAb3-M1.

TABLE 17

| | Incubation temperature | | | | | |
|---|---|---|---|---|---|---|
| Sample | 40° C. | 43.9° C. | 50° C. | 54° C. | 60.1° C. | 64° C. |
| C5 | 0.5 | 0.6 | 0.7 | 0.3 | 1.8 | 81.1 |
| Ab3 | 0.2 | 0.2 | 0.3 | 1.3 | 59.8 | 99.7 |
| C5xAb3-M1 | 1.7 | 1.7 | 4.4 | 7.9 | 13.7 | 99.7 |
| C5xAb3-M2 | 0.3 | 0.3 | 1.8 | 22.3 | 84.6 | 100.0 |

Example 31

Biacore Analysis CCL20-Clone 5 (C5)xIL13-Clone Ab3 (Ab3) Antigens: Human CCL20x Human IL13

Fab Arm Mutations Used from Pair 1 from Table 8 (Fab ID S1 and S1_Rev)

Using a BIAcore Surface Plasmon Resonance biosensor (T200 model; GE Healthcare) an analysis of binding stoichiometry was conducted. The binding analysis took place using a running buffer consisting of hepes buffered saline (HBS) containing 500 mM NaCl and 0.01% surfactant p20. 1500 RU of recombinant protein A (Pierce) was immobilized via amine coupling chemistry to a CM5 carboxymethylated dextran chip. The recombinant protein A was amine coupled to both the reference and test flow cell. In order to measure binding stoichiometry 100-200 RU of putative bispecific antibody was captured on the test flow cell at a flow rate of 10 uL/min for 30-60s at a concentration of 1-10 nM. Recombinant human CCL20 (Peprotech) was subsequently flowed over both flow cells at a flow rate of 50 uL/min saturating concentration over 100x the KD of the CCL20/antibody interaction, for 60s at which point the reaction had reached steady state. The cytokine and test antibody were stripped from the surface using 10 mM Glycine-HCL pH 1.7 which was exposed to the chip surface at 10 uL/min for 30s. The injection port was then washed with running buffer prior to the next cycle. The process described was then repeated using recombinant human IL13 (R&D Systems). Based on the molecular weight of the cytokine (MWC), the molecular weight of the antibody (MWA), the amount of test antibody captured (AB-RU) and the observed binding of cytokine at saturation (Rmax_Obs), the observed binding stoichiometry (OBST) was calculated. The equation for this was: OBST=[Rmax_Obs]/[(MWC/MWA)xAB-RU].

In these studies, the known elements of the equation are the MW of the cytokine and antibody, the RU of antibody captured and the RU of cytokine binding at saturation, with the latter two variables measured experimentally. From that information, observed binding stoichiometry was calculated which infers the % of captured antibody molecules with correctly formed Fab arms for each respective antigen, since Fab arms with incorrect heavy/light chain pairing will result in no detectable binding of a given Fab arm to a given cytokine and hence a reduction in the pooled binding stoichiometry which represents the entire antibody population. Data for Rmax_Obs was generated from reference subtracted data and adjusted for baseline drift caused by underlying dissociation of the antibody from the chip surface over time and for non-specific binding. The binding stoichiometries were normalized based on the saturation binding to the parental bivalent positive control antibody.

Saturation binding stoichiometries for CCL20 and IL13 of putative bispecific antibodies were compared with bivalent monospecific positive controls and a control with no Fab arm engineering which exhibits all permutations of light chain pairing thus impacting the overall stoichiometry. The data (Table 18) shows that the Fab arm engineered electrostatic interactions increase the correct light chain pairing to ~95% with binding stoichiometries close to 1:1 for each cytokine/chemokine.

TABLE 18

Binding stoichiometries for anti-CCL20-clone5 x anti-IL13-cloneAb3 bispecific antibodies.

| Clone | CCL20 Binding Ratio | | IL13 Binding Ratio | |
| --- | --- | --- | --- | --- |
| | N = 1 | N = 2 | N = 1 | N = 2 |
| C5 | 2 (2.15*) | 2 (2.18*) | 0.00 | 0.00 |
| Ab3 | 0.00 | 0.00 | 2 (1.93*) | 2 (1.93*) |
| C5xAb3-M1 (n = 1) | 0.91 | 0.96 | 0.98 | 1.03 |
| C5xAb3-M1 (n = 2) | 0.89 | 0.95 | 0.99 | 1.03 |
| C5xAb3-M1-NEGATIVE | 0.76 | 0.77 | 0.71 | 0.72 |
| C5xAb3-M2 (n = 1) | 0.95 | 0.99 | 0.96 | 1.00 |
| C5xAb3-M2 (n = 2) | 0.92 | 0.99 | 1.02 | 1.06 |
| C5xAb3-M2-NEGATIVE | 0.81 | 0.83 | 0.65 | 0.67 |

*Measured ratio. Used to normalize bispecific ratios.
** Negative control with heavy chain heterodimerizing mutations but no Fab arm engineering for correct light chain association.
M1—heavy chain heterodimerization method 1.
M2—heavy chain heterodimerization method 2

Example 32

Figure 12A:
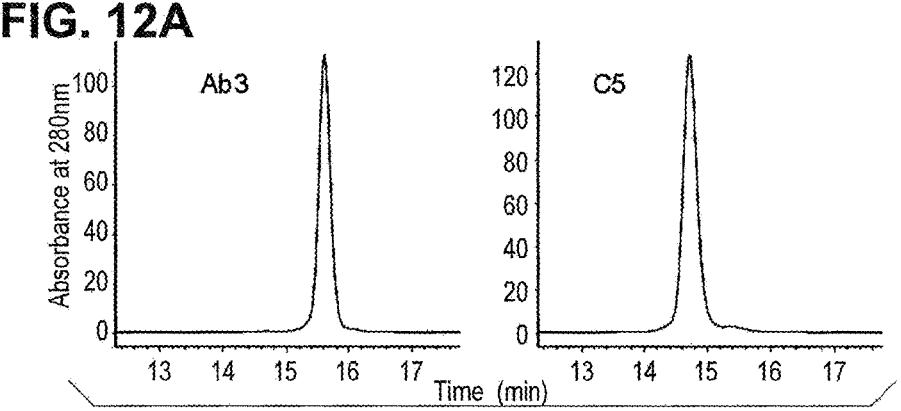
FIG. 12 depicts a graph showing separation of bispecific antibodies using hydrophobic interaction chromatography. The parental antibodies Ab3 and C5 shown in panel 12A(1) and panel 12A(2), respectively, each display an apparent single peak. The heterodimerization approach M1 is shown in panel 12C and heterodimerization approach M2 is shown in panel 12B. The chromatograms on the left for both panel 12B(1) and 12C(1) show the incorporation of the heavy-chain heterodimerization mutations alone. The chromatograms on the right (panels 12B(2) and 12C(2)) show bispecific antibodies that contain both the heavy-chain and light-chain mutations described in Example 5. These results demonstrate a reduction in the heterogeneity of antibody produced with the incorporation of both $C_H1$ and $C_L$-Kappa mutations for correct light chain pairing and $C_H3$ mutations compared with a bispecific (e.g., "NEGATIVE") comprising only the $C_H3/C_H3$ mutations.
Figure 12B:
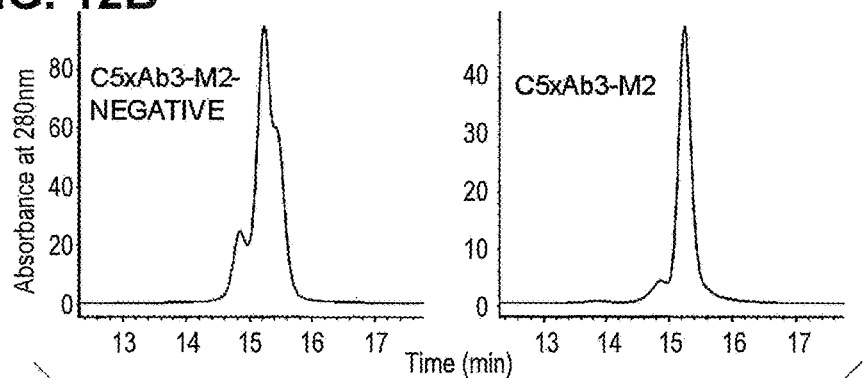
Figure 12C:
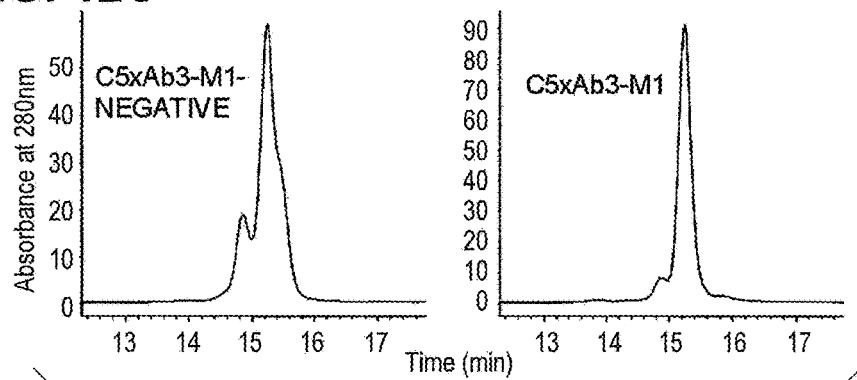
Figure 13:
FIG. 13 depicts the interface region between a $C_H1$ domain and a $C_L$ domain (from PDB entry 3QQ9). The view is along the interaction edge between the domains, with $C_H1$ in dark gray on the left, and $C_L$ in light gray on the right.
Figure 14:
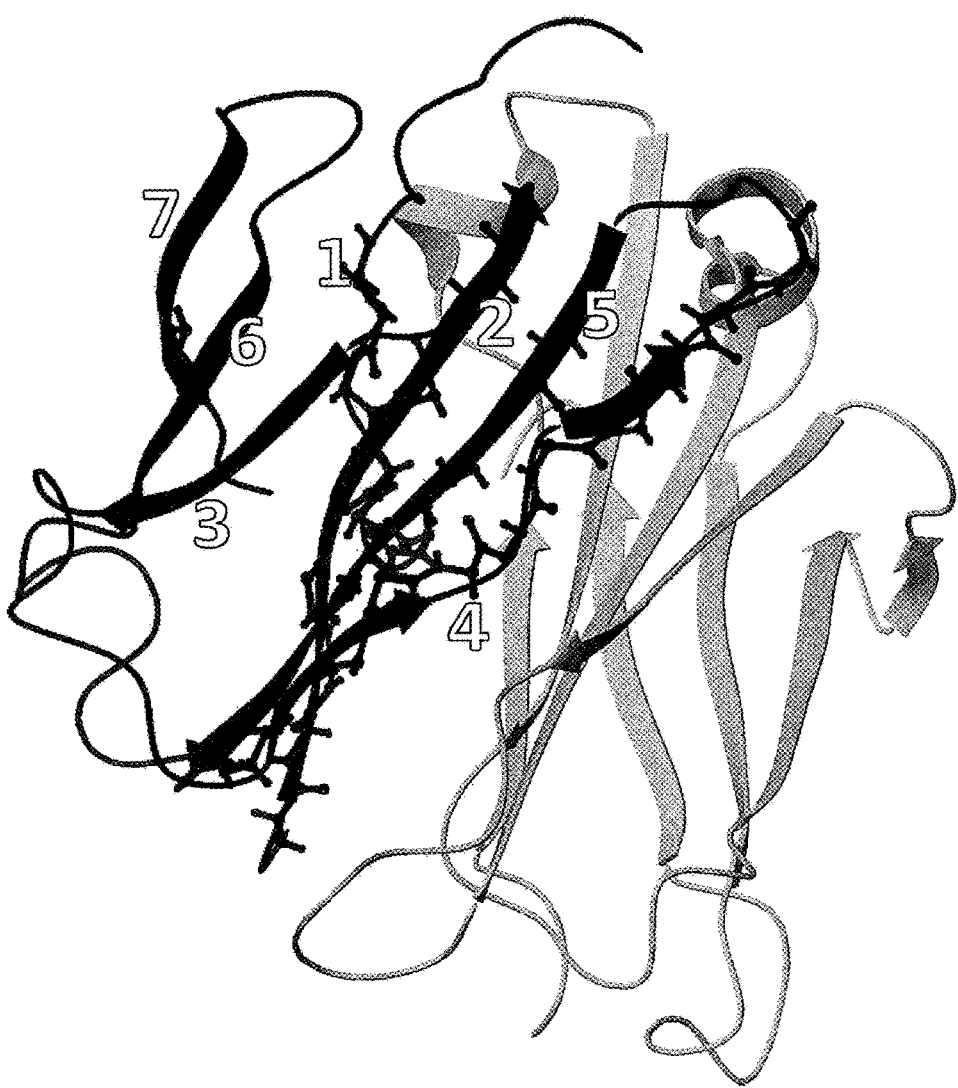
FIG. 14 depicts the interface region between a $C_H1$ domain and a $C_L$ domain (from PDB entry 3QQ9) with a drawing style similar to FIG. 13. This view highlights the regions of $C_H1$ that interact with $C_L$ (backbone atoms of interacting residues shown with ball and stick rendering). The primary Ig-fold β-strand regions are numbered 1 to 7 from N terminus to C terminus.
Figure 15:
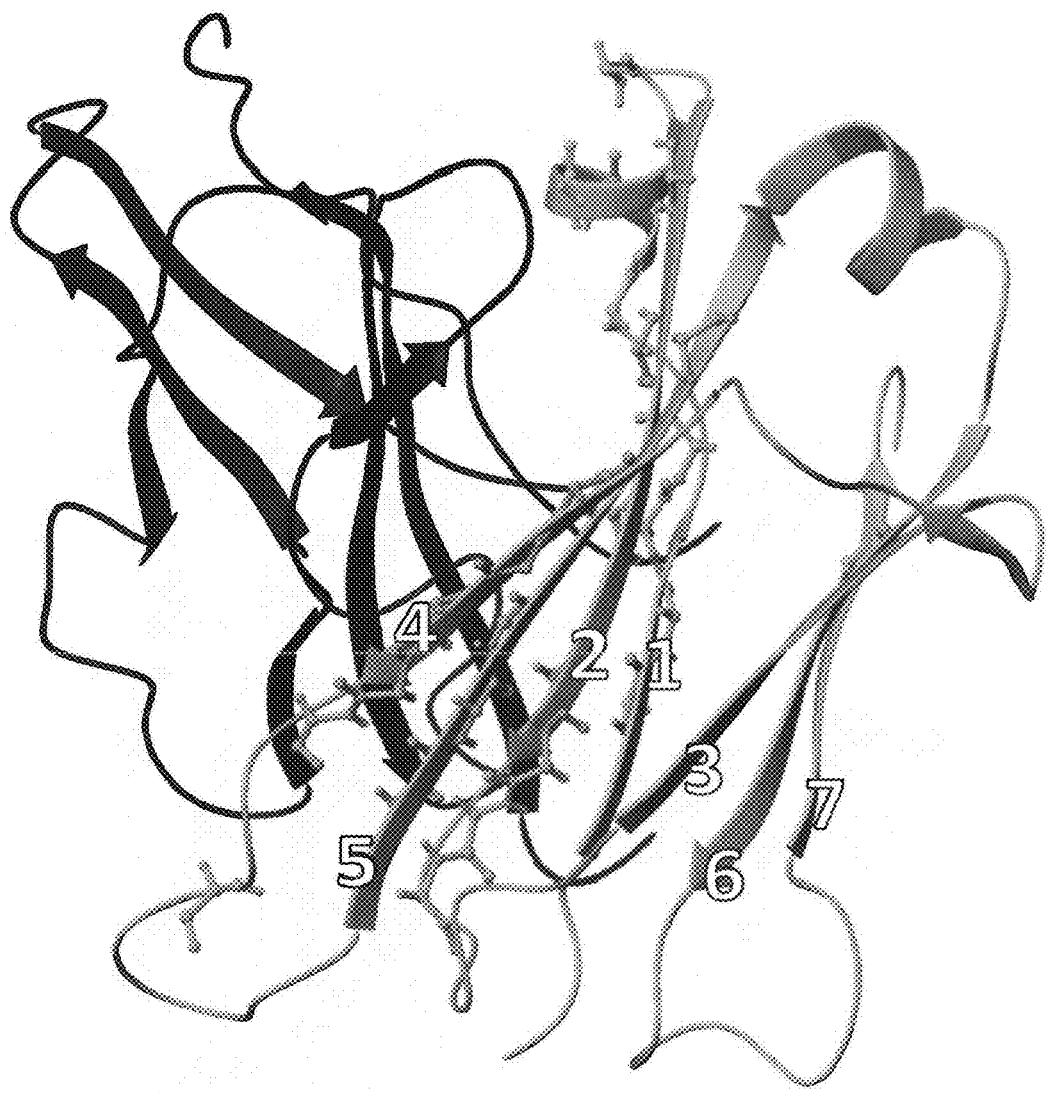
FIG. 15 depicts the interface region between a $C_H1$ domain and a $C_L$ domains (from PDB entry 3QQ9) with a drawing style similar to FIG. 13. This view highlights the regions of $C_L$ that interact with $C_H1$ (backbone atoms of interacting residues shown with ball and stick rendering). The primary Ig-fold β-strand regions are numbered 1 to 7 from N terminus to C terminus.

Separation of Bispecific Antibodies Using Hydrophobic Interaction Chromatography Hydrophobic interaction chromatography was used to assess protein heterogeneity following the two-step antibody purification process from conditioned media of constructs C5xAb3-M1, C5xAb3-M1-NEGATIVE, C5xAb3-M2 and C5xAb3-M2-NEGATIVE. Using an Agilent Infinity 1290 UHLPC (Agilent Technologies) fitted with a ProPac HIC-10 (Dionex), approximately 20 to 30 µg of protein was injected at a flow rate of 1 mL/min onto the column equilibrated in 100 mM sodium phosphate and 1M ammonium sulfate pH 7.0. The protein was then eluted with 100 mM sodium phosphate pH7.0 over a 7 minute linear gradient from 0-100%. Protein was detected by absorption at 280 nm. The results of this analysis are shown in FIG. 12. The parental C5 and Ab3 antibodies shown in FIG. 12 panel A display an apparent single peak. The heterodimerization approach M2 is shown in FIG. 12 panel C and heterodimerization approach M1 is shown in FIG. 12 panel B. The chromatograms on the left for both panel B and C show the incorporation of the heavy-chain heterodimerization mutations alone. The chromatograms on the right are of bispecific antibodies that contain both the heavy-chain and light-chain mutations. These results clearly show a reduction in the heterogeneity with the incorporation of both the heavy-chain and light-chain mutations Example 33

Calculation of Accessible Surface Area

When introducing non-human residues into antibodies intended for administration to human patients, there is a risk that the human immune system will recognize the modified residues as foreign and generate antibodies against the therapeutic (an anti-drug antibody or ADA response, which may result in faster clearance, reduced activity of circulating therapeutic, or both).

One method of minimizing these consequences of an ADA response is to choose mutations that are largely confined to the core of the therapeutic, meaning that they are not on the surface of the therapeutic, and therefore are inaccessible for binding by an ADA. Therefore, one way to rank the preferability of bispecific designs is to measure the accessible surface area (ASA) of the modified residues. All other factors being equal, a bispecific design with a lower ASA value for its mutated residues should have lower ADA risk than a bispecific design with a higher ASA value. The ASA of the complementary residue sets of Table 6 were measured, based on the molecular models described above, and also of designs S1 and S1_rev from Table 8, based on x-ray crystallographic analysis. As described above, the designs in Table 8 (Example 13) were specifically designed into a buried pocket, which minimizes ASA. Results are shown in Table 19, and were calculated using the molecular surface tool in Maestro 9.7 (Schrodinger, LLC, 2014) or Maestro 9.9 (Schrodinger, LLC, 2015) on the high resolution setting after removal of solvent and buffer molecules, using the structure of each involved domain as the context ('entry' as the context setting). The probe radius was set to 2.5 Å. The radius of a solvent molecule is often chosen as 1.4 Å; 2.5 Å was used here to account for experimental coordinate error in x-ray structures, side chain motion not apparent in the x-ray structure, and for the difficulty of an ADA accessing an extremely narrow opening in the surface as opposed to a water molecule as assumed in many other ASA calculations. A close approach of protein backbones, as observed in beta strand interactions, would generally result in 2.5 Å or longer hydrogen bond contacts and thus this is an approximate size for the smallest hole which can be penetrated by any protein chemical group wider than an unbranched side chain.

The consequences of an ADA response may vary by indication. In certain diseases where the immune system is suppressed, the risk of an ADA response may be lower, making designs with higher ASA more feasible. In certain diseases where the immune system is overactive, the ADA risk may be higher, thus requiring use of a bispecific design with a low (preferably <50 Å$^2$, <40 Å$^2$, <30 Å$^2$, <20 Å$^2$, <10 Å$^2$) or zero ASA value. Some designs previously reported (such as by Lewis et al. and in WO2014/150973A1) have higher ASA than certain designs (such as S1 and S1_rev) reported herein, and such previously reported designs may be more susceptible to an undesired ADA response. The various embodiments disclosed in WO2014150973 all have engineered residues whose ASA is at least 148 Å$^2$, or larger (calculated from PDB entry 4LLY (claim 1 of WO2014150973) or 4LLW (claim 7 of WO2014150973) as reported by Lewis et al. For the embodiment disclosed in claim 1 of WO2014150973 and related claims, the value reported is an underestimate, because the side chain of residue 1 on the light chain variable domain was disordered in the crystal structure. With the claimed arginine present, modeling suggests an increased value of 230.3).

The single exception is the mutation at position $C_L$-135, which in some variants is Phe rather than the larger Tyr of claim 1; however, this residue is buried and excluding it from the ASA calculation entirely still results in a value of 149 Å$^2$ when combining the residues disclosed at claim 1 and claim 7 of WO2014150973 (see also Table 19 of WO2014150973). In addition, for the crystal structure 4LLY reported by Lewis (which contains the mutations relevant to WO2014150973), residue 1 of the light chain, which is mutated to Arg, has a disordered side chain. If this residue is added by modeling it in its most commonly occurring rotamer conformation (using the rotamer library in the Maestro software), the total ASA of the mutated residues involved in WO2014150973 increases further to 230 Å$^2$. The exposed surface area of the designs reported herein, (most notably S1 and S1_rev), is considerably lower when implemented in the context of a bispecific with two different heavy chain sequences and two different light chain sequences.

In designing therapeutic antibodies with favorable properties, the introduction of some surface accessible foreign residues may be a necessary requirement to impart certain functional characteristics (including but not limited to stability). Thus, any minimization of the ASA footprint of foreign residues introduced during other engineering steps can be seen as advantageous in reducing the total final ASA of foreign residues.

TABLE 19

Accessible surface area for various heavyheavy chain/light chain heterodimerization designs computed with a probe radius of 2.5 Å (see text) and high resolution setting in Maestro. Only protein atoms were included in the calculation; solvent and ion atoms were removed. With the designs herein, combining S1 and S1_rev as analyzed in examples 14, 16, and 26-33 results in a bispecific antibody with low surface exposure of 18.0 Å$^2$.

| Construct | ASA (Å$^2$) |
| --- | --- |
| S1 | 3.5 |
| S1_rev | 14.5 |
| S1 (Arm 1), S1_rev (Arm 2) | 18.0 |
| S3 | 0 |
| S3_rev | 0 |
| S4a/b | 0 |
| S4a_rev | 0 |
| S4b_rev | 0 |
| S5 | 0.2 |
| S5_rev | 0 |
| R1.1 | 110 |
| R4.1 | 17.7 |
| R4.2 | 24.1 |
| R4.3 | 2.0 |
| H10.1 | 0 |
| H10.2 | 0 |
| H10.3 | 0 |
| H10.4 | 0 |

Example 34

Measurement of Pairing Fidelity

Using hydrophobic interaction chromatography it was not possible to differentiate between correct bispecific molecule and molecules containing mis-paired light chains for this particular bispecific antibody most likely because molecules with mis-paired light chains do not have sufficiently different propensity for interacting with the HIC column resin. However Anion Exchange Chromatography (FIG. 8B) was able to separate fully bispecific antibody (Peak 1 from FIG. 8B) from bispecific antibody containing mis-paired light chain/heavy chain interactions (Peak 2A from FIG. 8B). Unfortunately, a post-translational modification (Sulfation) of one of the parental antibodies, which carried through to the bispecific molecule (Peak 2B from FIG. 8B), lead to a change in the bispecific anion exchange elution time such that it was not baseline resolved from bispecific molecule containing mis-paired light chain. Therefore it was not possible to accurately quantify by anion exchange chromatography the % bispecific antibody. Addition of FIG. 8B Peak 1% AUC (60%) to the sulfated form (FIG. 8B Peak 2B), which amounted to 17% approximates % correct bispecific antibody to be 78% of the protein preparation. Table 20 below represents mass spec relative quantification of correctly paired Fab arm in the Ab1×Ab2 example preparations.

TABLE 20

% correct Fab species with correct heavy and light chain pairing based on % peak intensities following LCMS as depicted in FIG. 6 and FIG. 9.

| Sample | % Correctly paired Fab domains* |
| --- | --- |
| Ab1xAb2 v1.0 (FIG. 6A) | 90.5 |
| Ab1xAb2 NEGATIVE (FIG. 6B) | 66.8 |
| Ab1xAb2 v1.0 AEX** Peak 1 Fraction (FIG. 9C) | 99.7 |
| Ab1xAb2 v1.0 AEX* Peak 2A*** Fraction (FIG. 6A) | 64.3 |
| Ab1xAb2 v1.0 AEX* Peak 2B** Fraction (FIG. 6A) | 88.3 |

*% correct Fab species determined as a fraction of total peak intensity summed from all correct and incorrect Fab species detected.
**AEX = Anion exchange chromatography fractions.
***Peaks 2A and 2B were not baseline resolved and the species attributable to those peaks will have leaked into their adjacent overlapping peak for LCMS purposes.
The pairing fidelity of C5xAb3 was also analyzed; results are shown in Tables 21 and 22.

TABLE 21

% Peak of Interest of C5xAb3 antibodies after fractionation on a HIC Ethyl column as depicted in FIG. 12.

| Sample | % Peak of Interest* |
| --- | --- |
| C5 | 98.5 |
| Ab3 | 96.7 |
| C5xAb3-M1 | 92.1 |
| C5xAb3-M1-NEGATIVE | 59.3 |
| C5xAb3-M2 | 86.3 |
| C5xAb3-M2-NEGATIVE | 56.2 |

*% peak of interest is defined by the % area under curve representing either bivalent, monospecific IgG parental antibodies (C5 and Ab3) or bivalent bispecific IgG species (all other clones in table).

TABLE 22

% correct Fab species with correct heavy chain and light chain pairing based on % peak intensities following LCMS as depicted in FIG. 10 and FIG. 11.

| Sample | % Correctly Paired Fab Domains* |
| --- | --- |
| C5xAb3-M1 | 95.0 |
| C5xAb3-M1-NEGATIVE | 75.2 |
| C5xAb3-M2 | 96.4 |
| C5xAb3-M2-NEGATIVE | 71.5 |

*% correct Fab species determined as a fraction of total peak intensity summed from all correct and incorrect Fab species detected.

Example 35

Effect of Secondary Mutations in S1 and S1_rev

As shown in Table 8, design S1 consists of the primary mutations $C_H1$-L124K and $C_L$-S176D with secondary mutations $C_L$-V133S and $C_H1$-V190S. Design S1_rev consists of primary mutations $C_H1$-L124E and $C_L$-S176K, with secondary mutations $C_L$-V133S and $C_H1$-S188G. The secondary mutations were designed to optimize side chain packing in the interface. To test whether these mutations contribute to fidelity of light chain pairing, variants of C5×Ab3 were generated in which none, some, or all of the secondary mutations were omitted. The C5 Fab arm was used to test variations of S1_rev, while the Ab3 Fab arm was used to test variations of S1. The knobs-into-holes (Ridgway et al., supra and Merchant et al., supra) method, termed M1, was used to bias heavy chain heterodimerization of each combination. From M1, the $C_H3$ domain of each Ab3 variant made for this example had the following mutations for heavy chain heterodimerization: $C_H3$-Y370 was mutated to C and $C_H3$-T389 was mutated to W ("knob" chain). From M1, the $C_H3$ domain of each C5 variant made for this example had the following mutations for heavy chain heterodimerization: $C_H3$-S375C, $C_H3$-T389S, $C_H3$-L391A, and $C_H3$-Y438V ("hole" chain). The Cys-370 and Cys-375 form an interchain disulphide bond to stabilize the heterodimer. Six constructs were tested to deconvolute the role of the mutations. "Ab3 C5-M1-NEGATIVE", which contained only the M1 mutations described above for C5 and Ab3, but none of the S1 or S1_rev mutations. Deconvolute-2, was reused as a control and is also referred to for this example as Deconvolute-1. "Ab3 C5-M1", which contained the M1 mutations as described above, S1_rev in the C5 Fab arm, and S1 in the Ab3 arm, was reused as a control and is referred to for this example as Deconvolute-2. Deconvolute-3 was identical to Deconvolute-2, except that it did not include any of the "Secondary Mutations" for S1 and S1_rev as listed in Table 8. Deconvolute-4 was identical to Deconvolute-2, except that it omitted the secondary mutations of the $C_H1$ domain for both S1 and S1_rev. Thus, for clarity, the Ab3 Fab arm of Deconvolute-4 contained $C_H1$-L124K, $C_L$-S176D, and $C_L$-V133S but not $C_H1$-V190S. And, for clarity, the C5 Fab arm of Deconvolute-4 contained $C_H1$-L124E, $C_L$-S176K, and $C_L$-V133S but not $C_H1$-S188G. The parent monospecific constructs "C5" and "Ab3" (also referred to as Deconvolute-5 and Deconvolute-6 respectively), having neither M1 mutations nor S1 or S1_rev mutations ($C_H$ sequence 54 and $C_L$ sequence 9), and were tested as controls to establish the behavior of the monospecific variant of each antibody. All six designs were IgG1 with hinge/$C_H2$ effector function ablating mutations (L247A, L248A and G250A). For designs Deconvolute-1 through Deconvolute-4, a total of four chains comprising the heavy chain of Ab3, heavy chain of C5, light chain of Ab3 and light chain of C5 were simultaneously transfected into mammalian cells. The level of correct light chain pairing was assessed via various biophysical analysis techniques, and compared to the Ab3Ab3 C5-M1-NEGATIVE, C5, and Ab3Ab3 controls. Separate expressions were carried out for the constructs described. By comparing the level of correct light chain pairing present in control vs test, the effect of mutations can be assessed. The Abs were expressed and purified as discussed in Examples 16 and 17 for Ab1/Ab2. Expression of constructs Deconvolute-1 through Deconvolute-6 ranged from 9 to 200 mg/L.

Example 36

Mass Spectrometric Analysis of S1 and S1_Rev Deconvolution

Fab generation and LC/MS analysis of dual arm antibody constructs Deconvolute-1 through Deconvolute-6 (described in the previous example) were carried out using same methods as described above for Ab1/Ab2. A total of six constructs as described above were analyzed to determine the pairing of heavy and light chains based on Fab molecular weight.

Deconvoluted mass spectra are shown in FIG. 17. Panels A and B show that the monospecific control antibodies, C5C5 and Ab3Ab3, present one predominant peak corresponding to the predicted molecular mass of their respective Fab fragments. The negative control bispecific Ab3Ab3 C5-M1-NEGATIVE (Panel C), which lacks the S1 and S1_rev mutations, shows all four possible heavy/light chain pairings: two correct and two incorrect (Ab3 heavy+C5 light, and Ab3 light+C5 heavy). The analysis indicates that approximately 30% of the sample consists of mispaired Fabs. The positive control bispecific Ab3Ab3 C5-M1 (Panel D), which contains the full set of S1 and S1_rev mutations, shows no visible evidence of heavy/light mispairs, which have predicted masses of 47397 and 46906. Small readings at these values (not readily visible in the figure) lead to a prediction of 0.5% mispairing in this sample. In contrast, Deconvolute-3 (Panel E), in which the secondary S1 and S1_rev mutations (see Table 8) in the heavy and light chains are removed relative to Deconvolute-2, shows clear evidence of both possible heavy/light mispairs accounting for approximately 18% of the sample. Finally, Deconvolute-4 (Panel F) shows that removing the secondary S1 and S1_rev mutations from the heavy chain (but leaving them in the light chain) also allows mispaired chains to form at detectable levels, and 11% of the sample is estimated to be mispaired. In summary, the full set of mutations for S1 and S1_rev provides the highest fidelity, while partial implementations of the S1 and S1_rev designs provide detectable (but smaller) improvement over the negative control lacking CH1/CL bispecific engineering mutations.

Example 37

Hydrophobic Interaction Chromatography Analysis of S1 and S1_Rev Deconvolution Constructs Hydrophobic interaction chromatography was used to assess protein heterogeneity following the two-step antibody purification process from conditioned media for constructs Deconvolute-1 through Deconvolute-6. Using an Agilent Infinity 1290 UHLPC (Agilent Technologies) fitted with a ProPac HIC-10 (Dionex), approximately 20 to 30 µg of protein was injected at a flow rate of 1 mL/min onto the column equilibrated in 100 mM sodium phosphate and 1M ammonium sulfate pH 7.0. The protein was then eluted with 100 mM sodium phosphate pH7.0 over a 7 minute linear gradient from 0-100%. Protein was detected by absorption at 280 nm. The results of this analysis are shown in FIG. 18. Control monospecific antibodies "C5" and "Ab3" each show a sharp main peak (Panels E-F). If the two antibodies are assembled into a bispecific where only the $C_H3$ domains are engineered, there are overlapping peaks instead of a single main peak, indicating heterogeneity in the sample due to various combinations of the heavy and light chains (Panel A). When the S1 and S1_rev mutations are added to the $C_H1/C_L$ interface to favor only the correct heavy/light pairing, sample heterogeneity is greatly reduced (Panel B). The S1 and S1_rev designs contain primary mutations that directly form electrostatic interactions, as well as supporting secondary mutations as shown in Table 8. If the heavy chain supporting mutations are removed (Panel C) while the light chain supporting mutations are left intact, the level of heterogeneity is similar by HIC, but differences were detectable by mass spec (Example 36). If all supporting mutations are removed (Panel D), heterogeneity is reduced relative to ""Ab3 C5-M1-NEGATIVE", but is still more pronounced relative to Deconvolute-2. ""Ab3 C5-M1". Taken together with the mass spec data of example 36, these results collectively illustrate that the least amount of heterogeneity is produced when the full S1 and S1_rev designs are combined.

Example 38

Production of Bispecific Antibodies with Mixed Fab Arm Designs

Conceptually, bispecific Fabs could be engineered by using different combinations of the $C_{H1}/C_L$ engineering designs described herein, as discussed in Example 15. To test this hypothesis, bispecific antibodies having Ab3 and C5 Fab arms were produced, wherein the Ab3 Fab arm contained either no bispecific engineering mutations (negative control) or the S1 design of Table 8. The C5 arm contained either no bispecific engineering mutations (negative control), the S1_rev design of Table 8 (positive control), or one of the designs T1, T2, T3, T4, T9 as specified in Table 7. An additional control containing S1_rev mutations in C5, but no Fab arm bispecific mutations in Ab3, was also prepared. These 9 constructs, summarized and named in Table 23, were all produced as IgG1 with M1 knobs-into-holes (Ridgway et al., supra and Merchant et al., supra) mutations in the Ab3 and C5 heavy chains in the same configuration described in Example 35, and effector function ablating mutations in the $C_H2$ of both heavy chains, as previously described.

For each design, four chains comprising the heavy chain of Ab3, heavy chain of C5, light chain of Ab3 and light chain of C5 were simultaneously transfected into mammalian cells. The level of correct light chain pairing was assessed via various biophysical analysis techniques, and compared to a control containing the heavy chain heterodimerizing mutations but no mutations at the interface between the heavy and light chain. Separate expressions were carried out for the constructs just described. By comparing the level of correct light chain pairing present in control versus test, the effect of the mutations can be assessed. The antibodies were expressed and purified as discussed above in Examples 16 and 17 for Ab1/Ab2. Expression of the constructs in Table 23 ranged from 4 to 73 mg/L.

TABLE 23

Mixing and Matching of Fab Arm Bispecific Engineering Mutations. In addition to the mutations listed here, all constructs contained M1 heavy chain heterodimerization mutations, and effector function ablating mutations, as described for Example 35.

| Construct | Ab3 Fab Mutations | C5 Fab Mutations |
|---|---|---|
| Ab3-S1xC5-T1 | S1 (see Table 8) | T1 (see Table 7) |
| Ab3-S1xC5-T2 | S1 | T2 |
| Ab3-S1xC5-T3 | S1 | T3 |

TABLE 23-continued

Mixing and Matching of Fab Arm Bispecific Engineering Mutations. In addition to the mutations listed here, all constructs contained M1 heavy chain heterodimerization mutations, and effector function ablating mutations, as described for Example 35.

| Construct | Ab3 Fab Mutations | C5 Fab Mutations |
|---|---|---|
| Ab3-S1xC5-T4 | S1 | T4 |
| Ab3-S1xC5-T9 | S1 | T9 |
| Ab3-S1xC5-S1rev (AKA "Ab3 C5-M1")" from prior examples) | S1 | S1_rev (see Table 8) |
| Ab3-S1xC5 | S1 | None |
| Ab3xC5-S1rev | None | S1_rev |
| Ab3xC5 (AKA "Ab3-C5-M1-NEGATIVE")" from prior examples) | None | None |

Example 39

DSC Analysis of Mixed Fab Arm Designs

Proteins described in Example 38 and listed in Table 24 below were received in PBS (137 mM NaCl, 2.7 mM KCl, 8.1 mM $Na_2HPO_4$, and 1.47 mM $KH_2PO_4$, pH 7.2) and diluted in the same buffer to a concentration of 0.3 mg/mL. Samples and buffers (400 µL) were transferred to a 96 well deep well plate and placed in the autosampler of the DSC (Cap-DSC, Microcal/GE Healthcare). Following injection into the instrument, samples were heated from 10° C. to 110° C. at 100° C./h. The data were buffer- and baseline corrected prior to fitting to two or three, non-two-state transitions to determine the melting temperatures. Overall these were all stable proteins with high Tm values, Detailed melting temperature profiles of each antibody are provided in FIG. 19.

TABLE 24

Melting Temperature of Mixed Fab Arm Designs

| Protein | $T_m1$ (° C.) | $T_m2$ (° C.) | $T_m3$ (° C.) |
|---|---|---|---|
| Ab3-S1xC5-T1 | | 70.7 ± 0.0 | 76.6 ± 0.1 |
| Ab3-S1xC5-T2 | 67.9 ± 0.8 | 70.1 ± 0.1 | 76.6 ± 0.1 |
| Ab3-S1xC5-T3 | 67.7 ± 1.4 | 70.1 ± 0.0 | 76.7 ± 0.1 |
| Ab3-S1xC5-T4 | 68.5 ± 1.4 | 70.4 ± 0.1 | 76.6 ± 0.1 |
| Ab3-S1xC5-T9 | | 70.7 ± 0.0 | 75.4 ± 0.1 |
| Ab3-S1xC5-S1rev | | 70.8 ± 0.0 | 73.8 ± 0.4 |
| Ab3-S1xC5 | | 71.1 ± 0.0 | 75.2 ± 0.0 |
| Ab3xC5-S1rev | | 70.8 ± 0.3 | 73.9 ± 0.3 |
| Ab3xC5 | | 71.5 ± 0.0 | 75.3 ± 0.0 |

Example 40

Biacore Binding Stoichiometry Analysis of Mixed Fab Arm Designs

Fab Arm Mutations Used from Table 23 (Example 38)

Using a BIAcore Surface Plasmon Resonance biosensor (T200 model; GE Healthcare) an analysis of binding stoichiometry was conducted as described for Example 31. Saturation binding stoichiometries for CCL20 and IL13 of putative bispecific antibodies were compared with bivalent monospecific positive controls and a control with no Fab arm engineering which exhibits all permutations of light chain pairing thus impacting the overall binding stoichiometry. The data (Table 25) shows that all combinations with engineering in both Fab arms achieved binding stoichiometries close to 1:1 for each pair of antibody with the target cytokine and chemokine (no more than 10% variation from 1:1 binding), while combinations lacking engineering in one or both arms had stoichiometries of less than 0.7:1 in one arm. These results indicate that different combinations of the bispecific designs can be used to reduce heavy/light chain mispairing.

TABLE 25

Binding stoichiometries for anti-CCL20-clone5 × anti-IL13-cloneAb3 bispecific antibodies. Measurements were made in triplicate (N = 1, N = 2, N = 3). The first six constructs, with different combinations of bispecific engineering mutations in the C5 arm, all show binding stoichiometries within 10% of the expected 1:1 value. The remaining three constructs lack $CH_1/C_L$ bispecific mutations in one or both of the Fab arms, resulting in a drop in binding stoichiometry (underlined). The mutations in each clone are described in Table 23 and the text of Example 37.

| Clone | IL13 Binding Ratio | | | CCL20 Binding Ratio | | |
|---|---|---|---|---|---|---|
| | N = 1 | N = 2 | N = 3 | N = 1 | N = 2 | N = 3 |
| Ab3-S1xC5-T1 | 0.95 | 0.96 | 0.92 | 1.05 | 1.05 | 1.09 |
| Ab3-S1xC5-T2 | 0.90 | 0.89 | 0.92 | 1.08 | 1.06 | 1.09 |
| Ab3-S1xC5-T3 | 0.96 | 0.94 | 0.95 | 0.99 | 1.03 | 0.99 |
| Ab3-S1xC5-T4 | 0.95 | 0.94 | 0.94 | 0.99 | 0.97 | 1.01 |
| Ab3-S1xC5-T9 | 0.97 | 0.97 | 0.96 | 1.04 | 1.03 | 1.01 |
| Ab3-S1xC5-S1rev | 1.02 | 1.01 | 0.99 | 0.93 | 0.92 | 0.93 |
| Ab3-S1xC5 | 0.51 | 0.51 | 0.54 | 1.04 | 1.00 | 1.02 |
| Ab3xC5-S1rev | 0.99 | 0.99 | 1.02 | 0.65 | 0.68 | 0.68 |
| Ab3xC5 | 0.51 | 0.53 | 0.52 | 0.91 | 0.92 | 0.91 |

Example 41

Mass Spectrometric Analysis of Mixed Fab Arm Designs

Fab generation and LC/MS analysis of dual arm antibody constructs with various combinations of designs in each Fab arm (as described in Table 23 and Example 38) were carried out using same methods as described above for Ab1/Ab2. A total of 9 constructs as described above were analyzed to determine the pairing of heavy and light chains based on Fab molecular weight. Deconvoluted mass spectra are shown in FIG. 20. When the S1 design in the Ab3 Fab arm was paired with T1, T2, T3, T4, or T9 (FIG. 20, Panels A-E) in the C5 Fab arm, minimal amounts of mispaired Fab were detected: 0.5% for T1, T2, and T3; 0.4% for T4, and 1.3% for T9. Ab3×S1 paired with S1_rev in the C5 Fab arm also gave high fidelity, with only 3.2% mispaired (Panel F; note that this bispecific design used the same Fab arm mutations as Deconvolute-2 of Example 37 and is thus a second measurement of the effectiveness of this design). However, when either Fab arm was lacking a bispecific-favoring design, larger amounts of mispaired sample were produced: 19% with Ab3-S1 and native C5 (Panel G), 41% with native Ab3 and C5-S1rev (Panel H), and 35% with native Ab3 in one Fab arm and native C5 in the other (Panel I). Thus, in each case where different combinations were tried with each Fab arm using a different bispecific-favoring design, sample purity improved significantly as measured by mass spectrometry.

Example 42

Hydrophobic Interaction Chromatography Analysis of Mixed Fab Arms Designs

Hydrophobic interaction chromatography was used to assess protein heterogeneity following the two-step antibody purification process from conditioned media for constructs with various combinations of designs in each Fab arm (as described in Table 23 and Example 38). Using an Agilent Infinity 1290 UHLPC (Agilent Technologies) fitted with a TOSOH Butyl column, approximately 20 to 30 µg of protein was injected at a flow rate of 1 mL/min onto the column equilibrated in 50 mM sodium phosphate and 2M ammonium sulfate pH 7.2. The protein was then eluted with 50 mM sodium phosphate pH7.2 over a 7 minute linear gradient from 0-100%. Protein was detected by absorption at 280 nm. The results of this analysis are shown in FIG. 21. Bispecific antibodies with S1 in the Ab3 Fab arm and any of T1, T2, T3, T4, or T9 in the C5 Fab arm displayed high fidelity of heavy/light chain pairing (Panels A-E). A minor amount of mispairing is apparent as a small tail on the left side of the main peak. This tail on the peak is slightly larger for S1 on Ab3 paired with S1_rev on C5 (Panel F, see arrow). These results are consistent with the mass spectrographic analysis of Example 41 and FIG. 20. If one Fab arm (Panels G-H) or both Fab arms (Panel I) did not contain a bispecific-favoring design, larger amounts of mispaired Fab were detected, as indicated by the presence of additional peaks. For reference, Panels J-K show the corresponding profile of the monospecific Ab3 and C5 antibodies on which these bispecific designs were based; both show a sharp single peak. Thus, in each case where different combinations were tried with each Fab arm using a different bispecific-favoring design, sample purity improved significantly over designs lacking the Fab engineering designs, as measured by hydrophobic interaction chromatography.

Example 43

Mouse Anti-TrkB TOA-1 Antibody

The invention includes a humanized mouse antibody that specifically binds human TrkB.

Anti-TrkB antibodies were prepared in mice using human and mouse TrkB-extracellular domain antigens and standard methods for immunization Hybridoma cell line producing the TOA-1 antibody was produced by fusion of individual B cells with myeloma cells. The murine TOA-1 antibody, also referred to as "29D7," is disclosed in U.S. Pat. No. 7,750,122, herein incorporated by reference in its entirety.

The TOA-1 anti-TrkB antibody heavy chain and light chain variable regions were cloned using the SMART® cDNA synthesis system (Clontech Laboratories Incof Mountain View, Calif.) followed by PCR amplification The cDNA was synthesized from 1 µg total RNA isolated from TOA-1 hybridoma cells, using oligo (dT) and the SMART® IIA oligo (Clontech Laboratories Inc.) with POWERSCRIPT™ reverse transcriptase (Clontech Laboratories Inc.) The cDNA was then amplified by PCR using a primer which anneals to the SMART® IIA oligo sequence and mouse constant region specific primer (mouse Kappa for the light chain and mouse IgG1 for the heavy chain) with VENT® polymerase (New England Biolabs Incof Ipswich, Mass.) Heavy and light chain PCR products were subcloned into the pED6 expression vector and the nucleic acid sequence was determined This method is advantageous in that no prior knowledge of the DNA sequence is required In addition, the resultant DNA sequence is not altered by use of degenerate PCR primers The nucleotide sequences of the TOA-1 heavy chain variable region is set forth as nucleotides 58-411 of SEQ ID NO: 104. The amino acid sequences of the TOA-1 heavy chain variable region is set forth as residues 20-137 of SEQ ID NO: 105. The nucleotide sequences of the TOA-1 light chain variable region is set forth as nucleotides 61-381 of SEQ ID NO: 106. The amino acid sequences of the TOA-1 light chain variable region is set forth as residues 20-137 of SEQ ID NO:107.

Example 44

Construction of Chimeric TOA-1 Antibody

To verify that the mouse heavy and light chain variable region sequences were correct, chimeric TOA-1 antibody was constructed To generate chimeric TOA-1 heavy chain, the nucleotide sequences of the TOA-1 heavy chain variable region (nucleotides 58-411 of SEQ ID NO: 104) was ligated to cDNA encoding the human IgG1 constant domain mutated for minimal effector function These mutations change the human IgG1 amino acid sequence at residues 234, 235 and 237 defined by EU numbering from leucine, leucine and glycine to alanine, alanine and alanine respectively. Chimeric TOA-1 light chain was constructed be joining the nucleotide sequences of TOA-1 light chain variable region (nucleotides 61-381 of SEQ ID NO: 106) to DNA encoding the human Kappa constant region. The alanine present at residue 1 of the TOA-1 light chain variable region was changed to aspartic acid which is commonly found at this position and this was then fused to the human Kappa constant region to generate chimeric TOA-1 A1D light chain (nucleotide sequence SEQ ID NO: 108 and amino acid sequence SEQ ID NO: 109). DNA encoding both versions of chimeric TOA-1 antibody was transiently transfected into COS-1 cells to generate protein. The resultant conditioned medium containing the TOA-1 antibody was quantitated by total human IgG sandwich ELISA Activity of chimeric TOA-1 antibody was assessed by direct binding ELISA Direct binding assays were performed by coating ELISA plates with either human or mouse TrkB-extracellular domain protein (R and D Systems), adding serially diluted conditioned medium containing chimeric TOA-1 antibody and detecting the bound antibody with goat-anti-human IgG-HRP (Southern Biotech). Chimeric TOA-1 antibody bound human and mouse TrkB with comparable affinity as the mouse TOA-1 antibody (FIGS. 23 and 24). Changing the alanine to aspartic acid at position 1 of the TOA-1 light chain variable region did not affect binding properties to human or mouse TrkB (FIGS. 23 and 24). Chimeric TOA-1 antibody was purified by standard Protein A purification techniques from conditioned medium that was generated by transiently transfecting COS-1 cells with DNA encoding chimeric TOA-1.

Example 45

Humanization of Mouse TOA-1 Antibody

The CDRs of the mouse TOA-1 antibody were identified using the AbM definition, which is based on sequence variability as well as the location of the structural loop regions. A humanized TOA-1 heavy chain variable region was constructed to include the CDRs of mouse TOA-1 grafted onto a human DP-54 framework region and this amino acid sequence is set forth as SEQ ID NO: 51 huTOA-1 $V_H$ v1.0. The huTOA-1 $V_H$ V1.0 is encoded by the nucleic acid sequence in SEQ ID NO: 110. Additional mutations of the human framework acceptor sequences are made, for example, to restore mouse residues believed to be involved in antigen contacts and/or residues involved in the structural integrity of the antigen-binding site. A24T, R72V and L79A mutations predicted to be important for preserving TrkB binding properties were introduced to the DP-54 framework and this amino acid sequence is set forth as SEQ ID NO: 111 and is referred to herein as huTOA-1 $V_H$ v1.1. The huTOA-1 $V_H$ V1.1 is encoded by the nucleic acid sequence in SEQ ID NO: 112. Additionally, a humanized TOA-1 heavy chain variable region was constructed to include the CDRs of mouse TOA-1 grafted onto the DP-3 human germline acceptor framework selected on the basis that it is substantially similar to the framework regions of mouse TOA-1 heavy chain variable region and this amino acid sequence is set forth in SEQ ID NO: 113 huTOA-1 $V_H$ v2.0 The huTOA-1 $V_H$ v2.0 is encoded by the nucleic acid sequence in SEQ ID NO: 114. Similarly, the DPK21 human germline acceptor framework was used to construct a CDR grafted version of humanized TOA-1 light chain variable region since this germline framework exhibits high sequence identity to the TOA-1 light chain variable region and this amino acid sequence is set forth in SEQ ID NO: 132 huTOA-1 $V_L$ v2.0. The huTOA-1 $V_L$ v2.0 is encoded by the nucleic acid sequence in SEQ ID NO: 133. Another humanized TOA-1 light chain variable region was constructed to include the CDRs of mouse TOA-1 grafted onto a human DPK9 germline acceptor framework region and this amino acid sequence is set forth as SEQ ID NO: 115 huTOA-1 $V_L$ v1.0. The huTOA-1 $V_L$ v1.0 is encoded by the nucleic acid sequence in SEQ ID NO: 116. Additionally, K42E, A435 and Y49K mutations predicted to be important for preserving TrkB binding properties were introduced to the DPK9 framework containing the TOA-1 variable light region CDRs and this amino acid sequence is set forth as SEQ ID NO: 117 huTOA-1 $V_L$ v1.1. The huTOA-1 $V_L$ v1.1 is encoded by the nucleic acid sequence in SEQ ID NO: 118. The huTOA-1 comprising $V_H$ v1.0 and $V_L$ v1.4 is referred to interchangeably herein as huTOA-1 and TAM-163. Other variants based on the DPK9 framework were constructed and their corresponding nucleotide and amino acid sequences are represented by the SEQ ID NOS listed in Table 27. DNA encoding all possible versions of humanized TOA-1 antibody was transiently transfected into COS-1 cells to generate protein. The resultant conditioned medium containing the humanized TOA-1 antibody variants were quantitated by total human IgG sandwich ELISA. TrkB binding properties were evaluated using a competition ELISA with biotinylated chimeric TOA-1 antibody and by Surface Plasmon Resonance (SPR: Biacore).

TABLE 27

Sequence ID listing for the huTOA-1 $V_L$ variants

| huTOA-1 $V_L$ Variant | SEQ ID NO (Amino Acid) | SEQ ID NO (Nucleotide) |
|---|---|---|
| huTOA-1 v1.2 | 119 | 120 |
| huTOA-1 v1.3 | 121 | 122 |
| huTOA-1 v1.4 | 53 | 123 |
| huTOA-1 v1.5 | 124 | 125 |
| huTOA-1 v1.6 | 126 | 127 |
| huTOA-1 v1.7 | 128 | 129 |
| huTOA-1 v1.8 | 130 | 131 |

Example 46

Evaluation of TrkB Binding Properties of huTOA-1 Variants

TrkB binding properties were assessed for the huTOA-1 variants using a competition ELISA assay with biotinylated chimeric TOA-1 antibody. For this assay procedure, a 96-well plate was coated with rhTrkB-ECD (R&D #397-TR/CF) at 1 µg/ml, overnight at 4° C. The plate was then blocked with PBS+0.02% casein for 1 hour at room temperature Biotinylated chimeric TOA-1 at 25 ng/ml in PBS+

Figure 26:
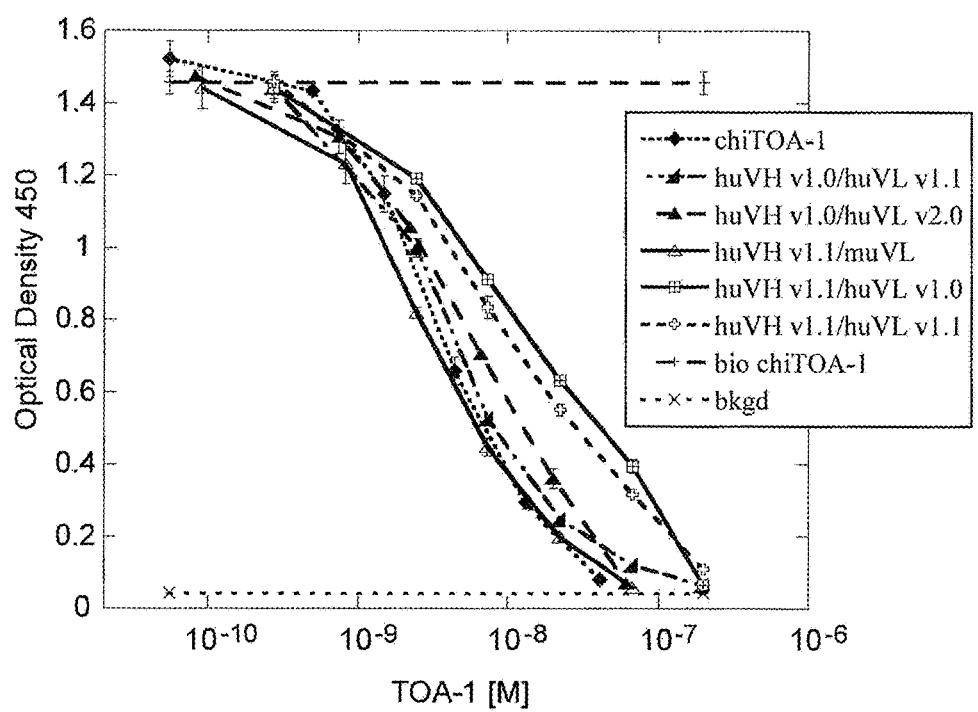
Figure 27:
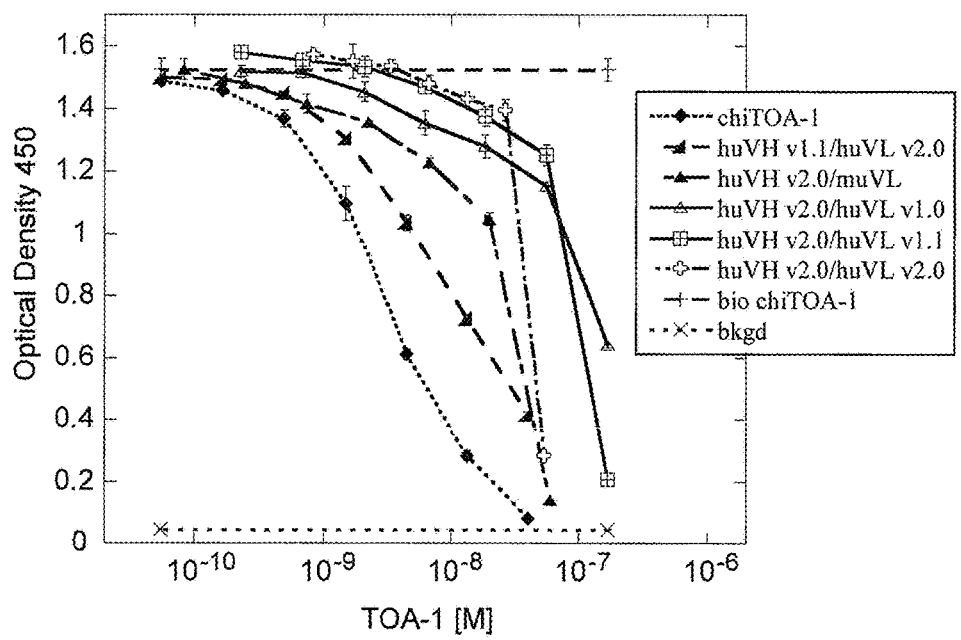
Figure 28:
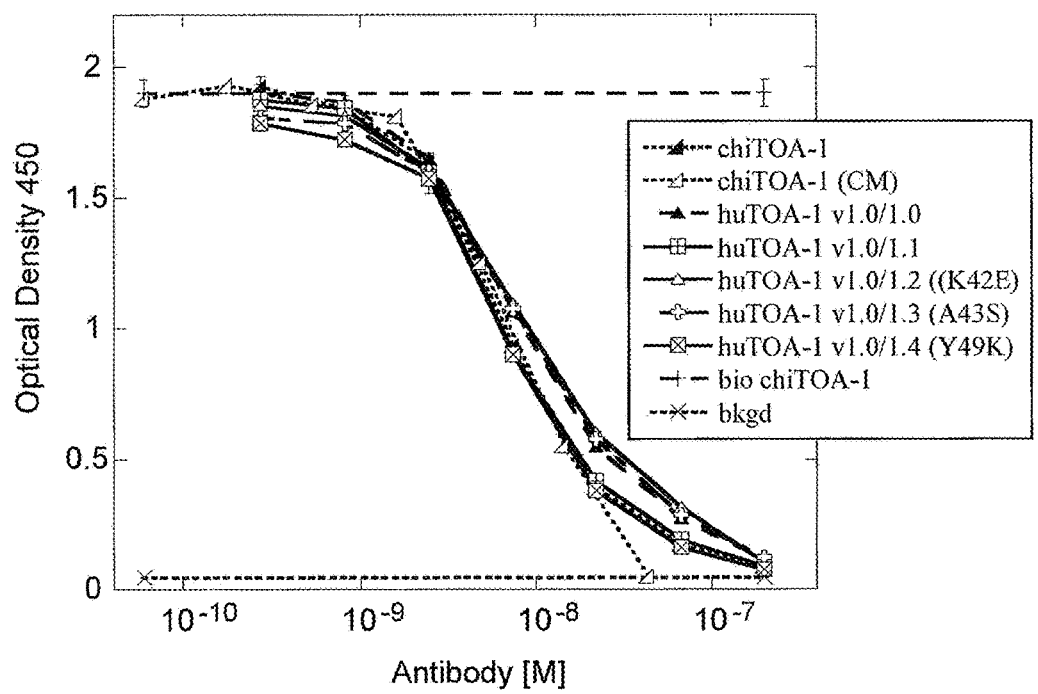

0.5% BSA+0.02% tween-20 was mixed with varying concentrations of huTOA-1 variants or unlabeled chimeric TOA-1 and incubated at room temperature for 1 hour. The wells were washed four times with PBS+0.03% tween-20 Streptavidin-HRP (Southern Biotech catalog #7100-05) diluted 1:10,000 was added and incubated for 30 minutes at room temperature. The wells were washed four times with PBS+0.03% tween-20 and TMB (BioFx) was added. The reaction developed for 5-10 minutes and was then quenched with 0.18 N $H_2SO_4$. The absorbance at 450 nm was determined. Results summarized in Table 28 show that humanized TOA-1 $V_H$ version 1.0 and $V_L$ version 1.1 completely retained TrkB binding properties relative to the chimeric TOA-1 antibody (FIGS. 25, 26 and 27). Further characterization was done to determine which mouse framework residues contained within TOA-1 $V_L$ version 1.1 are required for binding TrkB Humanized TOA-1 $V_L$ version 1.4 contains a single mouse framework residue K49 (Kabat numbering) and this version has comparable activity to TOA-1 $V_L$ version 1.1 (FIG. 28)

TABLE 28

Summary of Humanized TOA-1 Variants TrkB Binding Properties

| $V_H$ | $V_L$ | $IC_{50}$ [nM] |
|---|---|---|
| mouse | mouse | 3.6 |
| mouse | human v1.0 | 16.3 |
| mouse | human v1.1 | 13.6 |
| mouse | human v2.0 | 13.6 |
| human v1.0 | mouse | 3.6 |
| human v1.0 | human v1.0 | 6.2 |
| human v1.0 | human v1.1 | 4.3 |
| human v1.0 | human v2.0 | 5.9 |
| human v1.1 | mouse | 3.0 |
| human v1.1 | human v1.0 | 13.6 |
| human v1.1 | human v1.1 | 10.1 |
| human v1.1 | human v2.0 | 10.7 |
| human v2.0 | mouse | ~26.3 |
| human v2.0 | human v1.0 | ~126 |
| human v2.0 | human v1.1 | ~87.6 |
| human v2.0 | human v2.0 | ~37.8 |

Example 47

Kinetic Evaluation of huTOA-1 Variants

BIACORE® analysis was performed to determine the affinity constants for TOA-1 and the humanized TOA-1 variants to human and mouse TrkB. BIACORE® technology utilizes changes in the refractive index at the surface layer upon binding of the TOA-1 antibody variants to the TrkB protein immobilized on the layer Binding is detected by surface plasmon resonance (SPR) of laser light refracting from the surface. Analysis of the signal kinetics on-rate and off-rate allows the discrimination between non-specific and specific interactions Human and mouse TrkB ectodomain proteins (R&D Systems, #397/TR/CF and #1494-TB/CF) were immobilized at a low density on a CM5 chip (41 and 30 RUs respectively) and then various concentrations of TOA-1 and humanized TOA-1 variants were injected over the surface. The surface was regenerated with 4M $MgCl_2$ between injection cycles. Results show that the humanized TOA-1 variants have comparable affinity constants for both human and mouse relative to both the parental mouse TOA-1 antibody as well as the chimeric TOA-1 antibody (Table 29) demonstrating that these humanized variants have fully retained TrkB binding properties.

TABLE 29

Kinetic affinity constants for humanized TOA-1 variants binding human or mouse TrkB

| | Human TrkB | | | Mouse TrkB | | |
|---|---|---|---|---|---|---|
| Antibody | ka | kd | KD (nM) | ka | kd | KD (nM) |
| muTOA-1 | $2.1 \times 10^5$ | $3.1 \times 10^{-3}$ | 14.7 | $4.2 \times 10^5$ | $6.9 \times 10^{-3}$ | 16.3 |
| chiTOA-1 | $2.8 \times 10^5$ | $3.4 \times 10^{-3}$ | 12.1 | $2.6 \times 10^5$ | $4.4 \times 10^{-3}$ | 17.0 |
| semi-huTOA-1 | $4.6 \times 10^5$ | $3.2 \times 10^{-3}$ | 7.0 | $6.8 \times 10^5$ | $7.4 \times 10^{-3}$ | 10.9 |
| huTOA-1 v1.0/1.0 | $3.4 \times 10^5$ | $5.1 \times 10^{-3}$ | 14.9 | $2.6 \times 10^5$ | $4.8 \times 10^{-3}$ | 18.4 |
| huTOA-1 v1.0/1.1 | $3.5 \times 10^5$ | $4.2 \times 10^{-3}$ | 12.1 | $5.4 \times 10^5$ | $7.4 \times 10^{-3}$ | 13.8 |
| huTOA-1 v1.0/1.4 (TAM-163) | $4.3 \times 10^5$ | $4.1 \times 10^{-3}$ | 9.4 | $4.4 \times 10^5$ | $5.0 \times 10^{-3}$ | 11.4 |
| huTOA-1 v1.0/2.0 | $3.3 \times 10^5$ | $5.5 \times 10^{-3}$ | 16.5 | $5.3 \times 10^5$ | $1.1\times 10^{-2}$ | 20.9 |

Example 48

Agonist Activity of Anti-TrkB Antibodies

The ability of humanized anti-TrkB TOA-1 antibodies to activate the TrkB signaling cascade was assessed using 1) a transcriptional reporter to monitor TrkB signalling activation and 2) evaluating autophosphorylation of hTrkB and phosphorylation of ERK1/2, AKT, and PLCγ1, known mediators of TrkB signaling (reviewed in Friedman et al Exp Cell Res 1999; 253:131-142).

TrkB Expressing Stable Cell-lines

Stable cell lines of HEK-293 cells expressing both a CRE-luciferase reporter and rhuTrkB (nm_006180) or rmuTrkB (nm_001025074) were generated using standard techniques (Zhang et al, 2007, Neurosignals 15:29-39). Stable cell lines are designated rhuTrkB-CRE and rmuTrkB-CRE.

Transcriptional Reporter Assay

The luciferase reporter assay was performed as follows rhuTrkB-CRE cells were plated at 35,000 cells/100 ul/well in growth media (10% FCS-DMEM) in white bottom 96-well plates The next day, 10 ul/well of murine TOA1, humanized TOA-1 variants or isotype control (m IgG1 or hIgG1) antibody was added as 10× to the assay plates without changing media Luciferase activity was measured 16-18 hrs later using the Steady-Glo Luciferase Assay System (Promega,E2520) according to the manufacturer's protocol. In brief, media was replaced with 100 ul/well of 1×PBSNext, 100 ul/well of Steady-Glo reagent is added. Plates are sealed with TopSeal (PerkinElmer cat#6005185) and shaken at A Plate Shaker (IKA Works, Inc.) at speed 600 for 5 minutes. The luminescence was measured using VICTOR 3, 1420 Multilabel Counter (Perkin Elmer).

As exemplified in FIG. 29 and summarized in Table 30, TOA-1 antibody treatment resulted in a dose-dependent increase in luciferase activity with mouse TOA-1 and all humanized TOA-1 variants, indicating that these antibodies are able to activate the TrkB signalling cascade

TABLE 30

Agonist activity of Anti-TrkB TOA-1 antibodies in CRE-luciferase reporter assay

Humanized TOA-1 variant

| VH | VL | Relative Activity |
|---|---|---|
| mu | mu | ++++ |
| mu | hu v1.0 | ++ |
| mu | hu v1.1 | ++ |
| mu | hu v2.0 | ++ |
| hu v1.0 | mu | +++ |
| hu v1.0 | hu v1.0 | +++ |
| hu v1.0 | hu v1.1 | +++ |
| hu v1.0 | hu v1.2 | ++ |
| hu v1.0 | hu v1.3 | ++ |
| hu v1.0 | hu v1.4 | +++ |
| hu v1.0 | hu v1.5 | +++ |
| hu v1.0 | hu v1.6 | ++ |
| hu v1.0 | hu v1.7 | +++ |
| hu v1.0 | hu v1.8 | +++ |
| hu v1.0 | hu v2.0 | ++ |
| hu v1.1 | mu | +++ |
| hu v1.1 | hu v1.0 | ++ |
| hu v1.1 | hu v1.1 | ++ |
| hu v1.1 | hu v2.0 | ++ |
| hu v2.0 | mu | ++ |
| hu v2.0 | hu v1.0 | + |
| hu v2.0 | hu v1.1 | + |
| hu v2.0 | hu v2.0 | + |

Stimulation of TrkB Autophosphorylation and Phosphorylation of PLCγ1, AKT, and ERK1/2 by TOA-1 Antibodies Phosphorlyation analyses was performed to measure activation of proximal markers of TrkB signaling in engineered cell lines that overexpress TrkB (rhuTrkB-CRE and rmuTrkB-CRE stable cell lines generated as described above) and differentiated Human SH-SY5Y neuroblastoma cells that express human TrkB. Human TrkB expression in these cells was confirmed by Western analysis using standard techniques, as described below, using an anti-TrkB antibody (BD Transduction Labs Cat#610102). TrkB expressing cells were treated with TOA-1 antibodies and Western analyses performed to monitor autophosphorylation of hTrkB (Tyr490) and phosphorylation of ERK1/2 (Thr202/Tyr204), AKT (Ser473), p38 (Thr180/Tyr182) and PLCγ1 (Tyr783) as detailed below.

rhuTrkB-CRE or rmuTrkB-CRE cells were plated in 6-well plates at $5 \times 10^5$ cells/well in 10% FCS-DMEM growth media and cultured until the cells were 85-90% confluent. Cells were washed once with 0.1% FCS-DMEM (low serum media) and incubated for an additional 4 hours in low serum media. Next, cells were treated with BDNF (R&D #248BD) or TOA-1 antibody at the designated concentration for 15-60 min Medium was aspirated from the wells and 0.6 ml of 1× loading buffer (Invitrogen, with 1% b-ME) was added per well to lyse the cells. Cell lysates were transferred to Eppendoff tubes, and heated at 100° C. for 5 min 25 ul of each sample were resolved on a NuPAGE 4-20% Bis-Tris gradient gel (Invitrogen).

Western analysis was performed as follows: After electrophoresis, size-fractionated proteins were transferred onto nitrocellulose membranes. Membranes were blocked with 5% milk in T-TBS (0.15% Tween 20 in TBS), incubated with the appropriate primary antibody [anti-P-TrkB: Phosphor-TrkA (Tyr490), Cell signaling (CS) #9141; anti-Phospho-PLCγ1 (Tyr783), CS #2821; anti-Phospho AKT (Ser473), CS#9271; anti-P-ERK1/2 (Phospho-P44/P42 (Thr202/Tyr204), CS #9101; anti-Actin, Sigma A2066] in 1% milk T-TBS on a rocking platform at 4° C. overnight Membranes were washed 3× in T-TBS, then incubated with the appropriate HRP-conjugated secondary antibody (Cell Signaling #7974) for 2 hours. Next, membranes were washed 4 times in T-TBS and once in TBS. The signals were developed using ECL kit (GE RPN2106V) and the manufacturer's protocol followed by x-ray film exposure or Gel-Doc (Bio-Rad) to capture the image.

Human neuroblastoma SH-SYSY cells were plated in 6-well plates at $2 \times 10^5$ cells/well and cultured in growth media (DMEM:F12 (1:1) supplemented with 2 mM L-glutamine, 15% FBS and pen/strep). Cells were incubated with retinoic acid (10 uM) for 3 days to induce differentiation. Then, the cells were cultured in low serum media (growth media with 1% FBS) overnight, and further cultured in 0.1% FBS medium for 4 hours BDNF (R&D #248BD) or TOA-1 antibody at the designated concentration was added and cells incubated for 15-60 min. Medium was aspirated from the wells and 0.6 ml of 1× loading buffer (Invitrogen, with 1% b-ME) was added per well to lyse the cells. Cell lysates were transferred to Eppendoff tubes, and heated at 100° C. for 5 min 20 μl of each sample was resolved on a NuPAGE 4-20% Bis-Tris gradient gel (Invitrogen) Western analysis was performed as described above.

Figure 30A:
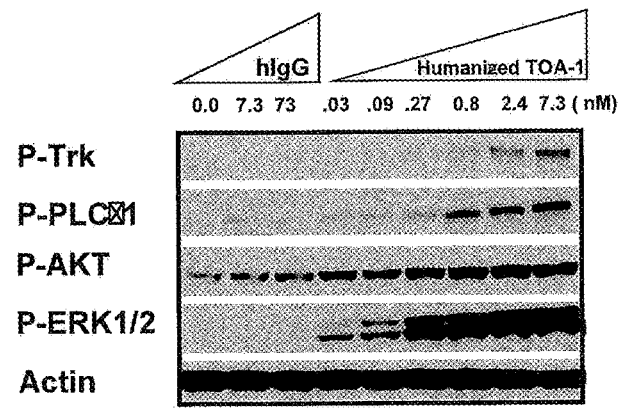
Figure 30B:
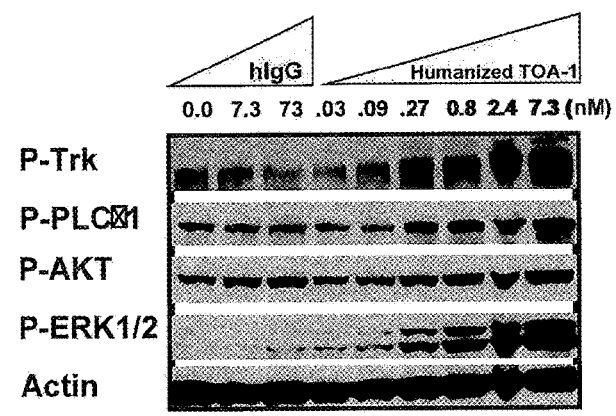
Figure 30C:
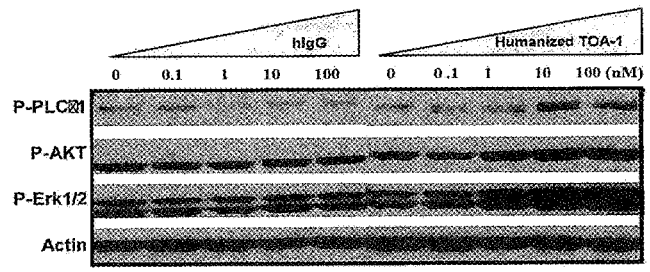

As shown in FIG. 30, treatment with humanized TOA-1 antibody induced dose-dependent auto-phosphorylation of TrkB and phosphorylation of the signaling molecules ERK1/2, AKT, and PLCγ1 in cells expressing human TrkB (both overexpressed TrkB, FIG. 30A, and endogenous TrkB, FIG. 30C) or mouse TrkB (FIG. 30B).

Figure 30D:
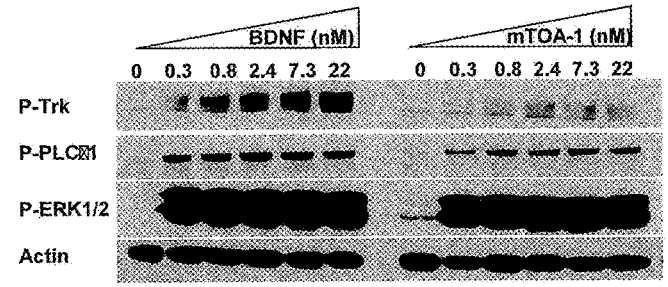

Also shown is the relative activity of BDNF and mTOA-1 in the phosphorylation assays performed as described above BDNF is a more potent stimulator of the TrkB signaling cascade as measured by TrkB autophosphorylation and PLCγ1 phosphorylation than mTOA-1 (FIG. 30D).

In summary, both the transcriptional reporter assay and phosphorylation assays demonstrated that TOA-1 antibodies activate the TrkB signalling pathway.

Example 49

Characterization of Antibody Binding Epitopes Relative to BDNF

Competition ELISAs were used to evaluate how the binding of anti-TrkB antibodies to TrkB protein affects the BDNF interaction with TrkB protein. In one format, a 96-well plate (Costar, cat#3590) was coated with BDNF (0.3 ug/ml, R&D systems, cat #248-BD) in PBS at 4 C and incubated overnight. The plate was washed with PBS, 0.1% Tween-20, then blocked wells with PBS, 1% BSA, 0.05% Tween-20 at Room temperature for 1 hour. Multiple concentrations of ProA purified anti-TrkB antibody were preincubated with rhTrkB/Fc Chimera (150 ng/ml, R&D systems, cat#688-TK) for 30 minutes at room temperature, then the mixtures were added to the plate and incubated for 1 hr at room temperature. The plate was washed with PBS, 0.1% Tween-20 6 times, peroxidase conjugated goat anti-human IgG (Fc) antibody (PIERCE, cat#31413) was added and incubated for 1 hr at room temperatue. The wells were washed with PBS 3 times and the substrate TMB (BioFX Laboratories, cat # TMBW-0100-01) added for 10 minutes. The reaction was stopped with 0.18N H2SO4 The absorbance at 450 nm was determined.

Figure 31:
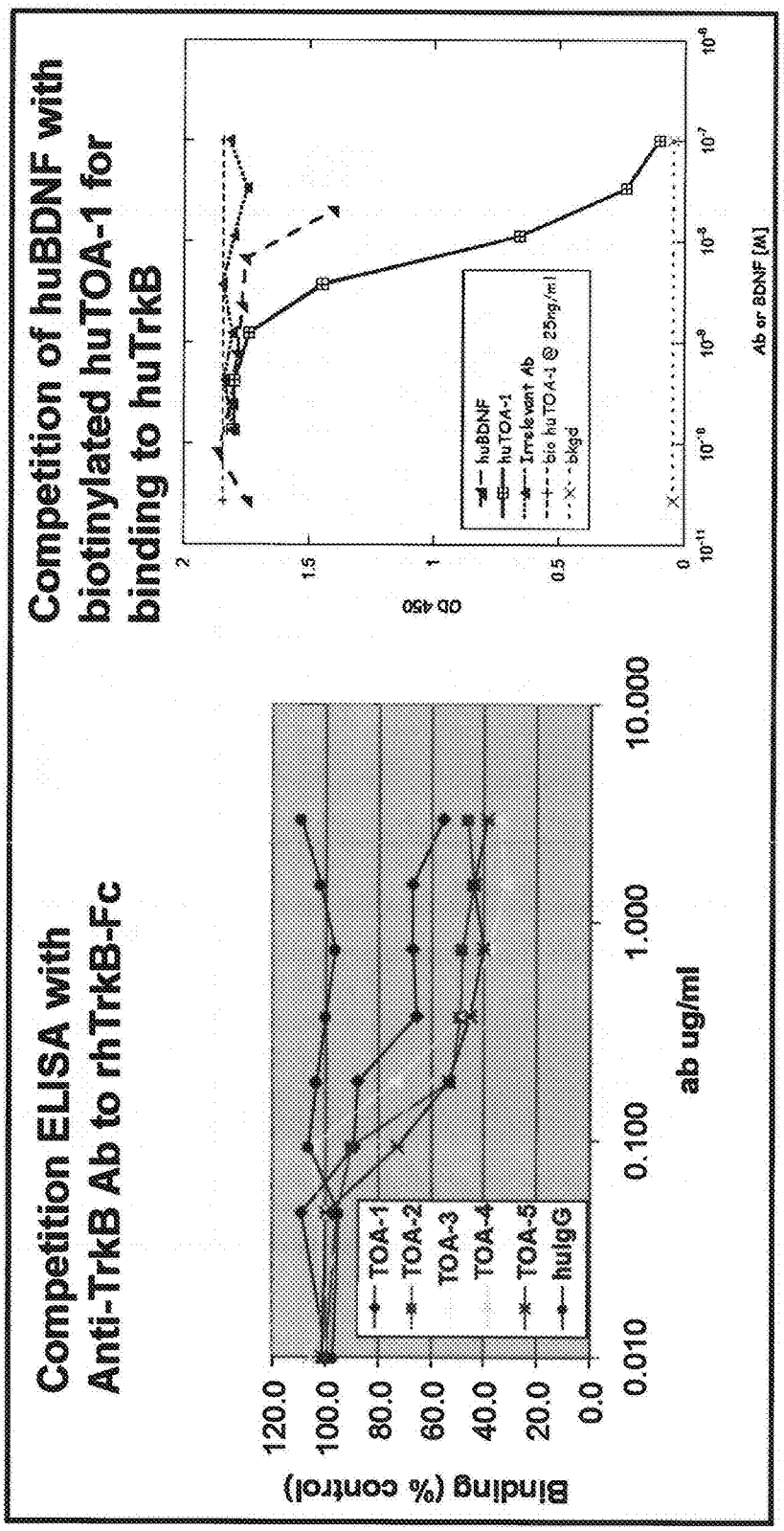
Figure 32:
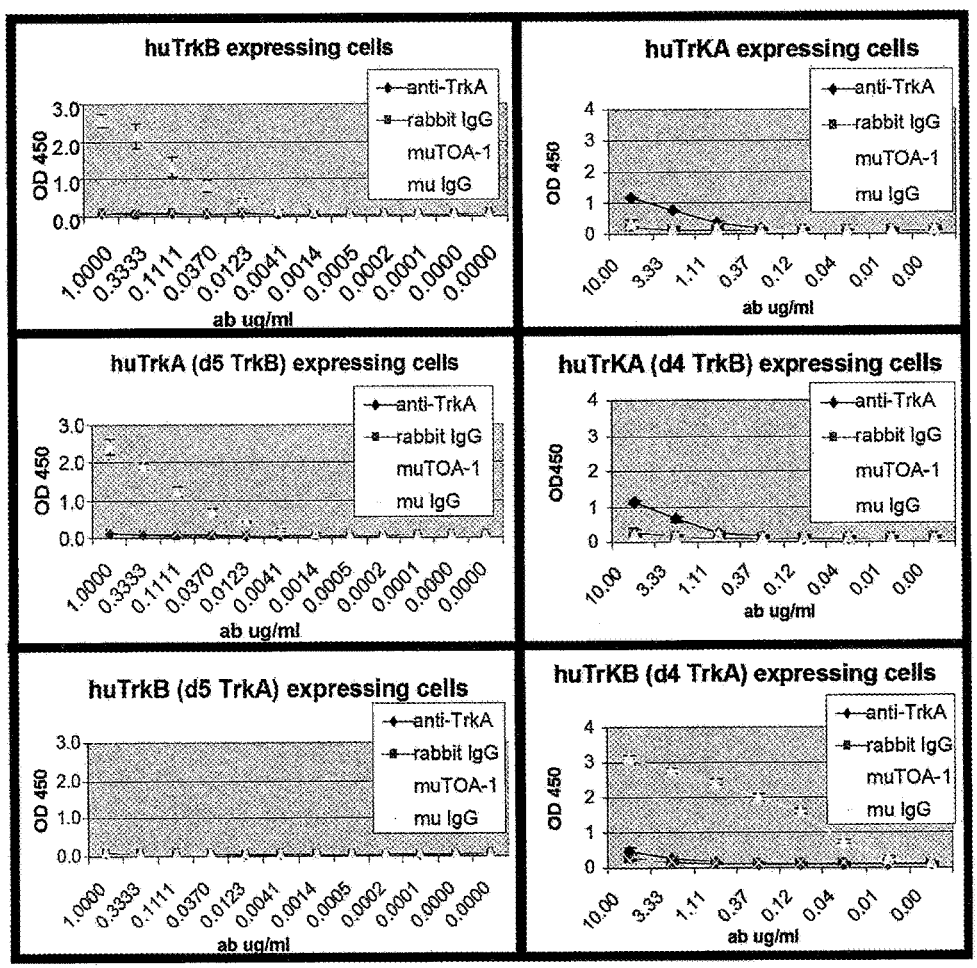

In a second format, a 96-well plate was coated with rhTrkB-ECD-His (1 µg/ml) in PBS overnight at 4° C. The plate was then blocked with PBS+0.02% casein for 1 hour at room temperature Biotinylated humanized TOA-1 at 25 ng/ml was incubated with varying concentrations of rhBDNF, unlabeled huTOA-1, or an irrelevant human IgG1 antibody and then the mixtures were added to the plate and incubated for 1 hour at room temperature. The plate was washed with PBS+0.03% tween-20 four times, Streptavidin-HRP (Southern Biotech catalog #7100-05) diluted 1:10,000 was added and incubated for 30 minutes at room temperature. The wells were washed four times with PBS+0.03% tween-20 and TMB (BioFx) was added. The reaction developed for 5-10 minutes and was then quenched with 0.18 N $H_2SO_4$. The absorbance at 450 nm was determined As shown in FIG. 31, results using both competition ELISA formats indicate that TOA-1 partially competes with BDNF for binding to human TrkB, suggesting that the TOA-1 binding site at least partially overlaps with the BDNF docking site on hTrkB Example 50

Mapping the TOA-1 Binding Site on Human TrkB

To further delineate the TOA-1 binding site on TrkB, a series of chimeric TrkB-TrkA receptors were generated and evaluated for TOA-1 binding in a cell-based ELISA.
Generation of TrkB-TrkA Chimeric Receptor Expression Constructs
TrkA-TrkB chimeric receptors were generated and cloned into the mammalian expression vector pcDNA3.1 (Invitrogen) using standard molecular cloning techniques. The chimeric TrkB(d5TrkA) receptor (Sequence 35) was generated by replacing residues 284-377 (np_001018074 Sequence 34), referred to as domain 5 of TrkB, with the TrkA domain 5 residues 280-377 (np_002520, Sequence 33). Similarly, chimeric TrkA(d5TrkB) was generated by replacing residues 283-377 of TrkA with residues 281-377 of TrkB (Sequence 36) Chimeric TrkB (d4TrkA) was generated by replacing residues 190-282 of TrkB with residues 187-281 of TrkA (Sequence 37) Chimeric TrkA(d4TrkB) was generated by replacing residues 187-281 of TrkA with residues 190-282 of TrkB (Sequence 38).
Cell-based ELISAs to evaluate the binding of humanized TOA-1 antibodies to TrkB-TrkA chimeric receptors were performed as follows:
Cell Transfection:
Human embryonic kidney 293 cells (ATCC) cells are plated at 4.5×10^6 cells per 10 cm² tissue culture plate and cultured overnight at 37 C. The next day cells are transfected with Chimeric TrkA-B expression plasmids using LF2000 reagent (Invitrogen, Cat #11668-019) at a 3:1 ratio of reagent to plasmid DNA using the manufacturers protocol. Cells are harvested 48 hrs after transfection using Trypsin, washed once with phosphate buffered saline (PBS), then suspended in growth media without serum at 2×10e6 cells/ml.
Cell-based ELISA Assay
Anti-TrkB or control antibodies at 1 µg/ml are serial diluted at 1:3 in PBS containing 1% BSA using 96-well plate 100 µl of the appropriate chimeric TrkA-B-transfected 293 cells or control parental 293 cells at 2×10e6 cells/ml in serum-free growth medium are added to U-bottom 96 well plate to get 1×10e5 cells/well. The cells are centrifuged down at 1600 cpm for 2 minutes. The supernatants are discarded with one-time swing and the plate is patted gently to loosen the cell pellet. 100 µl of diluted primary anti-TrkB or isotype-matching control antibodies in cold PBS containing 10% FCS are added to the cells and incubated on ice for 1 hour. The cells are then stained with 100 µl of diluted secondary anti-IgG antibody HRP conjugates (Donkey anti-Rabbit IgG, Thermo, cat #31458; goat anti-mouse IgG FC, Pierce, 31439; Goat anti-human IgG Fc, Pierce, cat #31413) on ice for 1 hour. Following each step of primary antibody and secondary antibody incubations, the cells are washed 3 times with ice-cold PBS100 µl of substrate TMB1 component (BIO FX, TMBW-0100-01) is added to the plate and incubated for 10 minutes at room temperature. The color development is stopped by adding 100 µl of 0.18M $H_2SO_4$. The cells are centrifuged down and the supernatants are transferred to fresh plate and read at 450 nm (Soft MAX pro 4.0, Molecular Device).

Figure 33:
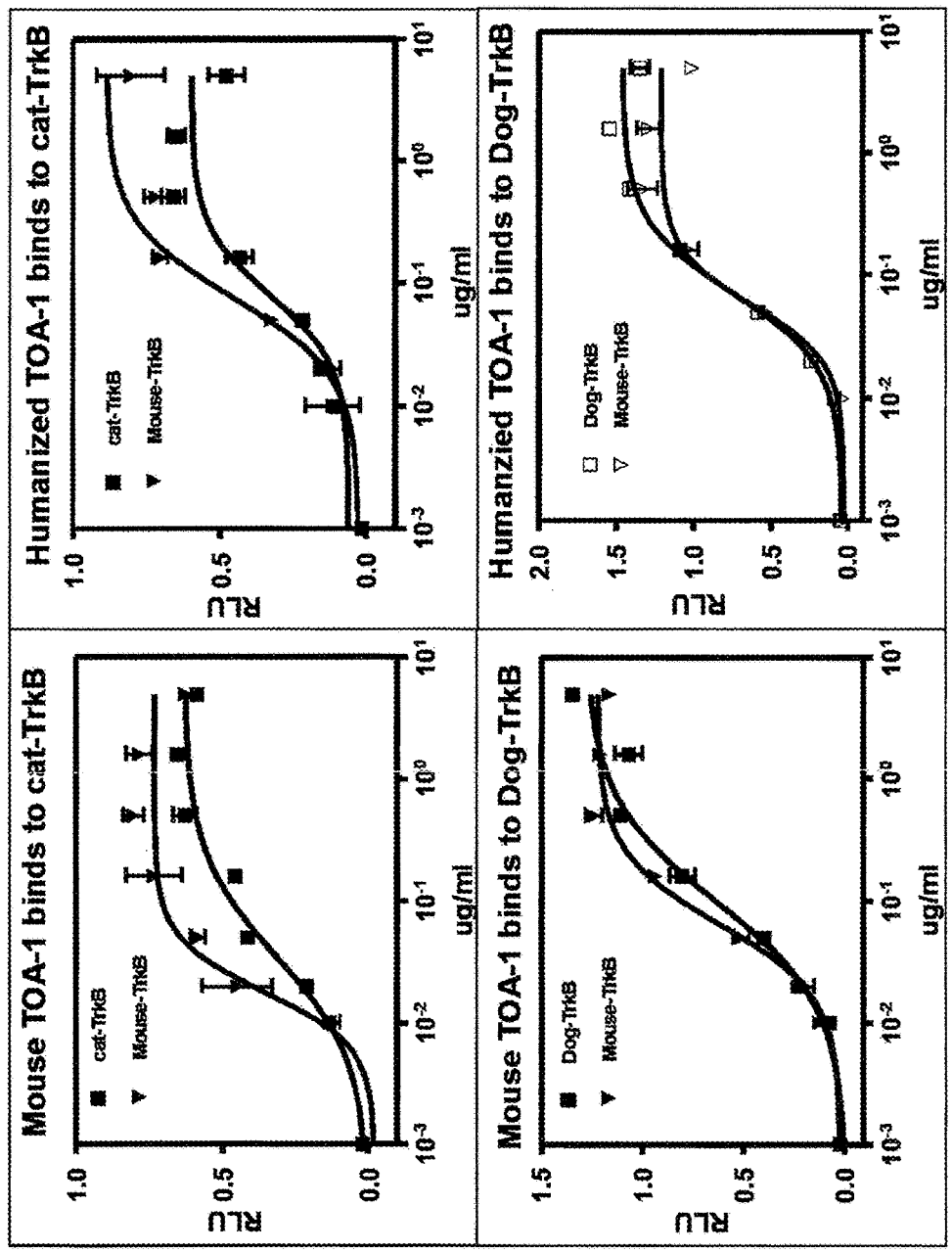

As shown in FIG. 33, in this cell-based ELISA the anti-TrkB antibody TOA-1 binds to cell-surface expressed TrkB (sequence 34), but not TrkA (sequence 33). In this same assay format, TOA-1 binds to chimeric TrkA (d5TrkB), but not TrkB (d5TrkA). Additionally, TOA-1 binds to TrkB (d4TrkA) and not to TrkA (d4TrkB). Together the results indicate that the TOA-1 antibody binds to domain 5 of TrkB, and domain 4 of TrkB is not sufficient for TOA-1 binding.

Example 51

Isolation of Cat NTRK2 (TrkB) cDNA

Methods
Isolation of Cat (*Felis domesticus*) TrkB
TrkB Cat coding sequences were isolated and cloned using standard Polymerase Chain reaction (PCR) methods. Full length cat (*Felis domesticus*) TrkB sequences were amplified from a cat brain cDNA pool (BioChain) using Stratagene Easy-A High-Fidelity system (cat#600640) and the suggested protocol using the oligonucleotides, 5'GGATCCGCCGCCACCATGTCGTCCTGGACGAG-GTGGCATGG (SEQ ID NO:144) and 5'GCGGCCGC-CTAGCCCAGAATATCCAGGTAGACCGGAGAT (SEQ ID NO:145), as primers. The cDNA was cloned into pCR2.1-TOPO vector (Invitrogen) and subsequently subcloned into pcDNA3.1-Hyg (Invitrogen) with BamHI and NotI restriction enzyme sites. The resultant plasmids were sequenced (SEQ ID NO:140, 141)

Dog (*Canis familiaris*) full length TrkB (XM_851329) coding sequence was amplified by PCR from a dog brain cDNA pool (BioChain) as described above using the oligonucleotides 5'GGATCCGCCGCCACCATGTCGTCCTG-GACGAGGTGGCATGG (SEQ ID NO:146) and 5'GCG-GCCGCCTAGCCTAGAATATCCAGGTAGACTGGAG (SEQ ID NO:147), as primers. The dog ortholog of human TrkB isoform c was selected for subcloning into pcDNA3.1-Hyg as described above. The resultant plasmids were sequenced (SEQ ID NO:142, 143)

Example 52

Antibody Binding to TrkB of Different Species was Measured by Cell-based ELISA

Cell-based ELISA was performed to evaluate the binding of anti-TrkB antibodies to mouse (nm_001025074), cat, and dog TrkB receptors Cell Transfection:

Human embryonic kidney 293 cells (ATCC) cells are plated at 5×10^6 cells per 10 cm2 tissue culture plate and cultured overnight at 37 C The next day cells are transfected with Human, dog, or cat TrkB expression plasmids using Fugene6 (Roche Applied Sciences) at a 3:1 ratio of reagent to plasmid DNA using the manufacturer's protocol. Cells are harvested 24 hrs after transfection using Accutase (Millipore), washed once with phosphate buffered saline (PBS), then suspended in DMEM with 0.2% BSA at 2×10e6 cells/ml.

Cell-based ELISA Assay

Anti-TrkB or control antibodies at 10 µg/ml are serial diluted at 1:3.17 in DMEM containing 0.2% BSA using 96-well plate 50 µl of the appropriate TrkB-transfected 293 cells or control LacZ-transfected 293 cells from the above are added to a U-bottom 96 well plate to get 1×10e5 cells/well. The plate is left at 4 C for 15 min before 50 µl of the diluted primary anti-TrkB or isotype-matching control antibodies are added to the cells. The cells and antibody are mixed by gentle pipetting then incubated at 4 C for 1 hour. The cells are washed 3 times with ice-cold PBS by centrifugation at 1600 cpm for 2 minutes. Each time the supernatants are discarded with one-time swing and the plate is patted gently to loose the cell pellet before adding the next buffer or medium Then, 100 µl of diluted secondary anti-IgG antibody HRP conjugates (Pierce) in DMEM with 0.2% BSA is added to the cells. Cells are incubated at 4 C for 1 hour, and washed 3 times as above. For staining, 100 µl of substrate TMB1 component (BIO FX, TMBW-0100-01) is added to each well and incubated for 5-30 minutes at room temperature. The color development is stopped by adding 100 µl of 0.18M $H_2SO_4$. The cells are centrifuged down and the supernatants are transferred to fresh plate and read at 450 nm (Soft MAX pro 4.0, Molecular Device).

The anti-TrkB antibodies mouse TOA-1 and humanized TOA-1 bind to mouse, cat and dog TrkB as determined by cell-based ELISA, shown in FIG. 33. The EC50 values for the binding of TOA-1 to cell surface mouse, dog, and cat TrkB, as determined by cell-based ELISA, are shown in Table 31.

TABLE 31

EC50 values for binding to TrkB determined by cell-based ELISA

|  | Humanized TOA1 | Mouse TOA1 |
| --- | --- | --- |
| 293-mouse TrkB | 0.33 nM | 0.40 nM |
| 293-cat TrkB | 0.52 nM | 0.23 nM |
| 293-dog TrkB | 0.55 nM | 0.65 nM |

Example 53

Selectivity of Anti-TrkB Antibodies Against TrkA, TrkC, and p75

Multiple experimental approaches were used to demonstrate that the anti-TrkB antibody, TOA-1, is selective for human TrkB versus human TrkA, TrkC, and the low affinity BDNF receptor p75 NTR.

Direct Binding ELISA

TOA-1 selectivity to TrkB was assessed by direct binding ELISA to recombinant human TrkA-Fc, TrkB-Fc or TrkC-Fc with biotinylated humanized TOA-1, chimeric TOA-1 and mouse TOA-1 antibodies as follows.

Figure 34:
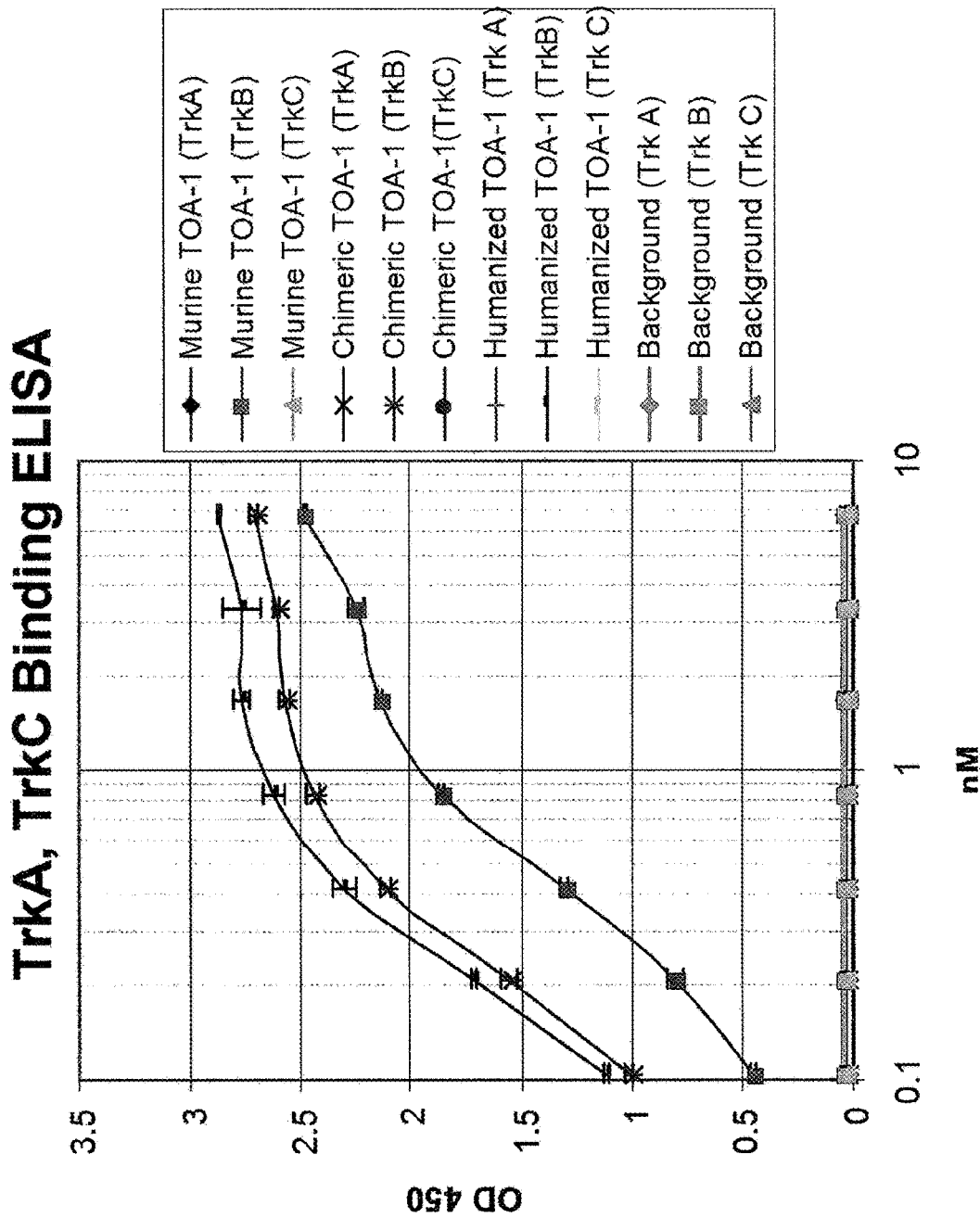

96-well plates (Costar) were coated with 1 µg/ml rhTrkB-ECD (R&D system, 688-TK), 5 µg/ml rhTrkA-ECD (R&D system, 175-TK), or 5 µg/ml rhTrkC-ECD (R&D system, 373-TC/TF) in PBS and incubated overnight at 4° C. Plates were blocked with PBS+0.2% casein (100 µl per well) for 3 hours at room temperature Next, 100 µl of biotinylated antibody (murine TOA1, chimeric TOA1, humanized TOA-1, or isotype control) at 6.7 nM was added to the wells and incubated for 1 hr at room temperature The wells were washed four times with PBS+0.03% tween-20 Streptavidin-HRP (Southern Biotech catalog #7100-05) diluted 1:10,000 was added and incubated for 30 minutes at room temperature The wells were washed four times with PBS+0.03% tween-20 and TMB (BioFx) was added The reaction developed for 5-10 minutes and was then quenched with 0.18 N $H_2SO_4$ The absorbance at 450 nm was determined As shown in FIG. 34, humanized TOA-1 (i.e., TAM-163), chimeric TOA-1 and mouse TOA-1 bind TrkB-Fc but not TrkA-Fc or TrkC-Fc.

FACs Analysis

90% confluent HEK293 cells were transiently transfected with plasmids expressing human TrkB (open reading frame from nm_006180 cloned into the mammalian expression vector pcDNA3.1-hyg, Invitrogen) or human p75NTR (open reading frame from NM_002507 cloned into vector pSMED2) using Fugene6 (Roche Applied Sciences) according to the manufacturer's directions Expression of human TrkB and human p75NTR was verified by Western analysis. At 24 hours post transfection, the cells were harvested, washed with PBS, resuspended in PBS/0.5% BSA 2.5×10^5 huTrkB and hu p75NTR cells were stained with antibodies as follows For p75NTR detection, cells were incubated with 1 ug/ml mouse anti-P75-Alexa488 (Millipore MAB5368X) for 30 min at 4° C., followed by a washing with PBS through centrifugation (1500 rpm for 5 min). For TrkB staining, cells were incubated with 1 µg/ml humanized TOA-1 antibody for 30 min at 4° C. followed by a PBS wash as described above Next, the cells were incubated with FITC labeled mouse anti-Human IgG (Southern Biotech S9670-02) for 30 min at 4° C., followed by a washing with PBS as described above Stained cells were analyzed on a FACSCalibur using CellQuest software (Becton Dickinson)

Figure 35:
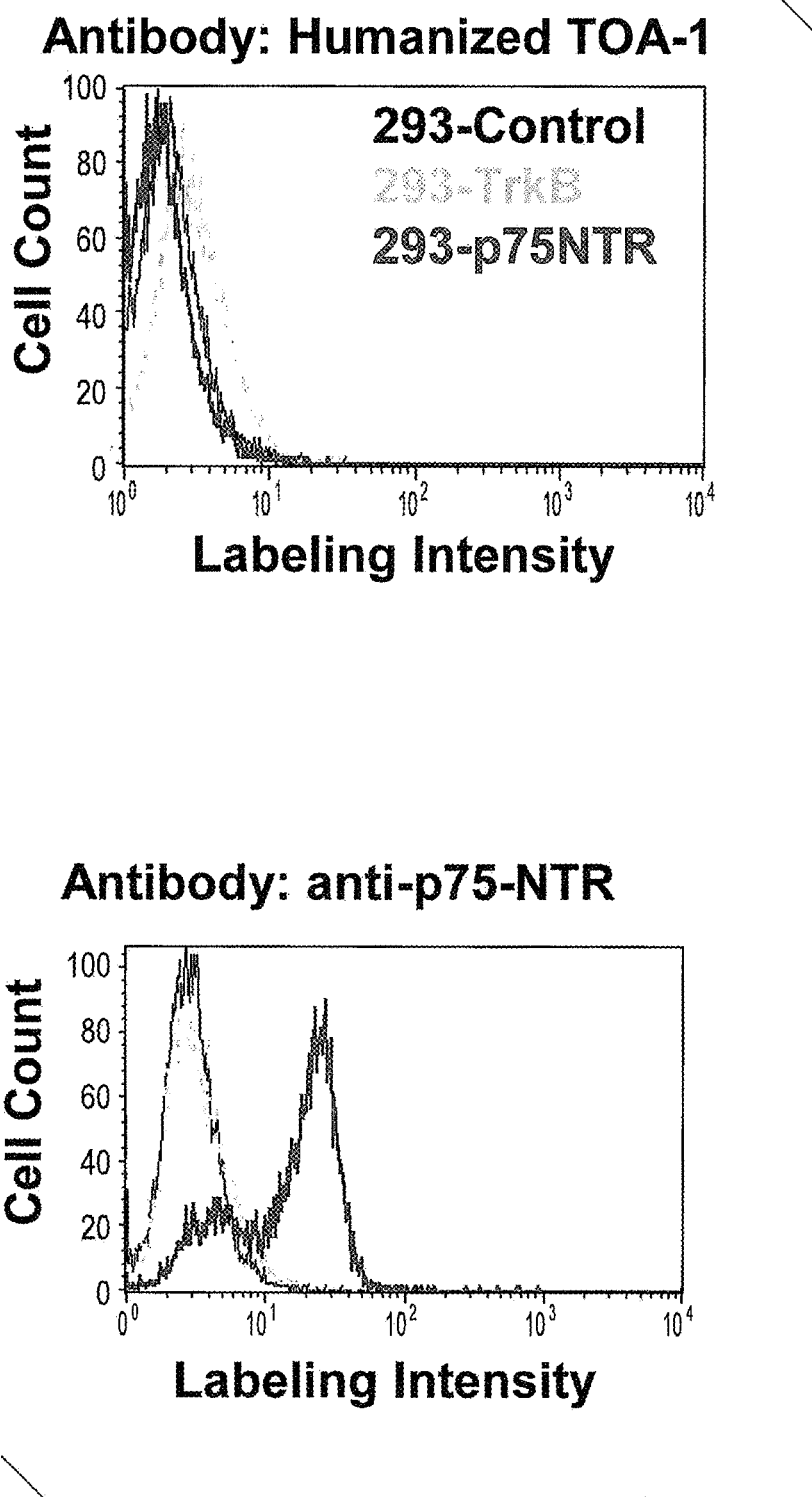

As shown in FIG. 35, using FACS analysis TOA-1 antibody binds to cell-surface expressed human TrkB, but does not bind to cell-surface expressed human p75NTR FACS analysis using anti-p75 on the respective cell lines confirms the cell-surface expression of p75 in these cell lines.

Cell-based ELISA

Cell-based ELISAs were performed to evaluate the binding of TOA-1 to human TrkB receptor but not to p75NTR.

Human embryonic kidney 293 cells were transfected and harvested as above except resuspended in DMEM containing 0.2% BSA at 2×10e6 cells/ml Anti-TrkB (TOA-1), control antibodies (anti-p75NTR, R&D AF367) or anti-huIgG isotype antibody, at 20 µg/ml are serial diluted at 1:3.17 in DMEM containing 0.2% BSA using 96-well plate 50 µl of the transfected or control 293 cells from the above are added to a U-bottom 96 well plate to get 1×10e5 cells/well. The plate is incubated at 4 C for 15 min before 50 µl of the diluted primary anti-TrkB or isotype-matching control antibodies in cold are added to the cells. The cells and antibody are mixed by pipetting up-down three times before incubated at 4 C for 1 hour. The cells are washed 3 times with ice-cold PBS by centrifugation at 1600 cpm for 2 minutes. Each time the supernatants are discarded with one-time swing and the plate is patted gently to loose the cell pellet before adding the next buffer or medium Then, 100 µl of diluted secondary anti-IgG antibody HRP conjugates (Pierce) in DMEM with 0.2% BSA is added to the cells. Cells are incubated at 4 C for 1 hour, and washed 3 times as above. For staining, 100 μl of substrate TMB1 component (BIO FX, TMBW-0100-01) is added to each well and incubated for 5-30 minutes at room temperature. The color development is stopped by adding 100 μl of 0.18M $H_2SO_4$ The cells are centrifuged down and the supernatants are transferred to fresh plate and read at 450 nm (Soft MAX pro 4.0, Molecular Device).

As shown in FIG. 36, the TOA-1 antibody binds to the cells expressing TrkB but not to the cells transfected with p75NTR construct (FIG. 36A), which does express p75NTR on the cell surface as detected by anti-p75NTR antibody (FIG. 36B)

Trk Signal Transduction

The ability of mouse, chimeric, and humanized anti-TrkB TOA-1 antibodies to activate the TrkB signaling cascade, but not the TrkA or TrkC cascades, was assessed by monitoring autophosphorylation of Trk and phosphorylation of ERK1/2, AKT, and PLCγ1, known mediators of Trk signaling (reviewed in Friedman et al Exp Cell Res 1999; 253: 131-142)

Stable cell lines of HEK-293 cells expressing both a CRE-luciferase reporter and rhuTrkA (open reading frame from NM_002529.3), rhuTrkB (open reading frame from nm_006180), and rhuTrkC (open reading frame from NM_001012338.1) were generated using standard techniques (Zhang et al, 2007, Neurosignals 15: 29-39) Stable cell lines are designated rhuTrkA-CRE, rhuTrkB-CRE, and rhuTrkC-CRE.

Trk-expressing cells were treated with TOA-1 antibodies, isotype control antibodies, or the neurotrophin ligands BDNF, NGF, and NT3 Western analyses was performed to evaluate autophosphorylation of hTrk (Tyr490) and phosphorylation of ERK1/2 (Thr202/Tyr204), AKT (Ser473), μ38 (Thr180/Tyr182) and PLCγ1 (Tyr783) as detailed below.

rhuTrkA-CRE, rhuTrkB-CRE, rhuTrkC, or parental HEK-293 cells were plated in 6-well plates at $5 \times 10^5$ cells/well in 10% FCS-DMEM growth media and cultured until the cells were 85-90% confluent. Cells were washed once with 0.1% FCS-DMEM (low serum media) and incubated for an additional 4 hours in low serum media. Next, cells were treated with TOA-1 antibody (final concentration 100 nM) or neurotrophin (TrkB: BDNF, R&D #248BD 10 nM final concentration; TrkA: NGF, R&D 256GF 10 nM final concentration; TrkC: NT3, R&D267N3, 25 nM final concentration) for 15-60 min. Medium was aspirated from the wells and 0.6 ml of 1× loading buffer (Invitrogen NP0007, with 1% b-ME) was added per well to lyse the cells. Cell lysates were transferred to Eppendoff tubes, and heated at 100° C. for 5 min 25 μl of each sample were resolved on a NuPAGE 4-20% Bis-Tris gradient gel (Invitrogen)

Western analysis was performed as follows. After electrophoresis, size-fractionated proteins were transferred onto nitrocellulose membranes Membranes were blocked with 5% milk in T-TBS (0.15% Tween20 in TBS), incubated with the appropriate primary antibody [anti-P-Trk: Phosphor-TrkA (Tyr490), Cell signaling (CS) #9141; anti-Phospho-PLCγ1 (Tyr783), CS #2821; anti-Phospho AKT (Ser473), CS#9271; anti-P-ERK1/2 (Phospho-P44/P42 (Thr202/Tyr204), CS #9101; anti-Actin, Sigma A2066] in 1% milk T-TBS on a rocking platform at 4° C. overnight Membranes were washed 3× in T-TBS, then incubated with the appropriate HRP-conjugated secondary antibody (Cell Signaling #7974) for 2 hours. Next, membranes were washed 4 times in T-TBS and once in TBS. The signals were developed using ECL kit (GE RPN2106V) and the manufacturer's protocol followed by x-ray film exposure or Gel-Doc (Bio-Rad) to capture the image.

As shown in FIG. 37, TOA-1 antibodies failed to cause a detectable increase above basal levels in Trk autophosphorylation, and PLCγ1, AKT, and ERK1/2 phosphorylation in TrkA and TrkC expressing cells. In contrast, the TrkA and TrkC ligands, NGF and NT3, respectively, induced a response indicating that the cellular signaling system is intact.

In all further examples, huTOA-1 (SEQ ID NOs: 51 and 53), is referred to as TAM-163.

Example 54 mRNA Expression of Catalytic and Non-catalytic TrkB Isoforms

In preparation for functional studies and to identify tissues and cell lines expressing high levels of endogenous TrkB, the tissue distribution of catalytic compared to non-catalytic isoforms of TrkB was examined using Taqman quantitative PCR (Q-PCR). Primer-probe pairs were designed to recognize either the extracellular domain (ECD) common to all hTrkB isoforms or the catalytic domain common to the catalytic hTrkB-a and hTrkB-c isoforms. A standard curve was generated for each primer probe pair using TrkB plasmid cDNA, and was used to convert raw data into TrkB cDNA molecules. Assuming similar efficiency of reverse transcription for different mRNA samples, this number reflects the molecules of TrkB mRNA for each tissue. Two independent primer-probe pairs were designed for each region and similar results were obtained with both pairs. As can be seen in Table 32, hTrkB is most highly expressed in the brain, and in this tissue the catalytic isoforms of TrkB accounts for ~35% of all TrkB isoforms. The neuroblastoma cell line SH-SYSY, when differentiated with retinoic acid, expresses levels of TrkB mRNA comparable to the ones found in human brain with 87% of the TrkB mRNA accounted for by the catalytic isoforms. This cell line was therefore chosen to evaluate the effects of TAM-163 on endogenous TrkB. Non-neuronal tissues showed <10% of the TrkB mRNA levels found in brain, when examining expression of all isoforms; expression of the catalytic isoforms was even lower and constituted <2% of the amount observed in brain. The lowest expression of TrkB was observed in peripheral blood leukocytes where TrkB mRNA was barely detectable.

TABLE 32 mRNA expression of TrkB in normal human tissues - comparison of catalytic isoforms versus total TrkB

| Human Tissue | Catalytic Isoforms | | All Isoforms (total) | | Ratio |
| --- | --- | --- | --- | --- | --- |
| | Molecules/ PCR | % of brain | Molecules/ PCR | % of brain | catalytic/ total (%) |
| Brain | 457311 | 100.00 | 1363034 | 100.00 | 33.55 |
| Kidney | 8849 | 1.94 | 116365 | 8.54 | 7.60 |
| Artery | 4780 | 1.05 | 63754 | 4.68 | 7.50 |
| Skin | 4079 | 0.89 | 113506 | 8.33 | 3.59 |
| Uterus | 3130 | 0.68 | 59566 | 4.37 | 5.26 |
| Heart | 2710 | 0.59 | 74769 | 5.49 | 3.62 |
| Vein | 2666 | 0.58 | 101286 | 7.43 | 2.63 |
| Adipose Tissue | 2183 | 0.48 | 67345 | 4.94 | 3.24 |
| Ovary | 1948 | 0.43 | 59626 | 4.37 | 3.27 |
| Pancreas | 1827 | 0.40 | 58539 | 4.29 | 3.12 |

TABLE 32-continued mRNA expression of TrkB in normal human tissues - comparison of catalytic isoforms versus total TrkB

| Human Tissue | Catalytic Isoforms | | All Isoforms (total) | | Ratio catalytic/total (%) |
| --- | --- | --- | --- | --- | --- |
| | Molecules/ PCR | % of brain | Molecules/ PCR | % of brain | |
| Thymus | 1246 | 0.27 | 33902 | 2.49 | 3.68 |
| Spleen | 1071 | 0.23 | 50565 | 3.71 | 2.12 |
| Skeletal Muscle | 777 | 0.17 | 12341 | 0.91 | 6.29 |
| Lymph Node | 774 | 0.17 | 24328 | 1.78 | 3.18 |
| Colon | 677 | 0.15 | 16491 | 1.21 | 4.10 |
| Bone Marrow | 411 | 0.09 | 13101 | 0.96 | 3.14 |
| Lung | 404 | 0.09 | 11215 | 0.82 | 3.60 |
| Ileum | 308 | 0.07 | 7048 | 0.52 | 4.38 |
| Jejunum | 173 | 0.04 | 4148 | 0.30 | 4.18 |
| Stomach | 114 | 0.03 | 2626 | 0.19 | 4.36 |
| Liver | 101 | 0.02 | 2672 | 0.20 | 3.76 |
| White Blood Cells (Buffy Coat) | 81 | 0.02 | 40 | 0.00 | N/A |
| Duodenum | 63 | 0.01 | 1878 | 0.14 | 3.35 |
| Peripheral Blood Leukocytes | 5 | 0.00 | 30 | 0.00 | N/A |
| SH-SY5Y Cells (differentiated) | 908417 | 198.64 | 1042645 | 76.49 | 87.13 |
| SH-SY5Y Cells (undifferentiated) | 3318 | 0.73 | 6056 | 0.44 | 54.78 |

Taqman quantitative PCR conditions, primer-probe pairs and conversion into molecules of cDNA/200 ng RNA is described in 3.2; the average value for the two primer-probe pairs available for catalytic and total trkB isoforms is shown. A ratio of catalytic/total was not calculated if the values for total were too low for accurate quantitation (indicated as N/A).

Example 55

Signaling by TAM-163 in Cell Lines Expressing Recombinant hTrkB, hTrkA and hTrkC The ability of TAM-163 to activate the TrkB signaling cascade was assessed using 1) a transcriptional reporter assay to monitor TrkB signaling activation, 2) an enzyme complementation assay to monitor recruitment of the signaling molecule SHC1 to TrkB and 3) evaluating autophosphorylation of hTrkB and phosphorylation of ERK1/2, AKT, and PLCγ1, known mediators of TrkB signaling. The same assays were also used to examine the ability of TAM-163 to activate TrkA and TrkC signaling pathways.

Example 56

TAM-163 Activates the Cre-luciferase Reporter Gene in Cell Lines Expressing hTrkB, but not in Cell Lines Expressing hTrkA or hTrkC The Cre-luciferase (Cre-luc) transcriptional reporter assay measures the ability of TrkB ligands to activate the CRE response element and as such integrates multiple upstream signaling pathways. The cell lines used for this assay, hTrkB-Cre, hTrkA-Cre and hTrkC-Cre, have been previously described and were shown to respond specifically to the appropriate endogenous ligands (Zhang et al. Neurosignals. 2006-2007; 15(1):26-39, Qian et al. J Neurosci. 2006 Sep. 13; 26(37):9394-9403). Treatment of hTrkB-Cre cells with TAM-163 resulted in a dose-dependent increase in luciferase activity; the $EC_{50}$ was 0.2 nM and the maximum fold-increase was 5-fold (FIG. 38). In the same experiment, human BDNF (Peprotech, Rocky Hill, N.J.) showed an $EC_{50}$ of 5.2 nM and a maximum fold-increase of 7.5-fold, while a hIgG control antibody had no effect (FIG. 38). Between experiments, $EC_{50}$ and maximum-fold induction ranged from 0.10 nM-0.79 nM and 2.5-5.4 fold for TAM-163, and from 5.2-8.2 nM and 6-7.5-fold for human BDNF. Individual activity data for different lots of TAM-163 tested in the hTrkB Cre-luc reporter assays multiple times are shown below (Table 33). Averaging across all assays, the $EC_{50}$ value for TAM-163 in this assay was determined to be 0.37±0.06 nM with a fold-induction of 4.2±0.3.

TABLE 33

Activity of different lots of TAM-163 in the hTrkB Cre-luc transcriptional reporter assay

| TAM-163 Lot# | $EC_{50}$ (nM) | Fold-increase | Reference |
| --- | --- | --- | --- |
| L40042-166 | 0.34 | 2.5 | L401310-192 |
| L40042-166 | 0.65 | 3.0 | L401310-207 |
| L40042-166 | 0.35 | 3.1 | L42358-41 |
| L40042-166 | 0.45 | 5.4 | L42358-41 |
| L40042-166 | 0.79 | 5.0 | L42358-52 |
| L40042-166 | 0.2 | 4.5 | L42358-173 |
| L40042-192 | 0.24 | 2.9 | L42358-41 |
| L40042-192 | 0.39 | 5.3 | L42358-41 |
| L40042-192 | 0.61 | 5.0 | L42358-52 |
| L42385-008 | 0.25 | 2.4 | L42358-41 |
| L42385-008 | 0.37 | 5.3 | L42358-41 |
| L42385-024 | 0.13 | 5.3 | L42358-195 |
| L42385-152 | 0.10 | 4.5 | L42358-173 |
| Average ± SEM | 0.37 ± 0.06 | 4.2 ± 0.3 | |

The crossreactivity of TAM-163 with human TrkA and TrkC was tested using hTrkB-Cre, hTrkA-Cre and hTrkC-Cre with the appropriate endogenous controls (NGF for hTrkA, BDNF for hTrkB and NT-3 for hTrkC) and 20 nM or 100 nM TAM-163 (FIG. 39). While the endogenous ligands resulted in the expected responses (NGF: 4.5-fold increase hTrkA-Cre; NT-3: 2.9-fold increase hTrkC-Cre), TAM-163 did not show any increased luciferase activity compared to hIgG control in either hTrkA or hTrkC cells. In the same experiment, TAM-163 did activate hTrkB-Cre cells 3.4-4.1-fold, demonstrating that TAM-163 was effective on TrkB, as expected.

Example 58

Figure 40:
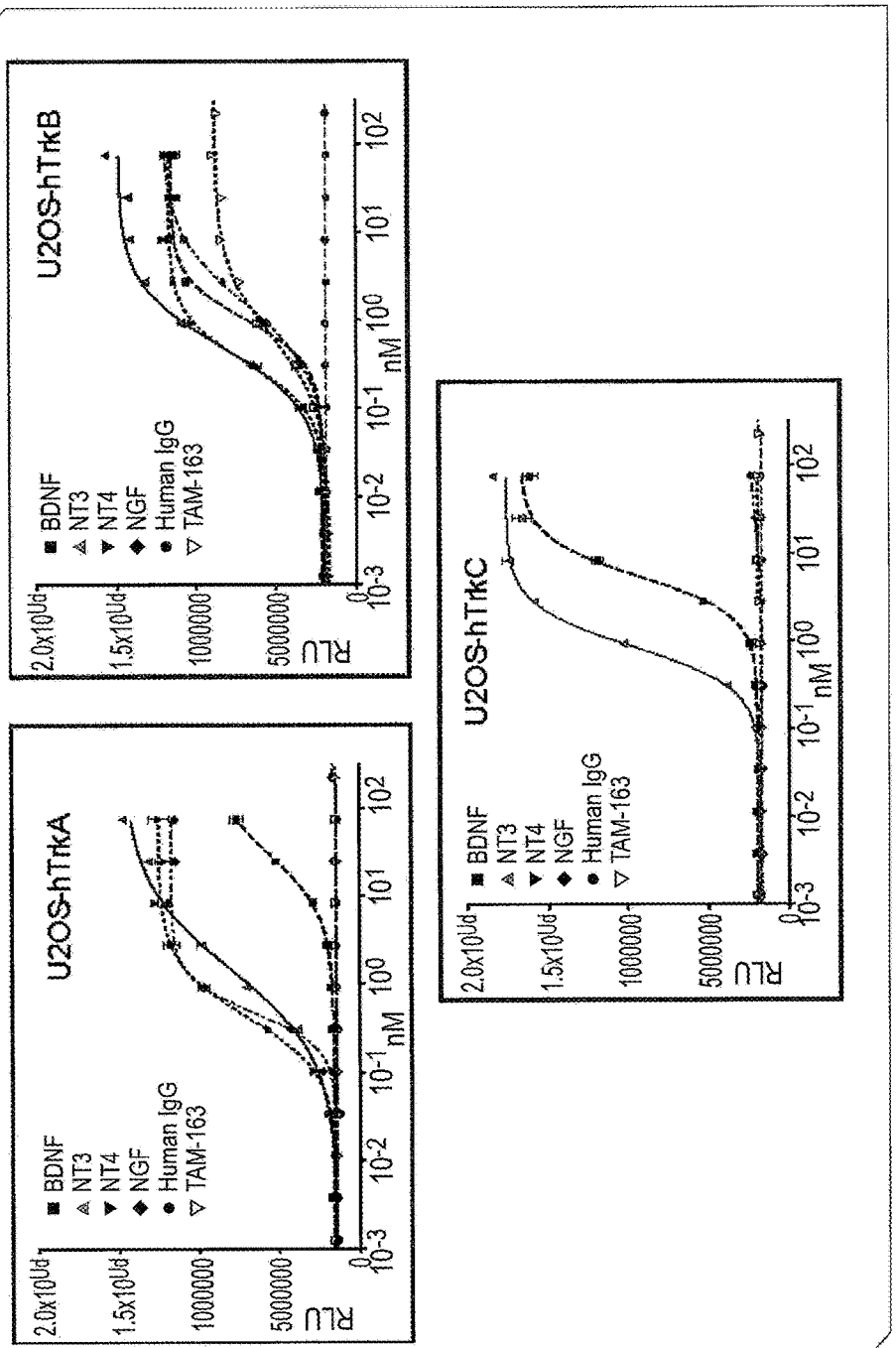
Figure 41:
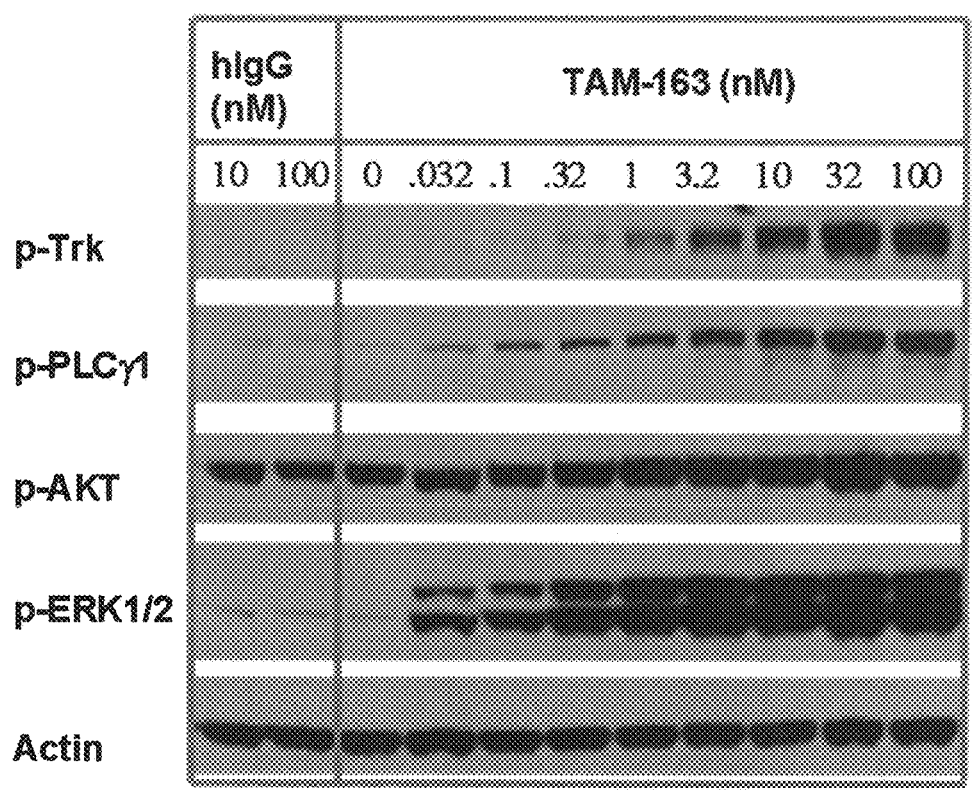

TAM-163 Mediates SHC1 Recruitment in Cells Expressing hTrkB, but not in Cells Expressing hTrkA or hTrkC The ability of TAM-163 to activate hTrkA, hTrkB and hTrkC was also assayed in an enzyme complementation assay (FIG. 40; Table 34). This assay monitors recruitment of the signaling molecule SHC1 to autophosphorylated TrkB in U2OS cells using the Discoverx Pathhunter technology. TAM-163 activated hTrkB in this assay with a potency similar to the one observed in the Cre-luciferase reporter assay ($EC_{50}$=0.67 nM) (FIG. 40; Table 34). Similar to the Cre-luciferase assay, the maximum signal induced by TAM-163 was significantly less than the maximum signal observed with BDNF, suggesting that TAM-163 is a partial agonist in this assay. Importantly, TAM-163 did not activate hTrkA or hTrkC at concentrations up to 670 nM, while the endogenous ligands for these receptors showed strong activation at very low concentrations (FIG. 40; Table 34). hTrkA, hTrkB and hTrkC were activated by an unusually broad array of endogenous Trk ligands in this assay which could reflect the particular signaling pathway assayed (SHC1 recruitment), the cell background (U2OS cells) or a peculiarity of the Pathhunter system (this assay uses the hTrkB-a isoform fused to a small peptide epitope, while our other assays are conducted with the native hTrkB-c isoform). It is remarkable that TAM-163 did not crossactivate hTrkA and hTrkC despite the apparent relaxed specificity for the endogenous ligands in this assay.

TABLE 34

Activity of TAM-163 on hTrkA, hTrkB and hTrkC in the SHC1 recruitment assay

|  |  | TAM-163 | hIgG | NGF | BDNF | NT-3 | NT-4 |
|---|---|---|---|---|---|---|---|
| hTrkA | EC50 (nM) | N/A | N/A | 0.48 | 30.13 | 1.49 | 0.43 |
|  | Fold-increase | 1.1 | 1.1 | 7.2 | 4.3 | 9.2 | 9.0 |
| hTrkB | EC50 (nM) | 0.67 | N/A | 1.59 | 1.02 | 0.50 | 0.33 |
|  | Fold-increase | 5.2 | 1.1 | 7.2 | 5.9 | 7.7 | 6.1 |
| hTrkC | EC50 (nM) | N/A | N/A | N/A | 5.45 | 0.86 | N/A |
|  | Fold-increase | 1.0 | 1.0 | 1.9 | 8.4 | 10.5 | 1.1 |

The maximum ligand concentration tested was 670 nM (antibodies) and 74 nM (endogenous ligands). The EC50 and maximum fold-increase reached is shown. EC50 = concentration at which 50% of maximum effect is reached. An EC50 was not calculated if a plateau was not reached (indicated as N/A).

Example 59

TAM-163 Activates Trk-dependent Phosphorylation Events in Cells Expressing hTrkB, but not in Cells Expressing hTrkA or hTrkC To directly monitor signaling events downstream of TrkB, we used Western blotting. Autophosphorylation of TrkB (Y490) as well phosphorylation of signaling molecules downstream of TrkB, including ERK1/2 (Thr202/Tyr204), PLCγ1 (Tyr783) and AKT (Ser473) were assessed using the hTrkA-Cre, hTrkB-Cre and hTrkC-Cre cell lines described above. TAM-163, but not a hIgG control antibody, induced dose-dependent phosphorylation of TrkB (Y490), ERK1/2 (Thr202/Tyr204), PLCγ1 (Tyr783) and AKT (Ser473) in hTrkB-Cre cells (FIG. 42).

Figure 42:
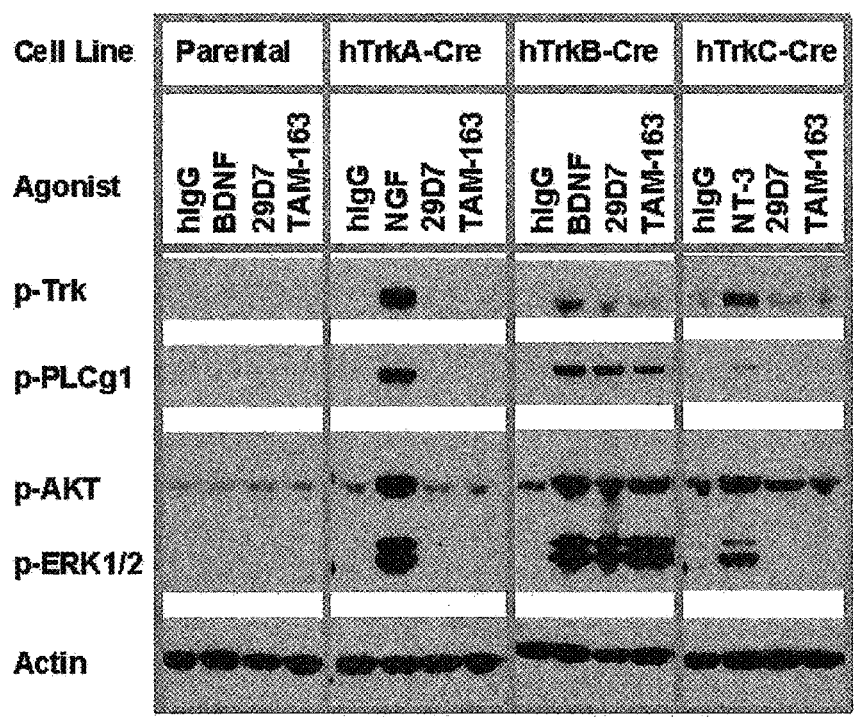

TAM-163 was unable to induce signaling in hTrkA-Cre or hTrkC-Cre cells (FIG. 42). The endogenous ligands for hTrkA (NGF) and hTrkC (NT-3) induced both Trk autophosphorylation and phosphorylation of the signaling intermediates ERK1/2 and PLCγ1 in hTrkA-Cre and hTrkC-Cre cells, demonstrating that these cell lines respond to their appropriate ligand. In the same experiment, TAM-163 was able to activate signaling downstream of hTrkB, demonstrating that TAM-163 was active.

Example 60

Figure 43:
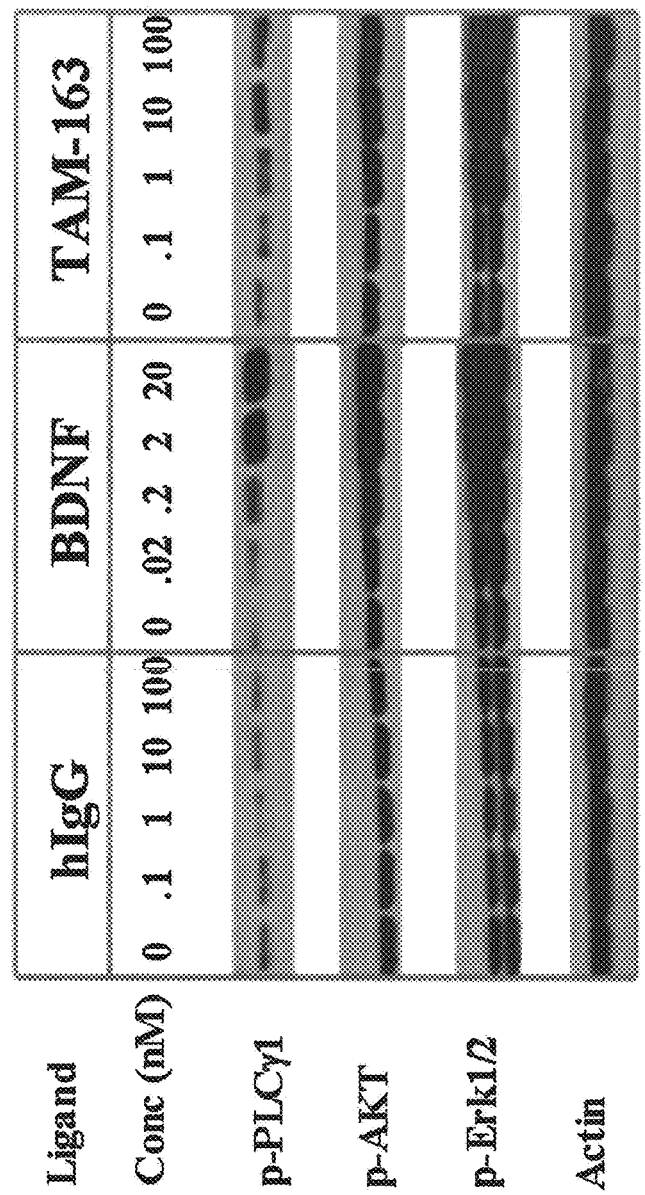

TAM-163 Activates Trk-dependent Phosphorylation Events in a Human Neuroblastoma Cell Line Expressing Endogenous hTrkB To examine the ability of TAM-163 to signal in cells expressing endogenous TrkB, we used differentiated human neuroblastoma SH-SY5Y cells. TAM-163, but not a hIgG control antibody, induced phosphorylation of ERK1/2, PLCγ1, and AKT in a dose-dependent manner in these cells; effects became apparent at concentrations 1 nM TAM-163 (FIG. 43). Compared to BDNF, TAM-163 appeared somewhat less potent and showed a significantly lower maximal stimulation of phosphorylation, suggesting that TAM-163 is a partial agonist in this system.

Example 61

TAM-163 Induces Internalization and Degradation of hTrkB

Figure 44:
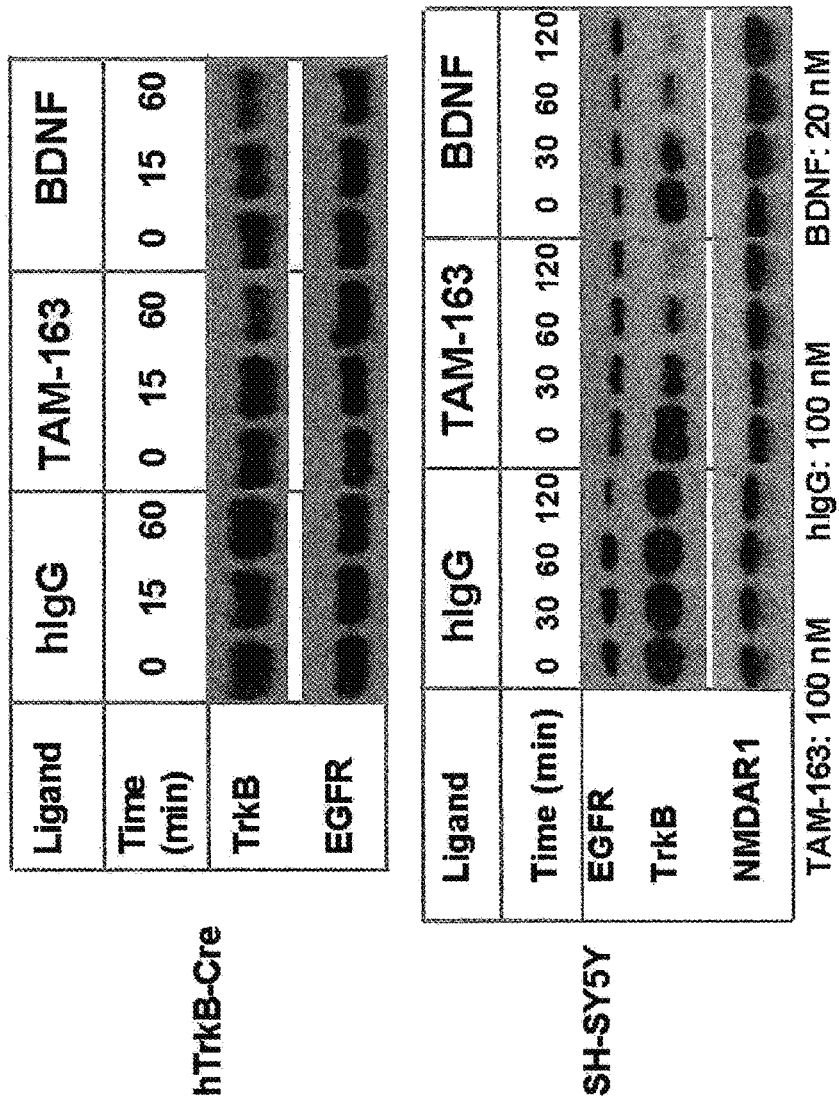

BDNF has been reported to mediate internalization and degradation of TrkB {8,9}. We examined the effect of TAM-163 on TrkB internalization and degradation using cell lines expressing either recombinant (hTrkB-Cre) or endogenous (SH-SY5Y) TrkB. To monitor internalization, cells were activated with TAM-163 or BDNF for the indicated times, cell surface proteins were then labeled with biotin, isolated by strepatavidin affinity purification and cell surface TrkB protein was identified by Western blotting. In this assay, biotinylated TrkB represents the TrkB remaining on the cell surface after activation. As can be seen in FIG. 44, TAM-163, but not a control hIgG antibody, induced significant internalization of TrkB in cells expressing recombinant TrkB (hTrkB-Cre) and in cells expressing endogenous TrkB (SH-SY5Y). TAM-163 did not affect cell surface levels of unrelated proteins (EGF-receptor, NMDA-receptor). The time-course and amount of TrkB internalization induced by TAM-163 was comparable to BDNF in both hTrkB-Cre and SH-SY5Y cells (FIG. 44).

Figure 45:
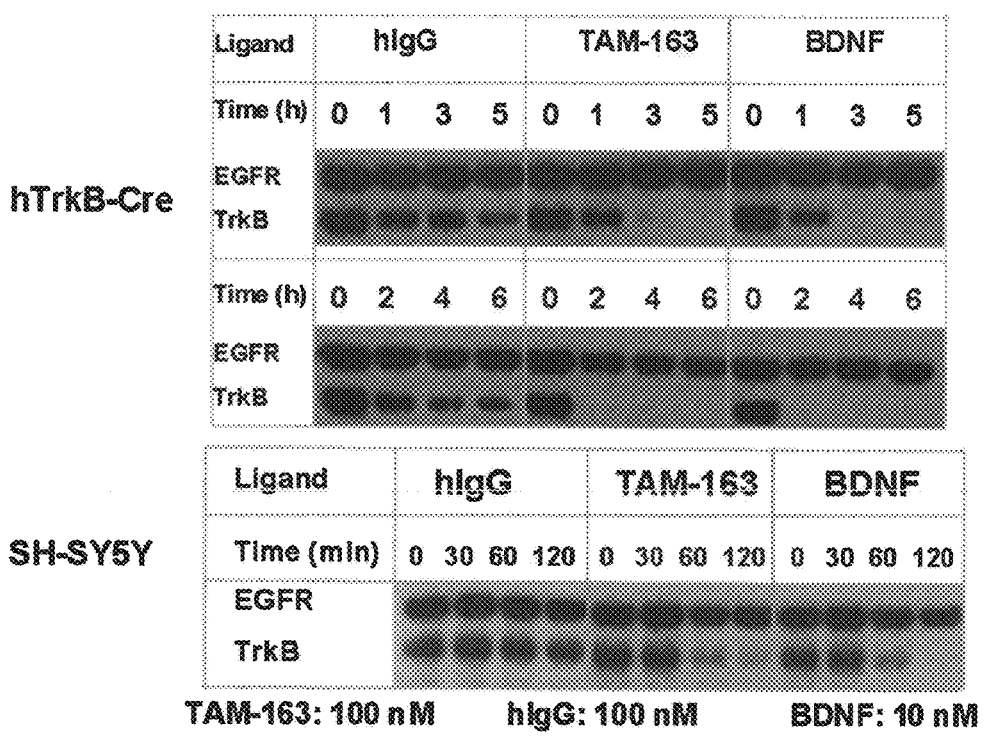

To monitor TrkB degradation, cell surface proteins were labeled with biotin prior to ligand exposure, and cells were then activated with TAM-163 or BDNF for the indicated times. Labeled proteins were isolated by strepatavidin affinity purification, and TrkB was identified by Western blotting. In this assay, biotinylated TrkB represents the total TrkB remaining after activation; the disappearance of labeled TrkB is a measure for its clearance from the cell. As can be seen in FIG. 45, TAM-163, but not a hIgG control antibody, induced degradation of cell-surface-labeled TrkB in cells expressing recombinant TrkB (hTrkB-Cre) and in cells expressing endogenous TrkB (SH-SY5Y). TAM-163 did not affect unrelated proteins (EGF-receptor, NMDA-receptor). The time-course and amount of TrkB degradation induced by TAM-163 was comparable to BDNF in both hTrkB-Cre and SH-SY5Y cells (FIG. 45).

Example 62

TAM-163 does not Bind to Human p75NTR

Figure 46:
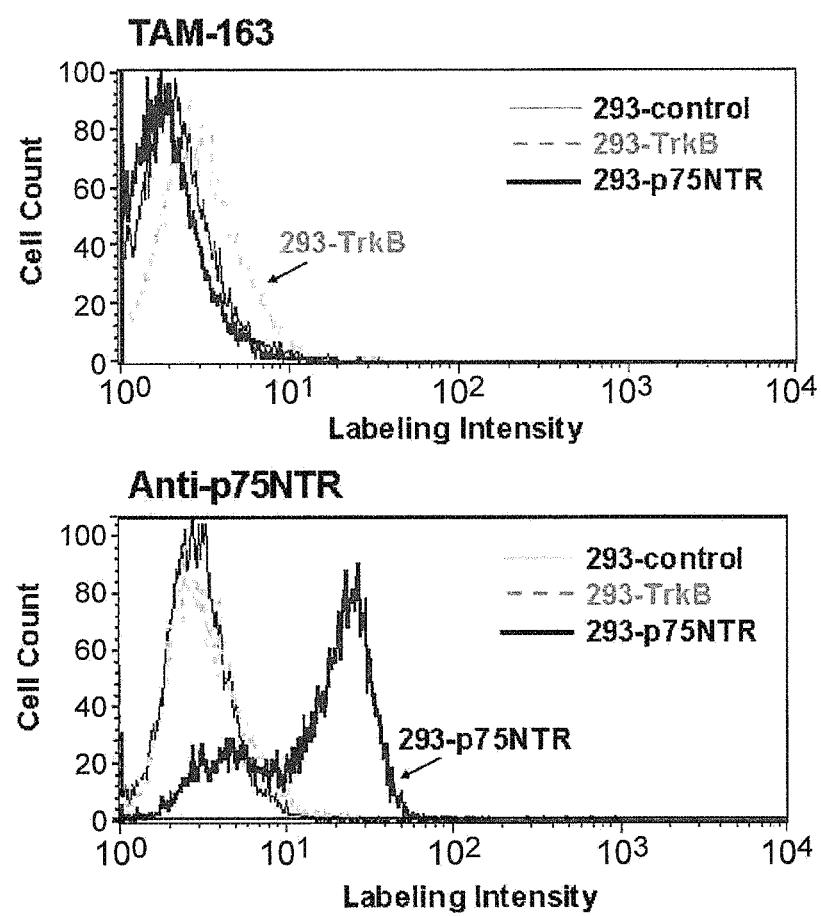

The crossreactivity of TAM-163 to human p75NTR was examined by fluorescence activated cell sorter (FACS) analysis using HEK293 cells transiently transfected with hTrkB or human p75NTR. TAM-163 (6.7 nM) was able to specifically bind to cells transfected with hTrkB, as evidenced by increased fluorescence compared with cells transfected with control empty vector (FIG. 46). TAM-163 did not show any binding to cells transfected with human p75NTR; in fact, staining was slightly less compared to control transfected cells (FIG. 46, top panel). To verify that p75NTR was indeed expressed and present at the cell surface, cells were stained with an ALEXA-labelled anti-p75NTR antibody. As can be seen in FIG. 46, bottom panel, the anti-p75NTR antibody strongly stained cells expressing p75NTR, but did not stain cells expressing hTrkB or a control vector.

As a second approach, we tested the binding of TAM-163 to cells expressing p75NTR using a cell-based ELISA. HEK293 cells transiently transfected with hTrkB, human p75NTR or control vector were incubated with either TAM-163 or anti-p75NTR antibody. TAM-163 specifically bound to cells expressing human TrkB with binding detectable at concentrations as low as 0.2 nM (FIG. 47). TAM-163 did not show any binding to cells expressing human p75NTR even at very high concentrations (67 nM). To verify that p75NTR was indeed expressed and present at the cell surface, staining with anti-p75NTR antibody was used. As expected, anti-p75NTR antibody stained cells expressing human p75NTR, but did not stain control cells or cells expressing hTrkB (FIG. 47).

Example 63

Crossreactivity of TAM-163 with Monkey, Mouse, Dog and Cat TrkB

Since no sequence information is available for cynomolgus monkey TrkB, we isolated TrkB cDNA from this species using standard cloning biology techniques and brain as a template. Sequencing revealed the presence of both TrkB-c and TrkB-a isoforms with the majority of clones (8/10) containing the TrkB-c isoform. Comparison of cynomolgus TrkB cDNA sequence with the human TrkB sequence shows that, with the exception of one amino acid change in the signal sequence, the mature cynomolgus monkey TrkB protein is identical in amino acid sequence to human TrkB. The rhesus monkey TrkB sequence (available in public databases as XP_001107264) is found to be identical to mature human TrkB (not shown). Since the monkey TrkB protein is identical to human, all the human TrkB binding and signaling data shown above are equally applicable to monkey TrkB.

Figure 48:
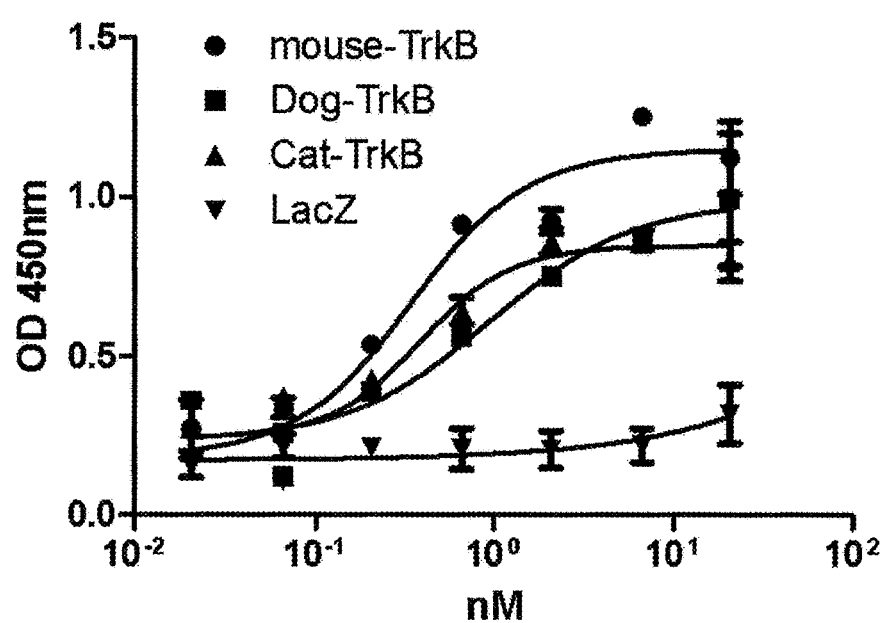

We evaluated the crossreactivity of TAM-163 with mouse and dog TrkB using both binding and signaling experiments. For binding, a cell-based ELISA was used. HEK293 cells transiently transfected with mouse, dog or cat TrkB, or a control vector, were incubated with various concentrations of the TAM-163 antibody. Dose-dependent binding was observed to TrkB from all species, while no binding was observed to a control cell line expressing lacz. The EC50s were similar between species (mouse TrkB=0.34 nM; dog TrkB=0.94 nM; cat TrkB=0.39 nM), indicating that TAM-163 binds to mouse, dog and cat TrkB with high affinity (FIG. 48).

To evaluate the ability of TAM-163 to induce signaling on mouse and dog TrkB, we generated stable cell lines expressing either mouse or dog TrkB. TAM-163, but not a hIgG control antibody, dose-dependently activated phosphorylation of TrkB (Y490), ERK1/2 (Thr202/Tyr204), PLCγ1 (Tyr783) and AKT (Ser473) in both mouse (FIG. 49; TAM-163) and dog (FIG. 50; TAM-163) TrkB cells. Activation of signaling pathways was detectable at concentrations ≤1 nM in both mouse and dog, consistent with the observed EC50 in the binding assay for mouse and dog TrkB.

Example 64

TrkB in Sensory Neuronal Hearing Loss

Temporary and permanent hearing loss is induced by various sources including overexposure to intense sound, chemo induced damage or neurodegeneration that occurs from aging (presbycusis). Recent evidence from Liberman, 2009, J. Neurosci. 29(45):14077-14085, suggests that the ribbon synapse is the first site of insult after both acute noise exposure and in presbycusis. This ribbon synapse damage preceeds spiral ganglia neuron (SGN) and hair cell loss, rendering the ribbon synapse an attractive target for hearing loss intervention.

It is known that factor-related peptides known as neurotrophins are essential for neural development and maintenance, and that several neurotrophins act on a number of neuronal receptors, promoting neuronal survival and differentiation. This class of peptides has been shown to impact the ribbon synapse, specifically the brain-derived neurotrophic factor (BDNF). The elegant work of Wise et al (J. Comp. Neurol. 2000, 487:147-165, whose contents are hereby incorporated by reference), clearly demonstrates that BDNF treatment prevented the loss of SGNs in response to deafening consistently across all cochlear regions. Specifically, application of BDNF prevented auditory neuron death, reduced continued neuronal loss, and enhanced cochlear performance in the models tested, producing a profound effect on hearing. Melster et al (Curr Biol, 2014: 24(6): 658-663, whose contents are hereby incorporated by reference) demonstrated TrkB mediated protection against circadian sensitivity to noise trauma in murine cochlea. Schimmang et al (Development, 2003, 130: 4741-4750, whose contents are hereby incorporated by reference) demonstrated that a lack of BDNF and TrkB signaling in the postnatal cochlea leads to a spatial reshaping of innervation along the tonotopic axis and hearing loss.

Tyrosine Kinase Receptor B (TrkB) is a high affinity catalytic receptor for several growth factor-related peptides (neurotrophins), in particular BDNF and neurotrophin-3 (NT-3). TrkB is expressed and functions predominantly in neurons throughout the central nervous system, including the ribbon synapse rendering it a strong potential therapeutic target for a variety of sensorineural hearing loss disorders including sudden hearing loss, noise induced hearing loss, age related hearing loss (presbycusis), noise induced hearing loss, drug induced hearing loss and genetic disorders of hearing. Thus, TrkB agonists may be potential therapeutics for treatment of such hearing loss disorders.

TAM-163 is a humanized monoclonal antibody designed as an agonist of the TrkB. TAM-163 (also referred to as huTOA-1 and PF-05230901) has been shown to be such a selective antibody TrkB agonist showing strong activation of downstream signaling cascades (FIG. 41, TRK, PLCγ1 and ERK ½) and demonstrating an excellent selectivity profile (FIG. 42). Thus, TAM-163 may be a potential therapeutic for treatment of hearing loss disorders that may be treated by a TrkB agonist in a patient in need of such treatment.

Such patients can be identified by a test to determine hearing loss which may be conducted by an audiologist using an audiometer to determine the individual's hearing sensitivity at different frequencies. Other hearing tests may be used, for example, the Weber test, the Rinne test, the Hearing in Noise test, the acoustic reflex test, and a tympanogram, among many such tests known in the art.

Example 65

Conclusions

The present data demonstrate that TAM-163 is a potent and specific agonist of human TrkB that activates all aspects of the TrkB signaling cascade. While the potency (EC50) of TAM-163 is comparable to the endogenous TrkB ligand BDNF, the maximum effect is less than what is observed with BDNF (~50-80% of maximal signal depending on the assay), suggesting that TAM-163 is a partial agonist of human TrkB. TAM-163 induces internalization and degradation of human TrkB in a manner similar to BDNF. TAM-163 does not crossreact with human TrkA, human TrkC or human p75NTR in cell-surface binding experiments and does not induce signaling in cell lines expressing human TrkA or TrkC. TAM-163 binds to and activates mouse and dog TrkB at low nanomolar concentrations, similar to its effect on human TrkB. Since monkey TrkB is 100% identical to human TrkB, TAM-163 also fully crossreacts with monkey TrkB. Examination of the mRNA expression of the catalytic isoforms of TrkB as well as all TrkB isoforms in normal human tissues confirms that the catalytic isoform of TrkB is most highly expressed in the brain and that the human neuroblastoma cell line SH-SY5Y can be used to examine signaling mediated by endogenous TrkB.

Further Embodiments of the Invention

E77. According to the 77$^{th}$ embodiment of the invention (E77), there is provided an isolated Human Tyrosine Receptor Kinase B (huTrkB) antibody which specifically binds to huTrkB wherein the VH region comprises an amino acid sequence selected from the group consisting of SEQ ID NO: 51, SEQ ID NO:111, and SEQ ID NO:113, and wherein the VL domain comprises an amino acid sequence selected from the group consisting of SEQ ID NO:53, SEQ ID NO:115, SEQ ID NO:117, SEQ ID NO:119, SEQ ID NO:121, SEQ ID NO:124, SEQ ID NO:126, SEQ ID NO:128, SEQ ID NO:130, and SEQ ID NO:132.

E78. The antibody as set forth in E77, wherein the VH region comprises the amino acid of SEQ ID NO:51 and the VH region comprises the amino acid sequence of SEQ ID NO:53.

E79. The antibody as set forth in any one of E77-E78, wherein the antibody is IgG1 subclass.

E80. The antibody as set forth in any one of E77-E79, wherein the HC comprises SEQ ID NO:75 and the LC comprises SEQ ID NO:78.

E81. An isolated Human Tyrosine Receptor Kinase B (huTrkB) antibody which specifically binds to huTrkB wherein the VH region comprises an amino acid sequence encoded by sequence selected from the group consisting of SEQ ID NO:110, SEQ ID NO:111, and SEQ ID NO:113; and wherein the wherein the VL region is encoded by a nucleic acid comprising a sequence selected from the group consisting of SEQ ID NO:123, SEQ ID NO:116, SEQ ID NO:118, SEQ ID NO:120, SEQ ID NO:122, SEQ ID NO:125, SEQ ID NO:127, SEQ ID NO:129, SEQ ID NO:131, and SEQ ID NO:133.

E82. An antibody as set forth in any one of E77-E81, wherein the VH region is encoded by a nucleic acid comprising SEQ ID NO:110, and the VL region is encoded by a nucleic acid comprising SEQ ID NO:123.

E83. A nucleic acid encoding the antibody as set forth in any one of E77-E82.

E84. A nucleic acid encoding the antibody as set forth in any one of E77-E82, wherein the VH region is encoded by a nucleic acid comprising a sequence selected from the group consisting of SEQ ID NO:110, SEQ ID NO:111, and SEQ ID NO:113; and wherein the wherein the VL region is encoded by a nucleic acid comprising a sequence selected from the group consisting of SEQ ID NO:123, SEQ ID NO:116, SEQ ID NO:118, SEQ ID NO:120, SEQ ID NO:122, SEQ ID NO:125, SEQ ID NO:127, SEQ ID NO:129, SEQ ID NO:131, and SEQ ID NO:133.

E85. A nucleic acid encoding the antibody as set forth in any one of E77-E82, wherein the VH region is encoded by a nucleic acid comprising SEQ ID NO:110, and the VL region is encoded by a nucleic acid comprising SEQ ID NO:123.

E86. A vector comprising the nucleic acid as set forth in any one of E83-E85.

E87. A vector comprising a nucleic acid encoding the antibody as set forth in any one of E83-E86

E88. A cell comprising the nucleic acid as set forth in any one of E83-E85.

E89. A cell comprising the vector as set forth in any one of E86-E87.

E90. A cell expressing the antibody as set forth in any one of E77-E82.

E91. A cell comprising the nucleic acid as set forth in any one of E83-E85.

E92. A method of generating an antibody, comprising culturing the cell as set forth in any one of E88-E91 under conditions conducive to antibody expression, and allowing said cell to express said antibody.

E93. A pharmaceutical composition comprising the antibody as set forth in any one of E77-E82 and a pharmaceutically acceptable carrier.

E94. A method of treating hearing loss in an individual, comprising administering to the individual a therapeutically effective amount of the pharmaceutical composition as set forth in E93.

E95. A method of preventing further hearing loss in an individual, comprising administering to the individual a therapeutically effective amount of the pharmaceutical composition as set forth in E93.

E96. The method as set forth in any one of E94-95, wherein the hearing loss is selected from the group consisting of sudden hearing loss, age related hearing loss, noise induced hearing loss, drug induced hearing loss and genetic disorders of hearing.

E97. The method as set forth in any one of E94-E96, wherein the hearing loss is characterized by auditory neuronal death.

E98. The method as set forth in any one of E94-E97, wherein the auditory neuronal death is minimized or inhibited by TrkB activation.

E99. The method as set forth in any one of E97-E98, wherein the auditory neuronal death occurs at the ribbon synapse.

E100. The method as set forth in any one of E94-E99, wherein the method improves cochlear performance.

E101. The antibody as set forth in any one of E77-E82, for use in the treatment of hearing loss.

E102. The antibody as set forth in any one of E77-E82, for use in the prevention of further hearing loss in an individual.

E103. The antibody as set forth in any one of E101-102, wherein the hearing loss is selected from the group consisting of sudden hearing loss, age related hearing loss, noise induced hearing loss, drug induced hearing loss and genetic disorders of hearing.

E104. The antibody as set forth in any one of E101-E103, wherein the hearing loss is characterized by auditory neuronal death.

E105. The antibody as set forth in E104, wherein the auditory neuronal death is minimized or inhibited by TrkB activation.

E106. The antibody as set forth in any one of E104-E105, wherein the auditory neuronal death occurs at the ribbon synapse.1097

E107. The antibody as set forth in any one of E101-E106, wherein administration of the antibody to an individual with hearing loss improves cochlear performance.

E108. The pharmaceutical composition as set forth in E93, for use in the treatment of hearing loss.

E109. The pharmaceutical composition as set forth in E93, for use in the prevention of further hearing loss in an individual E110. The pharmaceutical composition as set forth in any one of E108-109, wherein the hearing loss is selected from the group consisting of sudden hearing loss, age related hearing loss, noise induced hearing loss, drug induced hearing loss and genetic disorders of hearing.

E111. The pharmaceutical composition as set forth in any one of E108-E110, wherein the hearing loss is characterized by auditory neuronal death.

E112. The pharmaceutical composition as set forth in E111, wherein the auditory neuronal death is minimized or inhibited by TrkB activation.

E113. The pharmaceutical composition as set forth in any one of E111-E112, wherein the auditory neuronal death occurs at the ribbon synapse.

E114. The pharmaceutical composition as set forth in any one of E108-E113, wherein administration of the antibody to an individual with hearing loss improves cochlear performance.

E115. The antibody as set forth in any one of E1-71, and E77-E107.

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. In particular, any aspect of the invention described in the claims, alone or in combination with one or more additional claims and/or aspects of the description, is to be understood as being combinable with other aspects of the invention set out elsewhere in the claims and/or description and/or sequence listings and/or drawings.

In so far as specific examples found herein do not fall within the scope of an invention, said specific example may be explicitly disclaimed.

The use of the term "or" in the claims is used to mean "and/or" unless explicitly indicated to refer to alternatives only or the alternatives are mutually exclusive, although the disclosure supports a definition that refers to only alternatives and "and/or." As used herein the specification, "a" or "an" may mean one or more, unless clearly indicated otherwise. As used herein in the claim(s), when used in conjunction with the word "comprising", the words "a" or "an" may mean one or more than one. As used herein "another" may mean at least a second or more. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The words "comprises/comprising" and the words "having/including" when used herein with reference to the present invention are used to specify the presence of stated features, integers, steps or components but does not preclude the presence or addition of one or more other features, integers, steps, components or groups thereof.

Although the disclosed teachings have been described with reference to various applications, methods, and compositions, it will be appreciated that various changes and modifications can be made without departing from the teachings herein and the claimed invention below. The examples are provided to better illustrate the disclosed teachings and are not intended to limit the scope of the teachings presented herein. While the present teachings have been described in terms of these exemplary embodiments, numerous variations and modifications of these exemplary embodiments are possible without undue experimentation. All such variations and modifications are within the scope of the current teachings.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The description and examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

TABLE 26

SEQ IDs of antibodies and antibody domains used in examples. Each row indicates the seq IDs of sequences (see Table 1) used to construct the full sequence of the protein in column 1. ($C_H3$). N/A: Not Applicable (bivalent, monospecific control antibody). Empty cells indicate unique sequence not disclosed in this application version.

| Antibody | 1st Component | | | | | | | | | |
|---|---|---|---|---|---|---|---|---|---|---|
| | LC | VL | CL | HC | VH | CH | CH1 | HNGE | CH2 | CH3 |
| Ab1 | | 9 | | | | 54 | 1 | 42 | 45 | 18 |
| Ab2 | | 9 | | | | 54 | 1 | 42 | 45 | 18 |

TABLE 26-continued

SEQ IDs of antibodies and antibody domains used in examples. Each row indicates the seq IDs of sequences (see Table 1) used to construct the full sequence of the protein in column 1. ($C_H3$). N/A: Not Applicable (bivalent, monospecific control antibody). Empty cells indicate unique sequence not disclosed in this application version.

| Antibody | LC | VL | CL | HC | VH | CH | CH1 | HNGE | CH2 | CH3 |
|---|---|---|---|---|---|---|---|---|---|---|
| Ab1 Ab2 v1.0 | | | 24 | | | 55 | 33 | 42 | 45 | 46 |
| Ab1 Ab2 v2.0 | | | 24 | | | 55 | 33 | 42 | 45 | 46 |
| Ab1 Ab2 v1.0 NEGATIVE | | | 9 | | | 56 | 1 | 42 | 45 | 46 |
| Ab1 Ab2 v1.0 T1 | | | 9 | | | 56 | 1 | 42 | 45 | 46 |
| Ab1 Ab2 v1.0 T2 | | | 9 | | | 56 | 1 | 42 | 45 | 46 |
| Ab1 Ab2 v1.0 T3 | | | 9 | | | 56 | 1 | 42 | 45 | 46 |
| Ab1 Ab2 v1.0 T4 | | | 9 | | | 56 | 1 | 42 | 45 | 46 |
| Ab1 Ab2 v1.0 T9 | | | 9 | | | 56 | 1 | 42 | 45 | 46 |
| Ab1 Ab2 v1.0 T12 | | | 9 | | | 56 | 1 | 42 | 45 | 46 |
| Ab1 Ab2 v1.0 T18 | | | 9 | | | 56 | 1 | 42 | 45 | 46 |
| Ab1 Ab2 v1.0 T1* | | | 24 | | | 55 | 33 | 42 | 45 | 46 |
| Ab1 Ab2 v1.0 T2* | | | 24 | | | 55 | 33 | 42 | 45 | 46 |
| Ab1 Ab2 v1.0 T3* | | | 24 | | | 55 | 33 | 42 | 45 | 46 |
| Ab1 Ab2 v1.0 T4* | | | 24 | | | 55 | 33 | 42 | 45 | 46 |
| Ab1 Ab2 v1.0 T9* | | | 24 | | | 55 | 33 | 42 | 45 | 46 |
| C5 | 76 | 52 | 9 | 70 | 50 | 54 | 1 | 42 | 45 | 18 |
| Ab3 | | | 9 | | | 54 | 1 | 42 | 45 | 18 |
| Ab3 C5-M1 | | | 24 | | | 55 | 33 | 42 | 45 | 46 |
| Ab3 C5-M1-NEGATIVE | | | 9 | | | 56 | 1 | 42 | 45 | 46 |
| Ab3 C5-M2 | | | 24 | | | 57 | 33 | 44 | 45 | 49 |
| Ab3 C5-M2-NEGATIVE | | | 9 | | | 58 | 1 | 44 | 45 | 49 |
| 29D7 | 78 | 53 | 9 | 75 | 51 | 54 | 1 | 42 | 45 | 18 |
| Deconvolute-3 (Ab3,C5) | | | ×86 | | | ×91 | ×89 | 42 | 45 | 46 |
| Deconvolute-4 (Ab3,C5) | | | ×24 | | | ×91 | ×89 | 42 | 45 | 46 |
| Ab3-S1xC5-T1 | | | 24 | | | 55 | 33 | 42 | 45 | 46 |
| Ab3-S1xC5-T2 | | | 24 | | | 55 | 33 | 42 | 45 | 46 |
| Ab3-S1xC5-T3 | | | 24 | | | 55 | 33 | 42 | 45 | 46 |
| Ab3-S1xC5-T4 | | | 24 | | | 55 | 33 | 42 | 45 | 46 |
| Ab3-S1xC5-T9 | | | 24 | | | 55 | 33 | 42 | 45 | 46 |
| Ab3-S1xC5 | | | 24 | | | 55 | 33 | 42 | 45 | 46 |
| Ab3xC5-S1rev | | | 9 | | | 56 | 1 | 42 | 45 | 46 |

| | 2nd Component | | | | | | | | | |
|---|---|---|---|---|---|---|---|---|---|---|
| Antibody | LC | VL | CL | HC | VH | CH | CH1 | HNGE | CH2 | CH3 |
| Ab1 | N/A | N/A | N/A | N/A | N/A | N/A | N/A | N/A | N/A | N/A |
| Ab2 | N/A | N/A | N/A | N/A | N/A | N/A | N/A | N/A | N/A | N/A |
| Ab1 Ab2 v1.0 | | | 25 | | | 59 | 34 | 42 | 45 | 47 |
| Ab1 Ab2 v2.0 | | | 25 | | | 59 | 34 | 42 | 45 | 47 |
| Ab1 Ab2 v1.0 NEGATIVE | | | 9 | | | 60 | 1 | 42 | 45 | 47 |
| Ab1 Ab2 v1.0 T1 | | | 26 | | | 61 | 35 | 42 | 45 | 47 |
| Ab1 Ab2 v1.0 T2 | | | 27 | | | 62 | 36 | 42 | 45 | 47 |
| Ab1 Ab2 v1.0 T3 | | | 28 | | | 63 | 37 | 42 | 45 | 47 |
| Ab1 Ab2 v1.0 T4 | | | 29 | | | 64 | 38 | 42 | 45 | 47 |
| Ab1 Ab2 v1.0 T9 | | | 30 | | | 65 | 39 | 42 | 45 | 47 |
| Ab1 Ab2 v1.0 T12 | | | 31 | | | 66 | 40 | 42 | 45 | 47 |
| Ab1 Ab2 v1.0 T18 | | | 32 | | | 67 | 41 | 42 | 45 | 47 |
| Ab1 Ab2 v1.0 T1* | | | 26 | | | 61 | 35 | 42 | 45 | 47 |
| Ab1 Ab2 v1.0 T2* | | | 27 | | | 62 | 36 | 42 | 45 | 47 |
| Ab1 Ab2 v1.0 T3* | | | 28 | | | 63 | 37 | 42 | 45 | 47 |
| Ab1 Ab2 v1.0 T4* | | | 29 | | | 64 | 38 | 42 | 45 | 47 |
| Ab1 Ab2 v1.0 T9* | | | 30 | | | 65 | 39 | 42 | 45 | 47 |
| C5 | N/A | N/A | N/A | N/A | N/A | N/A | N/A | N/A | N/A | N/A |
| Ab3 | N/A | N/A | N/A | N/A | N/A | N/A | N/A | N/A | N/A | N/A |
| Ab3 C5-M1 | 77 | 52 | 25 | 71 | 50 | 59 | 34 | 42 | 45 | 47 |
| Ab3 C5-M1-NEGATIVE | 76 | 52 | 9 | 72 | 50 | 60 | 1 | 42 | 45 | 47 |
| Ab3 C5-M2 | 77 | 52 | 25 | 73 | 50 | 68 | 34 | 43 | 45 | 48 |
| Ab3 C5-M2-NEGATIVE | 76 | 52 | 9 | 74 | 50 | 69 | 1 | 43 | 45 | 48 |
| 29D7 | N/A | N/A | N/A | N/A | N/A | N/A | N/A | N/A | N/A | N/A |
| Deconvolute-3 (Ab3,C5) | ×88 | 52 | ×87 | ×93 | 50 | ×92 | ×90 | 42 | 45 | 47 |
| Deconvolute-4 (Ab3,C5) | ×77 | 52 | ×25 | ×93 | 50 | ×92 | ×90 | 42 | 45 | 47 |
| Ab3-S1xC5-T1 | 94 | 52 | 26 | 99 | 50 | 61 | 35 | 42 | 45 | 47 |
| Ab3-S1xC5-T2 | 95 | 52 | 27 | 100 | 50 | 62 | 36 | 42 | 45 | 47 |
| Ab3-S1xC5-T3 | 96 | 52 | 28 | 101 | 50 | 63 | 37 | 42 | 45 | 47 |
| Ab3-S1xC5-T4 | 97 | 52 | 29 | 102 | 50 | 64 | 38 | 42 | 45 | 47 |
| Ab3-S1xC5-T9 | 98 | 52 | 30 | 103 | 50 | 65 | 39 | 42 | 45 | 47 |
| Ab3-S1xC5 | 76 | 52 | 9 | 72 | 50 | 60 | 1 | 42 | 45 | 47 |
| Ab3xC5-S1rev | 77 | 52 | 25 | 71 | 50 | 59 | 34 | 42 | 45 | 47 |

What is claimed is:

1. A heterodimeric protein, comprising
 (i) a first $C_H1$ domain ($C_H1$) and a first $C_L$ domain ($C_L$), the first $C_H1$ and the first $C_L$ interacting together at a first $C_HC_L$ interface to form a first $C_HC_L$ domain ($C_HC_L$);
 (ii) a second $C_H1$ domain ($C_H1$) and a second $C_L$ domain ($C_L$), the second $C_H1$ and the second $C_L$ interacting together at a second $C_HC_L$ interface to form a second $C_HC_L$ domain ($C_HC_L$);
 wherein the first $C_H1$ is engineered to differ from the second $C_H1$ by at least one $C_H1$ mutant residue in the first $C_H1$; and
 wherein the first $C_L$ is engineered to differ from the second $C_L$ by at least one $C_L$ mutant residue in the first $C_L$;
 such that the at least one $C_H1$ mutant residue in the first $C_H1$ and the at least one $C_L$ mutant residue in the first $C_L$ interact with each other in preference to the corresponding at least one $C_H1$ mutant residue in the second $C_H1$ and at least one $C_L$ mutant residue in the second $C_L$;
 wherein the interacting mutant residues of the first $C_H1$ and first $C_L$ thereby form a first complementary residue set;
 wherein the location of the first complementary residue set is selected from the group consisting of:
 (i) $C_h1$-124 and $C_L$-176;
 (ii) $C_H1$-221 and $C_L$-123;
 (iii) $C_H1$-186 and $C_L$-131; and
 (iv) $C_H1$-122 and $C_L$-123;
 and wherein the first $C_H1$ is attached to a first variable heavy domain ($V_H$), and the first $C_L$ is attached to a first variable light domain ($V_L$), and the second $C_H1$ is attached to a second $V_H$, and the second $C_L$ is attached to a second $V_L$, such that when combined, the first $V_H$, first $V_L$, first $C_H1$ and first $C_L$ together form a first Fab, and when combined, the second $V_H$, second $V_L$, second $C_H1$, and second $C_L$ form a second Fab, and wherein preferential formation of the first Fab and the second Fab does not rely on complementary pairing of the variable domains.

2. The heterodimeric protein of claim 1, wherein the solvent accessible surface area of the first complementary residue set is less than 225 Å² as measured using a 2.50 probe.

3. The heterodimeric protein of claim 1, wherein formation of the first $C_HC_L$ and second $C_HC_L$ preferentially occur over formation of a $C_HC_L$ comprised of either the first $C_H1$ and second $C_L$, or second $C_H1$ and first $C_L$, by at least about 4-fold.

4. The heterodimeric protein of claim 1, wherein at least one of the $C_L$ domains is a kappa domain.

5. The heterodimeric protein of claim 1, comprising an engineered disulfide bond between the first $C_H1$ and the first $C_L$, and or the second $C_H1$ and the second $C_L$.

6. The heterodimeric protein of claim 5, wherein the engineered disulfide bond is located at $C_H1$-122 and $C_L$-123.

7. The heterodimeric protein of claim 5, wherein a wild type disulfide bond has been removed, by mutating one or both of $C_H1$-C230 and $C_L$-C214 to any residue except C, on the first $C_HC_L$ and/or second $C_HC_L$, and wherein the first and/or second $C_H1$-C230 and first, and/or second $C_L$-C214 are mutated to S.

8. The heterodimeric protein of claim 1,
wherein the second $C_H1$ is engineered to differ from the first $C_H1$ by at least one $C_H1$ mutant residue in the second $C_H1$;
wherein the second $C_L$ is engineered to differ from the first $C_L$ by at least one $C_L$ mutant residue in the second $C_L$;
such that the at least one $C_H1$ mutant residue in the second $C_H1$ and the at least one $C_L$ mutant residue in the second $C_L$ interact with each other in preference to the corresponding at least one $C_H1$ mutant residue in the first $C_H1$ and the at least one $C_L$ mutant residue in the first $C_L$; and
wherein the interacting mutant residues of the second $C_H1$ and second $C_L$ thereby form a second complementary residue set.

9. The heterodimeric protein of claim 8, wherein the first complementary residue set comprises a positively or negatively charged residue in the first $C_H1$ or first $C_L$, and either a polar residue, or an oppositely charged residue in the other domain; and wherein the second complementary residue set comprises a positively or negatively charged residue in the second $C_H1$ or second $C_L$, and either a polar residue, or an oppositely charged residue in the other domain.

10. The heterodimeric protein of claim 8,
wherein when the at least one $C_H1$ mutant residue in the first $C_H1$, the at least one $C_H1$ mutant residue in the second $C_H1$, or both is selected from the group consisting of W, H, K, R, S and T, the at least one $C_L$ mutant residue in the first $C_L$, the at least one $C_L$ mutant residue in the second $C_L$, or both is selected from the group consisting of S, M, D and E, or
wherein when the at least one $C_H1$ mutant residue in the first $C_H1$, the at least one $C_H1$ mutant residue in the second $C_H1$, or both is selected from the group consisting of E, and D, the at least one $C_L$ mutant residue in the first $C_L$, the at least one $C_L$ mutant residue in the second $C_L$, or both is selected from the group consisting of H, K, and R.

11. The heterodimeric protein of claim 8, wherein the first, second, or both complementary residue sets are selected from the following groups:
(i) $C_H1$-124K, $C_L$-176D, $C_H1$-190S, $C_L$-133S;
(ii) $C_H1$-124K, $C_L$-176D, $C_L$-133S;
(iii) $C_H1$-124E, $C_L$-176K;
(iv) $C_H1$-124E, $C_L$-176K, $C_H1$-188G, $C_L$-133S;
(v) $C_H1$-143R, $C_L$-131E, $C_H1$-186A;
(vi) $C_H1$-221D, $C_L$-123K;
(vii) $C_H1$-221D, $C_L$-123K, $C_H1$-190I, $C_L$-135I;
(viii) $C_H1$-143H, $C_H1$-179D, $C_H1$-186E, $C_L$-131H;
(ix) $C_H1$-186E, $C_L$-131H, $C_H1$-145S;
(x) $C_H1$-143H, $C_H1$-179D, $C_H1$-186E, $C_L$-131H, $C_H1$-190I, $C_L$-135I;
(xi) $C_H1$-186E, $C_L$-131H, $C_H1$-145S;
(xii) $C_H1$-124E, $C_L$-176K, $C_L$-133S;
(xiii) $C_H1$-221D, $C_L$-123K, $C_H1$-190I, $C_L$-135I, $C_H1$-174C, $C_H1$-230S, $C_L$-176C, $C_L$-214S
(xiv) $C_H1$-143H, $C_H1$-179D, $C_H1$-186E, $C_L$-131H, $C_H1$-190I, $C_L$-135I, $C_H1$-174C, $C_H1$-230S, $C_L$-176C, $C_L$-214S;
(xv) $C_H1$-186E, $C_L$-131H, $C_H1$-145S, $C_H1$-139C, $C_H1$-230S, $C_L$-116C, $C_L$-214S;
(xvi) $C_H1$-122C, $C_H1$-145E, $C_H1$-230S, $C_L$-123C, $C_L$-131H, $C_L$-214S;
(xvii) $C_H1$-143S, $C_H1$-188W, $C_H1$-122C, $C_H1$-230S, $C_L$-133M, $C_L$-178G, $C_L$-176G, $C_L$-123C, $C_L$-214S;
(xviii) $C_H1$-143S, $C_H1$-188W, $C_H1$-122C, $C_H1$-139C, $C_H1$-174C, $C_H1$-230S, $C_L$-133S, $C_L$-178S, $C_L$-131D, $C_L$-116C, $C_L$-123C, $C_L$-176C, $C_L$-214S;
and optionally,
wherein the second complementary residue set is selected from the following groups:
(i) $C_H1$-188E, $C_L$-178K, $C_H1$-143E;
(ii) $C_H1$-188K, $C_L$-178D, $C_H1$-143D;
(iii) $C_H1$-143K, $C_L$-178D;
(iv) $C_H1$-143D, $C_L$-178R;
(v) $C_H1$-143K, $C_L$-178D;
(vi) $C_H1$-143D, $C_L$-178K;
(vii) $C_H1$-143D, $C_L$-178K, $C_L$-176M;
(viii) $C_H1$-143E, $C_L$-131R;
(ix) $C_H1$-143R, $C_L$-131E;
(x) $C_H1$-145E, $C_L$-131H;
(xi) $C_H1$-143S, $C_L$-131D, $C_H1$-188W, $C_L$-133S, $C_L$-178S;
(xii) $C_H1$-143S, $C_H1$-188W, $C_L$-133M, $C_L$-176G, $C_L$-178G;
(xii) $C_H1$-143S, $C_L$-131D, $C_H1$-188W, $C_L$-133S, $C_L$-176C;
(xiv) C1-143S, $C_H1$-188W, $C_L$-133M, $C_L$-178G, $C_L$-176G;
(xv) $C_H1$-143S, $C_H1$-188W, $C_L$-131D; and
(xvi) $C_H1$-143S, $C_L$-131D, $C_H1$-188W, $C_L$-133S, $C_L$-178S, $C_H1$-174C, $C_H1$-230S, $C_L$-176C, $C_L$-214S.

12. The heterodimeric protein of claim 11, wherein the first and second complementary residue sets further comprise one or more mutations selected from the group consisting of: $C_H1$-143D, $C_H1$-145S, $C_H1$-186A, $C_H1$-186E, $C_H1$-188G, $C_H1$-143S, $C_H1$-190S, $C_H1$-190I, $C_L$-133S, $C_L$-135I, $C_L$-176G, $C_L$-176M, $C_L$-178G, and $C_L$-178S.

13. A bispecific antibody comprising a heterodimeric protein of claim 8, wherein the first $C_HC_L$ comprises $C_H1$-124K, $C_L$-176D, $C_H1$-190S, and $C_L$-133S, and the second $C_HC_L$ comprises $C_H1$-124E, $C_L$-176K, $C_H1$-188G, and $C_L$-133S.

14. An isolated nucleic acid encoding the heterodimeric protein of claim 1.

15. The isolated nucleic acid of claim 14, wherein the isolated nucleic acid encodes the first $C_H1$, the first $C_L$, the second $C_H1$, the second $C_L$, the first $V_H$, the first $V_L$, the second $V_H$, the second $V_L$ or a combination thereof.

16. A vector comprising the nucleic acid of claim 14.

17. A cell comprising the nucleic acid of claim 14.

18. A method of making the heterodimeric protein of claim 1, comprising:
   (i) cotransfecting a cell line with one or more vectors to express the first $C_H1$ and the first $C_L$ of the first $C_HC_L$; and the second $C_H1$ and the second $C_L$ of the second $C_HC_L$;
   (ii) culturing the cell line under conditions to express the one or more vectors and that allow the first $C_HC_L$ and second $C_HC_L$ to assemble; and
   (iii) purifying the heterodimeric protein from the cell culture.

19. An isolated antibody that specifically binds human TrkB, wherein the antibody comprises a VH region comprising the amino acid sequence of SEQ ID NO:51 and a VL region comprising the amino acid sequence of SEQ ID NO:53.

20. The antibody of claim 19, wherein the antibody comprises a heavy chain and a light chain, and wherein the heavy chain comprises the amino acid sequence of SEQ ID NO:75 and the light chain comprises the amino acid sequence of SEQ ID NO:78.

21. A pharmaceutical composition comprising the antibody of claim 19 and a pharmaceutically acceptable carrier.

22. An isolated nucleic acid encoding the antibody of claim 19.

23. The isolated nucleic acid of claim 22, wherein the isolated nucleic acid encodes the $V_H$, $V_L$ or both of an antibody or an antigen-binding fragment thereof that specifically binds TrkB, and wherein the nucleic acid encodes the amino acid sequence of SEQ ID NO:51, the amino acid sequence of SEQ ID NO:53, or both.

24. A method of treating a hearing loss disorder in a patient in need thereof, comprising administering a therapeutically effective amount of the pharmaceutical composition of claim 21 to the patient, thereby treating a hearing loss disorder.

* * * * *